United States Patent
Doudna et al.

(10) Patent No.: US 11,441,137 B2
(45) Date of Patent: *Sep. 13, 2022

(54) CASZ COMPOSITIONS AND METHODS OF USE

(71) Applicant: The Regents of the University of California, Oakland, CA (US)

(72) Inventors: Jennifer A. Doudna, Berkeley, CA (US); David Burstein, Berkeley, CA (US); Janice S. Chen, Berkeley, CA (US); Lucas B. Harrington, Berkeley, CA (US); David Paez-Espino, Walnut Creek, CA (US); Jillian F. Banfield, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/884,766

(22) Filed: May 27, 2020

(65) Prior Publication Data

US 2020/0370028 A1   Nov. 26, 2020

Related U.S. Application Data

(63) Continuation of application No. 16/694,720, filed on Nov. 25, 2019, which is a continuation of application No. PCT/US2018/058545, filed on Oct. 31, 2018.

(60) Provisional application No. 62/580,395, filed on Nov. 1, 2017.

(51) Int. Cl.
| | |
|---|---|
| *C12Q 1/6809* | (2018.01) |
| *C12N 9/22* | (2006.01) |
| *C12N 15/11* | (2006.01) |
| *C12N 15/113* | (2010.01) |

(52) U.S. Cl.
CPC .............. *C12N 9/22* (2013.01); *C12N 15/11* (2013.01); *C12N 15/113* (2013.01); *C07K 2319/09* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,773,885 B1 | 8/2004 | Walder et al. | |
| 8,597,886 B2 | 12/2013 | Smith et al. | |
| 8,815,782 B2 | 8/2014 | Zeiner et al. | |
| 9,730,967 B2 | 6/2017 | Kovarik et al. | |
| 9,790,490 B2 | 10/2017 | Zhang et al. | |
| 10,253,365 B1 * | 4/2019 | Doudna | C12Q 1/6823 |
| 10,316,324 B2 | 6/2019 | Begemann et al. | |
| 10,337,051 B2 | 7/2019 | Doudna et al. | |
| 10,494,664 B2 | 12/2019 | Doudna et al. | |
| 10,570,415 B2 | 2/2020 | Doudna et al. | |
| 2013/0261196 A1 | 10/2013 | Diamond et al. | |
| 2014/0068797 A1 | 3/2014 | Doudna et al. | |
| 2014/0093883 A1 | 4/2014 | Maples et al. | |
| 2014/0273226 A1 | 9/2014 | Wu | |
| 2015/0211058 A1 | 7/2015 | Carstens | |
| 2016/0138008 A1 | 5/2016 | Charpentier et al. | |
| 2016/0208243 A1 | 7/2016 | Zhang et al. | |
| 2016/0289659 A1 | 10/2016 | Doudna et al. | |
| 2017/0037432 A1 | 2/2017 | Donohoue et al. | |
| 2017/0051276 A1 | 2/2017 | May et al. | |
| 2017/0175104 A1 | 6/2017 | Doudna et al. | |
| 2017/0198277 A1 | 7/2017 | Kmiec et al. | |
| 2017/0211142 A1 | 7/2017 | Smargon et al. | |
| 2017/0233756 A1 | 8/2017 | Begemann et al. | |
| 2017/0306335 A1 | 10/2017 | Zhang et al. | |
| 2017/0321198 A1 | 11/2017 | Severinov et al. | |
| 2017/0321214 A1 | 11/2017 | Zhang et al. | |
| 2018/0320163 A1 | 11/2018 | Koonin et al. | |
| 2018/0340218 A1 | 11/2018 | Abudayyeh et al. | |
| 2019/0276842 A1 | 9/2019 | Doudna et al. | |

(Continued)

FOREIGN PATENT DOCUMENTS

| | | |
|---|---|---|
| CN | 106701830 A | 5/2017 |
| EP | 3009511 A2 | 4/2016 |

(Continued)

OTHER PUBLICATIONS

East-Seletsky et al., "Two distinct RNase activities of CRISPR-C2c2 enable guide-RNA processing and RNA detection", Nature, vol. 538, p. 270-275 plus supplemental, Oct. 13, 2016.*
Harrington et al. "Programmed DNA destruction by miniature CRISPR-Cas14 enzymes," Science; vol. 362, No. 6416, pp. 839-842 (Nov. 16, 2018).
Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).
Ngo, et al.; "Computational Complexity, Protein Structure Prediction, and the Levinthal Paradox"; The Protein Folding Problem and Tertiary Structure Prediction; 5 pages (1994).

(Continued)

*Primary Examiner* — Richard G Hutson
(74) *Attorney, Agent, or Firm* — Bozicevic Field & Francis, LLP; Paula A. Borden

(57) ABSTRACT

Provided are compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ transactivating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

29 Claims, 108 Drawing Sheets

Specification includes a Sequence Listing.

(56) References Cited

U.S. PATENT DOCUMENTS

| | | |
|---|---|---|
| 2019/0300908 A1 | 10/2019 | Doudna et al. |
| 2020/0017879 A1 | 1/2020 | Doudna et al. |
| 2020/0087640 A1 | 3/2020 | Doudna et al. |
| 2020/0172886 A1 | 6/2020 | Doudna et al. |
| 2021/0017508 A1 | 1/2021 | Doudna et al. |
| 2021/0166783 A1 | 6/2021 | Shmakov et al. |

FOREIGN PATENT DOCUMENTS

| | | | |
|---|---|---|---|
| EP | | 2825654 | 4/2017 |
| EP | | 3546573 | 10/2019 |
| EP | | 3283625 | 12/2019 |
| JP | | 2004521606 A | 7/2004 |
| WO | WO 2015/071474 | | 5/2015 |
| WO | WO 2015/139139 | | 9/2015 |
| WO | WO 2015/191693 | | 12/2015 |
| WO | WO 2016/094872 | | 12/2015 |
| WO | WO 2016/106236 | | 12/2015 |
| WO | WO 2016/028843 | | 2/2016 |
| WO | WO 2016/094867 | | 6/2016 |
| WO | WO 2016/205711 | | 6/2016 |
| WO | WO 2016/123243 | | 8/2016 |
| WO | WO 2016/166340 | | 10/2016 |
| WO | WO 2016/205613 | | 12/2016 |
| WO | WO 2016/205749 | | 12/2016 |
| WO | WO 2016/205764 | | 12/2016 |
| WO | WO 2017/070605 | | 4/2017 |
| WO | WO 2017/205668 | | 5/2017 |
| WO | WO 2017/120410 | | 7/2017 |
| WO | WO 2017/147345 | | 8/2017 |
| WO | WO 2017/176529 | | 10/2017 |
| WO | WO 2017/218573 | | 12/2017 |
| WO | WO 2017/219027 | | 12/2017 |
| WO | WO 2017/223538 | | 12/2017 |
| WO | WO 2018/035250 | | 2/2018 |
| WO | WO 2018/064352 | | 4/2018 |
| WO | WO 2018/064371 | | 4/2018 |
| WO | WO 2018/107129 | | 6/2018 |
| WO | WO 2018/195545 | | 10/2018 |
| WO | WO 2019/089796 | | 5/2019 |
| WO | WO 2019/089804 | | 5/2019 |
| WO | WO 2019/089808 | | 5/2019 |
| WO | WO 2019/089820 | | 5/2019 |
| WO | WO 2019/126577 | | 6/2019 |
| WO | WO-2019126577 A2 * | | 6/2019 ............... C12N 9/22 |

OTHER PUBLICATIONS

Shmakov, et al.; "Diversity and evolution of class 2 CRISPR-Cas systems"; Nature Reviews Microbiology; vol. 15, pp. 169-182 (Mar. 2017).
Abudayyeh, et al.; "C2c2 is a single-component programmable RNA-guided RNA-targeting CRISPR effector"; Science; vol. 353, No. 6299, 23 pages (Aug. 5, 2016).
Abudayyeh, et al.; "C2c2 is a single-component programmable RNA-guided RNA-targeting CRISPR effector; Supplementary Information"; Science; vol. 353, vol. 6299, 31 pages (Aug. 5, 2016).
Abudayyeh, et al.; "RNA targeting with CRISPR-Cas13"; Nature; vol. 550, 18 pages (Oct. 12, 2017).
Ambion; "RnaseAlert Lab Test Kit v2, User Guide"; 12 pages (Mar. 1, 2013).
Anantharaman, et al.; "Thousands of microbial genomes shed light on interconnected biogeochemical processes in an aquifer system"; Nature Communications; vol. 7, No. 13210, 11 pages (Oct. 24, 2016).
Applied Biosystems/Ambion; "RNaseAlert Lab Test Kit"; 12 pages (2008).
Armitage, et al.; "Hairpin-Forming Peptide Nucleic Acid Oligomers"; Biochemistry; vol. 37, No. 26, pp. 9417-9425 (1998).
Baker, et al.; "Enigmatic, ultrasmall, uncultivated Archaea"; PNAS; vol. 107, No. 19, pp. 8806-8811 (May 11, 2010).
Barrangou, et al.; "Expanding the CRISPR Toolbox: Targeting RNA with Cas13b"; Molecular Cell; vol. 65, No. 4, pp. 582-584 (Feb. 16, 2017).

Bautista, et al.; "Virus-Induced Dormancy in the Archaeon Sulfolobus islandicus"; mBio; vol. 6, No. 2, 8 pages (2015).
Burstein, et al.; "New CRISPR-Cas systems from uncultivated microbes"; Nature; vol. 542, No. 7640, pp. 237-241 (Feb. 9, 2017).
Choudhury, et al.; "CRISPR-dCas9 mediated TET1 targeting for selective DNA demethylation at BRCA1 promoter"; Oncotarget; vol. 7, No. 29, pp. 46545-46556 (2016).
Chylinski, et al.; "Classification and evolution of type II CRISPR-Cas systems"; Nucleic Acids Research; vol. 42, No. 10, pp. 6091-6105 (2014).
Cong, et al.; "Multiplex Genome Engineering Using CRISPR/Cas Systems"; Science; vol. 339, No. 6121, pp. 819-823 (Feb. 15, 2013).
Cox, et al.; "RNA editing with CRISPR-Cas13"; Science; vol. 358, No. 6366, 15 pages (Nov. 24, 2017).
CRZ3554.1 (hypothetical protein HHT344_2368 [Herbinix hemicellulosilytica], Gen Bank Accession sequence, priority to Jul. 24, 2015, 1 page) (Year: 2015).
Deltcheva, et al.; "CRISPR RNA maturation by trans-encoded small RNA and host factor RNase III"; Nature; vol. 471, pp. 1-19 (Mar. 31, 2011).
East-Seletsky, et al.; "RNA Targeting by Functionally Orthogonal Type VI-A CRISPR-Cas Enzymes"; Molecular Cell; vol. 66, pp. 373-383 (May 4, 2017).
Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
GenBank CRZ35554 1; "Hypothetical protein HHT355_2368 [Herbinix hemicellulosilytica]"; 1 page (Oct. 11, 2018).
GenBank OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).
Gootenberg, et al.; "Multiplexed and portable nucleic acid detection platform with Cas13, Cas12a, and Csm6"; Science; vol. 360, pp. 439-444 (2018).
Gootenberg, et al.; "Nucleic acid detection with CRISPR-Cas13a/C2c2"; Science; 9 pages (Apr. 13, 2017).
Hale, et al.; "RNA-Guided RNA Cleavage by a CRISPR RNA-Cas Protein Complex"; Cell; vol. 139, No. 5, pp. 945-956 (Nov. 25, 2009).
Hale, et al.; "Target RNA capture and cleavage by the Cmr type III-B CRISPR-Cas effector complex"; Genes & Development; vol. 28, No. 21, pp. 2432-2443 (Nov. 1, 2014).
Kelemen, et al.; "Hypersensitive substrate for ribonucleases"; Nucleic Acids Research; vol. 27, No. 18, pp. 3696-3701 (1999).
Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).
Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Le Cong, et al.; "Multiplex Genome Engineering Using CRISPR/Cas Systems"; Science; vol. 339, pp. 819-823 (Feb. 15, 2013).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "CasX enzymes comprise a distinct family of RNA-guided genome editors"; Nature; vol. 566, pp. 23 pages (Feb. 14, 2019).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Makarova, et al.; "Evolutionary classification of CRISPR-Cas systems: a burst of class 2 and derived variants"; Nature Reviews Microbiology; vol. 18, pp. 67-83 (Feb. 2020).
O'Connell; "Molecular Mechanisms of RNA Targeting by Cas13-containing Type VI CRISPR-Cas Systems"; J Mol Biol; vol. 431, pp. 66-87 (2019).

(56) References Cited

OTHER PUBLICATIONS

OHA03494.1 (hypothetical protein A3J58_03210 [Candidatus Sung bacteria bacterium RIFCSPH IGHO2_02_FU LL_52_23], NCBI Reference Sequence, priority to Oct. 21, 2016, 2 pages) (Year: 2016).
RNaseAlert Lab Test Kit (Applied Biosystems, Fluorometric RNase Detection Assay, 2008, 12 pages). (Year: 2008).
Sato, et al.; "Highly Sensitive Nuclease Assays Based on Chemically Modified DNA or RNA"; Sensors; vol. 14, No. 7, pp. 12437-12450 (2014).
Shmakov, et al.; "Discovery and functional characterization of diverse Class 2 CRISPR-Cas systems"; Mol. Cell.; vol. 60, No. 3, pp. 385-397 (Nov. 5, 2015).
Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Strauβ, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
Third Party Observations filed on Oct. 15, 2018 in UK patent application No. GB 1804822.3 (18 pages).
Yan, et al.; "Cas13d Is a Compact RNA-Targeting Type VI CRISPR Effector Positively Modulated by a WYL-Domain-Containing Accessory Protein"; Molecular Cell; vol. 70, pp. 327-339 (2018).
Yang, et al.; "New CRISPR-Cas systems discovered"; Cell Res.; vol. 27, pp. 313-314 (Feb. 21, 2017).
Yang, et al.; "Using Molecular Beacons for Sensitive Fluorescence Assays of the Enzymatic Cleavage of Nucleic Acids"; Methods in Molecular Biology, Fluorescent Energy Transfer Nucleic Acid Probes: Designs and Protocols; vol. 335, pp. 71-81 (2006).
Zhang, et al.; "Design of a Molecular Beacon DNA Probe with Two Fluorophores"; Angew. Chem.; vol. 113, No. 2, pp. 416-419 (2001).
Koonin, et al.; "Origins and evolution of CRISPR-Cas systems"; Phil. Trans. R. Soc. B.; vol. 374, No. 1772, 6 pages (Mar. 25, 2019).
JGI Accession No. 3300002502.a:C687J35174_100538264; 2 pages (obtained online Sep. 1, 2021).
JGI Accession No. 3300025142.a:Ga0210019_10421012; 2 pages (obtained online Sep. 1, 2021).
Chen, et al.; "CRISPR-Cas12a target binding unleashes indiscriminate single-stranded DNase activity"; Science; vol. 360, pp. 436-439 (2018).
JGI Accession No. (Taxon ID:Gene ID) 3300002105.a:C687J26635_100228363, available at https://img.jgi.doe.gov/cgi-bin/m/main.cgi?section=MetaGeneDetail&page=metaGeneDetail&data_type=assembled&taxon_oid=3300002105&gene_oid=C687J26635_100228363.
JGI Accession No. (Taxon ID:Gene ID) 3300002502.a:C687J35174_100538264, available at https://img.jgi.doe.gov/cgi-bin/m/main.cgi?section=MetaGeneDetail&page=metaGeneDetail&data_type=assembled&taxon_oid=3300002502&gene_oid=C687J35174_100538264.
JGI Accession No. (Taxon ID:Gene ID) 3300025308.a:Ga0209211_100536734, available at https://img.jgi.doe.gov/cgi-bin/m/main.cgi?section=MetaGeneDetail&page=metaGeneDetail&data_type=assembled&taxon_oid=3300025308&gene_oid=Ga0209211_100536734.
JGI Accession No. (Taxon ID:Gene ID) 3300025317.a:Ga0209541_100096836, available at https://img.jgi.doe.gov/cgi-bin/m/main.cgi?section=MetaGeneDetail&page=metaGeneDetail&data_type=assembled&taxon_oid=3300025317&gene_oid=Ga0209541_100096836.
JGI Accession No. (Taxon ID:Gene ID) 3300025323.a:Ga0209542_1000010711, available at https://img.jgi.doe.gov/cgi-bin/m/main.cgi?section=MetaGeneDetail&page=metaGeneDetail&data_type=assembled&taxon_oid=3300025323&gene_oid=Ga0209542_1000010711.
JGI Accession No. (Taxon ID:Gene ID) 3300025323.a:Ga0209542_10000107204, available at https://img.jgi.doe.gov/cgi-bin/m/main.cgi?section=MetaGeneDetail&page=metaGeneDetail&data_type=assembled&taxon_oid=3300025323&gene_oid=Ga0209542_10000107204.
Liu, et al.; "Delivery strategies of the CRISPR-Cas9 gene-editing system for therapeutic applications"; Journal of Controlled Release; vol. 266, pp. 17-26 (2017).
Makarova, et al.; "An updated evolutionary classification of CRISPR-Cas systems"; Nat. Rev. Microbiol.; vol. 13, No. 11, pp. 722-736 (Nov. 2015).
Price, et al.; "Cas9-mediated targeting of viral RNA in eukaryotic cells"; PNAS; vol. 112, No. 19, pp. 6164-6169 (May 12, 2015).
Sampson, et al.; "A CRISPR/Cas system mediates bacterial innate immune evasion and virulence"; Nature; vol. 497, No. 7448; pp. 254-257 (May 9, 2013).
U.S. Appl. No. 16/694,720 Final Office Action dated Sep. 16, 2020.
U.S. Appl. No. 16/694,720 Non-Final Office Action dated Jun. 17, 2021.
U.S. Appl. No. 16/896,711 Final Office Action dated Jan. 27, 2021.
U.S. Appl. No. 16/896,711 Non-Final Office Action dated Aug. 18, 2021.
U.S. Appl. No. 16/896,711 Non-Final Office Action dated Oct. 15, 2020.
U.S. Appl. No. 17/032,521 Non-Final Office Action dated Aug. 9, 2021.
U.S. Appl. No. 17/032,521 Non-Final Office Action dated Feb. 3, 2021.
Wright, et al.; "Biology and Applications of CRISPR Systems: Harnessing Nature's Toolbox for Genome Engineering"; Cell; vol. 164, pp. 29-44 (2016).
Yamano, et al.; "Crystal Structure of Cpf1 in Complex with Guide RNA and Target DNA"; Cell; vol. 165, pp. 949-962 (2016).
Zetsche, et al.; "Cpf1 Is a Single RNA-Guided Endonuclease of a Class 2 CRISPR-Cas System"; Cell; vol. 163, pp. 759-771 (Oct. 22, 2015).
Makarova, et al.; "Snapshot: Class 2 CRISPR-Cas Systems"; Cell; vol. 168, 2 pages (Jan. 12, 2017).
Mohanraju, et al.; "Diverse evolutionary roots and mechanistic variations of the CRISPR-Cas systems"; Science; vol. 353, No. 6299, 14 pages (Aug. 5, 2016).
JGI Accession No. (Taxon ID:Gene ID) 3300002105.a:C687J6635_100228363, available at https://img.jgi/doe/gov/cgi-bin/m/main.cgi?section=MetaGeneDetail&page=metaGeneDetail&data_type=assembled&taxon_oid=3300002105&gene_oid=C687J26635_100228363; Downloaded from the JGI website on Nov. 9, 2021.
JGI Accession No. (Taxon ID:Gene ID) 3300002502.a:C687J35174_100538264, available at http://img.jgi.doe.gov/cgi-bin/m/main.cgi?section=MetaGeneDetail&page=metaGeneDetail&data_type=assembled&taxon_oid=3300002502&gene_oid=C687J35174_100538264; Downloaded from the JGI website on Nov. 9, 2021.
JGI Accession No. (Taxon ID:Gene ID) 3300025308.a:Ga0209211_100536734, available at https://img.jgi.doe.gov/cgi-bin/m/main.cgi?section=MetaGeneDetail&page=metaGeneDetail&data_type=assembled&taxon_oid=3300025308&gene_oid=Ga0209211_100536734; Downloaded from the JGI website on Nov. 9, 2021.
JGI Accession No. (Taxon ID:Gene ID) 3300025317.a:Ga0209541_100096836, available at https://img.jgi/doe.gove/cgi-bin/m/main.cgi?section=MetaGeneDetail&page=metaGeneDetail&data_type=assembled&taxon_oid=3300025317&gene_oid=Ga0209541_100096836; Downloaded from the JGI website on Nov. 9, 2021.
JGI Accession No. (Taxon ID:Gene ID) 3300025323.a:Ga0209542_1000010711, available at https://img.jgi.doe.gov/cgi-bin/m/main.cgi?section=MetaGeneDetail&page=metaGeneDetail&data_type=assembled&taxon_oid=3300025323&gene_oid=Ga0209542_1000010711; Downloaded from the JGI website on Nov. 9, 2021.
JGI Accession No. (Taxon ID:Gene ID) 3300025323.a:Ga0209542_10000107204, available at https://img.jgi.doe.gov/cgi-bin/m/main.cgi?section=MetaGeneDetail&page=metaGeneDetail&data_type=assembled&taxon_oid=3300025323&gene_oid=Ga0209542_10000107204; Downloaded from the JGI website on Nov. 9, 2021.

(56) References Cited

OTHER PUBLICATIONS

Karvelis, et al.; "PAM recognition by miniature CRISPR-Cas12f nucleases triggers programmable double-stranded DNA target cleavage"; Nucleic Acids Research; pp. 1-8 (2020).

Koonin, et al.; "Diversity, classification and evolution of CRISPR-Cas systems"; Current Opinion in Microbiology; vol. 37, pp. 67-78 (2017).

Koonin, et al.; "CRISPR-Cas: an adaptive immunity system in prokaryotes"; F1000 Biology Reports; vol. 1, No. 95, 6 pages (Dec. 9, 2009).

* cited by examiner

FIG. 1A

>CasZa.1|rifcsphigho2_02_scaffold_2167_39 \N id=61050970
partial=0 scaf=rifcsphigho2_02_scaffold_2167
bin=RIFCSPHIGHO2_02_FULL_Archaea_Woesearchaeota_57_22
sample=Archaea-Rifle02 proj=Rifle Groundwater Metagenome
mEVQKTVMKTLSLRILRPLYSQEIEKEIKEEKERRKQAGGTGELDGGFYKKLEKKHSEMFSFDR
LNLLLNQLQREIAKVYNHAISELYIATIAQGNKSNKHYISSIVYNRAYGYFNAYIALGICSKV
EANFRSNELLTQQSALPTAKSDNFPIVLHQKGAEGEDGGFRISTEGSDLIFEIPIPFYEYNGE
NRKEPYKWVKKGGQKPVLKLILSTFRRQRNKGWAKDEGTDAEIRKVTEGKYQVSQIEINRGKKL
GEHQKWFANFSIEQPIYERKPNRSIVGGLDVGIRSPLVCAINNSFSRYSVDSNDVFKFSKQVFA
FRRRLLSKNSLKRKGHGAAHKLEPITEMTEKNDKFRKKIIERWAKEVTNFFVKNQVGIVQIEDL
STMKDREDHFFNQYLRGFWPYYQMQTLIENKLKEYGIEVKRVQAKYTSQLCSNPNCRYWNNYFN
FEYRKVNKFPKFKCEKCNLEISADYNAARNLSTPDIEKFVAKATKGINLPEK
        (SEQ ID NO: 1)

>CasZa.2|gwa2_scaffold_18027_12 Putative transposase DNA-binding
domain family id=2625699 partial=0 scaf=gwa2_scaffold_18027
bin=GWA2 Unbinned sample=GWA2 proj=Rifle Groundwater Metagenome
mEEAKTVSKTLSLRILRPLYSAEIEKEIKEEKERRKQGGKSGELDSGFYKKLEKKHTQMFGWDK
LNLMLSQLQRQIARVFNQSISELYIETVIQGKKSNKHYTSKIVYNRAYSVFYNAYLALGITSKV
EANFRSTELLMQKSSLPTAKSDNFPILLHKQKGVEGEEGGFKISADGNDLIFEIPIPFYEYDSA
NKKEPFKWIKKGGQKPTIKLILSTFRRQRNKGWAKDEGTDAEIRKVIEGKYQVSHIEINRGKKL
GDHQKWFVNFTIEQPIYERKLDKNIIGGIDVGIKSPLVCAVNNSFARYSVDSNDVLKFSKQAFA
FRRRLLSKNSLKRSGHGSKNKLDPITRMTEKNDRFRKKIIERWAKEVTNFFIKNQVGTVQIEDL
STMKDRQDNFFNQYLRGFWPYYQMQNLIENKLKEYGIETKRIKARYTSQLCSNPSCRHWNSYFS
FDHRKTNNFPKFKCEKCALEISADYNAARNISTPDIEKFVAKATKGINLPDKNENVILE
        (SEQ ID NO: 2)

>CasZa.3|gwa1_scaffold_1795_31 Transposase, IS605 OrfB family
id=2784443 partial=0 scaf=gwa1_scaffold_1795
bin=GWA1_Archaeon_57_19 sample=GWA1 proj=Rifle Groundwater
Metagenome
mAKNTITKTLKLRIVRPYNSAEVEKIVADEKNNREKIALEKNKDKVKEACSKHLKVAAYCTTQV
ERNACLFCKARKLDDKFYQKLRGQFPDAVFWQEISEIFRQLQKQAAEIYNQSLIELYYEIFIKG
KGIANASSVEHYLSDVCYTRAAELFKNAAIASGLRSKIKSNFRLKELKNMKSGLPTTKSDNFPI
PLVKQKGGQYTGFEISNHNSDFIIKIPFGRWQVKKEIDKYRPWEKFDFEQVQKSPKPISLLLST
QRRKRNKGWSKDEGTEAEIKKVMNGDYQTSYIEVKRGSKIGEKSAWMLNLSIDVPKIDKGVDPS
IIGGIDVGVKSPLVCAINNAFSRYSISDNDLFHFNKKMFARRRILLKKNRHKRAGHGAKNLKP
ITILTEKSERFRKKLIERWACEIADFFIKNKVGTVQmENLESMKRKEDSYFNIRLRGFWPYAEM
QNKIEFKLKQYGIEIRKVAPNNTSKTCSKCGHLNNYFNFEYRKKNKFPHFKCEKCNFKENADYN
AALNISNPKLKSTKEEP (SEQ ID NO: 3)

FIG. 1B

>CasZa.4|CG10_big_fil_rev_8_21_14_0.10_scaffold_20906_2 \N
id=132542232 partial=0
scaf=CG10_big_fil_rev_8_21_14_0.10_scaffold_20906
bin=CG10_big_fil_rev_8_21_14_0_10_UNK
sample=CG10_big_fil_rev_8_21_14_0_10 proj=Crystal Geyser
mERQKVPQIRKIVRVVPLRILRPKYSDVIENALKKFKEKGDDTNTNDFWRAIRDRDTEFFRKEL
NFSEDEINQLERDTLFRVGLDNRVLFSYFDFLQEKLMKDYNKIISKLFINRQSKSSFENDLTDE
EVEELIEKDVTPFYGAYIGKGIKSVIKSNLGGKFIKSVKIDRETKKVTKLTAINIGLMGLPVAK
SDTFPIKIIKTNPDYITFQKSTKENLQKIEDYETGIEYGDLLVQITIPWFKNENKDFSLIKTKE
AIEYYKLNGVGKKDLLNINLVLTTYHIRKKKSWQIDGSSQSLVREMANGELEEKWKSFFDTFIK
KYGDEGKSALVKRRVNKKSRAKGEKGRELNLDERIKRLYDSIKAKSFPSEINLIPENYKWKLHF
SIEIPPMVNDIDSNLYGGIDFGEQNIATLCVKNIEKDDYDFLTIYGNDLLKHAQASYARRRIMR
VQDEYKARGHGKSRKTKAQEDYSERMQKLRQKITERLVKQISDFFLWRNKFHMAVCSLRYEDLN
TLYKGESVKAKRMRQFINKQQLFNGIERLKDYNSEIYVNSRYPHYTSRLCSKCGKLNLYFDFL
KFRTKNIIIRKNPDGSEIKYMPFFICEFCGWKQAGDKNASANIADKDYQDKLNKEKEFCNIRKP
KSKKEDIGEENEEERDYSRRFNRNSFIYNSLKKDNKLNQEKLFDEWKNQLKRKIDGRNKFEPKE

YKDRFSYLFAYYQEIIKNESES (SEQ ID NO: 4)

>CasZa.5|rifcsplowo2_01_scaffold_34461_9 \N id=58382281
partial=0 scaf=rifcsplowo2_01_scaffold_34461
bin=RifCSPlowO2_01_full_UNK sample=RIFCSPLOWO2_01_FULL
proj=RifleCSP2_LowO2
mVPTELITKTLQLRVIRPLYFEEIEKELAELKEQKEKEFEETNSLLLESKKIDAKSLKKLKRKA
RSSAAVEFWKIAKEKYPDILTKPEMEFIFSEMQKMMARFYNKSMTNIFIEMNNDEKVNPLSLIS
KASTEANQVIKCSSISSGLNRKIAGSINKTKFQVRDGLISLPTARTETFPISFYKSTANKDEI
PISKINLPSEEEADLTITLPFPFFEIKKEKKGQKAYSYFNIIEKSGRSNNKIDLLLSTHRRQRR
KGWKEEGGTSAEIRRLMEGEFDKEWEIYLGEAEKSEKAKNDLIKNMTRGKLSKDIKEQLEDIQV
KYFSDNNVESWNDLSKEQKQELSKLRKKKVEELKDWKHVKEILKTRAKIGWVELKRGKRQRDRN
KWFVNITITRPPFINKELDDTKFGGIDLGVKVPFVCAVHGSPARLIIKENEILQFNKMVSARNR
QITKDSEQRKGRGKKNKFIKKEIFNERNELFRKKIIERWANQIVKFFEDQKCATVQIENLESFD

RTSYK (SEQ ID NO: 5)

>CasZa.6|037|3300012359.a:Ga0137385_10000156_01776
Zr6.cluA_1a.mostc10like protein
MKSDTKDKKIIIHQTKTLSLRIVKPQSIPMEEFTDLVRYHQMIIFPVYNNGAIDLYKKLFKAKI
QKGNEARAIKYFMNKIVYAPIANTVKNSYIALGYSTKMQSSFSGKRLWDLRFGEATPPTIKADF
PLPFYNQSGFKVSSENGEFIIGIPFGQYTKKTVSDIEKKTSFAWDKFTLEDTTKKTLIELLLST
KTRKMNEGWKNNEGTEAEIKRVMDGTYQVTSLEILQRDDSWFVNFNIAYDSLKKQPDRDKIAGI
HMGITRPLTAVIYNNKYRALSIYPNTVMHLTQKQLARIKEQRTNSKYATGGHGRNAKVTGTDTL
SEAYRQRRKKIIEDWIASIVKFAINNEIGTIYLEDISNTNSFFAAREQKLIYLEDISNTNSFLS
TYKYPISAISDTLQHKLEEKAIQVIRKKAYYVNQICSLCGHYNKGFTYQFRRKNKFPKMKCQGC

LEATSTEFNAAANVANPDYEKLLIKHGLLQLKK    (SEQ ID NO: 6)

FIG. 1C

>CasZa.7|127|3300009029.a:Ga0066793_10010091_01298
Zr6.cluA_1.c10.inclusive
MSTITRQVRLSPTPEQSRLLMAHCQQYISTVNVLVAAFDSEVLTGKVSTKDFRAALPSAVKNQA
LRDAQSVFKRSVELGCLPVLKKPHCQWNNQNWRVEGDQLILPICKDGKTQQERFRCAAVALEGK
AGILRIKKKRGKWIADLTVTQEDAPESSGSAIMGVDLGIKVPAVAHIGGKGTRFFGNGRSQRSM
RRRFYARRKTLQKAKKLRAVRKSKGKEARWMKTINHQLSRQIVNHAHALGVGTIKIEALQGIRK
GTTRKSRGAAARKNNRMTNTWSFSQLTLFITYKAQRQGITVEQVDPAYTSQDCPACRARNGAQD
RTYVCSECGWRGHRDTVGAINISRRAGLSGHRRGATGA (SEQ ID NO: 7)

>CasZb.1|bjp_ig2599_sub10_scaffold_488_2 transposase id=60827220
partial=0 scaf=bjp_ig2599_sub10_scaffold_488
bin=BJP_IG2599_SUB10_Micrarchaeota_NOVEL_41_24
sample=BJP_IG2599_SUB10 proj=Borehole JP
mIAQKTIKIKLNPTKEQIIKLNSIIEEYIKVSNFTAKKIAEIQESFTDSGLTQGTCSECGKEKT
YRKYHLLKKDNKLFCITCYKRKYSQFTLQKVEFQNKTGLRNVAKLPKTYYTNAIRFASDTFSGF
DEIIKKKQNRLNSIQNRLNFWKELLYNPSNRNEIKIKVVKYAPKTDTREHPHYYSEAEIKGRIK
RLEKQLKKFKMPKYPEFTSETISLQRELYSWKNPDELKISSITDKNESmNYYGKEYLKRYIDLI
NSQTPQILLEKENNSFYLCFPITKNIEMPKIDDTFEPVGIDWGITRNIAVVSILDSKTKKPKFV
KFYSAGYILGKRKHYKSLRKHFGQKKRQDKINKLGTKEDRFIDSNIHKLAFLIVKEIRNHSNKP
IILMENITDNREEAEKSMRQNILLHSVKSRLQNYIAYKALWNNIPTNLVKPEHTSQICNRCGHQ
DRENRPKGSKLFKCVKCNYMSNADFNASINIARKFYIGEYEPFYKDNEKMKSGVNSISM (SEQ
ID NO: 8)

>CasZb.2|rifcsplowo2_01_scaffold_239_52 IS605 OrfB family
transposase id=57672634 partial=0
scaf=rifcsplowo2_01_scaffold_239 bin=RifCSPlowO2_01_full_UNK
sample=RIFCSPLOWO2_01_FULL proj=RifleCSP2_LowO2
LKLSEQENITTGVKFKLKLDKETSEGLNDYFDEYGKAINFAIKVIQKELAEDRFAGKVRLDENK
KPLLNEDGKKIWDFPNEFCSCGKQVNRYVNGKSLCQECYKNKFTEYGIRKRMYSAKGRKAEQDI
NIKNSTNKISKTHFNYAIREAFILDKSIKKQRKERFRRLREMKKKLQEFIEIRDGNKILCPKIE
KQRVERYIHPSWINKEKKLEDFRGYSMSNVLGKIKILDRNIKREEKSLKEKGQINFKARRLMLD
KSVKFLNDNKISFTISKNLPKEYELDLPEKEKRLNWLKEKIKIIKNQKPKYAYLLRKDDNFYLQ
YTLETEFNLKEDYSGIVGIDRGVSHIAVYTFVHNNGKNERPLFLNSSEILRLKNLQKERDRFLR
RKHNKKRKKSNMRNIEKKIQLILHNYSKQIVDFAKNKNAFIVFEKLEKPKKNRSKMSKKSQYKL
SQFTFKKLSDLVDYKAKREGIKVLYISPEYTSKECSHCGEKVNTQRPFNGNSSLFKCNKCGVEL
NADYNASINIAKKGLNILNSTN
     (SEQ ID NO: 9)

FIG. 1D

>CasZb.3|rifcsplowo2_01_scaffold_282_93 IS605 OrfB family transposase id=57678680 partial=0 scaf=rifcsplowo2_01_scaffold_282 bin=RifCSPlowO2_01_full_UNK sample=RIFCSPLOWO2_01_FULL proj=RifleCSP2_LowO2
mEESIITGVKFKLRIDKETTKKLNEYFDEYGKAINFAVKIIQKELADDRFAGKAKLDQNKNPIL
DENGKKIYEFPDEFCSCGKQVNKYVNNKPFCQECYKIRFTENGIRKRMYSAKGRKAEHKINILN
STNKISKTHFNYAIREAFILDKSIKKQRKKRNERLRESKKRLQQFIDMRDGKREICPTIKGQKV
DRFIHPSWITKDKKLEDFRGYTLSIINSKIKILDRNIKREEKSLKEKGQIIFKAKRLMLDKSIR
FVGDRKVLFTISKTLPKEYELDLPSKEKRLNWLKEKIEIIKNQKPKYAYLLRKNIESEKKPNYE
YYLQYTLEIKPELKDFYDGAIGIDRGINHIAVCTFISNDGKVTPPKFFSSGEILRLKNLQKERD
RFLLRKHNKNRKKGNMRVIENKINLILHRYSKQIVDmAKKLNASIVFEELGRIGKSRTKMKKSQ
RYKLSLFIFKKLSDLVDYKSRREGIRVTYVPPEYTSKECSHCGEKVNTQRPFNGNYSLFKCNKC
GIQLNSDYNASINIAKKGLKIPNST
      (SEQ ID NO: 10)

>CasZb.4|rifcsphigho2_01_scaffold_36781_5 transposase, IS605 OrfB family id=55842010 partial=0 scaf=rifcsphigho2_01_scaffold_36781 bin=RifCSPhighO2_01_full_UNK sample=RIFCSPHIGHO2_01_FULL proj=RifleCSP2_HighO2
LWTIVIGDFIEMPKQDLVTTGIKFKLDVDKETRKKLDDYFDEYGKAINFAVKIIQKNLKEDRFA
GKIALGEDKKPLLDKDGKKIYNYPNESCSCGNQVRRYVNAKPFCVDCYKLKFTENGIRKRMYSA
RGRKADSDINIKNSTNKISKTHFNYAIREGFILDKSLKKQRSKRIKKLLELKRKLQEFIDIRQG
QMVLCPKIKNQRVDKFIHPSWLKRDKKLEEFRGYSLSVVEGKIKIFNRNILREEDSLRQRGHVN
FKANRIMLDKSVRFLDGGKVNFNLNKGLPKEYLLDLPKKENKLSWLNEKISLIKLQKPKYAYLL
RREGSFFIQYTIENVPKTFSDYLGAIGIDRGISHIAVCTFVSKNGVNKAPVFFSSGEILKLKSL
QKQRDLFLRGKHNKIRKKSNMRNIDNKINLILHKYSRNIVNLAKSEKAFIVFEKLEKIKKSRFK
MSKSLQYKLSQFTFKKLSDLVEYKAKIEGIKVDYVPPEYTSKECSHCGEKVDTQRPFNGNSSLF
KCNKCRVQLNADYNASINIAKKSLNISNN (SEQ ID NO: 11)

>CasZb.5|cg1_0.2_scaffold_785_c_37 transposase, IS605 OrfB family id=91826491 partial=0 scaf=cg1_0.2_scaffold_785_c bin=CG1_02_FULL_Micrarchaeota_47_40_curated sample=CG1_02_FULL proj=Crystal Geyser
mSKTTISVKLKIIDLSSEKKEFLDNYFNEYAKATTFCQLRIRRLLRNTHWLGKKEKSSKKWIFE
SGICDLCGENKELVNEDRNSGEPAKICKRCYNGRYGNQMIRKLFVSTKKREVQENMDIRRVAKL
NNTHYHRIPEEAFDMIKAADTAEKRRKKNVEYDKKRQMEFIEMFNDEKKRAARPKKPNERETRY
VHISKLESPSKGYTLNGIKRKIDGMGKKIERAEKGLSRKKIFGYQGNRIKLDSNWVRFDLAESE
ITIPSLFKEMKLRITGPTNVHSKSGQIYFAEWFERINKQPNNYCYLIRKTSSNGKYEYYLQYTY
EAEVEANKEYAGCLGVDIGCSKLAAAVYYDSKNKKAQKPIEIFTNPIKKIKMRREKLIKLLSRV
KVRHRRRKLMQLSKTEPIIDYTCHKTARKIVEMANTAKAFISMENLETGIKQKQQARETKKQKF
YRNMFLFRKLSKLIEYKALLKGIKIVYVKPDYTSQTCSSCGADKEKTERPSQAIFRCLNPTCRY
YQRDINADFNAAVNIAKKALNNTEVVTTLL    (SEQ ID NO: 12)

FIG. 1E

>CasZb.6|rifcsphigho2_02_scaffold_55589_5 transposase, IS605 OrfB family id=61682131 partial=0 scaf=rifcsphigho2_02_scaffold_55589 bin=RifCSPhighO2_02_full_UNK sample=RIFCSPHIGHO2_02_FULL proj=RifleCSP2_HighO2
mARAKNQPYQKLTTTTGIKFKLDLSEEEGKRFDEYFSEYAKAVNFCAKVIYQLRKNLKFAGKKE
LAAKEWKFEISNCDFCNKQKEIYYKNIANGQKVCKGCHRTNFSDNAIRKKMIPVKGRKVESKFN
IHNTTKKISGTHRHWAFEDAADIIESMDKQRKEKQKRLRREKRKLSYFFELFGDPAKRYELPKV
GKQRVPRYLHKIIDKDSLTKKRGYSLSYIKNKIKISERNIERDEKSLRKASPIAFGARKIKMSK
LDPKRAFDLENNVFKIPGKVIKGQYKFFGTNVANEHGKKFYKDRISKILAGKPKYFYLLRKKVA
ESDGNPIFEYYVQWSIDTETPAITSYDNILGIDAGITNLATTVLIPKNLSAEHCSHCGNNHVKP
IFTKFFSGKELKAIKIKSRKQKYFLRGKHNKLVKIKRIRPIEQKVDGYCHVVSKQIVEMAKERN
SCIALEKLEKPKKSKFRQRRREKYAVSMFVFKKLATFIKYKAAREGIEIIPVEPEGTSYTCSHC
KNAQNNQRPYFKPNSKKSWTSMFKCGKCGIELNSDYNAAFNIAQKALNMTSA
   (SEQ ID NO: 13)

>CasZb.7|CG03_land_8_20_14_0.80_scaffold_2214_9 transposase, IS605 OrfB family id=135165146 partial=0 scaf=CG03_land_8_20_14_0.80_scaffold_2214 bin=CG03_land_8_20_14_0_80_cor_UNK sample=CG03_land_8_20_14_0_80_cor proj=Crystal Geyser
mDEKHFFCSYCNKELKISKNLINKISKGSIREDEAVSKAISIHNKKEHSLILGIKFKLFIENKL
DKKKLNEYFDNYSKAVTFAARIFDKIRSPYKFIGLKDKNTKKWTFPKAKCVFCLEEKEVAYANE
KDNSKICTECYLKEFGENGIRKKIYSTRGRKVEPKYNIFNSTKELSSTHYNYAIRDAFQLLDAL
KKQRQKKLKSIFNQKLRLKEFEDIFSDPQKRIELSLKPHQREKRYIHLSKSGQESINRGYTLRF
VRGKIKSLTRNIEREEKSLRKKTPIHFKGNRLMIFPAGIKFDFASNKVKISISKNLPNEFNFSG
TNVKNEHGKSFFKSRIELIKTQKPKYAYVLRKIKREYSKLRNYEIEKIRLENPNADLCDFYLQY
TIETESRNNEEINGIIGIDRGITNLACLVLLKKGDKKPSGVKFYKGNKILGMKIAYRKHLYLLK
GKRNKLRKQRQIRAIEPKINLILHQISKDIVKIAKEKNFAIALEQLEKPKKARFAQRKKEKYKL
ALFTFKNLSTLIEYKSKREGIPVIYVPPEKTSQMCSHCAINGDEHVDTQRPYKKPNAQKPSYSL
FKCNKCGIELNADYNAAFNIAQKGLKTLMLNHSH   (SEQ ID NO: 14)

>CasZb.8|058|3300002172.a:JGI24730J26740_1002785_01697 Zr6.newTrpA
MLQTLLVKLDPSKEQYKMLYETMERFNEACNQIAETVFAIHSANKIEVQKTVYYPIREKFGLSA
QLTILAIRKVCEAYKRDKSIKPEFRLDGALVYDQRVLSWKGLDKVSLVTLQGRQIIPIKFGDYQ
KARMDRIRGQADLILVKGVFYLCVVVESEESPYDPKGVLGVDLGIKNLAVDSDGEVHSGEQTT
NTRERLDSLKARLQSKGTKSAKRHLKKLSGRMAKFSKDVNHCISKKLVAKAKGTLMSIALEDLQ
GIRDRVTVRKAQRRNLHTWNFGLLRMFVDYKAKIAGVPLVFVDPRNTSRTCPSCGHVAKANRPT
RDEFRCVSCGFAGAADHIAAMNIAFRAEVSQPIVTRFFVQSQAPSFRVG
   (SEQ ID NO: 15)

FIG. 1F

>CasZb.9|114|3300013125.a:Ga0172369_10000737_00842
Zr6.cluA_2b.c10_like protein
MDEEPDSAEPNLAPISVKLKLVKLDGEKLAALNDYFNEYAKAVNFCELKMQKIRKNLVNIRGTY
LKEKKAWINQTGECCICKKIDELRCEDKNPDINGKICKKCYNGRYGNQMIRKLFVSTNKRAVPK
SLDIRKVARLHNTHYHRIPPEAADIIKAIETAERKRRNRILFDERRYNELKDALENEEKRVARP
KKPKEREVRYVPISKKDTPSKGYTMNALVRKVSGMAKKIERAKRNLNKRKKIEYLGRRILLDKN
WVRFDFDKSEISIPTMKEFFGEMRFEITGPSNVMSPNGREYFTKWFDRIKAQPDNYCYLLRKES
EDETDFYLQYTWRPDAHPKKDYTGCLGIDIGGSKLASAVYFDADKNRAKQPIQIFSNPIGKWKT
KRQKVIKVLSKAAVRHKTKKLESLRNIEPRIDVHCHRIARKIVGMALAANAFISMENLEGGIRE
KQKAKETKKQKFSRNMFVFRKLSKLIEYKALMEGVKVVYIVPDYTSQLCSSCGTNNTKRPKQAI

FMCQNTECRYFGKNINADFNAAINIAKKALNRKDIVRELS (SEQ ID NO: 16)

>CasZb.10|115|3300013125.a:Ga0172369_10010464_01540
Zr6.cluA_2b.c10_like protein
MEKNNSEQTSITTGIKFKLKLDKETKEKLNNYFDEYGKAINFAVRIIQMQLNDDRLAGKYKRDE
KGKPILGEDGKKILEIPNDFCSCGNQVNHYVNGVSFCQECYKKRFSENGIRKRMYSAKGRKAEQ
DINIKNSTNKISKTHFNYAIREAFNLDKSIKKQREKRFKKLKDMKRKLQEFLEIRDGKRVICPK
IEKQKVERYIHPSWINKEKKLEEFRGYSLSIVNSKIKSFDRNIQREEKSLKEKGQINFKAQRLM
LDKSVKFLKDNKVSFTISKELPKTFELDLPKKEKKLNWLNEKLEIIKNQKPKYAYLLRKENNIF
LQYTLDSIPEIHSEYSGAVGIDRGVSHIAVYTFLDKDGKNERPFFLSSSGILRLKNLQKERDKF
LRKKHNKIRKKGNMRNIEQKINLILHEYSKQIVNFAKDKNAFIVFELLEKPKKSRERMSKKIQY
KLSQFTFKKLSDLVDYKAKREGIKVIYVEPAYTSKDCSHCGERVNTQRPFNGNFSLFKCNKCGI

VLNSDYNASLNIARKGLNISAN (SEQ ID NO: 17)

>CasZb.11|134|3300013127.a:Ga0172365_10004421_00828
Zr6.cluA_2b.c10_like protein
MAEEKFFFCEKCNKDIKIPKNYINKQGAEEKARAKHEHRVHALILGIKFKIYPKKEDISKLNDY
FDEYAKAVTFTAKIVDKLKAPFLFAGKRDKDTSKKKWVFPVDKCSFCKEKTEINYRTKQGKNIC
NSCYLTEFGEQGLLEKIYATKGRKVSSSFNLFNSTKKLTGTHNNYVVKESLQLLDALKKQRSKR
LKKLSNTRRKLKQFEEMFEKEDKRFQLPLKEKQRELRFIHVSQKDRATEFKGYTMNKIKSKIKV
LRRNIEREQRSLNRKSPVFFRGTRIRLSPSVQFDDKDNKIKLTLSKELPKEYSFSGLNVANEHG
RKFFAEKLKLIKENKSKYAYLLRRQVNKNNKKPIYDYYLQYTVEFLPNIITNYNGILGIDRGIN
TLACIVLLENKKEKPSFVKFFSGKGILNLKNKRRKQLYFLKGVHNKYRKQQKIRPIEPRIDQIL
HDISKQIIDLAKEKRVAISLEQLEKPQKPKFRQSRKAKYKLSQFNFKTLSNYIDYKAKKEGIRV
IYIAPEMTSQNCSRCAMKNDLHVNTQRPYKNTSSLFKCNKCGVELNADYNAAFNIAQKGLKILN

S (SEQ ID NO: 18)

FIG. 1G

>CasZc.1|CG08_land_8_20_14_0.20_scaffold_1609_10 Tax=CG_Micra_03
id=133381002 partial=0 scaf=CG08_land_8_20_14_0.20_scaffold_1609
bin=CG08_land_8_20_14_0_20_UNK sample=CG08_land_8_20_14_0_20
proj=Crystal Geyser
mISLKLKLLPDEEQKKLLDEMFWKWASICTRVGFGRADKEDLKPPKDAEGVWFSLTQLNQANTD
INDLREAMKHQKHRLEYEKNRLEAQRDDTQDALKNPDRREISTKRKDLFRPKASVEKGFLKLKY
HQERYWVRRLKEINKLIERKTKTLIKIEKGRIKFKATRITLHQGSFKIRFGDKPAFLIKALSGK
NQIDAPFVVVPEQPICGSVVNSKKYLDEITTNFLAYSVNAMLFGLSRSEEMLLKAKRPEKIKKK
EEKLAKKQSAFENKKKELQKLLGRELTQQEEAIIEETRNQFFQDFEVKITKQYSELLSKIANEL
KQKNDFLKVNKYPILLRKPLKKAKSKKINNLSPSEWKYYLQFGVKPLLKQKSRRKSRNVLGIDR
GLKHLLAVTVLEPDKKTFVWNKLYPNPITGWKWRRRKLLRSLKRLKRRIKSQKHETIHENQTRK
KLKSLQGRIDDLLHNISRKIVETAKEYDAVIVVEDLQSMRQHGRSKGNRLKTLNYALSLFDYAN
VMQLIKYKAGIEGIQIYDVKPAGTSQNCAYCLLAQRDSHEYKRSQENSKIGVCLNPNCQNHKKQ

IDADLNAARVIASCYALKINDSQPFGTRKRFKKRTTN (SEQ ID NO: 19)

>CasZc.2|CG_4_10_14_0.8_um_filter_scaffold_20762_4
Tax=CG_Micra_03 id=144037526 partial=0
scaf=CG_4_10_14_0.8_um_filter_scaffold_20762
bin=CG_4_10_14_0_8_um_filter_cor_UNK
sample=CG_4_10_14_0_8_um_filter_cor proj=Crystal Geyser
mETLSLKLKLNPSKEQLLVLDKMFWKWASICTRLGLKKAEMSDLEPPKDAEGVWFSKTQLNQAN
TDVNDLRKAMQHQGKRIEYELDKVENRRNEIQEMLEKPDRRDISPNRKDLFRPKAAVEKGYLKL
KYHKLGYWSKELKTANKLIERKRKTLAKIDAGKMFKPTRISLHTNSFRIKFGEEPKIALSTTS
KHEKIELPLITSLQRPLKTSCAKKSKTYLDAAILNFLAYSTNAALFGLSRSEEMLLKAKKPEKI
EKRDRKLATKRESFDKKLKTLEKLLERKLSEKEKSVFKRKQTEFFDKFCITLDETYVEALHRIA
EELVSKNKYLEIKKYPVLLRKPESRLRSKKLKNLKPEDWTYYIQFGFQPLLDTPKPIKTKTVLG
IDRGVRHLLAVSIFDPRTKTFTFNRLYSNPIVDWKWRRRKLLRSIKRLKRRLKSEKHVHLHENQ
FKAKLRSLEGRIEDHFHNLSKEIVDLAKENNSVIVVENLGGMRQHGRGRGKWLKALNYALSHFD
YAKVMQLIKYKAELAGVFVYDVAPAGTSINCAYCLLNDKDASNYTRGKVINGKKNTKIGECKTC

KKEFDADLNAARVIALCYEKRLNDPQPFGTRKQFKPKKP (SEQ ID NO: 20)

FIG. 1H

>CasZc.3|CG22_combo_CG10-13_8_21_14_all_scaffold_2003_2 IS605
OrfB family transposase id=130740989 partial=0
scaf=CG22_combo_CG10-13_8_21_14_all_scaffold_2003
bin=CG22_combo_CG10-13_8_21_14_all_UNK sample=CG22_combo_CG10-
13_8_21_14_all proj=Crystal Geyser
mKALKLQLIPTRKQYKILDEMFWKWASLANRVSQKGESKETLAPKKDIQKIQFNATQLNQIEKD
IKDLRGAMKEQQKQKERLLLQIQERRSTISEMLNDDNNKERDPHRPLNFRPKGWRKFHTSKHWV
GELSKILRQEDRVKKTIERIVAGKISFKPKRIGIWSSNYKINFFKRKISINPLNSKGFELTLMT
EPTQDLIGKNGGKSVLNNKRYLDDSIKSLLMFALHSRFFGLNNTDTYLLGGKINPSLVKYYKKN
QDMGEFGREIVEKFERKLKQEINEQQKKIIMSQIKEQYSNRDSAFNKDYLGLINEFSEVFNQRK
SERAEYLLDSFEDKIKQIKQEIGESLNISDWDFLIDEAKKAYGYEEGFTEYVYSKRYLEILNKI
VKAVLITDIYFDLRKYPILLRKPLDKIKKISNLKPDEWSYYIQFGYDSINPVQLMSTDKFLGID
RGLTHLLAYSVFDKEKKEFTINQLEPNPIMGWKWLRKVKRSLQHLERRIRAQKMVKLPENQMK
KKLKSIEPKIEVHYHNISRKIVNLAKDYNASIVVESLEGGGLKQHGRKKNARNRSLNYALSLFD
YGKIASLIKYKADLEGVPMYEVLPAYTSQQCAKCVLEKGSFVDPEIIGYVEDIGIKGSLLDSLF
EGTELSSIQVLKKIKNKIELSARDNHNKEINLILKYNFKGLVIVRGQDKEEIAEHPIKEINGKF
AILDFVYKRGKEKVGKKGNQKVRYTGNKKVGYCSKHGQVDADLNASRVIALCKYLDINDPILFG
EQRKSFK (SEQ ID NO: 21)

>CasZc.4|rifcsphigho2_01_scaffold_82367_2 Tax=CG_Micra_03
id=56177664 partial=0 scaf=rifcsphigho2_01_scaffold_82367
bin=RifCSPhighO2_01_full_UNK sample=RIFCSPHIGHO2_01_FULL
proj=RifleCSP2_HighO2
mVTRAIKLKLDPTKNQYKLLNEMFWKWASLANRFSQKGASKETLAPKDGTQKIQFNATQLNQIK
KDVDDLRGAMEKQGKQKERLLIQIQERLLTISEILRDDSKKEKDPHRPQNFRPFGWRRFHTSAY
WSSEASKLTRQVDRVRRTIERIKAGKINFKPKRIGLWSSTYKINFLKKKINISPLKSKSFELDL
ITEPQQKIIGKEGGKSVANSKKYLDDSIKSLLIFAIKSRLFGLNNKDKPLFENIITPNLVRYHK
KGQEQENFKKEVIKKFENKLKKEISQKQKEIIFSQIERQYENRDATFSEDYLRAISEFSEIFNQ
RKKERAKELLNSFNEKIRQLKKEVNGNISEEDLKILEVEAEKAYNYENGFIEWEYSEQFLGVLE
KIARAVLISDNYFDLKKYPILIRKPTNKSKKITNLKPEEWDYYIQFGYGLINSPMKIETKNFMG
IDRGLTHLLAYSIFDRDSEKFTINQLELNPIKGWKWKLRKVKRSLQHLERRMRAQKGVKLPENQ
MKKRLKSIEPKIESYYHNLSRKIVNLAKANNASIVVESLEGGGLKQHGRKKNSRHRALNYALSL
FDYGKIASLIKYKSDLEGVPMYEVLPAYTSQQCAKCVLKKGSFVEPEIIGYIEEIGFKENLLTL
LFEDTGLSSVQVLKKSKNKMTLSARDKEGKMVDLVLKYNFKGLVISQEKKKEEIVEFPIKEIDG
KFAVLDSAYKRGKERISKKGNQKLVYTGNKKVGYCSVHGQVDADLNASRVIALCKYLGINEPIV
FGEQRKSFK (SEQ ID NO: 22)

FIG. 1I

>CasZc.5|gwc1_scaffold_8732_6 Transposase, IS605 OrfB family
id=3520800 partial=0 scaf=gwc1_scaffold_8732 bin=GWC1 Unbinned
sample=GWC1 proj=Rifle Groundwater Metagenome
LDLITEPIQPHKSSSLRSKEFLEYQISDFLNFSLHSLFFGLASNEGPLVDFKIYDKIVIPKPEE
RFPKKESEEGKKLDSFDKRVEEYYSDKLEKKIERKLNTEEKNVIDREKTRIWGEVNKLEEIRSI
IDEINEIKKQKHISEKSKLLGEKWKKVNNIQETLLSQEYVSLISNLSDELTNKKKELLAKKYSK
FDDKIKKIKEDYGLEFDENTIKKEGEKAFLNPDKFSKYQFSSSYLKLIGEIARSLITYKGFLDL
NKYPIIFRKPINKVKKIHNLEPDEWKYYIQFGYEQINNPKLETENILGIDRGLTHILAYSVFEP
RSSKFILNKLEPNPIEGWKWKLRKLRRSIQNLERRWRAQDNVKLPENQMKKNLRSIEDKVENLY
HNLSRKIVDLAKEKNACIVFEKLEGQGMKQHGRKKSDRLRGLNYKLSLFDYGKIAKLIKYKAEI
EGIPIYRIDSAYTSQNCAKCVLESRRFAQPEEISCLDDFKEGDNLDKRILEGTGLVEAKIYKKL
LKEKKEDFEIEEDIAMFDTKKVIKENKEKTVILDYVYTRRKEIIGTNHKKNIKGIAKYTGNTKI
GYCMKHGQVDADLNASRTIALCKNFDINNPEIWK  (SEQ ID NO: 23)

>CasZc.6|109|3300010293.a:Ga0116204_1008574_00822
Zr6.cluA_2a.c10_like protein
MSDESLVSSEDKLAIKIKIVPNAEQAKMLDEMFKKWSSICNRISRGKEDIETLRPDEGKELQFN
STQLNSATMDVSDLKKAMARQGERLEAEVSKLRGRYETIDASLRDPSRRHTNPQKPSSFYPSDW
DISGRLTPRFHTARHYSTELRKLKAKEDKMLKTINKIKNGKIVFKPKRITLWPSSVNMAFKGSR
LLLKPFANGFEMELPIVISPQKTADGKSQKASAEYMRNALLGLAGYSINQLLFGMNRSQKMLAN
AKKPEKVEKFLEQMKNKDANFDKKIKALEGKWLLDRKLKESEKSSIAVVRTKFFKSGKVELNED
YLKLLKHMANEILERDGFVNLNKYPILSRKPMKRYKQKNIDNLKPNMWKYYIQFGYEPIFERKA
SGKPKNIMGIDRGLTHLLAVAVFSPDQQKFLFNHLESNPIMHWKWKLRKIRRSIQHMERRIRAE
KNKHIHEAQLKKRLGSIEEKTEQHYHIVSSKIINWAIEYEAAIVLESLSHMKQRGGKKSVRTRA
LNYALSLFDYEKVARLITYKARIRGIPVYDVLPGMTSKTCATCLLNGSQGAYVRGLETTKAAGK
ATKRKNMKIGKCMVCNSSENSMIDADLNAARVIAICKYKNLNDPQPAGSRKVFKRF
    (SEQ ID NO: 24)

>CasZc.7|126|3300005573.a:Ga0078972_1001015_00056
Zr6.cluA_2a.c10_like protein
MLALKLKIMPTEKQAEILDAMFWKWASICSRIAKMKKKVSVKENKKELSKKIPSNSDIWFSKTQ
LCQAEVDVGDHKKALKNFEKRQESLLDELKYVKAINEVINDESKREIDPNNPSKFRIKDSTKK
GNLNSPKFFTLKKWQKILQENEKRIKKKESTIEKLKRGNIFFNPTKISLHEEEYSINFGSSKLL
LNCFYKYNKKSGINSDQLENKFNEFQNGLNIICSPLQPIRGSSKRSFEFIRNSIINFLMYSLYA
KLFGIPRSVKALMKSNKDENKLKLEEKLKKKKSSFNKTVKEFEKMIGRKLSDNESKILNDESKK
FFEIIKSNNKYIPSEEYLKLLKDISEEIYNSNIDFKPYKYSILIRKPLSKFKSKKLYNLKPTDY
KYYLQLSYEPFSKQLIATKTILGIDRGLKHLLAVSVFDPSQNKFVYNKLIKNPVFKWKKRYHDL
KRSIRNRERRIRALTGVHIHENQLIKKLKSMKNKINVLYHNVSKNIVDLAKKYESTIVLERLEN
LKQHGRSKGKRYKKLNYVLSNFDYKKIESLISYKAKKEGVPVSNINPKYTSKTCAKCLLEVNQL
SELKNEYNRDSKNSKIGICNIHGQIDADLNAARVIALCYSKNLNEPHFK
    (SEQ ID NO: 25)

FIG. 1J

>CasZd.1|CG10_big_fil_rev_8_21_14_0.10_scaffold_4477_25 IS605
OrfB family transposase id=132383911 partial=0
scaf=CG10_big_fil_rev_8_21_14_0.10_scaffold_4477
bin=CG10_big_fil_rev_8_21_14_0_10_test2
sample=CG10_big_fil_rev_8_21_14_0_10 proj=Crystal Geyser
VINLFGYKFALYPNKTQEELLNKHLGECGWLYNKAIEQNEYYKADSNIEEAQKKFELLPDKNSD
EAKVLRGNISKDNYVYRTLVKKKKSEINVQIRKAVVLRPAETIRNLAKVKKKGLSVGRLKFIPI
REWDVLPFKQSDQIRLEENYLILEPYGRLKFKMHRPLLGKPKTFCIKRTATDRWTISFSTEYDD
SNMRKNDGGQVGIDVGLKTHLRLSNENPDEDPRYPNPKIWKRYDRRLTILQRRISKSKKLGKNR
TRLRLRLSRLWEKIRNSRADLIQNETYEILSENKLIAIEDLNVKGMQEKKDKKGRKGRTRAQEK
GLHRSISDAAFSEFRRVLEYKAKRFGSEVKPVSAIDSSKECHNCGNKKGMPLESRIYECPKCGL
KIDRDLNSAKVILARATGVRPGSNARADTKISATAGASVQTEGTVSEDFRQQMETSDQKPMQGE
GSKEPPMNPEHKSSGRGSKHVNIGCKNKVGLYNEDENSRSTEKQIMDENRSTTEDMVEIGALHS
PVLTT (SEQ ID NO: 26)

>CasZd.2|053|3300001245.a:JGI12048J13642_10201286_01511
Zr6.c9.inclusive
MIASIDYEAVSQALIVFEFKAKGKDSQYQAIDEAIRSYRFIRNSCLRYWMDNKKVGKYDLNKYC
KVLAKQYPFANKLNSQARQSAAECSWSAISRFYDNCKRKVSGKKGFPKFKKHARSVEYKTSGWK
LSENRKAITFTDKNGIGKLKLKGTYDLHFSQLEDMKRVRLVRRADGYYVQFCISVDVKVETEPT
GKAIGLDVGIKYFLADSSGNTIENPQFYRKAEKKLNRANRRKSKKYIRGVKPQSKNYHKARCRY
ARKHLRVSRQRKEYCKRVAYCVIHSNDVVAYEDLNVKGMVKNRHLAKSISDVAWSTFRHWLEYF
AIKYGKLTIPVAPHNTSQNCSNCDKKVPKSLSTRTHICHHCGYSEDRDVNAAKNILKKALSTVG
QTGSLKLGEIEPLLVLEQSCTRKFDL (SEQ ID NO: 27)

>CasZe.1|19ft_2_nophage_noknown_scaffold_0_545 \N id=8269792
partial=0 scaf=19ft_2_nophage_noknown_scaffold_0 bin=19ft_2_UNK
sample=19FT_2_THINNED proj=Rifle Sediment CSP1
LAEENTLHLTLAMSLPLNDLPENRTRSELWRRQWLPQKKLSLLLGVNQSVRKAAADCLRWFEPY
QELLWWEPTDPDGKKLLDKEGRPIKRTAGHMRVLRKLEEIAPFRGYQLGSAVKNGLRHKVADLL
LSYAKRKLDPQFTDKTSYPSIGDQFPIVWTGAFVCYEQSITGQLYLYLPLFPRGSHQEDITNNY
DPDRGPALQVFGEKEIARLSRSTSGLLLPLQFDKWGEATFIRGENNPPTWKATHRRSDKKWLSE
VLLREKDFQPKRVELLVRNGRIFVNVACEIPTKPLLEVENFMGVSFGLEHLVTVVVINRDGNVV
HQRQEPARRYEKTYFARLERLRRGGPFSQELETFHYRQVAQIVEEALRFKSVPAVEQVGNIPK
GRYNPRLNLRLSYWPFGKLADLTSYKAVKEGLPKPYSVYSATAKMLCSTCGAANKEGDQPISLK
GPTVYCGNCGTRHNTGFNTALNLARRAQELFVKGVVAR (SEQ ID NO: 28)

FIG. 1K

>CasZe.2|RIFCSPHIGHO2_01_FULL_CPR_46_36_rifcsphigho2_01_scaffold
_646_49 Tax=RIFCSPHIGHO2_01_FULL_RIF_OD1_04_46_36_curated
id=87353177 partial=0
scaf=RIFCSPHIGHO2_01_FULL_CPR_46_36_rifcsphigho2_01_scaffold_646
bin=RIFCSPHIGHO2_01_FULL_OD1_Andersenbacteria_46_36_curated
sample=2500-curated-genomes-non-redundant proj=2500_Genomes
mSQSLLKWHDMAGRDKDASRSLQKSAVEGVLLHLTASHRVALEMLEKSVSQTVAVTMEAAQQRL
VIVLEDDPTKATSRKRVISADLQFTREEFGSLPNWAQKLASTCPEIATKYADKHINSIRIAWGV
AKESTNGDAVEQKLQWQIRLLDVTMFLQQLVLQLADKALLEQIPSSIRGGIGQEVAQQVTSHIQ
LLDSGTVLKAELPTISDRNSELARKQWEDAIQTVCTYALPFSRERARILDPGKYAAEDPRGDRL
INIDPMWARVLKGPTVKSLPLLFVSGSSIRIVKLTLPRKHAAGHKHTFTATYLVLPVSREWINS
LPGTVQEKVQWWKKPDVLATQELLVGKGALKKSANTLVIPISAGKKRFFNHILPALQRGFPLQW
QRIVGRSYRRPATHRKWFAQLTIGYTNPSSLPEMALGIHFGMKDILWWALADKQGNILKDGSIP
GNSILDFSLQEKGKIERQQKAGKNVAGKKYGKSLLNATYRVVNGVLEFSKGISAEHASQPIGLG
LETIRFVDKASGSSPVNARHSNWNYGQLSGIFANKAGPAGFSVTEITLKKAQRDLSDAEQARVL
AIEATKRFASRIKRLATKRKDDTLFV  (SEQ ID NO: 29)

>CasZe.3|rifcsphigho2_01_scaffold_10981_6
Tax=RIFCSPHIGHO2_01_FULL_OD1_47_10b curated id=55513311
partial=0 scaf=rifcsphigho2_01_scaffold_10981
bin=RIFCSPHIGHO2_01_FULL_OD1_47_10b sample=2500-genomes
proj=2500_Genomes
VEPVEKERFYYRTYTFRLDGQPRTQNLTTQSGWGLLTKAVLDNTKHYWEIVHHARIANQPIVFE
NPVIDEQGNPKLNKLGQPRFWKRPISDIVNQLRALFENQNPYQLGSSLIQGTYWDVAENLASWY
ALNKEYLAGTATWGEPSFPEPHPLTEINQWMPLTFSSGKVVRLLKNASGRYFIGLPILGENNPC
YRMRTIEKLIPCDGKGRVTSGSLILFPLVGIYAQQHRRMTDICESIRTEKGKLAWAQVSIDYVR
EVDKRRRMRRTRKSQGWIQGPWQEVFILRLVLAHKAPKLYKPRCFAGISLGPKTLASCVILDQD
ERVVEKQQWSGSELLSLIHQGEERLRSLREQSKPTWNAAYRKQLKSLINTQVFTIVTFLRERGA
AVRLESIARVRKSTPAPPVNFLLSHWAYRQITERLKDLAIRNGMPLTHSNGSYGVRFTCSQCGA
TNQGIKDPTKYKVDIESETFLCSICSHREIAAVNTATNLAKQLLDE (SEQ ID NO: 30)

>CasZe.4b|rifcsplowo2_02_scaffold_57876_2 hypothetical protein
Tax=GWA2_OD1_56_11 id=66016044 partial=0
scaf=rifcsplowo2_02_scaffold_57876 bin=RifCSPlowO2_02_full_UNK
sample=RIFCSPLOWO2_02_FULL proj=RifleCSP2_LowO2
mNDTETSETLTSHRTVCAHLHVVGETGSLPRLVEAALAELITLNGRATQALLSLAKNGLVLRRD
KEENLIAAELTLPCRKNKYADVAAKAGEPILATRINNKGKLVTKKWYGEGNSYHIVRFTPETGM
FTVRVFDRYAFDEELLHLHSEVVFGSDLPKGIKAKTDSLPANFLQAVFTSFLELPFQGFPDIVV
KPAMKQAAEQLLSYVQLEAGENQQAEYPDTNERDPELRLVEWQKSLHELSVRTEPFEFVRARDI
DYYAETDRRGNRFVNITPEWTKFAESPFARRLPLKIPPEFCILLRRKTEGHAKIPNRIYLGLQI
FDGVTPDSTLGVLATAEDGKLFWWHDHLDEFSNLEGKPEPKLKNKPQLLMVSLEYDREQRFEES
VGGDRKICLVTLKETRNFRRGWNGRILGIHFQHNPVITWALMDHDAEVLEKGFIEGNAFLGKAL
DKQALNEYLQKGGKWVGDRSFGNLKGITHTLASLIVRLAREKDAWIALEEISWVQKQSADSVA
NHEIVEQPHHSLTR (SEQ ID NO: 31)

FIG. 1L

>CasZe.4|RIFCSPLOWO2_01_FULL_OD1_45_34b_rifcsplowo2_01_scaffold_
3495_33 hypothetical protein Tax=GWA2_OD1_56_11 id=88324948
partial=0
scaf=RIFCSPLOWO2_01_FULL_OD1_45_34b_rifcsplowo2_01_scaffold_3495
bin=RIFCSPLOWO2_01_FULL_OD1_Taylorbacteria_45_34b_curated
sample=2500-curated-genomes proj=2500 Genomes
mNDTETSETLTSHRTVCAHLHVVGETGSLPRLVEAALAELITLNGRATQALLSLAKNGLVLRRD
KEENLIAAELTLPCRKNKYADVAAKAGEPILATRINNKGKLVTKKWYGEGNSYHIVRFTPETGM
FTVRVFDRYAFDEELLHLHSEVVFGSDLPKGIKAKTDSLPANFLQAVFTSFLELPFQGFPDIVV
KPAMKQAAEQLLSYVQLEAGENQQAEYPDTNERDPELRLVEWQKSLHELSVRTEPFEFVRARDI
DYYAETDRRGNRFVNITPEWTKFAESPFARRLPLKIPPEFCILLRRKTEGHAKIPNRIYLGLQI
FDGVTPDSTLGVLATAEDGKLFWWHDHLDEFSNLEGKPEPKLKNKPQLLMVSLEYDREQRFEES
VGGDRKICLVTLKETRNFRRGRHGHTRTDRLPAGNTLWRADFATSAEVAAPKWNGRILGIHFQH
NPVITWALMDHDAEVLEKGFIEGNAFLGKALDKQALNEYLQKGGKWVGDRSFGNKLKGITHTLA
SLIVRLAREKDAWIALEEISWVQKQSADSVANRRFSMWNYSRLATLIEWLGTDIATRDCGTAAP
LAHKVSDYLTHFTCPECGACRKAGQKKEIADTVRAGDILTCRKCGFSGPIPDNFIAEFVAKKAL

ERMLKKKPV (SEQ ID NO: 32)

>CasZf.1|rifcsphigho2_01_scaffold_566_121
Tax=RIFCSPHIGHO2_01_FULL_RIF_OD1_10_44_22b_curated id=55167017
partial=0 scaf=rifcsphigho2_01_scaffold_566
bin=RifCSPhighO2_01_full_UNK sample=RIFCSPHIGHO2_01_FULL
proj=RifleCSP2_HighO2
mAKRNFGEKSEALYRAVRFEVRPSKEELSILLAVSEVLRMLFNSALAERQQVFTEFIASLYAEL
KSASVPEEISEIRKKLREAYKEHSISLFDQINALTARRVEDEAFASVTRNWQEETLDALDGAYK
SFLSLRRKGDYDAHSPRSRDSGFFQKIPGRSGFKIGEGRIALSCGAGRKLSFPIPDYQQGRLAE
TTKLKKFELYRDQPNLAKSGRFWISVVYELPKPEATTCQSEQVAFVALGASSIGVVSQRGEEVI
ALWRSDKHWVPKIEAVEERMKRRVKGSRGWLRLLNSGKRRMHMISSRQHVQDEREIVDYLVRNH
GSHFVVTELVVRSKEGKLADSSKPERGGSLGLNWAAQNTGSLSRLVRQLEEKVKEHGGSVRKHK

LTLTEAPPARGAENKLWMARKLRESFLKEV (SEQ ID NO: 33)

>CasZf.2|rifcsplowo2_01_scaffold_81231_1 transposase, IS605 OrfB
family, central region id=58737995 partial=0
scaf=rifcsplowo2_01_scaffold_81231 bin=RifCSPLowO2_01_full_UNK
sample=RIFCSPLOWO2_01_FULL proj=RifleCSP2_LowO2
LAKNDEKELLYQSVKFEIYPDESKIRVLTRVSNILVLVWNSALGERRARFELYIAPLYEELKKF
PRKSAESNALRQKIREGYKEHIPTFFDQLKKLLTPMRKEDPALLGSVPRAYQEETLNTLNGSFV
SFMTLRRNNDMDAKPPKGRAEDRFHEISGRSGFKIDGSEFVLSTKEQKLRFPIPNYQLEKLKEA
KQIKKFTLYQSRDRRFWISIAYEIELPDQRPFNPEEVIYIAFGASSIGVISPEGEKVIDFWRPD
KHWKPKIKEVENRMRSCKKGSRAWKKRAAARRKMYAMTQRQQKLNHREIVASLLRLGFHFVVTE
YTVRSKPGKLADGSNPKRGGAPQGFNWSAQNTGSFGEFILWLKQKVKEQGGTVQTFRLVLGQSE

RPEKRGRDNKIEMVRLLREKYLESQTIVV (SEQ ID NO: 34)

FIG. 1M

>CasZf.3|rifcsphigho2_01_scaffold_4702_81 IS605 OrfB family transposase id=55366684 partial=0 scaf=rifcsphigho2_01_scaffold_4702 bin=RifCSPhighO2_01_full_UNK sample=RIFCSPHIGHO2_01_FULL proj=RifleCSP2_HighO2
mAKGKKKEGKPLYRAVRFEIFPTSDQITLFLRVSKNLQQVWNEAWQERQSCYEQFFGSIYERIG
QAKKRAQEAGFSEVWENEAKKGLNKKLRQQEISMQLVSEKESLLQELSIAFQEHGVTLYDQING
LTARRIIGEFALIPRNWQEETLDSLDGSFKSFLALRKNGDPDAKPPRQRVSENSFYKIPGRSGF
KVSNGQIYLSFGKIGQTLTSVIPEFQLKRLETAIKLKKFELCRDERDMAKPGRFWISVAYEIPK
PEKVPVVSKQITYLAIGASRLGVVSPKGEFCLNLPRSDYHWKPQINALQERLEGVVKGSRKWKK
RMAACTRMFAKLGHQQKQHGQYEVVKKLLRHGVHFVVTELKVRSKPGALADASKSDRKGSPTGP
NWSAQNTGNIARLIQKLTDKASEHGGTVIKRNPPLLSLEERQLPDAQRKIFIAKKLREEFLADQ
K  (SEQ ID NO: 35)

>CasZg.1|rifcsp13_1_sub10_scaffold_3_54 \N id=12787801 partial=0 scaf=rifcsp13_1_sub10_scaffold_3 bin=RifCSP13_1_UNK sample=RIFCSP13_1 proj=Rifle Sediment CSP2
mAKREKKDDVVLRGTKMRIYPTDRQVTLMDMWRRRCISLWNLLLNLETAAYGAKNTRSKLGWRS
IWARVVEENHAKALIVYQHGKCKKDGSFVLKRDGTVKHPPRERFPGDRKILLGLFDALRHTLDK
GAKCKCNVNQPYALTRAWLDETGHGARTADIIAWLKDFKGECDCTAISTAAKYCPAPPTAELLT
KIKRAAPADDLPVDQAILLDLFGALRGGLKQKECDHTHARTVAYFEKHELAGRAEDILAWLIAH
GGTCDCKIVEEAANHCPGPRLFIWEHELAMIMARLKAEPRTEWIGDLPSHAAQTVVKDLVKALQ
TMLKERAKAAAGDESARKTGFPKFKKQAYAAGSVYFPNTTmFFDVAAGRVQLPNGCGSMRCEIP
RQLVAELLERNLKPGLVIGAQLGLLGGRIWRQGDRWYLSCQWERPQPTLLPKTGRTAGVKIAAS
IVFTTYDNRGQTKEYPMPPADKKLTAVHLVAGKQNSRALEAQKEKEKKLKARKERLRLGKLEKG
HDPNALKPLKRPRVRRSKLFYKSAARLAACEAIERDRRDGFLHRVTNEIVHKFDAVSVQKMSVA
PMMRRQKQKEKQIESKKNEAKKEDNGAAKKPRNLKPVRKLLRHVAMARGRQFLEYKYNDLRGPG
SVLIADRLEPEVQECSRCGTKNPQMKDGRRLLRCIGVLPDGTDCDAVLPRNRNAARNAEKRLRK
HREAHNA  (SEQ ID NO: 36)

>CasZg.2|033|3300009991.a:Ga0105042_100140_01533 Zr6.c9.inclusive
MNEVLPIPAVGEDAADTIMRGSKMRIYPSVRQAATMDLWRRRCIQLWNLLLELEQAAYSGENRR
TQIGWRSIWATVVEDSHAEAVRVAREGKKRKDGTFRKAPSGKEIPPLDPAMLAKIQRQMNGAVD
VDPKTGEVTPAQPRLFMWEHELQKIMARLKQAPRTHWIDDLPSHAAQSVVKDLIKALQAMLRER
KKRASGIGGRDTGFPKFKKNRYAAGSVYFANTQLRFEAKRGKAGDPDAVRGEFARVKLPNGVGW
MECRMPRHINAAHAYAQATLMGGRIWRQGENWYLSCQWKMPKPAPLPRAGRTAAIKIAAAIPIT
TVDNRGQTREYAMPPIDRERIAAHAAAGRAQSRALEARKRRAKKREAYAKKRHAKKLERGIAAK
PPGRARIKLSPGFYAAAAKLAKLEAEDANAREAWLHEITTQIVRNFDVIAVPRMEVAKLMKKPE
PPEEKEEQVKAPWQGKRRSLKAARVMMRRTAMALIQTTLKYKAVDLRGPQAYEEIAPLDVTAAA
CSGCGVLKPEWKMARAKGREIMRCQEPLPGGKTCNTVLTYTRNSARVIGRELAVRLAERQKA
(SEQ ID NO: 37)

FIG. 1N

>CasZh.1|rifcsp2_19_4_full_scaffold_168_120 transposase
id=102318404 partial=0 scaf=rifcsp2_19_4_full_scaffold_168
bin=RifCSP19_4_full_UNK sample=RIFCSP19_4_FULL proj=Rifle
Sediment CSP1
mTTQKTYNFCFYDQRFFELSKEAGEVYSRSLEEFWKIYDETGVWLSKFDLQKHMRNKLERKLLH
SDSFLGAMQQVHANLASWKQAKKVVPDACPPRKPKFLQAILFKKSQIKYKNGFLRLTLGTEKEF
LYLKWDINIPLPIYGSVTYSKTRGWKINLCLETEVEQKNLSENKYLSIDLGVKRVATIFDGENT
ITLSGKKFMGLMHYRNKLNGKTQSRLSHKKKGSNNYKKIQRAKRKTTDRLLNIQKEMLHKYSSF
IVNYAIRNDIGNIIIGDNSSTHDSPNMRGKTNQKISQNPEQKLKNYIKYKFESISGRVDIVPEP
YTSRKCPHCKNIKKSSPKGRTYKCKKCGFIFDRDGVGAINIYNENVSFGQIISPGRIRSLTEPI
GMKFHNEIYFKSYVAA   (SEQ ID NO: 38)

>CasZi.1|RBG_13_scaffold_1401_19
Tax=RBG_13_Planctomycetes_46_10_curated id=16386779 partial=0
scaf=RBG_13_scaffold_1401 bin=RBG_13_Planctomycetes_46_10
sample=2500-genomes proj=2500 Genomes
mSVRSFQARVECDKQTMEHLWRTHKVFNERLPEIIKILFKMKRGECGQNDKQKSLYKSISQSIL
EANAQNADYLLNSVSIKGWKPGTAKKYRNASFTWADDAAKLSSQGIHVYDKKQVLGDLPGMMSQ
MVCRQSVEAISGHIELTKKWEKEHNEWLKEKEKWESEDEHKKYLDLREKFEQFEQSIGGKITKR
RGRWHLYLKWLSDNPDFAAWRGNKAVINPLSEKAQIRINKAKPNKKNSVERDEFFKANPEMKAL
DNLHGYYERNFVRRRKTKKNPDGFDHKPTFTLPHPTIHPRWFVFNKPKTNPEGYRKLILPKKAG
DLGSLEMRLLTGEKNKGNYPDDWISVKFKADPRLSLIRPVKGRRVVRKGKEQGQTKETDSYEFF
DKHLKKWRPAKLSGVKLIFPDKTPKAAYLYFTCDIPDEPLTETAKKIQWLETGDVTKKGKKRKK
KVLPHGLVSCAVDLSMRRGTTGFATLCRYENGKIHILRSRNLWVGYKEGKGCHPYRWTEGPDLG
HIAKHKREIRILRSKRGKPVKGEESHIDLQKHIDYMGEDRFKKAARTIVNFALNTENAASKNGF
YPRADVLLLENLEGLIPDAEKERGINRALAGWNRRHLVERVIEMAKDAGFKRRVFEIPPYGTSQ
VCSKCGALGRRYSIIRENNRREIRFGYVEKLFACPNCGYCANADHNASVNLNRRFLIEDSFKSY
YDWKRLSEKKQKEEIETIESKLMDKLCAMHKISRGSISK (SEQ ID NO: 39)

FIG. 10

>CasZi.2|026|3300009652.a:Ga0123330_1010394_01528
Zr6.c2c1.inclusive
MHLWRTHCVFNQRLPALLKRLFAMRRGEVGGNEAQRQVYQRVAQFVLARDAKDSVDLLNAVSLR
KRSANSAFKKKATISCNGQAREVTGEEVFAEAVALASKGVFAYDKDDMRAGLPDSLFQPLTRDA
VACMRSHEELVATWKKEYREWRDRKSEWEAEPEHALYLNLRPKFEEGEAARGGRFRKRAERDHA
YLDWLEANPQLAAWRRKAPPAVVPIDEAGKRRIARAKAWKQASVRAEEFWKRNPELHALHKIHV
QYLREFVRPRRTRRNKRREGFKQRPTFTMPDPVRHPRWCLFNAPQTSPQGYRLLRLPQSRRTVG
SVELRLLTGPSDGAGFPDAWVNVRFKADPRLAQLRPVKVPRTVTRGKNKGAKVEADGFRYYDDQ
LLIERDAQVSGVKLLFRDIRMAPFADKPIEDRLLSATPYLVFAVEIKDEARTERAKAIRFDETS
ELTKSGKKRKTLPAGLVSVAVDLDTRGVGFLTRAVIGVPEIQQTHHGVRLLQSRYVAVGQVEAR
ASGEAEWSPGPDLAHIARHKREIRRLRQLRGKPVKGERSHVRLQAHIDRMGEDRFKKAARKIVN
EALRGSNPAAGDPYTRADVLLYESLETLLPDAERERGINRALLRWNRAKLIEHLKRMCDDAGIR
HFPVSPFGTSQVCSKCGALGRRYSLARENGRAVIRFGWVERLFACPNPECPGRRPDRPDRPFTC
NSDHNASVNLHRVFALGDQAVAAFRALAPRDSPARTLAVKRVEDTLRPQLMRVHKLADAGVDSP
F (SEQ ID NO: 40)

>CasZj.1|130|3300012532.a:Ga0137373_10000316_00700 c2c4
MATLVYRYGVRAHGSARQQDAVVSDPAMLEQLRLGHELRNALVGVQHRYEDGKRAVWSGFASVA
AADHRVTTGETAVAELEKQARAEHSADRTAATRQGTAESLKAARAAVKQARADRKAAMAAVAEQ
AKPKIQALGDDRDAEIKDLYRRFCQDGVLLPRCGRCAGDLRSDGDCTDCGAAHEPRKLYWATYN
AIREDHQTAVKLVEAKRKAGQPARLRFRRWTGDGTLTVQLQRMHGPACRCVTCAEKLTRRARKT
DPQAPAVAADPAYPPTDPPRDPALLASGQGKWRNVLQLGTWIPPGEWSAMSRAERRRVGRSHIG
WQLGGGRQLTLPVQLHRQMPADADVAMAQLTRVRVGGRHRMSVALTAKLPDPPQVQGLPPVALH
LGWRQRPDGSLRVATWACPQPLDLPPAVADVVVSHGGRWGEVIMPARWLADAEVPPRLLGRRDK
AMEPVLEALADWLEAHTEACTARMTPALVRRWRSQGRLAGLTNRWRGQPPTGSAEILTYLEAWR
IQDKLLWERESHLRRRLAARRDDAWRRVASWLARHAGVLVVDDADIAELRRRDDPADTDPTMPA
SAAQAARARAALAAPGRLRHLATITATRDGLVHTVASAGLTRLHRKCGHQAPDPRYAASAVV
TCPGCGNGYDQDYNAAMLMLDRQQQP (SEQ ID NO: 41)

>CasZk.1|012|3300005602.a:Ga0070762_10001740_01506
Zr6.c9.inclusive
MSRVELHRAYKFRLYPTPAQVAELAEWERQLRRLYNLAHSQRLAAMQRHVRPKSPGVLKSECLS
CGAVAVAEIGTDGKAKKTVKHAVGCSVLECRSCGGSPDAEGRTAHTAACSFVDYYRQGREMTQL
LEEDDQLARVVCSARQETLRDLEKAWQRWHKMPGFGKPHFKKRIDSCRIYFSTPKSWAVDLGYL
SFTGVASSVGRIKIRQDRVWPGDAKFSSCHVVRDVDEWYAVFPLTFTKEIEKPKGGAVGINRGA
VHAIADSTGRVVDSPKFYARSLGVIRHRARLLDRKVPFGRAVKPSPTKYHGLPKADIDAAAARV
NASPGRLVYEARARGSIAAAEAHLAALVLPAPRQTSQLPSEGRNRERARRFLALAHQRVRRQRE
WFLHNESAHYAQSYTKIAIEDWSTKEMTSSEPRDAEEMKRVTRARNRSILDVGWYELGRQIAYK
SEATGAEFAKVDPGLRETETHVPEAIVRERDVDVSGMLRGEAGISGTCSRCGGLLRASASGHAD
AECEVCLHVEVGDVNAAVNVLKRAMFPGAAPPSKEKAKVTIGIKGRKKKRAA
(SEQ ID NO: 42)

FIG. 1P

>CasZk.2|016|3300005921.a:Ga0070766_10011912_01491
Zr6.c9.inclusive
MSRVELHRAYKFRLYPTPVQVAELSEWERQLRRLYNLGHEQRLLTLTRHLRPKSPGVLKGECLS
CDSTQVQEVGADGRPKTTVRHAEQCPTLACRSCGALRDAEGRTAHTVACAFVDYYRQGREMTEL
LAADDQLARVVCSARQEVLRDLDKAWQRWRKMPGFGKPRFKRRTDSCRIYFSTPKAWKLEGGHL
SFTGAATTVGAIKMRQDRNWPASVQFSSCHVVRDVDEWYAVFPLTFVAEVARPKGGAVGINRGA
VHAIADSTGRVVDSPRYYARALGVIRHRARLFDRKVPSGHAVKPSPTKYRGLSAIEVDRVARAT
GFTPGRVVTEALNRGGVAYAECALAAIAVLGHGPERPLTSDGRNREKARKFLALAHQRVRRQRE
WFLHNESAHYARTYSKIAIEDWSTKEMTASEPQGEETRRVTRSRNRSILDVGWYELGRQLAYKT
EATGAEFAQVDPGLKETETNVPKAIADARDVDVSGMLRGEAGISGTCSKCGGLLRAPASGHADA
ECEICLNVEVGDVNAAVNVLKRAMFPGDAPPASGEKPKVSIGIKGRQKKKAA
    (SEQ ID NO: 43)

>CasZk.3|106|3300009698.a:Ga0116216_10000905_01565 c2c9
MEAIATGMSPERRVELGILPGSVELKRAYKFRLYPMKVQQAELSEWERQLRRLYNLAHEQRLAA
LLRYRDWDFQKGACPSCRVAVPGVHTAACDHVDYFRQAREMTQLLEVDAQLSRVICCARQEVLR
DLDKAWQRWRKKLGGRPRFKRRTDSCRIYLSTPKHWEIAGRYLRLSGLASSVGEIRIEQDRAFP
EGALLSSCSIVRDVDEWYACLPLTFTQPIERAPHRSVGLNRGVVHALADSDGRVVDSPKFFERA
LATVQKRSRDLARKVSGSRNAHKARIKLAKAHQRVRRQRAAFLHQESAYYSKGFDLVALEDMSV
RKMTATAGEAPEMGRGAQRDLNRGILDVGWYELARQIDYKRLAHGGELLRVDPGQTTPLACVTE
EQPARGISSACAVCGIPLARPASGNARMRCTACGSSQVGDVNAAENVLTRALSSAPSGPKSPKA
SIKIKGRQKRLGTPANRAGEASGGDPPVRGPVEGGTLAYVVEPVSESQSDT
    (SEQ ID NO: 44)

>CasZk.4|072|3300006028.a:Ga0070717_10000077_00263
Zr6.c9.inclusive
MTVRTYKYRAYPTPEQAEALTSWLRFASQLYNAALEHRKNAWGRHDAHGRGFRFWDGDAAPRKK
SDPPGRWVYRGGGGAHISKNDQGKLLTEFRREHAELLPPGMPALVQHEVLARLERSMAAFFQRA
TKGQKAGYPRWRSEHRYDSLTFGLTSPSKERFDPETGESLGRGKTVGAGTYHNGDLRLTGLGEL
RILEHRRIPMGAIPKSVIVRRSGKRWFVSIAMEMPSVEPAASGRPAVGLDMGVVTWGTAFTADT
SAAAALVADLRRMATDPSDCRRLEELEREAAQLSEVLAHCRARGLDPARPRRCPKELTKLYRRS
LHRLGELDRACARIRRRLQAAHDIAEPVPDEAGSAVLIEGSNAGMRHARRVARTQRRVARRTRA
GHAHSNRRKKAVQAYARAKERERSARGDHRHKVSRALVRQFEEISVEALDIKQLTVAPEHNPDP
QPDLPAHVQRRRNRGELDAAWGAFFAALDYKAADAGGRVARKPAPHTTQECARCGTLVPKPISL
RVHRCPACGYTAPRTVNSARNVLQRPLEEPGRAGPSGANGRGVPHAVA (SEQ ID NO: 45)

FIG. 1Q

>CasZ1.1|004|3300001256.a:JGI12210J13797_10004690_01983 c2c9
MNCRYRYRIYPTPGQRQSLARLFGCVRVVWNDALFLCRQSEKLPKNSELQKLCITQAKKTEARG
WLGQVSAIPLQQSVADLGVAFKNFFQSRSGKRKGKKVNPPRVKRRNNRQGARFTRGGFKVKTSK
VYLARIGDIKIKWSRPLPSEPSSVTVIKDCAGQYFLSFVVEVKPEIKPPKNPSIGIDLGLKTFA
SCSNGEKIDSPDYSRLYRKLKRCQRRLAKRQRGSKRRERMRVKVAKLNAQIRDKRKDFLHKLST
KVVNENQVIALEDLNVGGMLKNRKLSRAISQAGWYEFRSLCEGKAEKHNRDFRVISRWEPTSQV
CSECGYRWGKIDLSVRSIVCINCGVEHDRDDNASVNIEQAGLKVGVGHTHDSKRTGSACKTSNG

AVCVEPSTHREYVQLTLFDW     (SEQ ID NO: 46)

>CasZ1.2|014|3300005660.a:Ga0073904_10021651_01988 c2c9
MKSRWTFRCYPTPEQEQHLARTFGCVRFVWNWALRARTDAFRAGERIGYPATDKALTLLKQQPE
TVWLNEVSSVCLQQALRDLQVAFSNFFDKRAAHPSFKRKEARQSANYTERGFSFDHERRILKLA
KIGAIKVKWSRKAIPHPSSIRLIRTASGKYFVSLVVETQPAPMPETGESVGVDFGVARLATLSN
GERISNPKHGAKWQRRLAFYQKRLARATKGSKRRMRIKRHVARIHEKIGNSRSDTLHKLSTDLV
TRFDLICVEDLNLRGMVKNHSLARSLHDASIGSAIRMIEEKAERYGKNVVKIDRWFPSSKTCSD
CGHIVEQLPLNVREWTCPECGTTHDRDANAAANILAVGQTVSAHGGTVRRSRAKASERKSQRSA

NRQGVNRA    (SEQ ID NO: 47)

FIG. 2

|   | # | Cas1 | Organism | Locus example |
|---|---|------|----------|---------------|
| Za | 5 | I-B | DPANN | Cas1-2-4-CasZa (508aa) |
| Zb | 7 | I-B | DPANN | Cas1-2-4-CasZb (538aa) |
| Zc | 5 | I-B | DPANN | CasZc (614aa) - Cas1-2-4 |
| Zd | 1 | I-B | DPANN | Cas1-2-4-CasZd (518aa) |
| Ze | 4 | III-D* | CPR | CasZe (650aa) - Cas1 |
| Zf | 3 | III-D | CPR | CasZf (415aa) - Cas1 |
| Zg | 1 | I-E | Phage? | CasZg (712aa) - Cas1-2 |
| Zh | 1 | II-C | MGE | CasZh (401aa) - Trnsp - Cas1-2 |
| Zi | 1 | I-U | Plancto | Cas4+1 - 2 - CasZi (744aa) |

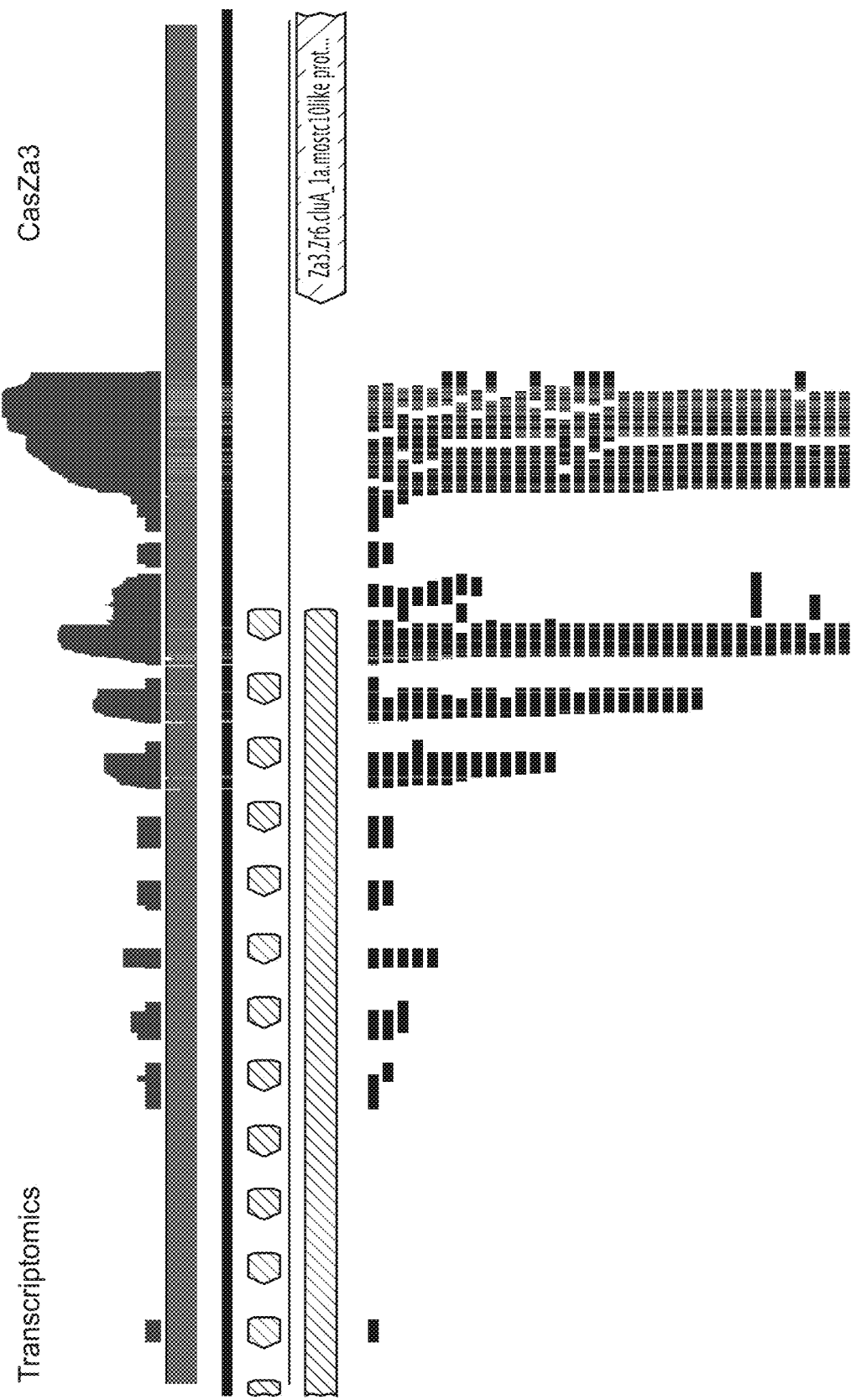

FIG. 7A

>Cas14a.1|gwa1_scaffold_1795_curated|25635..27224|revcom
PEEKTSKLKPNSINLAANYDANEKFNCKECKFHPFKNKKRYEFNFYNNLHGCKSCTKST
NNPAVKRIEIGYQKLKFEIKNQMEAYPWFGRLRINFYSDEKRKMSELNEMQVTGVKNKI
FFDAIECAWREILKKRFRESKETLITIPKLKNKAGHGARKHRNKKLLIRRRAFMKKNFH
FLDNDSISYRSFANNIACVLPSKVGVDIGGIISPDVGKDIKPVDISLNLMWASKEGIKS
GRKVEIYSTQYDGNMVKKIEAETGEDKSWGKNRKRRQTSLLLSIPKPSKQVQEFDFKEW
PRYKDIEKKVQWRGFPIKIIFDSNHNSIEFGTYQGGKQKVLPIPFNDSKTTPLGSKMNK
LEKLRFNSKIKSRLGSAIAANKFLEAARTYCVDSLYHEVSSANAIGKGKIFIEYYLEIL
SQNYIEAAQKQLQRFIESIEQWFVADPFQGRLKQYFKDDLKRAKCFLCANREVQTTCYA
AVKLHKSCAEKVKDKNKELAIKERNNKEDAVIKEVEASNYPRVIRLKLTKTITNKAM
(SEQ ID NO:306)

>Cas14a.2|gwa2_scaffold_18027_curated|7105..8628
ELIVNENKDPLNIGKTAKAVFKEIDPTSINRAANYDASIELACKECKFKPFNNTKRHDF
SFYSNWHRCSPNSCLQSTYRAKIRKTEIGYEKLKNEILNQMQYYPWFGRLYQNFFNDQR
DKMTSLDEIQVTGVQNKIFFNTVEKAWREIIKKRFRDNKETMRTIPDLKNKSGHGSRKL
SNKSLLRRRFAFAQKSFKLVDNSDVSYRAFSNNVACVLPSKIGVDIGGIINKDLKREYI
PQEITFNVFWKQHDGLKKGRNIEIHSVQYKGEIVKRIEADTGEDKAWGKNRQRRFTSLI
LKITPKQGGKKIWKFPEKKNASDYEYFPIPIEFILDNGDASIKFGGEEGEVGKQKHLLI
PFNDSKATPLSSKQMLLETSRFNAEVKSTIGLALYANYFVSYARNYVIKSTYHKNSKKG
QIVTEIYLESISQNFVRAIQRQLQSLMLNLKDWGFMQTHKKELKKYFGSDLEGSKGGQK
RREKEEKIEKEIEASYLPRLIRLSLTKSVTKAEEM (SEQ ID NO:305)

>Cas14a.3|rifcsphigho2_02_scaffold_2167_curated|30296..31798|revcom
KEPLNIGKTAKAVFKEIDPTSLNRAANYDASIELNCKECKFKPFKNVKRYEFNFYNNWY
RCNPNSCLQSTYKAQVRKVEIGYEKLKNEILTQMQYYPWFGRLYQNFFHDERDKMTSLD
EIQVIGVQNKVFFNTVEKAWREIIKKRFKDNKETMETIPELKHAAGHGKRKLSNKSLLR
RRFAFVQKSFKFVDNSDVSYRSFSNNIACVLPSRIGVDLGGVISRNPKREYIPQEISFN
AFWKQHEGLKKGRNIEIQSVQYKGETVKRIEADTGEDKAWGKNRQRRFTSLILKLVPKQ
GGKKVWKYPEKRNEGNYEYFPIPIEFILDSGETSIRFGGDEGEAGKQKHLVIPFNDSKA
TPLASQQTLLENSRFNAEVKSCIGLAIYANYFYGYARNYVISSIYHKNSKNGQAITAIY
LESIAHNYVKAIERQLQNLLLNLRDFSFMESHKKELKKYFGGDLEGTGGAQKRREKEEK
IEKEIEQSYLPRLIRLSLTKMVTKQVEM (SEQ ID NO:304)

FIG. 7B

>Cas14a.4|CG10_big_fil_rev_8_21_14_0.10_scaffold_20906_curated|649..2829
SESENKIIEQYYAFLYSFRDKYEKPEFKNRGDIKRKLQNKWEDFLKEQNLKNDKKLSNY
IFSNRNFRRSYDREEENEEGIDEKKSKPKRINCFEKEKNLKDQYDKDAINASANKDGAQ
KWGCFECIFFPMYKIESGDPNKRIIINKTRFKLFDFYLNLKGCKSCLRSTYHPYRSNVY
IESNYDKLKREIGNFLQQKNIFQRMRKAKVSEGKYLTNLDEYRLSCVAMHFKNRWLFFD
SIQKVLRETIKQRLKQMRESYDEQAKTKRSKGHGRAKYEDQVRMIRRRAYSAQAHKLLD
NGYITLFDYDDKEINKVCLTAINQEGFDIGGYLNSDIDNVMPPIEISFHLKWKYNEPIL
NIESPFSKAKISDYLRKIREDLNLERGKEGKARSKKNVRRKVLASKGEDGYKKIFTDFF
SKWKEELEGNAMERVLSQSSGDIQWSKKKRIHYTTLVLNINLLDKKGVGNLKYYEIAEK
TKILSFDKNENKFWPITIQVLLDGYEIGTEYDEIKQLNEKTSKQFTIYDPNTKIIKIPF
TDSKAVPLGMLGINIATLKTVKKTERDIKVSKIFKGGLNSKIVSKIGKGIYAGYFPTVD
KEILEEVEEDTLDNEFSSKSQRNIFLKSIIKNYDKMLKEQLFDFYSFLVRNDLGVRFLT
DRELQNIEDESFNLEKRFFETDRDRIARWFDNTNTDDGKEKFKKLANEIVDSYKPRLIR
LPVVRVIKRIQPVKQREM (SEQ ID NO:178)

>Cas14a.5|rifcsplowo2_01_scaffold_34461_curated|4968..6521
KYSTRDFSELNEIQVTACKQDEFFKVIQNAWREIIKKRFLENRENFIEKKIFKNKKGRG
KRQESDKTIQRNRASVMKNFQLIENEKIILRAPSGHVACVFPVKVGLDIGGFKTDDLEK
NIFPPRTITINVFWKNRDRQRKGRKLEVWGIKARTKLIEKVHKWDKLEEVKKKRLKSLE
QKQEKSLDNWSEVNNDSFYKVQIDELQEKIDKSLKGRTMNKILDNKAKESKEAEGLYIE
WEKDFEGEMLRRIEASTGGEEKWGKRRQRRHTSLLLDIKNNSRGSKEIINFYSYAKQGK
KEKKIEFFPFPLTITLDAEEESPLNIKSIPIEDKNATSKYFSIPFTETRATPLSILGDR
VQKFKTKNISGAIKRNLGSSISSCKIVQNAETSAKSILSLPNVKEDNNMEIFINTMSKN
YFRAMMKQMESFIFEMEPKTLIDPYKEKAIKWFEVAASSRAKRKLKKLSKADIKKSELL
LSNTEEFEKEKQEKLEALEKEIEEFYLPRIVRLQLTKTILETPVM (SEQ ID
NO:179)

>Cas14a.6|3300012359.a|Ga0137385_10000156|41289..42734
KKLQLLGHKILLKEYDPNAVNAAANFETSTAELCGQCKMKPFKNKRRFQYTFGKNYHGC
LSCIQNVYYAKKRIVQIAKEELKHQLTDSIASIPYKYTSLFSNTNSIDELYILKQERAA
FFSNTNSIDELYITGIENNIAFKVISAIWDEIIKKRRQRYAESLTDTGTVKANRGHGGT
AYKSNTRQEKIRALQKQTLHMVTNPYISLARYKNNYIVATLPRTIGMHIGAIKDRDPQK
KLSDYAINFNVFWSDDRQLIELSTVQYTGDMVRKIEAETGENNKWGENMKRTKTSLLLE
ILTKKTTDELTFKDWAFSTKKEIDSVTKKTYQGFPIGIIFEGNESSVKFGSQNYFPLPF
DAKITPPTAEGFRLDWLRKGSFSSQMKTSYGLAIYSNKVTNAIPAYVIKNMFYKIARAE
NGKQIKAKFLKKYLDIAGNNYVPFIIMQHYRVLDTFEEMPISQPKVIRLSLTKTQHIII
KKDKTDSKM (SEQ ID NO:180)

FIG. 7C

>Cas14b.1|rifcsplowo2_01_scaffold_239_curated|54653..56257
NTSNLINLGKKAINISANYDANLEVGCKNCKFLSSNGNFPRQTNVKEGCHSCEKSTYEP
SIYLVKIGERKAKYDVLDSLKKFTFQSLKYQSKKSMKSRNKKPKELKEFVIFANKNKAF
DVIQKSYNHLILQIKKEINRMNSKKRKKNHKRRLFRDREKQLNKLRLIESSNLFLPREN
KGNNHVFTYVAIHSVGRDIGVIGSYDEKLNFETELTYQLYFNDDKRLLYAYKPKQNKII
KIKEKLWNLRKEKEPLDLEYEKPLNKSITFSIKNDNLFKVSKDLMLRRAKFNIQGKEKL
SKEERKINRDLIKIKGLVNSMSYGRFDELKKEKNIWSPHIYREVRQKEIKPCLIKNGDR
IEIFEQLKKKMERLRRFREKRQKKISKDLIFAERIAYNFHTKSIKNTSNKINIDQEAKR
GKASYMRKRIGYETFKNKYCEQCLSKGNVYRNVQKGCSCFENPFDWIKKGDENLLPKKN
EDLRVKGAFRDEALEKQIVKIAFNIAKGYEDFYDNLGESTEKDLKLKFKVGTTINEQES
LKL (SEQ ID NO:181)

>Cas14b.2|rifcsplowo2_01_scaffold_282_curated|77370..78983
TSNPIKLGKKAINISANYDSNLQIGCKNCKFLSYNGNFPRQTNVKEGCHSCEKSTYEPP
VYTVRIGERRSKYDVLDSLKKFIFLSLKYRQSKKMKTRSKGIRGLEEFVISANLKKAMD
VIQKSYRHLILNIKNEIVRMNGKKRNKNHKRLLFRDREKQLNKLRLIEGSSFFKPPTVK
GDNSIFTCVAIHNIGRDIGIAGDYFDKLEPKIELTYQLYYEYNPKKESEINKRLLYAYK
PKQNKIIEIKEKLWNLRKEKSPLDLEYEKPLTKSITFLVKRDGVFRISKDLMLRKAKFI
IQGKEKLSKEERKINRDLIKIKSNIISLTYGRFDELKKDKTIWSPHIFRDVKQGKITPC
IERKGDRMDIFQQLRKKSERLRENRKKRQKKISKDLIFAERIAYNFHTKSIKNTSNLIN
IKHEAKRGKASYMRKRIGNETFRIKYCEQCFPKNNVYKNVQKGCSCFEDPFEYIKKGNE
DLIPNKNQDLKAKGAFRDDALEKQIIKVAFNIAKGYEDFYENLKKTTEKDIRLKFKVGT
IISEEM (SEQ ID NO:182)

>Cas14b.3|rifcsphigho2_01_scaffold_36781_curated|2592..4217
NNSINLSKKAINISANYDANLQVRCKNCKFLSSNGNFPRQTDVKEGCHSCEKSTYEPPV
YDVKIGEIKAKYEVLDSLKKFTFQSLKYQLSKSMKFRSKKIKELKEFVIFAKESKALNV
INRSYKHLILNIKNDINRMNSKKRIKNHKGRLFLDRQKQLSKLKLIEGSSFFVPAKNVG
NKSVFTCVAIHSIGRDIGIAGLYDSFTKPVNEITYQIFFSGERRLLYAYKPKQLKILSI
KENLWSLKNEKKPLDLLYEKPLGKNLNFNVKGGDLFRVSKDLMIRNAKFNVHGRQRLSD
EERLINRNFIKIKGEVVSLSYGRFEELKKDRKLWSPHIFKDVRQNKIKPCLVMQGQRID
IFEQLKRKLELLKKIRKSRQKKLSKDLIFGERIAYNFHTKSIKNTSNKINIDSDAKRGR
ASYMRKRIGNETFKLKYCDVCFPKANVYRRVQNGCSCSENPYNYIKKGDKDLLPKKDEG
LAIKGAFRDEKLNKQIIKVAFNIAKGYEDFYDDLKKRTEKDVDLKFKIGTTVLDQKPME
IFDGIVITWL (SEQ ID NO:183)

FIG. 7D

>Cas14b.4|cgl_0.2_scaffold_785_c_curated|32521..34155
LLTTVVETNNLAKKAINVAANFDANIDRQYYRCTPNLCRFIAQSPRETKEKDAGCSSCT
QSTYDPKVYVIKIGKLLAKYEILKSLKRFLFMNRYFKQKKTERAQQKQKIGTELNEMSI
FAKATNAMEVIKRATKHCTYDIIPETKSLQMLKRRRHRVKVRSLLKILKERRMKIKKIP
NTFIEIPKQAKKNKSDYYVAAALKSCGIDVGLCGAYEKNAEVEAEYTYQLYYEYKGNSS
TKRILYCYNNPQKNIREFWEAFYIQGSKSHVNTPGTIRLKMEKFLSPITIESEALDFRV
WNSDLKIRNGQYGFIKKRSLGKEAREIKKGMGDIKRKIGNLTYGKSPSELKSIHVYRTE
RENPKKPRAARKKEDNFMEIFEMQRKKDYEVNKKRRKEATDAAKIMDFAEEPIRHYHTN
NLKAVRRIDMNEQVERKKTSVFLKRIMQNGYRGNYCRKCIKAPEGSNRDENVLEKNEGC
LDCIGSEFIWKKSSKEKKGLWHTNRLLRRIRLQCFTTAKAYENFYNDLFEKKESSLDII
KLKVSITTKSM (SEQ ID NO:184)

>Cas14b.5|rifcsphigho2_02_scaffold_55589_curated|1904..3598
ASTMNLAKQAINFAANYDSNLEIGCKGCKFMSTWSKKSNPKFYPRQNNQANKCHSCTYS
TGEPEVPIIEIGERAAKYKIFTALKKFVFMSVAYKERRRQRFKSKKPKELKELAICSNR
EKAMEVIQKSVVHCYGDVKQEIPRIRKIKVLKNHKGRLFYKQKRSKIKIAKLEKGSFFK
TFIPKVHNNGCHSCHEASLNKPILVTTALNTIGADIGLINDYSTIAPTETDISWQVYYE
FIPNGDSEAVKKRLLYFYKPKGALIKSIRDKYFKKGHENAVNTGFFKYQGKIVKGPIKF
VNNELDFARKPDLKSMKIKRAGFAIPSAKRLSKEDREINRESIKIKNKIYSLSYGRKKT
LSDKDIIKHLYRPVRQKGVKPLEYRKAPDGFLEFFYSLKRKERRLRKQKEKRQKDMSEI
IDAADEFAWHRHTGSIKKTTNHINFKSEVKRGKVPIMKKRIANDSFNTRHCGKCVKQGN
AINKYYIEKQKNCFDCNSIEFKWEKAALEKKGAFKLNKRLQYIVKACFNVAKAYESFYE
DFRKGEEESLDLKFKIGTTTTLKQYPQNKARAM (SEQ ID NO:185)

>Cas14b.6|CG03_land_8_20_14_0.80_scaffold_2214_curated|6634
..8466|revcom
HSHNLMLTKLGKQAINFAANYDANLEIGCKNCKFLSYSPKQANPKKYPRQTDVHEDGNI
ACHSCMQSTKEPPVYIVPIGERKSKYEILTSLNKFTFLALKYKEKKRQAFRAKKPKELQ
ELAIAFNKEKAIKVIDKSIQHLILNIKPEIARIQRQKRLKNRKGKLLYLHKRYAIKMGL
IKNGKYFKVGSPKKDGKKLLVLCALNTIGRDIGIIGNIEENNRSETEITYQLYFDCLDA
NPNELRIKEIEYNRLKSYERKIKRLVYAYKPKQTKILEIRSKFFSKGHENKVNTGSFNF
ENPLNKSISIKVKNSAFDFKIGAPFIMLRNGKFHIPTKKRLSKEEREINRTLSKIKGRV
FRLTYGRNISEQGSKSLHIYRKERQHPKLSLEIRKQPDSFIDEFEKLRLKQNFISKLKK
QRQKKLADLLQFADRIAYNYHTSSLEKTSNFINYKPEVKRGRTSYIKKRIGNEGFEKLY
CETCIKSNDKENAYAVEKEELCFVCKAKPFTWKKTNKDLGIFKYPSRIKDFIRAAFTV
AKSYNDFYENLKKKDLKNEIFLKFKIGLILSHEKKNHISIAKSVAEDERISGKSIKNIL
NKSIKLEKNCYSCFFHKEDM (SEQ ID NO:186)

FIG. 7E

>Cas14b.7|3300013125.a|Ga0172369_10000737|994..2652|revcom
SLERVIDKRNLAKKAINIAANFDANINKGFYRCETNQCMFIAQKPRKTNNTGCSSCLQS
TYDPVIYVVKVGEMLAKYEILKSLKRFVFMNRSFKQKKTEKAKQKERIGGELNEMSIFA
NAALAMGVIKRAIRHCHVDIRPEINRLSELKKTKHRVAAKSLVKIVQRKTKWKGIPNS
FIQIPQKARNKDADFYVASALKSGGIDIGLCGTYDKKPHADPRWTYQLYFDTEDESEKR
LLYCYNDPQAKIRDFWKTFYERGNPSMVNSPGTIEFRMEGFFEKMTPISIESKDFDFRV
WNKDLLIRRGLYEIKKRKNLNRKAREIKKAMGSVKRVLANMTYGKSPTDKKSIPVYRVE
REKPKKPRAVRKEENELADKLENYRREDFLIRNRRKREATEIAKIIDAAEPPIRHYHTN
HLRAVKRIDLSKPVARKNTSVFLKRIMQNGYRGNYCKKCIKGNIDPNKDECRLEDIKKC
ICCEGTQNIWAKKEKLYTGRINVLNKRIKQMKLECFNVAKAYENFYDNLAALKEGDLKV
LKLKVSIPALNPEASDPEEDM (SEQ ID NO:187)

>Cas14b.8|3300013125.a|Ga0172369_10010464|885..2489|revcom
NASINLGKRAINLSANYDSNLVIGCKNCKFLSFNGNFPRQTNVREGCHSCDKSTYAPEV
YIVKIGERKAKYDVLDSLKKFTFQSLKYQIKKSMRERSKKPKELLEFVIFANKDKAFNV
IQKSYEHLILNIKQEINRMNGKKRIKNHKKRLFKDREKQLNKLRLIGSSSLFFPRENKG
DKDLFTYVAIHSVGRDIGVAGSYESHIEPISDLTYQLFINNEKRLLYAYKPKQNKIIEL
KENLWNLKKEKKPLDLEFTKPLEKSITFSVKNDKLFKVSKDLMLRQAKFNIQGKEKLSK
EERQINRDFSKIKSNVISLSYGRFEELKKEKNIWSPHIYREVKQKEIKPCIVRKGDRIE
LFEQLKRKMDKLKKFRKERQKKISKDLNFAERIAYNFHTKSIKNTSNKINIDQEAKRGK
ASYMRKRIGNESFRKKYCEQCFSVGNVYHNVQNGCSCFDNPIELIKKGDEGLIPKGKED
RKYKGALRDDNLQMQIIRVAFNIAKGYEDFYNNLKEKTEKDLKLKFKIGTTISTQESNN
KEM (SEQ ID NO:188)

>Cas14b.9|3300013127.a|Ga0172365_10004421|633..2366|revcom
SNLIKLGKQAINFAANYDANLEVGCKNCKFLSSTNKYPRQTNVHLDNKMACRSCNQSTM
EPAIYIVRIGEKKAKYDIYNSLTKFNFQSLKYKAKRSQRFKPKQPKELQELSIAVRKEK
ALDIIQKSIDHLIQDIRPEIPRIKQQKRYKNHVGKLFYLQKRRKNKLNLIGKGSFFKVF
SPKEKKNELLVICALTNIGRDIGLIGNYNTIINPLFEVTYQLYYDYIPKKNNKNVQRRL
LYAYKSKNEKILKLKEAFFKRGHENAVNLGSFSYEKPLEKSLTLKIKNDKDDFQVSPSL
RIRTGRFFVPSKRNLSRQEREINRRLVKIKSKIKNMTYGKFETARDKQSVHIFRLERQK
EKLPLQFRKDEKEFMEEFQKLKRRTNSLKKLRKSRQKKLADLLQLSEKVVYNNHTGTLK
KTSNFLNFSSVKRGKTAYIKELLGQEGFETLYCSNCINKGQKTRYNIETKEKCFSCKD
VPFVWKKKSTDKDRKGAFLFPAKLKDVIKATFTVAKAYEDFYDNLKSIDEKKPYIKFKI
GLILAHVRHEHKARAKEEAGQKNIYNKPIKIDKNCKECFFFKEEAM (SEQ ID NO:189
)

FIG. 7F

>Cas14b.10|CG08_land_8_20_14_0.20_scaffold_1609_curated|6134..7975
NTTRKKFRKRTGFPQSDNIKLAYCSAIVRAANLDADIQKKHNQCNPNLCVGIKSNEQSR
KYEHSDRQALLCYACNQSTGAPKVDYIQIGEIGAKYKILQMVNAYDFLSLAYNLTKLRN
GKSRGHQRMSQLDEVVIVADYEKATEVIKRSINHLLDDIRGQLSKLKKRTQNEHITEHK
QSKIRRKLRKLSRLLKRRRWKWGTIPNPYLKNVVFTKKDPELVTVALLHKLGRDIGLVN
RSKRRSKQKLLPKVGFQLYYKWESPSLNNIKKSKAKKLPKRLLIPYKNVKLFDNKQKLE
NAIKSLLESYQKTIKVEFDQFFQNRTEEIIAEEQQTLERGLLKQLEKKKNEFASQKKAL
KEEKKKIKEPRKAKLLMEESRSLGFLMANVSYALFNTTIEDLYKKSNVVSGCIPQEPVV
VFPADIQNKGSLAKILFAPKDGFRIKFSGQHLTIRTAKFKIRGKEIKILTKTKREILKN
IEKLRRVWYREQHYKLKLFGKEVSAKPRFLDKRKTSIERRDPNKLADQTDDRQAELRNK
EYELRHKQHKMAERLDNIDTNAQNLQTLSFWVGEADKPPKLDEKDARGFGVRTCISAWK
WFMEDLLKKQEEDPLLKLKLSIM (SEQ ID NO:190)

>Cas14b.11|CG_4_10_14_0.8_um_filter_scaffold_20762_curated|1372..3219
PKKPKFQKRTGFPQPDNLRKEYCLAIVRAANLDADFEKKCTKCEGIKTNKKGNIVKGRT
YNSADKDNLLCYACNISTGAPAVDYVFVGALEAKYKILQMVKAYDFHSLAYNLAKLWKG
RGRGHQRMGGLNEVVIVSNNEKALDVIEKSLNHFHDEIRGELSRLKAKFQNEHLHVHKE
SKLRRKLRKISRLLKRRRWKWDVIPNSYLRNFTFTKTRPDFISVALLHRVGRDIGLVTK
TKIPKPTDLLPQFGFQIYYTWDEPKLNKLKKSRLRSEPKRLLVPYKKIELYKNKSVLEE
AIRHLAEVYTEDLTICFKDFFETQKRKFVSKEKESLKRELLKELTKLKKDFSERKTALK
RDRKEIKEPKKAKLLMEESRSLGFLAANTSYALFNLIAADLYTKSKKACSTKLPRQLST
ILPLEIKEHKSTTSLAIKPEEGFKIRFSNTHLSIRTPKFKMKGADIKALTKRKREILKN
ATKLEKSWYGLKHYKLKLYGKEVAAKPRFLDKRNPSIDRRDPKELMEQIENRRNEVKDL
EYEIRKGQHQMAKRLDNVDTNAQNLQTKSFWVGEADKPPELDSMEAKKLGLRTCISAWK
WFMKDLVLLQEKSPNLKLKLSLTEM (SEQ ID NO:191)

>Cas14b.12|CG22_combo_CG10-13_8_21_14_all_scaffold_2003_curated|553..2880|revcom
KFSKRQEGFLIPDNIDLYKCLAIVRSANLDADVQGHKSCYGVKKNGTYRVKQNGKKGVK
EKGRKYVFDLIAFKGNIEKIPHEAIEEKDQGRVIVLGKFNYKLILNIEKNHNDRASLEI
KNKIKKLVQISSLETGEFLSDLLSGKIGIDEVYGIIEPDVFSGKELVCKACQQSTYAPL
VEYMPVGELDAKYKILSAIKGYDFLSLAYNLSRNRANKKRGHQKLGGGELSEVVISANY
DKALNVIKRSINHYHVEIKPEISKLKKKMQNEPLKVMKQARIRRELHQLSRKVKRLKWK
WGMIPNPELQNIIFEKKEKDFVSYALLHTLGRDIGLFKDTSMLQVPNISDYGFQIYYSW
EDPKLNSIKKIKDLPKRLLIPYKRLDFYIDTILVAKVIKNLIELYRKSYVYETFGEEYG
YAKKAEDILFDWDSINLSEGIEQKIQKIKDEFSDLLYEARESKRQNFVESFENILGLYD
KNFASDRNSYQEKIQSMIIKKQQENIEQKLKREFKEVIERGFEGMDQNKKYYKVLSPNI
KGGLLYTDTNNLGFFRSHLAFMLLSKISDDLYRKNNLVSKGGNKGILDQTPETMLTLEF
GKSNLPNISIKRKFFNIKYNSSWIGIRKPKFSIKGAVIREITKKVRDEQRLIKSLEGVW
HKSTHFKRWGKPRFNLPRHPDREKNNDDNLMESITSRREQIQLLLREKQKQQEKMAGRL
DKIDKEIQNLQTANFQIKQIDKKPALTEKSEGKQSVRNALSAWKWFMEDLIKYQKRTPI
LQLKLAKM (SEQ ID NO: 192)

FIG. 7G

>Cas14b.13|rifcsphigho2_01_scaffold_82367_curated|1523..3856|revcom
KFSKRQEGFVIPENIGLYKCLAIVRSANLDADVQGHVSCYGVKKNGTYVLKQNGKKSIR
EKGRKYASDLVAFKGDIEKIPFEVIEEKKKEQSIVLGKFNYKLVLDVMKGEKDRASLTM
KNKSKKLVQVSSLGTDEFLLTLLNEKFGIEEIYGIIEPEVFSGKKLVCKACQQSTYAPL
VEYMPVGELDSKYKILSAIKGYDFLSLAYNLARHRSNKKRGHQKLGGGELSEVVISANN
AKALNVIKRSLNHYYSEIKPEISKLRKKMQNEPLKVGKQARMRRELHQLSRKVKRLKWK
WGKIPNLELQNITFKESDRDFISYALLHTLGRDIGMFNKTEIKMPSNILGYGFQIYYDW
EEPKLNTIKKSKNTPKRILIPYKKLDFYNDSILVARAIKELVGLFQESYEWEIFGNEYN
YAKEAEVELIKLDEESINGNVEKKLQRIKENFSNLLEKAREKKRQNFIESFESIARLYD
ESFTADRNEYQREIQSFIIEKQKQSIEKKLKNEFKKIVEKKFNEQEQGKKHYRVLNPTI
INEFLPKDKNNLGFLRSKIAFILLSKISDDLYKKSNAVSKGGEKGIIKQQPETILDLEF
SKSKLPSINIKKKLFNIKYTSSWLGIRKPKFNIKGAKIREITRRVRDVQRTLKSAESSW
YASTHFRRWGFPRFNQPRHPDKEKKSDDRLIESITLLREQIQILLREKQKGQKEMAGRL
DDVDKKIQNLQTANFQIKQTGDKPALTEKSAGKQSFRNALSAWKWFMENLLKYQNKTPD
LKLKIARTVM (SEQ ID NO: 193)

>Cas14b.14|gwcl_scaffold_8732_curated|2705..4537
KWIEPNNIDFNKCLAITRSANLDADVQGHKMCYGIKTNGTYKAIGKINKKHNTGIIEKR
RTYVYDLIVTKEKNEKIVKKTDFMAIDEEIEFDEKKEKLLKKYIKAEVLGTGELIRKDL
NDGEKFDDLCSIEEPQAFRRSELVCKACNQSTYASDIRYIPIGEIEAKYKILKAIKGYD
FLSLKYNLGRLRDSKKRGHQKMGQGELKEFVICANKEKALDVIKRSLNHYLNEVKDEIS
RLNKKMQNEPLKVNDQARWRRELNQISRRLKRLKWKWGEIPNPELKNLIFKSSRPEFVS
YALIHTLGRDIGLINETELKPNNIQEYGFQIYYKWEDPELNHIKKVKNIPKRFIIPYKN
LDLFGKYTILSRAIEGILKLYSSSFQYKSFKDPNLFAKEGEKKITNEDFELGYDEKIKK
IKDDFKSYKKALLEKKKNTLEDSLNSILSVYEQSLLTEQINNVKKWKEGLLKSKESIHK
QKKIENIEDIISRIEELKNVEGWIRTKERDIVNKEETNLKREIKKELKDSYYEEVRKDF
SDLKKGEESEKKPFREEPKPIVIKDYIKFDVLPGENSALGFFLSHLSFNLFDSIQYELF
EKSRLSSSKHPQIPETILDL (SEQ ID NO: 194)

>Cas14b.15|3300010293.a|Ga0116204_1008574|2134..4032
FRKFVKRSGAPQPDNLNKYKCIAIVRAANLDADIMSNESSNCVMCKGIKMNKRKTAKGA
AKTTELGRVYAGQSGNLLCTACTKSTMGPLVDYVPIGRIRAKYTILRAVKEYDFLSLAY
NLARTRVSKKGGRQKMHSLSELVIAAEYEIAWNIIKSSVIHYHQETKEEISGLRKKLQA
EHIHKNKEARIRREMHQISRRIKRLKWKWHMIPNSELHNFLFKQQDPSFVAVALLHTLG
RDIGMINKPKGSAKREFIPEYGFQIYYKWMNPKLNDINKQKYRKMPKRSLIPYKNLNVF
GDRELIENAMHKLLKLYDENLEVKGSKFFKTRVVAISSKESEKLKRDLLWKGELAKIKK
DFNADKNKMQELFKEVKEPKKANALMKQSRNMGFLLQNISYGALGLLANRMYEASAKQS
KGDATKQPSIVIPLEMEFGNAFPKLLLRSGKFAMNVSSPWLTIRKPKFVIKGNKIKNIT
KLMKDEKAKLKRLETSYHRATHFRPTLRGSIDWDSPYFSSPKQPNTHRRSPDRLSADIT
EYRGRLKSVEAELREGQRAMAKKLDSVDMTASNLQTSNFQLEKGEDPRLTEIDEKGRSI
RNCISSWKKFMEDLMKAQEANPVIKIKIALKDESSVLSEDSM (SEQ ID NO: 195)

FIG. 7H

>Cas14b.16|3300005573.a|Ga0078972_1001015a|33750..35627
KFHPENLNKSYCLAIVRAANLDADIQGHINCIGIKSNKSDRNYENKLESLQNVELLCKA
CTKSTYKPNINSVPVGEKKAKYSILSEIKKYDFNSLVYNLKKYRKGKSRGHQKLNELRE
LVITSEYKKALDVINKSVNHYLVNIKNKMSKLKKILQNEHIHVGTLARIRRERNRISRK
LDHYRKKWKFVPNKILKNYVFKNQSPDFVSVALLHKLGRDIGLITKTAILQKSFPEYSL
QLYYKYDTPKLNYLKKSKFKSLPKRILISYKYPKFDINSNYIEESIDKLLKLYEESPIY
KNNSKIIEFFKKSEDNLIKSENDSLRGIMKEFEKVTKNFSSKKKKLKEELKLKNEDKN
SKMLAKVSRPIGFLKAYLSYMLFNIISNRIFEFSRKSSGRIPQLPSCIINLGNQFENFK
NELQDSNIGSKKNYKYFCNLLLKSSGFNISYEEEHLSIKTPNFFINGRKLKEITSEKKK
IRKENEQLIKQWKKLTFFKPSNLNGKKTSDKIRFKSPNNPDIERKSEDNIVENIAKVKY
KLEDLLSEQRKEFNKLAKKHDGVDVEAQCLQTKSFWIDSNSPIKKSLEKKNEKVSVKKK
MKAIRSCISAWKWFMADLIEAQKETPMIKLKLALM (SEQ ID NO: 196)

>Cas14c.1|CG10_big_fil_rev_8_21_14_0.10_scaffold_4477_curat
ed|19327..20880|revcom
TTLVPSHLAGIEVMDETTSRNEDMIQKETSRSNEDENYLGVKNKCGINVHKSGRGSSKH
EPNMPPEKSGEGQMPKQDSTEMQQRFDESVTGETQVSAGATASIKTDARANSGPRVGTA
RALIVKASNLDRDIKLGCKPCEYIRSELPMGKKNGCNHCEKSSDIASVPKVESGFRKAK
YELVRRFESFAADSISRHLGKEQARTRGKRGKKDKKEQMGKVNLDEIAILKNESLIEYT
ENQILDARSNRIKEWLRSLRLRLRTRNKGLKKSKSIRRQLITLRRDYRKWIKPNPYRPD
EDPNENSLRLHTKLGVDIGVQGGDNKRMNSDDYETSFSITWRDTATRKICFTKPKGLLP
RHMKFKLRGYPELILYNEELRIQDSQKFPLVDWERIPIFKLRGVSLGKKKVKALNRITE
APRLVVAKRIQVNIESKKKKVLTRYVYNDKSINGRLVKAEDSNKDPLLEFKKQAEEINS
DAKYYENQEIAKNYLWGCEGLHKNLLEEQTKNPYLAFKYGFLNIV (SEQ ID
NO:197)

>Cas14c.2|3300001245.a|JGI12048J13642_1020128|4257..5489|r
evcom
LDFKRTCSQELVLLPEIEGLKLSGTQGVTSLAKKLINKAANVDRDESYGCHHCIHTRTS
LSKPVKKDCNSCNQSTNHPAVPITLKGYKIAFYELWHRFTSWAVDSISKALHRNKVMGK
VNLDEYAVVDNSHIVCYAVRKCYEKRQRSVRLHKRAYRCRAKHYNKSQPKVGRIYKKSK
RRNARNLKKEAKRYFQPNEITNGSSDALFYKIGVDLGIAKGTPETEVKVDVSICFQVYY
GDARRVLRVRKMDELQSFHLDYTGKLKLKGIGNKDTFTIAKRNESLKWGSTKYEVSRAH
KKFKPFGKKGSVKRKCNDYFRSIASWSCEAASQRAQSNLKNAFPYQKALVKCYKNLDYK
GVKKNDMWYRLCSNRIFRYSRIAEDIAQYQSDKGKAKFEFVILAQSVAEYDISAIM
 (SEQ ID NO: 198)

FIG. 71

>Cas14d.1|RIFCSPHIGHO2_01_FULL_CPR_46_36_rifcsphigho2_01_sc
affold_646_curated|49808..51616|revcom
VFLTDDKRKTALRKIRSAFRKTAEIALVRAQEADSLDRQAKKLTIETVSFGAPGAKNAF
IGSLQGYNWNSHRANVPSSGSAKDVFRITELGLGIPQSAHEASIGKSFELVGNVVRYTA
NLLSKGYKKGAVNKGAKQQREIKGKEQLSFDLISNGPISGDKLINGQKDALAWWLIDKM
GFHIGLAMEPLSSPNTYGITLQAFWKRHTAPRRYSRGVIRQWQLPFGRQLAPLIHNFFR
KKGASIPIVLTNASKKLAGKGVLLEQTALVDPKKWWQVKEQVTGPLSNIWERSVPLVLY
TATFTHKHGAAHKRPLTLKVIRISSGSVFLLPLSKVTPGKLVRAWMPDINILRDGRPDE
AAYKGPDLIRARERSFPLAYTCVTQIADEWQKRALESNRDSITPLEAKLVTGSDLLQIH
STVQQAVEQGIGGRISSPIQELLAKDALQLVLQQLFMTVDLLRIQWQLKQEVADGNTSE
KAVGWAIRISNIHKDAYKTAIEPCTSALKQAWNPLSGFEERTFQLDASIVRKRSTAKTP
DDELVIVLRQQAAEMTVAVTQSVSKELMELAVRHSATLHLLVGEVASKQLSRSADKDRG
AMDHWKLLSQSM (SEQ ID NO: 199)

>Cas14d.2|rifcsphigho2_01_scaffold_10981_curated|5762..7246
|revcom
EDLLQKALNTATNVAAIERHSCISCLFTESEIDVKYKTPDKIGQNTAGCQSCTFRVGYS
GNSHTLPMGNRIALDKLRETIQRYAWHSLLFNVPPAPTSKRVRAISELRVAAGRERLFT
VITFVQTNILSKLQKRYAANWTPKSQERLSRLREEGQHILSLLESGSWQQKEVVREDQD
LIVCSALTKPGLSIGAFCRPKYLKPAKHALVLRLIFVEQWPGQIWGQSKRTRRMRRRKD
VERVYDISVQAWALKGKETRISECIDTMRRHQQAYIGVLPFLILSGSTVRGKGDCPILK
EITRMRYCPNNEGLIPLGIFYRGSANKLLRVVKGSSFTLPMWQNIETLPHPEPFSPEGW
TATGALYEKNLAYWSALNEAVDWYTGQILSSGLQYPNQNEFLARLQNVIDSIPRKWFRP
QGLKNLKPNGQEDIVPNEFVIPQNAIRAHHVIEWYHKTNDLVAKTLLGWGSQTTLNQTR
PQGDLRFTYTRYYFREKEVPEV (SEQ ID NO: 200)

>Cas14d.3|RIFCSPLOWO2_01_FULL_OD1_45_34b_rifcsplowo2_01_sca
ffold_3495_curated|25656..27605|revcom
VPKKKLMRELAKKAVFEAIFNDPIPGSFGCKRCTLIDGARVTDAIEKKQGAKRCAGCEP
CTFHTLYDSVKHALPAATGCDRTAIDTGLWEILTALRSYNWMSFRRNAVSDASQKQVWS
IEELAIWADKERALRVILSALTHTIGKLKNGFSRDGVWKGGKQLYENLAQKDLAKGLFA
NGEIFGKELVEADHDMLAWTIVPNHQFHIGLIRGNWKPAAVEASTAFDARWLTNGAPLR
DTRTHGHRGRRFNRTEKLTVLCIKRDGGVSEEFRQERDYELSVMLLQPKNKLKPEPKGE
LNSFEDLHDHWWFLKGDEATALVGLTSDPTVGDFIQLGLYIRNPIKAHGETKRRLLICF
EPPIKLPLRRAFPSEAFKTWEPTINVFRNGRRDTEAYYDIDRARVFEFPETRVSLEHLS
KQWEVLRLEPDRENTDPYEAQQNEGAELQVYSLLQEAAQKMAPKVVIDPFGQFPLELFS
TFVAQLFNAPLSDTKAKIGKPLDSGFVVESHLHLLEEDFAYRDFVRVTFMGTEPTFRVI
HYSNGEGYWKKTVLKGKNNIRTALIPEGAKAAVDAYKNKRCPLTLEAAILNEEKDRRLV
LGNKALSLLAQTARGNLTILEALAAEVLRPLSGTEGVVHLHACVTRHSTLTESTETDNM
(SEQ ID NO: 201)

FIG. 7J

>Cas14e.1|rifcsphigho2_01_scaffold_566_curated|113069..1143
13
VEKLFSERLKRAMWLKNEAGRAPPAETLTLKHKRVSGGHEKVKEELQRVLRSLSGTNQA
AWNLGLSGGREPKSSDALKGEKSRVVLETVVFHSGHNRVLYDVIEREDQVHQRSSIMHM
RRKGSNLLRLWGRSGKVRRKMREEVAEIKPVWHKDSRWLAIVEEGRQSVVGISSAGLAV
FAVQESQCTTAEPKPLEYVVSIWFRGSKALNPQDRYLEFKKLKTTEALRGQQYDPIPFS
LKRGAGCSLAIRGEGIKFGSRGPIKQFFGSDRSRPSHADYDGKRRLSLFSKYAGDLADL
TEEQWNRTVSAFAEDEVRRATLANIQDFLSISHEKYAERLKKRIESIEEPVSASKLEAY
LSAIFETFVQQREALASNFLMRLVESVALLISLEEKSPRVEFRVARYLAESKEGFNRKA
M (SEQ ID NO: 202)

>Cas14e.2|rifcsplowo2_01_scaffold_81231_curated|976..2217
VVITQSELYKERLLRVMEIKNDRGRKEPRESQGLVLRFTQVTGGQEKVQKLWLIFEGF
SGTNQASWNFGQPAGGRKPNSGDALKGPKSRVTYETVVFHFGLRLLSAVIERHNLKQQR
QTMAYMKRRAAARKKWARSGKKCSRMRNEVEKIKPKWHKDPRWFDIVKEGEPSIVGISS
AGFAIYIVEEPNFPRQDPLEIEYAISIWFRRDRSQYLTFKKIQKAEKLKELQYNPIPFR
LKQEKTSLVFESGDIKFGSRGSIEHFRDEARGKPPKADMDNNRRLTMFSVFSGNLTNLT
EEQYARPVSGLLAPDEKRMPTLLKKLQDFFTPIHEKYGERIKQRLANSEASKRPFKKLE
EYLPAIYLEFRARREGLASNWLVLINSVRTLVRIKSEDPYIEFKVSQYLLEKEDNKAL
(SEQ ID NO: 203)

>Cas14e.3|rifcsphigho2_01_scaffold_4702_curated|82881..8423
0|revcom
KQDALFEERLKKAIFIKRQADPLQREELSLLPPNRKIVTGGHESAKDTLKQILRAINGT
NQASWNPGTPSGKRDSKSADALAGPKSRVKLETVVFHVGHRLLKKVVEYQGHQKQQHGL
KAFMRTCAAMRKKWKRSGKVVGELREQLANIQPKWHYDSRPLNLCFEGKPSVVGLRSAG
IALYTIQKSVVPVKEPKPIEYAVSIWFRGPKAMDREDRCLEFKKLKIATELRKLQFEPI
VSTLTQGIKGFSLYIQGNSVKFGSRGPIKYFSNESVRQRPPKADPDGNKRLALFSKFSG
DLSDLTEEQWNRPILAFEGIIRRATLGNIQDYLTVGHEQFAISLEQLLSEKESVLQMSI
EQQRLKKNLGKKAENEWVESFGAEQARKKAQGIREYISGFFQEYCSQREQWAENWVQQL
NKSVRLFLTIQDSTPFIEFRVARYLPKGEKKKGKAM (SEQ ID NO: 204)

>Cas14f.1|rifcsp13_1_sub10_scaffold_3_curated|38906..41041
ANHAERHKRLRKEANRAANRNRPLVADCDTGDPLVGICRLLRRGDKMQPNKTGCRSCEQ
VEPELRDAILVSGPGRLDNYKYELFQRGRAMAVHRLLKRVPKLNRPKKAAGNDEKKAEN
KKSEIQKEKQQRRMMPAVSMKQVSVADFKHVIENTVRHLFGDRRDREIAECAALRAAS
KYFLKSRRVRPRKLPKLANPDHGKELKGLRLREKRAKLKKEKEKQAELARSNQKGAVLH
VATLKKDAPPMPYEKTQGRNDYTTFVISAAIKVGATRGTKPLLTPQPREWQCSLYWRDG
QRWIRGGLLGLQAGIVLGPKLNRELLEAVLQRPIECRMSGCGNPLQVRGAAVDFFMTTN
PFYVSGAAYAQKKFKPFGTKRASEDGAAAKAREKLMTQLAKVLDKVVTQAAHSPLDGIW
ETRPEAKLRAMIMALEHEWIFLRPGPCHNAAEEVIKCDCTGGHAILWALIDEARGALEH
KEFYAVTRAHTHDCEKQKLGGRLAGFLDLLIAQDVPLDDAPAARKIKTLLEATPPAPCY
KAATSIATCDCEGKFDKLWAIIDATRAGHGTEDLWARTLAYPQNVNCKCKAGKDLTHRL
ADFLGLLIKRDGPFRERPPHKVTGDRKLVFSGDKKCKGHQYVILAKAHNEEVVRAWISR
WGLKSRTNKAGYAATELNLLLNWLSICRRRWMDMLTVQRDTPYIRMKTGRLVVDDKKER
KAM (SEQ ID NO: 205)

FIG. 7K

>Cas14f.2|3300009991.a|Ga0105042_100140|1624..3348
AKQREALRVALERGIVRASNRTYTLVTNCTKGGPLPEQCRMIERGKARAMKWEPKLVGC
GSCAAATVDLPAIEEYAQPGRLDVAKYKLTTQILAMATRRMMVRAAKLSRRKGQWPAKV
QEEKEEPPEPKKMLKAVEMRPVAIVDFNRVIQTTIEHLWAERANADEAELKALKAAAAY
FGPSLKIRARGPPKAAIGRELKKAHRKKAYAERKKARRKRAELARSQARGAAAHAAIRE
RDIPPMAYERTQGRNDVTTIPIAAAIKIAATRGARPLPAPKPMKWQCSLYWNEGQRWIR
GGMLTAQAYAHAANIHRPMRCEMWGVGNPLKVRAFEGRVADPDGAKGRKAEFRLQTNAF
YVSGAAYRNKKFKPFGTDRGGIGSARKKRERLMAQLAKILDKVVSQAAHSPLDDIWHTR
PAQKLRAMIKQLEHEWMFLRPQAPTVEGTKPDVDVAGNMQRQIKALMAPDLPPIEKGSP
AKRFTGDKRKKGERAVRVAEAHSDEVVTAWISRWGIQTRRNEGSYAAQELELLLNWLQI
CRRRWLDMTAAQRVSPYIRMKSGRMITDAADEGVAPIPLVENM (SEQ ID NO: 206
)

>Cas14g.1|RBG_13_scaffold_1401_curated|15949..18180
KSISGRSIKHMACLKDMLKSEITEIEEKQKKESLRKWDYYSKFSDEILFRRNLNVSANH
DANACYGCNPCAFLKEVYGFRIERRNNERIISYRRGLAGCKSCVQSTGYPPIEFVRRKF
GADKAMEIVREVLHRRNWGALARNIGREKEADPILGELNELLLVDARPYFGNKSAANET
NLAFNVITRAAKKFRDEGMYDIHKQLDIHSEEGKVPKGRKSRLIRIERKHKAIHGLDPG
ETWRYPHCGKGEKYGVWLNRSRLIHIKGNEYRCLTAFGTTGRRMSLDVACSVLGHPLVK
KKRKKGKKTVDGTELWQIKKATETLPEDPIDCTFYLYAAKPTKDPFILKVGSLKAPRWK
KLHKDFFEYSDTEKTQGQEKGKRVVRRGKVPRILSLRPDAKFKVSIWDDPYNGKNKEGT
LLRMELSGLDGAKKPLILKRYGEPNTKPKNFVFWRPHITPHPLTFTPKHDFGDPNKKTK
RRRVFNREYYGHLNDLAKMEPNAKFFEDREVSNKKNPKAKNIRIQAKESLPNIVAKNGR
WAAFDPNDSLWKLYLHWRGRRKTIKGGISQEFQEFKERLDLYKKHEDESEWKEKEKLWE
NHEKEWKKTLEIHGSIAEVSQRCVMQSMMGPLDGLVQKKDYVHIGQSSLKAADDAWTFS
ANRYKKATGPKWGKISVSNLLYDANQANAELISQSISKYLSKQKDNQGCEGRKMKFLIK
IIEPLRENFVKHTRWLHEMTQKDCEVRAQFSRVSM (SEQ ID NO:207)

>Cas14g.2|3300009652.a|Ga0123330_1010394|2814..5123
FPSDVGADALKHVRMLQPRLTDEVRKVALTRAPSDRPALARFAAVAQDGLAFVRHLNVS
ANHDSNCTFPRDPRDPRRGPCEPNPCAFLREVWGFRIVARGNERALSYRRGLAGCKSCV
QSTGFPSVPFHRIGADDCMRKLHEILKARNWRLLARNIGREREADPLLTELSEYLLVDA
RTYPDGAAPNSGRLAENVIKRAAKKFRDEGMRDIHAQLRVHSREGKVPKGRLQRLRRIE
RKHRAIHALDPGPSWEAEGSARAEVQGVAVYRSQLLRVGHHTQQIEPVGIVARTLFGVG
RTDLDVAVSVLGAPLTKRKKGSKTLESTEDFRIAKARETRAEDKIEVAFVLYPTASLLR
DEIPKDAFPAMRIDRFLLKVSVQADREILLQDDYYRFGDAEVKAGKNKGRTVTRPVKV
PRLQALRPDAKFRVNVWADPFGAGDSPGTLLRLEVSGVTRRSQPLRLLRYGQPSTQPAN
FLCWRPHRVPDPMTFTPRQKFGERRKNRRTRRPVFERLYQVHIKHLAHLEPNRKWFEE
ARVSAQKWAKARAIRRKGAEDIPVVAPPAKRRWAALQPNAELWDLYAHDREARKRFGG
RAAEGEEFKPRLNLYLAHEPEAEWESKRDRWERYEKKWTAVLEEHSRMCAVADRTLPQF
LSDPLGARMDDKDYAFVGKSALAVAEAFVEEGTVERAQGNCSITAKKKFASNASRKRLS
VANLLDVSDKADRALVFQAVRQYVQRQAENGGVEGRRMAFLRKLLAPLRQNFVCHTRWL
HM (SEQ ID NO: 208)

FIG. 7L

>Cas14h.1|3300005602.a|Ga0070762_10001740|7377..9071|revcom
AARKKKRGKIGITVKAKEKSPPAAGPFMARKLVNVAANVDGVEVHLCVECEADAHGSAS
ARLLGGCRSCTGSIGAEGRLMGSVDVDRERVIAEPVHTETERLGPDVKAFEAGTAESKY
AIQRGLEYWGVDLISRNRARTVRKMEEADRPESSTMEKTSWDEIAIKTYSQAYHASENH
LFWERQRRVRQHALALFRRARERNRGESPLQSTQRPAPLVLAALHAEAAAISGRARAEY
VLRGPSANVRAAAADIDAKPLGHYKTPSPKVARGFPVKRDLLRARHRIVGLSRAYFKPS
DVVRGTSDAIAHVAGRNIGVAGGKPKEIEKTFTLPFVAYWEDVDRVVHCSSFKADGPWV
RDQRIKIRGVSSAVGTFSLYGLDVAWSKPTSFYIRCSDIRKKFHPKGFGPMKHWRQWAK
ELDRLTEQRASCVVRALQDDEELLQTMERGQRYYDVFSCAATHATRGEADPSGGCSRCE
LVSCGVAHKVTKKAKGDTGIEAVAVAGCSLCESKLVGPSKPRVHRQMAALRQSHALNYL
RRLQREWEALEAVQAPTPYLRFKYARHLEVRSM (SEQ ID NO: 209)

>Cas14h.2|3300005921.a|Ga0070766_10011912|384..2081
AAKKKQRGKIGISVKPKEGSAPPADGPFMARKLVNVAANVDGVEVNLCIECEADAHGS
APARLLGGCKSCTGSIGAEGRLMGSVDVDRADAIAKPVNTETEKLGPDVQAFEAGTAET
KYALQRGLEYWGVDLISRNRSRTVRRTEEGQPESATMEKTSWDEIAIKSYTRAYHASEN
HLFWERQRRVRQHALALFKRAKERNRGDSTLPREPGHGLVAIAALCEAYAVGGRNLAE
TVVRGPTFGTARAVRDVEIASLGRYKTPSPKVAHGSPVKRDFLRARHRIVGLARAYYRP
SDVVRGTSDAIAHVAGRNIGVAGGKPRAVEAVFTLPFVAYWEDVDRVVHCSSFQVSAPW
NRDQRMKIAGVTTAAGTFSLHGGELKWAKPTSFYIRCSDTRRKFRPKGFGPMKRWRQWA
KDLDRLVEQRASCVVRALQDDAALLETMERGQRYYDVFACAVTHATRGEADRLAGCSRC
ALTPCQEAHRVTTKPRGDAGVEQVQTSDCSLCEGKLVGPSKPRLHRTLTLLRQEHGLNY
LRRLQREWESLEAVQVPTPYLRFKYARHLEVRSM (SEQ ID NO: 210)

>Cas14h.3|3300009698.a|Ga0116216_10000905|8005..9504
TDSQSESVPEVVYALTGGEVPGRVPPDGGSAEGARNAPTGLRKQRGKIKISAKPSKPGS
PASSLARTLVNEAANVDGVQSSGCATCRMRANGSAPRALPIGCVACASSIGRAPQEETV
CALPTTQGPDVRLLEGGHALRKYDIQRALEYWGVDLIGRNLDRQAGRGMEPAEGATATM
KRVSMDELAVLDFGKSYYASEQHLFAARQRRVRQHAKALKIRAKHANRSGSVKRALDRS
RKQVTALAREFFKPSDVVRGDSDALAHVVGRNLGVSRHPAREIPQTFTLPLCAYWEDVD
RVISCSSLLAGEPFARDQEIRIEGVSSALGSLRLYRGAIEWHKPTSLYIRCSDTRRKFR
PRGGLKKRWRQWAKDLDRLVEQRACCIVRSLQADVELLQTMERAQRFYDVHDCAATHVG
PVAVRCSPCAGKQFDWDRYRLLAALRQEHALNYLRRLQREWESLEAQQVKMPYLRFKYA
RKLEVSGPLIGLEVRREPSMGTAIAEM (SEQ ID NO: 211)

>Cas14u.1|3300009029.a|Ga0066793_10010091|37..1113|revcom
AGTAGRRHGSLGARRSINIAGVTDRHGRWGCESCVYTRDQAGNRARCAPCDQSTYAPDV
QEVTIGQRQAKYTIFLTQSFSWTNTMRNNKRAAAGRSKRTTGKRIGQLAEIKITGVGL
AHAHNVIQRSLQHNITKMWRAEKGKSKRVARLKKAKQLTKRRAYFRRRMSRQSRGNGFF
RTGKGGIHAVAPVKIGLDVGMIASGSSEPADEQTVTLDAIWKGRKKKIRLIGAKGELAV
AACRFREQQTKGDKCIPLILQDGEVRWQNNWQCHPKKLVPLCGLEVSRKFVSQADRLA
QNKVASPLAARFDKTSVKGTLVESDFAAVLVNVTSIYQQCHAMLLRSQEPTPSLRVQRT
ITSM (SEQ ID NO: 212)

FIG. 7M

>Cas14u.2|3300002172.a|JGI24730J26740_1002785|496..1605|rev
com
GVRFSPAQSQVFFRTVIPQSVEARFAINMAAIHDAAGAFGCSVCRFEDRTPRNAKAVHG
CSPCTRSTNRPDVFVLPVGAIKAKYDVFMRLLGFNWTHLNRRQAKRVTVRDRIGQLDEL
AISMLTGKAKAVLKKSICHNVDKSFKAMRGSLKKLHRKASKTGKSQLRAKLSDLRERTN
TTQEGSHVEGDSDVALNKIGLDVGLVGKPDYPSEESVEVVVCLYFVGKVLILDAQGRIR
DMRAKQYDGFKIPIIQRGQLTVLSVKDLGKWSLVRQDYVLAGDLRFEPKISKDRKYAEC
VKRIALITLQASLGFKERIPYYVTKQVEIKNASHIAFVTEAIQNCAENFREMTEYLMKY
QEKSPDLKVLLTQLM (SEQ ID NO: 213)

>Cas14u.3|19ft_2_nophage_noknown_scaffold_0_curated|508188.
.509648
RAVVGKVFLEQARRALNLATNFGTNHRTGCNGCYVTPGKLSIPQDGEKNAAGCTSCLMK
ATASYVSYPKPLGEKVAKYSTLDALKGFPWYSLRLNLRPNYRGKPINGVQEVAPVSKFR
LAEEVIQAVQRYHFTELEQSFPGGRRRLRELRAFYTKEYRRAPEQRQHVVNGDRNIVVV
TVLHELGFSVGMFNEVELLPKTPIECAVNVFIRGNRVLLEVRKPQFDKERLLVESLWKK
DSRRHTAKWTPPNNEGRIFTAEGWKDFQLPLLLGSTSRSLRAIEKEGFVQLAPGRDPDY
NNTIDEQHSGRPFLPLYLYLQGTISQEYCVFAGTWVIPFQDGISPYSTKDFQPDLKRK
AYSLLLDAVKHRLGNKVASGLQYGRFPAIEELKRLVRMHGATRKIPRGEKDLLKKGDPD
TPEWWLLEQYPEFWRLCDAAAKRVSQNVGLLLSLKKQPLWQRRWLESRTRNEPLDNLPL
SMALTLHLTNEEAL (SEQ ID NO: 214)

>Cas14u.4|rifcsp2_19_4_full_scaffold_168_curated|84455..856
57
AAVYSKFYIENHFKMGIPETLSRIRGPSIIQGFSVNENYINIAGVGDRDFIFGCKKCKY
TRGKPSSKKINKCHPCKRSTYPEPVIDVRGSISEFKYKIYNKLKQEPNQSIKQNTKGRM
NPSDHTSSNDGIIINGIDNRIAYNVIFSSYKHLMEKQINLLRDTTKRKARQIKKYNNSG
KKKHSLRSQTKGNLKNRYHMLGMFKKGSLTITNEGDFITAVRKVGLDISLYKNESLNKQ
EVETELCLNIKWGRTKSYTVSGYIPLPINIDWKLYLFEKETGLTRLFGNYKIQSKKF
LIAQLFKPKRPPCADPVVKKAQKWSALNAHVQQMAGLFSDSHLLKRELKNRMHKQLDFK
SLWVGTEDYIKWFEELSRSYVEGAEKSLEFFRQDYFCFNYTKQTTM (SEQ ID NO: 215
)

>Cas14u.5|3300012532.a|Ga0137373_10000316|3286..5286
PQQQRDLMLMAANYDQDYGNGCGPCTVVASAAYRPDPQAQHGCKRHLRTLGASAVTHVG
LGDRTATITALHRLRGPAALAARARAAQAASAPMTPDTDAPDDRRRLEAIDADDVVLVG
AHRALWSAVRRWADDRRAALRRRLHSEREWLLKDQIRWAELYTLIEASGTPPQGRWRNT
LGALRGQSRWRRVLAPTMRATCAETHAELWDALAELVPEMAKDRRGLLRPPVEADALWR
APMIVEGWRGGHSVVVDAVAPPLDLPQPCAWTAVRLSGDPRQRWGLHLAVPPLGQVQPP
DPLKATLAVSMRHGGVRVRTLQAMAVDADAPMQRHLQVPLTLQRGGGLQWGIHSRGVR
RREARSMASWEGPPIWTGLQLVNRWKGQGSALLAPDRPPDTPPYAPDAAVAPAQPDTKR
ARRTLKEACTVCRCAPGHMRQLQVTLTGDGTWRRFRLRAPQGAKRKAEVLKVATQHDER
IANYTAWYLKRPEHAAGCDTCDGDSRLDGACRGCRPLLVGDQCFRRYLDKIEADRDDGL
AQIKPKAQEAVAAMAAKRDARAQKVAARAAKLSEATGQRTAATRDASHEARAQKELEAV
ATEGTTVRHDAAAVSAFGSWVARKGDEYRHQVGVLANRLEHGLRLQELMAPDSVVADQQ
RASGHARVGYRYVLTAM (SEQ ID NO:216)

FIG. 7N

>Cas14u.6|3300006028.a|Ga0070717_10000077|54519..56201|revcom
AVAHPVGRGNAGSPGARGPEELPRQLVNRASNVTRPATYGCAPCRHVRLSIPKPVLTGC
RACEQTTHPAPKRAVRGGADAAKYDLAAFFAGWAADLEGRNRRRQVHAPLDPQPDPNHE
PAVTLQKIDLAEVSIEEFQRVLARSVKHRHDGRASREREKARAYAQVAKKRRNSHAHGA
RTRRAVRRQTRAVRRAHRMGANSGEILVASGAEDPVPEAIDHAAQLRRRIRACARDLEG
LRHLSRRYLKTLEKPCRRPRAPDLGRARCHALVESLQAAERELEELRRCDSPDTAMRRL
DAVLAAAASTDATFATGWTVVGMDLGVAPRGSAAPEVSPMEMAISVFWRKGSRRVIVSK
PIAGMPIRRHELIRLEGLGTLRLDGNHYTGAGVTKGRGLSEGTEPDFREKSPSTLGFTL
SDYRHESRWRPYGAKQGKTARQFFAAMSRELRALVEHQVLAPMGPPLLEAHERRFETLL
KGQDNKSIHAGGGGRYVWRGPPDSKKRPAADGDWFRFGRGHADHRGWANKRHELAANYL
QSAFRLWSTLAEAQEPTPYARYKYTRVTM (SEQ ID NO:217)

>Cas14u.7|3300001256.a|JGI12210J13797_10004690|5792..7006
WDFLTLQVYERHTSPEVCVAGNSTKCASGTRKSDHTHGVGVKLGAQEINVSANDDRDHE
VGCNICVISRVSLDIKGWRYGCESCVQSTPEWRSIVRFDRNHKEAKGECLSRFEYWGAQ
SIARSLKRNKLMGGVNLDELAIVQNENVVKTSLKHLFDKRKDRIQANLKAVKVRMRERR
KSGRQRKALRRQCRKLKRYLRSYDPSDIKEGNSCSAFTKLGLDIGISPNKPPKIEPKVE
VVFSLFYQGACDKIVTVSSPESPLPRSWKIKIDGIRALYVKSTKVKFGGRTFRAGQRNN
RRKVRPPNVKKGKRKGSRSQFFNKFAVGLDAVSQQLPIASVQGLWGRAETKKAQTICLK
QLESNKPLKESQRCLFLADNWVVRVCGFLRALSQRQGPTPYIRYRYRCNM (SEQ ID
NO:218)

>Cas14u.8|3300005660.a|Ga0073904_10021651|765..1943
ARNVGQRNASRQSKRESAKARSRRVTGGHASVTQGVALINAAANADRDHTTGCEPCTWE
RVNLPLQEVIHGCDSCTKSSPFWRDIKVVNKGYREAKEEIMRIASGISADHLSRALSHN
KVMGRLNLDEVCILDFRTVLDTSLKHLTDSRSNGIKEHIRAVHRKIRMRRKSGKTARAL
RKQYFALRRQWKAGHKPNSIREGNSLTALRAVGFDVGSEGTEPMPAPQTEVVLSVFYK
GSATRILRISSPHPIAKRSWKVKIAGIKALKLIRREHDFSFGRETYNASQRAEKRKFSP
HAARKDFFNSFAVQLDRLAQQLCVSSVENLWVTEPQQKLLTLAKDTAPYGIREGARFAD
TRARLAWNWVFRVCGFTRALHQEQEPTPYCRFTWRSKM (SEQ ID NO:219)

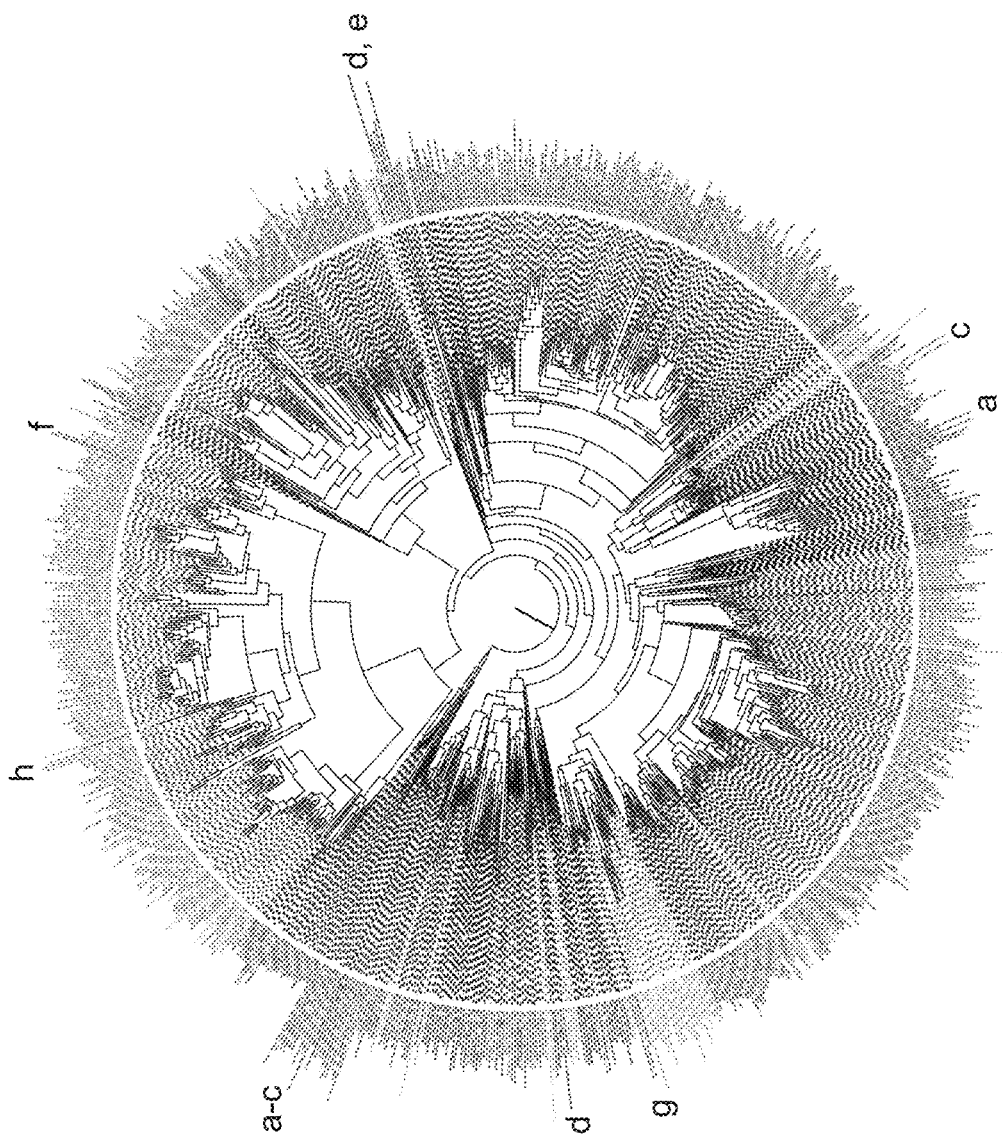
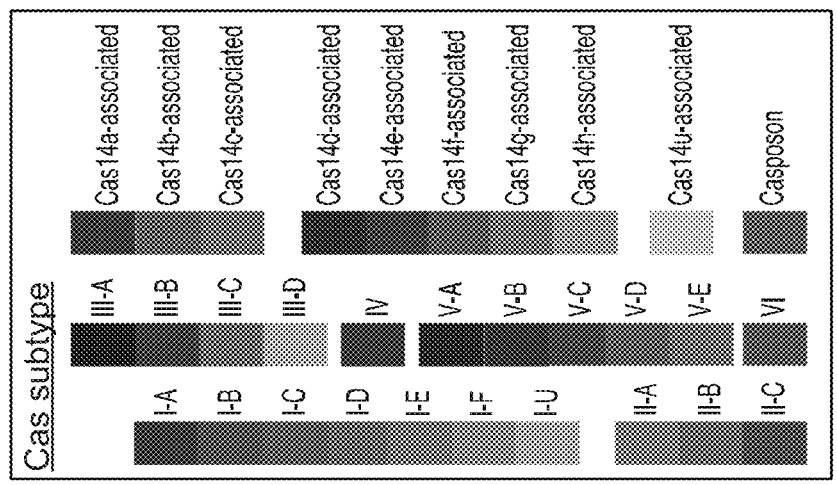
FIG. 10

FIG. 14A

| | Bin | | | | | | | |
|---|---|---|---|---|---|---|---|---|
| | Cas14c1 | Cas14b15 | Cas14b13 | Cas14b11 | Cas14b6 | Cas14b4 | Cas14a1 | Cas14a2 |
| RNase-I | | | | | | | | |
| RNase-II | ● | | | | | | | |
| RNase-III | | | | | | | | |
| RNase-III family | | | | | | | | |
| RNase-D | | | | | | | | |
| RNase-E | | | | | | | | |
| RNase-G | | | | | | | | |
| RNase-H | | | | | | | | |
| RNase-H2 subunit A | ● | ● | ● | ● | ● | ● | | |
| RNase-H2 subunit B | | | | | | | | |
| RNase-HI | | | | | ● | | | |
| RNase-HII | | | | | | | ○ | ○ |
| RNase-HIII | | | | | | | | |
| RNase-J | ○ | ● | ● | ● | ● | ○ | ● | ● |
| RNase-L | | | | | | | | |
| RNase M5 | | | | | | | | |
| RNase-MPR subunit RMP1 | | | | | | | | |
| RNase-MPR subunit SNM1 | | | | | | | | |
| RNase-P component C5 | | | | | | | | |
| RNase-P subunit POP1 | | | | | | | | |
| RNase-P subunit POP3 | | | | | | | | |
| RNase-P subunit POP4 | ● | ● | | | ● | ● | ● | ● |
| RNase-P subunit POP5 | ● | ● | | ○ | ● | ● | ● | ● |
| RNase-P subunit POP6 | | | | | | | | |
| RNase-P subunit POP7 | | | | | | | | |
| RNase-P subunit POP8 | | | | | | | | |
| RNase-P subunit RPP1 | ● | | | ○ | ○ | ● | ○ | ● |
| RNase-P subunit RPR2 | ● | | | | ● | ● | ● | ● |
| RNase-P subunit RPP14 | | | | | | | | |
| RNase-P subunit RPP20 | | | | | | | | |
| RNase-P subunit RPP25 | | | | | | | | |
| RNase-P subunit RPP38 | | | | | | | | |
| RNase-P subunit RPP40 | | | | | | | | |
| RNase-PH | | | | | | | | |
| RNase-R | | | | | | | | |
| RNase-T | | | | | | | | |
| RNase-T1 | | | | | | | | |
| RNase-T2 | | | | | | | | |
| RNase-Y | | | | | | | | |
| RNase-Z | ● | ● | ● | ● | ● | ● | | ● |
| RNase-4 RNASE4 | | | | | | | | |
| RNase-11 | | | | | | | | |
| RNase-6/7/8 | | | | | | | | |
| Oligo-RNase NrnB | | | | | | | | |
| Oligo-RNase & PAP phosphatase NrnA | ● | | | | ● | | ● | |
| Cas6 endo-RNase | | | | | | | | |
| Cbf1 3'-5' exo-RNase | | | | | ● | ● | | |
| Dicer | | | | | | | | |
| Endo-RNase Nob1 | | | | | | | | |

● Reliable
○ Low quality hit

FIG. 15B
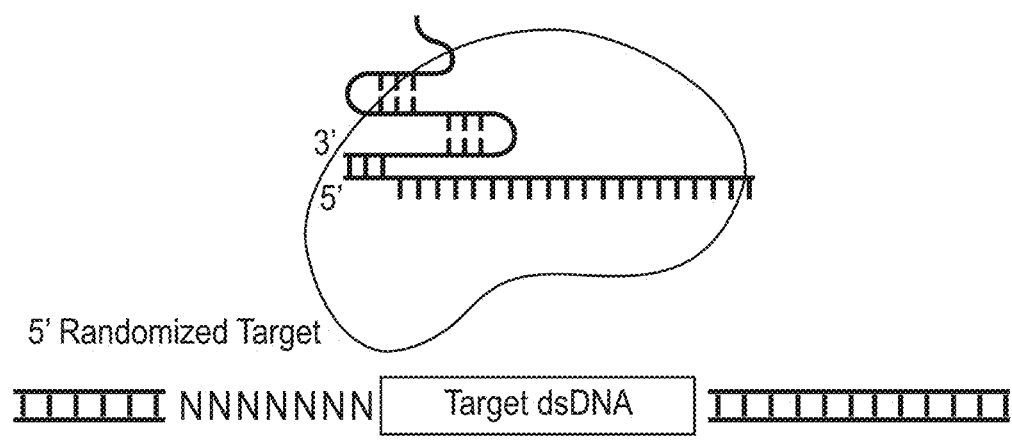
PDVT
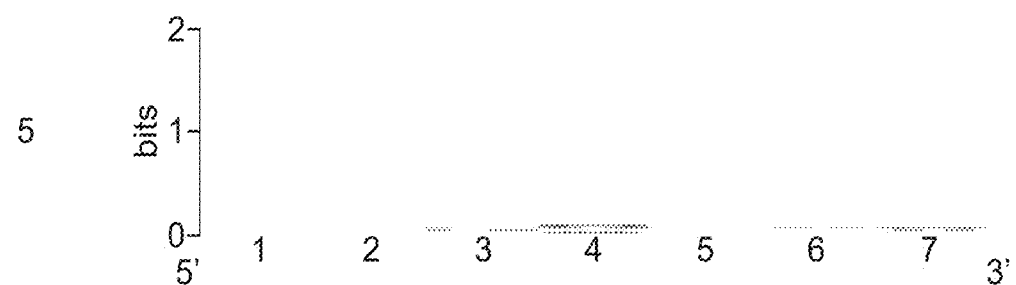

FIG. 15C
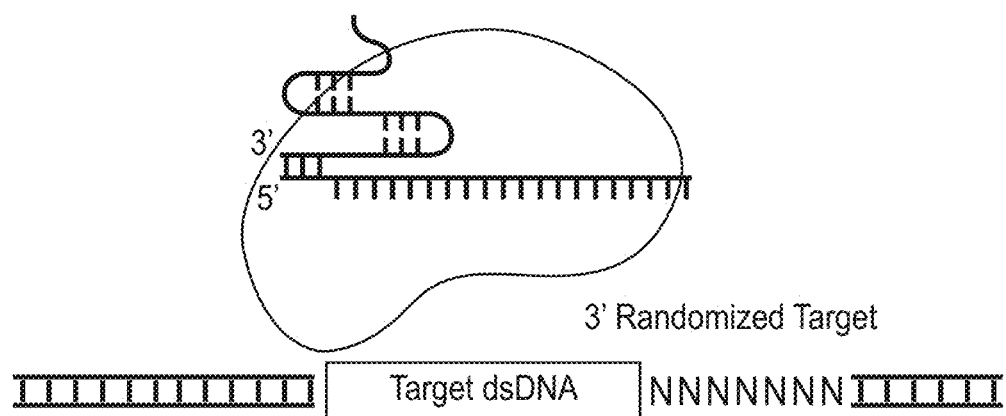
PDVT
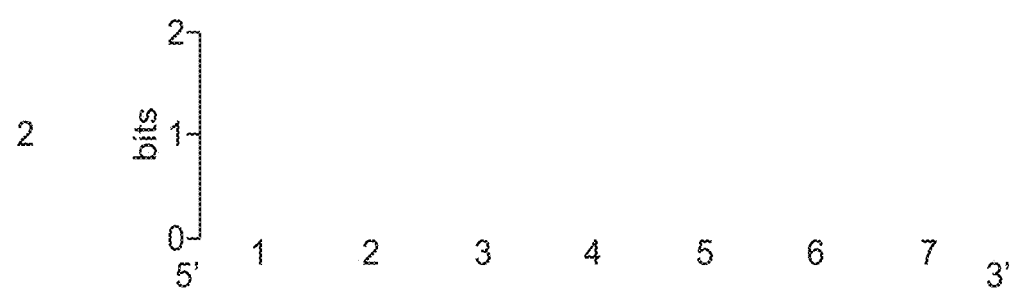
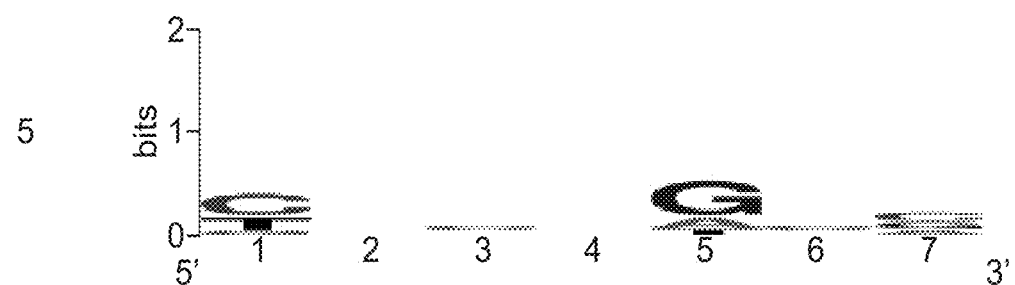

FIG. 16B
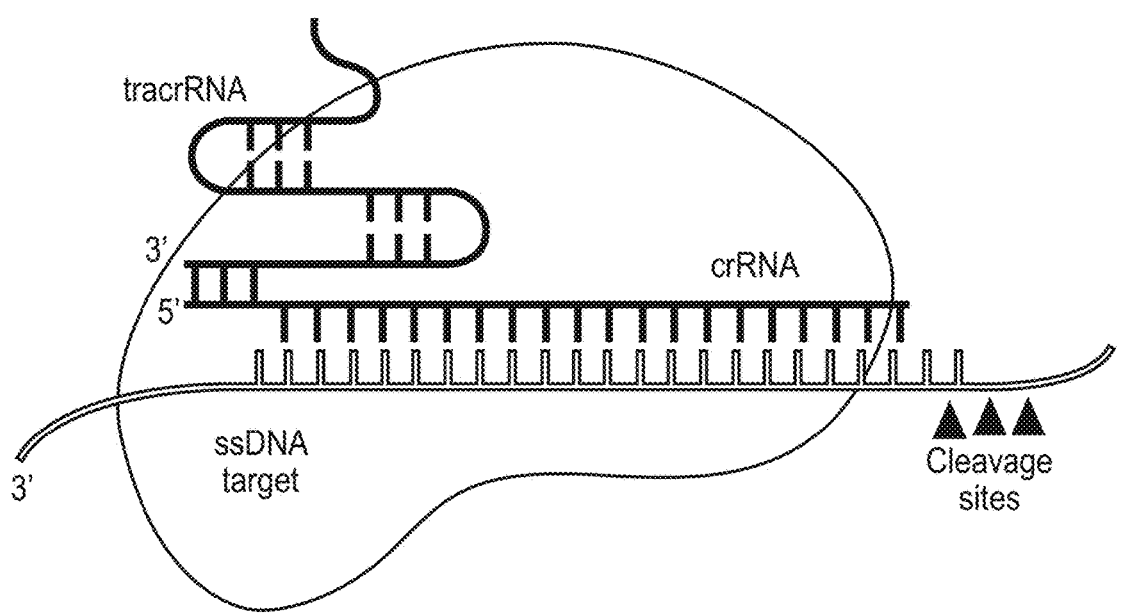
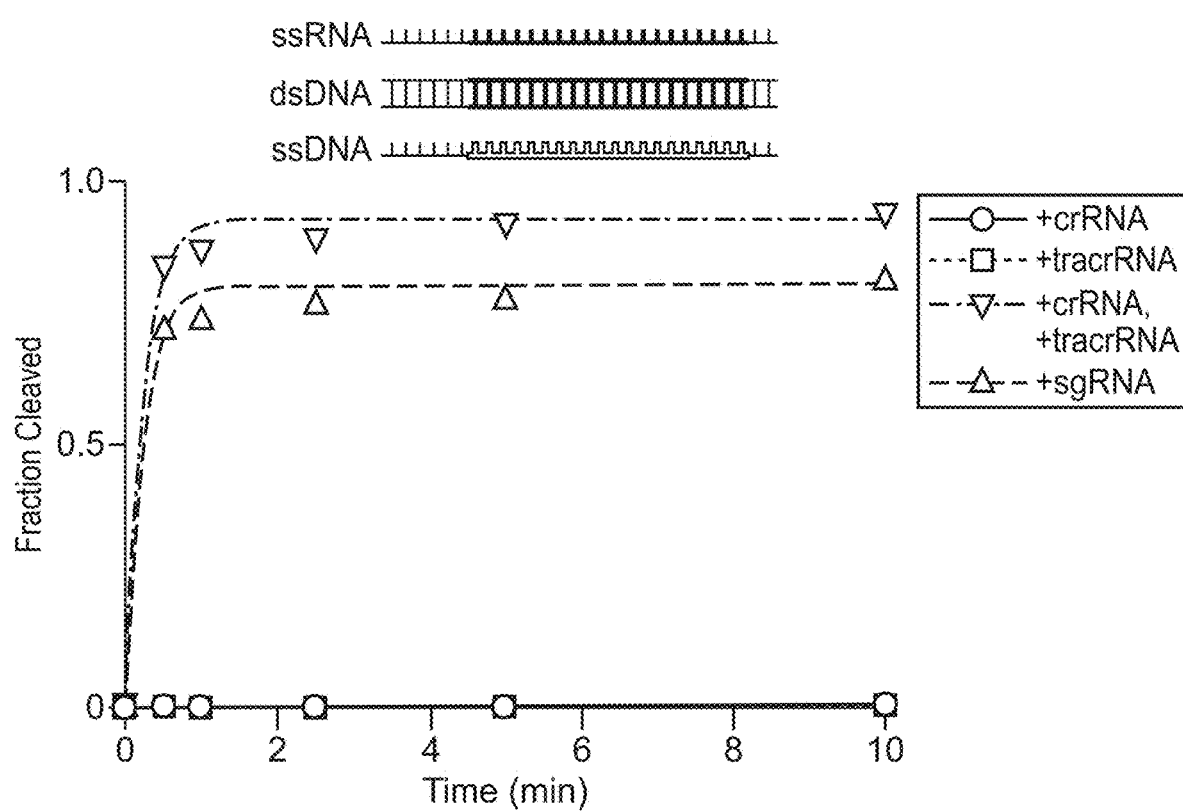

FIG. 17E

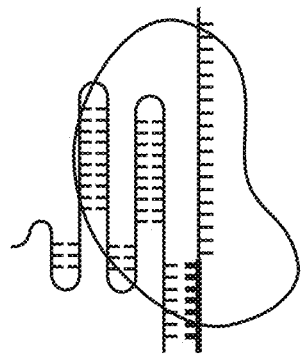
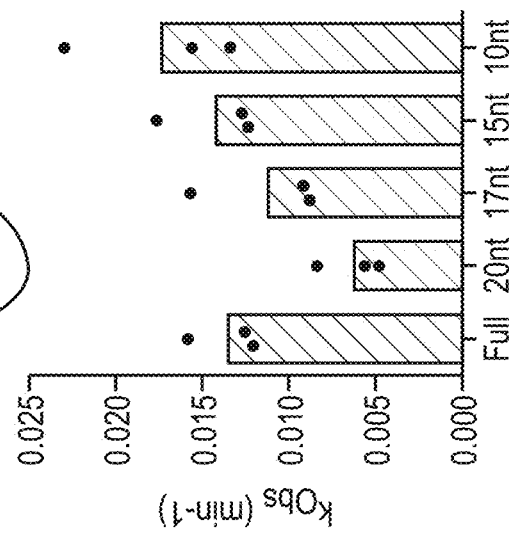
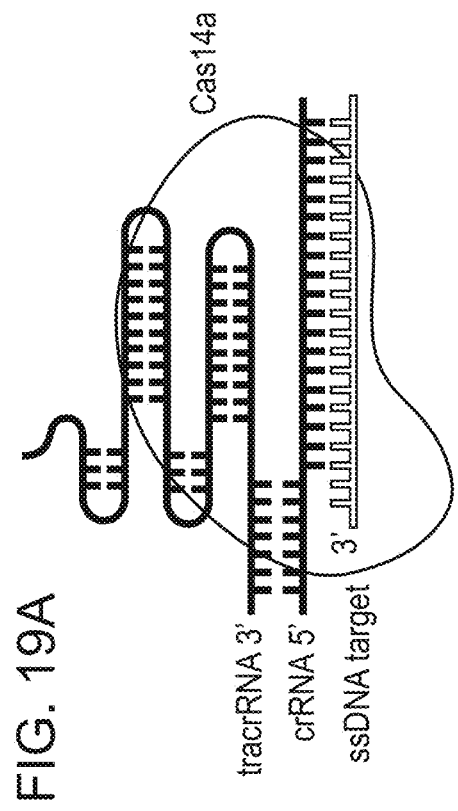
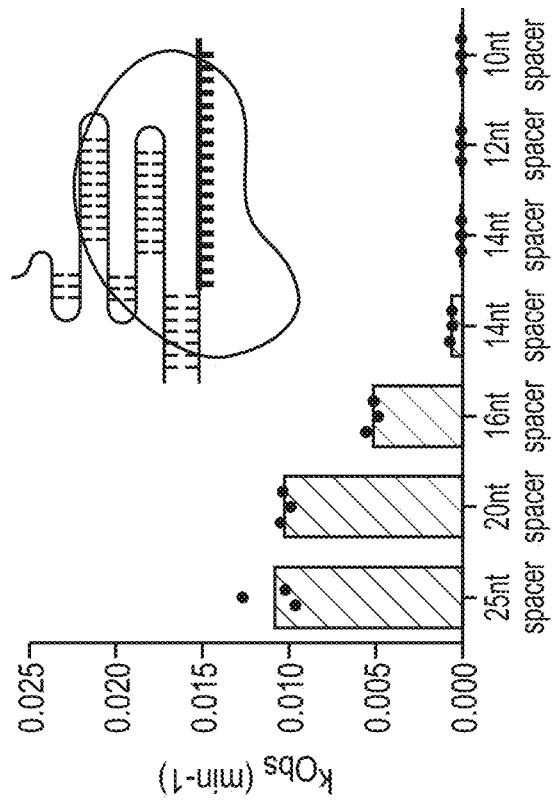

FIG. 19F
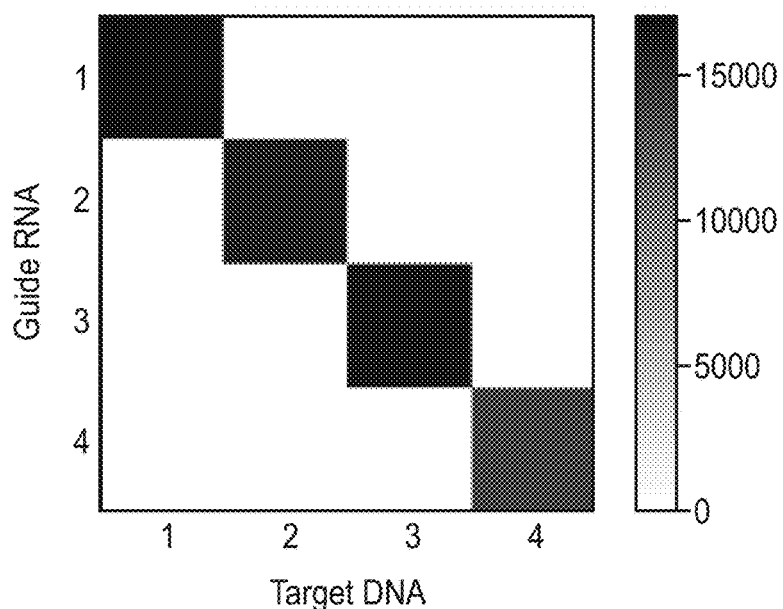
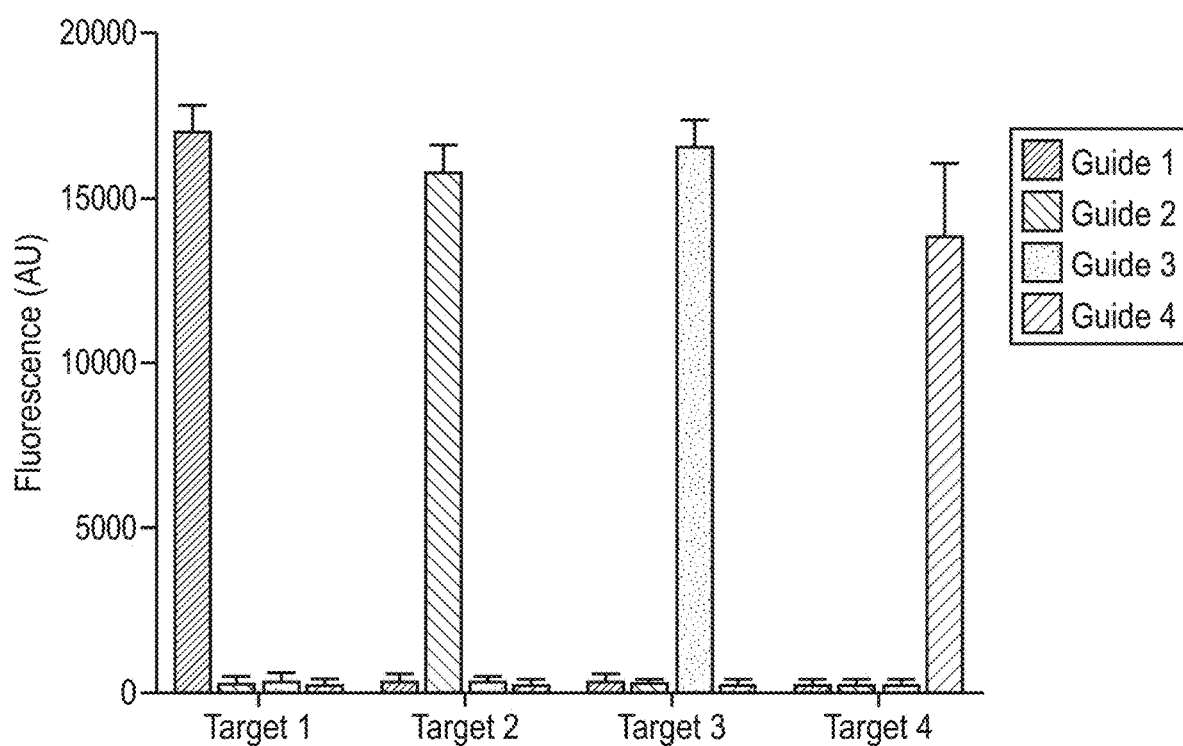

FIG. 20A
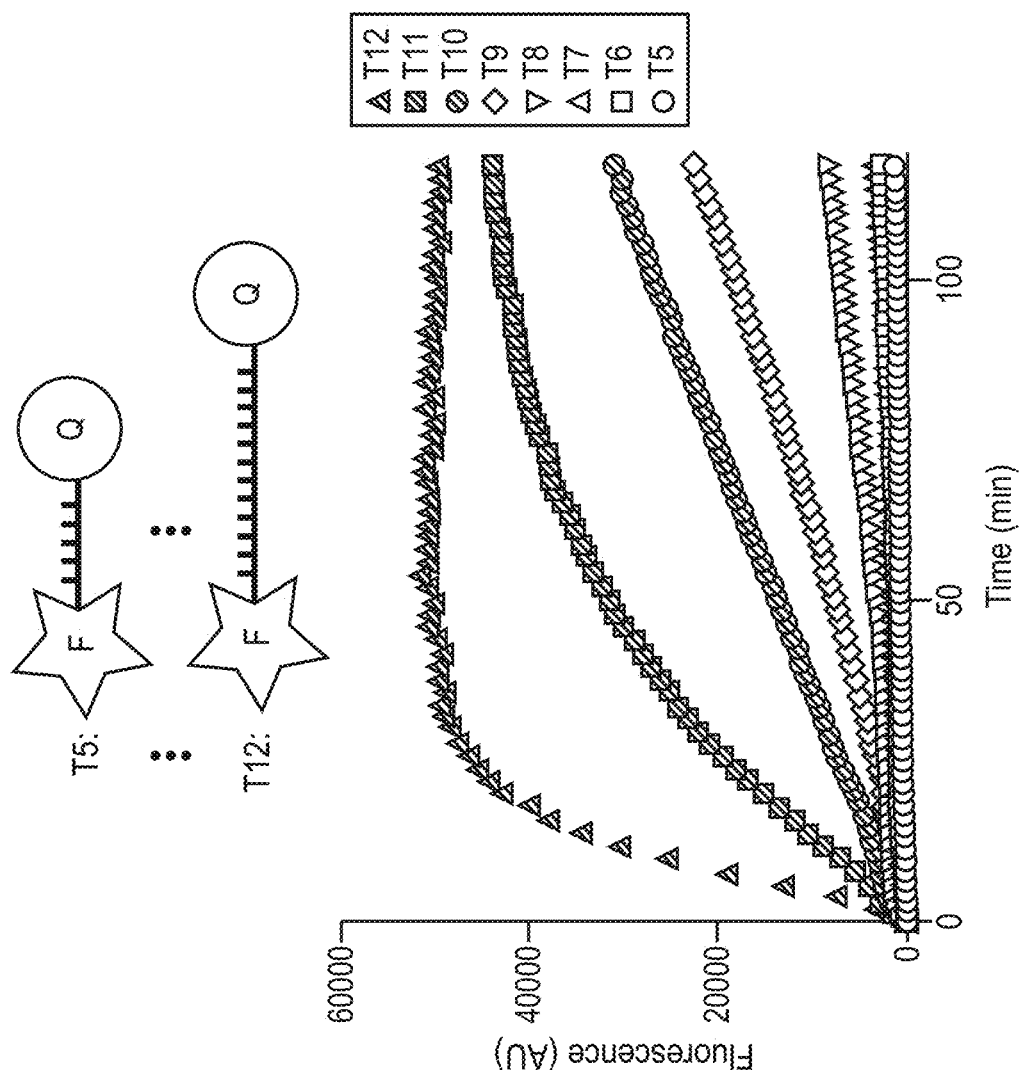
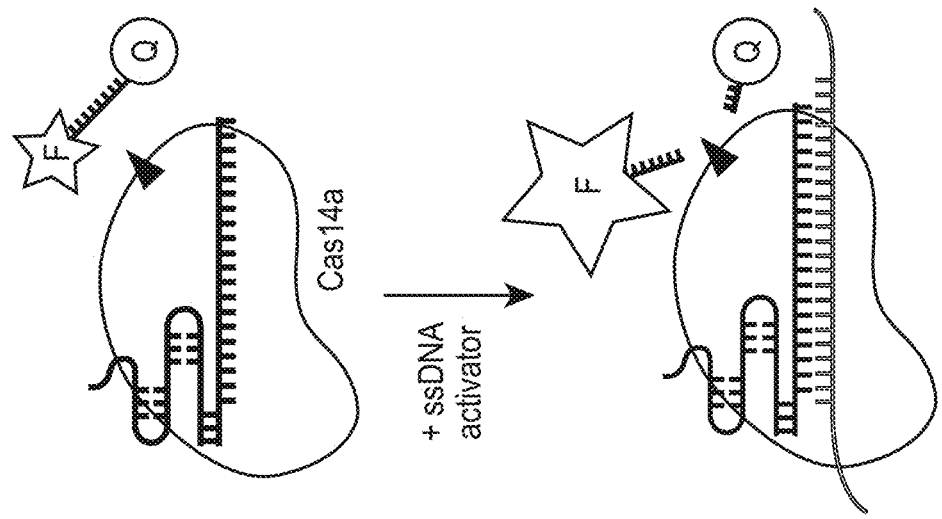

FIG. 21A
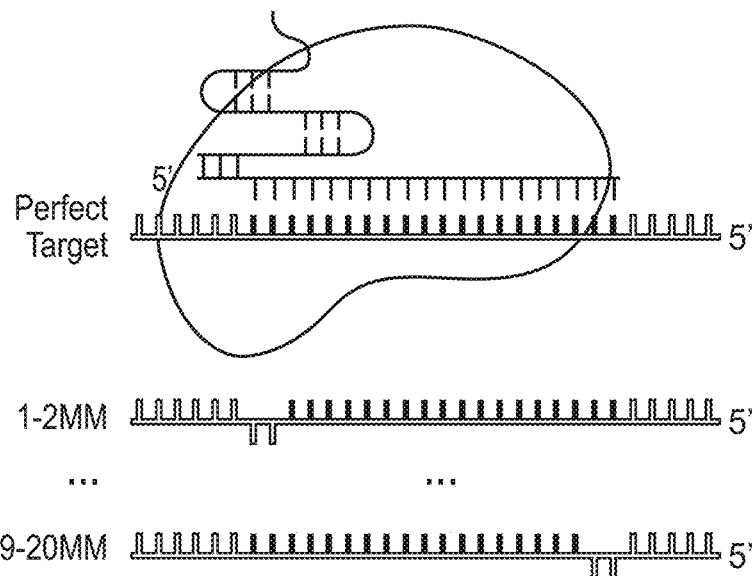
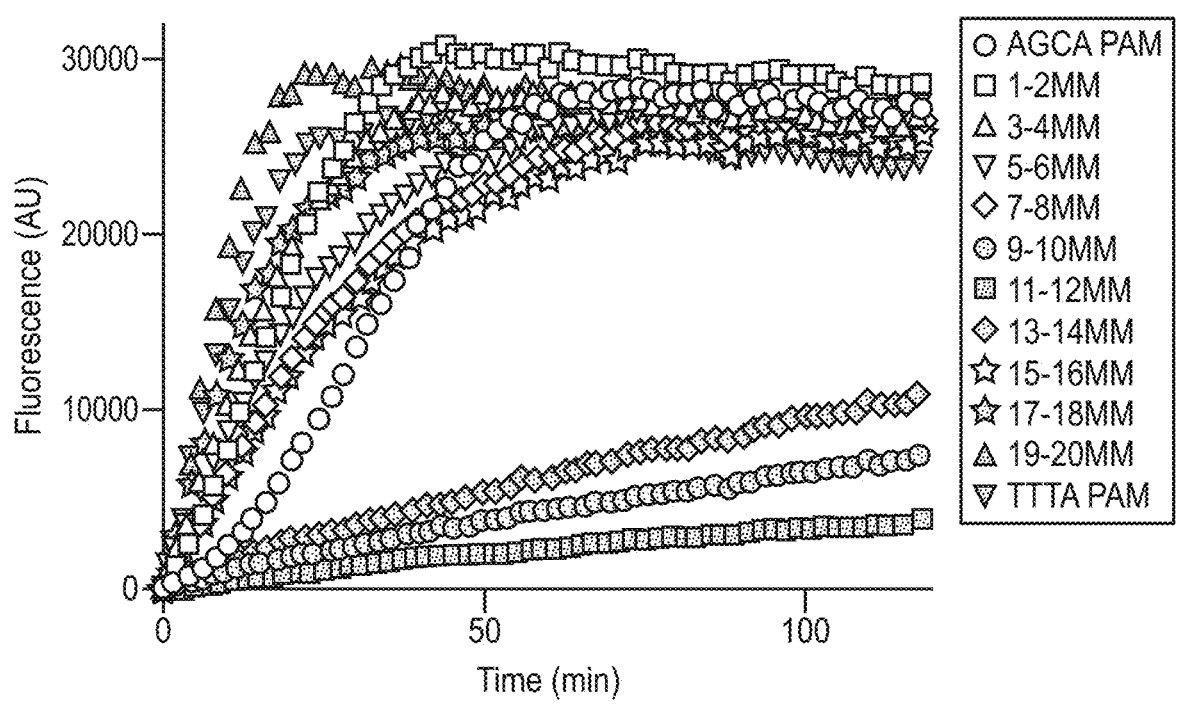

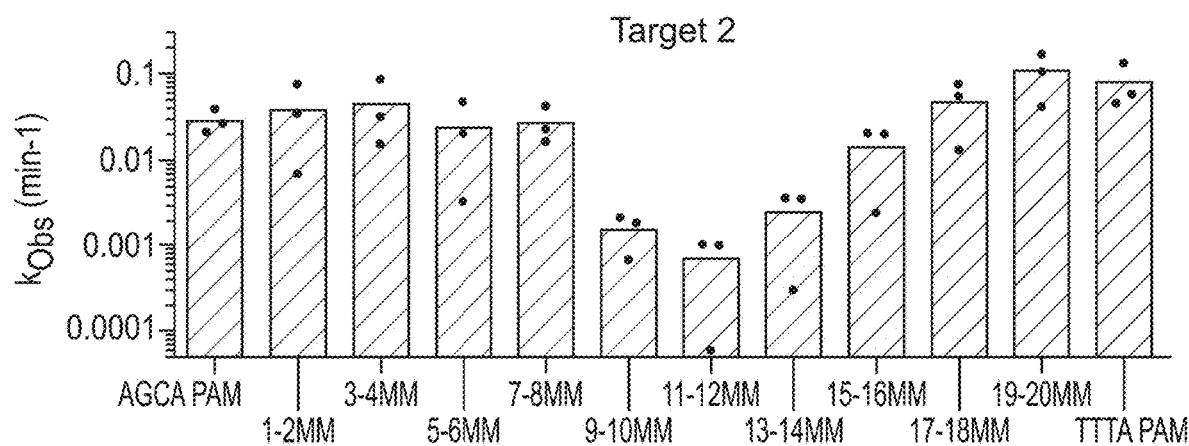
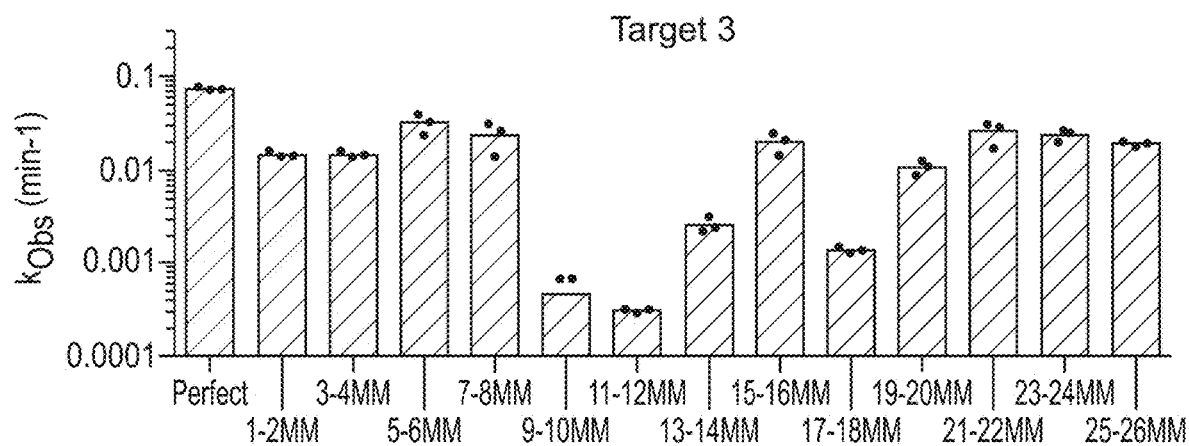
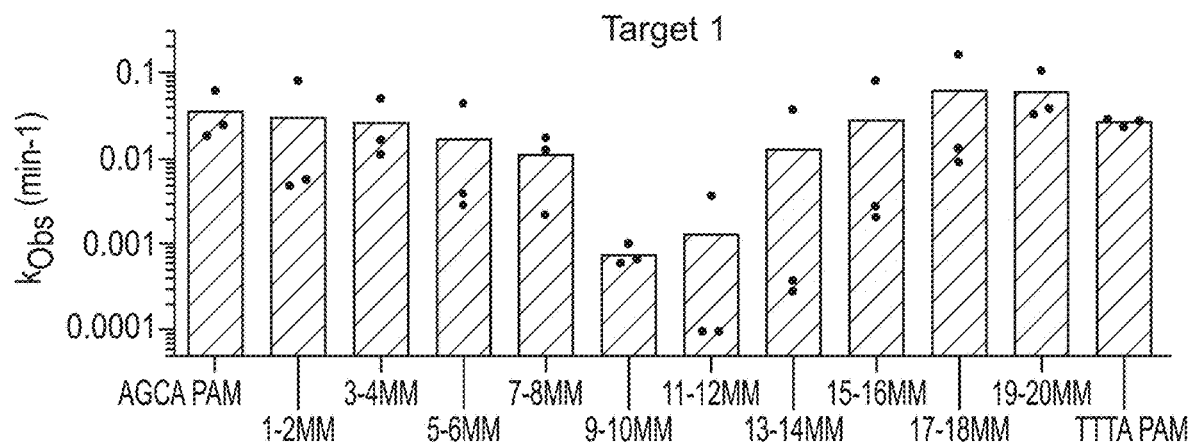

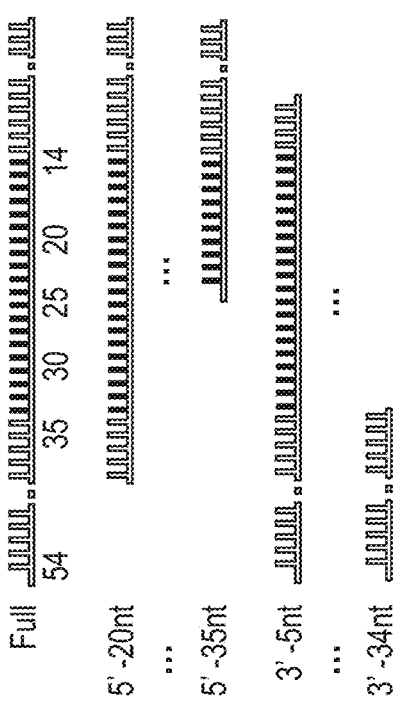
FIG. 21E
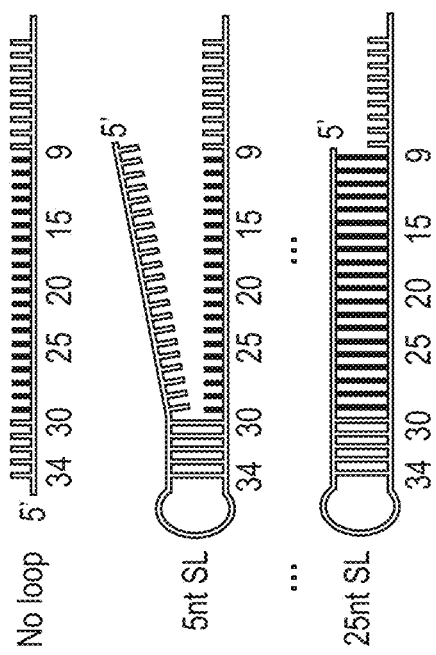
FIG. 21F
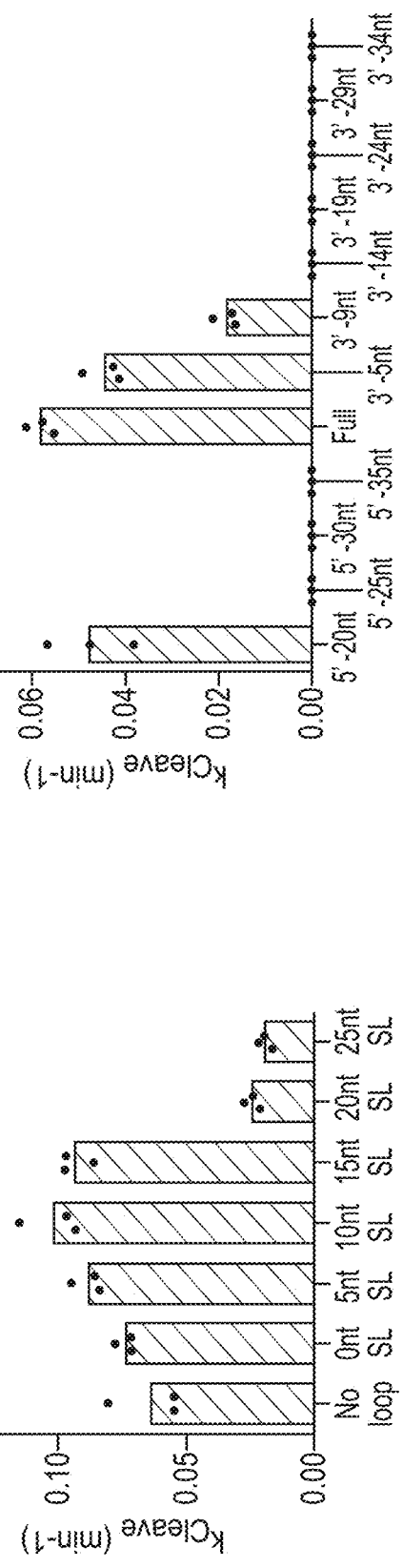

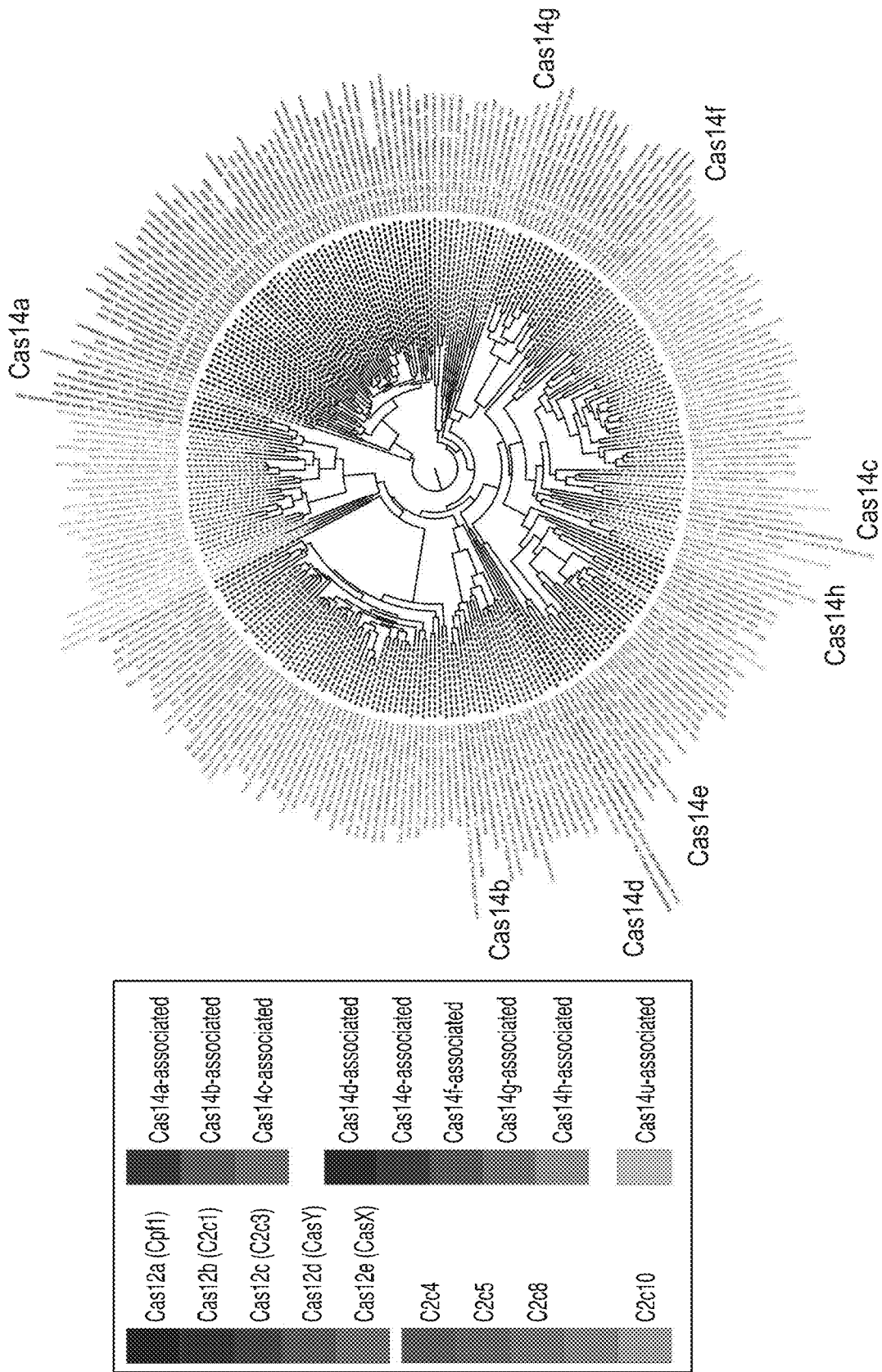

FIG. 24A

Plasmid pLBH533_MBP-Cas14b2 expression (Addgene Plasmid Number 112506)

GCAACCCGCACCTGTGGCGCCGGTGATGCCCGGCCACGATGCGTCCGGCGTAGAGGATCGAGATCGATCC
CGGCGAATTAATACGACTCACTATAGGGAGACCACAACGGTTCCCTCTAGTGCCGGTCGCCGGAGAGCTC
TTTAATTAAGCGGCCGCCCCGTCAGGACTCGAGTTCTAGAAATAATTTTGTTTAACTTTAAGAAGGAGATA
TACATATGAAAATCTCTCACCATCACCATCACCATCACCATGGTTCTTCTATGAAAATCGAAGA
AGGTAAACTGGTAATCTGGATTAACGGCGATAAAGGCTATAACGGTCTCGCTGAAGTCGGTAAGAAATTC
GAGAAAGATACCGGAATTAAAGTCACGGTTGAGCATCGGATAAACTGGAAGAGAAATTCCACAGGTTG
CGGCAACTGCCGATGCCCCTGACATTATCTTCTGGCACCACGACCCTTTGGTGGCTACCCTCAATCTGG
CCTGTTGCTGAAATCACCCGGACAAGGTTCCAGGACAAGCTGTATCCGTTTACCTGGGATGCCGTA
CGTTACAACGCAAGCTGCTTACCGGATGCTGTTGAAGCGTTATCGCTGATTTATAACAAAGATC
TGCTGCCGAACCCGCAAAAACCTGGGAAGAGATCCGGGCTGGATAAAGAACTGAAAGGAAAGGTAA
GAGCCGCGTCAGTGTCCAAGGCTAAGAACCGTACTTCACCTGCCCCTGATTGCTGCTGACGGGGTTAT
GCGGTTCAAGTATGAAAACGGCAAGTACGACATTAAAGACGCAAGCAGCAGCATCAGCGAAAGCGG
GTCTGACCTTCCGGGTTGACCTGATTAAAAACAACAATGAATGCAGACATGGGAACGATTACTCATCGACAGA
AGCTGCCTTAATAAGGGAAACAGCAGCGATGACCATCAACGGCGACCTTCAGGGTCAACCATCGACACC
AGCAAAGGTGAATTATGGGTGTAACGGTACTGCCGACCCAGTTCAAAAGAGCTGGCCAAAGAGTTCTGAAACTATCT
TGCTGAGCGGCAGGTATTACGCCCGCGCCAGTCTGAAGCGGTTAATAACGCGGTTAATGCGGTCCGCCGTAAACGCG
CTGACTGATGAAGGTTGGCGAAGATCCAGCTTTGAAGAAAAACCGCAGACTACTTCCAAATGCAATGGAAGACTGAATCATGC
GAGGAAGAGTTGGCGAAGATCCAGCTTCGCTTCGGCTTATGCCGGATATGCCGGTATCAACGCGCCAGGGTCG
CGAACATCCCGCAGATGTCCGCTTTCGGCTTATGCCGGTATCAACGAGTACTTGCCGGTATCAACGCGCCAGGGTCG
TCAGACTGTGCATGAAGCCTGATGAAGACCGGCAGATAATTCGAGCTGAACACAACAACAATAACAAT
AACAACAACCTGCAGATCGGGAAAACCGATCTGGATGAAGAGACTGGCAGATGATCGTTTGCAGGTAAAGCA
GTGTGAAATTCAAACTGCGCATCGACATGCTGATATAAAACCGATCTAACAAGTACGTTAACAAGTACGTTTTGCCAAGAGTGCTATAAAT
CAAAGCAATTAACTTGCGCGTGAATAAAACCGATCTAACAACGTTAACAACAACCGTTTGCCAAGAGTGCTATAAAT
TTGCAGCTGTGTAAACAGGTTAACAAGTACGTTTAACAACAACGTTTGCCAAGAGTGCTATAAAT
CCGCTTTACCGAAATGGTATTGCAAAACAGTGTATATAGCGCAAAGGTCGTAAGCCGAACATAAATC
AATATCCTGAACGCAACACAGCAGCAAAATGTTAACTATGCCATTGCCGAAGCCTTCATTC
TGGATAAAAGCATCAAAAGCAGCGCAAAACGTAATGAACGTCTGCGTGAAGTAAAAACGTCTGCA
GCAGTTTATCGATATGCCGTGATGGTAAACGTGAAATTTGCCGACCATTAAAGGTCAGAAGTGGATCGT
TTTATTCATCCGAGCTGGATCACCAAAGATAAAAAGCTGGAAGATTTTCGGGTTATACCCTGAGCATTA

FIG. 24B

TCAACAGCAAAATTAAGATTCTGGATCGCAACATCAAACGCGAAGAAAAGCCTGAAAGAAAAGGCCA
GATCATCTTTAAAGCCAAACGTCTGATGCTGGATAAATCCATTCGTTTGTTGTGTGTGATCCAAAGTGCTG
TTTACAATTAGTAAACCCTGCCGAAAGAGTATGAACTGGATCTGCCGAGCAAAGAAAACGGCTGAATT
GGCTGAAAGAGAGATGAGAGATTATCAAGAACCGAAAATATGCTATCTGCTGCCAAAACAT
TGAGGCGAAAAAAACCGAACTATGAGTACTATCTGCAGTACACCCTGGAAATTAAACCGAACTGAAA
GATTTTATGATGGTGCCATTGGTATTGACCGTGGCATTAATCATATTGCCGTTTGCACCTTTATTAGCA
ACGATGGTAAAGTTACCCCTCCGAAATTTTCAGCAGCGGTGAAATTCTGCGTCTGAAAAATCTGCAGAA
AGAGCGTGATCGGTTTCTGCTGCGTAAACACAACAAAATGCAAAAATGCAACATGCGGTGATCGAA
AACAAAATCAATCTGATCCTGCACCGTTATAGCAAGCAGATTGTTGATATGGCCAAAAAGCTGAATGCCA
GCATTGGTTTTGAAGAACTGGGTCGTATTGGTAAAAGCCGCACCAAAATGAAAAAAAGCCAGCGTTATAA
ACTGAGCCCTGTTCATCTTCAAGAAACTGAGCGATCTGGTTGATTACAAAACCGTCGTGAAGGTATTCCGT
GTTACCTATGTTCGCCTGAATATACCAGCAAAGAAGAATGTAGCCATTGCGGTGAAAAGTTAATACCCAGC
GTCCGTTTAATGCAACTATGCCTGTTTAAATGCAACAAATGTGGCATCCAGCGGTGAACAGCGATTATAA
TGCAAGCATCAACATTGCAAAAGGGCCTGAAAAATTCCGAAATAGCACCTAATAACATTGAAGTGGATA
ACGGAAATCCGCGATCGCGCCGATCCAAGCGCCCGGTGTACCCACGCGGTCGTGCGCTGTGCT
AACAAGCCCGAAGGAAGCTGAGTTGGCTGTGCCACCGTGCCACCGCAATAACTAGCATAACCCCTTGGGG
CCTCTAAACGGGTCTTGAGGCGTTTTGCTGAAGAGAACTATATCGGATATCCACAGGACGGGTG
TGGTCGCCATGATCGGTAGTTCGATAGTGGCTCCAAGTAGGACGAGCGAGCGACTGGGCGGGCCAA
GCGGTGCCGACAGTCGAGAACGGGTGCCGCATAGGATATCCCAAGAGGCCGGCAGTAGGCTAGCAGCACG
CCATAGTGACTGGCGATGCTGGAATGGACGAATATCCAAGAGGCCGGCAGTAGGCTACCGGCATAACCA
AGCCTATGCCTACAGCATCCAGGGTGACGGTGCGAGGATGACGAGCCATTGTTAGATTTCATACA
CGGTGCCTGACTGCGTTAGCATGCAATTTAACTGTGATAAACTACCGCATTAAAGCTTATCGATGATAAGCTGT
CAAACATGAGAATCTTGAAGACGAAAGGGCCTCGTGATACGCCTATTTTATAGGTAATGTCATGATA
ATAATGGTTTCTTAGACGTCAGGTGGCACTTTCGGGGAAATGTGCGCGGAACCCCTATTTGTTATTTT
TCTAAATACATTCAAATATGTATATTCAACATTCCGCATGGTGAAATAACCTGATAAATGCTCAATAACATTGAAA
AGGAAGAGTATGAGTTTCAACGCTGGTGAAAAAGTAGTGCTGAAGATCAGTGGGTGCACGAGTGGGTT
GTTTGCTCACCAGAATCTCAACAGCGGTAAGATCCTTGAGAGTTTCGCCCGAAGAACGTTTCCAATGAT
ACATCGAACTGGATCTCATATGTGGCGGTATTATCCGTGTTGACGCGGGCAAGAGCAACTCGGT
GAGCACTTTAAAGTTCTGCTATGTGGGCGGGTATTATCCGTGTTGACGCGGGCAAGAGCAACTCGGT
CGCGCATACACTGGTTGAAATGACTGGTTGCTGCCATAACCATGAGTGATAACCATCGACCATTACTTCT
GCATGACAGTAAGAGAATTATGCAGTGCTGCACAAAGCAGCTAACCTACTGGAATCATCGAACTGGATG
GACAACGATCGGAGGACCGAAGGAGCTAACCGCTTTTGCACAACATGGGGATCATGTAACTCGCCTT

FIG. 24C

GATCGTTGGAACCGGAGCTGAATGAAGCTGAACCGGAGCCATACCAAACGACGAGCGTGACACCACGATGCCTGCAGCAA
TGGCAACAAGGTTGCGCAAACTATTAACTGGGAACTACTACTCTAGCTTCCGCTGCGCCTTCCGCTGCCTGGTTTATTGCT
CTGGATGGAGGCGGATAAAGTTGCAGGACCACTTCTGCCTCCGCCACTTCTGCAGCACTGGGCCAGATGGTAAGCCCT
GATAAATCTGGAGCCGGTGAGGGTGGGTCTCGGGTATCATTGCAGCACTGGGCCAGATGGTAAGCCCT
CCGTATCGTAGTTATCTACGACGGGGAGTCAGCACTATGGAACGAACGAAATAGACGACATCGCTGA
GATAGGTGCCTCACTGATTAAGCATTGGTAACTGTCAGACCAAGTTACTCATATATACTTTAGATTGAT
TTAAAACTTCATTTTTAATTTAAAGGATCTAGGTGAAGATCCTTTTTGATATCATGACCAAATCC
CTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAACACCCCTACCAGCGGTGGTTTGTTTGCCG
GATCAAGAGCTACCAACTCTTTTTCCGAAGGTAACTGGCTTCAGCAGAGCGCAGATACCAAATACTGTCC
TTCTAGTGTAGCCGTAGTAGGCCACCACTTCAAGAACTCTGTAGCACCGCTACATACCTCGCTCTGCT
AATCCTGTTACCAGTGGCTGCTGCCAGTGGCGATAAGTCGTGTCTTACCGGGTTGGACTCAAGACGATAG
TTACCGGATAAGGCGCAGCGGGGTCGGGCTGAACGGGTTCGTGCACACGAGCCCAGCTGGAGCGAACGA
CCTACACCGAACTGAGATACCTACACGGTGATATGAGAAAGCGCCACGCTTCCGAAGGGAGAAAGGC
GGACAGGTATCCGGTAAGCGGCAGGGTCGGAACAGGAGAGCGCACGAGGGAGCTCCAGGGGAAACGCC
TGGTATCTTTATAGTCCTGTCGGGTTTCGCCACCTCTGACTTGAGCGTCGATTTTTGTGATGCTCGTCAG
GGGGGCGGAGCTATGGAAAACGCCAGCAAGCGCGGCCTTTTACGGTTCCTGGCCTTTTGCTGGCCTTT
TGCTCACATGTTCTTTCCTGCGTTATCCCCTGATTCTGTGGATAAGTCAGCGATTACCGCCTTTGAGTGAGCT
GATACCGCTCGCCGCAGCCGAACGACCGAGCGCAGCGAGTCAGTGAGCGAGGAAGCGGAAGAGCGCCTGA
TGCGGTATTTTCTCCTTACGCATCTGTGCGGTATTTCACACCGCATATGTGCACTCTCAGTACAATCTGC
TCTGATGCCGCATAGTTAAGCCAGTATACACTCCGCTATCGCTACGGACTGCCTCGTCCCGCCATCCGCTTACAGACAACT
ACACCCGCCAACACCGCTGGTCGTGAAGCGATTCACAGATGTCTGCCTGTTCATCCGCGTCATGTTAAGGGCGGTTTTTTCCTGTT
GTGACCGTCTCCGGGAGCTGCATGTGTCAGAGGTTTTCACCGTCATCACCGAAACGCGCGAGGCAGCTGC
GGTAAAGCTCATCAGCGTGGTCGTGAAGCGATTCACAGATGTCTGCCTGTTCATCCGCGTCATGGTTAAGGGCGGTTTTTTCCTGTT
GAGTTTCTCCAGAAGCGTTAATGTCTGGCTTCTGATAAAGCGGGCCATGTTAAGGGCGGTTTTTTCCTGTT
TTGGTCACTGATGCCTCCGTGTAAGGGGGATTTCTGTTCATGGGGGTAATGATACCGATGAAACGAGAGA
GGATGCTCACGATACGGGTTACTGATGATGAACATGCCCGGTTACTGGAACGTGTGAGGGTAAACAACT
GCGGTATGGATGCGGCGGGACCAGAGAAAATCACTCAGGGTCAATGCCAGCGCTTCGTTAATACAGAT
GTAGGTGTTCCACAGGGTAGCCACAGATCCGGATGCAGAACCGAAGACCATTCATTGGTTGCTAACCAGTAAGGCAA
ACTTCCGGGTTCAGAAGCGTTCAGTGCTTCACGTTCGCTCGCGTATCGGTGATTCATTCTGCTAACCAGTAAGGCAA
CGTTTTGCAGCAGCAGTCGCTTCACGTTCGCTCGCGTATCGGTGATTCATTCTGCTAACCAGTAAGGCAA
CCCCGCCAGCCTAGCCGGGTCTTCAACGACAGGAGCACGATCATGCGCACCCGTGGCCACCCGTGGCGACCCAACGC

FIG. 24D

TGCCCGAGATGCGCGCGGTGCGGCTGCTGGAGATGGGGACGCGATGGATATGTTCTGCCAAGGGTTGGT
TTGCGCATTCACAGTTCTCCGCAAGATTGATGGCTCCAATTCTTGGAGTGGTGAATCCGTTAGCGAGG
TGCCGCCGGCTTCCATTCAGTTCGAGGTGGCCCGGCTCCATGCACCGGCGACGCAACGCGGGAGGCAGAC
AAGTATAGGCGCGCCTACAATCCATGCCAACCGTTCTGCCCGAGCCGGCATAAATCGCC
GTGACGATCAGCGGTCCAATGATCGAAGTTAGGCTGGTAAGAGCCGGAGGATCCTTGAAGCTGTCCT
GATGGTCGTCATCTACCTGCCTGGACAGCATGGCCGTCAACGCGGGCATCCGATGCGCCGGAAGCGAG
AAGAATCATAATGGGGAAGGCCATCCAGCCTCGCGTGCGGAAGCCAGCAAGACGAAGCCAGCGCGTCG
GCCGCCATGCCGGCGATAATGCCGGCTTCTCGCCGAAACGTTGGTGGCGGACCAGTGACGAAGGTT
GAGGGAGGGCGTGCAAGATTCCGAATACCGCAAGCGACAGGCCGATCATCGTCGCTCCAGCGAAAGCG
GTCCTGCGCGAAAATGACCCAGAGCGCTGCCGCCACCGTCCTACGAGTTGCATGATAAAGAAGACAGTC
ATAAGTGCGGCGACGATAGTCATGCCCCGCCCACCGGAAGGAGCTGACTGGGTTGAAGGCTCTCAAGG
GCATCGGTCGACGCTCTCCCTTATGCGACTCCTGCATTAGGAAGCAGCCAGTAGTAGTTGAGGCCGTT
GAGCACCGCGCCGCGCAAGGAATGGTGCATGCAAGGAGATGGCGCCAACAGTCCCCGGCCACGGGCCT
GCCACCATACCCAGCGAAACAAGGCGTCATGACCCGAAGTGGCGAGCCGAAGTGCGAGCCGAAGTCGGCATCCCCATCGGTGA
TGTCGGCGATATAGGCGGCCA (SEQ ID NO: 493)

FIG. 24E

Plasmid pLBH547_Tet-Cas14b2Locus (AddGene Plasmid Number: 112504)

ATGGTTGATAGAGTTATTTTACCACTCCCTATCCAGTGATAGAGAAAAGAATTCAAAGATCTAAAGAGGA
GAAGGATCTATGGAAGAAAGCATTATTACCGGTGTGAAATTCAAACTGCCATCGATAAGAACCACC
AAAAACTGAACGAGTACTTCGATGAATATGGCAAAGCAATTAACTTCGCCGTGAAGATCATTCAGAAG
AACTGGCAGATGATCGTTTTGCAGTGAAAGCAAAACTGGACCAGAATAAAAACCGATCCTGATGAAA
CGGCAAAAAATCTATGAAAATTCCCGGATGAATTTTGCAGCTGTGGTAAACAGGTTAACAAGTACGTTAAC
AACAAACCGTTTGCCAGAGTGCTATAAAATCCGTTTACGGAAAATGGTATTGCGAAACGTATGTATA
GCGCCAAGGTCGTAAAGCCGAACATAAATCAATATCCTGAACGCACCAACAGATCAGCAAAACCA
TTTTAACTATGCCATTCGCGAAGTCTGCAGCCTTCATTCTGATAAAAGCATCAAAAGCAGCGCAAACGTAAT
GAACGTCTGCGGTGAAAGTAAAAACGTCTGCAGCAGTTTATCGATATGCGTGATGGTAAACGTGAAATTT
GCCGACCATTAAAGGTCAGAAGTGATGTTTATTCATCGAGCTGATCACCAAAGATAAAAGCT
GGAAGATTTCGCGGTTATATCCCTGAGCATTATCAACAGCAAAATTAAGATTCTGGATGCAACATCAA
CGCGAAGAAAAAGCCTGAAAGAAAAGGCCAGAATCATCTTTAAAGCCAAACCCTGCGATGCTGGATAAAT
CCATTCGTTTGTTGGTGATCGCAAAGTGCTGTTTACAATTAGTAAACCCTGCCGAAAGAGTATGAACT
GGATCTGCCGAGCAAAGAAATGGCTGAATTGGCTGAAAGAGAAGATGGAGATTATCAAGAACCAGAAA
CCGAAATATGCCTATCTGCTGCAAAAACATTGAGCGGCGAAAAAACCGAACTATGAGTACTATCTGC
AGTACACCCTGGAAATTAACCGGAACTGAAAGATTTTATGATGGTGCCATTGGTATTGACCGTGGCAT
TAATCATATTGCCGTTTGCACCTTTATTGCAACGATGGTAAGTTACCCTCGGCTTTCTGCGTAAACACAACAAAA
GGTGAAATTCTGCGTCGAAAAATGCAACATGCGCGTGATGAAAACAAATCAATCTGCATCCTGCGTTATACCAAGCA
GATTGTGATATGGCCAAAATGAAAGCTGAATGCCAGCATGTTTTGAAGAACTGGGTCGTATTGGTAAAGC
CGCACCAAAATGAAAAAACCGTCGTGAAGGTATTCGTGTTACCGTTCCGCCTGAATATACCAGCAAAGAATG
TTGATTACAAAAGCCGTCGGTGAAAATGAAAGCCGTTATACGATTAATCAACCCAGCCAGATTATCGGAAGGACAATGCAAC
TAGCCATTGCGGGTGAAAAGTAATACCAGCGTCCGTTAATGCAACTATAGCCTGTTTAATGCAAC
AATGTGGCATCCAGCTGAACAGCGATTATAATGCAAGCATCAACATTGCGAAAAAGGCCTGAAATTC
CGAATAGCCACCTAATAATGTTGGTAAGCCACAATATGGAAGATTTGGCGTTGTGGTTAACGCAATAAGGGTAACCCTGAA
ATTAATAATCTTCGAAGGCTATATGCCGGAAGATTTTATTGAGTTTAACCGCAATAAAGGACAGTATGACTTAA
AAGGTTGAAATCATATAAACCTAGTTTATTGAGTTTAGGCTCAGATAAAAGTGAACAGACCAATTCTAA
AATTCCGGTTCGTGATTTAAAAAATCAGAATCTCTTTATAATAGTATTACAAAAGTGTACATTCCAAAT

FIG. 24F

```
CCGAAAGCAGAATTGACCCTTTTAAGCCTAAAAAGCCAAATTTCAAGCCTCTTTCATACTCAGAACAAA
GGGATTAAGGAATGCAACTACCTTACACCGCTTGCGAAAGTTGTCAGAAGATAAATCTTTCATACTCAGAA
CAAGGGATTAAGGAATGCAACTATCTTATCCATTTCTTGACATCAAATTTCTTGCAGCATCTGAATTG
CTTAATTGCTTTCCTTGCTTGCTTGCAGCAGGAAATAGCCAAGATTTTCCAGTTCTGCTGGCGTTATTGCAAGCA
CGGGGGATTTGTCTTGCTGTGTAGATTTTGTTTCTCAGGACCTCTTTTCCATGCTAGAGTGACTGGC
TCACCTTCGGGTGGCCTTTCTGCGTTTATACCTAGGGATATATCCGCTTCCTGCTCACTGACTGCT
ACGCTCGGTCGTTCGACTGCGGCCGAGCGGAAATGCTTACGAACGGGGCGGAGATTCCTGAAGATGCC
AGGAAGATACTTAACAGGGAAGTGAGAGGGCGCGGCAAAGCCGTTTTCCATAGCTCGCGCCCCTGA
CAAGCATCACGAAATCGACGTCAAATCAGTGGTGCGGCGAAACCGACACAGGACTATAAAGATACCAGGCG
TTTCCCCCCTGCGGCTCCCTGGTGGCGCTCCGTGTTCCTGCGCTTTACGGTGTCATTCCGCGT
TATGGCCGGTTTGTCTTCCACGCCTGACACTCAGTTCCGGGTAGGCAGTTCGCTCCAAGCTGGACT
GTATGCACGAACCCCGTTCAGTCCGCGGCCCTTATCCGGTAACTATCGTCTTGAGTCAACCC
GAAAGACATGCAAAAGCACAGCTGGCAGCGCCACTGGTAATTGATTTAGAGAGGAGTTAGTCTGAAGTC
ATGCGGCCGGTTAAGCTAAACTGAAAGGACAAGTTTTTGGTGACTGCGCCTCCAAGCCAGTTACCTCCG
TTCAAAGAGTTGGTAGCTCAGGAGTCCAAGGAACCTTCGAAAAACCGCTCGAAGGCGGTTTTCGTTTCAGAGC
AAGAGATTACGGCCAGACCAAAACGATCTCAGAAGAATCATCTTATTAATCAGATAAATATTCTAGAT
TCAGTGCAATTATCTTCAAATGTAGCACCTGAAGTCAGGCCCATACGACCGAGTATAAGTTGTACTAGTG
CTTGGATTCTCACCAATAAAAACCGGGAGGAGTCCAAGCGAGCTGATAATCAAATTACGCCCCGCCACT
AGGTCATTACTGGATCATCAACAGGAGTCCAAGCGAGCTCGATATCAAATTACGCCCCCGCCACT
CATCGCAGTACTGTTGTAATTCATTAAGCATTCTGCCGACATGGAAGCCATCACACGATAACACGATGAAC
CTGAATGCGCCAGGGCATCAGCACCTTGTCGCCTTGCCTATAAATTGGCCATGGTGAAAACGGGGGCG
AAGAAGTTGTCCATATTGGCCACGTTTAGGGAAATAGGCCAGTTTCACCGTAACACGCCACATCTTGCGA
AAAACATATTCTCAATAAACCTTTAGGGAAATAGGCCAGTTTCACCGTAACACGCCACATCTTGCGA
ATATATGTGTAGAAACTGCCGGAAATCGTCGTGGTATTCACTCCAGAGCCGATGAAACGTTTCAGTTGC
TCATGGAAAACGGTGTAACAAGGGTGAACACTATCCATATCCACCAGCTCACCGTCTTCATTGCCATAC
GAAATTCCGGATGAGCATTCATCAGCGGGCAAGAATGTGAATAAGGCCGGATAAACTGTGCTTATT
TTTTCTCCATTTAGCTTCCTTAGCTCCTGAAAATCTGATAACTCAAAAATACGCCCGGTAGTGATCT
TATTCATTATGTGAAGTTGAAGCTTCTTAAGTTGTTTTCTAATCCGCATATGATCAATTCAAGGCGAATAAGA
TCTTAAGACCCACTTGACCCTGGTGACCCTGGTGTCGTAATAATTCGATAGCTTGTCGTAATAATTCGATAGCTTGTCGTAATGGCGGCATACTATCAGT
AGGCTGGCTCTGCACCTGGTGATCAAATAATTCGATAGCTTGTCGTAATAATGGCGGCATACTATCAGT
```

FIG. 24G

AGTAGGTGTTTCCCTTCTTCTTTAGGGACTTGATGCTCTTGATCTTCCAATACGCAACCTAAAGTAAAA
TGCCCCACAGGCTGAGTGCATATAATGCATTCTCTAGTGAAAAACCTTGTTGGCATAAAAGGCTAATT
GATTTCGAGAGTTTCATACTGTTTTTCTGTAGGCCGTGTACCTAAATGTACTTTGCTCCATCGCGATG
ACTTAGTAAAGCACATCTAAAACTTTTAGCGGTTATTACGTAAAAAATCTTGCCAGCTTCCCTTCTAAA
GGGCAAAAGTGAGTATGGTGCCTATCTCAACATCTCAATGGCTAAGGCGTCGAGCAAAGCCCGCTATTTT
TTACATGCCAATACAAATGTAGGCTGCTCTACACCTAGCTTCTGGCGAGTTTACGGGTTGTTAAACCTTC
GATTCCGACCTCATTAAGCACAGCTCTAATGCGCTGTTAATCACTTTACTTTTATCTAATCTAGACATCATT
AATTCCTAATTTTTGTTGACACTCT (SEQ ID NO: 494)

FIG. 24H

Plasmid pLBHS9_Tet-HisCas14a1Locus (AddGene Plasmid Number: 112502)

TAATTCCTAATTTTTGTTGACACTCTATCGTTGATAGAGTTATTTACCACTCCCTATCAGTGATAGAGA
AAGAATTCAAAAGATCTAAAGAGGAGAAAGGATCTATGAAATCTATGAAATCTACCATCACCATGAAACC
TGTACTTCCAATATTGGAAGTTGGAATGGCCAAAAACACCATTACCAAACACTGAAACTGCGTAT
TGTGGGTCCGTATAATAGCGCAGAAGTGGAAAAATTGTTGCCGACGAAAAAACAACCGCGAAAAATC
GCACTGGAAAAGAACAAAGACAAAGTGAAGAGCTGCAAATCTGAAGTTGCAGCATATTGTA
CCACACAGGTTGAACGTAATGCATGCCTGTTTTGTAAAGCACGTAAACTGGATGACAAATTCTACCAAAA
ACTGCGTGGTCAGTTCCGATGCAGTTTTTGGCAAGAAATCAGCGAAATTTTTGCCAGCTGCAGAAA
CAGGCAGCAGAAATCTATAATCAGAGCCTGATCGAACTGTACTACGAGATTTTTATCAAGGCAAGGTA
TGCAAATGCAGCAGCGGTTGAACATTATCGAGTAGTTTGTTATACCGTGCAGCAGCTGTTAA
AACCGCAGCAATTGCAAGCGGTCTGCGTAGCAAATCAAAAGCAATTTTCGTCTGAAGAACTGAAAAC
ATGAAAAGTGGTCTGCCGACCACCAAAGCGATAATATTCCGCGATTCCGCTGGTAAACAGAAGGTGGTC
AGTATACCGGTTTTGAAATTAGCAATCATAATAGCGACTTCATCATCAAGATTCCGTTTGGTGTTGGCA
GGTCAAAAAAGAGATTGATAAATATCGTCGTGGGGAGAAATTTGACTTTGAACAGGTCAGAAAAGCCCG
AAACCGATTAGCCTGCTGCTGAGCACCCAGCGTGTAAACGTAATAACAAGTTGGAGCAAGGTACAATGAAGGCA
CCGAAGCCGAAAAAAACGGCAATGAAGCCAGTACATTGATGTTCCGAAATTGATAATGATAAAGGTGTG
CAAATCGGTTGAAAAAAAGCGCATGATGATGTGGTATGATGTTATCACCGCTGGTTTGCCGAATAACAATGCAT
GATCCGAGCATTATTGGTGGTATTAGCGATAACGACCTGTTGCACTTCAGGAAAAATGTTTGCACGTCGTGTAT
TTAGCCGTTATATGCATCAGCGATAAACCGTCATAAAACCGTGCAGGTCAGGTGCAAAAACTGAACCGATCACCATT
CCTGCTGAAAAAAACCGATAACGTTTCCCAAAGTTGGCATGAACGTTGGCATGTGAATCGCGGATTTCT
CTGACCCGAAAAAGTGACGTTTCGTAAAGTTGCACCGCAGAAAAGCTGATTAAAATCTGGAAAGCATGAAACGTAAAGAGGACAGTA
TCATTAAAACAAGTTGGCACCGTCAGATGGAAATCTGGAAAGCATGAAACGTAAAGTAAAGAGGACAGTA
TTTTAACATTCGCCTGCGTGCCTGCGCGCAGAAATGCAGAACAACAAATTCAAACTGAAG
CAGTATGGCATCGAATTCGTAAAGTTGCACCGAAGCCCCACTGTAAAATGCGAAAATGCCATC
CTTCAAAGAAAAAGCCGATTATAATGCAGCCCTGAATATTTCAAACCCGAACTTAAATGCGAAAAGAG
GAACCGTAAATATTTATACTTTATCTTCATTTGACAAATGAGAATGTTATCCCAGATAACATTTG
ATGTACACAGATTCACACTTCACTGATAAATGGAGAACCGTTCACCAAAAGTCCTTAAGGGGATT
AGAACTGAGTGAAGTGGGCTGCTTGCATCAGCCTAATGTCGAGAAGTCGTTTCTCGAAAGTAACCC
TCGAACAATTCATTTTCCTCTCCAATTCTGCACAAAAAGGTGAGTCCTTATAACCGGCGTGCAG

FIG. 24I

```
AACGCCCGGCTCACCTTTTTCTTCATTCGATTTATGCTTAAAGCCGTAAAAACGCGGAATTCGGCGCC
GTTGCAGAACCCGAATAGACGAATGAAGGAATGCAACTACCTTACACCGCTTGCCAAAGTTGTCAGAAGA
TAATCTTGCAGAACCGAATAGAACGAATGAAGGAATGCAATCTTGACAGAGCCGATTGCGTTATCTCCA
GGAGAACATATAAAGCATCAACCCTGATCGGACTAGAGTCACACTGGCTCACCTTCGGGTGGCCTT
TCTGGGTTTATACCTAGGGATATATATTCCGCTTCCTCGCTCACTGACTCGCTACGCTCGGTCGTTGACTG
CGGCGACGGAAATGCTTACGACGGGGGCGGAGATTTCCTGAAGATGCCAGGAAGATACTTAACAGG
AAGTGAGAGGCCGCGGCAAAGCCGTTTTCCATAGCGCTCCGCCCCCGTCGACAAGCATCACGAAATCGA
CGGTCAAATCAGTGGTGCGAAACCGACAGGACTATAAAGATACCAGGCGTTTCCCCTGCCGCTCCC
TCGTGCGCTCTCGTTCCTGCCTTTGCGGGTTTACCGGGTGCATTCCGGTTATGGCCGCGTTGTCTCA
TTCCACGCCTGACACTCAGTTCCGGGTAGCGCAGTTCGCTCCAAGTCTGACTGTATGCACGAACCCCGT
TCAGTCCGACGCTGCGCCTTATCCGGTAACTATGTCTTGAGTCCAACCGGAAAGACATGCAAAGCA
CCACTGCAGCAGCACTGGTAATTGATTTAGAGGAGTTAGTCTTGAAGTCATGCGCCGGTTAAGCTAA
ACTGAAAGGACAAGTTTGGTGACTGCGCTCTCCAAGCCAGTACCTCGGTTCAAGAGTTGGTAGCTC
AGAGAACCTTGAAAACCGCCTGCAAACCGGGCTGCAAGAAGATTACGCGCAGACC
AAACGATCTCAAGAAGATCATCTTATTAATCAGATAAATATTTCTAGAGTTCAGTGCAATTTATCTCT
TCAAATGTAGCACCTGAAGTCAGCCCATACGATATAAGTTGTTACTAGTGGTATTCTCACCAATAA
AAACGCCGGGCAACCGAGGTTCTGAACAAATCCAGAATGGAGTTCTGAGGTCATTACTGGATCTAT
CAACAGGAGTCAAGCGAGCTGATATCAATTACGCCCGCCATCATGAACTGCACGTGTGTAA
TTCATTAAGCATTCTGCCGACATTGCCAGGAAGCCATGCACAAACGCATGATGAACTGAATGCCAGCGATC
AGCAGCTTGTGCCTTGCTTGCGTATATATTGCCATGGTGAAAACGGGGCGAAGAAGTTGTCCATATTGG
CCACGTTTAAATCAACTGGGTAAACTCACCCCAGGATTGGCTGAGACGAAAAACATATTCTCAATAAA
CCCTTTAGGGAAATAGGCCAGGTTTCACTCCAGAGCCACGTCTTCATTGCCATACGAATTCCGGATGAGCATT
CGGAAATGTCGTGGTATTCACTCCAGAGCCGATGAAACGTTCAGTTTGCTCAGTAAACGGTGTAAC
AAGGGTGAACACTATCCCATATCACCAGTCGAAGAATTGAGGCAAACTTGTCTTATTCTTACGGTCTTAAA
CATCAGGCGGGCAAGAATGTAATAAGGCCCGATAAACCTCGAAATGTACATTAGTAAGCAACTGAATGAGCAAT
AAGGCCGTAATATCCAGTGAACGGTCTGGTTATAGGTACATTGAGCAACTGAAATGCCTCAAAAT
GTTCTTTACGATGCCATTGGGATATATCAACGGTGTATATCAACGGTGTATATCACGGGATATTTTTCTCCATTTAGCTTC
CTTAGCTCCCTGAAATCTGATAACTCAAAAAATACGCCCGGTAGTATCTTATTCATTATGGTGAAAG
TTGGAACTCTTACGTGCCGATCAACGTCTCATTTCGCCAGATATCGACGTCTTAAGACCCACTTCAC
ATTTAAGTTGTTTTCTAATCCGCATATGAAATCAAGGCCGAATAAGAAGGCTGGCTCGCACCTTG
GTGATCAAATAATTCGATAGCTTGTCGTAATACGCAACTAAAGTAGTAGGCATATCAGTAGTAGGCCCACAGCGCTGAGTG
TCTTAGCGACTTGATGTCTCTTGATCTTCCAATACGCAACTAAAGTAAAAGTAAATGCCCCACAGCGCTGAGTG
```

FIG. 24J

CATATAATGCATTCTCTAGTGAAAAACCCTGTTGTTGGCATAAAAAGGCTAATTGATTTTCGAGAGTTTCATA
CTGTTTTCTGTAGGCCGTGTACCTAAATGTACTTTTGATCCATCGCGATGACTTAGTAAAGCACATCTA
AAACTTTTAGCGTTATTACGTAAAAAATCTTGCCAGCTTTCCCCTTCTAAAGGGCAAAGTGAGTATGGT
GCCTATCTAACATCTCAATGGCTAAGGCGTCGAGCAAAGCCCGCTTATTTTTACATGCCAATACAATGT
AGGCTGCTCTACACCTAGCTTCTGGGCGAGTTTACGGGTTGTTAAACCTTGATTCCGACCTCATTAAGC
AGCTCTAATGCGCTGTTAATCACTTTTATCTAATCTAGACACATCAT (SEQ ID NO: 495)

FIG. 24K

Plasmid pLBH545_Tet-Cas14a1_Locus (Addgene Plasmid Number: 112501)

```
TTACTTTTATCTAATCTAGACATCATTAATTCCTAATTTTTGTTGACACTCTATCGTTGATAGAGTTATT
TTACCACTCCCTATCAGTGATAGAGAAAAGAATTCAAAAGATCTAAAGAGGAGAAAGGATCTATGGCCAA
AAACACCATTACCAAACACTGAAACTGCGTATTGTGCGTCCGTATAATAGCGCAGAAGTGGAAAAATT
GTTGCCGACGAAAAAACAACCCGGAAAAAATGCACTGGAAAAGAACAAAGACAAAGTGAAAGAAGCCT
GCAGCAAACATCGAAAGTTGCAGCATATTGTACCACACAGGTTGAACGTAATGCATGCCGTTTTGTAA
AGCACGTAAACTGGATGACAAATTCTACCAAAAAACTGGGTGGTCAGTTCCGGATGCAGTTTTTGGCAA
GAAATCAGCGAAATTTTGCCAGCAGCTGCAGAAACAGGCAGCAGCAGAAATCTATATCAGAGCCTGAAC
TGTACTACGAGATTTTATCAAAGGCAAAGGTATTGCAAATGCCAGCAGGTTGAAACATTATCTGAGTGA
TGTTTGTTATACCGGTCAGCAGCAAACTGTTAAAACGCAGCAATTGCAAGGTCTGCGTAGCAAATC
AAAAGCAATTTTCGTCTGAAAGAACATGAAAAACATGGGTCTGCCGACCACCAAAGCGATAATT
TCCGATTCCGCTGGTTAACAGAAAGGTGGTCAGTATACCGGTTTGAAATTAGCAATCATAATAGCGA
CTTCATCATCAAGATTCCGTTTGGTCGTTGGCAGGTCAAAAAGAGATTGATAAATATCGTCGTGGGAG
AAATTTGACTTGAACAGGTTCAGAAAAAAAGCCGAAAACCGATTAGCCTGCTGCGAAATCAAAAGTTATGCCGATTA
AGCATTAAAAGGTTGGAGCAAAGATGAAGGCACCGAAGCACCGCAGCAAATCAAAAAGTTATGCCGATTA
TCAGACCAGTACATTGAAGTTAAACGTGGCAGCAAACGTGGTGGTATGCATTATTGGTGGTATGTTGGTGTTA
AGCATTGATGTTCCGAAATTGATAAAGGTACAGTGATAACAATTGCATTTAGCCGTTATAGCCGGATAACGACCGTTTCA
AATCACCGCTGGTTGCGCAATTAACAATGCATTTAGCCGTTATAGCCGGATAACGACCGTTTCA
CTTCAACAAGAAATGTTTGCAGTCTGTCGTATCCTCTGCTGAAAAAAAACCGTCATAAACGTGCAGGTCAT
GGTTGCAAAAAACTGAAACTGAAACCGATCACCATTCTGACCGAAAAAAAGTGAACGTTTCGCAAAAGCTGA
TTGAACGGTTGGCATGTGAAATCGCGGATTCTTCTTCATTAAAACAAGTTGGCACCGTGCACGTATGCA
TCTGGAAAGCATGAAAGCATGAAACGTAAAGAGGACAGCTATTTTAACATTGCCTGCGTGGCCGTATGCA
GAAATGCAGAACAAATCGAATTCAAACTGAAGCATGGCATGGCATGCAATGCAAATTGTAAGTGCACCGAATA
ATACCAGCAAAACCTGTAGCAAATGTGGCATCTGAACAACTATTCAACTCGAGTACCGCAAGAAAAA
CAAATTCCGCACTTTAAATGCGAAAAATGCAAACTTCAAAGAGGAACCGTAATATCAGCCCTGAAT
ATTCAAACCGCACTTGGAAAATGTTATCCCAGATAACATTGATGTACACAGATTCACACTTCACTGATAAGTGAGA
CAAAAATGAGAATGTTATCCCAGATAACATTGATGTACACAGATTCACACTTCACTGATAAGTGAGA
ACCGCTTCACCAAAAGCTGTCCCTTAGGGATTAGAACTTGAGTGAAGTTGGGCTGCTTGCATCAGCCTA
ATGTCGAGAAGTGCTTCTTCGAAAGTAACCCTCGAAACAAATTCATTTTCCTCTCCAATTCTGCACA
```

FIG. 24L

AAAAAAGGTGAGTCCTTATAAACCGGCGTGCAGAACGGCCGGCTCACCTTTTTCTTCATTCGATTTTATG
CTTAAAGCCGTAAAACGCGGAATTCGCGCCGTTGCAGCCCGTTGCAGAACCGGAATAGACGAATGAAGGAATCCAAC
TACCTTACACCGCTTGCGAAAGTTGTCAGAAGATAATCTGCAGAACCGAATAGACGAATAGAAGGAATG
CAATCTGACAGAGCCCGATTGCGTTATCCGTTATCCAGGAGAAACATATAAAGCATCACACGCTGATCGGACT
AGAGTCACACTGGCTCACCTTCGGGTGGCCTTTCTGCGTTTATACCTAGGGATATATTCCGCTCCTCG
CTCACTGACTGCTACGCTCGGTCGGTCGTTGACGCGGAGCGGAAATGGCTTACGAACGGGGCGAGATT
TCCTGGAAGATGCCAGGAAGATACTTAACAGGAAGTGAGAGGGCGGGCAAAGCCGTTTTCCATAGG
CTCCGCCCCCCTGACAAGCATCAGCGAAATCGACGCTCAAATCAGTGGTGGCGAAACCGACAGACTAT
AAGATACCAGGCGTTTCCCCTGGCGTCCCCTGGCCTCTCGTGCCTCTCCTGTTCCTGCCTTTCGGTTTACCGG
TGTCATTCCGCTGTTATGGCGTGTTTATGCCGGTGTTGTCATCCACGCCACACTGGCAGCCACTGGTAACTCAGTTCCGGGTAGCAGTTCG
CTCCAAGTCTGACTGTATGCACGAACCCGGTAAACTGAAGGACAAGTTTGGTGACTGCGCTCTCCAA
TTAGTCTTGAAGTCATGCGCCGGTTAAGGCCTAAACTGAAAGGACAAGTTTGGTGACTGCGCTCTCCAA
GCCAGTTACCTCGGTTCAAGAGTTGGTAGCTCAGAGACAACTTGAAAACGCCCTGCAAGGCGGTTTT
TCGTTTTTCAGAGCAAGAGATTACGCCAGACCAAACGATCTCAAGAAGATCATCTTATTAATCAGATA
AAATATTTCTAGATTCAGTGCAATTTATCTCTTCAAATGTAGCACCTGAAGTCAGCCCATACGATATA
AGTTGTTACTAGTGCTTGGATTCTCACCAATAAAAAACGCCGGCGCAACCGAGCGTTCTGAACAATC
CAGATGGAGTTCTGAGGTCATTACTGGATCTATCAACAGGAGTCCAAGCGAGCTGATATCAAATTACGC
CCCGCCCTGCCACTCATCGCAGTACTGTTGTCATTAAGCATTCTGCCGACATGCCAAGCCATCACAA
ACGGGCATGATGAACCTGGAATCGCCAGCGATCAGCACCTTGCGCCTTGCGTATTAAATATTTGCCATGG
TGAAAACGGGGGCGAAGAGAGTTGTCATATTGGCCACGTTGTCCAATCAAACTGGTGAACCTGAACCTCACCCAGGG
ATTGGCTGAGACGAAAACATATTCTCAATAAACCCTTTAGGAAATAGGCCAGTTCACCGTAACAC
GCCACACTGTTCGAATATGTGTAGAACCTGTAGAACCTTCACTTCACACTCAGAGCGATGAA
ACGTTCAGTTGCTCATGGAAACGGTGTAACAAGGGTGAACACTATCCATATCACCAGCTCACCGTC
TTTCATTGCCATAGACGAAATTCCGATGAGCATTCATCCGGGCAAGAATGTGAATAAGGCCGGATAA
AACTTGTGCTTATTTCTTTACGGTCTTAAAAGGCCGTAATATCCAGCTGAACGGTCGGTTATAGG
TACATTGAGCAACTGACGAAATGCCTCAAAGTTCTTTACGATGCCATTGGGATATATCAACGGTGGT
ATATCCAGTGATTTTTCCATTTAGCTTCCTTAGCTCCTGAAATCTGATAACTCAAAATACG
CCCGGTAGTGATCTTATTCATTATGGTGAAAGTTGAACCTCTACGTCCGATCACGTCTCATTTC
GCCAGATATGACGTCTTAAGACCACTTCACATTTAAGTTGTTTCTAATCCGCATATGATCAATTC
AAGGCGAATAAGAAGGCTGGCTCGCACCTGGTCAACCTGGTGATCAAATAATTCGATAGCTTGTCGTAATAATGGC
GGCATACTACTATCAGTAGTAGGTGTTTCCCTTCTCTTTAGGACTTGATGCTCTGATCTTGATCTTCCAATAGC

FIG. 24M

AACCTAAAGTAAAATGCCCCACAGCGCTGAGTGCATATAATGCATTCTCTAGTGAAAAACCTTGTTGGCA
TAAAAGGCTAAATTGATTTCGAGAGTTTCATACTGTTTTCTGTAGGCCGTGTACCTAAATGTACTTTT
GCTCCATGCGATGACTTAGTAAAGCACATCTAAAACTTTAGCGTTATTACGTAAAAAATCTTGCCAGC
TTTCCCTTCTAAAGGGCAAAGTGAGTATGGTGCCTATCTAACATCTCAATGGCTAAGGCGTCGAGCAA
AGCCCGCTTATTTTTACATGCCAATACAATGTAGGCTCTCTACACCTAGCTTCTGGGCGAGTTACGG
GTTGTTAAACCTTCGATTCCGACCTCATTAAGCAGCTCTAATGCGCTGTTAATCACT (SEQ ID NO. 496)

FIG. 24N

Plasmid pLBH31_MBP-Cas14a1 expression (Addgene Plasmid Number: 112500)

ACCCACGCCGAAACAAGGCTCATGAGCCGAAGTGGCGAGCCCGATCTTCCCCATCGGTGATGTCGGCG
ATATAGGGCCAGCAACCGCACCTGTGGCCGGCCGGTGATGCCGGCCACGATGCGTCCGCGTAGAGGATCG
AGATCTCGATCCCGGAAATTAATACGACTCACTATAGGGAGACCACAACGGTTTCCCTCTAGTGCCGGC
TCCGGAGAGCTCTTTAATTAAGCGGCCGCCCTCGCAGACTGCGAGTTCTAGAAATAATTTTGTTTAACTTT
AAGAAGGAGATATACATATGAAATCTTCTCACCATCACCATCACCATCACCATGGTTCTTCTAT
GAAATCGAAGAAGGTAAACTGGTAATCTGATTAACGGCGATAAAGGCTATAACGGTCGCTGAAGTC
GGTAAGAAATTCGAGAAGATACCGGAACATTAAGTCACCGTTGAGCATCCGGATAAACTGGAAGAGAAAT
TCCCACAGGTTGCGCAACTGGGATGCCCTGACATTATCTTCTGGCACACGACCGCTTGGTGGCTA
CGGTCAATCTGGCCTGTTGGCTGAAATCACCCGGACAAAGGTTCCAGACAAGTGTATCCGTTACC
TGGGATGCCGTACGTTACAACGGCAAGTGATTGCTTACCGTGTTGAACCGTGTTATCGCTGATTT
ATAACAAAGATCTGCTGCCGAACCGCCAAAACCTGGAAGAGATCCCGGCTGTGATAAGAACTGAA
AGCGAAAGGTAAGAGCGCGCTGATGTTCAACCTGAGTCCGTACTTCACCTGCCGCTGATTGCTGCT
GACGGGGTTATGCGTTCAAGTAGTGAAAACGGCATATGATGAAAACACATTAAAGACGTGGGCCTGATAACGCTG
GCGCGAAAGCGGGTCTGAACCTTCCTGGTTGACCTGATTAAAACAAACATGAATGCAGACACCGATTA
CTCCATTGCCAGAAGCTGCCTTTAATAAAGCGAACAGCGATGACCATCAACGCCCCGTGGGCATGGTCC
AACATCGACACCAGCAAGTGAATTATGGTGTAACGGTTACTGCCGACCTTCAAGGGTCAACCATCCAAAC
CGTTCGTTGCGGTTGACCCAGGCGCAGTATTAACGCGCCCAGTCGAACAGCAAAGAGCTGCAAAGAGTTCCT
CGAAAACTATCTGCTGACTGAAGGTCTGGAAGGGTTAATAAAGACAAACCGCTGGGTGCCGTAGCG
CTGAAGTCTTACGAGGAAGAGTTGGCGAAGATCCACGTTTCGTTTGCGTATGCCGGGTACTGCCGGTGATCAACGC
GTGAAATCATGCCGAACATCCCGCAGATGTCCGTTGCGGAACCGCCAGACTAATTGAGCTCGAACAACAAC
CGCCAGCGGTCGTCAGACTGTGATGAAGCCTGGAAGCCCTGAAAGAAAACCTGTACTTCCAATCCAATGGCCAAA
AACAATAACAATAACAAACCTGGAATCGAAACTGCGTATTGTGCGTATATATGCGAAAGAACAAAGACAAGAAGGAAAAATTGT
ACCATTACCAAAAACAACCGGACAAACCTGAAACTGCACTGAAAAAGAACAAAGACAAGTGAAGAAGCCTGC
AGCAAACATCGAAAACAACCGGAGCATATGTACCACACAGGTTGAAGTAATGCATGCCTGTTTGTAAAG
CACGTAAACTGGATGACAAATTCTACCAAAAACTGGGTCAGTTTCCGGATGCAGTTTCCGCAAGA
AATCAGCGAAATTTTCGCCAGCTGCAGAAACAGGCAGCAGAAATCTATAATCAGAGCCTGATCGAACTG

ATCTCAACAGCGGTAAGATCCTTGAGAGTTTGCCCGAAGAAGTTTCCAATGATGAGCACTTTAA
AGTTCTGCTATGTGGCGCGGTATTATCCCGTTGACGCGGGCAAGAGCAACTCGGTCGCCGCATACAC
TATTCTCAGAATGACTTGGTTGACTACTCACCAGTCACAGTGATAAAAGCATCTTACGGATGGCATGACAGTAA
GAGAATTATGCAGTGCTGCCATAACCATGAGTGATAACACTGCGGCCAACTTACTTCTGACAACGATCGG
AGGACCGAAGGAGCTAACGCTTTTTGCACAACGATCATGTAACTGCCTTGATCGTTGGGAA
CCGGAGCTGAATGAAGCCATACCAAACGTGACCGTGACCACGATGCTGCAGCAATGGCAACACGT
TGCGCAAACTATTAACTGGCGAACTACTTCACTCCGGCAACAATTAATAGACTGGATGGAGGC
GGATAAAGTTGCAGGACCACTTCTGCGCTCGCCGTTCGGCTGCCTGGTTTATTGCTGATAAATCTGGA
GCCGGTGAGCGTGGGTCTCGCGGTATCATTGCAGCACTGGGCCAGATGGTAAGCCCTCCGTATCGTAG
TTATCTACACGACGGGGAGTCAGGCACCTATGGATGAACGAAATAGACAGATCCGTGAGATAGGTGCCTC
ACTGATTAAGCATGGTAACTGTCAGACCAAGTTTACTCATATATACTTTAGATTGATTAAAACTTCAT
TTTAATTTAAAGGATCTAGGTGAAGATCCTTTTTGATAATCTCATGACCAAATCCTTAACGTGAGT
TTCGTTCCACTGAGCGTCAGACCCCGTAGAAAAGATCAAAGGATCTTCTTGAGATCCTTTTTCTGCG
CGTAATCTGCTGCTTGCAAACAAAAAAACCACCGCTACCAGCGGTGGTTTGTTTGCCGGATCAAGAGCTA
CCAACTCTTTTTCGAAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCGGACAGGTATCC
GGTAAGCGGCAGGGTCTGGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGGGGCGGAGCC
TATGGAAAAACGCCAGCAACGCGGCCTTTTTACGGTTCCTGGCCTTTTGCTGCGCTTTTGCTCACATGTT
CTTTCCTGCGTTATCCCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCGCTGATGCGGTATTTTC
TCCTTACGCATCTGTGCGGTATTTCACACCGCAATGGTGCACTCTCAGTACAATCTGCTCTGATGCCGCA
TAGTTAAGCCAGTATACACTCCGCTATCGCTACGTGACTGGGTCATGGCTGCGCCCCGACACCGTCTCC
GGGAGCTGCATGTGTCAGAGGTTTTCACCGTCATCACCGAAACGCGCGAGGCAGCTGCGGTAAAGCTCAT
CAGCGTGGTCGTGAAGCGATTCACAGATGTCTGCCTGTTCATCCGCGTCCAGCTCGTTGAGTTTCTCCAG
AAGCGTTAATGTCTGGCTTCTGATAAAGCGGGCCATGTTAAGGGCGGTTTTTTCCTGTTTGGTCACTGAT
GCCTCCGTGTAAGGGGGATTTCTGTTCATGGGGGTAATGATACCGATGAAACGAGAGAGGATGCTCACGA
TACGGGTTACTGATGATGAACAATGCCCGGTACTGAACGTTGTGAGGGTAAAACAACTGGCGGTATGGAT

FIG. 24Q

GCGGCGGACCAGAGAAAATCACTCAGGGTCAATGCCAGGCCTTCGTTAATACAGATGTAGGTGTCCA
CAGGGTAGCCAGCAGCATCCTGCGATGCAGATCCGAAGACATAATGGTCAGGGCGCTGACTTCCGCGTTT
CCAGACTTTACGAAACACGGAAACCGAAGACCATTCATGTTGTTGCTCAGGTCGCAGACGTTTGCAGCA
GCAGTCGCTTCGCTTCACGTTCGCTCGCGTATCGGTGATTCATTCGCTAACCAGTAAGGCAACCCCGCCAGCCT
AGCCGGGTCCTCAACGACAGGAGCACGATCATGCGCACCCGTGGCCAGGACCCAACGCTGCCCGAGATGC
GCCGCGTGCGGCTGCTGAGATGGCGGACGCGATGGATATGTTCTGCCAAGGGTTGCGTTTGCGCATTCAC
AGTTCTCCGCAAGAATTGATTGGCTCCAATTCTTGGAGTGGTGAATCCGTTAGCGAGTGCCGGGCTT
CCATTCAGGTCGAGGTGCCCGGCTCCATGCACCGGCAACGCGGAGGAGCAGACAAGTATAGGC
GGCGCCTACAATCCATGCCAATGCCAACCCGTTCCATGTGCTCGCCGAGGCGGGCATAAATCGCCGTGACGATCAGC
GGTTCCAATGATGAAGTTAGGCTGGTAAGAGCCGGAGATCTTGAAGCTGTCCTGATGTCGTCAT
CTACCTGCCTGGACAGCAGCCATGGCCTGCGTCGCGAACGCCAGCGTAGCGCAAGACCCAGCGTCGCCATGCCG
GGGAAGGCCATCCAGCCTTCTGCCGAAACGTTTGGCGGACCAGTAGCGAAGGCTTGAGCGAGGGGT
GCGATAATGGCCGCTTCTCGCCGAAACGTTTGGCGGGACCAGTAGCGAAGGCTTGAGCGAGGGGT
GCAAGATTCCGAATACCGCAAGCGACAGGCCGACCATCGTCGCCTCCAGGAAAGCGTCCTCGCGAA
AATGACCCAGAGCGCTGCCGCCACCTGTCCTACGAGTTGCATGATAAAGAAGACAGTCATAAGTGCGGCG
ACGATAGTCATGCCCCGCCTGCATTAGGAAGCAGCCAGTAGTAGGTTGAAGGCTCTCAAGGCATCGGTGAC
GCTCTCCCTTATGCGACTCCTGCATTAGGAAGCAGCCAGTAGTAGGTTGAGGCGTTGAGCACCGCGC
CGCAAGGAATGGTGCATGCAAGGAGATGGCGCCAACAGTCCCCGGCCCACGGGGCCTGCCACCAT (SEQ ID NO: 497)

SEQUENCE LISTING

<160> NUMBER OF SEQ ID NOS: 373

<210> SEQ ID NO 1
<211> LENGTH: 500
<212> TYPE: PRT
<213> ORGANISM: Artificial sequence
<220> FEATURE:
<223> OTHER INFORMATION: Synthetic sequence

<400> SEQUENCE: 1

```
Met Glu Val Gln Lys Thr Val Met Lys Thr Leu Ser Leu Arg Ile Leu
1               5                   10                  15

Arg Pro Leu Tyr Ser Gln Glu Ile Glu Lys Glu Ile Lys Glu Glu Lys
            20                  25                  30

Glu Arg Arg Lys Gln Ala Gly Gly Thr Gly Glu Leu Asp Gly Gly Phe
        35                  40                  45

Tyr Lys Lys Leu Glu Lys Lys His Ser Glu Met Phe Ser Phe Asp Arg
    50                  55                  60

Leu Asn Leu Leu Leu Asn Gln Leu Gln Arg Glu Ile Ala Lys Val Tyr
65                  70                  75                  80

Asn His Ala Ile Ser Glu Leu Tyr Ile Ala Thr Ile Ala Gln Gly Asn
                85                  90                  95

Lys Ser Asn Lys His Tyr Ile Ser Ser Ile Val Tyr Asn Arg Ala Tyr
            100                 105                 110

Gly Tyr Phe Tyr Asn Ala Tyr Ile Ala Leu Gly Ile Cys Ser Lys Val
        115                 120                 125

Glu Ala Asn Phe Arg Ser Asn Glu Leu Leu Thr Gln Gln Ser Ala Leu
    130                 135                 140
```

```
Pro Thr Ala Lys Ser Asp Asn Phe Pro Ile Val Leu His Lys Gln Lys
145                 150                 155                 160

Gly Ala Glu Gly Glu Asp Gly Phe Arg Ile Ser Thr Glu Gly Ser
            165                 170                 175

Asp Leu Ile Phe Glu Ile Pro Ile Pro Phe Tyr Glu Tyr Asn Gly Glu
                180                 185                 190

Asn Arg Lys Glu Pro Tyr Lys Trp Val Lys Gly Gly Gln Lys Pro
            195                 200                 205

Val Leu Lys Leu Ile Leu Ser Thr Phe Arg Arg Gln Arg Asn Lys Gly
210                 215                 220

Trp Ala Lys Asp Glu Gly Thr Asp Ala Glu Ile Arg Lys Val Thr Glu
225                 230                 235                 240

Gly Lys Tyr Gln Val Ser Gln Ile Glu Ile Asn Arg Gly Lys Lys Leu
            245                 250                 255

Gly Glu His Gln Lys Trp Phe Ala Asn Phe Ser Ile Glu Gln Pro Ile
            260                 265                 270

Tyr Glu Arg Lys Pro Asn Arg Ser Ile Val Gly Gly Leu Asp Val Gly
            275                 280                 285

Ile Arg Ser Pro Leu Val Cys Ala Ile Asn Asn Ser Phe Ser Arg Tyr
290                 295                 300

Ser Val Asp Ser Asn Asp Val Phe Lys Phe Ser Lys Gln Val Phe Ala
305                 310                 315                 320

Phe Arg Arg Arg Leu Leu Ser Lys Asn Ser Leu Lys Arg Lys Gly His
                325                 330                 335

Gly Ala Ala His Lys Leu Glu Pro Ile Thr Glu Met Thr Glu Lys Asn
            340                 345                 350

Asp Lys Phe Arg Lys Ile Ile Glu Arg Trp Ala Lys Glu Val Thr
            355                 360                 365

Asn Phe Phe Val Lys Asn Gln Val Gly Ile Val Gln Ile Glu Asp Leu
370                 375                 380

Ser Thr Met Lys Asp Arg Glu Asp His Phe Phe Asn Gln Tyr Leu Arg
385                 390                 395                 400

Gly Phe Trp Pro Tyr Tyr Gln Met Gln Thr Leu Ile Glu Asn Lys Leu
                405                 410                 415

Lys Glu Tyr Gly Ile Glu Val Lys Arg Val Gln Ala Lys Tyr Thr Ser
            420                 425                 430

Gln Leu Cys Ser Asn Pro Asn Cys Arg Tyr Trp Asn Asn Tyr Phe Asn
            435                 440                 445

Phe Glu Tyr Arg Lys Val Asn Lys Phe Pro Lys Phe Lys Cys Glu Lys
            450                 455                 460

Cys Asn Leu Glu Ile Ser Ala Asp Tyr Asn Ala Ala Arg Asn Leu Ser
465                 470                 475                 480

Thr Pro Asp Ile Glu Lys Phe Val Ala Lys Ala Thr Lys Gly Ile Asn
                485                 490                 495

Leu Pro Glu Lys
            500

<210> SEQ ID NO 2
<211> LENGTH: 507
<212> TYPE: PRT
<213> ORGANISM: Artificial sequence
<220> FEATURE:
<223> OTHER INFORMATION: Synthetic sequence

<400> SEQUENCE: 2
```

```
Met Glu Glu Ala Lys Thr Val Ser Lys Thr Leu Ser Leu Arg Ile Leu
1               5                   10                  15

Arg Pro Leu Tyr Ser Ala Glu Ile Glu Lys Ile Lys Glu Lys
            20                  25                  30

Glu Arg Arg Lys Gln Gly Gly Lys Ser Gly Glu Leu Asp Ser Gly Phe
            35                  40                  45

Tyr Lys Lys Leu Glu Lys Lys His Thr Gln Met Phe Gly Trp Asp Lys
    50                  55                  60

Leu Asn Leu Met Leu Ser Gln Leu Gln Arg Gln Ile Ala Arg Val Phe
65                  70                  75                  80

Asn Gln Ser Ile Ser Glu Leu Tyr Ile Glu Thr Val Ile Gln Gly Lys
                85                  90                  95

Lys Ser Asn Lys His Tyr Thr Ser Lys Ile Val Tyr Asn Arg Ala Tyr
            100                 105                 110

Ser Val Phe Tyr Asn Ala Tyr Leu Ala Leu Gly Ile Thr Ser Lys Val
            115                 120                 125

Glu Ala Asn Phe Arg Ser Thr Glu Leu Leu Met Gln Lys Ser Ser Leu
130                 135                 140

Pro Thr Ala Lys Ser Asp Asn Phe Pro Ile Leu Leu His Lys Gln Lys
145                 150                 155                 160

Gly Val Glu Gly Glu Glu Gly Gly Phe Lys Ile Ser Ala Asp Gly Asn
                165                 170                 175

Asp Leu Ile Phe Glu Ile Pro Ile Pro Phe Tyr Glu Tyr Asp Ser Ala
            180                 185                 190

Asn Lys Lys Glu Pro Phe Lys Trp Ile Lys Gly Gly Gln Lys Pro
            195                 200                 205

Thr Ile Lys Leu Ile Leu Ser Thr Phe Arg Arg Gln Arg Asn Lys Gly
            210                 215                 220

Trp Ala Lys Asp Glu Gly Thr Asp Ala Glu Ile Arg Lys Val Ile Glu
225                 230                 235                 240

Gly Lys Tyr Gln Val Ser His Ile Glu Ile Asn Arg Gly Lys Lys Leu
                245                 250                 255

Gly Asp His Gln Lys Trp Phe Val Asn Phe Thr Ile Glu Gln Pro Ile
            260                 265                 270

Tyr Glu Arg Lys Leu Asp Lys Asn Ile Ile Gly Gly Ile Asp Val Gly
            275                 280                 285

Ile Lys Ser Pro Leu Val Cys Ala Val Asn Asn Ser Phe Ala Arg Tyr
            290                 295                 300

Ser Val Asp Ser Asn Asp Val Leu Lys Phe Ser Lys Gln Ala Phe Ala
305                 310                 315                 320

Phe Arg Arg Arg Leu Leu Ser Lys Asn Ser Leu Lys Arg Ser Gly His
            325                 330                 335

Gly Ser Lys Asn Lys Leu Asp Pro Ile Thr Arg Met Thr Glu Lys Asn
            340                 345                 350

Asp Arg Phe Arg Lys Lys Ile Ile Glu Arg Trp Ala Lys Glu Val Thr
            355                 360                 365

Asn Phe Phe Ile Lys Asn Gln Val Gly Thr Val Gln Ile Glu Asp Leu
            370                 375                 380

Ser Thr Met Lys Asp Arg Gln Asp Asn Phe Phe Asn Gln Tyr Leu Arg
385                 390                 395                 400

Gly Phe Trp Pro Tyr Tyr Gln Met Gln Asn Leu Ile Glu Asn Lys Leu
            405                 410                 415
```

```
Lys Glu Tyr Gly Ile Glu Thr Lys Arg Ile Lys Ala Arg Tyr Thr Ser
            420                 425                 430

Gln Leu Cys Ser Asn Pro Ser Cys Arg His Trp Asn Ser Tyr Phe Ser
        435                 440                 445

Phe Asp His Arg Lys Thr Asn Asn Phe Pro Lys Phe Lys Cys Glu Lys
    450                 455                 460

Cys Ala Leu Glu Ile Ser Ala Asp Tyr Asn Ala Ala Arg Asn Ile Ser
465                 470                 475                 480

Thr Pro Asp Ile Glu Lys Phe Val Ala Lys Ala Thr Lys Gly Ile Asn
                485                 490                 495

Leu Pro Asp Lys Asn Glu Asn Val Ile Leu Glu
            500                 505

<210> SEQ ID NO 3
<211> LENGTH: 529
<212> TYPE: PRT
<213> ORGANISM: Artificial sequence
<220> FEATURE:
<223> OTHER INFORMATION: Synthetic sequence

<400> SEQUENCE: 3

Met Ala Lys Asn Thr Ile Thr Lys Thr Leu Lys Leu Arg Ile Val Arg
1               5                   10                  15

Pro Tyr Asn Ser Ala Glu Val Glu Lys Ile Val Ala Asp Glu Lys Asn
            20                  25                  30

Asn Arg Glu Lys Ile Ala Leu Glu Lys Asn Lys Asp Lys Val Lys Glu
        35                  40                  45

Ala Cys Ser Lys His Leu Lys Val Ala Ala Tyr Cys Thr Thr Gln Val
    50                  55                  60

Glu Arg Asn Ala Cys Leu Phe Cys Lys Ala Arg Lys Leu Asp Asp Lys
65                  70                  75                  80

Phe Tyr Gln Lys Leu Arg Gly Gln Phe Pro Asp Ala Val Phe Trp Gln
                85                  90                  95

Glu Ile Ser Glu Ile Phe Arg Gln Leu Gln Lys Gln Ala Ala Glu Ile
            100                 105                 110

Tyr Asn Gln Ser Leu Ile Glu Leu Tyr Glu Ile Phe Ile Lys Gly
        115                 120                 125

Lys Gly Ile Ala Asn Ala Ser Ser Val Glu His Tyr Leu Ser Asp Val
130                 135                 140

Cys Tyr Thr Arg Ala Ala Glu Leu Phe Lys Asn Ala Ala Ile Ala Ser
145                 150                 155                 160

Gly Leu Arg Ser Lys Ile Lys Ser Asn Phe Arg Leu Lys Glu Leu Lys
                165                 170                 175

Asn Met Lys Ser Gly Leu Pro Thr Thr Lys Ser Asp Asn Phe Pro Ile
            180                 185                 190

Pro Leu Val Lys Gln Lys Gly Gly Gln Tyr Thr Gly Phe Glu Ile Ser
        195                 200                 205

Asn His Asn Ser Asp Phe Ile Ile Lys Ile Pro Phe Gly Arg Trp Gln
    210                 215                 220

Val Lys Lys Glu Ile Asp Lys Tyr Arg Pro Trp Glu Lys Phe Asp Phe
225                 230                 235                 240

Glu Gln Val Gln Lys Ser Pro Lys Pro Ile Ser Leu Leu Leu Ser Thr
                245                 250                 255

Gln Arg Arg Lys Arg Asn Lys Gly Trp Ser Lys Asp Glu Gly Thr Glu
            260                 265                 270
```

Ala Glu Ile Lys Lys Val Met Asn Gly Asp Tyr Gln Thr Ser Tyr Ile
            275                 280                 285

Glu Val Lys Arg Gly Ser Lys Ile Gly Glu Lys Ser Ala Trp Met Leu
        290                 295                 300

Asn Leu Ser Ile Asp Val Pro Lys Ile Asp Lys Gly Val Asp Pro Ser
305                 310                 315                 320

Ile Ile Gly Gly Ile Asp Val Gly Val Lys Ser Pro Leu Val Cys Ala
                325                 330                 335

Ile Asn Asn Ala Phe Ser Arg Tyr Ser Ile Ser Asp Asn Asp Leu Phe
            340                 345                 350

His Phe Asn Lys Lys Met Phe Ala Arg Arg Ile Leu Leu Lys Lys
            355                 360                 365

Asn Arg His Lys Arg Ala Gly His Gly Ala Lys Asn Lys Leu Lys Pro
        370                 375                 380

Ile Thr Ile Leu Thr Glu Lys Ser Glu Arg Phe Arg Lys Lys Leu Ile
385                 390                 395                 400

Glu Arg Trp Ala Cys Glu Ile Ala Asp Phe Phe Ile Lys Asn Lys Val
                405                 410                 415

Gly Thr Val Gln Met Glu Asn Leu Glu Ser Met Lys Arg Lys Glu Asp
            420                 425                 430

Ser Tyr Phe Asn Ile Arg Leu Arg Gly Phe Trp Pro Tyr Ala Glu Met
        435                 440                 445

Gln Asn Lys Ile Glu Phe Lys Leu Lys Gln Tyr Gly Ile Glu Ile Arg
        450                 455                 460

Lys Val Ala Pro Asn Asn Thr Ser Lys Thr Cys Ser Lys Cys Gly His
465                 470                 475                 480

Leu Asn Asn Tyr Phe Asn Phe Glu Tyr Arg Lys Lys Asn Lys Phe Pro
                485                 490                 495

His Phe Lys Cys Glu Lys Cys Asn Phe Lys Glu Asn Ala Asp Tyr Asn
            500                 505                 510

Ala Ala Leu Asn Ile Ser Asn Pro Lys Leu Lys Ser Thr Lys Glu Glu
            515                 520                 525

Pro

<210> SEQ ID NO 4
<211> LENGTH: 726
<212> TYPE: PRT
<213> ORGANISM: Artificial sequence
<220> FEATURE:
<223> OTHER INFORMATION: Synthetic sequence

<400> SEQUENCE: 4

Met Glu Arg Gln Lys Val Pro Gln Ile Arg Lys Ile Val Arg Val Val
1               5                   10                  15

Pro Leu Arg Ile Leu Arg Pro Lys Tyr Ser Asp Val Ile Glu Asn Ala
            20                  25                  30

Leu Lys Lys Phe Lys Glu Lys Gly Asp Asp Thr Asn Thr Asn Asp Phe
        35                  40                  45

Trp Arg Ala Ile Arg Asp Arg Asp Thr Glu Phe Phe Arg Lys Glu Leu
    50                  55                  60

Asn Phe Ser Glu Asp Glu Ile Asn Gln Leu Glu Arg Asp Thr Leu Phe
65                  70                  75                  80

Arg Val Gly Leu Asp Asn Arg Val Leu Phe Ser Tyr Phe Asp Phe Leu
                85                  90                  95

Gln Glu Lys Leu Met Lys Asp Tyr Asn Lys Ile Ile Ser Lys Leu Phe

```
            100                 105                 110
Ile Asn Arg Gln Ser Lys Ser Ser Phe Glu Asn Asp Leu Thr Asp Glu
            115                 120                 125

Glu Val Glu Glu Leu Ile Glu Lys Asp Val Thr Pro Phe Tyr Gly Ala
            130                 135             140

Tyr Ile Gly Lys Gly Ile Lys Ser Val Ile Lys Ser Asn Leu Gly Gly
145                 150                 155                 160

Lys Phe Ile Lys Ser Val Lys Ile Asp Arg Glu Thr Lys Lys Val Thr
                165                 170                 175

Lys Leu Thr Ala Ile Asn Ile Gly Leu Met Gly Leu Pro Val Ala Lys
                180                 185                 190

Ser Asp Thr Phe Pro Ile Lys Ile Lys Thr Asn Pro Asp Tyr Ile
            195                 200                 205

Thr Phe Gln Lys Ser Thr Lys Glu Asn Leu Gln Lys Ile Glu Asp Tyr
            210                 215                 220

Glu Thr Gly Ile Glu Tyr Gly Asp Leu Leu Val Gln Ile Thr Ile Pro
225                 230                 235                 240

Trp Phe Lys Asn Glu Asn Lys Asp Phe Ser Leu Ile Lys Thr Lys Glu
                245                 250                 255

Ala Ile Glu Tyr Tyr Lys Leu Asn Gly Val Gly Lys Lys Asp Leu Leu
                260                 265                 270

Asn Ile Asn Leu Val Leu Thr Thr Tyr His Ile Arg Lys Lys Lys Ser
                275                 280                 285

Trp Gln Ile Asp Gly Ser Ser Gln Ser Leu Val Arg Glu Met Ala Asn
                290                 295                 300

Gly Glu Leu Glu Glu Lys Trp Lys Ser Phe Phe Asp Thr Phe Ile Lys
305                 310                 315                 320

Lys Tyr Gly Asp Glu Gly Lys Ser Ala Leu Val Lys Arg Arg Val Asn
                325                 330                 335

Lys Lys Ser Arg Ala Lys Gly Glu Lys Gly Arg Glu Leu Asn Leu Asp
                340                 345                 350

Glu Arg Ile Lys Arg Leu Tyr Asp Ser Ile Lys Ala Lys Ser Phe Pro
                355                 360                 365

Ser Glu Ile Asn Leu Ile Pro Glu Asn Tyr Lys Trp Lys Leu His Phe
                370                 375                 380

Ser Ile Glu Ile Pro Pro Met Val Asn Asp Ile Asp Ser Asn Leu Tyr
385                 390                 395                 400

Gly Gly Ile Asp Phe Gly Glu Gln Asn Ile Ala Thr Leu Cys Val Lys
                405                 410                 415

Asn Ile Glu Lys Asp Asp Tyr Asp Phe Leu Thr Ile Tyr Gly Asn Asp
                420                 425                 430

Leu Leu Lys His Ala Gln Ala Ser Tyr Ala Arg Arg Ile Met Arg
                435                 440                 445

Val Gln Asp Glu Tyr Lys Ala Arg Gly His Gly Lys Ser Arg Lys Thr
            450                 455                 460

Lys Ala Gln Glu Asp Tyr Ser Glu Arg Met Gln Lys Leu Arg Gln Lys
465                 470                 475                 480

Ile Thr Glu Arg Leu Val Lys Gln Ile Ser Asp Phe Phe Leu Trp Arg
                485                 490                 495

Asn Lys Phe His Met Ala Val Cys Ser Leu Arg Tyr Glu Asp Leu Asn
                500                 505                 510

Thr Leu Tyr Lys Gly Glu Ser Val Lys Ala Lys Arg Met Arg Gln Phe
                515                 520                 525
```

-continued

```
Ile Asn Lys Gln Gln Leu Phe Asn Gly Ile Glu Arg Lys Leu Lys Asp
    530                 535                 540

Tyr Asn Ser Glu Ile Tyr Val Asn Ser Arg Tyr Pro His Tyr Thr Ser
545                 550                 555                 560

Arg Leu Cys Ser Lys Cys Gly Lys Leu Asn Leu Tyr Phe Asp Phe Leu
                565                 570                 575

Lys Phe Arg Thr Lys Asn Ile Ile Arg Lys Asn Pro Asp Gly Ser
                580                 585                 590

Glu Ile Lys Tyr Met Pro Phe Phe Ile Cys Glu Phe Cys Gly Trp Lys
    595                 600                 605

Gln Ala Gly Asp Lys Asn Ala Ser Ala Asn Ile Ala Asp Lys Asp Tyr
    610                 615                 620

Gln Asp Lys Leu Asn Lys Glu Lys Glu Phe Cys Asn Ile Arg Lys Pro
625                 630                 635                 640

Lys Ser Lys Lys Glu Asp Ile Gly Glu Glu Asn Glu Glu Arg Asp
                645                 650                 655

Tyr Ser Arg Arg Phe Asn Arg Asn Ser Phe Ile Tyr Asn Ser Leu Lys
                660                 665                 670

Lys Asp Asn Lys Leu Asn Gln Glu Lys Leu Phe Asp Glu Trp Lys Asn
                675                 680                 685

Gln Leu Lys Arg Lys Ile Asp Gly Arg Asn Lys Phe Glu Pro Lys Glu
    690                 695                 700

Tyr Lys Asp Arg Phe Ser Tyr Leu Phe Ala Tyr Tyr Gln Glu Ile Ile
705                 710                 715                 720

Lys Asn Glu Ser Glu Ser
                725

<210> SEQ ID NO 5
<211> LENGTH: 517
<212> TYPE: PRT
<213> ORGANISM: Artificial sequence
<220> FEATURE:
<223> OTHER INFORMATION: Synthetic sequence

<400> SEQUENCE: 5

Met Val Pro Thr Glu Leu Ile Thr Lys Thr Leu Gln Leu Arg Val Ile
1               5                   10                  15

Arg Pro Leu Tyr Phe Glu Glu Ile Glu Lys Glu Leu Ala Glu Leu Lys
                20                  25                  30

Glu Gln Lys Glu Lys Glu Phe Glu Thr Asn Ser Leu Leu Leu Glu
            35                  40                  45

Ser Lys Lys Ile Asp Ala Lys Ser Leu Lys Lys Leu Lys Arg Lys Ala
    50                  55                  60

Arg Ser Ser Ala Ala Val Glu Phe Trp Lys Ile Ala Lys Glu Lys Tyr
65                  70                  75                  80

Pro Asp Ile Leu Thr Lys Pro Glu Met Glu Phe Ile Phe Ser Glu Met
                85                  90                  95

Gln Lys Met Met Ala Arg Phe Tyr Asn Lys Ser Met Thr Asn Ile Phe
            100                 105                 110

Ile Glu Met Asn Asn Asp Glu Lys Val Asn Pro Leu Ser Leu Ile Ser
        115                 120                 125

Lys Ala Ser Thr Glu Ala Asn Gln Val Ile Lys Cys Ser Ser Ile Ser
    130                 135                 140

Ser Gly Leu Asn Arg Lys Ile Ala Gly Ser Ile Asn Lys Thr Lys Phe
145                 150                 155                 160
```

Lys Gln Val Arg Asp Gly Leu Ile Ser Leu Pro Thr Ala Arg Thr Glu
                165                 170                 175

Thr Phe Pro Ile Ser Phe Tyr Lys Ser Thr Ala Asn Lys Asp Glu Ile
            180                 185                 190

Pro Ile Ser Lys Ile Asn Leu Pro Ser Glu Glu Ala Asp Leu Thr
        195                 200                 205

Ile Thr Leu Pro Phe Pro Phe Phe Glu Ile Lys Lys Glu Lys Lys Gly
    210                 215                 220

Gln Lys Ala Tyr Ser Tyr Phe Asn Ile Ile Glu Lys Ser Gly Arg Ser
225                 230                 235                 240

Asn Asn Lys Ile Asp Leu Leu Leu Ser Thr His Arg Arg Gln Arg Arg
                245                 250                 255

Lys Gly Trp Lys Glu Glu Gly Gly Thr Ser Ala Glu Ile Arg Arg Leu
            260                 265                 270

Met Glu Gly Glu Phe Asp Lys Glu Trp Glu Ile Tyr Leu Gly Glu Ala
        275                 280                 285

Glu Lys Ser Glu Lys Ala Lys Asn Asp Leu Ile Lys Asn Met Thr Arg
    290                 295                 300

Gly Lys Leu Ser Lys Asp Ile Lys Glu Gln Leu Glu Asp Ile Gln Val
305                 310                 315                 320

Lys Tyr Phe Ser Asp Asn Asn Val Glu Ser Trp Asn Asp Leu Ser Lys
                325                 330                 335

Glu Gln Lys Gln Glu Leu Ser Lys Leu Arg Lys Lys Val Glu Glu
            340                 345                 350

Leu Lys Asp Trp Lys His Val Lys Glu Ile Leu Lys Thr Arg Ala Lys
        355                 360                 365

Ile Gly Trp Val Glu Leu Lys Arg Gly Lys Arg Gln Arg Asp Arg Asn
    370                 375                 380

Lys Trp Phe Val Asn Ile Thr Ile Thr Arg Pro Pro Phe Ile Asn Lys
385                 390                 395                 400

Glu Leu Asp Asp Thr Lys Phe Gly Gly Ile Asp Leu Gly Val Lys Val
                405                 410                 415

Pro Phe Val Cys Ala Val His Gly Ser Pro Ala Arg Leu Ile Ile Lys
            420                 425                 430

Glu Asn Glu Ile Leu Gln Phe Asn Lys Met Val Ser Ala Arg Asn Arg
        435                 440                 445

Gln Ile Thr Lys Asp Ser Glu Gln Arg Lys Gly Arg Gly Lys Lys Asn
    450                 455                 460

Lys Phe Ile Lys Lys Glu Ile Phe Asn Glu Arg Asn Glu Leu Phe Arg
465                 470                 475                 480

Lys Lys Ile Ile Glu Arg Trp Ala Asn Gln Ile Val Lys Phe Phe Glu
                485                 490                 495

Asp Gln Lys Cys Ala Thr Val Gln Ile Glu Asn Leu Glu Ser Phe Asp
            500                 505                 510

Arg Thr Ser Tyr Lys
        515

<210> SEQ ID NO 6
<211> LENGTH: 481
<212> TYPE: PRT
<213> ORGANISM: Artificial sequence
<220> FEATURE:
<223> OTHER INFORMATION: Synthetic sequence

<400> SEQUENCE: 6

-continued

```
Met Lys Ser Asp Thr Lys Asp Lys Lys Ile Ile Ile His Gln Thr Lys
1               5                   10                  15

Thr Leu Ser Leu Arg Ile Val Lys Pro Gln Ser Ile Pro Met Glu Glu
            20                  25                  30

Phe Thr Asp Leu Val Arg Tyr His Gln Met Ile Ile Phe Pro Val Tyr
        35                  40                  45

Asn Asn Gly Ala Ile Asp Leu Tyr Lys Lys Leu Phe Lys Ala Lys Ile
    50                  55                  60

Gln Lys Gly Asn Glu Ala Arg Ala Ile Lys Tyr Phe Met Asn Lys Ile
65                  70                  75                  80

Val Tyr Ala Pro Ile Ala Asn Thr Val Lys Asn Ser Tyr Ile Ala Leu
                85                  90                  95

Gly Tyr Ser Thr Lys Met Gln Ser Ser Phe Ser Gly Lys Arg Leu Trp
            100                 105                 110

Asp Leu Arg Phe Gly Glu Ala Thr Pro Pro Thr Ile Lys Ala Asp Phe
        115                 120                 125

Pro Leu Pro Phe Tyr Asn Gln Ser Gly Phe Lys Val Ser Ser Glu Asn
    130                 135                 140

Gly Glu Phe Ile Ile Gly Ile Pro Phe Gly Gln Tyr Thr Lys Lys Thr
145                 150                 155                 160

Val Ser Asp Ile Glu Lys Lys Thr Ser Phe Ala Trp Asp Lys Phe Thr
                165                 170                 175

Leu Glu Asp Thr Thr Lys Lys Thr Leu Ile Glu Leu Leu Ser Thr
            180                 185                 190

Lys Thr Arg Lys Met Asn Glu Gly Trp Lys Asn Asn Gly Thr Glu
            195                 200                 205

Ala Glu Ile Lys Arg Val Met Asp Gly Thr Tyr Gln Val Thr Ser Leu
210                 215                 220

Glu Ile Leu Gln Arg Asp Asp Ser Trp Phe Val Asn Phe Asn Ile Ala
225                 230                 235                 240

Tyr Asp Ser Leu Lys Lys Gln Pro Asp Arg Asp Lys Ile Ala Gly Ile
            245                 250                 255

His Met Gly Ile Thr Arg Pro Leu Thr Ala Val Ile Tyr Asn Asn Lys
            260                 265                 270

Tyr Arg Ala Leu Ser Ile Tyr Pro Asn Thr Val Met His Leu Thr Gln
            275                 280                 285

Lys Gln Leu Ala Arg Ile Lys Glu Gln Arg Thr Asn Ser Lys Tyr Ala
            290                 295                 300

Thr Gly Gly His Gly Arg Asn Ala Lys Val Thr Gly Thr Asp Thr Leu
305                 310                 315                 320

Ser Glu Ala Tyr Arg Gln Arg Lys Lys Ile Ile Glu Asp Trp Ile
            325                 330                 335

Ala Ser Ile Val Lys Phe Ala Ile Asn Asn Glu Ile Gly Thr Ile Tyr
            340                 345                 350

Leu Glu Asp Ile Ser Asn Thr Asn Ser Phe Phe Ala Ala Arg Glu Gln
            355                 360                 365

Lys Leu Ile Tyr Leu Glu Asp Ile Ser Asn Thr Asn Ser Phe Leu Ser
    370                 375                 380

Thr Tyr Lys Tyr Pro Ile Ser Ala Ile Ser Asp Thr Leu Gln His Lys
385                 390                 395                 400

Leu Glu Glu Lys Ala Ile Gln Val Ile Arg Lys Lys Ala Tyr Tyr Val
                405                 410                 415
```

Asn Gln Ile Cys Ser Leu Cys Gly His Tyr Asn Lys Gly Phe Thr Tyr
                420                 425                 430

Gln Phe Arg Arg Lys Asn Lys Phe Pro Lys Met Lys Cys Gln Gly Cys
            435                 440                 445

Leu Glu Ala Thr Ser Thr Glu Phe Asn Ala Ala Ala Asn Val Ala Asn
450                 455                 460

Pro Asp Tyr Glu Lys Leu Leu Ile Lys His Gly Leu Leu Gln Leu Lys
465                 470                 475                 480

Lys

<210> SEQ ID NO 7
<211> LENGTH: 358
<212> TYPE: PRT
<213> ORGANISM: Artificial sequence
<220> FEATURE:
<223> OTHER INFORMATION: Synthetic sequence

<400> SEQUENCE: 7

Met Ser Thr Ile Thr Arg Gln Val Arg Leu Ser Pro Thr Pro Glu Gln
1               5                   10                  15

Ser Arg Leu Leu Met Ala His Cys Gln Gln Tyr Ile Ser Thr Val Asn
            20                  25                  30

Val Leu Val Ala Ala Phe Asp Ser Glu Val Leu Thr Gly Lys Val Ser
        35                  40                  45

Thr Lys Asp Phe Arg Ala Ala Leu Pro Ser Ala Val Lys Asn Gln Ala
50                  55                  60

Leu Arg Asp Ala Gln Ser Val Phe Lys Arg Ser Val Glu Leu Gly Cys
65                  70                  75                  80

Leu Pro Val Leu Lys Lys Pro His Cys Gln Trp Asn Gln Asn Trp
                85                  90                  95

Arg Val Glu Gly Asp Gln Leu Ile Leu Pro Ile Cys Lys Asp Gly Lys
                100                 105                 110

Thr Gln Gln Glu Arg Phe Arg Cys Ala Ala Val Ala Leu Glu Gly Lys
            115                 120                 125

Ala Gly Ile Leu Arg Ile Lys Lys Lys Arg Gly Lys Trp Ile Ala Asp
        130                 135                 140

Leu Thr Val Thr Gln Glu Asp Ala Pro Glu Ser Ser Gly Ser Ala Ile
145                 150                 155                 160

Met Gly Val Asp Leu Gly Ile Lys Val Pro Ala Val Ala His Ile Gly
                165                 170                 175

Gly Lys Gly Thr Arg Phe Phe Gly Asn Gly Arg Ser Gln Arg Ser Met
            180                 185                 190

Arg Arg Arg Phe Tyr Ala Arg Arg Lys Thr Leu Gln Lys Ala Lys Lys
        195                 200                 205

Leu Arg Ala Val Arg Lys Ser Lys Gly Lys Glu Ala Arg Trp Met Lys
210                 215                 220

Thr Ile Asn His Gln Leu Ser Arg Gln Ile Val Asn His Ala His Ala
225                 230                 235                 240

Leu Gly Val Gly Thr Ile Lys Ile Glu Ala Leu Gln Gly Ile Arg Lys
                245                 250                 255

Gly Thr Thr Arg Lys Ser Arg Gly Ala Ala Ala Arg Lys Asn Asn Arg
            260                 265                 270

Met Thr Asn Thr Trp Ser Phe Ser Gln Leu Thr Leu Phe Ile Thr Tyr
        275                 280                 285

Lys Ala Gln Arg Gln Gly Ile Thr Val Glu Gln Val Asp Pro Ala Tyr

```
                290                 295                 300
Thr Ser Gln Asp Cys Pro Ala Cys Arg Ala Arg Asn Gly Ala Gln Asp
305                 310                 315                 320

Arg Thr Tyr Val Cys Ser Glu Cys Gly Trp Arg Gly His Arg Asp Thr
                325                 330                 335

Val Gly Ala Ile Asn Ile Ser Arg Arg Ala Gly Leu Ser Gly His Arg
            340                 345                 350

Arg Gly Ala Thr Gly Ala
        355

<210> SEQ ID NO 8
<211> LENGTH: 507
<212> TYPE: PRT
<213> ORGANISM: Artificial sequence
<220> FEATURE:
<223> OTHER INFORMATION: Synthetic sequence

<400> SEQUENCE: 8

Met Ile Ala Gln Lys Thr Ile Lys Ile Lys Leu Asn Pro Thr Lys Glu
1               5                   10                  15

Gln Ile Ile Lys Leu Asn Ser Ile Ile Glu Glu Tyr Ile Lys Val Ser
            20                  25                  30

Asn Phe Thr Ala Lys Lys Ile Ala Glu Ile Gln Glu Ser Phe Thr Asp
        35                  40                  45

Ser Gly Leu Thr Gln Gly Thr Cys Ser Glu Cys Gly Lys Glu Lys Thr
    50                  55                  60

Tyr Arg Lys Tyr His Leu Leu Lys Lys Asp Asn Lys Leu Phe Cys Ile
65                  70                  75                  80

Thr Cys Tyr Lys Arg Lys Tyr Ser Gln Phe Thr Leu Gln Lys Val Glu
                85                  90                  95

Phe Gln Asn Lys Thr Gly Leu Arg Asn Val Ala Lys Leu Pro Lys Thr
            100                 105                 110

Tyr Tyr Thr Asn Ala Ile Arg Phe Ala Ser Asp Thr Phe Ser Gly Phe
        115                 120                 125

Asp Glu Ile Ile Lys Lys Gln Asn Arg Leu Asn Ser Ile Gln Asn
    130                 135                 140

Arg Leu Asn Phe Trp Lys Glu Leu Leu Tyr Asn Pro Ser Asn Arg Asn
145                 150                 155                 160

Glu Ile Lys Ile Lys Val Val Lys Tyr Ala Pro Lys Thr Asp Thr Arg
                165                 170                 175

Glu His Pro His Tyr Tyr Ser Glu Ala Glu Ile Lys Gly Arg Ile Lys
            180                 185                 190

Arg Leu Glu Lys Gln Leu Lys Lys Phe Lys Met Pro Lys Tyr Pro Glu
        195                 200                 205

Phe Thr Ser Glu Thr Ile Ser Leu Gln Arg Glu Leu Tyr Ser Trp Lys
    210                 215                 220

Asn Pro Asp Glu Leu Lys Ile Ser Ser Ile Thr Asp Lys Asn Glu Ser
225                 230                 235                 240

Met Asn Tyr Tyr Gly Lys Glu Tyr Leu Lys Arg Tyr Ile Asp Leu Ile
                245                 250                 255

Asn Ser Gln Thr Pro Gln Ile Leu Leu Glu Lys Glu Asn Asn Ser Phe
            260                 265                 270

Tyr Leu Cys Phe Pro Ile Thr Lys Asn Ile Glu Met Pro Lys Ile Asp
        275                 280                 285

Asp Thr Phe Glu Pro Val Gly Ile Asp Trp Gly Ile Thr Arg Asn Ile
```

```
                290                 295                 300
Ala Val Val Ser Ile Leu Asp Ser Lys Thr Lys Lys Pro Lys Phe Val
305                 310                 315                 320

Lys Phe Tyr Ser Ala Gly Tyr Ile Leu Gly Lys Arg Lys His Tyr Lys
                325                 330                 335

Ser Leu Arg Lys His Phe Gly Gln Lys Lys Arg Gln Asp Lys Ile Asn
                340                 345                 350

Lys Leu Gly Thr Lys Glu Asp Arg Phe Ile Asp Ser Asn Ile His Lys
                355                 360                 365

Leu Ala Phe Leu Ile Val Lys Glu Ile Arg Asn His Ser Asn Lys Pro
                370                 375                 380

Ile Ile Leu Met Glu Asn Ile Thr Asp Asn Arg Glu Glu Ala Glu Lys
385                 390                 395                 400

Ser Met Arg Gln Asn Ile Leu Leu His Ser Val Lys Ser Arg Leu Gln
                405                 410                 415

Asn Tyr Ile Ala Tyr Lys Ala Leu Trp Asn Asn Ile Pro Thr Asn Leu
                420                 425                 430

Val Lys Pro Glu His Thr Ser Gln Ile Cys Asn Arg Cys Gly His Gln
                435                 440                 445

Asp Arg Glu Asn Arg Pro Lys Gly Ser Lys Leu Phe Lys Cys Val Lys
                450                 455                 460

Cys Asn Tyr Met Ser Asn Ala Asp Phe Asn Ala Ser Ile Asn Ile Ala
465                 470                 475                 480

Arg Lys Phe Tyr Ile Gly Glu Tyr Gly Pro Phe Tyr Lys Asp Asn Glu
                485                 490                 495

Lys Met Lys Ser Gly Val Asn Ser Ile Ser Met
                500                 505

<210> SEQ ID NO 9
<211> LENGTH: 534
<212> TYPE: PRT
<213> ORGANISM: Artificial sequence
<220> FEATURE:
<223> OTHER INFORMATION: Synthetic sequence

<400> SEQUENCE: 9

Leu Lys Leu Ser Glu Gln Glu Asn Ile Thr Thr Gly Val Lys Phe Lys
1               5                   10                  15

Leu Lys Leu Asp Lys Glu Thr Ser Glu Gly Leu Asn Asp Tyr Phe Asp
                20                  25                  30

Glu Tyr Gly Lys Ala Ile Asn Phe Ala Ile Lys Val Ile Gln Lys Glu
            35                  40                  45

Leu Ala Glu Asp Arg Phe Ala Gly Lys Val Arg Leu Asp Glu Asn Lys
        50                  55                  60

Lys Pro Leu Leu Asn Glu Asp Gly Lys Ile Trp Asp Phe Pro Asn
65                  70                  75                  80

Glu Phe Cys Ser Cys Gly Lys Gln Val Asn Arg Tyr Val Asn Gly Lys
                85                  90                  95

Ser Leu Cys Gln Glu Cys Tyr Lys Asn Lys Phe Thr Glu Tyr Gly Ile
            100                 105                 110

Arg Lys Arg Met Tyr Ser Ala Lys Gly Arg Lys Ala Glu Gln Asp Ile
        115                 120                 125

Asn Ile Lys Asn Ser Thr Asn Lys Ile Ser Lys Thr His Phe Asn Tyr
    130                 135                 140

Ala Ile Arg Glu Ala Phe Ile Leu Asp Lys Ser Ile Lys Lys Gln Arg
```

```
                145                 150                 155                 160
Lys Glu Arg Phe Arg Arg Leu Arg Glu Met Lys Lys Leu Gln Glu
                    165                 170                 175
Phe Ile Glu Ile Arg Asp Gly Asn Lys Ile Leu Cys Pro Lys Ile Glu
                    180                 185                 190
Lys Gln Arg Val Glu Arg Tyr Ile His Pro Ser Trp Ile Asn Lys Glu
                    195                 200                 205
Lys Lys Leu Glu Asp Phe Arg Gly Tyr Ser Met Ser Asn Val Leu Gly
                    210                 215                 220
Lys Ile Lys Ile Leu Asp Arg Asn Ile Lys Arg Glu Lys Ser Leu
225                 230                 235                 240
Lys Glu Lys Gly Gln Ile Asn Phe Lys Ala Arg Arg Leu Met Leu Asp
                    245                 250                 255
Lys Ser Val Lys Phe Leu Asn Asp Asn Lys Ile Ser Phe Thr Ile Ser
                    260                 265                 270
Lys Asn Leu Pro Lys Glu Tyr Glu Leu Asp Leu Pro Glu Lys Glu Lys
                    275                 280                 285
Arg Leu Asn Trp Leu Lys Glu Lys Ile Lys Ile Ile Lys Asn Gln Lys
                    290                 295                 300
Pro Lys Tyr Ala Tyr Leu Leu Arg Lys Asp Asp Asn Phe Tyr Leu Gln
305                 310                 315                 320
Tyr Thr Leu Glu Thr Glu Phe Asn Leu Lys Glu Asp Tyr Ser Gly Ile
                    325                 330                 335
Val Gly Ile Asp Arg Gly Val Ser His Ile Ala Val Tyr Thr Phe Val
                    340                 345                 350
His Asn Asn Gly Lys Asn Glu Arg Pro Leu Phe Leu Asn Ser Ser Glu
                    355                 360                 365
Ile Leu Arg Leu Lys Asn Leu Gln Lys Glu Arg Asp Arg Phe Leu Arg
                    370                 375                 380
Arg Lys His Asn Lys Lys Arg Lys Lys Ser Asn Met Arg Asn Ile Glu
385                 390                 395                 400
Lys Lys Ile Gln Leu Ile Leu His Asn Tyr Ser Lys Gln Ile Val Asp
                    405                 410                 415
Phe Ala Lys Asn Lys Asn Ala Phe Ile Val Phe Glu Lys Leu Glu Lys
                    420                 425                 430
Pro Lys Lys Asn Arg Ser Lys Met Ser Lys Lys Ser Gln Tyr Lys Leu
                    435                 440                 445
Ser Gln Phe Thr Phe Lys Lys Leu Ser Asp Leu Val Asp Tyr Lys Ala
                    450                 455                 460
Lys Arg Glu Gly Ile Lys Val Leu Tyr Ile Ser Pro Glu Tyr Thr Ser
465                 470                 475                 480
Lys Glu Cys Ser His Cys Gly Glu Lys Val Asn Thr Gln Arg Pro Phe
                    485                 490                 495
Asn Gly Asn Ser Ser Leu Phe Lys Cys Asn Lys Cys Gly Val Glu Leu
                    500                 505                 510
Asn Ala Asp Tyr Asn Ala Ser Ile Asn Ile Ala Lys Lys Gly Leu Asn
                    515                 520                 525
Ile Leu Asn Ser Thr Asn
        530

<210> SEQ ID NO 10
<211> LENGTH: 537
<212> TYPE: PRT
<213> ORGANISM: Artificial sequence
```

<220> FEATURE:
<223> OTHER INFORMATION: Synthetic sequence

<400> SEQUENCE: 10

```
Met Glu Glu Ser Ile Ile Thr Gly Val Lys Phe Lys Leu Arg Ile Asp
1               5                   10                  15

Lys Glu Thr Thr Lys Lys Leu Asn Glu Tyr Phe Asp Glu Tyr Gly Lys
            20                  25                  30

Ala Ile Asn Phe Ala Val Lys Ile Ile Gln Lys Glu Leu Ala Asp Asp
        35                  40                  45

Arg Phe Ala Gly Lys Ala Lys Leu Asp Gln Asn Lys Asn Pro Ile Leu
    50                  55                  60

Asp Glu Asn Gly Lys Lys Ile Tyr Glu Phe Pro Asp Glu Phe Cys Ser
65                  70                  75                  80

Cys Gly Lys Gln Val Asn Lys Tyr Val Asn Asn Lys Pro Phe Cys Gln
                85                  90                  95

Glu Cys Tyr Lys Ile Arg Phe Thr Glu Asn Gly Ile Arg Lys Arg Met
            100                 105                 110

Tyr Ser Ala Lys Gly Arg Lys Ala Glu His Lys Ile Asn Ile Leu Asn
        115                 120                 125

Ser Thr Asn Lys Ile Ser Lys Thr His Phe Asn Tyr Ala Ile Arg Glu
    130                 135                 140

Ala Phe Ile Leu Asp Lys Ser Ile Lys Lys Gln Arg Lys Lys Arg Asn
145                 150                 155                 160

Glu Arg Leu Arg Glu Ser Lys Lys Arg Leu Gln Gln Phe Ile Asp Met
                165                 170                 175

Arg Asp Gly Lys Arg Glu Ile Cys Pro Thr Ile Lys Gly Gln Lys Val
            180                 185                 190

Asp Arg Phe Ile His Pro Ser Trp Ile Thr Lys Asp Lys Lys Leu Glu
        195                 200                 205

Asp Phe Arg Gly Tyr Thr Leu Ser Ile Ile Asn Ser Lys Ile Lys Ile
    210                 215                 220

Leu Asp Arg Asn Ile Lys Arg Glu Glu Lys Ser Leu Lys Glu Lys Gly
225                 230                 235                 240

Gln Ile Ile Phe Lys Ala Lys Arg Leu Met Leu Asp Lys Ser Ile Arg
                245                 250                 255

Phe Val Gly Asp Arg Lys Val Leu Phe Thr Ile Ser Lys Thr Leu Pro
            260                 265                 270

Lys Glu Tyr Glu Leu Asp Leu Pro Ser Lys Glu Lys Arg Leu Asn Trp
        275                 280                 285

Leu Lys Glu Lys Ile Glu Ile Ile Lys Asn Gln Lys Pro Lys Tyr Ala
    290                 295                 300

Tyr Leu Leu Arg Lys Asn Ile Glu Ser Glu Lys Pro Asn Tyr Glu
305                 310                 315                 320

Tyr Tyr Leu Gln Tyr Thr Leu Glu Ile Lys Pro Glu Leu Lys Asp Phe
                325                 330                 335

Tyr Asp Gly Ala Ile Gly Ile Asp Arg Gly Ile Asn His Ile Ala Val
            340                 345                 350

Cys Thr Phe Ile Ser Asn Asp Gly Lys Val Thr Pro Pro Lys Phe Phe
        355                 360                 365

Ser Ser Gly Glu Ile Leu Arg Leu Lys Asn Leu Gln Lys Glu Arg Asp
    370                 375                 380

Arg Phe Leu Leu Arg Lys His Asn Lys Asn Arg Lys Lys Gly Asn Met
385                 390                 395                 400
```

```
Arg Val Ile Glu Asn Lys Ile Asn Leu Ile Leu His Arg Tyr Ser Lys
                405                 410                 415

Gln Ile Val Asp Met Ala Lys Lys Leu Asn Ala Ser Ile Val Phe Glu
            420                 425                 430

Glu Leu Gly Arg Ile Gly Lys Ser Arg Thr Lys Met Lys Lys Ser Gln
        435                 440                 445

Arg Tyr Lys Leu Ser Leu Phe Ile Phe Lys Lys Leu Ser Asp Leu Val
    450                 455                 460

Asp Tyr Lys Ser Arg Arg Glu Gly Ile Arg Val Thr Tyr Val Pro Pro
465                 470                 475                 480

Glu Tyr Thr Ser Lys Glu Cys Ser His Cys Gly Glu Lys Val Asn Thr
                485                 490                 495

Gln Arg Pro Phe Asn Gly Asn Tyr Ser Leu Phe Lys Cys Asn Lys Cys
            500                 505                 510

Gly Ile Gln Leu Asn Ser Asp Tyr Asn Ala Ser Ile Asn Ile Ala Lys
        515                 520                 525

Lys Gly Leu Lys Ile Pro Asn Ser Thr
    530                 535

<210> SEQ ID NO 11
<211> LENGTH: 540
<212> TYPE: PRT
<213> ORGANISM: Artificial sequence
<220> FEATURE:
<223> OTHER INFORMATION: Synthetic sequence

<400> SEQUENCE: 11

Leu Trp Thr Ile Val Ile Gly Asp Phe Ile Glu Met Pro Lys Gln Asp
1               5                   10                  15

Leu Val Thr Thr Gly Ile Lys Phe Lys Leu Asp Val Asp Lys Glu Thr
            20                  25                  30

Arg Lys Lys Leu Asp Asp Tyr Phe Asp Glu Tyr Gly Lys Ala Ile Asn
        35                  40                  45

Phe Ala Val Lys Ile Ile Gln Lys Asn Leu Lys Glu Asp Arg Phe Ala
    50                  55                  60

Gly Lys Ile Ala Leu Gly Glu Asp Lys Lys Pro Leu Leu Asp Lys Asp
65                  70                  75                  80

Gly Lys Lys Ile Tyr Asn Tyr Pro Asn Glu Ser Cys Ser Cys Gly Asn
                85                  90                  95

Gln Val Arg Arg Tyr Val Asn Ala Lys Pro Phe Cys Val Asp Cys Tyr
            100                 105                 110

Lys Leu Lys Phe Thr Glu Asn Gly Ile Arg Lys Arg Met Tyr Ser Ala
        115                 120                 125

Arg Gly Arg Lys Ala Asp Ser Asp Ile Asn Ile Lys Asn Ser Thr Asn
    130                 135                 140

Lys Ile Ser Lys Thr His Phe Asn Tyr Ala Ile Arg Glu Gly Phe Ile
145                 150                 155                 160

Leu Asp Lys Ser Leu Lys Lys Gln Arg Ser Lys Arg Ile Lys Lys Leu
                165                 170                 175

Leu Glu Leu Lys Arg Lys Leu Gln Glu Phe Ile Asp Ile Arg Gln Gly
            180                 185                 190

Gln Met Val Leu Cys Pro Lys Ile Lys Asn Gln Arg Val Asp Lys Phe
        195                 200                 205

Ile His Pro Ser Trp Leu Lys Arg Asp Lys Lys Leu Glu Glu Phe Arg
    210                 215                 220
```

```
Gly Tyr Ser Leu Ser Val Val Glu Gly Lys Ile Lys Ile Phe Asn Arg
225                 230                 235                 240

Asn Ile Leu Arg Glu Glu Asp Ser Leu Arg Gln Arg Gly His Val Asn
            245                 250                 255

Phe Lys Ala Asn Arg Ile Met Leu Asp Lys Ser Val Arg Phe Leu Asp
        260                 265                 270

Gly Gly Lys Val Asn Phe Asn Leu Asn Lys Gly Leu Pro Lys Glu Tyr
    275                 280                 285

Leu Leu Asp Leu Pro Lys Lys Glu Asn Lys Leu Ser Trp Leu Asn Glu
290                 295                 300

Lys Ile Ser Leu Ile Lys Leu Gln Lys Pro Lys Tyr Ala Tyr Leu Leu
305                 310                 315                 320

Arg Arg Glu Gly Ser Phe Phe Ile Gln Tyr Thr Ile Glu Asn Val Pro
            325                 330                 335

Lys Thr Phe Ser Asp Tyr Leu Gly Ala Ile Gly Ile Asp Arg Gly Ile
        340                 345                 350

Ser His Ile Ala Val Cys Thr Phe Val Ser Lys Asn Gly Val Asn Lys
    355                 360                 365

Ala Pro Val Phe Phe Ser Ser Gly Glu Ile Leu Lys Leu Lys Ser Leu
370                 375                 380

Gln Lys Gln Arg Asp Leu Phe Leu Arg Gly Lys His Asn Lys Ile Arg
385                 390                 395                 400

Lys Lys Ser Asn Met Arg Asn Ile Asp Asn Lys Ile Asn Leu Ile Leu
            405                 410                 415

His Lys Tyr Ser Arg Asn Ile Val Asn Leu Ala Lys Ser Glu Lys Ala
        420                 425                 430

Phe Ile Val Phe Glu Lys Leu Glu Lys Ile Lys Lys Ser Arg Phe Lys
    435                 440                 445

Met Ser Lys Ser Leu Gln Tyr Lys Leu Ser Gln Phe Thr Phe Lys Lys
450                 455                 460

Leu Ser Asp Leu Val Glu Tyr Lys Ala Lys Ile Glu Gly Ile Lys Val
465                 470                 475                 480

Asp Tyr Val Pro Pro Glu Tyr Thr Ser Lys Cys Ser His Cys Gly
            485                 490                 495

Glu Lys Val Asp Thr Gln Arg Pro Phe Asn Gly Asn Ser Ser Leu Phe
        500                 505                 510

Lys Cys Asn Lys Cys Arg Val Gln Leu Asn Ala Asp Tyr Asn Ala Ser
    515                 520                 525

Ile Asn Ile Ala Lys Lys Ser Leu Asn Ile Ser Asn
530                 535                 540
```

<210> SEQ ID NO 12
<211> LENGTH: 542
<212> TYPE: PRT
<213> ORGANISM: Artificial sequence
<220> FEATURE:
<223> OTHER INFORMATION: Synthetic sequence

<400> SEQUENCE: 12

```
Met Ser Lys Thr Thr Ile Ser Val Lys Leu Lys Ile Ile Asp Leu Ser
1               5                   10                  15

Ser Glu Lys Lys Glu Phe Leu Asp Asn Tyr Phe Asn Glu Tyr Ala Lys
            20                  25                  30

Ala Thr Thr Phe Cys Gln Leu Arg Ile Arg Arg Leu Leu Arg Asn Thr
        35                  40                  45
```

```
His Trp Leu Gly Lys Lys Glu Lys Ser Ser Lys Lys Trp Ile Phe Glu
    50                  55                  60
Ser Gly Ile Cys Asp Leu Cys Gly Glu Asn Lys Glu Leu Val Asn Glu
65                  70                  75                  80
Asp Arg Asn Ser Gly Glu Pro Ala Lys Ile Cys Lys Arg Cys Tyr Asn
                85                  90                  95
Gly Arg Tyr Gly Asn Gln Met Ile Arg Lys Leu Phe Val Ser Thr Lys
            100                 105                 110
Lys Arg Glu Val Gln Glu Asn Met Asp Ile Arg Arg Val Ala Lys Leu
        115                 120                 125
Asn Asn Thr His Tyr His Arg Ile Pro Glu Glu Ala Phe Asp Met Ile
130                 135                 140
Lys Ala Ala Asp Thr Ala Glu Lys Arg Arg Lys Lys Asn Val Glu Tyr
145                 150                 155                 160
Asp Lys Lys Arg Gln Met Glu Phe Ile Glu Met Phe Asn Asp Glu Lys
                165                 170                 175
Lys Arg Ala Ala Arg Pro Lys Lys Pro Asn Glu Arg Glu Thr Arg Tyr
            180                 185                 190
Val His Ile Ser Lys Leu Glu Ser Pro Ser Lys Gly Tyr Thr Leu Asn
        195                 200                 205
Gly Ile Lys Arg Lys Ile Asp Gly Met Gly Lys Lys Ile Glu Arg Ala
210                 215                 220
Glu Lys Gly Leu Ser Arg Lys Lys Ile Phe Gly Tyr Gln Gly Asn Arg
225                 230                 235                 240
Ile Lys Leu Asp Ser Asn Trp Val Arg Phe Asp Leu Ala Glu Ser Glu
                245                 250                 255
Ile Thr Ile Pro Ser Leu Phe Lys Glu Met Lys Leu Arg Ile Thr Gly
            260                 265                 270
Pro Thr Asn Val His Ser Lys Ser Gly Gln Ile Tyr Phe Ala Glu Trp
        275                 280                 285
Phe Glu Arg Ile Asn Lys Gln Pro Asn Asn Tyr Cys Tyr Leu Ile Arg
290                 295                 300
Lys Thr Ser Ser Asn Gly Lys Tyr Glu Tyr Tyr Leu Gln Tyr Thr Tyr
305                 310                 315                 320
Glu Ala Glu Val Glu Ala Asn Lys Glu Tyr Ala Gly Cys Leu Gly Val
                325                 330                 335
Asp Ile Gly Cys Ser Lys Leu Ala Ala Ala Val Tyr Tyr Asp Ser Lys
            340                 345                 350
Asn Lys Lys Ala Gln Lys Pro Ile Glu Ile Phe Thr Asn Pro Ile Lys
        355                 360                 365
Lys Ile Lys Met Arg Arg Glu Lys Leu Ile Lys Leu Leu Ser Arg Val
370                 375                 380
Lys Val Arg His Arg Arg Lys Leu Met Gln Leu Ser Lys Thr Glu
385                 390                 395                 400
Pro Ile Ile Asp Tyr Thr Cys His Lys Thr Ala Arg Lys Ile Val Glu
                405                 410                 415
Met Ala Asn Thr Ala Lys Ala Phe Ile Ser Met Glu Asn Leu Glu Thr
            420                 425                 430
Gly Ile Lys Gln Lys Gln Gln Ala Arg Glu Thr Lys Lys Gln Lys Phe
        435                 440                 445
Tyr Arg Asn Met Phe Leu Phe Arg Lys Leu Ser Lys Leu Ile Glu Tyr
450                 455                 460
```

```
Lys Ala Leu Leu Lys Gly Ile Lys Ile Val Tyr Val Lys Pro Asp Tyr
465                 470                 475                 480

Thr Ser Gln Thr Cys Ser Ser Cys Gly Ala Asp Lys Glu Lys Thr Glu
            485                 490                 495

Arg Pro Ser Gln Ala Ile Phe Arg Cys Leu Asn Pro Thr Cys Arg Tyr
            500                 505                 510

Tyr Gln Arg Asp Ile Asn Ala Asp Phe Asn Ala Ala Val Asn Ile Ala
            515                 520                 525

Lys Lys Ala Leu Asn Asn Thr Glu Val Val Thr Thr Leu Leu
            530                 535                 540

<210> SEQ ID NO 13
<211> LENGTH: 564
<212> TYPE: PRT
<213> ORGANISM: Artificial sequence
<220> FEATURE:
<223> OTHER INFORMATION: Synthetic sequence

<400> SEQUENCE: 13

Met Ala Arg Ala Lys Asn Gln Pro Tyr Gln Lys Leu Thr Thr Thr Thr
1               5                   10                  15

Gly Ile Lys Phe Lys Leu Asp Leu Ser Glu Glu Glu Gly Lys Arg Phe
                20                  25                  30

Asp Glu Tyr Phe Ser Glu Tyr Ala Lys Ala Val Asn Phe Cys Ala Lys
            35                  40                  45

Val Ile Tyr Gln Leu Arg Lys Asn Leu Lys Phe Ala Gly Lys Lys Glu
        50                  55                  60

Leu Ala Ala Lys Glu Trp Lys Phe Glu Ile Ser Asn Cys Asp Phe Cys
65                  70                  75                  80

Asn Lys Gln Lys Glu Ile Tyr Tyr Lys Asn Ile Ala Asn Gly Gln Lys
                85                  90                  95

Val Cys Lys Gly Cys His Arg Thr Asn Phe Ser Asp Asn Ala Ile Arg
            100                 105                 110

Lys Lys Met Ile Pro Val Lys Gly Arg Lys Val Glu Ser Lys Phe Asn
        115                 120                 125

Ile His Asn Thr Thr Lys Lys Ile Ser Gly Thr His Arg His Trp Ala
    130                 135                 140

Phe Glu Asp Ala Ala Asp Ile Ile Glu Ser Met Asp Lys Gln Arg Lys
145                 150                 155                 160

Glu Lys Gln Lys Arg Leu Arg Arg Glu Lys Arg Lys Leu Ser Tyr Phe
                165                 170                 175

Phe Glu Leu Phe Gly Asp Pro Ala Lys Arg Tyr Glu Leu Pro Lys Val
            180                 185                 190

Gly Lys Gln Arg Val Pro Arg Tyr Leu His Lys Ile Ile Asp Lys Asp
        195                 200                 205

Ser Leu Thr Lys Lys Arg Gly Tyr Ser Leu Ser Tyr Ile Lys Asn Lys
    210                 215                 220

Ile Lys Ile Ser Glu Arg Asn Ile Glu Arg Asp Glu Lys Ser Leu Arg
225                 230                 235                 240

Lys Ala Ser Pro Ile Ala Phe Gly Ala Arg Lys Ile Lys Met Ser Lys
                245                 250                 255

Leu Asp Pro Lys Arg Ala Phe Asp Leu Glu Asn Asn Val Phe Lys Ile
            260                 265                 270

Pro Gly Lys Val Ile Lys Gly Gln Tyr Lys Phe Phe Gly Thr Asn Val
        275                 280                 285
```

-continued

```
Ala Asn Glu His Gly Lys Lys Phe Tyr Lys Asp Arg Ile Ser Lys Ile
    290                 295                 300
Leu Ala Gly Lys Pro Lys Tyr Phe Tyr Leu Leu Arg Lys Lys Val Ala
305                 310                 315                 320
Glu Ser Asp Gly Asn Pro Ile Phe Glu Tyr Tyr Val Gln Trp Ser Ile
                325                 330                 335
Asp Thr Glu Thr Pro Ala Ile Thr Ser Tyr Asp Asn Ile Leu Gly Ile
            340                 345                 350
Asp Ala Gly Ile Thr Asn Leu Ala Thr Thr Val Leu Ile Pro Lys Asn
        355                 360                 365
Leu Ser Ala Glu His Cys Ser His Cys Gly Asn Asn His Val Lys Pro
370                 375                 380
Ile Phe Thr Lys Phe Phe Ser Gly Lys Glu Leu Lys Ala Ile Lys Ile
385                 390                 395                 400
Lys Ser Arg Lys Gln Lys Tyr Phe Leu Arg Gly Lys His Asn Lys Leu
                405                 410                 415
Val Lys Ile Lys Arg Ile Arg Pro Ile Glu Gln Lys Val Asp Gly Tyr
            420                 425                 430
Cys His Val Val Ser Lys Gln Ile Val Glu Met Ala Lys Glu Arg Asn
        435                 440                 445
Ser Cys Ile Ala Leu Glu Lys Leu Glu Lys Pro Lys Lys Ser Lys Phe
    450                 455                 460
Arg Gln Arg Arg Glu Lys Tyr Ala Val Ser Met Phe Val Phe Lys
465                 470                 475                 480
Lys Leu Ala Thr Phe Ile Lys Tyr Lys Ala Ala Arg Glu Gly Ile Glu
                485                 490                 495
Ile Ile Pro Val Glu Pro Glu Gly Thr Ser Tyr Thr Cys Ser His Cys
            500                 505                 510
Lys Asn Ala Gln Asn Asn Gln Arg Pro Tyr Phe Lys Pro Asn Ser Lys
        515                 520                 525
Lys Ser Trp Thr Ser Met Phe Lys Cys Gly Lys Cys Gly Ile Glu Leu
    530                 535                 540
Asn Ser Asp Tyr Asn Ala Ala Phe Asn Ile Ala Gln Lys Ala Leu Asn
545                 550                 555                 560
Met Thr Ser Ala

<210> SEQ ID NO 14
<211> LENGTH: 610
<212> TYPE: PRT
<213> ORGANISM: Artificial sequence
<220> FEATURE:
<223> OTHER INFORMATION: Synthetic sequence

<400> SEQUENCE: 14

Met Asp Glu Lys His Phe Phe Cys Ser Tyr Cys Asn Lys Glu Leu Lys
1               5                   10                  15
Ile Ser Lys Asn Leu Ile Asn Lys Ile Ser Lys Gly Ser Ile Arg Glu
                20                  25                  30
Asp Glu Ala Val Ser Lys Ala Ile Ser Ile His Asn Lys Lys Glu His
            35                  40                  45
Ser Leu Ile Leu Gly Ile Lys Phe Lys Leu Phe Ile Glu Asn Lys Leu
        50                  55                  60
Asp Lys Lys Lys Leu Asn Glu Tyr Phe Asp Asn Tyr Ser Lys Ala Val
65                  70                  75                  80
Thr Phe Ala Ala Arg Ile Phe Asp Lys Ile Arg Ser Pro Tyr Lys Phe
```

```
                      85                  90                  95
Ile Gly Leu Lys Asp Lys Asn Thr Lys Lys Trp Thr Phe Pro Lys Ala
                100                 105                 110

Lys Cys Val Phe Cys Leu Glu Glu Lys Glu Val Ala Tyr Ala Asn Glu
                115                 120                 125

Lys Asp Asn Ser Lys Ile Cys Thr Glu Cys Tyr Leu Lys Glu Phe Gly
            130                 135                 140

Glu Asn Gly Ile Arg Lys Ile Tyr Ser Thr Arg Gly Arg Lys Val
145                 150                 155                 160

Glu Pro Lys Tyr Asn Ile Phe Asn Ser Thr Lys Glu Leu Ser Ser Thr
                165                 170                 175

His Tyr Asn Tyr Ala Ile Arg Asp Ala Phe Gln Leu Leu Asp Ala Leu
                180                 185                 190

Lys Lys Gln Arg Gln Lys Lys Leu Lys Ser Ile Phe Asn Gln Lys Leu
            195                 200                 205

Arg Leu Lys Glu Phe Glu Asp Ile Phe Ser Asp Pro Gln Lys Arg Ile
            210                 215                 220

Glu Leu Ser Leu Lys Pro His Gln Arg Glu Lys Arg Tyr Ile His Leu
225                 230                 235                 240

Ser Lys Ser Gly Gln Glu Ser Ile Asn Arg Gly Tyr Thr Leu Arg Phe
                245                 250                 255

Val Arg Gly Lys Ile Lys Ser Leu Thr Arg Asn Ile Glu Arg Glu Glu
                260                 265                 270

Lys Ser Leu Arg Lys Lys Thr Pro Ile His Phe Lys Gly Asn Arg Leu
            275                 280                 285

Met Ile Phe Pro Ala Gly Ile Lys Phe Asp Phe Ala Ser Asn Lys Val
            290                 295                 300

Lys Ile Ser Ile Ser Lys Asn Leu Pro Asn Glu Phe Asn Phe Ser Gly
305                 310                 315                 320

Thr Asn Val Lys Asn Glu His Gly Lys Ser Phe Phe Lys Ser Arg Ile
                325                 330                 335

Glu Leu Ile Lys Thr Gln Lys Pro Lys Tyr Ala Tyr Val Leu Arg Lys
            340                 345                 350

Ile Lys Arg Glu Tyr Ser Lys Leu Arg Asn Tyr Glu Ile Glu Lys Ile
            355                 360                 365

Arg Leu Glu Asn Pro Asn Ala Asp Leu Cys Asp Phe Tyr Leu Gln Tyr
            370                 375                 380

Thr Ile Glu Thr Glu Ser Arg Asn Asn Glu Glu Ile Asn Gly Ile Ile
385                 390                 395                 400

Gly Ile Asp Arg Gly Ile Thr Asn Leu Ala Cys Leu Val Leu Leu Lys
                405                 410                 415

Lys Gly Asp Lys Lys Pro Ser Gly Val Lys Phe Tyr Lys Gly Asn Lys
            420                 425                 430

Ile Leu Gly Met Lys Ile Ala Tyr Arg Lys His Leu Tyr Leu Leu Lys
            435                 440                 445

Gly Lys Arg Asn Lys Leu Arg Lys Gln Arg Gln Ile Arg Ala Ile Glu
            450                 455                 460

Pro Lys Ile Asn Leu Ile Leu His Gln Ile Ser Lys Asp Ile Val Lys
465                 470                 475                 480

Ile Ala Lys Glu Lys Asn Phe Ala Ile Ala Leu Glu Gln Leu Glu Lys
                485                 490                 495

Pro Lys Lys Ala Arg Phe Ala Gln Arg Lys Lys Glu Lys Tyr Lys Leu
                500                 505                 510
```

```
Ala Leu Phe Thr Phe Lys Asn Leu Ser Thr Leu Ile Glu Tyr Lys Ser
            515                 520                 525

Lys Arg Glu Gly Ile Pro Val Ile Tyr Val Pro Pro Glu Lys Thr Ser
        530                 535                 540

Gln Met Cys Ser His Cys Ala Ile Asn Gly Asp Glu His Val Asp Thr
545                 550                 555                 560

Gln Arg Pro Tyr Lys Lys Pro Asn Ala Gln Lys Pro Ser Tyr Ser Leu
                565                 570                 575

Phe Lys Cys Asn Lys Cys Gly Ile Glu Leu Asn Ala Asp Tyr Asn Ala
            580                 585                 590

Ala Phe Asn Ile Ala Gln Lys Gly Leu Lys Thr Leu Met Leu Asn His
        595                 600                 605

Ser His
    610

<210> SEQ ID NO 15
<211> LENGTH: 369
<212> TYPE: PRT
<213> ORGANISM: Artificial sequence
<220> FEATURE:
<223> OTHER INFORMATION: Synthetic sequence

<400> SEQUENCE: 15

Met Leu Gln Thr Leu Leu Val Lys Leu Asp Pro Ser Lys Glu Gln Tyr
1               5                   10                  15

Lys Met Leu Tyr Glu Thr Met Glu Arg Phe Asn Glu Ala Cys Asn Gln
            20                  25                  30

Ile Ala Glu Thr Val Phe Ala Ile His Ser Ala Asn Lys Ile Glu Val
        35                  40                  45

Gln Lys Thr Val Tyr Tyr Pro Ile Arg Glu Lys Phe Gly Leu Ser Ala
    50                  55                  60

Gln Leu Thr Ile Leu Ala Ile Arg Lys Val Cys Glu Ala Tyr Lys Arg
65                  70                  75                  80

Asp Lys Ser Ile Lys Pro Glu Phe Arg Leu Asp Gly Ala Leu Val Tyr
                85                  90                  95

Asp Gln Arg Val Leu Ser Trp Lys Gly Leu Asp Lys Val Ser Leu Val
            100                 105                 110

Thr Leu Gln Gly Arg Gln Ile Ile Pro Ile Lys Phe Gly Asp Tyr Gln
        115                 120                 125

Lys Ala Arg Met Asp Arg Ile Arg Gly Gln Ala Asp Leu Ile Leu Val
    130                 135                 140

Lys Gly Val Phe Tyr Leu Cys Val Val Val Glu Val Ser Glu Glu Ser
145                 150                 155                 160

Pro Tyr Asp Pro Lys Gly Val Leu Gly Val Asp Leu Gly Ile Lys Asn
                165                 170                 175

Leu Ala Val Asp Ser Asp Gly Glu Val His Ser Gly Gln Thr Thr
            180                 185                 190

Asn Thr Arg Glu Arg Leu Asp Ser Leu Lys Ala Arg Leu Gln Ser Lys
        195                 200                 205

Gly Thr Lys Ser Ala Lys Arg His Leu Lys Leu Ser Gly Arg Met
    210                 215                 220

Ala Lys Phe Ser Lys Asp Val Asn His Cys Ile Ser Lys Lys Leu Val
225                 230                 235                 240

Ala Lys Ala Lys Gly Thr Leu Met Ser Ile Ala Leu Glu Asp Leu Gln
                245                 250                 255
```

Gly Ile Arg Asp Arg Val Thr Val Arg Lys Ala Gln Arg Arg Asn Leu
            260                 265                 270

His Thr Trp Asn Phe Gly Leu Leu Arg Met Phe Val Asp Tyr Lys Ala
            275                 280                 285

Lys Ile Ala Gly Val Pro Leu Val Phe Val Asp Pro Arg Asn Thr Ser
            290                 295                 300

Arg Thr Cys Pro Ser Cys Gly His Val Ala Lys Ala Asn Arg Pro Thr
305                 310                 315                 320

Arg Asp Glu Phe Arg Cys Val Ser Cys Gly Phe Ala Gly Ala Ala Asp
            325                 330                 335

His Ile Ala Ala Met Asn Ile Ala Phe Arg Ala Glu Val Ser Gln Pro
            340                 345                 350

Ile Val Thr Arg Phe Phe Val Gln Ser Gln Ala Pro Ser Phe Arg Val
            355                 360                 365

Gly

<210> SEQ ID NO 16
<211> LENGTH: 552
<212> TYPE: PRT
<213> ORGANISM: Artificial sequence
<220> FEATURE:
<223> OTHER INFORMATION: Synthetic sequence

<400> SEQUENCE: 16

Met Asp Glu Glu Pro Asp Ser Ala Glu Pro Asn Leu Ala Pro Ile Ser
1               5                   10                  15

Val Lys Leu Lys Leu Val Lys Leu Asp Gly Glu Lys Leu Ala Ala Leu
            20                  25                  30

Asn Asp Tyr Phe Asn Glu Tyr Ala Lys Ala Val Asn Phe Cys Glu Leu
            35                  40                  45

Lys Met Gln Lys Ile Arg Lys Asn Leu Val Asn Ile Arg Gly Thr Tyr
            50                  55                  60

Leu Lys Glu Lys Lys Ala Trp Ile Asn Gln Thr Gly Glu Cys Cys Ile
65                  70                  75                  80

Cys Lys Lys Ile Asp Glu Leu Arg Cys Glu Asp Lys Asn Pro Asp Ile
            85                  90                  95

Asn Gly Lys Ile Cys Lys Lys Cys Tyr Asn Gly Arg Tyr Gly Asn Gln
            100                 105                 110

Met Ile Arg Lys Leu Phe Val Ser Thr Asn Lys Arg Ala Val Pro Lys
            115                 120                 125

Ser Leu Asp Ile Arg Lys Val Ala Arg Leu His Asn Thr His Tyr His
            130                 135                 140

Arg Ile Pro Pro Glu Ala Ala Asp Ile Ile Lys Ala Ile Glu Thr Ala
145                 150                 155                 160

Glu Arg Lys Arg Arg Asn Arg Ile Leu Phe Asp Glu Arg Arg Tyr Asn
            165                 170                 175

Glu Leu Lys Asp Ala Leu Glu Asn Glu Lys Arg Val Ala Arg Pro
            180                 185                 190

Lys Lys Pro Lys Glu Arg Glu Val Arg Tyr Val Pro Ile Ser Lys Lys
            195                 200                 205

Asp Thr Pro Ser Lys Gly Tyr Thr Met Asn Ala Leu Val Arg Lys Val
            210                 215                 220

Ser Gly Met Ala Lys Lys Ile Glu Arg Ala Lys Arg Asn Leu Asn Lys
225                 230                 235                 240

```
Arg Lys Lys Ile Glu Tyr Leu Gly Arg Arg Ile Leu Leu Asp Lys Asn
                245                 250                 255

Trp Val Arg Phe Asp Phe Asp Lys Ser Glu Ile Ser Ile Pro Thr Met
            260                 265                 270

Lys Glu Phe Phe Gly Glu Met Arg Phe Glu Ile Thr Gly Pro Ser Asn
            275                 280                 285

Val Met Ser Pro Asn Gly Arg Glu Tyr Phe Thr Lys Trp Phe Asp Arg
        290                 295                 300

Ile Lys Ala Gln Pro Asp Asn Tyr Cys Tyr Leu Leu Arg Lys Glu Ser
305                 310                 315                 320

Glu Asp Glu Thr Asp Phe Tyr Leu Gln Tyr Thr Trp Arg Pro Asp Ala
                325                 330                 335

His Pro Lys Lys Asp Tyr Thr Gly Cys Leu Gly Ile Asp Ile Gly Gly
            340                 345                 350

Ser Lys Leu Ala Ser Ala Val Tyr Phe Asp Ala Asp Lys Asn Arg Ala
        355                 360                 365

Lys Gln Pro Ile Gln Ile Phe Ser Asn Pro Ile Gly Lys Trp Lys Thr
    370                 375                 380

Lys Arg Gln Lys Val Ile Lys Val Leu Ser Lys Ala Ala Val Arg His
385                 390                 395                 400

Lys Thr Lys Lys Leu Glu Ser Leu Arg Asn Ile Glu Pro Arg Ile Asp
                405                 410                 415

Val His Cys His Arg Ile Ala Arg Lys Ile Val Gly Met Ala Leu Ala
            420                 425                 430

Ala Asn Ala Phe Ile Ser Met Glu Asn Leu Glu Gly Ile Arg Glu
        435                 440                 445

Lys Gln Lys Ala Lys Glu Thr Lys Lys Gln Lys Phe Ser Arg Asn Met
    450                 455                 460

Phe Val Phe Arg Lys Leu Ser Lys Leu Ile Glu Tyr Lys Ala Leu Met
465                 470                 475                 480

Glu Gly Val Lys Val Val Tyr Ile Val Pro Asp Tyr Thr Ser Gln Leu
                485                 490                 495

Cys Ser Ser Cys Gly Thr Asn Asn Thr Lys Arg Pro Lys Gln Ala Ile
            500                 505                 510

Phe Met Cys Gln Asn Thr Glu Cys Arg Tyr Phe Gly Lys Asn Ile Asn
        515                 520                 525

Ala Asp Phe Asn Ala Ala Ile Asn Ile Ala Lys Lys Ala Leu Asn Arg
    530                 535                 540

Lys Asp Ile Val Arg Glu Leu Ser
545                 550

<210> SEQ ID NO 17
<211> LENGTH: 534
<212> TYPE: PRT
<213> ORGANISM: Artificial sequence
<220> FEATURE:
<223> OTHER INFORMATION: Synthetic sequence

<400> SEQUENCE: 17

Met Glu Lys Asn Asn Ser Glu Gln Thr Ser Ile Thr Thr Gly Ile Lys
1               5                   10                  15

Phe Lys Leu Lys Leu Asp Lys Glu Thr Lys Glu Lys Leu Asn Asn Tyr
                20                  25                  30

Phe Asp Glu Tyr Gly Lys Ala Ile Asn Phe Ala Val Arg Ile Ile Gln
            35                  40                  45
```

```
Met Gln Leu Asn Asp Asp Arg Leu Ala Gly Lys Tyr Lys Arg Asp Glu
    50                  55                  60

Lys Gly Lys Pro Ile Leu Gly Glu Asp Gly Lys Lys Ile Leu Glu Ile
65                  70                  75                  80

Pro Asn Asp Phe Cys Ser Cys Gly Asn Gln Val Asn His Tyr Val Asn
                    85                  90                  95

Gly Val Ser Phe Cys Gln Glu Cys Tyr Lys Lys Arg Phe Ser Glu Asn
                100                 105                 110

Gly Ile Arg Lys Arg Met Tyr Ser Ala Lys Gly Arg Lys Ala Glu Gln
            115                 120                 125

Asp Ile Asn Ile Lys Asn Ser Thr Asn Lys Ile Ser Lys Thr His Phe
        130                 135                 140

Asn Tyr Ala Ile Arg Glu Ala Phe Asn Leu Asp Lys Ser Ile Lys Lys
145                 150                 155                 160

Gln Arg Glu Lys Arg Phe Lys Lys Leu Lys Asp Met Lys Arg Lys Leu
                165                 170                 175

Gln Glu Phe Leu Glu Ile Arg Asp Gly Lys Arg Val Ile Cys Pro Lys
            180                 185                 190

Ile Glu Lys Gln Lys Val Glu Arg Tyr Ile His Pro Ser Trp Ile Asn
        195                 200                 205

Lys Glu Lys Lys Leu Glu Glu Phe Arg Gly Tyr Ser Leu Ser Ile Val
210                 215                 220

Asn Ser Lys Ile Lys Ser Phe Asp Arg Asn Ile Gln Arg Glu Glu Lys
225                 230                 235                 240

Ser Leu Lys Glu Lys Gly Gln Ile Asn Phe Lys Ala Gln Arg Leu Met
                245                 250                 255

Leu Asp Lys Ser Val Lys Phe Leu Lys Asp Asn Lys Val Ser Phe Thr
            260                 265                 270

Ile Ser Lys Glu Leu Pro Lys Thr Phe Glu Leu Asp Leu Pro Lys Lys
        275                 280                 285

Glu Lys Lys Leu Asn Trp Leu Asn Glu Lys Leu Glu Ile Ile Lys Asn
                295                 300
    290

Gln Lys Pro Lys Tyr Ala Tyr Leu Leu Arg Lys Glu Asn Asn Ile Phe
305                 310                 315                 320

Leu Gln Tyr Thr Leu Asp Ser Ile Pro Glu Ile His Ser Glu Tyr Ser
                325                 330                 335

Gly Ala Val Gly Ile Asp Arg Gly Val Ser His Ile Ala Val Tyr Thr
            340                 345                 350

Phe Leu Asp Lys Asp Gly Lys Asn Glu Arg Pro Phe Phe Leu Ser Ser
        355                 360                 365

Ser Gly Ile Leu Arg Leu Lys Asn Leu Gln Lys Glu Arg Asp Lys Phe
    370                 375                 380

Leu Arg Lys Lys His Asn Lys Ile Arg Lys Lys Gly Asn Met Arg Asn
385                 390                 395                 400

Ile Glu Gln Lys Ile Asn Leu Ile Leu His Glu Tyr Ser Lys Gln Ile
                405                 410                 415

Val Asn Phe Ala Lys Asp Lys Asn Ala Phe Ile Val Phe Glu Leu Leu
            420                 425                 430

Glu Lys Pro Lys Lys Ser Arg Glu Arg Met Ser Lys Lys Ile Gln Tyr
        435                 440                 445

Lys Leu Ser Gln Phe Thr Phe Lys Lys Leu Ser Asp Leu Val Asp Tyr
    450                 455                 460

Lys Ala Lys Arg Glu Gly Ile Lys Val Ile Tyr Val Glu Pro Ala Tyr
```

```
              465                 470                 475                 480
        Thr Ser Lys Asp Cys Ser His Cys Gly Glu Arg Val Asn Thr Gln Arg
                        485                 490                 495

Pro Phe Asn Gly Asn Phe Ser Leu Phe Lys Cys Asn Lys Cys Gly Ile
                    500                 505                 510

Val Leu Asn Ser Asp Tyr Asn Ala Ser Leu Asn Ile Ala Arg Lys Gly
                    515                 520                 525

Leu Asn Ile Ser Ala Asn
                    530

<210> SEQ ID NO 18
<211> LENGTH: 577
<212> TYPE: PRT
<213> ORGANISM: Artificial sequence
<220> FEATURE:
<223> OTHER INFORMATION: Synthetic sequence

<400> SEQUENCE: 18

Met Ala Glu Glu Lys Phe Phe Cys Glu Lys Cys Asn Lys Asp Ile
1               5                   10                  15

Lys Ile Pro Lys Asn Tyr Ile Asn Lys Gln Gly Ala Glu Glu Lys Ala
            20                  25                  30

Arg Ala Lys His Glu His Arg Val His Ala Leu Ile Leu Gly Ile Lys
        35                  40                  45

Phe Lys Ile Tyr Pro Lys Lys Glu Asp Ile Ser Lys Leu Asn Asp Tyr
    50                  55                  60

Phe Asp Glu Tyr Ala Lys Ala Val Thr Phe Thr Ala Lys Ile Val Asp
65                  70                  75                  80

Lys Leu Lys Ala Pro Phe Leu Phe Ala Gly Lys Arg Asp Lys Asp Thr
                85                  90                  95

Ser Lys Lys Lys Trp Val Phe Pro Val Asp Lys Cys Ser Phe Cys Lys
            100                 105                 110

Glu Lys Thr Glu Ile Asn Tyr Arg Thr Lys Gln Gly Lys Asn Ile Cys
        115                 120                 125

Asn Ser Cys Tyr Leu Thr Glu Phe Gly Glu Gln Gly Leu Leu Glu Lys
    130                 135                 140

Ile Tyr Ala Thr Lys Gly Arg Lys Val Ser Ser Phe Asn Leu Phe
145                 150                 155                 160

Asn Ser Thr Lys Lys Leu Thr Gly Thr His Asn Asn Tyr Val Val Lys
                165                 170                 175

Glu Ser Leu Gln Leu Leu Asp Ala Leu Lys Lys Gln Arg Ser Lys Arg
            180                 185                 190

Leu Lys Lys Leu Ser Asn Thr Arg Arg Lys Leu Lys Gln Phe Glu Glu
        195                 200                 205

Met Phe Glu Lys Glu Asp Lys Arg Phe Gln Leu Pro Leu Lys Glu Lys
    210                 215                 220

Gln Arg Glu Leu Arg Phe Ile His Val Ser Gln Lys Asp Arg Ala Thr
225                 230                 235                 240

Glu Phe Lys Gly Tyr Thr Met Asn Lys Ile Lys Ser Lys Ile Lys Val
                245                 250                 255

Leu Arg Arg Asn Ile Glu Arg Glu Gln Arg Ser Leu Asn Arg Lys Ser
            260                 265                 270

Pro Val Phe Phe Arg Gly Thr Arg Ile Arg Leu Ser Pro Ser Val Gln
        275                 280                 285

Phe Asp Asp Lys Asp Asn Lys Ile Lys Leu Thr Leu Ser Lys Glu Leu
```

```
                290                 295                 300
Pro Lys Glu Tyr Ser Phe Ser Gly Leu Asn Val Ala Asn Glu His Gly
305                 310                 315                 320

Arg Lys Phe Phe Ala Glu Lys Leu Lys Leu Ile Lys Glu Asn Lys Ser
                325                 330                 335

Lys Tyr Ala Tyr Leu Leu Arg Arg Gln Val Asn Lys Asn Asn Lys Lys
            340                 345                 350

Pro Ile Tyr Asp Tyr Tyr Leu Gln Tyr Thr Val Glu Phe Leu Pro Asn
        355                 360                 365

Ile Ile Thr Asn Tyr Asn Gly Ile Leu Gly Ile Asp Arg Gly Ile Asn
370                 375                 380

Thr Leu Ala Cys Ile Val Leu Leu Glu Asn Lys Lys Glu Lys Pro Ser
385                 390                 395                 400

Phe Val Lys Phe Phe Ser Gly Lys Gly Ile Leu Asn Leu Lys Asn Lys
                405                 410                 415

Arg Arg Lys Gln Leu Tyr Phe Leu Lys Gly Val His Asn Lys Tyr Arg
            420                 425                 430

Lys Gln Gln Lys Ile Arg Pro Ile Glu Pro Arg Ile Asp Gln Ile Leu
        435                 440                 445

His Asp Ile Ser Lys Gln Ile Ile Asp Leu Ala Lys Glu Lys Arg Val
450                 455                 460

Ala Ile Ser Leu Glu Gln Leu Glu Lys Pro Gln Lys Pro Lys Phe Arg
465                 470                 475                 480

Gln Ser Arg Lys Ala Lys Tyr Lys Leu Ser Gln Phe Asn Phe Lys Thr
                485                 490                 495

Leu Ser Asn Tyr Ile Asp Tyr Lys Ala Lys Lys Glu Gly Ile Arg Val
            500                 505                 510

Ile Tyr Ile Ala Pro Glu Met Thr Ser Gln Asn Cys Ser Arg Cys Ala
        515                 520                 525

Met Lys Asn Asp Leu His Val Asn Thr Gln Arg Pro Tyr Lys Asn Thr
530                 535                 540

Ser Ser Leu Phe Lys Cys Asn Lys Cys Gly Val Glu Leu Asn Ala Asp
545                 550                 555                 560

Tyr Asn Ala Ala Phe Asn Ile Ala Gln Lys Gly Leu Lys Ile Leu Asn
                565                 570                 575

Ser

<210> SEQ ID NO 19
<211> LENGTH: 613
<212> TYPE: PRT
<213> ORGANISM: Artificial sequence
<220> FEATURE:
<223> OTHER INFORMATION: Synthetic sequence

<400> SEQUENCE: 19

Met Ile Ser Leu Lys Leu Lys Leu Leu Pro Asp Glu Glu Gln Lys Lys
1               5                   10                  15

Leu Leu Asp Glu Met Phe Trp Lys Trp Ala Ser Ile Cys Thr Arg Val
                20                  25                  30

Gly Phe Gly Arg Ala Asp Lys Glu Asp Leu Lys Pro Pro Lys Asp Ala
            35                  40                  45

Glu Gly Val Trp Phe Ser Leu Thr Gln Leu Asn Gln Ala Asn Thr Asp
        50                  55                  60

Ile Asn Asp Leu Arg Glu Ala Met Lys His Gln Lys His Arg Leu Glu
65                  70                  75                  80
```

```
Tyr Glu Lys Asn Arg Leu Glu Ala Gln Arg Asp Asp Thr Gln Asp Ala
                85                  90                  95

Leu Lys Asn Pro Asp Arg Arg Glu Ile Ser Thr Lys Arg Lys Asp Leu
            100                 105                 110

Phe Arg Pro Lys Ala Ser Val Glu Lys Gly Phe Leu Lys Leu Lys Tyr
        115                 120                 125

His Gln Glu Arg Tyr Trp Val Arg Arg Leu Lys Glu Ile Asn Lys Leu
    130                 135                 140

Ile Glu Arg Lys Thr Lys Thr Leu Ile Lys Ile Glu Lys Gly Arg Ile
145                 150                 155                 160

Lys Phe Lys Ala Thr Arg Ile Thr Leu His Gln Gly Ser Phe Lys Ile
                165                 170                 175

Arg Phe Gly Asp Lys Pro Ala Phe Leu Ile Lys Ala Leu Ser Gly Lys
            180                 185                 190

Asn Gln Ile Asp Ala Pro Phe Val Val Pro Glu Gln Pro Ile Cys
        195                 200                 205

Gly Ser Val Val Asn Ser Lys Lys Tyr Leu Asp Glu Ile Thr Thr Asn
    210                 215                 220

Phe Leu Ala Tyr Ser Val Asn Ala Met Leu Phe Gly Leu Ser Arg Ser
225                 230                 235                 240

Glu Glu Met Leu Leu Lys Ala Lys Arg Pro Glu Lys Ile Lys Lys Lys
            245                 250                 255

Glu Glu Lys Leu Ala Lys Lys Gln Ser Ala Phe Glu Asn Lys Lys Lys
            260                 265                 270

Glu Leu Gln Lys Leu Leu Gly Arg Glu Leu Thr Gln Gln Glu Glu Ala
        275                 280                 285

Ile Ile Glu Glu Thr Arg Asn Gln Phe Phe Gln Asp Phe Glu Val Lys
290                 295                 300

Ile Thr Lys Gln Tyr Ser Glu Leu Leu Ser Lys Ile Ala Asn Glu Leu
305                 310                 315                 320

Lys Gln Lys Asn Asp Phe Leu Lys Val Asn Lys Tyr Pro Ile Leu Leu
                325                 330                 335

Arg Lys Pro Leu Lys Lys Ala Lys Ser Lys Lys Ile Asn Asn Leu Ser
            340                 345                 350

Pro Ser Glu Trp Lys Tyr Tyr Leu Gln Phe Gly Val Lys Pro Leu Leu
        355                 360                 365

Lys Gln Lys Ser Arg Arg Lys Ser Arg Asn Val Leu Gly Ile Asp Arg
        370                 375                 380

Gly Leu Lys His Leu Leu Ala Val Thr Val Leu Glu Pro Asp Lys Lys
385                 390                 395                 400

Thr Phe Val Trp Asn Lys Leu Tyr Pro Asn Pro Ile Thr Gly Trp Lys
                405                 410                 415

Trp Arg Arg Arg Lys Leu Leu Arg Ser Leu Lys Arg Leu Lys Arg Arg
            420                 425                 430

Ile Lys Ser Gln Lys His Glu Thr Ile His Glu Asn Gln Thr Arg Lys
        435                 440                 445

Lys Leu Lys Ser Leu Gln Gly Arg Ile Asp Asp Leu Leu His Asn Ile
    450                 455                 460

Ser Arg Lys Ile Val Glu Thr Ala Lys Glu Tyr Asp Ala Val Ile Val
465                 470                 475                 480

Val Glu Asp Leu Gln Ser Met Arg Gln His Gly Arg Ser Lys Gly Asn
            485                 490                 495
```

```
Arg Leu Lys Thr Leu Asn Tyr Ala Leu Ser Leu Phe Asp Tyr Ala Asn
            500                 505                 510

Val Met Gln Leu Ile Lys Tyr Lys Ala Gly Ile Glu Gly Ile Gln Ile
        515                 520                 525

Tyr Asp Val Lys Pro Ala Gly Thr Ser Gln Asn Cys Ala Tyr Cys Leu
    530                 535                 540

Leu Ala Gln Arg Asp Ser His Glu Tyr Lys Arg Ser Gln Glu Asn Ser
545                 550                 555                 560

Lys Ile Gly Val Cys Leu Asn Pro Asn Cys Gln Asn His Lys Lys Gln
                565                 570                 575

Ile Asp Ala Asp Leu Asn Ala Ala Arg Val Ile Ala Ser Cys Tyr Ala
            580                 585                 590

Leu Lys Ile Asn Asp Ser Gln Pro Phe Gly Thr Arg Lys Arg Phe Lys
        595                 600                 605

Lys Arg Thr Thr Asn
    610
```

<210> SEQ ID NO 20
<211> LENGTH: 615
<212> TYPE: PRT
<213> ORGANISM: Artificial sequence
<220> FEATURE:
<223> OTHER INFORMATION: Synthetic sequence

<400> SEQUENCE: 20

```
Met Glu Thr Leu Ser Leu Lys Leu Lys Leu Asn Pro Ser Lys Glu Gln
1               5                   10                  15

Leu Leu Val Leu Asp Lys Met Phe Trp Lys Trp Ala Ser Ile Cys Thr
            20                  25                  30

Arg Leu Gly Leu Lys Lys Ala Glu Met Ser Asp Leu Glu Pro Pro Lys
        35                  40                  45

Asp Ala Glu Gly Val Trp Phe Ser Lys Thr Gln Leu Asn Gln Ala Asn
    50                  55                  60

Thr Asp Val Asn Asp Leu Arg Lys Ala Met Gln His Gln Gly Lys Arg
65                  70                  75                  80

Ile Glu Tyr Glu Leu Asp Lys Val Glu Asn Arg Arg Asn Glu Ile Gln
                85                  90                  95

Glu Met Leu Glu Lys Pro Asp Arg Arg Asp Ile Ser Pro Asn Arg Lys
            100                 105                 110

Asp Leu Phe Arg Pro Lys Ala Ala Val Glu Lys Gly Tyr Leu Lys Leu
        115                 120                 125

Lys Tyr His Lys Leu Gly Tyr Trp Ser Lys Glu Leu Lys Thr Ala Asn
    130                 135                 140

Lys Leu Ile Glu Arg Lys Arg Lys Thr Leu Ala Lys Ile Asp Ala Gly
145                 150                 155                 160

Lys Met Lys Phe Lys Pro Thr Arg Ile Ser Leu His Thr Asn Ser Phe
                165                 170                 175

Arg Ile Lys Phe Gly Glu Glu Pro Lys Ile Ala Leu Ser Thr Thr Ser
            180                 185                 190

Lys His Glu Lys Ile Glu Leu Pro Leu Ile Thr Ser Leu Gln Arg Pro
        195                 200                 205

Leu Lys Thr Ser Cys Ala Lys Lys Ser Lys Thr Tyr Leu Asp Ala Ala
    210                 215                 220

Ile Leu Asn Phe Leu Ala Tyr Ser Thr Asn Ala Ala Leu Phe Gly Leu
225                 230                 235                 240
```

```
Ser Arg Ser Glu Glu Met Leu Leu Lys Ala Lys Lys Pro Glu Lys Ile
            245                 250                 255

Glu Lys Arg Asp Arg Lys Leu Ala Thr Lys Arg Glu Ser Phe Asp Lys
        260                 265                 270

Lys Leu Lys Thr Leu Glu Lys Leu Leu Glu Arg Lys Leu Ser Glu Lys
            275                 280                 285

Glu Lys Ser Val Phe Lys Arg Lys Gln Thr Glu Phe Phe Asp Lys Phe
        290                 295                 300

Cys Ile Thr Leu Asp Glu Thr Tyr Val Glu Ala Leu His Arg Ile Ala
305                 310                 315                 320

Glu Glu Leu Val Ser Lys Asn Lys Tyr Leu Glu Ile Lys Lys Tyr Pro
            325                 330                 335

Val Leu Leu Arg Lys Pro Glu Ser Arg Leu Arg Ser Lys Lys Leu Lys
            340                 345                 350

Asn Leu Lys Pro Glu Asp Trp Thr Tyr Tyr Ile Gln Phe Gly Phe Gln
            355                 360                 365

Pro Leu Leu Asp Thr Pro Lys Pro Ile Lys Thr Lys Thr Val Leu Gly
    370                 375                 380

Ile Asp Arg Gly Val Arg His Leu Leu Ala Val Ser Ile Phe Asp Pro
385                 390                 395                 400

Arg Thr Lys Thr Phe Thr Phe Asn Arg Leu Tyr Ser Asn Pro Ile Val
                405                 410                 415

Asp Trp Lys Trp Arg Arg Arg Lys Leu Leu Arg Ser Ile Lys Arg Leu
            420                 425                 430

Lys Arg Arg Leu Lys Ser Glu Lys His Val His Leu His Glu Asn Gln
            435                 440                 445

Phe Lys Ala Lys Leu Arg Ser Leu Glu Gly Arg Ile Glu Asp His Phe
    450                 455                 460

His Asn Leu Ser Lys Glu Ile Val Asp Leu Ala Lys Glu Asn Asn Ser
465                 470                 475                 480

Val Ile Val Val Glu Asn Leu Gly Gly Met Arg Gln His Gly Arg Gly
            485                 490                 495

Arg Gly Lys Trp Leu Lys Ala Leu Asn Tyr Ala Leu Ser His Phe Asp
            500                 505                 510

Tyr Ala Lys Val Met Gln Leu Ile Lys Tyr Lys Ala Glu Leu Ala Gly
    515                 520                 525

Val Phe Val Tyr Asp Val Ala Pro Ala Gly Thr Ser Ile Asn Cys Ala
    530                 535                 540

Tyr Cys Leu Leu Asn Asp Lys Asp Ala Ser Asn Tyr Thr Arg Gly Lys
545                 550                 555                 560

Val Ile Asn Gly Lys Lys Asn Thr Lys Ile Gly Glu Cys Lys Thr Cys
            565                 570                 575

Lys Lys Glu Phe Asp Ala Asp Leu Asn Ala Ala Arg Val Ile Ala Leu
        580                 585                 590

Cys Tyr Glu Lys Arg Leu Asn Asp Pro Gln Pro Phe Gly Thr Arg Lys
    595                 600                 605

Gln Phe Lys Pro Lys Lys Pro
    610                 615

<210> SEQ ID NO 21
<211> LENGTH: 775
<212> TYPE: PRT
<213> ORGANISM: Artificial sequence
<220> FEATURE:
<223> OTHER INFORMATION: Synthetic sequence
```

<400> SEQUENCE: 21

Met Lys Ala Leu Lys Leu Gln Leu Ile Pro Thr Arg Lys Gln Tyr Lys
1               5                   10                  15

Ile Leu Asp Glu Met Phe Trp Lys Trp Ala Ser Leu Ala Asn Arg Val
            20                  25                  30

Ser Gln Lys Gly Glu Ser Lys Glu Thr Leu Ala Pro Lys Lys Asp Ile
        35                  40                  45

Gln Lys Ile Gln Phe Asn Ala Thr Gln Leu Asn Gln Ile Glu Lys Asp
    50                  55                  60

Ile Lys Asp Leu Arg Gly Ala Met Lys Glu Gln Gln Lys Gln Lys Glu
65                  70                  75                  80

Arg Leu Leu Gln Ile Gln Glu Arg Arg Ser Thr Ile Ser Glu Met
                85                  90                  95

Leu Asn Asp Asp Asn Asn Lys Glu Arg Asp Pro His Arg Pro Leu Asn
            100                 105                 110

Phe Arg Pro Lys Gly Trp Arg Lys Phe His Thr Ser Lys His Trp Val
        115                 120                 125

Gly Glu Leu Ser Lys Ile Leu Arg Gln Glu Asp Arg Val Lys Lys Thr
    130                 135                 140

Ile Glu Arg Ile Val Ala Gly Lys Ile Ser Phe Lys Pro Lys Arg Ile
145                 150                 155                 160

Gly Ile Trp Ser Ser Asn Tyr Lys Ile Asn Phe Lys Arg Lys Ile
                165                 170                 175

Ser Ile Asn Pro Leu Asn Ser Lys Gly Phe Glu Leu Thr Leu Met Thr
            180                 185                 190

Glu Pro Thr Gln Asp Leu Ile Gly Lys Asn Gly Gly Lys Ser Val Leu
        195                 200                 205

Asn Asn Lys Arg Tyr Leu Asp Asp Ser Ile Lys Ser Leu Leu Met Phe
    210                 215                 220

Ala Leu His Ser Arg Phe Phe Gly Leu Asn Asn Thr Asp Thr Tyr Leu
225                 230                 235                 240

Leu Gly Gly Lys Ile Asn Pro Ser Leu Val Lys Tyr Tyr Lys Asn
                245                 250                 255

Gln Asp Met Gly Glu Phe Gly Arg Glu Ile Val Glu Lys Phe Glu Arg
        260                 265                 270

Lys Leu Lys Gln Glu Ile Asn Glu Gln Gln Lys Lys Ile Ile Met Ser
    275                 280                 285

Gln Ile Lys Glu Gln Tyr Ser Asn Arg Asp Ser Ala Phe Asn Lys Asp
    290                 295                 300

Tyr Leu Gly Leu Ile Asn Glu Phe Ser Glu Val Phe Asn Gln Arg Lys
305                 310                 315                 320

Ser Glu Arg Ala Glu Tyr Leu Leu Asp Ser Phe Glu Asp Lys Ile Lys
            325                 330                 335

Gln Ile Lys Gln Glu Ile Gly Ser Leu Asn Ile Ser Asp Trp Asp
        340                 345                 350

Phe Leu Ile Asp Glu Ala Lys Lys Ala Tyr Gly Tyr Glu Glu Gly Phe
    355                 360                 365

Thr Glu Tyr Val Tyr Ser Lys Arg Tyr Leu Glu Ile Leu Asn Lys Ile
        370                 375                 380

Val Lys Ala Val Leu Ile Thr Asp Ile Tyr Phe Asp Leu Arg Lys Tyr
385                 390                 395                 400

Pro Ile Leu Leu Arg Lys Pro Leu Asp Lys Ile Lys Lys Ile Ser Asn

```
                405                 410                 415
Leu Lys Pro Asp Glu Trp Ser Tyr Tyr Ile Gln Phe Gly Tyr Asp Ser
            420                 425                 430

Ile Asn Pro Val Gln Leu Met Ser Thr Asp Lys Phe Leu Gly Ile Asp
            435                 440                 445

Arg Gly Leu Thr His Leu Leu Ala Tyr Ser Val Phe Asp Lys Glu Lys
            450                 455                 460

Lys Glu Phe Ile Ile Asn Gln Leu Glu Pro Asn Pro Ile Met Gly Trp
465                 470                 475                 480

Lys Trp Lys Leu Arg Lys Val Lys Arg Ser Leu Gln His Leu Glu Arg
                485                 490                 495

Arg Ile Arg Ala Gln Lys Met Val Lys Leu Pro Glu Asn Gln Met Lys
            500                 505                 510

Lys Lys Leu Lys Ser Ile Glu Pro Lys Ile Glu Val His Tyr His Asn
            515                 520                 525

Ile Ser Arg Lys Ile Val Asn Leu Ala Lys Asp Tyr Asn Ala Ser Ile
            530                 535                 540

Val Val Glu Ser Leu Glu Gly Gly Leu Lys Gln His Gly Arg Lys
545                 550                 555                 560

Lys Asn Ala Arg Asn Arg Ser Leu Asn Tyr Ala Leu Ser Leu Phe Asp
                565                 570                 575

Tyr Gly Lys Ile Ala Ser Leu Ile Lys Tyr Lys Ala Asp Leu Glu Gly
            580                 585                 590

Val Pro Met Tyr Glu Val Leu Pro Ala Tyr Thr Ser Gln Gln Cys Ala
            595                 600                 605

Lys Cys Val Leu Glu Lys Gly Ser Phe Val Asp Pro Glu Ile Ile Gly
610                 615                 620

Tyr Val Glu Asp Ile Gly Ile Lys Gly Ser Leu Leu Asp Ser Leu Phe
625                 630                 635                 640

Glu Gly Thr Glu Leu Ser Ser Ile Gln Val Leu Lys Lys Ile Lys Asn
                645                 650                 655

Lys Ile Glu Leu Ser Ala Arg Asp Asn His Asn Lys Glu Ile Asn Leu
            660                 665                 670

Ile Leu Lys Tyr Asn Phe Lys Gly Leu Val Ile Val Arg Gly Gln Asp
            675                 680                 685

Lys Glu Glu Ile Ala Glu His Pro Ile Lys Glu Ile Asn Gly Lys Phe
            690                 695                 700

Ala Ile Leu Asp Phe Val Tyr Lys Arg Gly Lys Glu Lys Val Gly Lys
705                 710                 715                 720

Lys Gly Asn Gln Lys Val Arg Tyr Thr Gly Asn Lys Lys Val Gly Tyr
                725                 730                 735

Cys Ser Lys His Gly Gln Val Asp Ala Asp Leu Asn Ala Ser Arg Val
            740                 745                 750

Ile Ala Leu Cys Lys Tyr Leu Asp Ile Asn Asp Pro Ile Leu Phe Gly
            755                 760                 765

Glu Gln Arg Lys Ser Phe Lys
            770                 775
```

<210> SEQ ID NO 22
<211> LENGTH: 777
<212> TYPE: PRT
<213> ORGANISM: Artificial sequence
<220> FEATURE:
<223> OTHER INFORMATION: Synthetic sequence

```
<400> SEQUENCE: 22

Met Val Thr Arg Ala Ile Lys Leu Lys Leu Asp Pro Thr Lys Asn Gln
1               5                   10                  15

Tyr Lys Leu Leu Asn Glu Met Phe Trp Lys Trp Ala Ser Leu Ala Asn
            20                  25                  30

Arg Phe Ser Gln Lys Gly Ala Ser Lys Glu Thr Leu Ala Pro Lys Asp
        35                  40                  45

Gly Thr Gln Lys Ile Gln Phe Asn Ala Thr Gln Leu Asn Gln Ile Lys
    50                  55                  60

Lys Asp Val Asp Leu Arg Gly Ala Met Glu Lys Gln Gly Lys Gln
65                  70                  75                  80

Lys Glu Arg Leu Leu Ile Gln Ile Gln Glu Arg Leu Leu Thr Ile Ser
                85                  90                  95

Glu Ile Leu Arg Asp Asp Ser Lys Lys Glu Lys Asp Pro His Arg Pro
            100                 105                 110

Gln Asn Phe Arg Pro Phe Gly Trp Arg Arg Phe His Thr Ser Ala Tyr
        115                 120                 125

Trp Ser Ser Glu Ala Ser Lys Leu Thr Arg Gln Val Asp Arg Val Arg
    130                 135                 140

Arg Thr Ile Glu Arg Ile Lys Ala Gly Lys Ile Asn Phe Lys Pro Lys
145                 150                 155                 160

Arg Ile Gly Leu Trp Ser Ser Thr Tyr Lys Ile Asn Phe Leu Lys Lys
                165                 170                 175

Lys Ile Asn Ile Ser Pro Leu Lys Ser Lys Ser Phe Glu Leu Asp Leu
            180                 185                 190

Ile Thr Glu Pro Gln Gln Lys Ile Ile Gly Lys Glu Gly Lys Ser
        195                 200                 205

Val Ala Asn Ser Lys Lys Tyr Leu Asp Asp Ser Ile Lys Ser Leu Leu
    210                 215                 220

Ile Phe Ala Ile Lys Ser Arg Leu Phe Gly Leu Asn Asn Lys Asp Lys
225                 230                 235                 240

Pro Leu Phe Glu Asn Ile Ile Thr Pro Asn Leu Val Arg Tyr His Lys
                245                 250                 255

Lys Gly Gln Glu Gln Glu Asn Phe Lys Lys Glu Val Ile Lys Lys Phe
            260                 265                 270

Glu Asn Lys Leu Lys Lys Glu Ile Ser Gln Lys Gln Lys Glu Ile Ile
        275                 280                 285

Phe Ser Gln Ile Glu Arg Gln Tyr Glu Asn Arg Asp Ala Thr Phe Ser
    290                 295                 300

Glu Asp Tyr Leu Arg Ala Ile Ser Glu Phe Ser Glu Ile Phe Asn Gln
305                 310                 315                 320

Arg Lys Lys Glu Arg Ala Lys Glu Leu Leu Asn Ser Phe Asn Glu Lys
                325                 330                 335

Ile Arg Gln Leu Lys Lys Glu Val Asn Gly Asn Ile Ser Glu Glu Asp
            340                 345                 350

Leu Lys Ile Leu Glu Val Glu Ala Glu Lys Ala Tyr Asn Tyr Glu Asn
        355                 360                 365

Gly Phe Ile Glu Trp Glu Tyr Ser Glu Gln Phe Leu Gly Val Leu Glu
    370                 375                 380

Lys Ile Ala Arg Ala Val Leu Ile Ser Asp Asn Tyr Phe Asp Leu Lys
385                 390                 395                 400

Lys Tyr Pro Ile Leu Ile Arg Lys Pro Thr Asn Lys Ser Lys Lys Ile
                405                 410                 415
```

```
Thr Asn Leu Lys Pro Glu Trp Asp Tyr Tyr Ile Gln Phe Gly Tyr
            420                 425                 430

Gly Leu Ile Asn Ser Pro Met Lys Ile Glu Thr Lys Asn Phe Met Gly
            435                 440                 445

Ile Asp Arg Gly Leu Thr His Leu Leu Ala Tyr Ser Ile Phe Asp Arg
450                 455                 460

Asp Ser Glu Lys Phe Thr Ile Asn Gln Leu Glu Leu Asn Pro Ile Lys
465                 470                 475                 480

Gly Trp Lys Trp Lys Leu Arg Lys Val Lys Arg Ser Leu Gln His Leu
                485                 490                 495

Glu Arg Arg Met Arg Ala Gln Lys Gly Val Lys Leu Pro Glu Asn Gln
            500                 505                 510

Met Lys Lys Arg Leu Lys Ser Ile Glu Pro Lys Ile Glu Ser Tyr Tyr
            515                 520                 525

His Asn Leu Ser Arg Lys Ile Val Asn Leu Ala Lys Ala Asn Asn Ala
        530                 535                 540

Ser Ile Val Val Glu Ser Leu Glu Gly Gly Leu Lys Gln His Gly
545                 550                 555                 560

Arg Lys Lys Asn Ser Arg His Arg Ala Leu Asn Tyr Ala Leu Ser Leu
                565                 570                 575

Phe Asp Tyr Gly Lys Ile Ala Ser Leu Ile Lys Tyr Lys Ser Asp Leu
            580                 585                 590

Glu Gly Val Pro Met Tyr Glu Val Leu Pro Ala Tyr Thr Ser Gln Gln
            595                 600                 605

Cys Ala Lys Cys Val Leu Lys Lys Gly Ser Phe Val Glu Pro Glu Ile
610                 615                 620

Ile Gly Tyr Ile Glu Glu Ile Gly Phe Lys Glu Asn Leu Leu Thr Leu
625                 630                 635                 640

Leu Phe Glu Asp Thr Gly Leu Ser Ser Val Gln Val Leu Lys Lys Ser
                645                 650                 655

Lys Asn Lys Met Thr Leu Ser Ala Arg Asp Lys Glu Gly Lys Met Val
            660                 665                 670

Asp Leu Val Leu Lys Tyr Asn Phe Lys Gly Leu Val Ile Ser Gln Glu
            675                 680                 685

Lys Lys Lys Glu Glu Ile Val Glu Phe Pro Ile Lys Glu Ile Asp Gly
690                 695                 700

Lys Phe Ala Val Leu Asp Ser Ala Tyr Lys Arg Gly Lys Glu Arg Ile
705                 710                 715                 720

Ser Lys Lys Gly Asn Gln Lys Leu Val Tyr Thr Gly Asn Lys Lys Val
                725                 730                 735

Gly Tyr Cys Ser Val His Gly Gln Val Asp Ala Asp Leu Asn Ala Ser
            740                 745                 750

Arg Val Ile Ala Leu Cys Lys Tyr Leu Gly Ile Asn Glu Pro Ile Val
            755                 760                 765

Phe Gly Glu Gln Arg Lys Ser Phe Lys
770                 775
```

<210> SEQ ID NO 23
<211> LENGTH: 610
<212> TYPE: PRT
<213> ORGANISM: Artificial sequence
<220> FEATURE:
<223> OTHER INFORMATION: Synthetic sequence

<400> SEQUENCE: 23

```
Leu Asp Leu Ile Thr Glu Pro Ile Gln Pro His Lys Ser Ser Leu
1               5                   10                  15

Arg Ser Lys Glu Phe Leu Glu Tyr Gln Ile Ser Asp Phe Leu Asn Phe
            20                  25                  30

Ser Leu His Ser Leu Phe Phe Gly Leu Ala Ser Asn Glu Gly Pro Leu
            35                  40                  45

Val Asp Phe Lys Ile Tyr Asp Lys Ile Val Ile Pro Lys Pro Glu Glu
50                  55                  60

Arg Phe Pro Lys Lys Glu Ser Glu Gly Lys Lys Leu Asp Ser Phe
65                  70                  75                  80

Asp Lys Arg Val Glu Glu Tyr Tyr Ser Asp Lys Leu Glu Lys Lys Ile
                85                  90                  95

Glu Arg Lys Leu Asn Thr Glu Glu Lys Asn Val Ile Asp Arg Glu Lys
                100                 105                 110

Thr Arg Ile Trp Gly Glu Val Asn Lys Leu Glu Glu Ile Arg Ser Ile
                115                 120                 125

Ile Asp Glu Ile Asn Glu Ile Lys Lys Gln Lys His Ile Ser Glu Lys
130                 135                 140

Ser Lys Leu Leu Gly Glu Lys Trp Lys Lys Val Asn Asn Ile Gln Glu
145                 150                 155                 160

Thr Leu Leu Ser Gln Glu Tyr Val Ser Leu Ile Ser Asn Leu Ser Asp
                165                 170                 175

Glu Leu Thr Asn Lys Lys Glu Leu Leu Ala Lys Lys Tyr Ser Lys
                180                 185                 190

Phe Asp Asp Lys Ile Lys Lys Ile Lys Glu Asp Tyr Gly Leu Glu Phe
                195                 200                 205

Asp Glu Asn Thr Ile Lys Lys Glu Gly Glu Lys Ala Phe Leu Asn Pro
210                 215                 220

Asp Lys Phe Ser Lys Tyr Gln Phe Ser Ser Tyr Leu Lys Leu Ile
225                 230                 235                 240

Gly Glu Ile Ala Arg Ser Leu Ile Thr Tyr Lys Gly Phe Leu Asp Leu
                245                 250                 255

Asn Lys Tyr Pro Ile Ile Phe Arg Lys Pro Ile Asn Lys Val Lys Lys
                260                 265                 270

Ile His Asn Leu Glu Pro Asp Glu Trp Lys Tyr Tyr Ile Gln Phe Gly
                275                 280                 285

Tyr Glu Gln Ile Asn Asn Pro Lys Leu Glu Thr Glu Asn Ile Leu Gly
                290                 295                 300

Ile Asp Arg Gly Leu Thr His Ile Leu Ala Tyr Ser Val Phe Glu Pro
305                 310                 315                 320

Arg Ser Ser Lys Phe Ile Leu Asn Lys Leu Glu Pro Asn Pro Ile Glu
                325                 330                 335

Gly Trp Lys Trp Lys Leu Arg Lys Leu Arg Arg Ser Ile Gln Asn Leu
                340                 345                 350

Glu Arg Arg Trp Arg Ala Gln Asp Asn Val Lys Leu Pro Glu Asn Gln
                355                 360                 365

Met Lys Lys Asn Leu Arg Ser Ile Glu Asp Lys Val Glu Asn Leu Tyr
370                 375                 380

His Asn Leu Ser Arg Lys Ile Val Asp Leu Ala Lys Glu Lys Asn Ala
385                 390                 395                 400

Cys Ile Val Phe Glu Lys Leu Glu Gly Gln Gly Met Lys Gln His Gly
                405                 410                 415
```

```
Arg Lys Lys Ser Asp Arg Leu Arg Gly Leu Asn Tyr Lys Leu Ser Leu
                420                 425                 430

Phe Asp Tyr Gly Lys Ile Ala Lys Leu Ile Lys Tyr Lys Ala Glu Ile
            435                 440                 445

Glu Gly Ile Pro Ile Tyr Arg Ile Asp Ser Ala Tyr Thr Ser Gln Asn
        450                 455                 460

Cys Ala Lys Cys Val Leu Glu Ser Arg Arg Phe Ala Gln Pro Glu Glu
465                 470                 475                 480

Ile Ser Cys Leu Asp Asp Phe Lys Glu Gly Asp Asn Leu Asp Lys Arg
                485                 490                 495

Ile Leu Glu Gly Thr Gly Leu Val Glu Ala Lys Ile Tyr Lys Lys Leu
            500                 505                 510

Leu Lys Glu Lys Lys Glu Asp Phe Glu Ile Glu Glu Asp Ile Ala Met
        515                 520                 525

Phe Asp Thr Lys Lys Val Ile Lys Glu Asn Lys Glu Lys Thr Val Ile
530                 535                 540

Leu Asp Tyr Val Tyr Thr Arg Arg Lys Glu Ile Ile Gly Thr Asn His
545                 550                 555                 560

Lys Lys Asn Ile Lys Gly Ile Ala Lys Tyr Thr Gly Asn Thr Lys Ile
                565                 570                 575

Gly Tyr Cys Met Lys His Gly Gln Val Asp Ala Asp Leu Asn Ala Ser
            580                 585                 590

Arg Thr Ile Ala Leu Cys Lys Asn Phe Asp Ile Asn Asn Pro Glu Ile
        595                 600                 605

Trp Lys
    610

<210> SEQ ID NO 24
<211> LENGTH: 632
<212> TYPE: PRT
<213> ORGANISM: Artificial sequence
<220> FEATURE:
<223> OTHER INFORMATION: Synthetic sequence

<400> SEQUENCE: 24

Met Ser Asp Glu Ser Leu Val Ser Glu Asp Lys Leu Ala Ile Lys
1               5                   10                  15

Ile Lys Ile Val Pro Asn Ala Glu Gln Ala Lys Met Leu Asp Glu Met
            20                  25                  30

Phe Lys Lys Trp Ser Ser Ile Cys Asn Arg Ile Ser Arg Gly Lys Glu
        35                  40                  45

Asp Ile Glu Thr Leu Arg Pro Asp Glu Gly Lys Glu Leu Gln Phe Asn
    50                  55                  60

Ser Thr Gln Leu Asn Ser Ala Thr Met Asp Val Ser Asp Leu Lys Lys
65                  70                  75                  80

Ala Met Ala Arg Gln Gly Glu Arg Leu Glu Ala Glu Val Ser Lys Leu
                85                  90                  95

Arg Gly Arg Tyr Glu Thr Ile Asp Ala Ser Leu Arg Asp Pro Ser Arg
            100                 105                 110

Arg His Thr Asn Pro Gln Lys Pro Ser Ser Phe Tyr Pro Ser Asp Trp
        115                 120                 125

Asp Ile Ser Gly Arg Leu Thr Pro Arg Phe His Thr Ala Arg His Tyr
    130                 135                 140

Ser Thr Glu Leu Arg Lys Leu Lys Ala Lys Glu Asp Lys Met Leu Lys
145                 150                 155                 160
```

```
Thr Ile Asn Lys Ile Lys Asn Gly Lys Ile Val Phe Lys Pro Lys Arg
            165                 170                 175
Ile Thr Leu Trp Pro Ser Ser Val Asn Met Ala Phe Lys Gly Ser Arg
        180                 185                 190
Leu Leu Leu Lys Pro Phe Ala Asn Gly Phe Glu Met Glu Leu Pro Ile
        195                 200                 205
Val Ile Ser Pro Gln Lys Thr Ala Asp Gly Lys Ser Gln Lys Ala Ser
210                 215                 220
Ala Glu Tyr Met Arg Asn Ala Leu Leu Gly Leu Ala Gly Tyr Ser Ile
225                 230                 235                 240
Asn Gln Leu Leu Phe Gly Met Asn Arg Ser Gln Lys Met Leu Ala Asn
            245                 250                 255
Ala Lys Lys Pro Glu Lys Val Glu Lys Phe Leu Glu Gln Met Lys Asn
        260                 265                 270
Lys Asp Ala Asn Phe Asp Lys Lys Ile Lys Ala Leu Glu Gly Lys Trp
        275                 280                 285
Leu Leu Asp Arg Lys Leu Lys Glu Ser Glu Lys Ser Ser Ile Ala Val
        290                 295                 300
Val Arg Thr Lys Phe Phe Lys Ser Gly Lys Val Glu Leu Asn Glu Asp
305                 310                 315                 320
Tyr Leu Lys Leu Leu Lys His Met Ala Asn Glu Ile Leu Glu Arg Asp
            325                 330                 335
Gly Phe Val Asn Leu Asn Lys Tyr Pro Ile Leu Ser Arg Lys Pro Met
            340                 345                 350
Lys Arg Tyr Lys Gln Lys Asn Ile Asp Asn Leu Lys Pro Asn Met Trp
        355                 360                 365
Lys Tyr Tyr Ile Gln Phe Gly Tyr Glu Pro Ile Phe Glu Arg Lys Ala
        370                 375                 380
Ser Gly Lys Pro Lys Asn Ile Met Gly Ile Asp Arg Gly Leu Thr His
385                 390                 395                 400
Leu Leu Ala Val Ala Val Phe Ser Pro Asp Gln Gln Lys Phe Leu Phe
            405                 410                 415
Asn His Leu Glu Ser Asn Pro Ile Met His Trp Lys Trp Lys Leu Arg
            420                 425                 430
Lys Ile Arg Arg Ser Ile Gln His Met Glu Arg Arg Ile Arg Ala Glu
        435                 440                 445
Lys Asn Lys His Ile His Glu Ala Gln Leu Lys Lys Arg Leu Gly Ser
        450                 455                 460
Ile Glu Glu Lys Thr Glu Gln His Tyr His Ile Val Ser Ser Lys Ile
465                 470                 475                 480
Ile Asn Trp Ala Ile Glu Tyr Glu Ala Ala Ile Val Leu Glu Ser Leu
            485                 490                 495
Ser His Met Lys Gln Arg Gly Gly Lys Lys Ser Val Arg Thr Arg Ala
            500                 505                 510
Leu Asn Tyr Ala Leu Ser Leu Phe Asp Tyr Glu Lys Val Ala Arg Leu
        515                 520                 525
Ile Thr Tyr Lys Ala Arg Ile Arg Gly Ile Pro Val Tyr Asp Val Leu
        530                 535                 540
Pro Gly Met Thr Ser Lys Thr Cys Ala Thr Cys Leu Leu Asn Gly Ser
545                 550                 555                 560
Gln Gly Ala Tyr Val Arg Gly Leu Glu Thr Thr Lys Ala Ala Gly Lys
            565                 570                 575
Ala Thr Lys Arg Lys Asn Met Lys Ile Gly Lys Cys Met Val Cys Asn
```

```
                    580             585             590
Ser Ser Glu Asn Ser Met Ile Asp Ala Asp Leu Asn Ala Ala Arg Val
            595             600             605

Ile Ala Ile Cys Lys Tyr Lys Asn Leu Asn Asp Pro Gln Pro Ala Gly
            610             615             620

Ser Arg Lys Val Phe Lys Arg Phe
625             630

<210> SEQ ID NO 25
<211> LENGTH: 625
<212> TYPE: PRT
<213> ORGANISM: Artificial sequence
<220> FEATURE:
<223> OTHER INFORMATION: Synthetic sequence

<400> SEQUENCE: 25

Met Leu Ala Leu Lys Leu Lys Ile Met Pro Thr Glu Lys Gln Ala Glu
1               5                   10                  15

Ile Leu Asp Ala Met Phe Trp Lys Trp Ala Ser Ile Cys Ser Arg Ile
            20                  25                  30

Ala Lys Met Lys Lys Lys Val Ser Val Lys Glu Asn Lys Lys Glu Leu
        35                  40                  45

Ser Lys Lys Ile Pro Ser Asn Ser Asp Ile Trp Phe Ser Lys Thr Gln
    50                  55                  60

Leu Cys Gln Ala Glu Val Asp Val Gly Asp His Lys Lys Ala Leu Lys
65                  70                  75                  80

Asn Phe Glu Lys Arg Gln Glu Ser Leu Leu Asp Glu Leu Lys Tyr Lys
                85                  90                  95

Val Lys Ala Ile Asn Glu Val Ile Asn Asp Glu Ser Lys Arg Glu Ile
            100                 105                 110

Asp Pro Asn Asn Pro Ser Lys Phe Arg Ile Lys Asp Ser Thr Lys Lys
        115                 120                 125

Gly Asn Leu Asn Ser Pro Lys Phe Phe Thr Leu Lys Lys Trp Gln Lys
    130                 135                 140

Ile Leu Gln Glu Asn Glu Lys Arg Ile Lys Lys Glu Ser Thr Ile
145                 150                 155                 160

Glu Lys Leu Lys Arg Gly Asn Ile Phe Phe Asn Pro Thr Lys Ile Ser
                165                 170                 175

Leu His Glu Glu Glu Tyr Ser Ile Asn Phe Gly Ser Ser Lys Leu Leu
            180                 185                 190

Leu Asn Cys Phe Tyr Lys Tyr Asn Lys Lys Ser Gly Ile Asn Ser Asp
        195                 200                 205

Gln Leu Glu Asn Lys Phe Asn Glu Phe Gln Asn Gly Leu Asn Ile Ile
    210                 215                 220

Cys Ser Pro Leu Gln Pro Ile Arg Gly Ser Ser Lys Arg Ser Phe Glu
225                 230                 235                 240

Phe Ile Arg Asn Ser Ile Ile Asn Phe Leu Met Tyr Ser Leu Tyr Ala
                245                 250                 255

Lys Leu Phe Gly Ile Pro Arg Ser Val Lys Ala Leu Met Lys Ser Asn
            260                 265                 270

Lys Asp Glu Asn Lys Leu Lys Leu Glu Glu Lys Leu Lys Lys Lys
        275                 280                 285

Ser Ser Phe Asn Lys Thr Val Lys Glu Phe Glu Lys Met Ile Gly Arg
    290                 295                 300

Lys Leu Ser Asp Asn Glu Ser Lys Ile Leu Asn Asp Glu Ser Lys Lys
```

```
                305                 310                 315                 320
        Phe Phe Glu Ile Ile Lys Ser Asn Asn Lys Tyr Ile Pro Ser Glu Glu
                            325                 330                 335

Tyr Leu Lys Leu Leu Lys Asp Ile Ser Glu Glu Ile Tyr Asn Ser Asn
                            340                 345                 350

Ile Asp Phe Lys Pro Tyr Lys Tyr Ser Ile Leu Ile Arg Lys Pro Leu
                            355                 360                 365

Ser Lys Phe Lys Ser Lys Lys Leu Tyr Asn Leu Lys Pro Thr Asp Tyr
                            370                 375                 380

Lys Tyr Tyr Leu Gln Leu Ser Tyr Glu Pro Phe Ser Lys Gln Leu Ile
        385                 390                 395                 400

Ala Thr Lys Thr Ile Leu Gly Ile Asp Arg Gly Leu Lys His Leu Leu
                            405                 410                 415

Ala Val Ser Val Phe Asp Pro Ser Gln Asn Lys Phe Val Tyr Asn Lys
                            420                 425                 430

Leu Ile Lys Asn Pro Val Phe Lys Trp Lys Arg Tyr His Asp Leu
                            435                 440                 445

Lys Arg Ser Ile Arg Asn Arg Glu Arg Ile Arg Ala Leu Thr Gly
                            450                 455                 460

Val His Ile His Glu Asn Gln Leu Ile Lys Lys Leu Lys Ser Met Lys
        465                 470                 475                 480

Asn Lys Ile Asn Val Leu Tyr His Asn Val Ser Lys Asn Ile Val Asp
                            485                 490                 495

Leu Ala Lys Lys Tyr Glu Ser Thr Ile Val Leu Glu Arg Leu Glu Asn
                            500                 505                 510

Leu Lys Gln His Gly Arg Ser Lys Gly Lys Arg Tyr Lys Lys Leu Asn
                            515                 520                 525

Tyr Val Leu Ser Asn Phe Asp Tyr Lys Lys Ile Glu Ser Leu Ile Ser
                            530                 535                 540

Tyr Lys Ala Lys Lys Glu Gly Val Pro Val Ser Asn Ile Asn Pro Lys
        545                 550                 555                 560

Tyr Thr Ser Lys Thr Cys Ala Lys Cys Leu Leu Glu Val Asn Gln Leu
                            565                 570                 575

Ser Glu Leu Lys Asn Glu Tyr Asn Arg Asp Ser Lys Asn Ser Lys Ile
                            580                 585                 590

Gly Ile Cys Asn Ile His Gly Gln Ile Asp Ala Asp Leu Asn Ala Ala
                            595                 600                 605

Arg Val Ile Ala Leu Cys Tyr Ser Lys Asn Leu Asn Glu Pro His Phe
                            610                 615                 620

Lys
        625

<210> SEQ ID NO 26
<211> LENGTH: 517
<212> TYPE: PRT
<213> ORGANISM: Artificial sequence
<220> FEATURE:
<223> OTHER INFORMATION: Synthetic sequence

<400> SEQUENCE: 26

Val Ile Asn Leu Phe Gly Tyr Lys Phe Ala Leu Tyr Pro Asn Lys Thr
        1               5                   10                  15

Gln Glu Glu Leu Leu Asn Lys His Leu Gly Glu Cys Gly Trp Leu Tyr
                            20                  25                  30

Asn Lys Ala Ile Glu Gln Asn Glu Tyr Tyr Lys Ala Asp Ser Asn Ile
```

-continued

```
                35                  40                  45
Glu Glu Ala Gln Lys Lys Phe Glu Leu Leu Pro Asp Lys Asn Ser Asp
 50                  55                  60

Glu Ala Lys Val Leu Arg Gly Asn Ile Ser Lys Asp Asn Tyr Val Tyr
 65                  70                  75                  80

Arg Thr Leu Val Lys Lys Lys Ser Glu Ile Asn Val Gln Ile Arg
                 85                  90                  95

Lys Ala Val Val Leu Arg Pro Ala Glu Thr Ile Arg Asn Leu Ala Lys
                100                 105                 110

Val Lys Lys Lys Gly Leu Ser Val Gly Arg Leu Lys Phe Ile Pro Ile
                115                 120                 125

Arg Glu Trp Asp Val Leu Pro Phe Lys Gln Ser Asp Gln Ile Arg Leu
                130                 135                 140

Glu Glu Asn Tyr Leu Ile Leu Glu Pro Tyr Gly Arg Leu Lys Phe Lys
145                 150                 155                 160

Met His Arg Pro Leu Leu Gly Lys Pro Lys Thr Phe Cys Ile Lys Arg
                165                 170                 175

Thr Ala Thr Asp Arg Trp Thr Ile Ser Phe Ser Thr Glu Tyr Asp Asp
                180                 185                 190

Ser Asn Met Arg Lys Asn Asp Gly Gln Val Gly Ile Asp Val Gly
                195                 200                 205

Leu Lys Thr His Leu Arg Leu Ser Asn Glu Asn Pro Asp Glu Asp Pro
210                 215                 220

Arg Tyr Pro Asn Pro Lys Ile Trp Lys Arg Tyr Asp Arg Arg Leu Thr
225                 230                 235                 240

Ile Leu Gln Arg Arg Ile Ser Lys Ser Lys Lys Leu Gly Lys Asn Arg
                245                 250                 255

Thr Arg Leu Arg Leu Arg Leu Ser Arg Leu Trp Glu Lys Ile Arg Asn
                260                 265                 270

Ser Arg Ala Asp Leu Ile Gln Asn Glu Thr Tyr Glu Ile Leu Ser Glu
                275                 280                 285

Asn Lys Leu Ile Ala Ile Glu Asp Leu Asn Val Lys Gly Met Gln Glu
                290                 295                 300

Lys Lys Asp Lys Lys Gly Arg Lys Gly Arg Thr Arg Ala Gln Glu Lys
305                 310                 315                 320

Gly Leu His Arg Ser Ile Ser Asp Ala Ala Phe Ser Glu Phe Arg Arg
                325                 330                 335

Val Leu Glu Tyr Lys Ala Lys Arg Phe Gly Ser Glu Val Lys Pro Val
                340                 345                 350

Ser Ala Ile Asp Ser Ser Lys Glu Cys His Asn Cys Gly Asn Lys Lys
                355                 360                 365

Gly Met Pro Leu Glu Ser Arg Ile Tyr Glu Cys Pro Lys Cys Gly Leu
                370                 375                 380

Lys Ile Asp Arg Asp Leu Asn Ser Ala Lys Val Ile Leu Ala Arg Ala
385                 390                 395                 400

Thr Gly Val Arg Pro Gly Ser Asn Ala Arg Ala Asp Thr Lys Ile Ser
                405                 410                 415

Ala Thr Ala Gly Ala Ser Val Gln Thr Glu Gly Thr Val Ser Glu Asp
                420                 425                 430

Phe Arg Gln Gln Met Glu Thr Ser Asp Gln Lys Pro Met Gln Gly Glu
                435                 440                 445

Gly Ser Lys Glu Pro Pro Met Asn Pro Glu His Lys Ser Ser Gly Arg
450                 455                 460
```

Gly Ser Lys His Val Asn Ile Gly Cys Lys Asn Lys Val Gly Leu Tyr
465                 470                 475                 480

Asn Glu Asp Glu Asn Ser Arg Ser Thr Glu Lys Gln Ile Met Asp Glu
                485                 490                 495

Asn Arg Ser Thr Thr Glu Asp Met Val Glu Ile Gly Ala Leu His Ser
            500                 505                 510

Pro Val Leu Thr Thr
        515

<210> SEQ ID NO 27
<211> LENGTH: 410
<212> TYPE: PRT
<213> ORGANISM: Artificial sequence
<220> FEATURE:
<223> OTHER INFORMATION: Synthetic sequence

<400> SEQUENCE: 27

Met Ile Ala Ser Ile Asp Tyr Glu Ala Val Ser Gln Ala Leu Ile Val
1               5                   10                  15

Phe Glu Phe Lys Ala Lys Gly Lys Asp Ser Gln Tyr Gln Ala Ile Asp
                20                  25                  30

Glu Ala Ile Arg Ser Tyr Arg Phe Ile Arg Asn Ser Cys Leu Arg Tyr
            35                  40                  45

Trp Met Asp Asn Lys Val Gly Lys Tyr Asp Leu Asn Lys Tyr Cys
    50                  55                  60

Lys Val Leu Ala Lys Gln Tyr Pro Phe Ala Asn Lys Leu Asn Ser Gln
65                  70                  75                  80

Ala Arg Gln Ser Ala Ala Glu Cys Ser Trp Ser Ala Ile Ser Arg Phe
                85                  90                  95

Tyr Asp Asn Cys Lys Arg Lys Val Ser Gly Lys Gly Phe Pro Lys
                100                 105                 110

Phe Lys Lys His Ala Arg Ser Val Glu Tyr Lys Thr Ser Gly Trp Lys
                115                 120                 125

Leu Ser Glu Asn Arg Lys Ala Ile Thr Phe Thr Asp Lys Asn Gly Ile
130                 135                 140

Gly Lys Leu Lys Leu Lys Gly Thr Tyr Asp Leu His Phe Ser Gln Leu
145                 150                 155                 160

Glu Asp Met Lys Arg Val Arg Leu Val Arg Arg Ala Asp Gly Tyr Tyr
                165                 170                 175

Val Gln Phe Cys Ile Ser Val Asp Val Lys Val Glu Thr Glu Pro Thr
                180                 185                 190

Gly Lys Ala Ile Gly Leu Asp Val Gly Ile Lys Tyr Phe Leu Ala Asp
            195                 200                 205

Ser Ser Gly Asn Thr Ile Glu Asn Pro Gln Phe Tyr Arg Lys Ala Glu
210                 215                 220

Lys Lys Leu Asn Arg Ala Asn Arg Arg Lys Ser Lys Lys Tyr Ile Arg
225                 230                 235                 240

Gly Val Lys Pro Gln Ser Lys Asn Tyr His Lys Ala Arg Cys Arg Tyr
                245                 250                 255

Ala Arg Lys His Leu Arg Val Ser Arg Gln Arg Lys Glu Tyr Cys Lys
            260                 265                 270

Arg Val Ala Tyr Cys Val Ile His Ser Asn Asp Val Val Ala Tyr Glu
        275                 280                 285

Asp Leu Asn Val Lys Gly Met Val Lys Asn Arg His Leu Ala Lys Ser
290                 295                 300

```
Ile Ser Asp Val Ala Trp Ser Thr Phe Arg His Trp Leu Glu Tyr Phe
305                 310                 315                 320

Ala Ile Lys Tyr Gly Lys Leu Thr Ile Pro Val Ala Pro His Asn Thr
                325                 330                 335

Ser Gln Asn Cys Ser Asn Cys Asp Lys Lys Val Pro Lys Ser Leu Ser
            340                 345                 350

Thr Arg Thr His Ile Cys His His Cys Gly Tyr Ser Glu Asp Arg Asp
        355                 360                 365

Val Asn Ala Ala Lys Asn Ile Leu Lys Lys Ala Leu Ser Thr Val Gly
    370                 375                 380

Gln Thr Gly Ser Leu Lys Leu Gly Glu Ile Glu Pro Leu Leu Val Leu
385                 390                 395                 400

Glu Gln Ser Cys Thr Arg Lys Phe Asp Leu
                405                 410

<210> SEQ ID NO 28
<211> LENGTH: 486
<212> TYPE: PRT
<213> ORGANISM: Artificial sequence
<220> FEATURE:
<223> OTHER INFORMATION: Synthetic sequence

<400> SEQUENCE: 28

Leu Ala Glu Glu Asn Thr Leu His Leu Thr Leu Ala Met Ser Leu Pro
1               5                   10                  15

Leu Asn Asp Leu Pro Glu Asn Arg Thr Arg Ser Glu Leu Trp Arg Arg
                20                  25                  30

Gln Trp Leu Pro Gln Lys Lys Leu Ser Leu Leu Gly Val Asn Gln
            35                  40                  45

Ser Val Arg Lys Ala Ala Asp Cys Leu Arg Trp Phe Glu Pro Tyr
    50                  55                  60

Gln Glu Leu Leu Trp Trp Glu Pro Thr Asp Pro Asp Gly Lys Lys Leu
65                  70                  75                  80

Leu Asp Lys Glu Gly Arg Pro Ile Lys Arg Thr Ala Gly His Met Arg
                85                  90                  95

Val Leu Arg Lys Leu Glu Glu Ile Ala Pro Phe Arg Gly Tyr Gln Leu
                100                 105                 110

Gly Ser Ala Val Lys Asn Gly Leu Arg His Lys Val Ala Asp Leu Leu
            115                 120                 125

Leu Ser Tyr Ala Lys Arg Lys Leu Asp Pro Gln Phe Thr Asp Lys Thr
    130                 135                 140

Ser Tyr Pro Ser Ile Gly Asp Gln Phe Pro Ile Val Trp Thr Gly Ala
145                 150                 155                 160

Phe Val Cys Tyr Glu Gln Ser Ile Thr Gly Gln Leu Tyr Leu Tyr Leu
                165                 170                 175

Pro Leu Phe Pro Arg Gly Ser His Gln Glu Asp Ile Thr Asn Tyr
                180                 185                 190

Asp Pro Asp Arg Gly Pro Ala Leu Gln Val Phe Gly Glu Lys Glu Ile
            195                 200                 205

Ala Arg Leu Ser Arg Ser Thr Ser Gly Leu Leu Leu Pro Leu Gln Phe
    210                 215                 220

Asp Lys Trp Gly Glu Ala Thr Phe Ile Arg Gly Glu Asn Asn Pro Pro
225                 230                 235                 240

Thr Trp Lys Ala Thr His Arg Arg Ser Asp Lys Lys Trp Leu Ser Glu
                245                 250                 255
```

Val Leu Leu Arg Glu Lys Asp Phe Gln Pro Lys Arg Val Glu Leu Leu
                260                 265                 270

Val Arg Asn Gly Arg Ile Phe Val Asn Val Ala Cys Glu Ile Pro Thr
            275                 280                 285

Lys Pro Leu Leu Glu Val Glu Asn Phe Met Gly Val Ser Phe Gly Leu
290                 295                 300

Glu His Leu Val Thr Val Val Ile Asn Arg Asp Gly Asn Val Val
305                 310                 315                 320

His Gln Arg Gln Glu Pro Ala Arg Arg Tyr Glu Lys Thr Tyr Phe Ala
                325                 330                 335

Arg Leu Glu Arg Leu Arg Arg Gly Gly Pro Phe Ser Gln Glu Leu
            340                 345                 350

Glu Thr Phe His Tyr Arg Gln Val Ala Gln Ile Val Glu Glu Ala Leu
                355                 360                 365

Arg Phe Lys Ser Val Pro Ala Val Glu Gln Val Gly Asn Ile Pro Lys
            370                 375                 380

Gly Arg Tyr Asn Pro Arg Leu Asn Leu Arg Leu Ser Tyr Trp Pro Phe
385                 390                 395                 400

Gly Lys Leu Ala Asp Leu Thr Ser Tyr Lys Ala Val Lys Glu Gly Leu
                405                 410                 415

Pro Lys Pro Tyr Ser Val Tyr Ser Ala Thr Ala Lys Met Leu Cys Ser
            420                 425                 430

Thr Cys Gly Ala Ala Asn Lys Glu Gly Asp Gln Pro Ile Ser Leu Lys
            435                 440                 445

Gly Pro Thr Val Tyr Cys Gly Asn Cys Gly Thr Arg His Asn Thr Gly
            450                 455                 460

Phe Asn Thr Ala Leu Asn Leu Ala Arg Arg Ala Gln Glu Leu Phe Val
465                 470                 475                 480

Lys Gly Val Val Ala Arg
                485

<210> SEQ ID NO 29
<211> LENGTH: 602
<212> TYPE: PRT
<213> ORGANISM: Artificial sequence
<220> FEATURE:
<223> OTHER INFORMATION: Synthetic sequence

<400> SEQUENCE: 29

Met Ser Gln Ser Leu Leu Lys Trp His Asp Met Ala Gly Arg Asp Lys
1               5                   10                  15

Asp Ala Ser Arg Ser Leu Gln Lys Ser Ala Val Glu Gly Val Leu Leu
                20                  25                  30

His Leu Thr Ala Ser His Arg Val Ala Leu Glu Met Leu Glu Lys Ser
            35                  40                  45

Val Ser Gln Thr Val Ala Val Thr Met Glu Ala Gln Gln Arg Leu
        50                  55                  60

Val Ile Val Leu Glu Asp Asp Pro Thr Lys Ala Thr Ser Arg Lys Arg
65                  70                  75                  80

Val Ile Ser Ala Asp Leu Gln Phe Thr Arg Glu Glu Phe Gly Ser Leu
                85                  90                  95

Pro Asn Trp Ala Gln Lys Leu Ala Ser Thr Cys Pro Glu Ile Ala Thr
            100                 105                 110

Lys Tyr Ala Asp Lys His Ile Asn Ser Ile Arg Ile Ala Trp Gly Val
        115                 120                 125

```
Ala Lys Glu Ser Thr Asn Gly Asp Ala Val Glu Gln Lys Leu Gln Trp
    130                 135                 140

Gln Ile Arg Leu Leu Asp Val Thr Met Phe Leu Gln Gln Leu Val Leu
145                 150                 155                 160

Gln Leu Ala Asp Lys Ala Leu Leu Glu Gln Ile Pro Ser Ser Ile Arg
                165                 170                 175

Gly Gly Ile Gly Gln Glu Val Ala Gln Val Thr Ser His Ile Gln
            180                 185                 190

Leu Leu Asp Ser Gly Thr Val Leu Lys Ala Glu Leu Pro Thr Ile Ser
        195                 200                 205

Asp Arg Asn Ser Glu Leu Ala Arg Lys Gln Trp Glu Asp Ala Ile Gln
    210                 215                 220

Thr Val Cys Thr Tyr Ala Leu Pro Phe Ser Arg Glu Arg Ala Arg Ile
225                 230                 235                 240

Leu Asp Pro Gly Lys Tyr Ala Ala Glu Asp Pro Arg Gly Asp Arg Leu
                245                 250                 255

Ile Asn Ile Asp Pro Met Trp Ala Arg Val Leu Lys Gly Pro Thr Val
            260                 265                 270

Lys Ser Leu Pro Leu Leu Phe Val Ser Gly Ser Ile Arg Ile Val
        275                 280                 285

Lys Leu Thr Leu Pro Arg Lys His Ala Ala Gly His Lys His Thr Phe
    290                 295                 300

Thr Ala Thr Tyr Leu Val Leu Pro Val Ser Arg Glu Trp Ile Asn Ser
305                 310                 315                 320

Leu Pro Gly Thr Val Gln Glu Lys Val Gln Trp Trp Lys Lys Pro Asp
                325                 330                 335

Val Leu Ala Thr Gln Glu Leu Leu Val Gly Lys Gly Ala Leu Lys Lys
            340                 345                 350

Ser Ala Asn Thr Leu Val Ile Pro Ile Ser Ala Gly Lys Lys Arg Phe
        355                 360                 365

Phe Asn His Ile Leu Pro Ala Leu Gln Arg Gly Phe Pro Leu Gln Trp
    370                 375                 380

Gln Arg Ile Val Gly Arg Ser Tyr Arg Pro Ala Thr His Arg Lys
385                 390                 395                 400

Trp Phe Ala Gln Leu Thr Ile Gly Tyr Thr Asn Pro Ser Ser Leu Pro
                405                 410                 415

Glu Met Ala Leu Gly Ile His Phe Gly Met Lys Asp Ile Leu Trp Trp
            420                 425                 430

Ala Leu Ala Asp Lys Gln Gly Asn Ile Leu Lys Asp Gly Ser Ile Pro
        435                 440                 445

Gly Asn Ser Ile Leu Asp Phe Ser Leu Gln Glu Lys Gly Lys Ile Glu
    450                 455                 460

Arg Gln Gln Lys Ala Gly Lys Asn Val Ala Gly Lys Tyr Gly Lys
465                 470                 475                 480

Ser Leu Leu Asn Ala Thr Tyr Arg Val Val Asn Gly Val Leu Glu Phe
                485                 490                 495

Ser Lys Gly Ile Ser Ala Glu His Ala Ser Gln Pro Ile Gly Leu Gly
            500                 505                 510

Leu Glu Thr Ile Arg Phe Val Asp Lys Ala Ser Gly Ser Ser Pro Val
        515                 520                 525

Asn Ala Arg His Ser Asn Trp Asn Tyr Gly Gln Leu Ser Gly Ile Phe
    530                 535                 540
```

```
Ala Asn Lys Ala Gly Pro Ala Gly Phe Ser Val Thr Glu Ile Thr Leu
545                 550                 555                 560

Lys Lys Ala Gln Arg Asp Leu Ser Asp Ala Glu Gln Ala Arg Val Leu
                565                 570                 575

Ala Ile Glu Ala Thr Lys Arg Phe Ala Ser Arg Ile Lys Arg Leu Ala
            580                 585                 590

Thr Lys Arg Lys Asp Asp Thr Leu Phe Val
        595                 600

<210> SEQ ID NO 30
<211> LENGTH: 494
<212> TYPE: PRT
<213> ORGANISM: Artificial sequence
<220> FEATURE:
<223> OTHER INFORMATION: Synthetic sequence

<400> SEQUENCE: 30

Val Glu Pro Val Glu Lys Glu Arg Phe Tyr Tyr Arg Thr Tyr Thr Phe
1               5                   10                  15

Arg Leu Asp Gly Gln Pro Arg Thr Gln Asn Leu Thr Thr Gln Ser Gly
            20                  25                  30

Trp Gly Leu Leu Thr Lys Ala Val Leu Asp Asn Thr Lys His Tyr Trp
        35                  40                  45

Glu Ile Val His His Ala Arg Ile Ala Asn Gln Pro Ile Val Phe Glu
50                  55                  60

Asn Pro Val Ile Asp Glu Gln Gly Asn Pro Lys Leu Asn Lys Leu Gly
65                  70                  75                  80

Gln Pro Arg Phe Trp Lys Arg Pro Ile Ser Asp Ile Val Asn Gln Leu
                85                  90                  95

Arg Ala Leu Phe Glu Asn Gln Asn Pro Tyr Gln Leu Gly Ser Ser Leu
            100                 105                 110

Ile Gln Gly Thr Tyr Trp Asp Val Ala Glu Asn Leu Ala Ser Trp Tyr
        115                 120                 125

Ala Leu Asn Lys Glu Tyr Leu Ala Gly Thr Ala Thr Trp Gly Glu Pro
130                 135                 140

Ser Phe Pro Glu Pro His Pro Leu Thr Glu Ile Asn Gln Trp Met Pro
145                 150                 155                 160

Leu Thr Phe Ser Ser Gly Lys Val Val Arg Leu Leu Lys Asn Ala Ser
                165                 170                 175

Gly Arg Tyr Phe Ile Gly Leu Pro Ile Leu Gly Glu Asn Asn Pro Cys
            180                 185                 190

Tyr Arg Met Arg Thr Ile Glu Lys Leu Ile Pro Cys Asp Gly Lys Gly
        195                 200                 205

Arg Val Thr Ser Gly Ser Leu Ile Leu Phe Pro Leu Val Gly Ile Tyr
210                 215                 220

Ala Gln Gln His Arg Arg Met Thr Asp Ile Cys Glu Ser Ile Arg Thr
225                 230                 235                 240

Glu Lys Gly Lys Leu Ala Trp Ala Gln Val Ser Ile Asp Tyr Val Arg
                245                 250                 255

Glu Val Asp Lys Arg Arg Arg Met Arg Arg Thr Arg Lys Ser Gln Gly
            260                 265                 270

Trp Ile Gln Gly Pro Trp Gln Glu Val Phe Ile Leu Arg Leu Val Leu
        275                 280                 285

Ala His Lys Ala Pro Lys Leu Tyr Lys Pro Arg Cys Phe Ala Gly Ile
290                 295                 300
```

```
Ser Leu Gly Pro Lys Thr Leu Ala Ser Cys Val Ile Leu Asp Gln Asp
305                 310                 315                 320

Glu Arg Val Val Glu Lys Gln Gln Trp Ser Gly Ser Glu Leu Leu Ser
                325                 330                 335

Leu Ile His Gln Gly Glu Arg Leu Arg Ser Leu Arg Glu Gln Ser
            340                 345                 350

Lys Pro Thr Trp Asn Ala Ala Tyr Arg Lys Gln Leu Lys Ser Leu Ile
                355                 360                 365

Asn Thr Gln Val Phe Thr Ile Val Thr Phe Leu Arg Glu Arg Gly Ala
            370                 375                 380

Ala Val Arg Leu Glu Ser Ile Ala Arg Val Arg Lys Ser Thr Pro Ala
385                 390                 395                 400

Pro Pro Val Asn Phe Leu Leu Ser His Trp Ala Tyr Arg Gln Ile Thr
                405                 410                 415

Glu Arg Leu Lys Asp Leu Ala Ile Arg Asn Gly Met Pro Leu Thr His
                420                 425                 430

Ser Asn Gly Ser Tyr Gly Val Arg Phe Thr Cys Ser Gln Cys Gly Ala
            435                 440                 445

Thr Asn Gln Gly Ile Lys Asp Pro Thr Lys Tyr Lys Val Asp Ile Glu
450                 455                 460

Ser Glu Thr Phe Leu Cys Ser Ile Cys Ser His Arg Glu Ile Ala Ala
465                 470                 475                 480

Val Asn Thr Ala Thr Asn Leu Ala Lys Gln Leu Leu Asp Glu
            485                 490

<210> SEQ ID NO 31
<211> LENGTH: 526
<212> TYPE: PRT
<213> ORGANISM: Artificial sequence
<220> FEATURE:
<223> OTHER INFORMATION: Synthetic sequence

<400> SEQUENCE: 31

Met Asn Asp Thr Glu Thr Ser Glu Thr Leu Thr Ser His Arg Thr Val
1               5                   10                  15

Cys Ala His Leu His Val Val Gly Glu Thr Gly Ser Leu Pro Arg Leu
                20                  25                  30

Val Glu Ala Ala Leu Ala Glu Leu Ile Thr Leu Asn Gly Arg Ala Thr
            35                  40                  45

Gln Ala Leu Leu Ser Leu Ala Lys Asn Gly Leu Val Leu Arg Arg Asp
        50                  55                  60

Lys Glu Glu Asn Leu Ile Ala Ala Glu Leu Thr Leu Pro Cys Arg Lys
65                  70                  75                  80

Asn Lys Tyr Ala Asp Val Ala Lys Ala Gly Glu Pro Ile Leu Ala
                85                  90                  95

Thr Arg Ile Asn Asn Lys Gly Lys Leu Val Thr Lys Lys Trp Tyr Gly
                100                 105                 110

Glu Gly Asn Ser Tyr His Ile Val Arg Phe Thr Pro Glu Thr Gly Met
            115                 120                 125

Phe Thr Val Arg Val Phe Asp Arg Tyr Ala Phe Asp Glu Glu Leu Leu
130                 135                 140

His Leu His Ser Glu Val Val Phe Gly Ser Asp Leu Pro Lys Gly Ile
145                 150                 155                 160

Lys Ala Lys Thr Asp Ser Leu Pro Ala Asn Phe Leu Gln Ala Val Phe
                165                 170                 175
```

```
Thr Ser Phe Leu Glu Leu Pro Phe Gln Gly Phe Pro Asp Ile Val Val
            180                 185                 190

Lys Pro Ala Met Lys Gln Ala Ala Glu Gln Leu Leu Ser Tyr Val Gln
        195                 200                 205

Leu Glu Ala Gly Glu Asn Gln Gln Ala Glu Tyr Pro Asp Thr Asn Glu
    210                 215                 220

Arg Asp Pro Glu Leu Arg Leu Val Glu Trp Gln Lys Ser Leu His Glu
225                 230                 235                 240

Leu Ser Val Arg Thr Glu Pro Phe Glu Phe Val Arg Ala Arg Asp Ile
                245                 250                 255

Asp Tyr Tyr Ala Glu Thr Asp Arg Arg Gly Asn Arg Phe Val Asn Ile
                260                 265                 270

Thr Pro Glu Trp Thr Lys Phe Ala Glu Ser Pro Phe Ala Arg Arg Leu
            275                 280                 285

Pro Leu Lys Ile Pro Pro Glu Phe Cys Ile Leu Leu Arg Arg Lys Thr
        290                 295                 300

Glu Gly His Ala Lys Ile Pro Asn Arg Ile Tyr Leu Gly Leu Gln Ile
305                 310                 315                 320

Phe Asp Gly Val Thr Pro Asp Ser Thr Leu Gly Val Leu Ala Thr Ala
                325                 330                 335

Glu Asp Gly Lys Leu Phe Trp Trp His Asp His Leu Asp Glu Phe Ser
            340                 345                 350

Asn Leu Glu Gly Lys Pro Glu Pro Lys Leu Lys Asn Lys Pro Gln Leu
        355                 360                 365

Leu Met Val Ser Leu Glu Tyr Asp Arg Glu Gln Arg Phe Glu Glu Ser
    370                 375                 380

Val Gly Gly Asp Arg Lys Ile Cys Leu Val Thr Leu Lys Glu Thr Arg
385                 390                 395                 400

Asn Phe Arg Arg Gly Trp Asn Gly Arg Ile Leu Gly Ile His Phe Gln
                405                 410                 415

His Asn Pro Val Ile Thr Trp Ala Leu Met Asp His Asp Ala Glu Val
            420                 425                 430

Leu Glu Lys Gly Phe Ile Glu Gly Asn Ala Phe Leu Gly Lys Ala Leu
        435                 440                 445

Asp Lys Gln Ala Leu Asn Glu Tyr Leu Gln Lys Gly Gly Lys Trp Val
    450                 455                 460

Gly Asp Arg Ser Phe Gly Asn Lys Leu Lys Gly Ile Thr His Thr Leu
465                 470                 475                 480

Ala Ser Leu Ile Val Arg Leu Ala Arg Glu Lys Asp Ala Trp Ile Ala
                485                 490                 495

Leu Glu Glu Ile Ser Trp Val Gln Lys Gln Ser Ala Asp Ser Val Ala
            500                 505                 510

Asn His Glu Ile Val Glu Gln Pro His His Ser Leu Thr Arg
        515                 520                 525

<210> SEQ ID NO 32
<211> LENGTH: 649
<212> TYPE: PRT
<213> ORGANISM: Artificial sequence
<220> FEATURE:
<223> OTHER INFORMATION: Synthetic sequence

<400> SEQUENCE: 32

Met Asn Asp Thr Glu Thr Ser Glu Thr Leu Thr Ser His Arg Thr Val
1               5                   10                  15
```

```
Cys Ala His Leu His Val Val Gly Glu Thr Gly Ser Leu Pro Arg Leu
                 20              25                  30

Val Glu Ala Ala Leu Ala Glu Leu Ile Thr Leu Asn Gly Arg Ala Thr
             35              40                  45

Gln Ala Leu Leu Ser Leu Ala Lys Asn Gly Leu Val Leu Arg Arg Asp
 50              55                  60

Lys Glu Glu Asn Leu Ile Ala Ala Glu Leu Thr Leu Pro Cys Arg Lys
 65              70                  75                      80

Asn Lys Tyr Ala Asp Val Ala Ala Lys Ala Gly Glu Pro Ile Leu Ala
                 85              90                  95

Thr Arg Ile Asn Asn Lys Gly Lys Leu Val Thr Lys Lys Trp Tyr Gly
                100             105                 110

Glu Gly Asn Ser Tyr His Ile Val Arg Phe Thr Pro Glu Thr Gly Met
                115             120                 125

Phe Thr Val Arg Val Phe Asp Arg Tyr Ala Phe Asp Glu Glu Leu Leu
                130             135                 140

His Leu His Ser Glu Val Val Phe Gly Ser Asp Leu Pro Lys Gly Ile
145             150                 155                     160

Lys Ala Lys Thr Asp Ser Leu Pro Ala Asn Phe Leu Gln Ala Val Phe
                165             170                 175

Thr Ser Phe Leu Glu Leu Pro Phe Gln Gly Phe Pro Asp Ile Val Val
                180             185                 190

Lys Pro Ala Met Lys Gln Ala Ala Glu Gln Leu Leu Ser Tyr Val Gln
                195             200                 205

Leu Glu Ala Gly Glu Asn Gln Gln Ala Glu Tyr Pro Asp Thr Asn Glu
210             215                 220

Arg Asp Pro Glu Leu Arg Leu Val Glu Trp Gln Lys Ser Leu His Glu
225             230                 235                     240

Leu Ser Val Arg Thr Glu Pro Phe Glu Phe Val Arg Ala Arg Asp Ile
                245             250                 255

Asp Tyr Tyr Ala Glu Thr Asp Arg Arg Gly Asn Arg Phe Val Asn Ile
                260             265                 270

Thr Pro Glu Trp Thr Lys Phe Ala Glu Ser Pro Phe Ala Arg Arg Leu
                275             280                 285

Pro Leu Lys Ile Pro Pro Glu Phe Cys Ile Leu Leu Arg Arg Lys Thr
290             295                 300

Glu Gly His Ala Lys Ile Pro Asn Arg Ile Tyr Leu Gly Leu Gln Ile
305             310                 315                     320

Phe Asp Gly Val Thr Pro Asp Ser Thr Leu Gly Val Leu Ala Thr Ala
                325             330                 335

Glu Asp Gly Lys Leu Phe Trp Trp His Asp His Leu Asp Glu Phe Ser
                340             345                 350

Asn Leu Glu Gly Lys Pro Glu Pro Lys Leu Lys Asn Lys Pro Gln Leu
                355             360                 365

Leu Met Val Ser Leu Glu Tyr Asp Arg Glu Gln Arg Phe Glu Glu Ser
                370             375                 380

Val Gly Gly Asp Arg Lys Ile Cys Leu Val Thr Leu Lys Glu Thr Arg
385             390                 395                     400

Asn Phe Arg Arg Gly Arg His Gly His Thr Arg Thr Asp Arg Leu Pro
                405             410                 415

Ala Gly Asn Thr Leu Trp Arg Ala Asp Phe Ala Thr Ser Ala Glu Val
                420             425                 430

Ala Ala Pro Lys Trp Asn Gly Arg Ile Leu Gly Ile His Phe Gln His
```

```
               435                 440                 445
Asn Pro Val Ile Thr Trp Ala Leu Met Asp His Asp Ala Glu Val Leu
450                 455                 460
Glu Lys Gly Phe Ile Glu Gly Asn Ala Phe Leu Gly Lys Ala Leu Asp
465                 470                 475                 480
Lys Gln Ala Leu Asn Glu Tyr Leu Gln Lys Gly Lys Trp Val Gly
                    485                 490                 495
Asp Arg Ser Phe Gly Asn Lys Leu Lys Gly Ile Thr His Thr Leu Ala
                500                 505                 510
Ser Leu Ile Val Arg Leu Ala Arg Glu Lys Asp Ala Trp Ile Ala Leu
                515                 520                 525
Glu Glu Ile Ser Trp Val Gln Lys Gln Ser Ala Asp Ser Val Ala Asn
530                 535                 540
Arg Arg Phe Ser Met Trp Asn Tyr Ser Arg Leu Ala Thr Leu Ile Glu
545                 550                 555                 560
Trp Leu Gly Thr Asp Ile Ala Thr Arg Asp Cys Gly Thr Ala Ala Pro
                565                 570                 575
Leu Ala His Lys Val Ser Asp Tyr Leu Thr His Phe Thr Cys Pro Glu
                580                 585                 590
Cys Gly Ala Cys Arg Lys Ala Gly Gln Lys Lys Glu Ile Ala Asp Thr
                595                 600                 605
Val Arg Ala Gly Asp Ile Leu Thr Cys Arg Lys Cys Gly Phe Ser Gly
610                 615                 620
Pro Ile Pro Asp Asn Phe Ile Ala Glu Phe Val Ala Lys Lys Ala Leu
625                 630                 635                 640
Glu Arg Met Leu Lys Lys Pro Val
                645

<210> SEQ ID NO 33
<211> LENGTH: 414
<212> TYPE: PRT
<213> ORGANISM: Artificial sequence
<220> FEATURE:
<223> OTHER INFORMATION: Synthetic sequence

<400> SEQUENCE: 33

Met Ala Lys Arg Asn Phe Gly Glu Lys Ser Glu Ala Leu Tyr Arg Ala
1               5                   10                  15
Val Arg Phe Glu Val Arg Pro Ser Lys Glu Glu Leu Ser Ile Leu Leu
                20                  25                  30
Ala Val Ser Glu Val Leu Arg Met Leu Phe Asn Ser Ala Leu Ala Glu
                35                  40                  45
Arg Gln Gln Val Phe Thr Glu Phe Ile Ala Ser Leu Tyr Ala Glu Leu
                50                  55                  60
Lys Ser Ala Ser Val Pro Glu Glu Ile Ser Glu Ile Arg Lys Lys Leu
65                  70                  75                  80
Arg Glu Ala Tyr Lys Glu His Ser Ile Ser Leu Phe Asp Gln Ile Asn
                85                  90                  95
Ala Leu Thr Ala Arg Arg Val Glu Asp Glu Ala Phe Ala Ser Val Thr
                100                 105                 110
Arg Asn Trp Gln Glu Glu Thr Leu Asp Ala Leu Asp Gly Ala Tyr Lys
                115                 120                 125
Ser Phe Leu Ser Leu Arg Arg Lys Gly Asp Tyr Asp Ala His Ser Pro
                130                 135                 140
Arg Ser Arg Asp Ser Gly Phe Phe Gln Lys Ile Pro Gly Arg Ser Gly
```

```
145                 150                 155                 160
    Phe Lys Ile Gly Glu Gly Arg Ile Ala Leu Ser Cys Gly Ala Gly Arg
                    165                 170                 175

Lys Leu Ser Phe Pro Ile Pro Asp Tyr Gln Gln Gly Arg Leu Ala Glu
                    180                 185                 190

Thr Thr Lys Leu Lys Lys Phe Glu Leu Tyr Arg Asp Gln Pro Asn Leu
                    195                 200                 205

Ala Lys Ser Gly Arg Phe Trp Ile Ser Val Val Tyr Glu Leu Pro Lys
                210                 215                 220

Pro Glu Ala Thr Thr Cys Gln Ser Glu Gln Val Ala Phe Val Ala Leu
    225                 230                 235                 240

Gly Ala Ser Ser Ile Gly Val Val Ser Gln Arg Gly Glu Glu Val Ile
                    245                 250                 255

Ala Leu Trp Arg Ser Asp Lys His Trp Val Pro Lys Ile Glu Ala Val
                    260                 265                 270

Glu Glu Arg Met Lys Arg Val Lys Gly Ser Arg Gly Trp Leu Arg
                    275                 280                 285

Leu Leu Asn Ser Gly Lys Arg Arg Met His Met Ile Ser Ser Arg Gln
                290                 295                 300

His Val Gln Asp Glu Arg Glu Ile Val Asp Tyr Leu Val Arg Asn His
    305                 310                 315                 320

Gly Ser His Phe Val Val Thr Glu Leu Val Val Arg Ser Lys Glu Gly
                    325                 330                 335

Lys Leu Ala Asp Ser Ser Lys Pro Glu Arg Gly Gly Ser Leu Gly Leu
                    340                 345                 350

Asn Trp Ala Ala Gln Asn Thr Gly Ser Leu Ser Arg Leu Val Arg Gln
                    355                 360                 365

Leu Glu Glu Lys Val Lys Glu His Gly Gly Ser Val Arg Lys His Lys
                370                 375                 380

Leu Thr Leu Thr Glu Ala Pro Pro Ala Arg Gly Ala Glu Asn Lys Leu
    385                 390                 395                 400

Trp Met Ala Arg Lys Leu Arg Glu Ser Phe Leu Lys Glu Val
                    405                 410

<210> SEQ ID NO 34
<211> LENGTH: 413
<212> TYPE: PRT
<213> ORGANISM: Artificial sequence
<220> FEATURE:
<223> OTHER INFORMATION: Synthetic sequence

<400> SEQUENCE: 34

Leu Ala Lys Asn Asp Glu Lys Glu Leu Leu Tyr Gln Ser Val Lys Phe
    1               5                   10                  15

Glu Ile Tyr Pro Asp Glu Ser Lys Ile Arg Val Leu Thr Arg Val Ser
                    20                  25                  30

Asn Ile Leu Val Leu Val Trp Asn Ser Ala Leu Gly Glu Arg Arg Ala
                    35                  40                  45

Arg Phe Glu Leu Tyr Ile Ala Pro Leu Tyr Glu Glu Leu Lys Lys Phe
                50                  55                  60

Pro Arg Lys Ser Ala Glu Ser Asn Ala Leu Arg Gln Lys Ile Arg Glu
    65                  70                  75                  80

Gly Tyr Lys Glu His Ile Pro Thr Phe Phe Asp Gln Leu Lys Lys Leu
                    85                  90                  95

Leu Thr Pro Met Arg Lys Glu Asp Pro Ala Leu Leu Gly Ser Val Pro
```

```
            100                 105                 110
Arg Ala Tyr Gln Glu Glu Thr Leu Asn Thr Leu Asn Gly Ser Phe Val
            115                 120                 125

Ser Phe Met Thr Leu Arg Arg Asn Asn Asp Met Asp Ala Lys Pro Pro
            130                 135                 140

Lys Gly Arg Ala Glu Asp Arg Phe His Glu Ile Ser Gly Arg Ser Gly
145                 150                 155                 160

Phe Lys Ile Asp Gly Ser Glu Phe Val Leu Ser Thr Lys Glu Gln Lys
                165                 170                 175

Leu Arg Phe Pro Ile Pro Asn Tyr Gln Leu Glu Lys Leu Lys Glu Ala
            180                 185                 190

Lys Gln Ile Lys Lys Phe Thr Leu Tyr Gln Ser Arg Asp Arg Arg Phe
            195                 200                 205

Trp Ile Ser Ile Ala Tyr Glu Ile Glu Leu Pro Asp Gln Arg Pro Phe
            210                 215                 220

Asn Pro Glu Glu Val Ile Tyr Ile Ala Phe Gly Ala Ser Ser Ile Gly
225                 230                 235                 240

Val Ile Ser Pro Glu Gly Glu Lys Val Ile Asp Phe Trp Arg Pro Asp
                245                 250                 255

Lys His Trp Lys Pro Lys Ile Lys Glu Val Glu Asn Arg Met Arg Ser
            260                 265                 270

Cys Lys Lys Gly Ser Arg Ala Trp Lys Lys Arg Ala Ala Ala Arg Arg
            275                 280                 285

Lys Met Tyr Ala Met Thr Gln Arg Gln Gln Lys Leu Asn His Arg Glu
            290                 295                 300

Ile Val Ala Ser Leu Leu Arg Leu Gly Phe His Phe Val Val Thr Glu
305                 310                 315                 320

Tyr Thr Val Arg Ser Lys Pro Gly Lys Leu Ala Asp Gly Ser Asn Pro
                325                 330                 335

Lys Arg Gly Gly Ala Pro Gln Gly Phe Asn Trp Ser Ala Gln Asn Thr
            340                 345                 350

Gly Ser Phe Gly Glu Phe Ile Leu Trp Leu Lys Gln Lys Val Lys Glu
            355                 360                 365

Gln Gly Gly Thr Val Gln Thr Phe Arg Leu Val Leu Gly Gln Ser Glu
            370                 375                 380

Arg Pro Glu Lys Arg Gly Arg Asp Asn Lys Ile Glu Met Val Arg Leu
385                 390                 395                 400

Leu Arg Glu Lys Tyr Leu Glu Ser Gln Thr Ile Val Val
                405                 410

<210> SEQ ID NO 35
<211> LENGTH: 449
<212> TYPE: PRT
<213> ORGANISM: Artificial sequence
<220> FEATURE:
<223> OTHER INFORMATION: Synthetic sequence

<400> SEQUENCE: 35

Met Ala Lys Gly Lys Lys Glu Gly Lys Pro Leu Tyr Arg Ala Val
1               5                   10                  15

Arg Phe Glu Ile Phe Pro Thr Ser Asp Gln Ile Thr Leu Phe Leu Arg
            20                  25                  30

Val Ser Lys Asn Leu Gln Gln Val Trp Asn Glu Ala Trp Gln Glu Arg
            35                  40                  45

Gln Ser Cys Tyr Glu Gln Phe Phe Gly Ser Ile Tyr Glu Arg Ile Gly
```

```
            50                  55                  60
Gln Ala Lys Lys Arg Ala Gln Glu Ala Gly Phe Ser Glu Val Trp Glu
 65                  70                  75                  80
Asn Glu Ala Lys Lys Gly Leu Asn Lys Lys Leu Arg Gln Gln Glu Ile
                 85                  90                  95
Ser Met Gln Leu Val Ser Lys Glu Ser Leu Leu Gln Glu Leu Ser
                100                 105                 110
Ile Ala Phe Gln Glu His Gly Val Thr Leu Tyr Asp Gln Ile Asn Gly
            115                 120                 125
Leu Thr Ala Arg Arg Ile Ile Gly Glu Phe Ala Leu Ile Pro Arg Asn
130                 135                 140
Trp Gln Glu Glu Thr Leu Asp Ser Leu Asp Gly Ser Phe Lys Ser Phe
145                 150                 155                 160
Leu Ala Leu Arg Lys Asn Gly Asp Pro Asp Ala Lys Pro Pro Arg Gln
                165                 170                 175
Arg Val Ser Glu Asn Ser Phe Tyr Lys Ile Pro Gly Arg Ser Gly Phe
                180                 185                 190
Lys Val Ser Asn Gly Gln Ile Tyr Leu Ser Phe Gly Lys Ile Gly Gln
                195                 200                 205
Thr Leu Thr Ser Val Ile Pro Glu Phe Gln Leu Lys Arg Leu Glu Thr
            210                 215                 220
Ala Ile Lys Leu Lys Lys Phe Glu Leu Cys Arg Asp Glu Arg Asp Met
225                 230                 235                 240
Ala Lys Pro Gly Arg Phe Trp Ile Ser Val Ala Tyr Glu Ile Pro Lys
                245                 250                 255
Pro Glu Lys Val Pro Val Val Ser Lys Gln Ile Thr Tyr Leu Ala Ile
                260                 265                 270
Gly Ala Ser Arg Leu Gly Val Val Ser Pro Lys Gly Glu Phe Cys Leu
                275                 280                 285
Asn Leu Pro Arg Ser Asp Tyr His Trp Lys Pro Gln Ile Asn Ala Leu
            290                 295                 300
Gln Glu Arg Leu Glu Gly Val Val Lys Gly Ser Arg Lys Trp Lys Lys
305                 310                 315                 320
Arg Met Ala Ala Cys Thr Arg Met Phe Ala Lys Leu Gly His Gln Gln
                325                 330                 335
Lys Gln His Gly Gln Tyr Glu Val Val Lys Lys Leu Leu Arg His Gly
                340                 345                 350
Val His Phe Val Val Thr Glu Leu Lys Val Arg Ser Lys Pro Gly Ala
                355                 360                 365
Leu Ala Asp Ala Ser Lys Ser Asp Arg Lys Gly Ser Pro Thr Gly Pro
370                 375                 380
Asn Trp Ser Ala Gln Asn Thr Gly Asn Ile Ala Arg Leu Ile Gln Lys
385                 390                 395                 400
Leu Thr Asp Lys Ala Ser Glu His Gly Gly Thr Val Ile Lys Arg Asn
                405                 410                 415
Pro Pro Leu Leu Ser Leu Glu Glu Arg Gln Leu Pro Asp Ala Gln Arg
                420                 425                 430
Lys Ile Phe Ile Ala Lys Lys Leu Arg Glu Glu Phe Leu Ala Asp Gln
                435                 440                 445

Lys

<210> SEQ ID NO 36
<211> LENGTH: 711
```

<212> TYPE: PRT
<213> ORGANISM: Artificial sequence
<220> FEATURE:
<223> OTHER INFORMATION: Synthetic sequence

<400> SEQUENCE: 36

```
Met Ala Lys Arg Glu Lys Lys Asp Asp Val Val Leu Arg Gly Thr Lys
1               5                   10                  15

Met Arg Ile Tyr Pro Thr Asp Arg Gln Val Thr Leu Met Asp Met Trp
            20                  25                  30

Arg Arg Arg Cys Ile Ser Leu Trp Asn Leu Leu Leu Asn Leu Glu Thr
        35                  40                  45

Ala Ala Tyr Gly Ala Lys Asn Thr Arg Ser Lys Leu Gly Trp Arg Ser
    50                  55                  60

Ile Trp Ala Arg Val Val Glu Glu Asn His Ala Lys Ala Leu Ile Val
65                  70                  75                  80

Tyr Gln His Gly Lys Cys Lys Lys Asp Gly Ser Phe Val Leu Lys Arg
                85                  90                  95

Asp Gly Thr Val Lys His Pro Pro Arg Glu Arg Phe Pro Gly Asp Arg
            100                 105                 110

Lys Ile Leu Leu Gly Leu Phe Asp Ala Leu Arg His Thr Leu Asp Lys
        115                 120                 125

Gly Ala Lys Cys Lys Cys Asn Val Asn Gln Pro Tyr Ala Leu Thr Arg
    130                 135                 140

Ala Trp Leu Asp Glu Thr Gly His Gly Ala Arg Thr Ala Asp Ile Ile
145                 150                 155                 160

Ala Trp Leu Lys Asp Phe Lys Gly Glu Cys Asp Cys Thr Ala Ile Ser
                165                 170                 175

Thr Ala Ala Lys Tyr Cys Pro Ala Pro Pro Thr Ala Glu Leu Leu Thr
            180                 185                 190

Lys Ile Lys Arg Ala Ala Pro Ala Asp Asp Leu Pro Val Asp Gln Ala
        195                 200                 205

Ile Leu Leu Asp Leu Phe Gly Ala Leu Arg Gly Gly Leu Lys Gln Lys
    210                 215                 220

Glu Cys Asp His Thr His Ala Arg Thr Val Ala Tyr Phe Glu Lys His
225                 230                 235                 240

Glu Leu Ala Gly Arg Ala Glu Asp Ile Leu Ala Trp Leu Ile Ala His
                245                 250                 255

Gly Gly Thr Cys Asp Cys Lys Ile Val Glu Glu Ala Ala Asn His Cys
            260                 265                 270

Pro Gly Pro Arg Leu Phe Ile Trp Glu His Glu Leu Ala Met Ile Met
        275                 280                 285

Ala Arg Leu Lys Ala Glu Pro Arg Thr Glu Trp Ile Gly Asp Leu Pro
    290                 295                 300

Ser His Ala Ala Gln Thr Val Val Lys Asp Leu Val Lys Ala Leu Gln
305                 310                 315                 320

Thr Met Leu Lys Glu Arg Ala Lys Ala Ala Gly Asp Glu Ser Ala
                325                 330                 335

Arg Lys Thr Gly Phe Pro Lys Phe Lys Lys Gln Ala Tyr Ala Ala Gly
            340                 345                 350

Ser Val Tyr Phe Pro Asn Thr Thr Met Phe Phe Asp Val Ala Ala Gly
        355                 360                 365

Arg Val Gln Leu Pro Asn Gly Cys Gly Ser Met Arg Cys Glu Ile Pro
    370                 375                 380
```

```
Arg Gln Leu Val Ala Glu Leu Leu Glu Arg Asn Leu Lys Pro Gly Leu
385                 390                 395                 400

Val Ile Gly Ala Gln Leu Gly Leu Leu Gly Gly Arg Ile Trp Arg Gln
                405                 410                 415

Gly Asp Arg Trp Tyr Leu Ser Cys Gln Trp Glu Arg Pro Gln Pro Thr
            420                 425                 430

Leu Leu Pro Lys Thr Gly Arg Thr Ala Gly Val Lys Ile Ala Ala Ser
        435                 440                 445

Ile Val Phe Thr Thr Tyr Asp Asn Arg Gly Gln Thr Lys Glu Tyr Pro
    450                 455                 460

Met Pro Pro Ala Asp Lys Lys Leu Thr Ala Val His Leu Val Ala Gly
465                 470                 475                 480

Lys Gln Asn Ser Arg Ala Leu Glu Ala Gln Lys Glu Lys Glu Lys Lys
                485                 490                 495

Leu Lys Ala Arg Lys Glu Arg Leu Arg Leu Gly Lys Leu Glu Lys Gly
            500                 505                 510

His Asp Pro Asn Ala Leu Lys Pro Leu Lys Arg Pro Arg Val Arg Arg
        515                 520                 525

Ser Lys Leu Phe Tyr Lys Ser Ala Ala Arg Leu Ala Ala Cys Glu Ala
    530                 535                 540

Ile Glu Arg Asp Arg Arg Asp Gly Phe Leu His Arg Val Thr Asn Glu
545                 550                 555                 560

Ile Val His Lys Phe Asp Ala Val Ser Val Gln Lys Met Ser Val Ala
                565                 570                 575

Pro Met Met Arg Arg Gln Lys Gln Lys Glu Lys Gln Ile Glu Ser Lys
            580                 585                 590

Lys Asn Glu Ala Lys Lys Glu Asp Asn Gly Ala Ala Lys Lys Pro Arg
        595                 600                 605

Asn Leu Lys Pro Val Arg Lys Leu Leu Arg His Val Ala Met Ala Arg
    610                 615                 620

Gly Arg Gln Phe Leu Glu Tyr Lys Tyr Asn Asp Leu Arg Gly Pro Gly
625                 630                 635                 640

Ser Val Leu Ile Ala Asp Arg Leu Glu Pro Glu Val Gln Glu Cys Ser
                645                 650                 655

Arg Cys Gly Thr Lys Asn Pro Gln Met Lys Asp Gly Arg Arg Leu Leu
            660                 665                 670

Arg Cys Ile Gly Val Leu Pro Asp Gly Thr Asp Cys Asp Ala Val Leu
        675                 680                 685

Pro Arg Asn Arg Asn Ala Ala Arg Asn Ala Glu Lys Arg Leu Arg Lys
    690                 695                 700

His Arg Glu Ala His Asn Ala
705                 710

<210> SEQ ID NO 37
<211> LENGTH: 574
<212> TYPE: PRT
<213> ORGANISM: Artificial sequence
<220> FEATURE:
<223> OTHER INFORMATION: Synthetic sequence

<400> SEQUENCE: 37

Met Asn Glu Val Leu Pro Ile Pro Ala Val Gly Glu Asp Ala Ala Asp
1               5                   10                  15

Thr Ile Met Arg Gly Ser Lys Met Arg Ile Tyr Pro Ser Val Arg Gln
                20                  25                  30
```

-continued

```
Ala Ala Thr Met Asp Leu Trp Arg Arg Cys Ile Gln Leu Trp Asn
            35                  40                  45

Leu Leu Leu Glu Leu Glu Gln Ala Ala Tyr Ser Gly Glu Asn Arg Arg
 50                  55                  60

Thr Gln Ile Gly Trp Arg Ser Ile Trp Ala Thr Val Glu Asp Ser
 65                  70                  75                  80

His Ala Glu Ala Val Arg Val Ala Arg Glu Gly Lys Lys Arg Lys Asp
                85                  90                  95

Gly Thr Phe Arg Lys Ala Pro Ser Gly Lys Glu Ile Pro Pro Leu Asp
                100                 105                 110

Pro Ala Met Leu Ala Lys Ile Gln Arg Gln Met Asn Gly Ala Val Asp
                115                 120                 125

Val Asp Pro Lys Thr Gly Glu Val Thr Pro Ala Gln Pro Arg Leu Phe
 130                 135                 140

Met Trp Glu His Glu Leu Gln Lys Ile Met Ala Arg Leu Lys Gln Ala
 145                 150                 155                 160

Pro Arg Thr His Trp Ile Asp Asp Leu Pro Ser His Ala Ala Gln Ser
                165                 170                 175

Val Val Lys Asp Leu Ile Lys Ala Leu Gln Ala Met Leu Arg Glu Arg
                180                 185                 190

Lys Lys Arg Ala Ser Gly Ile Gly Gly Arg Asp Thr Gly Phe Pro Lys
                195                 200                 205

Phe Lys Lys Asn Arg Tyr Ala Ala Gly Ser Val Tyr Phe Ala Asn Thr
                210                 215                 220

Gln Leu Arg Phe Glu Ala Lys Arg Gly Lys Ala Gly Asp Pro Asp Ala
225                 230                 235                 240

Val Arg Gly Glu Phe Ala Arg Val Lys Leu Pro Asn Gly Val Gly Trp
                245                 250                 255

Met Glu Cys Arg Met Pro Arg His Ile Asn Ala Ala His Ala Tyr Ala
                260                 265                 270

Gln Ala Thr Leu Met Gly Gly Arg Ile Trp Arg Gln Gly Glu Asn Trp
                275                 280                 285

Tyr Leu Ser Cys Gln Trp Lys Met Pro Lys Pro Ala Pro Leu Pro Arg
                290                 295                 300

Ala Gly Arg Thr Ala Ala Ile Lys Ile Ala Ala Ile Pro Ile Thr
305                 310                 315                 320

Thr Val Asp Asn Arg Gly Gln Thr Arg Glu Tyr Ala Met Pro Pro Ile
                325                 330                 335

Asp Arg Glu Arg Ile Ala Ala His Ala Ala Gly Arg Ala Gln Ser
                340                 345                 350

Arg Ala Leu Glu Ala Arg Lys Arg Ala Lys Lys Arg Glu Ala Tyr
                355                 360                 365

Ala Lys Lys Arg His Ala Lys Lys Leu Glu Arg Gly Ile Ala Ala Lys
                370                 375                 380

Pro Pro Gly Arg Ala Arg Ile Lys Leu Ser Pro Gly Phe Tyr Ala Ala
385                 390                 395                 400

Ala Ala Lys Leu Ala Lys Leu Glu Ala Glu Asp Ala Asn Ala Arg Glu
                405                 410                 415

Ala Trp Leu His Glu Ile Thr Thr Gln Ile Val Arg Asn Phe Asp Val
                420                 425                 430

Ile Ala Val Pro Arg Met Glu Val Ala Lys Leu Met Lys Lys Pro Glu
                435                 440                 445

Pro Pro Glu Glu Lys Glu Glu Gln Val Lys Ala Pro Trp Gln Gly Lys
```

```
                450           455           460
Arg Arg Ser Leu Lys Ala Ala Arg Val Met Met Arg Thr Ala Met
465               470               475               480

Ala Leu Ile Gln Thr Thr Leu Lys Tyr Lys Ala Val Asp Leu Arg Gly
              485               490               495

Pro Gln Ala Tyr Glu Glu Ile Ala Pro Leu Asp Val Thr Ala Ala Ala
              500               505               510

Cys Ser Gly Cys Gly Val Leu Lys Pro Glu Trp Lys Met Ala Arg Ala
              515               520               525

Lys Gly Arg Glu Ile Met Arg Cys Gln Glu Pro Leu Pro Gly Gly Lys
              530               535               540

Thr Cys Asn Thr Val Leu Thr Tyr Thr Arg Asn Ser Ala Arg Val Ile
545               550               555               560

Gly Arg Glu Leu Ala Val Arg Leu Ala Glu Arg Gln Lys Ala
              565               570
```

<210> SEQ ID NO 38
<211> LENGTH: 400
<212> TYPE: PRT
<213> ORGANISM: Artificial sequence
<220> FEATURE:
<223> OTHER INFORMATION: Synthetic sequence

<400> SEQUENCE: 38

```
Met Thr Thr Gln Lys Thr Tyr Asn Phe Cys Phe Tyr Asp Gln Arg Phe
1               5                   10                  15

Phe Glu Leu Ser Lys Glu Ala Gly Glu Val Tyr Ser Arg Ser Leu Glu
              20                  25                  30

Glu Phe Trp Lys Ile Tyr Asp Glu Thr Gly Val Trp Leu Ser Lys Phe
          35                  40                  45

Asp Leu Gln Lys His Met Arg Asn Lys Leu Glu Arg Lys Leu Leu His
      50                  55                  60

Ser Asp Ser Phe Leu Gly Ala Met Gln Gln Val His Ala Asn Leu Ala
65                  70                  75                  80

Ser Trp Lys Gln Ala Lys Lys Val Val Pro Asp Ala Cys Pro Pro Arg
              85                  90                  95

Lys Pro Lys Phe Leu Gln Ala Ile Leu Phe Lys Lys Ser Gln Ile Lys
              100                 105                 110

Tyr Lys Asn Gly Phe Leu Arg Leu Thr Leu Gly Thr Glu Lys Glu Phe
          115                 120                 125

Leu Tyr Leu Lys Trp Asp Ile Asn Ile Pro Leu Pro Ile Tyr Gly Ser
      130                 135                 140

Val Thr Tyr Ser Lys Thr Arg Gly Trp Lys Ile Asn Leu Cys Leu Glu
145                 150                 155                 160

Thr Glu Val Glu Gln Lys Asn Leu Ser Glu Asn Lys Tyr Leu Ser Ile
              165                 170                 175

Asp Leu Gly Val Lys Arg Val Ala Thr Ile Phe Asp Gly Glu Asn Thr
              180                 185                 190

Ile Thr Leu Ser Gly Lys Lys Phe Met Gly Leu Met His Tyr Arg Asn
          195                 200                 205

Lys Leu Asn Gly Lys Thr Gln Ser Arg Leu Ser His Lys Lys Lys Gly
      210                 215                 220

Ser Asn Tyr Lys Lys Ile Gln Arg Ala Lys Arg Lys Thr Thr Asp
225                 230                 235                 240

Arg Leu Leu Asn Ile Gln Lys Glu Met Leu His Lys Tyr Ser Ser Phe
```

-continued

```
                245                 250                 255
Ile Val Asn Tyr Ala Ile Arg Asn Asp Ile Gly Asn Ile Ile Gly
            260                 265                 270

Asp Asn Ser Ser Thr His Asp Ser Pro Asn Met Arg Gly Lys Thr Asn
            275                 280                 285

Gln Lys Ile Ser Gln Asn Pro Glu Gln Lys Leu Lys Asn Tyr Ile Lys
    290                 295                 300

Tyr Lys Phe Glu Ser Ile Ser Gly Arg Val Asp Ile Val Pro Glu Pro
305                 310                 315                 320

Tyr Thr Ser Arg Lys Cys Pro His Cys Lys Asn Ile Lys Lys Ser Ser
                325                 330                 335

Pro Lys Gly Arg Thr Tyr Lys Cys Lys Cys Gly Phe Ile Phe Asp
            340                 345                 350

Arg Asp Gly Val Gly Ala Ile Asn Ile Tyr Asn Glu Asn Val Ser Phe
                355                 360                 365

Gly Gln Ile Ile Ser Pro Gly Arg Ile Arg Ser Leu Thr Glu Pro Ile
    370                 375                 380

Gly Met Lys Phe His Asn Glu Ile Tyr Phe Lys Ser Tyr Val Ala Ala
385                 390                 395                 400
```

<210> SEQ ID NO 39
<211> LENGTH: 743
<212> TYPE: PRT
<213> ORGANISM: Artificial sequence
<220> FEATURE:
<223> OTHER INFORMATION: Synthetic sequence
<400> SEQUENCE: 39

```
Met Ser Val Arg Ser Phe Gln Ala Arg Val Glu Cys Asp Lys Gln Thr
1               5                   10                  15

Met Glu His Leu Trp Arg Thr His Lys Val Phe Asn Glu Arg Leu Pro
                20                  25                  30

Glu Ile Ile Lys Ile Leu Phe Lys Met Lys Arg Gly Glu Cys Gly Gln
            35                  40                  45

Asn Asp Lys Gln Lys Ser Leu Tyr Lys Ser Ile Ser Gln Ser Ile Leu
50                  55                  60

Glu Ala Asn Ala Gln Asn Ala Asp Tyr Leu Leu Asn Ser Val Ser Ile
65                  70                  75                  80

Lys Gly Trp Lys Pro Gly Thr Ala Lys Lys Tyr Arg Asn Ala Ser Phe
                85                  90                  95

Thr Trp Ala Asp Asp Ala Ala Lys Leu Ser Ser Gln Gly Ile His Val
            100                 105                 110

Tyr Asp Lys Lys Gln Val Leu Gly Asp Leu Pro Gly Met Met Ser Gln
        115                 120                 125

Met Val Cys Arg Gln Ser Val Glu Ala Ile Ser Gly His Ile Glu Leu
130                 135                 140

Thr Lys Lys Trp Glu Lys Glu His Asn Glu Trp Leu Lys Glu Lys Glu
145                 150                 155                 160

Lys Trp Glu Ser Glu Asp Glu His Lys Lys Tyr Leu Asp Leu Arg Glu
                165                 170                 175

Lys Phe Glu Gln Phe Glu Gln Ser Ile Gly Gly Lys Ile Thr Lys Arg
            180                 185                 190

Arg Gly Arg Trp His Leu Tyr Leu Lys Trp Leu Ser Asp Asn Pro Asp
        195                 200                 205

Phe Ala Ala Trp Arg Gly Asn Lys Ala Val Ile Asn Pro Leu Ser Glu
```

```
                210                 215                 220
Lys Ala Gln Ile Arg Ile Asn Lys Ala Lys Pro Asn Lys Lys Asn Ser
225                 230                 235                 240

Val Glu Arg Asp Glu Phe Phe Lys Ala Asn Pro Glu Met Lys Ala Leu
                245                 250                 255

Asp Asn Leu His Gly Tyr Tyr Glu Arg Asn Phe Val Arg Arg Arg Lys
                260                 265                 270

Thr Lys Lys Asn Pro Asp Gly Phe Asp His Lys Pro Thr Phe Thr Leu
                275                 280                 285

Pro His Pro Thr Ile His Pro Arg Trp Phe Val Phe Asn Lys Pro Lys
                290                 295                 300

Thr Asn Pro Glu Gly Tyr Arg Lys Leu Ile Leu Pro Lys Lys Ala Gly
305                 310                 315                 320

Asp Leu Gly Ser Leu Glu Met Arg Leu Leu Thr Gly Glu Lys Asn Lys
                325                 330                 335

Gly Asn Tyr Pro Asp Asp Trp Ile Ser Val Lys Phe Lys Ala Asp Pro
                340                 345                 350

Arg Leu Ser Leu Ile Arg Pro Val Lys Gly Arg Arg Val Val Arg Lys
                355                 360                 365

Gly Lys Glu Gln Gly Gln Thr Lys Glu Thr Asp Ser Tyr Glu Phe Phe
                370                 375                 380

Asp Lys His Leu Lys Lys Trp Arg Pro Ala Lys Leu Ser Gly Val Lys
385                 390                 395                 400

Leu Ile Phe Pro Asp Lys Thr Pro Lys Ala Ala Tyr Leu Tyr Phe Thr
                405                 410                 415

Cys Asp Ile Pro Asp Glu Pro Leu Thr Glu Thr Ala Lys Lys Ile Gln
                420                 425                 430

Trp Leu Glu Thr Gly Asp Val Thr Lys Gly Lys Lys Arg Lys Lys
                435                 440                 445

Lys Val Leu Pro His Gly Leu Val Ser Cys Ala Val Asp Leu Ser Met
450                 455                 460

Arg Arg Gly Thr Thr Gly Phe Ala Thr Leu Cys Arg Tyr Glu Asn Gly
465                 470                 475                 480

Lys Ile His Ile Leu Arg Ser Arg Asn Leu Trp Val Gly Tyr Lys Glu
                485                 490                 495

Gly Lys Gly Cys His Pro Tyr Arg Trp Thr Glu Gly Pro Asp Leu Gly
                500                 505                 510

His Ile Ala Lys His Lys Arg Glu Ile Arg Ile Leu Arg Ser Lys Arg
                515                 520                 525

Gly Lys Pro Val Lys Gly Glu Glu Ser His Ile Asp Leu Gln Lys His
                530                 535                 540

Ile Asp Tyr Met Gly Glu Asp Arg Phe Lys Lys Ala Ala Arg Thr Ile
545                 550                 555                 560

Val Asn Phe Ala Leu Asn Thr Glu Asn Ala Ala Ser Lys Asn Gly Phe
                565                 570                 575

Tyr Pro Arg Ala Asp Val Leu Leu Leu Glu Asn Leu Glu Gly Leu Ile
                580                 585                 590

Pro Asp Ala Glu Lys Glu Arg Gly Ile Asn Arg Ala Leu Ala Gly Trp
                595                 600                 605

Asn Arg Arg His Leu Val Glu Arg Val Ile Glu Met Ala Lys Asp Ala
                610                 615                 620

Gly Phe Lys Arg Arg Val Phe Glu Ile Pro Pro Tyr Gly Thr Ser Gln
625                 630                 635                 640
```

```
Val Cys Ser Lys Cys Gly Ala Leu Gly Arg Arg Tyr Ser Ile Ile Arg
            645                 650                 655

Glu Asn Asn Arg Arg Glu Ile Arg Phe Gly Tyr Val Glu Lys Leu Phe
            660                 665                 670

Ala Cys Pro Asn Cys Gly Tyr Cys Ala Asn Ala Asp His Asn Ala Ser
            675                 680                 685

Val Asn Leu Asn Arg Arg Phe Leu Ile Glu Asp Ser Phe Lys Ser Tyr
            690                 695                 700

Tyr Asp Trp Lys Arg Leu Ser Glu Lys Lys Gln Lys Glu Ile Glu
705                 710                 715                 720

Thr Ile Glu Ser Lys Leu Met Asp Lys Leu Cys Ala Met His Lys Ile
            725                 730                 735

Ser Arg Gly Ser Ile Ser Lys
            740

<210> SEQ ID NO 40
<211> LENGTH: 769
<212> TYPE: PRT
<213> ORGANISM: Artificial sequence
<220> FEATURE:
<223> OTHER INFORMATION: Synthetic sequence

<400> SEQUENCE: 40

Met His Leu Trp Arg Thr His Cys Val Phe Asn Gln Arg Leu Pro Ala
1               5                   10                  15

Leu Leu Lys Arg Leu Phe Ala Met Arg Arg Gly Glu Val Gly Gly Asn
            20                  25                  30

Glu Ala Gln Arg Gln Val Tyr Gln Arg Val Ala Gln Phe Val Leu Ala
            35                  40                  45

Arg Asp Ala Lys Asp Ser Val Asp Leu Leu Asn Ala Val Ser Leu Arg
        50                  55                  60

Lys Arg Ser Ala Asn Ser Ala Phe Lys Lys Ala Thr Ile Ser Cys
65                  70                  75                  80

Asn Gly Gln Ala Arg Glu Val Thr Gly Glu Glu Val Phe Ala Glu Ala
                85                  90                  95

Val Ala Leu Ala Ser Lys Gly Val Phe Ala Tyr Asp Lys Asp Asp Met
            100                 105                 110

Arg Ala Gly Leu Pro Asp Ser Leu Phe Gln Pro Leu Thr Arg Asp Ala
            115                 120                 125

Val Ala Cys Met Arg Ser His Glu Glu Leu Val Ala Thr Trp Lys Lys
        130                 135                 140

Glu Tyr Arg Glu Trp Arg Asp Arg Lys Ser Glu Trp Glu Ala Glu Pro
145                 150                 155                 160

Glu His Ala Leu Tyr Leu Asn Leu Arg Pro Lys Phe Glu Glu Gly Glu
                165                 170                 175

Ala Ala Arg Gly Gly Arg Phe Arg Lys Arg Ala Glu Arg Asp His Ala
            180                 185                 190

Tyr Leu Asp Trp Leu Glu Ala Asn Pro Gln Leu Ala Ala Trp Arg Arg
            195                 200                 205

Lys Ala Pro Pro Ala Val Val Pro Ile Asp Glu Ala Gly Lys Arg Arg
        210                 215                 220

Ile Ala Arg Ala Lys Ala Trp Lys Gln Ala Ser Val Arg Ala Glu Glu
225                 230                 235                 240

Phe Trp Lys Arg Asn Pro Glu Leu His Ala Leu His Lys Ile His Val
                245                 250                 255
```

-continued

```
Gln Tyr Leu Arg Glu Phe Val Arg Pro Arg Thr Arg Arg Asn Lys
        260                 265                 270

Arg Arg Glu Gly Phe Lys Gln Arg Pro Thr Phe Thr Met Pro Asp Pro
            275                 280                 285

Val Arg His Pro Arg Trp Cys Leu Phe Asn Ala Pro Gln Thr Ser Pro
290                 295                 300

Gln Gly Tyr Arg Leu Leu Arg Leu Pro Gln Ser Arg Arg Thr Val Gly
305                 310                 315                 320

Ser Val Glu Leu Arg Leu Leu Thr Gly Pro Ser Asp Gly Ala Gly Phe
                325                 330                 335

Pro Asp Ala Trp Val Asn Val Arg Phe Lys Ala Asp Pro Arg Leu Ala
            340                 345                 350

Gln Leu Arg Pro Val Lys Val Pro Arg Thr Val Thr Arg Gly Lys Asn
        355                 360                 365

Lys Gly Ala Lys Val Glu Ala Asp Gly Phe Arg Tyr Tyr Asp Asp Gln
370                 375                 380

Leu Leu Ile Glu Arg Asp Ala Gln Val Ser Gly Val Lys Leu Leu Phe
385                 390                 395                 400

Arg Asp Ile Arg Met Ala Pro Phe Ala Asp Lys Pro Ile Glu Asp Arg
                405                 410                 415

Leu Leu Ser Ala Thr Pro Tyr Leu Val Phe Ala Val Glu Ile Lys Asp
            420                 425                 430

Glu Ala Arg Thr Glu Arg Ala Lys Ala Ile Arg Phe Asp Glu Thr Ser
        435                 440                 445

Glu Leu Thr Lys Ser Gly Lys Lys Arg Lys Thr Leu Pro Ala Gly Leu
    450                 455                 460

Val Ser Val Ala Val Asp Leu Asp Thr Arg Gly Val Gly Phe Leu Thr
465                 470                 475                 480

Arg Ala Val Ile Gly Val Pro Glu Ile Gln Gln Thr His His Gly Val
                485                 490                 495

Arg Leu Leu Gln Ser Arg Tyr Val Ala Val Gly Gln Val Glu Ala Arg
            500                 505                 510

Ala Ser Gly Glu Ala Glu Trp Ser Pro Gly Pro Asp Leu Ala His Ile
        515                 520                 525

Ala Arg His Lys Arg Glu Ile Arg Arg Leu Arg Gln Leu Arg Gly Lys
    530                 535                 540

Pro Val Lys Gly Glu Arg Ser His Val Arg Leu Gln Ala His Ile Asp
545                 550                 555                 560

Arg Met Gly Glu Asp Arg Phe Lys Lys Ala Ala Arg Lys Ile Val Asn
                565                 570                 575

Glu Ala Leu Arg Gly Ser Asn Pro Ala Ala Gly Asp Pro Tyr Thr Arg
            580                 585                 590

Ala Asp Val Leu Leu Tyr Glu Ser Leu Glu Thr Leu Leu Pro Asp Ala
        595                 600                 605

Glu Arg Glu Arg Gly Ile Asn Arg Ala Leu Leu Arg Trp Asn Arg Ala
    610                 615                 620

Lys Leu Ile Glu His Leu Lys Arg Met Cys Asp Asp Ala Gly Ile Arg
625                 630                 635                 640

His Phe Pro Val Ser Pro Phe Gly Thr Ser Gln Val Cys Ser Lys Cys
                645                 650                 655

Gly Ala Leu Gly Arg Arg Tyr Ser Leu Ala Arg Glu Asn Gly Arg Ala
            660                 665                 670
```

-continued

```
Val Ile Arg Phe Gly Trp Val Glu Arg Leu Phe Ala Cys Pro Asn Pro
            675                 680                 685

Glu Cys Pro Gly Arg Arg Pro Asp Arg Pro Asp Arg Pro Phe Thr Cys
690                 695                 700

Asn Ser Asp His Asn Ala Ser Val Asn Leu His Arg Val Phe Ala Leu
705                 710                 715                 720

Gly Asp Gln Ala Val Ala Ala Phe Arg Ala Leu Ala Pro Arg Asp Ser
                725                 730                 735

Pro Ala Arg Thr Leu Ala Val Lys Arg Val Glu Asp Thr Leu Arg Pro
            740                 745                 750

Gln Leu Met Arg Val His Lys Leu Ala Asp Ala Gly Val Asp Ser Pro
            755                 760                 765

Phe

<210> SEQ ID NO 41
<211> LENGTH: 666
<212> TYPE: PRT
<213> ORGANISM: Artificial sequence
<220> FEATURE:
<223> OTHER INFORMATION: Synthetic sequence

<400> SEQUENCE: 41

Met Ala Thr Leu Val Tyr Arg Tyr Gly Val Arg Ala His Gly Ser Ala
1               5                   10                  15

Arg Gln Gln Asp Ala Val Val Ser Asp Pro Ala Met Leu Glu Gln Leu
            20                  25                  30

Arg Leu Gly His Glu Leu Arg Asn Ala Leu Val Gly Val Gln His Arg
        35                  40                  45

Tyr Glu Asp Gly Lys Arg Ala Val Trp Ser Gly Phe Ala Ser Val Ala
    50                  55                  60

Ala Ala Asp His Arg Val Thr Thr Gly Glu Thr Ala Val Ala Glu Leu
65                  70                  75                  80

Glu Lys Gln Ala Arg Ala Glu His Ser Ala Asp Arg Thr Ala Ala Thr
                85                  90                  95

Arg Gln Gly Thr Ala Glu Ser Leu Lys Ala Ala Arg Ala Ala Val Lys
            100                 105                 110

Gln Ala Arg Ala Asp Arg Lys Ala Ala Met Ala Ala Val Ala Glu Gln
        115                 120                 125

Ala Lys Pro Lys Ile Gln Ala Leu Gly Asp Asp Arg Asp Ala Glu Ile
    130                 135                 140

Lys Asp Leu Tyr Arg Arg Phe Cys Gln Asp Gly Val Leu Leu Pro Arg
145                 150                 155                 160

Cys Gly Arg Cys Ala Gly Asp Leu Arg Ser Asp Gly Asp Cys Thr Asp
                165                 170                 175

Cys Gly Ala Ala His Glu Pro Arg Lys Leu Tyr Trp Ala Thr Tyr Asn
            180                 185                 190

Ala Ile Arg Glu Asp His Gln Thr Ala Val Lys Leu Val Glu Ala Lys
        195                 200                 205

Arg Lys Ala Gly Gln Pro Ala Arg Leu Arg Phe Arg Arg Trp Thr Gly
    210                 215                 220

Asp Gly Thr Leu Thr Val Gln Leu Gln Arg Met His Gly Pro Ala Cys
225                 230                 235                 240

Arg Cys Val Thr Cys Ala Glu Lys Leu Thr Arg Arg Ala Arg Lys Thr
                245                 250                 255

Asp Pro Gln Ala Pro Ala Val Ala Ala Asp Pro Ala Tyr Pro Pro Thr
```

```
              260                 265                 270
Asp Pro Pro Arg Asp Pro Ala Leu Leu Ala Ser Gly Gln Gly Lys Trp
            275                 280                 285

Arg Asn Val Leu Gln Leu Gly Thr Trp Ile Pro Gly Glu Trp Ser
290                 295                 300

Ala Met Ser Arg Ala Glu Arg Arg Val Gly Arg Ser His Ile Gly
305                 310                 315                 320

Trp Gln Leu Gly Gly Gly Arg Gln Leu Thr Leu Pro Val Gln Leu His
            325                 330                 335

Arg Gln Met Pro Ala Asp Ala Asp Val Ala Met Ala Gln Leu Thr Arg
            340                 345                 350

Val Arg Val Gly Gly Arg His Arg Met Ser Val Ala Leu Thr Ala Lys
            355                 360                 365

Leu Pro Asp Pro Pro Gln Val Gln Gly Leu Pro Pro Val Ala Leu His
            370                 375                 380

Leu Gly Trp Arg Gln Arg Pro Asp Gly Ser Leu Arg Val Ala Thr Trp
385                 390                 395                 400

Ala Cys Pro Gln Pro Leu Asp Leu Pro Pro Ala Val Ala Asp Val Val
            405                 410                 415

Val Ser His Gly Gly Arg Trp Gly Glu Val Ile Met Pro Ala Arg Trp
            420                 425                 430

Leu Ala Asp Ala Glu Val Pro Pro Arg Leu Leu Gly Arg Arg Asp Lys
            435                 440                 445

Ala Met Glu Pro Val Leu Glu Ala Leu Ala Asp Trp Leu Glu Ala His
            450                 455                 460

Thr Glu Ala Cys Thr Ala Arg Met Thr Pro Ala Leu Val Arg Arg Trp
465                 470                 475                 480

Arg Ser Gln Gly Arg Leu Ala Gly Leu Thr Asn Arg Trp Arg Gly Gln
            485                 490                 495

Pro Pro Thr Gly Ser Ala Glu Ile Leu Thr Tyr Leu Glu Ala Trp Arg
            500                 505                 510

Ile Gln Asp Lys Leu Leu Trp Glu Arg Glu Ser His Leu Arg Arg Arg
            515                 520                 525

Leu Ala Ala Arg Arg Asp Asp Ala Trp Arg Arg Val Ala Ser Trp Leu
530                 535                 540

Ala Arg His Ala Gly Val Leu Val Val Asp Ala Asp Ile Ala Glu
545                 550                 555                 560

Leu Arg Arg Arg Asp Asp Pro Ala Asp Thr Asp Pro Thr Met Pro Ala
            565                 570                 575

Ser Ala Ala Gln Ala Ala Arg Ala Arg Ala Ala Leu Ala Ala Pro Gly
            580                 585                 590

Arg Leu Arg His Leu Ala Thr Ile Thr Ala Thr Arg Asp Gly Leu Gly
            595                 600                 605

Val His Thr Val Ala Ser Ala Gly Leu Thr Arg Leu His Arg Lys Cys
            610                 615                 620

Gly His Gln Ala Gln Pro Asp Pro Arg Tyr Ala Ala Ser Ala Val Val
625                 630                 635                 640

Thr Cys Pro Gly Cys Gly Asn Gly Tyr Asp Gln Asp Tyr Asn Ala Ala
            645                 650                 655

Met Leu Met Leu Asp Arg Gln Gln Gln Pro
            660                 665
```

<210> SEQ ID NO 42

<211> LENGTH: 564
<212> TYPE: PRT
<213> ORGANISM: Artificial sequence
<220> FEATURE:
<223> OTHER INFORMATION: Synthetic sequence

<400> SEQUENCE: 42

Met Ser Arg Val Glu Leu His Arg Ala Tyr Lys Phe Arg Leu Tyr Pro
1               5                   10                  15

Thr Pro Ala Gln Val Ala Glu Leu Ala Glu Trp Glu Arg Gln Leu Arg
            20                  25                  30

Arg Leu Tyr Asn Leu Ala His Ser Gln Arg Leu Ala Ala Met Gln Arg
        35                  40                  45

His Val Arg Pro Lys Ser Pro Gly Val Leu Lys Ser Glu Cys Leu Ser
    50                  55                  60

Cys Gly Ala Val Ala Val Ala Glu Ile Gly Thr Asp Gly Lys Ala Lys
65                  70                  75                  80

Lys Thr Val Lys His Ala Val Gly Cys Ser Val Leu Glu Cys Arg Ser
                85                  90                  95

Cys Gly Gly Ser Pro Asp Ala Glu Gly Arg Thr Ala His Thr Ala Ala
            100                 105                 110

Cys Ser Phe Val Asp Tyr Tyr Arg Gln Gly Arg Glu Met Thr Gln Leu
        115                 120                 125

Leu Glu Glu Asp Asp Gln Leu Ala Arg Val Val Cys Ser Ala Arg Gln
    130                 135                 140

Glu Thr Leu Arg Asp Leu Glu Lys Ala Trp Gln Arg Trp His Lys Met
145                 150                 155                 160

Pro Gly Phe Gly Lys Pro His Phe Lys Lys Arg Ile Asp Ser Cys Arg
                165                 170                 175

Ile Tyr Phe Ser Thr Pro Lys Ser Trp Ala Val Asp Leu Gly Tyr Leu
            180                 185                 190

Ser Phe Thr Gly Val Ala Ser Ser Val Gly Arg Ile Lys Ile Arg Gln
        195                 200                 205

Asp Arg Val Trp Pro Gly Asp Ala Lys Phe Ser Ser Cys His Val Val
    210                 215                 220

Arg Asp Val Asp Glu Trp Tyr Ala Val Phe Pro Leu Thr Phe Thr Lys
225                 230                 235                 240

Glu Ile Glu Lys Pro Lys Gly Gly Ala Val Gly Ile Asn Arg Gly Ala
                245                 250                 255

Val His Ala Ile Ala Asp Ser Thr Gly Arg Val Val Asp Ser Pro Lys
            260                 265                 270

Phe Tyr Ala Arg Ser Leu Gly Val Ile Arg His Arg Ala Arg Leu Leu
        275                 280                 285

Asp Arg Lys Val Pro Phe Gly Arg Ala Val Lys Pro Ser Pro Thr Lys
    290                 295                 300

Tyr His Gly Leu Pro Lys Ala Asp Ile Asp Ala Ala Ala Ala Arg Val
305                 310                 315                 320

Asn Ala Ser Pro Gly Arg Leu Val Tyr Glu Ala Arg Ala Arg Gly Ser
                325                 330                 335

Ile Ala Ala Ala Glu Ala His Leu Ala Ala Leu Val Leu Pro Ala Pro
            340                 345                 350

Arg Gln Thr Ser Gln Leu Pro Ser Glu Gly Arg Asn Arg Glu Arg Ala
        355                 360                 365

Arg Arg Phe Leu Ala Leu Ala His Gln Arg Val Arg Arg Gln Arg Glu
    370                 375                 380

Trp Phe Leu His Asn Glu Ser Ala His Tyr Ala Gln Ser Tyr Thr Lys
385                 390                 395                 400

Ile Ala Ile Glu Asp Trp Ser Thr Lys Glu Met Thr Ser Ser Glu Pro
            405                 410                 415

Arg Asp Ala Glu Glu Met Lys Arg Val Thr Arg Ala Arg Asn Arg Ser
        420                 425                 430

Ile Leu Asp Val Gly Trp Tyr Glu Leu Gly Arg Gln Ile Ala Tyr Lys
    435                 440                 445

Ser Glu Ala Thr Gly Ala Glu Phe Ala Lys Val Asp Pro Gly Leu Arg
450                 455                 460

Glu Thr Glu Thr His Val Pro Glu Ala Ile Val Arg Glu Arg Asp Val
465                 470                 475                 480

Asp Val Ser Gly Met Leu Arg Gly Glu Ala Gly Ile Ser Gly Thr Cys
            485                 490                 495

Ser Arg Cys Gly Gly Leu Leu Arg Ala Ser Ala Ser Gly His Ala Asp
        500                 505                 510

Ala Glu Cys Glu Val Cys Leu His Val Glu Val Gly Asp Val Asn Ala
    515                 520                 525

Ala Val Asn Val Leu Lys Arg Ala Met Phe Pro Gly Ala Ala Pro Pro
530                 535                 540

Ser Lys Glu Lys Ala Lys Val Thr Ile Gly Ile Lys Gly Arg Lys Lys
545                 550                 555                 560

Lys Arg Ala Ala

<210> SEQ ID NO 43
<211> LENGTH: 565
<212> TYPE: PRT
<213> ORGANISM: Artificial sequence
<220> FEATURE:
<223> OTHER INFORMATION: Synthetic sequence

<400> SEQUENCE: 43

Met Ser Arg Val Glu Leu His Arg Ala Tyr Lys Phe Arg Leu Tyr Pro
1               5                   10                  15

Thr Pro Val Gln Val Ala Glu Leu Ser Glu Trp Glu Arg Gln Leu Arg
            20                  25                  30

Arg Leu Tyr Asn Leu Gly His Glu Gln Arg Leu Leu Thr Leu Thr Arg
        35                  40                  45

His Leu Arg Pro Lys Ser Pro Gly Val Leu Lys Gly Glu Cys Leu Ser
    50                  55                  60

Cys Asp Ser Thr Gln Val Gln Glu Val Gly Ala Asp Gly Arg Pro Lys
65                  70                  75                  80

Thr Thr Val Arg His Ala Glu Gln Cys Pro Thr Leu Ala Cys Arg Ser
            85                  90                  95

Cys Gly Ala Leu Arg Asp Ala Glu Gly Arg Thr Ala His Thr Val Ala
        100                 105                 110

Cys Ala Phe Val Asp Tyr Tyr Arg Gln Gly Arg Glu Met Thr Glu Leu
    115                 120                 125

Leu Ala Ala Asp Asp Gln Leu Ala Arg Val Val Cys Ser Ala Arg Gln
130                 135                 140

Glu Val Leu Arg Asp Leu Asp Lys Ala Trp Gln Arg Trp Arg Lys Met
145                 150                 155                 160

Pro Gly Phe Gly Lys Pro Arg Phe Lys Arg Arg Thr Asp Ser Cys Arg
            165                 170                 175

```
Ile Tyr Phe Ser Thr Pro Lys Ala Trp Lys Leu Glu Gly Gly His Leu
            180                 185                 190

Ser Phe Thr Gly Ala Ala Thr Thr Val Gly Ala Ile Lys Met Arg Gln
            195                 200                 205

Asp Arg Asn Trp Pro Ala Ser Val Gln Phe Ser Ser Cys His Val Val
            210                 215                 220

Arg Asp Val Asp Glu Trp Tyr Ala Val Phe Pro Leu Thr Phe Val Ala
225                 230                 235                 240

Glu Val Ala Arg Pro Lys Gly Gly Ala Gly Ile Asn Arg Gly Ala
                245                 250                 255

Val His Ala Ile Ala Asp Ser Thr Gly Arg Val Val Asp Ser Pro Arg
            260                 265                 270

Tyr Tyr Ala Arg Ala Leu Gly Val Ile Arg His Arg Ala Arg Leu Phe
            275                 280                 285

Asp Arg Lys Val Pro Ser Gly His Ala Val Lys Pro Ser Pro Thr Lys
            290                 295                 300

Tyr Arg Gly Leu Ser Ala Ile Glu Val Asp Arg Val Ala Arg Ala Thr
305                 310                 315                 320

Gly Phe Thr Pro Gly Arg Val Val Thr Glu Ala Leu Asn Arg Gly Gly
                325                 330                 335

Val Ala Tyr Ala Glu Cys Ala Leu Ala Ala Ile Ala Val Leu Gly His
            340                 345                 350

Gly Pro Glu Arg Pro Leu Thr Ser Asp Gly Arg Asn Arg Glu Lys Ala
            355                 360                 365

Arg Lys Phe Leu Ala Leu Ala His Gln Arg Val Arg Arg Gln Arg Glu
            370                 375                 380

Trp Phe Leu His Asn Glu Ser Ala His Tyr Ala Arg Thr Tyr Ser Lys
385                 390                 395                 400

Ile Ala Ile Glu Asp Trp Ser Thr Lys Glu Met Thr Ala Ser Glu Pro
                405                 410                 415

Gln Gly Glu Glu Thr Arg Arg Val Thr Arg Ser Arg Asn Arg Ser Ile
            420                 425                 430

Leu Asp Val Gly Trp Tyr Glu Leu Gly Arg Gln Leu Ala Tyr Lys Thr
            435                 440                 445

Glu Ala Thr Gly Ala Glu Phe Ala Gln Val Asp Pro Gly Leu Lys Glu
450                 455                 460

Thr Glu Thr Asn Val Pro Lys Ala Ile Ala Asp Ala Arg Asp Val Asp
465                 470                 475                 480

Val Ser Gly Met Leu Arg Gly Glu Ala Gly Ile Ser Gly Thr Cys Ser
                485                 490                 495

Lys Cys Gly Gly Leu Leu Arg Ala Pro Ala Ser Gly His Ala Asp Ala
            500                 505                 510

Glu Cys Glu Ile Cys Leu Asn Val Glu Val Gly Asp Val Asn Ala Ala
            515                 520                 525

Val Asn Val Leu Lys Arg Ala Met Phe Pro Gly Asp Ala Pro Ala
            530                 535                 540

Ser Gly Glu Lys Pro Lys Val Ser Ile Gly Ile Lys Gly Arg Gln Lys
545                 550                 555                 560

Lys Lys Lys Ala Ala
                565
```

<210> SEQ ID NO 44
<211> LENGTH: 499
<212> TYPE: PRT

<213> ORGANISM: Artificial sequence
<220> FEATURE:
<223> OTHER INFORMATION: Synthetic sequence

<400> SEQUENCE: 44

Met Glu Ala Ile Ala Thr Gly Met Ser Pro Glu Arg Arg Val Glu Leu
1               5                   10                  15

Gly Ile Leu Pro Gly Ser Val Glu Leu Lys Arg Ala Tyr Lys Phe Arg
            20                  25                  30

Leu Tyr Pro Met Lys Val Gln Gln Ala Glu Leu Ser Glu Trp Glu Arg
        35                  40                  45

Gln Leu Arg Arg Leu Tyr Asn Leu Ala His Glu Gln Arg Leu Ala Ala
    50                  55                  60

Leu Leu Arg Tyr Arg Asp Trp Asp Phe Gln Lys Gly Ala Cys Pro Ser
65                  70                  75                  80

Cys Arg Val Ala Val Pro Gly Val His Thr Ala Ala Cys Asp His Val
                85                  90                  95

Asp Tyr Phe Arg Gln Ala Arg Glu Met Thr Gln Leu Leu Glu Val Asp
            100                 105                 110

Ala Gln Leu Ser Arg Val Ile Cys Cys Ala Arg Gln Glu Val Leu Arg
        115                 120                 125

Asp Leu Asp Lys Ala Trp Gln Arg Trp Arg Lys Lys Leu Gly Gly Arg
    130                 135                 140

Pro Arg Phe Lys Arg Arg Thr Asp Ser Cys Arg Ile Tyr Leu Ser Thr
145                 150                 155                 160

Pro Lys His Trp Glu Ile Ala Gly Arg Tyr Leu Arg Leu Ser Gly Leu
                165                 170                 175

Ala Ser Ser Val Gly Glu Ile Arg Ile Glu Gln Asp Arg Ala Phe Pro
            180                 185                 190

Glu Gly Ala Leu Leu Ser Ser Cys Ser Ile Val Arg Asp Val Asp Glu
        195                 200                 205

Trp Tyr Ala Cys Leu Pro Leu Thr Phe Thr Gln Pro Ile Glu Arg Ala
    210                 215                 220

Pro His Arg Ser Val Gly Leu Asn Arg Gly Val Val His Ala Leu Ala
225                 230                 235                 240

Asp Ser Asp Gly Arg Val Val Asp Ser Pro Lys Phe Phe Glu Arg Ala
                245                 250                 255

Leu Ala Thr Val Gln Lys Arg Ser Arg Asp Leu Ala Arg Lys Val Ser
            260                 265                 270

Gly Ser Arg Asn Ala His Lys Ala Arg Ile Lys Leu Ala Lys Ala His
        275                 280                 285

Gln Arg Val Arg Arg Gln Arg Ala Ala Phe Leu His Gln Glu Ser Ala
    290                 295                 300

Tyr Tyr Ser Lys Gly Phe Asp Leu Val Ala Leu Glu Asp Met Ser Val
305                 310                 315                 320

Arg Lys Met Thr Ala Thr Ala Gly Glu Ala Pro Glu Met Gly Arg Gly
                325                 330                 335

Ala Gln Arg Asp Leu Asn Arg Gly Ile Leu Asp Val Gly Trp Tyr Glu
            340                 345                 350

Leu Ala Arg Gln Ile Asp Tyr Lys Arg Leu Ala His Gly Gly Glu Leu
        355                 360                 365

Leu Arg Val Asp Pro Gly Gln Thr Thr Pro Leu Ala Cys Val Thr Glu
    370                 375                 380

Glu Gln Pro Ala Arg Gly Ile Ser Ser Ala Cys Ala Val Cys Gly Ile

```
            385                 390                 395                 400
    Pro Leu Ala Arg Pro Ala Ser Gly Asn Ala Arg Met Arg Cys Thr Ala
                    405                 410                 415

Cys Gly Ser Ser Gln Val Gly Asp Val Asn Ala Ala Glu Asn Val Leu
                420                 425                 430

Thr Arg Ala Leu Ser Ser Ala Pro Ser Gly Pro Lys Ser Pro Lys Ala
                435                 440                 445

Ser Ile Lys Ile Lys Gly Arg Gln Lys Arg Leu Gly Thr Pro Ala Asn
            450                 455                 460

Arg Ala Gly Glu Ala Ser Gly Gly Asp Pro Pro Val Arg Gly Pro Val
    465                 470                 475                 480

Glu Gly Gly Thr Leu Ala Tyr Val Val Glu Pro Val Ser Glu Ser Gln
                    485                 490                 495

Ser Asp Thr

<210> SEQ ID NO 45
<211> LENGTH: 560
<212> TYPE: PRT
<213> ORGANISM: Artificial sequence
<220> FEATURE:
<223> OTHER INFORMATION: Synthetic sequence

<400> SEQUENCE: 45

Met Thr Val Arg Thr Tyr Lys Tyr Arg Ala Tyr Pro Thr Pro Glu Gln
    1               5                   10                  15

Ala Glu Ala Leu Thr Ser Trp Leu Arg Phe Ala Ser Gln Leu Tyr Asn
                20                  25                  30

Ala Ala Leu Glu His Arg Lys Asn Ala Trp Gly Arg His Asp Ala His
                35                  40                  45

Gly Arg Gly Phe Arg Phe Trp Asp Gly Asp Ala Ala Pro Arg Lys Lys
            50                  55                  60

Ser Asp Pro Pro Gly Arg Trp Val Tyr Arg Gly Gly Gly Ala His
    65                  70                  75                  80

Ile Ser Lys Asn Asp Gln Gly Lys Leu Leu Thr Glu Phe Arg Arg Glu
                    85                  90                  95

His Ala Glu Leu Leu Pro Pro Gly Met Pro Ala Leu Val Gln His Glu
                100                 105                 110

Val Leu Ala Arg Leu Glu Arg Ser Met Ala Ala Phe Gln Arg Ala
                115                 120                 125

Thr Lys Gly Gln Lys Ala Gly Tyr Pro Arg Trp Arg Ser Glu His Arg
    130                 135                 140

Tyr Asp Ser Leu Thr Phe Gly Leu Thr Ser Pro Ser Lys Glu Arg Phe
    145                 150                 155                 160

Asp Pro Glu Thr Gly Glu Ser Leu Gly Arg Gly Lys Thr Val Gly Ala
                    165                 170                 175

Gly Thr Tyr His Asn Gly Asp Leu Arg Leu Thr Gly Leu Gly Glu Leu
                180                 185                 190

Arg Ile Leu Glu His Arg Ile Pro Met Gly Ala Ile Pro Lys Ser
                195                 200                 205

Val Ile Val Arg Arg Ser Gly Lys Arg Trp Phe Val Ser Ile Ala Met
        210                 215                 220

Glu Met Pro Ser Val Glu Pro Ala Ala Ser Gly Arg Pro Ala Val Gly
    225                 230                 235                 240

Leu Asp Met Gly Val Val Thr Trp Gly Thr Ala Phe Thr Ala Asp Thr
                    245                 250                 255
```

```
Ser Ala Ala Ala Ala Leu Val Ala Asp Leu Arg Arg Met Ala Thr Asp
                260                 265                 270

Pro Ser Asp Cys Arg Arg Leu Glu Glu Leu Glu Arg Glu Ala Ala Gln
            275                 280                 285

Leu Ser Glu Val Leu Ala His Cys Arg Ala Arg Gly Leu Asp Pro Ala
        290                 295                 300

Arg Pro Arg Arg Cys Pro Lys Glu Leu Thr Lys Leu Tyr Arg Arg Ser
305                 310                 315                 320

Leu His Arg Leu Gly Glu Leu Asp Arg Ala Cys Ala Arg Ile Arg Arg
                325                 330                 335

Arg Leu Gln Ala Ala His Asp Ile Ala Glu Pro Val Pro Asp Glu Ala
            340                 345                 350

Gly Ser Ala Val Leu Ile Glu Gly Ser Asn Ala Gly Met Arg His Ala
        355                 360                 365

Arg Arg Val Ala Arg Thr Gln Arg Val Ala Arg Thr Arg Ala
370                 375                 380

Gly His Ala His Ser Asn Arg Arg Lys Lys Ala Val Gln Ala Tyr Ala
385                 390                 395                 400

Arg Ala Lys Glu Arg Glu Arg Ser Ala Arg Gly Asp His Arg His Lys
                405                 410                 415

Val Ser Arg Ala Leu Val Arg Gln Phe Glu Glu Ile Ser Val Glu Ala
            420                 425                 430

Leu Asp Ile Lys Gln Leu Thr Val Ala Pro Glu His Asn Pro Asp Pro
        435                 440                 445

Gln Pro Asp Leu Pro Ala His Val Gln Arg Arg Arg Asn Arg Gly Glu
    450                 455                 460

Leu Asp Ala Ala Trp Gly Ala Phe Phe Ala Ala Leu Asp Tyr Lys Ala
465                 470                 475                 480

Ala Asp Ala Gly Gly Arg Val Ala Arg Lys Pro Ala Pro His Thr Thr
                485                 490                 495

Gln Glu Cys Ala Arg Cys Gly Thr Leu Val Pro Lys Pro Ile Ser Leu
            500                 505                 510

Arg Val His Arg Cys Pro Ala Cys Gly Tyr Thr Ala Pro Arg Thr Val
        515                 520                 525

Asn Ser Ala Arg Asn Val Leu Gln Arg Pro Leu Glu Glu Pro Gly Arg
    530                 535                 540

Ala Gly Pro Ser Gly Ala Asn Gly Arg Gly Val Pro His Ala Val Ala
545                 550                 555                 560

<210> SEQ ID NO 46
<211> LENGTH: 404
<212> TYPE: PRT
<213> ORGANISM: Artificial sequence
<220> FEATURE:
<223> OTHER INFORMATION: Synthetic sequence

<400> SEQUENCE: 46

Met Asn Cys Arg Tyr Arg Tyr Arg Ile Tyr Pro Thr Pro Gly Gln Arg
1               5                   10                  15

Gln Ser Leu Ala Arg Leu Phe Gly Cys Val Arg Val Val Trp Asn Asp
            20                  25                  30

Ala Leu Phe Leu Cys Arg Gln Ser Glu Lys Leu Pro Lys Asn Ser Glu
        35                  40                  45

Leu Gln Lys Leu Cys Ile Thr Gln Ala Lys Lys Thr Glu Ala Arg Gly
    50                  55                  60
```

Trp Leu Gly Gln Val Ser Ala Ile Pro Leu Gln Gln Ser Val Ala Asp
65                  70                  75                  80

Leu Gly Val Ala Phe Lys Asn Phe Phe Gln Ser Arg Ser Gly Lys Arg
            85                  90                  95

Lys Gly Lys Lys Val Asn Pro Pro Arg Val Arg Arg Asn Asn Arg
        100                 105                 110

Gln Gly Ala Arg Phe Thr Arg Gly Gly Phe Lys Val Lys Thr Ser Lys
        115                 120                 125

Val Tyr Leu Ala Arg Ile Gly Asp Ile Lys Ile Lys Trp Ser Arg Pro
        130                 135                 140

Leu Pro Ser Glu Pro Ser Ser Val Thr Val Ile Lys Asp Cys Ala Gly
145                 150                 155                 160

Gln Tyr Phe Leu Ser Phe Val Val Glu Val Lys Pro Glu Ile Lys Pro
                165                 170                 175

Pro Lys Asn Pro Ser Ile Gly Ile Asp Leu Gly Leu Lys Thr Phe Ala
            180                 185                 190

Ser Cys Ser Asn Gly Glu Lys Ile Asp Ser Pro Asp Tyr Ser Arg Leu
        195                 200                 205

Tyr Arg Lys Leu Lys Arg Cys Gln Arg Arg Leu Ala Lys Arg Gln Arg
210                 215                 220

Gly Ser Lys Arg Arg Glu Arg Met Arg Val Lys Val Ala Lys Leu Asn
225                 230                 235                 240

Ala Gln Ile Arg Asp Lys Arg Lys Asp Phe Leu His Lys Leu Ser Thr
            245                 250                 255

Lys Val Val Asn Glu Asn Gln Val Ile Ala Leu Glu Asp Leu Asn Val
                260                 265                 270

Gly Gly Met Leu Lys Asn Arg Lys Leu Ser Arg Ala Ile Ser Gln Ala
        275                 280                 285

Gly Trp Tyr Glu Phe Arg Ser Leu Cys Glu Gly Lys Ala Glu Lys His
        290                 295                 300

Asn Arg Asp Phe Arg Val Ile Ser Arg Trp Glu Pro Thr Ser Gln Val
305                 310                 315                 320

Cys Ser Glu Cys Gly Tyr Arg Trp Gly Lys Ile Asp Leu Ser Val Arg
                325                 330                 335

Ser Ile Val Cys Ile Asn Cys Gly Val Glu His Asp Arg Asp Asp Asn
            340                 345                 350

Ala Ser Val Asn Ile Glu Gln Ala Gly Leu Lys Val Gly Val Gly His
        355                 360                 365

Thr His Asp Ser Lys Arg Thr Gly Ser Ala Cys Lys Thr Ser Asn Gly
        370                 375                 380

Ala Val Cys Val Glu Pro Ser Thr His Arg Glu Tyr Val Gln Leu Thr
385                 390                 395                 400

Leu Phe Asp Trp

<210> SEQ ID NO 47
<211> LENGTH: 392
<212> TYPE: PRT
<213> ORGANISM: Artificial sequence
<220> FEATURE:
<223> OTHER INFORMATION: Synthetic sequence

<400> SEQUENCE: 47

Met Lys Ser Arg Trp Thr Phe Arg Cys Tyr Pro Thr Pro Glu Gln Glu
1               5                   10                  15

Gln His Leu Ala Arg Thr Phe Gly Cys Val Arg Phe Val Trp Asn Trp
            20                  25                  30

Ala Leu Arg Ala Arg Thr Asp Ala Phe Arg Ala Gly Glu Arg Ile Gly
        35                  40                  45

Tyr Pro Ala Thr Asp Lys Ala Leu Thr Leu Leu Lys Gln Gln Pro Glu
50                  55                  60

Thr Val Trp Leu Asn Glu Val Ser Ser Val Cys Leu Gln Gln Ala Leu
65                  70                  75                  80

Arg Asp Leu Gln Val Ala Phe Ser Asn Phe Phe Asp Lys Arg Ala Ala
                85                  90                  95

His Pro Ser Phe Lys Lys Glu Ala Arg Gln Ser Ala Asn Tyr Thr
            100                 105                 110

Glu Arg Gly Phe Ser Phe Asp His Glu Arg Arg Ile Leu Lys Leu Ala
        115                 120                 125

Lys Ile Gly Ala Ile Lys Val Lys Trp Ser Arg Lys Ala Ile Pro His
130                 135                 140

Pro Ser Ser Ile Arg Leu Ile Arg Thr Ala Ser Gly Lys Tyr Phe Val
145                 150                 155                 160

Ser Leu Val Val Glu Thr Gln Pro Ala Pro Met Pro Glu Thr Gly Glu
                165                 170                 175

Ser Val Gly Val Asp Phe Gly Val Ala Arg Leu Ala Thr Leu Ser Asn
            180                 185                 190

Gly Glu Arg Ile Ser Asn Pro Lys His Gly Ala Lys Trp Gln Arg Arg
        195                 200                 205

Leu Ala Phe Tyr Gln Lys Arg Leu Ala Arg Ala Thr Lys Gly Ser Lys
210                 215                 220

Arg Arg Met Arg Ile Lys Arg His Val Ala Arg Ile His Glu Lys Ile
225                 230                 235                 240

Gly Asn Ser Arg Ser Asp Thr Leu His Lys Leu Ser Thr Asp Leu Val
                245                 250                 255

Thr Arg Phe Asp Leu Ile Cys Val Glu Asp Leu Asn Leu Arg Gly Met
            260                 265                 270

Val Lys Asn His Ser Leu Ala Arg Ser Leu His Asp Ala Ser Ile Gly
        275                 280                 285

Ser Ala Ile Arg Met Ile Glu Glu Lys Ala Glu Arg Tyr Gly Lys Asn
290                 295                 300

Val Val Lys Ile Asp Arg Trp Phe Pro Ser Ser Lys Thr Cys Ser Asp
305                 310                 315                 320

Cys Gly His Ile Val Glu Gln Leu Pro Leu Asn Val Arg Glu Trp Thr
                325                 330                 335

Cys Pro Glu Cys Gly Thr Thr His Asp Arg Asp Ala Asn Ala Ala
            340                 345                 350

Asn Ile Leu Ala Val Gly Gln Thr Val Ser Ala His Gly Gly Thr Val
        355                 360                 365

Arg Arg Ser Arg Ala Lys Ala Ser Glu Arg Lys Ser Gln Arg Ser Ala
370                 375                 380

Asn Arg Gln Gly Val Asn Arg Ala
385                 390

<210> SEQ ID NO 48
<211> LENGTH: 10
<212> TYPE: PRT
<213> ORGANISM: Artificial sequence
<220> FEATURE:
<223> OTHER INFORMATION: Synthetic sequence

<400> SEQUENCE: 48

Ala Ala Ala Ala Ala Ala Ala Ala Ala Ala
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic sequence

<400> SEQUENCE: 49

Ala Ala Ala Ala Ala Ala Ala Ala Ala Ala
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic sequence

<400> SEQUENCE: 50

Ala Ala Ala Ala Ala Ala Ala Ala Ala Ala
1               5                   10

<210> SEQ ID NO 51
<211> LENGTH: 37
<212> TYPE: DNA
<213> ORGANISM: Artificial sequence
<220> FEATURE:
<223> OTHER INFORMATION: Synthetic sequence

<400> SEQUENCE: 51
gttgcattcc ttcattcgtc tattcgggtt ctgcaac                    37

<210> SEQ ID NO 52
<211> LENGTH: 37
<212> TYPE: DNA
<213> ORGANISM: Artificial sequence
<220> FEATURE:
<223> OTHER INFORMATION: Synthetic sequence

<400> SEQUENCE: 52
gttgcattcc ttcattcgtc tatccgggtt ctgcaag                    37

<210> SEQ ID NO 53
<211> LENGTH: 37
<212> TYPE: DNA
<213> ORGANISM: Artificial sequence
<220> FEATURE:
<223> OTHER INFORMATION: Synthetic sequence

<400> SEQUENCE: 53
gttgcagaac ccgaatagac gaatgaagga atgcaac                    37

<210> SEQ ID NO 54
<211> LENGTH: 37
<212> TYPE: DNA
<213> ORGANISM: Artificial sequence
<220> FEATURE:
<223> OTHER INFORMATION: Synthetic sequence

<400> SEQUENCE: 54
ctatcatatt cagaacaaag ggattaagga atgcaac                    37

<210> SEQ ID NO 55
<211> LENGTH: 37
<212> TYPE: DNA
<213> ORGANISM: Artificial sequence
<220> FEATURE:
<223> OTHER INFORMATION: Synthetic sequence

<400> SEQUENCE: 55
ctttcatact cagaacaaag ggattaagga atgcaac        37

<210> SEQ ID NO 56
<211> LENGTH: 37
<212> TYPE: DNA
<213> ORGANISM: Artificial sequence
<220> FEATURE:
<223> OTHER INFORMATION: Synthetic sequence

<400> SEQUENCE: 56
gtctacaact cattgataga aatcaatgag ttagaca        37

<210> SEQ ID NO 57
<211> LENGTH: 37
<212> TYPE: DNA
<213> ORGANISM: Artificial sequence
<220> FEATURE:
<223> OTHER INFORMATION: Synthetic sequence

<400> SEQUENCE: 57
gttataaagg cggggatcgc gaccgagcga ttgaaag        37

<210> SEQ ID NO 58
<211> LENGTH: 37
<212> TYPE: DNA
<213> ORGANISM: Artificial sequence
<220> FEATURE:
<223> OTHER INFORMATION: Synthetic sequence

<400> SEQUENCE: 58
gttgcattcc ttaattcatt ttctcaatat cggaaac        37

<210> SEQ ID NO 59
<211> LENGTH: 37
<212> TYPE: DNA
<213> ORGANISM: Artificial sequence
<220> FEATURE:
<223> OTHER INFORMATION: Synthetic sequence

<400> SEQUENCE: 59
gttgcagaaa tagaataaag gaattaagga atgcaac        37

<210> SEQ ID NO 60
<211> LENGTH: 37
<212> TYPE: DNA
<213> ORGANISM: Artificial sequence
<220> FEATURE:
<223> OTHER INFORMATION: Synthetic sequence

<400> SEQUENCE: 60
ctttcatact cagaacaaag ggattaagga atgcaac        37

<210> SEQ ID NO 61
<211> LENGTH: 37
<212> TYPE: DNA
<213> ORGANISM: Artificial sequence
<220> FEATURE:

<223> OTHER INFORMATION: Synthetic sequence

<400> SEQUENCE: 61
atttcatact cagaacaaag ggattaagga atgcaac              37

<210> SEQ ID NO 62
<211> LENGTH: 38
<212> TYPE: DNA
<213> ORGANISM: Artificial sequence
<220> FEATURE:
<223> OTHER INFORMATION: Synthetic sequence

<400> SEQUENCE: 62
gtttcagcgc acgaattaac gagatgagag atgcaact             38

<210> SEQ ID NO 63
<211> LENGTH: 37
<212> TYPE: DNA
<213> ORGANISM: Artificial sequence
<220> FEATURE:
<223> OTHER INFORMATION: Synthetic sequence

<400> SEQUENCE: 63
cttgcagaag ctgaatagac gaatcaagga atgcaac              37

<210> SEQ ID NO 64
<211> LENGTH: 39
<212> TYPE: DNA
<213> ORGANISM: Artificial sequence
<220> FEATURE:
<223> OTHER INFORMATION: Synthetic sequence

<400> SEQUENCE: 64
cacttgcagg ccttgaatag aggagttaag gaatgcaac            39

<210> SEQ ID NO 65
<211> LENGTH: 36
<212> TYPE: DNA
<213> ORGANISM: Artificial sequence
<220> FEATURE:
<223> OTHER INFORMATION: Synthetic sequence

<400> SEQUENCE: 65
gtctccatga ctgaaaagtc gtggccgaat tgaaac               36

<210> SEQ ID NO 66
<211> LENGTH: 37
<212> TYPE: DNA
<213> ORGANISM: Artificial sequence
<220> FEATURE:
<223> OTHER INFORMATION: Synthetic sequence

<400> SEQUENCE: 66
gttgcagcgc ccgaactgac gagacgagag atgcaac              37

<210> SEQ ID NO 67
<211> LENGTH: 37
<212> TYPE: DNA
<213> ORGANISM: Artificial sequence
<220> FEATURE:
<223> OTHER INFORMATION: Synthetic sequence

<400> SEQUENCE: 67
gttgcgcgaa tagaataaag gaattaagga atgcaac              37

```
<210> SEQ ID NO 68
<211> LENGTH: 38
<212> TYPE: DNA
<213> ORGANISM: Artificial sequence
<220> FEATURE:
<223> OTHER INFORMATION: Synthetic sequence

<400> SEQUENCE: 68
agttgcattc cttaatccct ctgttcagtt tgtgcaat                              38

<210> SEQ ID NO 69
<211> LENGTH: 37
<212> TYPE: DNA
<213> ORGANISM: Artificial sequence
<220> FEATURE:
<223> OTHER INFORMATION: Synthetic sequence

<400> SEQUENCE: 69
gttgcattcc tagtttctct aattagcact gtgcaac                               37

<210> SEQ ID NO 70
<211> LENGTH: 37
<212> TYPE: DNA
<213> ORGANISM: Artificial sequence
<220> FEATURE:
<223> OTHER INFORMATION: Synthetic sequence

<400> SEQUENCE: 70
gttgcggcgc gcgaataaac gagactagga atgcaac                               37

<210> SEQ ID NO 71
<211> LENGTH: 41
<212> TYPE: DNA
<213> ORGANISM: Artificial sequence
<220> FEATURE:
<223> OTHER INFORMATION: Synthetic sequence

<400> SEQUENCE: 71
actagttgca ttccttaatc cctttgttct gaatatgcta g                          41

<210> SEQ ID NO 72
<211> LENGTH: 37
<212> TYPE: DNA
<213> ORGANISM: Artificial sequence
<220> FEATURE:
<223> OTHER INFORMATION: Synthetic sequence

<400> SEQUENCE: 72
ctttcatatt cagaacaaag ggattaagga atgcaac                               37

<210> SEQ ID NO 73
<211> LENGTH: 39
<212> TYPE: DNA
<213> ORGANISM: Artificial sequence
<220> FEATURE:
<223> OTHER INFORMATION: Synthetic sequence

<400> SEQUENCE: 73
gttgcagtcc ttaacccta gtttctgaat atgaaagat                              39

<210> SEQ ID NO 74
<211> LENGTH: 37
<212> TYPE: DNA
<213> ORGANISM: Artificial sequence
<220> FEATURE:
<223> OTHER INFORMATION: Synthetic sequence
```

```
<400> SEQUENCE: 74
gttgcagccc ccgaactaac gagatgagag atgcaac                              37

<210> SEQ ID NO 75
<211> LENGTH: 38
<212> TYPE: DNA
<213> ORGANISM: Artificial sequence
<220> FEATURE:
<223> OTHER INFORMATION: Synthetic sequence

<400> SEQUENCE: 75
cttgcagaac aatcatatat gactaatcag actgcaac                             38

<210> SEQ ID NO 76
<211> LENGTH: 37
<212> TYPE: DNA
<213> ORGANISM: Artificial sequence
<220> FEATURE:
<223> OTHER INFORMATION: Synthetic sequence

<400> SEQUENCE: 76
gttgcactca ccggtgctca cgacgtaggg atgcaac                              37

<210> SEQ ID NO 77
<211> LENGTH: 36
<212> TYPE: DNA
<213> ORGANISM: Artificial sequence
<220> FEATURE:
<223> OTHER INFORMATION: Synthetic sequence

<400> SEQUENCE: 77
gtccctactc gctagggaaa ctaattgaat ggaaac                               36

<210> SEQ ID NO 78
<211> LENGTH: 37
<212> TYPE: DNA
<213> ORGANISM: Artificial sequence
<220> FEATURE:
<223> OTHER INFORMATION: Synthetic sequence

<400> SEQUENCE: 78
gttgcattcg ggtgcaaaac agggagtaga gtgtaac                              37

<210> SEQ ID NO 79
<211> LENGTH: 35
<212> TYPE: DNA
<213> ORGANISM: Artificial sequence
<220> FEATURE:
<223> OTHER INFORMATION: Synthetic sequence

<400> SEQUENCE: 79
cttccaaact cgagccagtg gggagagaag tggca                                35

<210> SEQ ID NO 80
<211> LENGTH: 38
<212> TYPE: DNA
<213> ORGANISM: Artificial sequence
<220> FEATURE:
<223> OTHER INFORMATION: Synthetic sequence

<400> SEQUENCE: 80
cctgtagacc ggtctcattc tgagaggggt atgcaact                             38

<210> SEQ ID NO 81
<211> LENGTH: 37
```

```
<212> TYPE: DNA
<213> ORGANISM: Artificial sequence
<220> FEATURE:
<223> OTHER INFORMATION: Synthetic sequence

<400> SEQUENCE: 81
gtctcgagac cctacagatt ttggagaggg gtgggac                              37

<210> SEQ ID NO 82
<211> LENGTH: 37
<212> TYPE: DNA
<213> ORGANISM: Artificial sequence
<220> FEATURE:
<223> OTHER INFORMATION: Synthetic sequence

<400> SEQUENCE: 82
gtcccacccc tctccaaaat ctgtagggtc tcgagac                              37

<210> SEQ ID NO 83
<211> LENGTH: 37
<212> TYPE: DNA
<213> ORGANISM: Artificial sequence
<220> FEATURE:
<223> OTHER INFORMATION: Synthetic sequence

<400> SEQUENCE: 83
gtagcaggac tctcctcgag agaaacaggg gtatgct                              37

<210> SEQ ID NO 84
<211> LENGTH: 40
<212> TYPE: DNA
<213> ORGANISM: Artificial sequence
<220> FEATURE:
<223> OTHER INFORMATION: Synthetic sequence

<400> SEQUENCE: 84
gtacaatacc tcctctttaa gagagggagg ggtacgctac                           40

<210> SEQ ID NO 85
<211> LENGTH: 31
<212> TYPE: DNA
<213> ORGANISM: Artificial sequence
<220> FEATURE:
<223> OTHER INFORMATION: Synthetic sequence

<400> SEQUENCE: 85 cccccctcgtt tccttcaggg gattcctttc c                                   31

<210> SEQ ID NO 86
<211> LENGTH: 28
<212> TYPE: DNA
<213> ORGANISM: Artificial sequence
<220> FEATURE:
<223> OTHER INFORMATION: Synthetic sequence

<400> SEQUENCE: 86
ggttcccccg ggcgcgggtg gggtggcg                                        28

<210> SEQ ID NO 87
<211> LENGTH: 28
<212> TYPE: DNA
<213> ORGANISM: Artificial sequence
<220> FEATURE:
<223> OTHER INFORMATION: Synthetic sequence

<400> SEQUENCE: 87
```
ggctgctccg ggtgcgcgtg gagcgagg                                      28

<210> SEQ ID NO 88
<211> LENGTH: 35
<212> TYPE: DNA
<213> ORGANISM: Artificial sequence
<220> FEATURE:
<223> OTHER INFORMATION: Synthetic sequence

<400> SEQUENCE: 88
gttttatacc ctttagaatt taaactgtct aaaag                              35

<210> SEQ ID NO 89
<211> LENGTH: 36
<212> TYPE: DNA
<213> ORGANISM: Artificial sequence
<220> FEATURE:
<223> OTHER INFORMATION: Synthetic sequence

<400> SEQUENCE: 89
attgcaccgg ccaacgcaaa tctgattgat ggacac                             36

<210> SEQ ID NO 90
<211> LENGTH: 36
<212> TYPE: DNA
<213> ORGANISM: Artificial sequence
<220> FEATURE:
<223> OTHER INFORMATION: Synthetic sequence

<400> SEQUENCE: 90
gccgcagcgg ccgacgcggc cctgatcgat ggacac                             36

<210> SEQ ID NO 91
<211> LENGTH: 36
<212> TYPE: DNA
<213> ORGANISM: Artificial sequence
<220> FEATURE:
<223> OTHER INFORMATION: Synthetic sequence

<400> SEQUENCE: 91
gtcgaaatgc ccgcgcgggg gcgtcgtacc cgcgac                             36

<210> SEQ ID NO 92
<211> LENGTH: 29
<212> TYPE: DNA
<213> ORGANISM: Artificial sequence
<220> FEATURE:
<223> OTHER INFORMATION: Synthetic sequence

<400> SEQUENCE: 92
ggctagcccg tgcgcgcagg gacgagtgg                                     29

<210> SEQ ID NO 93
<211> LENGTH: 24
<212> TYPE: DNA
<213> ORGANISM: Artificial sequence
<220> FEATURE:
<223> OTHER INFORMATION: Synthetic sequence

<400> SEQUENCE: 93
gcccgtgcgc gcagggacga gtgg                                          24

<210> SEQ ID NO 94
<211> LENGTH: 37
<212> TYPE: DNA
<213> ORGANISM: Artificial sequence

```
<220> FEATURE:
<223> OTHER INFORMATION: Synthetic sequence

<400> SEQUENCE: 94
gttgcagcgg ccgacggagc gcgagcgtgg atgccac                                37

<210> SEQ ID NO 95
<211> LENGTH: 29
<212> TYPE: DNA
<213> ORGANISM: Artificial sequence
<220> FEATURE:
<223> OTHER INFORMATION: Synthetic sequence

<400> SEQUENCE: 95
ccatcgcccc gcgcgcacgt ggatgagcc                                         29

<210> SEQ ID NO 96
<211> LENGTH: 35
<212> TYPE: DNA
<213> ORGANISM: Artificial sequence
<220> FEATURE:
<223> OTHER INFORMATION: Synthetic sequence

<400> SEQUENCE: 96
ctttagactt ctccggaagt cgaattaatg gaaac                                  35

<210> SEQ ID NO 97
<211> LENGTH: 28
<212> TYPE: DNA
<213> ORGANISM: Artificial sequence
<220> FEATURE:
<223> OTHER INFORMATION: Synthetic sequence

<400> SEQUENCE: 97
gggcgccccg cgcgagcggg ggttgaag                                          28

<210> SEQ ID NO 98
<211> LENGTH: 10
<212> TYPE: PRT
<213> ORGANISM: Artificial sequence
<220> FEATURE:
<223> OTHER INFORMATION: Synthetic sequence

<400> SEQUENCE: 98

Ala Ala Ala Ala Ala Ala Ala Ala Ala Ala
1               5                   10

<210> SEQ ID NO 99
<211> LENGTH: 10
<212> TYPE: PRT
<213> ORGANISM: Artificial sequence
<220> FEATURE:
<223> OTHER INFORMATION: Synthetic sequence

<400> SEQUENCE: 99

Ala Ala Ala Ala Ala Ala Ala Ala Ala Ala
1               5                   10

<210> SEQ ID NO 100
<211> LENGTH: 10
<212> TYPE: PRT
<213> ORGANISM: Artificial sequence
<220> FEATURE:
<223> OTHER INFORMATION: Synthetic sequence

<400> SEQUENCE: 100
```

Ala Ala Ala Ala Ala Ala Ala Ala Ala Ala
1               5                   10

<210> SEQ ID NO 101
<211> LENGTH: 84
<212> TYPE: PRT
<213> ORGANISM: Artificial sequence
<220> FEATURE:
<223> OTHER INFORMATION: Synthetic sequence

<400> SEQUENCE: 101

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 102
<211> LENGTH: 57
<212> TYPE: PRT
<213> ORGANISM: Artificial sequence
<220> FEATURE:
<223> OTHER INFORMATION: Synthetic sequence

<400> SEQUENCE: 102

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 103
<211> LENGTH: 85
<212> TYPE: PRT
<213> ORGANISM: Artificial sequence
<220> FEATURE:
<223> OTHER INFORMATION: Synthetic sequence

<400> SEQUENCE: 103

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 104
<211> LENGTH: 76
<212> TYPE: PRT
<213> ORGANISM: Artificial sequence
<220> FEATURE:
<223> OTHER INFORMATION: Synthetic sequence

<400> SEQUENCE: 104

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 105
<211> LENGTH: 76
<212> TYPE: PRT
<213> ORGANISM: Artificial sequence
<220> FEATURE:
<223> OTHER INFORMATION: Synthetic sequence

<400> SEQUENCE: 105

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 106
<211> LENGTH: 72
<212> TYPE: PRT
<213> ORGANISM: Artificial sequence
<220> FEATURE:
<223> OTHER INFORMATION: Synthetic sequence

<400> SEQUENCE: 106

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70

<210> SEQ ID NO 107
<211> LENGTH: 69

<212> TYPE: PRT
<213> ORGANISM: Artificial sequence
<220> FEATURE:
<223> OTHER INFORMATION: Synthetic sequence

<400> SEQUENCE: 107

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 108
<211> LENGTH: 77
<212> TYPE: PRT
<213> ORGANISM: Artificial sequence
<220> FEATURE:
<223> OTHER INFORMATION: Synthetic sequence

<400> SEQUENCE: 108

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
65                  70                  75

<210> SEQ ID NO 109
<211> LENGTH: 57
<212> TYPE: PRT
<213> ORGANISM: Artificial sequence
<220> FEATURE:
<223> OTHER INFORMATION: Synthetic sequence

<400> SEQUENCE: 109

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 110
<211> LENGTH: 65
<212> TYPE: PRT
<213> ORGANISM: Artificial sequence
<220> FEATURE:
<223> OTHER INFORMATION: Synthetic sequence

<400> SEQUENCE: 110

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Pro Thr
            20                  25                  30

Arg Arg Thr Ser Ser Thr Ser Gly Thr Ser Gly Val Lys Cys Ser Ala
            35                  40                  45

Ala Val Thr Pro Gln Ala Ser Pro Val Ile Ser Arg Ser Ala Ala Ala
            50                  55                  60

Ala
65
```

<210> SEQ ID NO 111
<211> LENGTH: 72
<212> TYPE: PRT
<213> ORGANISM: Artificial sequence
<220> FEATURE:
<223> OTHER INFORMATION: Synthetic sequence

<400> SEQUENCE: 111

```
Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
            35                  40                  45

Cys Ala Ser Ser Trp Asn Ser Thr Ile Asn Gly Ala Ala Thr Thr
            50                  55                  60

Asn Gly Ala Ser Ala Ala Ser Ser
65                  70
```

<210> SEQ ID NO 112
<211> LENGTH: 20
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 112

```
Gly Leu Phe Xaa Ala Leu Leu Xaa Leu Leu Xaa Ser Leu Trp Xaa Leu
1               5                   10                  15

Leu Leu Xaa Ala
            20
```

<210> SEQ ID NO 113
<211> LENGTH: 20

```
<212> TYPE: PRT
<213> ORGANISM: Artificial sequence
<220> FEATURE:
<223> OTHER INFORMATION: Synthetic sequence

<400> SEQUENCE: 113

Gly Leu Phe His Ala Leu Leu His Leu His Ser Leu Trp His Leu
1               5                   10                  15

Leu Leu His Ala
            20

<210> SEQ ID NO 114
<211> LENGTH: 7
<212> TYPE: PRT
<213> ORGANISM: Artificial sequence
<220> FEATURE:
<223> OTHER INFORMATION: Synthetic sequence

<400> SEQUENCE: 114

Pro Lys Lys Lys Arg Lys Val
1               5

<210> SEQ ID NO 115
<211> LENGTH: 16
<212> TYPE: PRT
<213> ORGANISM: Artificial sequence
<220> FEATURE:
<223> OTHER INFORMATION: Synthetic sequence

<400> SEQUENCE: 115

Lys Arg Pro Ala Ala Thr Lys Lys Ala Gly Gln Ala Lys Lys Lys Lys
1               5                   10                  15

<210> SEQ ID NO 116
<211> LENGTH: 9
<212> TYPE: PRT
<213> ORGANISM: Artificial sequence
<220> FEATURE:
<223> OTHER INFORMATION: Synthetic sequence

<400> SEQUENCE: 116

Pro Ala Ala Lys Arg Val Lys Leu Asp
1               5

<210> SEQ ID NO 117
<211> LENGTH: 11
<212> TYPE: PRT
<213> ORGANISM: Artificial sequence
<220> FEATURE:
<223> OTHER INFORMATION: Synthetic sequence

<400> SEQUENCE: 117

Arg Gln Arg Arg Asn Glu Leu Lys Arg Ser Pro
1               5                   10

<210> SEQ ID NO 118
<211> LENGTH: 38
<212> TYPE: PRT
<213> ORGANISM: Artificial sequence
<220> FEATURE:
<223> OTHER INFORMATION: Synthetic sequence

<400> SEQUENCE: 118

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
```

Arg Asn Gln Gly Gly Tyr
        35

<210> SEQ ID NO 119
<211> LENGTH: 42
<212> TYPE: PRT
<213> ORGANISM: Artificial sequence
<220> FEATURE:
<223> OTHER INFORMATION: Synthetic sequence

<400> SEQUENCE: 119

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 120
<211> LENGTH: 8
<212> TYPE: PRT
<213> ORGANISM: Artificial sequence
<220> FEATURE:
<223> OTHER INFORMATION: Synthetic sequence

<400> SEQUENCE: 120

Val Ser Arg Lys Arg Pro Arg Pro
1               5

<210> SEQ ID NO 121
<211> LENGTH: 8
<212> TYPE: PRT
<213> ORGANISM: Artificial sequence
<220> FEATURE:
<223> OTHER INFORMATION: Synthetic sequence

<400> SEQUENCE: 121

Pro Pro Lys Lys Ala Arg Glu Asp
1               5

<210> SEQ ID NO 122
<211> LENGTH: 8
<212> TYPE: PRT
<213> ORGANISM: Artificial sequence
<220> FEATURE:
<223> OTHER INFORMATION: Synthetic sequence

<400> SEQUENCE: 122

Pro Gln Pro Lys Lys Lys Pro Leu
1               5

<210> SEQ ID NO 123
<211> LENGTH: 12
<212> TYPE: PRT
<213> ORGANISM: Artificial sequence
<220> FEATURE:
<223> OTHER INFORMATION: Synthetic sequence

<400> SEQUENCE: 123

Ser Ala Leu Ile Lys Lys Lys Lys Lys Met Ala Pro
1               5                   10

<210> SEQ ID NO 124
<211> LENGTH: 5

```
<212> TYPE: PRT
<213> ORGANISM: Artificial sequence
<220> FEATURE:
<223> OTHER INFORMATION: Synthetic sequence

<400> SEQUENCE: 124

Asp Arg Leu Arg Arg
1               5

<210> SEQ ID NO 125
<211> LENGTH: 7
<212> TYPE: PRT
<213> ORGANISM: Artificial sequence
<220> FEATURE:
<223> OTHER INFORMATION: Synthetic sequence

<400> SEQUENCE: 125

Pro Lys Gln Lys Lys Arg Lys
1               5

<210> SEQ ID NO 126
<211> LENGTH: 10
<212> TYPE: PRT
<213> ORGANISM: Artificial sequence
<220> FEATURE:
<223> OTHER INFORMATION: Synthetic sequence

<400> SEQUENCE: 126

Arg Lys Leu Lys Lys Lys Ile Lys Lys Leu
1               5                   10

<210> SEQ ID NO 127
<211> LENGTH: 10
<212> TYPE: PRT
<213> ORGANISM: Artificial sequence
<220> FEATURE:
<223> OTHER INFORMATION: Synthetic sequence

<400> SEQUENCE: 127

Arg Glu Lys Lys Lys Phe Leu Lys Arg Arg
1               5                   10

<210> SEQ ID NO 128
<211> LENGTH: 20
<212> TYPE: PRT
<213> ORGANISM: Artificial sequence
<220> FEATURE:
<223> OTHER INFORMATION: Synthetic sequence

<400> SEQUENCE: 128

Lys Arg Lys Gly Asp Glu Val Asp Gly Val Asp Glu Val Ala Lys Lys
1               5                   10                  15

Lys Ser Lys Lys
            20

<210> SEQ ID NO 129
<211> LENGTH: 17
<212> TYPE: PRT
<213> ORGANISM: Artificial sequence
<220> FEATURE:
<223> OTHER INFORMATION: Synthetic sequence

<400> SEQUENCE: 129

Arg Lys Cys Leu Gln Ala Gly Met Asn Leu Glu Ala Arg Lys Thr Lys
1               5                   10                  15

Lys
```

```
<210> SEQ ID NO 130
<211> LENGTH: 11
<212> TYPE: PRT
<213> ORGANISM: Artificial sequence
<220> FEATURE:
<223> OTHER INFORMATION: Synthetic sequence

<400> SEQUENCE: 130

Tyr Gly Arg Lys Lys Arg Arg Gln Arg Arg Arg
1               5                   10

<210> SEQ ID NO 131
<211> LENGTH: 12
<212> TYPE: PRT
<213> ORGANISM: Artificial sequence
<220> FEATURE:
<223> OTHER INFORMATION: Synthetic sequence

<400> SEQUENCE: 131

Arg Arg Gln Arg Arg Thr Ser Lys Leu Met Lys Arg
1               5                   10

<210> SEQ ID NO 132
<211> LENGTH: 27
<212> TYPE: PRT
<213> ORGANISM: Artificial sequence
<220> FEATURE:
<223> OTHER INFORMATION: Synthetic sequence

<400> SEQUENCE: 132

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 133
<211> LENGTH: 33
<212> TYPE: PRT
<213> ORGANISM: Artificial sequence
<220> FEATURE:
<223> OTHER INFORMATION: Synthetic sequence

<400> SEQUENCE: 133

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 134
<211> LENGTH: 16
<212> TYPE: PRT
<213> ORGANISM: Artificial sequence
<220> FEATURE:
<223> OTHER INFORMATION: Synthetic sequence

<400> SEQUENCE: 134

Arg Gln Ile Lys Ile Trp Phe Gln Asn Arg Arg Met Lys Trp Lys Lys
1               5                   10                  15

<210> SEQ ID NO 135
<211> LENGTH: 9
<212> TYPE: PRT
<213> ORGANISM: Artificial sequence
```

```
<220> FEATURE:
<223> OTHER INFORMATION: Synthetic sequence

<400> SEQUENCE: 135

Arg Lys Lys Arg Arg Gln Arg Arg Arg
1               5

<210> SEQ ID NO 136
<211> LENGTH: 8
<212> TYPE: PRT
<213> ORGANISM: Artificial sequence
<220> FEATURE:
<223> OTHER INFORMATION: Synthetic sequence

<400> SEQUENCE: 136

Arg Lys Lys Arg Arg Gln Arg Arg
1               5

<210> SEQ ID NO 137
<211> LENGTH: 11
<212> TYPE: PRT
<213> ORGANISM: Artificial sequence
<220> FEATURE:
<223> OTHER INFORMATION: Synthetic sequence

<400> SEQUENCE: 137

Tyr Ala Arg Ala Ala Ala Arg Gln Ala Arg Ala
1               5                   10

<210> SEQ ID NO 138
<211> LENGTH: 11
<212> TYPE: PRT
<213> ORGANISM: Artificial sequence
<220> FEATURE:
<223> OTHER INFORMATION: Synthetic sequence

<400> SEQUENCE: 138

Thr His Arg Leu Pro Arg Arg Arg Arg Arg Arg
1               5                   10

<210> SEQ ID NO 139
<211> LENGTH: 11
<212> TYPE: PRT
<213> ORGANISM: Artificial sequence
<220> FEATURE:
<223> OTHER INFORMATION: Synthetic sequence

<400> SEQUENCE: 139

Gly Gly Arg Arg Ala Arg Arg Arg Arg Arg Arg
1               5                   10

<210> SEQ ID NO 140
<211> LENGTH: 5
<212> TYPE: PRT
<213> ORGANISM: Artificial sequence
<220> FEATURE:
<223> OTHER INFORMATION: Synthetic sequence

<400> SEQUENCE: 140

Gly Ser Gly Gly Ser
1               5

<210> SEQ ID NO 141
<211> LENGTH: 6
<212> TYPE: PRT
<213> ORGANISM: Artificial sequence
<220> FEATURE:
```

```
<223> OTHER INFORMATION: Synthetic sequence

<400> SEQUENCE: 141

Gly Gly Ser Gly Gly Ser
1               5

<210> SEQ ID NO 142
<211> LENGTH: 4
<212> TYPE: PRT
<213> ORGANISM: Artificial sequence
<220> FEATURE:
<223> OTHER INFORMATION: Synthetic sequence

<400> SEQUENCE: 142

Gly Gly Gly Ser
1

<210> SEQ ID NO 143
<211> LENGTH: 4
<212> TYPE: PRT
<213> ORGANISM: Artificial sequence
<220> FEATURE:
<223> OTHER INFORMATION: Synthetic sequence

<400> SEQUENCE: 143

Gly Gly Ser Gly
1

<210> SEQ ID NO 144
<211> LENGTH: 5
<212> TYPE: PRT
<213> ORGANISM: Artificial sequence
<220> FEATURE:
<223> OTHER INFORMATION: Synthetic sequence

<400> SEQUENCE: 144

Gly Gly Ser Gly Gly
1               5

<210> SEQ ID NO 145
<211> LENGTH: 5
<212> TYPE: PRT
<213> ORGANISM: Artificial sequence
<220> FEATURE:
<223> OTHER INFORMATION: Synthetic sequence

<400> SEQUENCE: 145

Gly Ser Gly Ser Gly
1               5

<210> SEQ ID NO 146
<211> LENGTH: 5
<212> TYPE: PRT
<213> ORGANISM: Artificial sequence
<220> FEATURE:
<223> OTHER INFORMATION: Synthetic sequence

<400> SEQUENCE: 146

Gly Ser Gly Gly Gly
1               5

<210> SEQ ID NO 147
<211> LENGTH: 5
<212> TYPE: PRT
<213> ORGANISM: Artificial sequence
<220> FEATURE:
<223> OTHER INFORMATION: Synthetic sequence
```

<210> SEQ ID NO 148
<211> LENGTH: 5
<212> TYPE: PRT
<213> ORGANISM: Artificial sequence
<220> FEATURE:
<223> OTHER INFORMATION: Synthetic sequence

<400> SEQUENCE: 147

Gly Gly Gly Ser Gly
1               5

<210> SEQ ID NO 148
<211> LENGTH: 5
<212> TYPE: PRT
<213> ORGANISM: Artificial sequence
<220> FEATURE:
<223> OTHER INFORMATION: Synthetic sequence

<400> SEQUENCE: 148

Gly Ser Ser Ser Gly
1               5

<210> SEQ ID NO 149
<211> LENGTH: 4
<212> TYPE: PRT
<213> ORGANISM: Artificial sequence
<220> FEATURE:
<223> OTHER INFORMATION: Synthetic sequence

<400> SEQUENCE: 149

Ala Ala Ala Ala
1

<210> SEQ ID NO 150
<211> LENGTH: 4
<212> TYPE: PRT
<213> ORGANISM: Artificial sequence
<220> FEATURE:
<223> OTHER INFORMATION: Synthetic sequence

<400> SEQUENCE: 150

Ala Ala Ala Ala
1

<210> SEQ ID NO 151
<211> LENGTH: 80
<212> TYPE: DNA
<213> ORGANISM: Artificial sequence
<220> FEATURE:
<223> OTHER INFORMATION: Synthetic sequence

<400> SEQUENCE: 151
cgattcctcc ctacagtagt taggtatagc cgaaaggtag agactaaatc tgtagttgga      60
gtgggccgct tgcatcggcc                                                 80

<210> SEQ ID NO 152
<211> LENGTH: 122
<212> TYPE: DNA
<213> ORGANISM: Artificial sequence
<220> FEATURE:
<223> OTHER INFORMATION: Synthetic sequence

<400> SEQUENCE: 152
tcgtctcgag ggttaccaaa attggcactt ctcgacttta ggccgatgca agcggcccac      60
tccactacag atttagtctc taccttgcgg ctatacctaa cttactgtag ggaggaatcg     120
tg                                                                   122

<210> SEQ ID NO 153
<211> LENGTH: 91
<212> TYPE: DNA

```
<213> ORGANISM: Artificial sequence
<220> FEATURE:
<223> OTHER INFORMATION: Synthetic sequence

<400> SEQUENCE: 153
cttcactgat aaagtggaga accgcttcac caaaagctgt cccttagggg attagaactt     60
gagtgaaggt gggctgcttg catcagccta a                                   91

<210> SEQ ID NO 154
<211> LENGTH: 114
<212> TYPE: DNA
<213> ORGANISM: Artificial sequence
<220> FEATURE:
<223> OTHER INFORMATION: Synthetic sequence

<400> SEQUENCE: 154
cagaataata ctgacttact aagatatctt gagggtatac ccgaaaagat tggcgttgtt     60
gcaacgcaat aagatgtaaa tctgaaaagg tttggaatca tataataat ttta           114

<210> SEQ ID NO 155
<211> LENGTH: 104
<212> TYPE: DNA
<213> ORGANISM: Artificial sequence
<220> FEATURE:
<223> OTHER INFORMATION: Synthetic sequence

<400> SEQUENCE: 155
aagccaagat atggaatgcc attgtaatat tatggtgttg acttagttta gatttaaaca     60
atcttcgatg gctatatgcg gaaggtttgg cgtcgttgta acgc                    104

<210> SEQ ID NO 156
<211> LENGTH: 213
<212> TYPE: DNA
<213> ORGANISM: Artificial sequence
<220> FEATURE:
<223> OTHER INFORMATION: Synthetic sequence

<400> SEQUENCE: 156
cagtgtgcat agctataaca ctacgcaaag actgctaaag agcgatgtgc tctatcgcag     60
tctcaccttt aatggactta cggatctttt ggagcactaa gctccgctgc ggtgcaacac    120 cgccctttc ttgcctctgc ttgccctttc cggttattat agccgggaga gtgcggaaga    180
ttaccgctct agctcgcagc atgttactga gtc                                213

<210> SEQ ID NO 157
<211> LENGTH: 94
<212> TYPE: DNA
<213> ORGANISM: Artificial sequence
<220> FEATURE:
<223> OTHER INFORMATION: Synthetic sequence

<400> SEQUENCE: 157
gcaagtcatt cggggacact ttttgttatt taaagtgttt tagataaatc agtgtcatgc     60
tgaataacga cccgacctat aaataacata atcc                                94

<210> SEQ ID NO 158
<211> LENGTH: 252
<212> TYPE: DNA
<213> ORGANISM: Artificial sequence
<220> FEATURE:
<223> OTHER INFORMATION: Synthetic sequence

<400> SEQUENCE: 158
```

```
gtccttaagg tactacacat tacatgtgaa cgtggagcta ataatagaaa tattattaga    60
ctacacctta ttaataacgg taggagatct atatggtctt gaatggaata gtaattgtga   120
aattataatt tctgttctta gctacttaag atggctcgtt gcaagccact cgggggctct   180
cttgaagtca aagagcttta gacaaatcag tgtcaaactg aataacgacc cgaccatgac   240
ttcataatcc cg                                                       252
```

<210> SEQ ID NO 159
<211> LENGTH: 152
<212> TYPE: DNA
<213> ORGANISM: Artificial sequence
<220> FEATURE:
<223> OTHER INFORMATION: Synthetic sequence

<400> SEQUENCE: 159

```
ctcgaggcta tttcatactc agaacaaagg gattaaggaa tgcaacccat ttcaaaatct    60
gtggaattat cacaaccatt aacatttcat actcagaaca aagggattaa ggaatgcaac   120
ggacaccttg ctatgtcctt tgatgtatg tg                                  152
```

<210> SEQ ID NO 160
<211> LENGTH: 61
<212> TYPE: DNA
<213> ORGANISM: Artificial sequence
<220> FEATURE:
<223> OTHER INFORMATION: Synthetic sequence

<400> SEQUENCE: 160

```
ctcgaggcta tttcatactc agaacaaagc tcagaacaaa gggataagg aatgcaacgg     60 a                                                                    61
```

<210> SEQ ID NO 161
<211> LENGTH: 101
<212> TYPE: DNA
<213> ORGANISM: Artificial sequence
<220> FEATURE:
<223> OTHER INFORMATION: Synthetic sequence

<400> SEQUENCE: 161

```
ctcagaaaca aagggattaa ggaatgcaac ccatttcaaa atctgtggaa actcagaaca    60
aagggattaa ggaatgcaac ggacaccttg ctatgtcctt c                       101
```

<210> SEQ ID NO 162
<211> LENGTH: 86
<212> TYPE: DNA
<213> ORGANISM: Artificial sequence
<220> FEATURE:
<223> OTHER INFORMATION: Synthetic sequence

<400> SEQUENCE: 162

```
ctcagaacaa agggattaag gaatgcaacc catttcctca gaacaaaggg attaaggaat    60
gcaacggaca ccttgctatg tccttc                                         86
```

<210> SEQ ID NO 163
<211> LENGTH: 76
<212> TYPE: DNA
<213> ORGANISM: Artificial sequence
<220> FEATURE:
<223> OTHER INFORMATION: Synthetic sequence

<400> SEQUENCE: 163
ctcagaacaa agggattaag gaatgcaacc catttctcag aacaaaggga ttaaggaatg    60
caacggacac cttgct                                                   76

<210> SEQ ID NO 164
<211> LENGTH: 82
<212> TYPE: DNA
<213> ORGANISM: Artificial sequence
<220> FEATURE:
<223> OTHER INFORMATION: Synthetic sequence

<400> SEQUENCE: 164
ctcagaacaa agggattaag gaatgcaacc catttcaaaa ctcagaacaa agggattaag    60
gaatgcaacg gacaccttgc ta                                            82

<210> SEQ ID NO 165
<211> LENGTH: 72
<212> TYPE: DNA
<213> ORGANISM: Artificial sequence
<220> FEATURE:
<223> OTHER INFORMATION: Synthetic sequence

<400> SEQUENCE: 165
ctcagaacaa agggattaag gaatgcaacc catttcctca gaacaaaggg attaaggaat    60
gcaacggaca cc                                                       72

<210> SEQ ID NO 166
<211> LENGTH: 59
<212> TYPE: DNA
<213> ORGANISM: Artificial sequence
<220> FEATURE:
<223> OTHER INFORMATION: Synthetic sequence

<400> SEQUENCE: 166
ctcagaacaa agggattaag gaatgcaacc cgggattaag gaatgcaacg gacaccttg     59

<210> SEQ ID NO 167
<211> LENGTH: 50
<212> TYPE: DNA
<213> ORGANISM: Artificial sequence
<220> FEATURE:
<223> OTHER INFORMATION: Synthetic sequence

<400> SEQUENCE: 167
ctcagaacaa agggattaag gaatgcaacc aacggacacc ttgctatgtc               50

<210> SEQ ID NO 168
<211> LENGTH: 45
<212> TYPE: DNA
<213> ORGANISM: Artificial sequence
<220> FEATURE:
<223> OTHER INFORMATION: Synthetic sequence

<400> SEQUENCE: 168
ctcagaacaa agggattaag gaatgcaacc catttcaaaa tctgt                    45

<210> SEQ ID NO 169
<211> LENGTH: 41
<212> TYPE: DNA
<213> ORGANISM: Artificial sequence
<220> FEATURE:
<223> OTHER INFORMATION: Synthetic sequence

<400> SEQUENCE: 169
ctcagaacaa agggattaag gaatgcaacc catttcaaaa t                        41

```
<210> SEQ ID NO 170
<211> LENGTH: 36
<212> TYPE: DNA
<213> ORGANISM: Artificial sequence
<220> FEATURE:
<223> OTHER INFORMATION: Synthetic sequence

<400> SEQUENCE: 170
ctcagaacaa agggattaag gaatgcaacc catttc                                 36

<210> SEQ ID NO 171
<211> LENGTH: 36
<212> TYPE: DNA
<213> ORGANISM: Artificial sequence
<220> FEATURE:
<223> OTHER INFORMATION: Synthetic sequence

<400> SEQUENCE: 171
ctcagaacaa agggattaag gaatgcaacc catttc                                 36

<210> SEQ ID NO 172
<211> LENGTH: 36
<212> TYPE: DNA
<213> ORGANISM: Artificial sequence
<220> FEATURE:
<223> OTHER INFORMATION: Synthetic sequence

<400> SEQUENCE: 172
ctcagaacaa agggattaag gaatgcaacc catttc                                 36

<210> SEQ ID NO 173
<211> LENGTH: 37
<212> TYPE: DNA
<213> ORGANISM: Artificial sequence
<220> FEATURE:
<223> OTHER INFORMATION: Synthetic sequence

<400> SEQUENCE: 173
ctcagaacaa agggattaag gaatgcaacc catttca                                37

<210> SEQ ID NO 174
<211> LENGTH: 38
<212> TYPE: DNA
<213> ORGANISM: Artificial sequence
<220> FEATURE:
<223> OTHER INFORMATION: Synthetic sequence

<400> SEQUENCE: 174
ctcagaacaa agggattaag gaatgcaacc catttcaa                               38

<210> SEQ ID NO 175
<211> LENGTH: 46
<212> TYPE: DNA
<213> ORGANISM: Artificial sequence
<220> FEATURE:
<223> OTHER INFORMATION: Synthetic sequence

<400> SEQUENCE: 175
ctcagaacaa agggattaag gaatgcaacc catttcaaaa tctgtg                      46

<210> SEQ ID NO 176
<211> LENGTH: 46
<212> TYPE: DNA
<213> ORGANISM: Artificial sequence
<220> FEATURE:
```

<223> OTHER INFORMATION: Synthetic sequence

<400> SEQUENCE: 176
ctcagaacaa agggattaag gaatgcaacc catttcaaaa tctgtg          46

<210> SEQ ID NO 177
<211> LENGTH: 44
<212> TYPE: DNA
<213> ORGANISM: Artificial sequence
<220> FEATURE:
<223> OTHER INFORMATION: Synthetic sequence

<400> SEQUENCE: 177
ctcagaacaa agggattaag gaatgcaacc catttcaaaa tctg            44

<210> SEQ ID NO 178
<211> LENGTH: 726
<212> TYPE: PRT
<213> ORGANISM: Artificial sequence
<220> FEATURE:
<223> OTHER INFORMATION: Synthetic sequence

<400> SEQUENCE: 178

```
Ser Glu Ser Glu Asn Lys Ile Ile Glu Gln Tyr Tyr Ala Phe Leu Tyr
1               5                   10                  15

Ser Phe Arg Asp Lys Tyr Glu Lys Pro Glu Phe Lys Asn Arg Gly Asp
            20                  25                  30

Ile Lys Arg Lys Leu Gln Asn Lys Trp Glu Asp Phe Leu Lys Glu Gln
        35                  40                  45

Asn Leu Lys Asn Asp Lys Lys Leu Ser Asn Tyr Ile Phe Ser Asn Arg
    50                  55                  60

Asn Phe Arg Arg Ser Tyr Asp Arg Glu Glu Asn Glu Glu Gly Ile
65                  70                  75                  80

Asp Glu Lys Lys Ser Lys Pro Lys Arg Ile Asn Cys Phe Glu Lys Glu
                85                  90                  95

Lys Asn Leu Lys Asp Gln Tyr Asp Lys Asp Ala Ile Asn Ala Ser Ala
            100                 105                 110

Asn Lys Asp Gly Ala Gln Lys Trp Gly Cys Phe Glu Cys Ile Phe Phe
        115                 120                 125

Pro Met Tyr Lys Ile Glu Ser Gly Asp Pro Asn Lys Arg Ile Ile Ile
    130                 135                 140

Asn Lys Thr Arg Phe Lys Leu Phe Asp Phe Tyr Leu Asn Leu Lys Gly
145                 150                 155                 160

Cys Lys Ser Cys Leu Arg Ser Thr Tyr His Pro Tyr Arg Ser Asn Val
                165                 170                 175

Tyr Ile Glu Ser Asn Tyr Asp Lys Leu Lys Arg Glu Ile Gly Asn Phe
            180                 185                 190

Leu Gln Gln Lys Asn Ile Phe Gln Arg Met Arg Lys Ala Lys Val Ser
        195                 200                 205

Glu Gly Lys Tyr Leu Thr Asn Leu Asp Glu Tyr Arg Leu Ser Cys Val
    210                 215                 220

Ala Met His Phe Lys Asn Arg Trp Leu Phe Phe Asp Ser Ile Gln Lys
225                 230                 235                 240

Val Leu Arg Glu Thr Ile Lys Gln Arg Leu Lys Gln Met Arg Glu Ser
                245                 250                 255

Tyr Asp Glu Gln Ala Lys Thr Leu Arg Ser Lys Gly His Gly Arg Ala
            260                 265                 270
```

```
Lys Tyr Glu Asp Gln Val Arg Met Ile Arg Arg Ala Tyr Ser Ala
            275                 280                 285
Gln Ala His Lys Leu Leu Asp Asn Gly Tyr Ile Thr Leu Phe Asp Tyr
    290                 295                 300
Asp Asp Lys Glu Ile Asn Lys Val Cys Leu Thr Ala Ile Asn Gln Glu
305                 310                 315                 320
Gly Phe Asp Ile Gly Gly Tyr Leu Asn Ser Asp Ile Asp Asn Val Met
                325                 330                 335
Pro Pro Ile Glu Ile Ser Phe His Lys Trp Lys Tyr Asn Glu Pro
            340                 345                 350
Ile Leu Asn Ile Glu Ser Pro Phe Ser Lys Ala Lys Ile Ser Asp Tyr
            355                 360                 365
Leu Arg Lys Ile Arg Glu Asp Leu Asn Leu Glu Arg Gly Lys Glu Gly
    370                 375                 380
Lys Ala Arg Ser Lys Lys Asn Val Arg Arg Lys Val Leu Ala Ser Lys
385                 390                 395                 400
Gly Glu Asp Gly Tyr Lys Lys Ile Phe Thr Asp Phe Phe Ser Lys Trp
                405                 410                 415
Lys Glu Glu Leu Glu Gly Asn Ala Met Glu Arg Val Leu Ser Gln Ser
            420                 425                 430
Ser Gly Asp Ile Gln Trp Ser Lys Lys Arg Ile His Tyr Thr Thr
    435                 440                 445
Leu Val Leu Asn Ile Asn Leu Leu Asp Lys Lys Gly Val Gly Asn Leu
    450                 455                 460
Lys Tyr Tyr Glu Ile Ala Glu Lys Thr Lys Ile Leu Ser Phe Asp Lys
465                 470                 475                 480
Asn Glu Asn Lys Phe Trp Pro Ile Thr Ile Gln Val Leu Leu Asp Gly
                485                 490                 495
Tyr Glu Ile Gly Thr Glu Tyr Asp Glu Ile Lys Gln Leu Asn Glu Lys
                500                 505                 510
Thr Ser Lys Gln Phe Thr Ile Tyr Asp Pro Asn Thr Lys Ile Ile Lys
            515                 520                 525
Ile Pro Phe Thr Asp Ser Lys Ala Val Pro Leu Gly Met Leu Gly Ile
    530                 535                 540
Asn Ile Ala Thr Leu Lys Thr Val Lys Lys Thr Glu Arg Asp Ile Lys
545                 550                 555                 560
Val Ser Lys Ile Phe Lys Gly Gly Leu Asn Ser Lys Ile Val Ser Lys
                565                 570                 575
Ile Gly Lys Gly Ile Tyr Ala Gly Tyr Phe Pro Thr Val Asp Lys Glu
            580                 585                 590
Ile Leu Glu Glu Val Glu Glu Asp Thr Leu Asp Asn Glu Phe Ser Ser
            595                 600                 605
Lys Ser Gln Arg Asn Ile Phe Leu Lys Ser Ile Ile Lys Asn Tyr Asp
    610                 615                 620
Lys Met Leu Lys Glu Gln Leu Phe Asp Phe Tyr Ser Phe Leu Val Arg
625                 630                 635                 640
Asn Asp Leu Gly Val Arg Phe Leu Thr Asp Arg Glu Leu Gln Asn Ile
                645                 650                 655
Glu Asp Glu Ser Phe Asn Leu Glu Lys Arg Phe Glu Thr Asp Arg
            660                 665                 670
Asp Arg Ile Ala Arg Trp Phe Asp Asn Thr Asn Thr Asp Asp Gly Lys
    675                 680                 685
Glu Lys Phe Lys Lys Leu Ala Asn Glu Ile Val Asp Ser Tyr Lys Pro
```

```
                    690                 695                 700
Arg Leu Ile Arg Leu Pro Val Arg Val Ile Lys Arg Ile Gln Pro
705                 710                 715                 720

Val Lys Gln Arg Glu Met
                725

<210> SEQ ID NO 179
<211> LENGTH: 517
<212> TYPE: PRT
<213> ORGANISM: Artificial sequence
<220> FEATURE:
<223> OTHER INFORMATION: Synthetic sequence

<400> SEQUENCE: 179

Lys Tyr Ser Thr Arg Asp Phe Ser Glu Leu Asn Glu Ile Gln Val Thr
1               5                   10                  15

Ala Cys Lys Gln Asp Glu Phe Phe Lys Val Ile Gln Asn Ala Trp Arg
            20                  25                  30

Glu Ile Ile Lys Lys Arg Phe Leu Glu Asn Arg Glu Asn Phe Ile Glu
        35                  40                  45

Lys Lys Ile Phe Lys Asn Lys Gly Arg Gly Lys Arg Gln Glu Ser
    50                  55                  60

Asp Lys Thr Ile Gln Arg Asn Arg Ala Ser Val Met Lys Asn Phe Gln
65                  70                  75                  80

Leu Ile Glu Asn Glu Lys Ile Ile Leu Arg Ala Pro Ser Gly His Val
                85                  90                  95

Ala Cys Val Phe Pro Val Lys Val Gly Leu Asp Ile Gly Phe Lys
            100                 105                 110

Thr Asp Asp Leu Glu Lys Asn Ile Phe Pro Pro Arg Thr Ile Thr Ile
        115                 120                 125

Asn Val Phe Trp Lys Asn Arg Asp Arg Gln Arg Lys Gly Arg Lys Leu
    130                 135                 140

Glu Val Trp Gly Ile Lys Ala Arg Thr Lys Leu Ile Glu Lys Val His
145                 150                 155                 160

Lys Trp Asp Lys Leu Glu Glu Val Lys Lys Arg Leu Lys Ser Leu
                165                 170                 175

Glu Gln Lys Gln Glu Lys Ser Leu Asp Asn Trp Ser Glu Val Asn Asn
            180                 185                 190

Asp Ser Phe Tyr Lys Val Gln Ile Asp Glu Leu Gln Glu Lys Ile Asp
        195                 200                 205

Lys Ser Leu Lys Gly Arg Thr Met Asn Lys Ile Leu Asp Asn Lys Ala
    210                 215                 220

Lys Glu Ser Lys Glu Ala Glu Gly Leu Tyr Ile Glu Trp Glu Lys Asp
225                 230                 235                 240

Phe Glu Gly Glu Met Leu Arg Arg Ile Glu Ala Ser Thr Gly Gly Glu
                245                 250                 255

Glu Lys Trp Gly Lys Arg Arg Gln Arg Arg His Thr Ser Leu Leu Leu
            260                 265                 270

Asp Ile Lys Asn Asn Ser Arg Gly Ser Lys Glu Ile Ile Asn Phe Tyr
        275                 280                 285

Ser Tyr Ala Lys Gln Gly Lys Lys Glu Lys Lys Ile Glu Phe Pro
    290                 295                 300

Phe Pro Leu Thr Ile Thr Leu Asp Ala Glu Glu Ser Pro Leu Asn
305                 310                 315                 320

Ile Lys Ser Ile Pro Ile Glu Asp Lys Asn Ala Thr Ser Lys Tyr Phe
```

325                 330                 335

Ser Ile Pro Phe Thr Glu Thr Arg Ala Thr Pro Leu Ser Ile Leu Gly
                340                 345                 350

Asp Arg Val Gln Lys Phe Lys Thr Lys Asn Ile Ser Gly Ala Ile Lys
            355                 360                 365

Arg Asn Leu Gly Ser Ser Ile Ser Ser Cys Lys Ile Val Gln Asn Ala
        370                 375                 380

Glu Thr Ser Ala Lys Ser Ile Leu Ser Leu Pro Asn Val Lys Glu Asp
385                 390                 395                 400

Asn Asn Met Glu Ile Phe Ile Asn Thr Met Ser Lys Asn Tyr Phe Arg
                405                 410                 415

Ala Met Met Lys Gln Met Glu Ser Phe Ile Phe Glu Met Glu Pro Lys
                420                 425                 430

Thr Leu Ile Asp Pro Tyr Lys Glu Lys Ala Ile Lys Trp Phe Glu Val
            435                 440                 445

Ala Ala Ser Ser Arg Ala Lys Arg Lys Leu Lys Leu Ser Lys Ala
        450                 455                 460

Asp Ile Lys Lys Ser Glu Leu Leu Ser Asn Thr Glu Glu Phe Glu
465                 470                 475                 480

Lys Glu Lys Gln Glu Lys Leu Glu Ala Leu Glu Lys Glu Ile Glu Glu
                485                 490                 495

Phe Tyr Leu Pro Arg Ile Val Arg Leu Gln Leu Thr Lys Thr Ile Leu
            500                 505                 510

Glu Thr Pro Val Met
        515

<210> SEQ ID NO 180
<211> LENGTH: 481
<212> TYPE: PRT
<213> ORGANISM: Artificial sequence
<220> FEATURE:
<223> OTHER INFORMATION: Synthetic sequence

<400> SEQUENCE: 180

Lys Lys Leu Gln Leu Leu Gly His Lys Ile Leu Leu Lys Glu Tyr Asp
1               5                   10                  15

Pro Asn Ala Val Asn Ala Ala Asn Phe Glu Thr Ser Thr Ala Glu
                20                  25                  30

Leu Cys Gly Gln Cys Lys Met Lys Pro Phe Lys Asn Lys Arg Arg Phe
            35                  40                  45

Gln Tyr Thr Phe Gly Lys Asn Tyr His Gly Cys Leu Ser Cys Ile Gln
        50                  55                  60

Asn Val Tyr Tyr Ala Lys Lys Arg Ile Val Gln Ile Ala Lys Glu Glu
65                  70                  75                  80

Leu Lys His Gln Leu Thr Asp Ser Ile Ala Ser Ile Pro Tyr Lys Tyr
                85                  90                  95

Thr Ser Leu Phe Ser Asn Thr Asn Ser Ile Asp Glu Leu Tyr Ile Leu
            100                 105                 110

Lys Gln Glu Arg Ala Ala Phe Phe Ser Asn Thr Asn Ser Ile Asp Glu
        115                 120                 125

Leu Tyr Ile Thr Gly Ile Glu Asn Asn Ile Ala Phe Lys Val Ile Ser
    130                 135                 140

Ala Ile Trp Asp Glu Ile Ile Lys Lys Arg Arg Gln Arg Tyr Ala Glu
145                 150                 155                 160

Ser Leu Thr Asp Thr Gly Thr Val Lys Ala Asn Arg Gly His Gly Gly

```
                    165                 170                 175

Thr Ala Tyr Lys Ser Asn Thr Arg Gln Glu Lys Ile Arg Ala Leu Gln
                180                 185                 190

Lys Gln Thr Leu His Met Val Thr Asn Pro Tyr Ile Ser Leu Ala Arg
            195                 200                 205

Tyr Lys Asn Asn Tyr Ile Val Ala Thr Leu Pro Arg Thr Ile Gly Met
        210                 215                 220

His Ile Gly Ala Ile Lys Asp Arg Asp Pro Gln Lys Lys Leu Ser Asp
225                 230                 235                 240

Tyr Ala Ile Asn Phe Asn Val Phe Trp Ser Asp Arg Gln Leu Ile
                245                 250                 255

Glu Leu Ser Thr Val Gln Tyr Thr Gly Asp Met Val Arg Lys Ile Glu
            260                 265                 270

Ala Glu Thr Gly Glu Asn Lys Trp Gly Glu Asn Met Lys Arg Thr
        275                 280                 285

Lys Thr Ser Leu Leu Leu Glu Ile Leu Thr Lys Thr Thr Asp Glu
        290                 295                 300

Leu Thr Phe Lys Asp Trp Ala Phe Ser Thr Lys Lys Glu Ile Asp Ser
305                 310                 315                 320

Val Thr Lys Lys Thr Tyr Gln Gly Phe Pro Ile Gly Ile Ile Phe Glu
                325                 330                 335

Gly Asn Glu Ser Ser Val Lys Phe Gly Ser Gln Asn Tyr Phe Pro Leu
            340                 345                 350

Pro Phe Asp Ala Lys Ile Thr Pro Pro Thr Ala Glu Gly Phe Arg Leu
        355                 360                 365

Asp Trp Leu Arg Lys Gly Ser Phe Ser Ser Gln Met Lys Thr Ser Tyr
        370                 375                 380

Gly Leu Ala Ile Tyr Ser Asn Lys Val Thr Asn Ala Ile Pro Ala Tyr
385                 390                 395                 400

Val Ile Lys Asn Met Phe Tyr Lys Ile Ala Arg Ala Glu Asn Gly Lys
                405                 410                 415

Gln Ile Lys Ala Lys Phe Leu Lys Lys Tyr Leu Asp Ile Ala Gly Asn
            420                 425                 430

Asn Tyr Val Pro Phe Ile Ile Met Gln His Tyr Arg Val Leu Asp Thr
        435                 440                 445

Phe Glu Glu Met Pro Ile Ser Gln Pro Lys Val Ile Arg Leu Ser Leu
        450                 455                 460

Thr Lys Thr Gln His Ile Ile Ile Lys Lys Asp Lys Thr Asp Ser Lys
465                 470                 475                 480

Met
```

<210> SEQ ID NO 181
<211> LENGTH: 534
<212> TYPE: PRT
<213> ORGANISM: Artificial sequence
<220> FEATURE:
<223> OTHER INFORMATION: Synthetic sequence

<400> SEQUENCE: 181

```
Asn Thr Ser Asn Leu Ile Asn Leu Gly Lys Lys Ala Ile Asn Ile Ser
1               5                   10                  15

Ala Asn Tyr Asp Ala Asn Leu Glu Val Gly Cys Lys Asn Cys Lys Phe
            20                  25                  30

Leu Ser Ser Asn Gly Asn Phe Pro Arg Gln Thr Asn Val Lys Glu Gly
        35                  40                  45
```

```
Cys His Ser Cys Glu Lys Ser Thr Tyr Glu Pro Ser Ile Tyr Leu Val
    50                  55                  60

Lys Ile Gly Glu Arg Lys Ala Lys Tyr Asp Val Leu Asp Ser Leu Lys
65                  70                  75                  80

Lys Phe Thr Phe Gln Ser Leu Lys Tyr Gln Ser Lys Lys Ser Met Lys
                85                  90                  95

Ser Arg Asn Lys Lys Pro Lys Glu Leu Lys Glu Phe Val Ile Phe Ala
            100                 105                 110

Asn Lys Asn Lys Ala Phe Asp Val Ile Gln Lys Ser Tyr Asn His Leu
        115                 120                 125

Ile Leu Gln Ile Lys Lys Glu Ile Asn Arg Met Asn Ser Lys Lys Arg
    130                 135                 140

Lys Lys Asn His Lys Arg Arg Leu Phe Arg Asp Arg Glu Lys Gln Leu
145                 150                 155                 160

Asn Lys Leu Arg Leu Ile Glu Ser Ser Asn Leu Phe Leu Pro Arg Glu
                165                 170                 175

Asn Lys Gly Asn Asn His Val Phe Thr Tyr Val Ala Ile His Ser Val
            180                 185                 190

Gly Arg Asp Ile Gly Val Ile Gly Ser Tyr Asp Glu Lys Leu Asn Phe
        195                 200                 205

Glu Thr Glu Leu Thr Tyr Gln Leu Tyr Phe Asn Asp Asp Lys Arg Leu
    210                 215                 220

Leu Tyr Ala Tyr Lys Pro Lys Gln Asn Lys Ile Ile Lys Ile Lys Glu
225                 230                 235                 240

Lys Leu Trp Asn Leu Arg Lys Glu Lys Glu Pro Leu Asp Leu Glu Tyr
                245                 250                 255

Glu Lys Pro Leu Asn Lys Ser Ile Thr Phe Ser Ile Lys Asn Asp Asn
            260                 265                 270

Leu Phe Lys Val Ser Lys Asp Leu Met Leu Arg Arg Ala Lys Phe Asn
        275                 280                 285

Ile Gln Gly Lys Glu Lys Leu Ser Lys Glu Arg Lys Ile Asn Arg
    290                 295                 300

Asp Leu Ile Lys Ile Lys Gly Leu Val Asn Ser Met Ser Tyr Gly Arg
305                 310                 315                 320

Phe Asp Glu Leu Lys Lys Glu Lys Asn Ile Trp Ser Pro His Ile Tyr
                325                 330                 335

Arg Glu Val Arg Gln Lys Glu Ile Lys Pro Cys Leu Ile Lys Asn Gly
            340                 345                 350

Asp Arg Ile Glu Ile Phe Glu Gln Leu Lys Lys Met Glu Arg Leu
        355                 360                 365

Arg Arg Phe Arg Glu Lys Arg Gln Lys Lys Ile Ser Lys Asp Leu Ile
    370                 375                 380

Phe Ala Glu Arg Ile Ala Tyr Asn Phe His Thr Lys Ser Ile Lys Asn
385                 390                 395                 400

Thr Ser Asn Lys Ile Asn Ile Asp Gln Glu Ala Lys Arg Gly Lys Ala
                405                 410                 415

Ser Tyr Met Arg Lys Arg Ile Gly Tyr Glu Thr Phe Lys Asn Lys Tyr
            420                 425                 430

Cys Glu Gln Cys Leu Ser Lys Gly Asn Val Tyr Arg Asn Val Gln Lys
        435                 440                 445

Gly Cys Ser Cys Phe Glu Asn Pro Phe Asp Trp Ile Lys Lys Gly Asp
    450                 455                 460
```

```
Glu Asn Leu Leu Pro Lys Lys Asn Glu Asp Leu Arg Val Lys Gly Ala
465                 470                 475                 480

Phe Arg Asp Glu Ala Leu Glu Lys Gln Ile Val Lys Ile Ala Phe Asn
                485                 490                 495

Ile Ala Lys Gly Tyr Glu Asp Phe Tyr Asp Asn Leu Gly Glu Ser Thr
            500                 505                 510

Glu Lys Asp Leu Lys Leu Lys Phe Lys Val Gly Thr Thr Ile Asn Glu
        515                 520                 525

Gln Glu Ser Leu Lys Leu
    530
```

<210> SEQ ID NO 182
<211> LENGTH: 537
<212> TYPE: PRT
<213> ORGANISM: Artificial sequence
<220> FEATURE:
<223> OTHER INFORMATION: Synthetic sequence

<400> SEQUENCE: 182

```
Thr Ser Asn Pro Ile Lys Leu Gly Lys Lys Ala Ile Asn Ile Ser Ala
1               5                   10                  15

Asn Tyr Asp Ser Asn Leu Gln Ile Gly Cys Lys Asn Cys Lys Phe Leu
            20                  25                  30

Ser Tyr Asn Gly Asn Phe Pro Arg Gln Thr Asn Val Lys Glu Gly Cys
        35                  40                  45

His Ser Cys Glu Lys Ser Thr Tyr Glu Pro Pro Val Tyr Thr Val Arg
    50                  55                  60

Ile Gly Glu Arg Arg Ser Lys Tyr Asp Val Leu Asp Ser Leu Lys Lys
65                  70                  75                  80

Phe Ile Phe Leu Ser Leu Lys Tyr Arg Gln Ser Lys Lys Met Lys Thr
                85                  90                  95

Arg Ser Lys Gly Ile Arg Gly Leu Glu Glu Phe Val Ile Ser Ala Asn
            100                 105                 110

Leu Lys Lys Ala Met Asp Val Ile Gln Lys Ser Tyr Arg His Leu Ile
        115                 120                 125

Leu Asn Ile Lys Asn Glu Ile Val Arg Met Asn Gly Lys Lys Arg Asn
    130                 135                 140

Lys Asn His Lys Arg Leu Leu Phe Arg Asp Arg Glu Lys Gln Leu Asn
145                 150                 155                 160

Lys Leu Arg Leu Ile Glu Gly Ser Ser Phe Phe Lys Pro Pro Thr Val
                165                 170                 175

Lys Gly Asp Asn Ser Ile Phe Thr Cys Val Ala Ile His Asn Ile Gly
            180                 185                 190

Arg Asp Ile Gly Ile Ala Gly Asp Tyr Phe Asp Lys Leu Glu Pro Lys
        195                 200                 205

Ile Glu Leu Thr Tyr Gln Leu Tyr Tyr Glu Tyr Asn Pro Lys Lys Glu
    210                 215                 220

Ser Glu Ile Asn Lys Arg Leu Leu Tyr Ala Tyr Lys Pro Lys Gln Asn
225                 230                 235                 240

Lys Ile Ile Glu Ile Lys Glu Lys Leu Trp Asn Leu Arg Lys Glu Lys
                245                 250                 255

Ser Pro Leu Asp Leu Glu Tyr Glu Lys Pro Leu Thr Lys Ser Ile Thr
            260                 265                 270

Phe Leu Val Lys Arg Asp Gly Val Phe Arg Ile Ser Lys Asp Leu Met
        275                 280                 285
```

```
Leu Arg Lys Ala Lys Phe Ile Ile Gln Gly Lys Glu Lys Leu Ser Lys
    290                 295                 300
Glu Glu Arg Lys Ile Asn Arg Asp Leu Ile Lys Ile Lys Ser Asn Ile
305                 310                 315                 320
Ile Ser Leu Thr Tyr Gly Arg Phe Asp Glu Leu Lys Lys Asp Lys Thr
                325                 330                 335
Ile Trp Ser Pro His Ile Phe Arg Asp Val Lys Gln Gly Lys Ile Thr
            340                 345                 350
Pro Cys Ile Glu Arg Lys Gly Asp Arg Met Asp Ile Phe Gln Gln Leu
        355                 360                 365
Arg Lys Lys Ser Glu Arg Leu Arg Glu Asn Arg Lys Lys Arg Gln Lys
    370                 375                 380
Lys Ile Ser Lys Asp Leu Ile Phe Ala Glu Arg Ile Ala Tyr Asn Phe
385                 390                 395                 400
His Thr Lys Ser Ile Lys Asn Thr Ser Asn Leu Ile Asn Ile Lys His
                405                 410                 415
Glu Ala Lys Arg Gly Lys Ala Ser Tyr Met Arg Lys Arg Ile Gly Asn
            420                 425                 430
Glu Thr Phe Arg Ile Lys Tyr Cys Glu Gln Cys Phe Pro Lys Asn Asn
        435                 440                 445
Val Tyr Lys Asn Val Gln Lys Gly Cys Ser Cys Phe Glu Asp Pro Phe
    450                 455                 460
Glu Tyr Ile Lys Lys Gly Asn Glu Asp Leu Ile Pro Asn Lys Asn Gln
465                 470                 475                 480
Asp Leu Lys Ala Lys Gly Ala Phe Arg Asp Asp Ala Leu Glu Lys Gln
                485                 490                 495
Ile Ile Lys Val Ala Phe Asn Ile Ala Lys Gly Tyr Glu Asp Phe Tyr
            500                 505                 510
Glu Asn Leu Lys Lys Thr Thr Glu Lys Asp Ile Arg Leu Lys Phe Lys
        515                 520                 525
Val Gly Thr Ile Ile Ser Glu Glu Met
    530                 535

<210> SEQ ID NO 183
<211> LENGTH: 541
<212> TYPE: PRT
<213> ORGANISM: Artificial sequence
<220> FEATURE:
<223> OTHER INFORMATION: Synthetic sequence

<400> SEQUENCE: 183

Asn Asn Ser Ile Asn Leu Ser Lys Lys Ala Ile Asn Ile Ser Ala Asn
1               5                   10                  15
Tyr Asp Ala Asn Leu Gln Val Arg Cys Lys Asn Cys Lys Phe Leu Ser
                20                  25                  30
Ser Asn Gly Asn Phe Pro Arg Gln Thr Asp Val Lys Glu Gly Cys His
            35                  40                  45
Ser Cys Glu Lys Ser Thr Tyr Glu Pro Pro Val Tyr Asp Val Lys Ile
        50                  55                  60
Gly Glu Ile Lys Ala Lys Tyr Glu Val Leu Asp Ser Leu Lys Lys Phe
65                  70                  75                  80
Thr Phe Gln Ser Leu Lys Tyr Gln Leu Ser Lys Ser Met Lys Phe Arg
                85                  90                  95
Ser Lys Lys Ile Lys Glu Leu Lys Glu Phe Val Ile Phe Ala Lys Glu
            100                 105                 110
```

```
Ser Lys Ala Leu Asn Val Ile Asn Arg Ser Tyr Lys His Leu Ile Leu
            115                 120                 125

Asn Ile Lys Asn Asp Ile Asn Arg Met Asn Ser Lys Lys Arg Ile Lys
130                 135                 140

Asn His Lys Gly Arg Leu Phe Leu Asp Arg Gln Lys Gln Leu Ser Lys
145                 150                 155                 160

Leu Lys Leu Ile Glu Gly Ser Ser Phe Phe Val Pro Ala Lys Asn Val
                165                 170                 175

Gly Asn Lys Ser Val Phe Thr Cys Val Ala Ile His Ser Ile Gly Arg
            180                 185                 190

Asp Ile Gly Ile Ala Gly Leu Tyr Asp Ser Phe Thr Lys Pro Val Asn
            195                 200                 205

Glu Ile Thr Tyr Gln Ile Phe Phe Ser Gly Glu Arg Arg Leu Leu Tyr
            210                 215                 220

Ala Tyr Lys Pro Lys Gln Leu Lys Ile Leu Ser Ile Lys Glu Asn Leu
225                 230                 235                 240

Trp Ser Leu Lys Asn Glu Lys Lys Pro Leu Asp Leu Leu Tyr Glu Lys
                245                 250                 255

Pro Leu Gly Lys Asn Leu Asn Phe Asn Val Lys Gly Gly Asp Leu Phe
            260                 265                 270

Arg Val Ser Lys Asp Leu Met Ile Arg Asn Ala Lys Phe Asn Val His
            275                 280                 285

Gly Arg Gln Arg Leu Ser Asp Glu Glu Arg Leu Ile Asn Arg Asn Phe
            290                 295                 300

Ile Lys Ile Lys Gly Glu Val Val Ser Leu Ser Tyr Gly Arg Phe Glu
305                 310                 315                 320

Glu Leu Lys Lys Asp Arg Lys Leu Trp Ser Pro His Ile Phe Lys Asp
                325                 330                 335

Val Arg Gln Asn Lys Ile Lys Pro Cys Leu Val Met Gln Gly Gln Arg
            340                 345                 350

Ile Asp Ile Phe Glu Gln Leu Lys Arg Lys Leu Glu Leu Leu Lys Lys
            355                 360                 365

Ile Arg Lys Ser Arg Gln Lys Lys Leu Ser Lys Asp Leu Ile Phe Gly
            370                 375                 380

Glu Arg Ile Ala Tyr Asn Phe His Thr Lys Ser Ile Lys Asn Thr Ser
385                 390                 395                 400

Asn Lys Ile Asn Ile Asp Ser Asp Ala Lys Arg Gly Arg Ala Ser Tyr
                405                 410                 415

Met Arg Lys Arg Ile Gly Asn Glu Thr Phe Lys Leu Lys Tyr Cys Asp
            420                 425                 430

Val Cys Phe Pro Lys Ala Asn Val Tyr Arg Arg Val Gln Asn Gly Cys
            435                 440                 445

Ser Cys Ser Glu Asn Pro Tyr Asn Tyr Ile Lys Lys Gly Asp Lys Asp
            450                 455                 460

Leu Leu Pro Lys Lys Asp Glu Gly Leu Ala Ile Lys Gly Ala Phe Arg
465                 470                 475                 480

Asp Glu Lys Leu Asn Lys Gln Ile Ile Lys Val Ala Phe Asn Ile Ala
                485                 490                 495

Lys Gly Tyr Glu Asp Phe Tyr Asp Asp Leu Lys Lys Arg Thr Glu Lys
            500                 505                 510

Asp Val Asp Leu Lys Phe Lys Ile Gly Thr Thr Val Leu Asp Gln Lys
            515                 520                 525

Pro Met Glu Ile Phe Asp Gly Ile Val Ile Thr Trp Leu
```

-continued

```
            530             535             540

<210> SEQ ID NO 184
<211> LENGTH: 542
<212> TYPE: PRT
<213> ORGANISM: Artificial sequence
<220> FEATURE:
<223> OTHER INFORMATION: Synthetic sequence

<400> SEQUENCE: 184

Leu Leu Thr Thr Val Val Glu Thr Asn Asn Leu Ala Lys Lys Ala Ile
1               5                   10                  15

Asn Val Ala Ala Asn Phe Asp Ala Asn Ile Asp Arg Gln Tyr Tyr Arg
            20                  25                  30

Cys Thr Pro Asn Leu Cys Arg Phe Ile Ala Gln Ser Pro Arg Glu Thr
        35                  40                  45

Lys Glu Lys Asp Ala Gly Cys Ser Ser Cys Thr Gln Ser Thr Tyr Asp
    50                  55                  60

Pro Lys Val Tyr Val Ile Lys Ile Gly Lys Leu Leu Ala Lys Tyr Glu
65                  70                  75                  80

Ile Leu Lys Ser Leu Lys Arg Phe Leu Phe Met Asn Arg Tyr Phe Lys
                85                  90                  95

Gln Lys Lys Thr Glu Arg Ala Gln Gln Lys Gln Lys Ile Gly Thr Glu
            100                 105                 110

Leu Asn Glu Met Ser Ile Phe Ala Lys Ala Thr Asn Ala Met Glu Val
        115                 120                 125

Ile Lys Arg Ala Thr Lys His Cys Thr Tyr Asp Ile Ile Pro Glu Thr
    130                 135                 140

Lys Ser Leu Gln Met Leu Lys Arg Arg His Arg Val Lys Val Arg
145                 150                 155                 160

Ser Leu Leu Lys Ile Leu Lys Glu Arg Arg Met Lys Ile Lys Lys Ile
                165                 170                 175

Pro Asn Thr Phe Ile Glu Ile Pro Lys Gln Ala Lys Lys Asn Lys Ser
            180                 185                 190

Asp Tyr Tyr Val Ala Ala Ala Leu Lys Ser Cys Gly Ile Asp Val Gly
        195                 200                 205

Leu Cys Gly Ala Tyr Glu Lys Asn Ala Glu Val Glu Ala Glu Tyr Thr
    210                 215                 220

Tyr Gln Leu Tyr Tyr Glu Tyr Lys Gly Asn Ser Ser Thr Lys Arg Ile
225                 230                 235                 240

Leu Tyr Cys Tyr Asn Asn Pro Gln Lys Asn Ile Arg Glu Phe Trp Glu
                245                 250                 255

Ala Phe Tyr Ile Gln Gly Ser Lys Ser His Val Asn Thr Pro Gly Thr
            260                 265                 270

Ile Arg Leu Lys Met Glu Lys Phe Leu Ser Pro Ile Thr Ile Glu Ser
        275                 280                 285

Glu Ala Leu Asp Phe Arg Val Trp Asn Ser Asp Leu Lys Ile Arg Asn
    290                 295                 300

Gly Gln Tyr Gly Phe Ile Lys Lys Arg Ser Leu Gly Lys Glu Ala Arg
305                 310                 315                 320

Glu Ile Lys Lys Gly Met Gly Asp Ile Lys Arg Ile Gly Asn Leu
                325                 330                 335

Thr Tyr Gly Lys Ser Pro Ser Glu Leu Lys Ser Ile His Val Tyr Arg
            340                 345                 350

Thr Glu Arg Glu Asn Pro Lys Lys Pro Arg Ala Ala Arg Lys Lys Glu
```

```
                355                 360                 365
Asp Asn Phe Met Glu Ile Phe Glu Met Gln Arg Lys Lys Asp Tyr Glu
    370                 375                 380

Val Asn Lys Lys Arg Arg Lys Glu Ala Thr Asp Ala Ala Lys Ile Met
385                 390                 395                 400

Asp Phe Ala Glu Glu Pro Ile Arg His Tyr His Thr Asn Asn Leu Lys
                405                 410                 415

Ala Val Arg Arg Ile Asp Met Asn Glu Gln Val Glu Arg Lys Lys Thr
            420                 425                 430

Ser Val Phe Leu Lys Arg Ile Met Gln Asn Gly Tyr Arg Gly Asn Tyr
        435                 440                 445

Cys Arg Lys Cys Ile Lys Ala Pro Glu Gly Ser Asn Arg Asp Glu Asn
    450                 455                 460

Val Leu Glu Lys Asn Glu Gly Cys Leu Asp Cys Ile Gly Ser Glu Phe
465                 470                 475                 480

Ile Trp Lys Lys Ser Lys Glu Lys Lys Gly Leu Trp His Thr Asn
                485                 490                 495

Arg Leu Leu Arg Arg Ile Arg Leu Gln Cys Phe Thr Thr Ala Lys Ala
            500                 505                 510

Tyr Glu Asn Phe Tyr Asn Asp Leu Phe Glu Lys Lys Glu Ser Ser Leu
        515                 520                 525

Asp Ile Ile Lys Leu Lys Val Ser Ile Thr Thr Lys Ser Met
    530                 535                 540

<210> SEQ ID NO 185
<211> LENGTH: 564
<212> TYPE: PRT
<213> ORGANISM: Artificial sequence
<220> FEATURE:
<223> OTHER INFORMATION: Synthetic sequence

<400> SEQUENCE: 185

Ala Ser Thr Met Asn Leu Ala Lys Gln Ala Ile Asn Phe Ala Ala Asn
1               5                   10                  15

Tyr Asp Ser Asn Leu Glu Ile Gly Cys Lys Gly Cys Lys Phe Met Ser
            20                  25                  30

Thr Trp Ser Lys Lys Ser Asn Pro Lys Phe Tyr Pro Arg Gln Asn Asn
        35                  40                  45

Gln Ala Asn Lys Cys His Ser Cys Thr Tyr Ser Thr Gly Glu Pro Glu
    50                  55                  60

Val Pro Ile Ile Glu Ile Gly Glu Arg Ala Ala Lys Tyr Lys Ile Phe
65              70                  75                  80

Thr Ala Leu Lys Lys Phe Val Phe Met Ser Val Ala Tyr Lys Glu Arg
            85                  90                  95

Arg Arg Gln Arg Phe Lys Ser Lys Lys Pro Lys Glu Leu Lys Glu Leu
        100                 105                 110

Ala Ile Cys Ser Asn Arg Glu Lys Ala Met Glu Val Ile Gln Lys Ser
    115                 120                 125

Val Val His Cys Tyr Gly Asp Val Lys Gln Glu Ile Pro Arg Ile Arg
130                 135                 140

Lys Ile Lys Val Leu Lys Asn His Lys Gly Arg Leu Phe Tyr Lys Gln
145                 150                 155                 160

Lys Arg Ser Lys Ile Lys Ile Ala Lys Leu Glu Lys Gly Ser Phe Phe
            165                 170                 175

Lys Thr Phe Ile Pro Lys Val His Asn Asn Gly Cys His Ser Cys His
```

```
                180                 185                 190
Glu Ala Ser Leu Asn Lys Pro Ile Leu Val Thr Thr Ala Leu Asn Thr
            195                 200                 205
Ile Gly Ala Asp Ile Gly Leu Ile Asn Asp Tyr Ser Thr Ile Ala Pro
        210                 215                 220
Thr Glu Thr Asp Ile Ser Trp Gln Val Tyr Tyr Glu Phe Ile Pro Asn
225                 230                 235                 240
Gly Asp Ser Glu Ala Val Lys Lys Arg Leu Leu Tyr Phe Tyr Lys Pro
                245                 250                 255
Lys Gly Ala Leu Ile Lys Ser Ile Arg Asp Lys Tyr Phe Lys Lys Gly
            260                 265                 270
His Glu Asn Ala Val Asn Thr Gly Phe Phe Lys Tyr Gln Gly Lys Ile
        275                 280                 285
Val Lys Gly Pro Ile Lys Phe Val Asn Asn Glu Leu Asp Phe Ala Arg
    290                 295                 300
Lys Pro Asp Leu Lys Ser Met Lys Ile Lys Arg Ala Gly Phe Ala Ile
305                 310                 315                 320
Pro Ser Ala Lys Arg Leu Ser Lys Glu Asp Arg Glu Ile Asn Arg Glu
                325                 330                 335
Ser Ile Lys Ile Lys Asn Lys Ile Tyr Ser Leu Ser Tyr Gly Arg Lys
            340                 345                 350
Lys Thr Leu Ser Asp Lys Asp Ile Ile Lys His Leu Tyr Arg Pro Val
        355                 360                 365
Arg Gln Lys Gly Val Lys Pro Leu Glu Tyr Arg Lys Ala Pro Asp Gly
    370                 375                 380
Phe Leu Glu Phe Phe Tyr Ser Leu Lys Arg Lys Glu Arg Arg Leu Arg
385                 390                 395                 400
Lys Gln Lys Glu Lys Arg Gln Lys Asp Met Ser Glu Ile Ile Asp Ala
                405                 410                 415
Ala Asp Glu Phe Ala Trp His Arg His Thr Gly Ser Ile Lys Lys Thr
            420                 425                 430
Thr Asn His Ile Asn Phe Lys Ser Glu Val Lys Arg Gly Lys Val Pro
        435                 440                 445
Ile Met Lys Lys Arg Ile Ala Asn Asp Ser Phe Asn Thr Arg His Cys
    450                 455                 460
Gly Lys Cys Val Lys Gln Gly Asn Ala Ile Asn Lys Tyr Tyr Ile Glu
465                 470                 475                 480
Lys Gln Lys Asn Cys Phe Asp Cys Asn Ser Ile Glu Phe Lys Trp Glu
                485                 490                 495
Lys Ala Ala Leu Glu Lys Lys Gly Ala Phe Lys Leu Asn Lys Arg Leu
            500                 505                 510
Gln Tyr Ile Val Lys Ala Cys Phe Asn Val Ala Lys Ala Tyr Glu Ser
        515                 520                 525
Phe Tyr Glu Asp Phe Arg Lys Gly Glu Glu Ser Leu Asp Leu Lys
    530                 535                 540
Phe Lys Ile Gly Thr Thr Thr Thr Leu Lys Gln Tyr Pro Gln Asn Lys
545                 550                 555                 560
Ala Arg Ala Met

<210> SEQ ID NO 186
<211> LENGTH: 610
<212> TYPE: PRT
<213> ORGANISM: Artificial sequence
<220> FEATURE:
```

-continued

<223> OTHER INFORMATION: Synthetic sequence

<400> SEQUENCE: 186

```
His Ser His Asn Leu Met Leu Thr Lys Leu Gly Lys Gln Ala Ile Asn
1               5                   10                  15

Phe Ala Ala Asn Tyr Asp Ala Asn Leu Glu Ile Gly Cys Lys Asn Cys
            20                  25                  30

Lys Phe Leu Ser Tyr Ser Pro Lys Gln Ala Asn Pro Lys Lys Tyr Pro
        35                  40                  45

Arg Gln Thr Asp Val His Glu Asp Gly Asn Ile Ala Cys His Ser Cys
    50                  55                  60

Met Gln Ser Thr Lys Glu Pro Pro Val Tyr Ile Val Pro Ile Gly Glu
65                  70                  75                  80

Arg Lys Ser Lys Tyr Glu Ile Leu Thr Ser Leu Asn Lys Phe Thr Phe
                85                  90                  95

Leu Ala Leu Lys Tyr Lys Glu Lys Lys Arg Gln Ala Phe Arg Ala Lys
            100                 105                 110

Lys Pro Lys Glu Leu Gln Glu Leu Ala Ile Ala Phe Asn Lys Glu Lys
        115                 120                 125

Ala Ile Lys Val Ile Asp Lys Ser Ile Gln His Leu Ile Leu Asn Ile
    130                 135                 140

Lys Pro Glu Ile Ala Arg Ile Gln Arg Gln Lys Arg Leu Lys Asn Arg
145                 150                 155                 160

Lys Gly Lys Leu Leu Tyr Leu His Lys Arg Tyr Ala Ile Lys Met Gly
                165                 170                 175

Leu Ile Lys Asn Gly Lys Tyr Phe Lys Val Gly Ser Pro Lys Lys Asp
            180                 185                 190

Gly Lys Lys Leu Leu Val Leu Cys Ala Leu Asn Thr Ile Gly Arg Asp
        195                 200                 205

Ile Gly Ile Ile Gly Asn Ile Glu Glu Asn Asn Arg Ser Glu Thr Glu
    210                 215                 220

Ile Thr Tyr Gln Leu Tyr Phe Asp Cys Leu Asp Ala Asn Pro Asn Glu
225                 230                 235                 240

Leu Arg Ile Lys Glu Ile Glu Tyr Asn Arg Leu Lys Ser Tyr Glu Arg
                245                 250                 255

Lys Ile Lys Arg Leu Val Tyr Ala Tyr Lys Pro Lys Gln Thr Lys Ile
            260                 265                 270

Leu Glu Ile Arg Ser Lys Phe Phe Ser Lys Gly His Glu Asn Lys Val
        275                 280                 285

Asn Thr Gly Ser Phe Asn Phe Glu Asn Pro Leu Asn Lys Ser Ile Ser
    290                 295                 300

Ile Lys Val Lys Asn Ser Ala Phe Asp Phe Lys Ile Gly Ala Pro Phe
305                 310                 315                 320

Ile Met Leu Arg Asn Gly Lys Phe His Ile Pro Thr Lys Lys Arg Leu
                325                 330                 335

Ser Lys Glu Glu Arg Glu Ile Asn Arg Thr Leu Ser Lys Ile Lys Gly
            340                 345                 350

Arg Val Phe Arg Leu Thr Tyr Gly Arg Asn Ile Ser Glu Gln Gly Ser
        355                 360                 365

Lys Ser Leu His Ile Tyr Arg Lys Glu Arg Gln His Pro Lys Leu Ser
    370                 375                 380

Leu Glu Ile Arg Lys Gln Pro Asp Ser Phe Ile Asp Glu Phe Glu Lys
385                 390                 395                 400
```

```
Leu Arg Leu Lys Gln Asn Phe Ile Ser Lys Leu Lys Lys Gln Arg Gln
                405                 410                 415

Lys Lys Leu Ala Asp Leu Leu Gln Phe Ala Asp Arg Ile Ala Tyr Asn
            420                 425                 430

Tyr His Thr Ser Ser Leu Glu Lys Thr Ser Asn Phe Ile Asn Tyr Lys
            435                 440                 445

Pro Glu Val Lys Arg Gly Arg Thr Ser Tyr Ile Lys Lys Arg Ile Gly
        450                 455                 460

Asn Glu Gly Phe Glu Lys Leu Tyr Cys Glu Thr Cys Ile Lys Ser Asn
465                 470                 475                 480

Asp Lys Glu Asn Ala Tyr Ala Val Glu Lys Glu Glu Leu Cys Phe Val
            485                 490                 495

Cys Lys Ala Lys Pro Phe Thr Trp Lys Lys Thr Asn Lys Asp Lys Leu
            500                 505                 510

Gly Ile Phe Lys Tyr Pro Ser Arg Ile Lys Asp Phe Ile Arg Ala Ala
            515                 520                 525

Phe Thr Val Ala Lys Ser Tyr Asn Asp Phe Tyr Glu Asn Leu Lys Lys
        530                 535                 540

Lys Asp Leu Lys Asn Glu Ile Phe Leu Lys Phe Lys Ile Gly Leu Ile
545                 550                 555                 560

Leu Ser His Glu Lys Lys Asn His Ile Ser Ile Ala Lys Ser Val Ala
                565                 570                 575

Glu Asp Glu Arg Ile Ser Gly Lys Ser Ile Lys Asn Ile Leu Asn Lys
            580                 585                 590

Ser Ile Lys Leu Glu Lys Asn Cys Tyr Ser Cys Phe Phe His Lys Glu
        595                 600                 605

Asp Met
    610

<210> SEQ ID NO 187
<211> LENGTH: 552
<212> TYPE: PRT
<213> ORGANISM: Artificial sequence
<220> FEATURE:
<223> OTHER INFORMATION: Synthetic sequence

<400> SEQUENCE: 187

Ser Leu Glu Arg Val Ile Asp Lys Arg Asn Leu Ala Lys Lys Ala Ile
1               5                   10                  15

Asn Ile Ala Ala Asn Phe Asp Ala Asn Ile Asn Lys Gly Phe Tyr Arg
            20                  25                  30

Cys Glu Thr Asn Gln Cys Met Phe Ile Ala Gln Lys Pro Arg Lys Thr
        35                  40                  45

Asn Asn Thr Gly Cys Ser Ser Cys Leu Gln Ser Thr Tyr Asp Pro Val
    50                  55                  60

Ile Tyr Val Val Lys Val Gly Glu Met Leu Ala Lys Tyr Glu Ile Leu
65                  70                  75                  80

Lys Ser Leu Lys Arg Phe Val Phe Met Asn Arg Ser Phe Lys Gln Lys
                85                  90                  95

Lys Thr Glu Lys Ala Lys Gln Lys Glu Arg Ile Gly Gly Glu Leu Asn
            100                 105                 110

Glu Met Ser Ile Phe Ala Asn Ala Ala Leu Ala Met Gly Val Ile Lys
        115                 120                 125

Arg Ala Ile Arg His Cys His Val Asp Ile Arg Pro Glu Ile Asn Arg
    130                 135                 140
```

```
Leu Ser Glu Leu Lys Lys Thr Lys His Arg Val Ala Ala Lys Ser Leu
145                 150                 155                 160

Val Lys Ile Val Lys Gln Arg Lys Thr Lys Trp Lys Gly Ile Pro Asn
                165                 170                 175

Ser Phe Ile Gln Ile Pro Gln Lys Ala Arg Asn Lys Asp Ala Asp Phe
            180                 185                 190

Tyr Val Ala Ser Ala Leu Lys Ser Gly Gly Ile Asp Ile Gly Leu Cys
        195                 200                 205

Gly Thr Tyr Asp Lys Lys Pro His Ala Asp Pro Arg Trp Thr Tyr Gln
    210                 215                 220

Leu Tyr Phe Asp Thr Glu Asp Glu Ser Glu Lys Arg Leu Leu Tyr Cys
225                 230                 235                 240

Tyr Asn Asp Pro Gln Ala Lys Ile Arg Asp Phe Trp Lys Thr Phe Tyr
            245                 250                 255

Glu Arg Gly Asn Pro Ser Met Val Asn Ser Pro Gly Thr Ile Glu Phe
            260                 265                 270

Arg Met Glu Gly Phe Phe Glu Lys Met Thr Pro Ile Ser Ile Glu Ser
            275                 280                 285

Lys Asp Phe Asp Phe Arg Val Trp Asn Lys Asp Leu Leu Ile Arg Arg
290                 295                 300

Gly Leu Tyr Glu Ile Lys Lys Arg Lys Asn Leu Asn Arg Lys Ala Arg
305                 310                 315                 320

Glu Ile Lys Lys Ala Met Gly Ser Val Lys Arg Val Leu Ala Asn Met
                325                 330                 335

Thr Tyr Gly Lys Ser Pro Thr Asp Lys Lys Ser Ile Pro Val Tyr Arg
            340                 345                 350

Val Glu Arg Glu Lys Pro Lys Lys Pro Arg Ala Val Arg Lys Glu Glu
            355                 360                 365

Asn Glu Leu Ala Asp Lys Leu Glu Asn Tyr Arg Arg Glu Asp Phe Leu
            370                 375                 380

Ile Arg Asn Arg Arg Lys Arg Glu Ala Thr Glu Ile Ala Lys Ile Ile
385                 390                 395                 400

Asp Ala Ala Glu Pro Pro Ile Arg His Tyr His Thr Asn His Leu Arg
            405                 410                 415

Ala Val Lys Arg Ile Asp Leu Ser Lys Pro Val Ala Arg Lys Asn Thr
            420                 425                 430

Ser Val Phe Leu Lys Arg Ile Met Gln Asn Gly Tyr Arg Gly Asn Tyr
            435                 440                 445

Cys Lys Lys Cys Ile Lys Gly Asn Ile Asp Pro Asn Lys Asp Glu Cys
            450                 455                 460

Arg Leu Glu Asp Ile Lys Lys Cys Ile Cys Glu Gly Thr Gln Asn
465                 470                 475                 480

Ile Trp Ala Lys Lys Glu Lys Leu Tyr Thr Gly Arg Ile Asn Val Leu
            485                 490                 495

Asn Lys Arg Ile Lys Gln Met Lys Leu Glu Cys Phe Asn Val Ala Lys
            500                 505                 510

Ala Tyr Glu Asn Phe Tyr Asp Asn Leu Ala Ala Leu Lys Glu Gly Asp
            515                 520                 525

Leu Lys Val Leu Lys Leu Val Ser Ile Pro Ala Leu Asn Pro Glu
            530                 535                 540

Ala Ser Asp Pro Glu Glu Asp Met
545                 550
```

-continued

```
<210> SEQ ID NO 188
<211> LENGTH: 534
<212> TYPE: PRT
<213> ORGANISM: Artificial sequence
<220> FEATURE:
<223> OTHER INFORMATION: Synthetic sequence

<400> SEQUENCE: 188

Asn Ala Ser Ile Asn Leu Gly Lys Arg Ala Ile Asn Leu Ser Ala Asn
1               5                   10                  15

Tyr Asp Ser Asn Leu Val Ile Gly Cys Lys Asn Cys Lys Phe Leu Ser
                20                  25                  30

Phe Asn Gly Asn Phe Pro Arg Gln Thr Asn Val Arg Glu Gly Cys His
            35                  40                  45

Ser Cys Asp Lys Ser Thr Tyr Ala Pro Glu Val Tyr Ile Val Lys Ile
        50                  55                  60

Gly Glu Arg Lys Ala Lys Tyr Asp Val Leu Asp Ser Leu Lys Lys Phe
65                  70                  75                  80

Thr Phe Gln Ser Leu Lys Tyr Gln Ile Lys Lys Ser Met Arg Glu Arg
                85                  90                  95

Ser Lys Lys Pro Lys Glu Leu Leu Glu Phe Val Ile Phe Ala Asn Lys
            100                 105                 110

Asp Lys Ala Phe Asn Val Ile Gln Lys Ser Tyr Glu His Leu Ile Leu
        115                 120                 125

Asn Ile Lys Gln Glu Ile Asn Arg Met Asn Gly Lys Lys Arg Ile Lys
    130                 135                 140

Asn His Lys Lys Arg Leu Phe Lys Asp Arg Glu Lys Gln Leu Asn Lys
145                 150                 155                 160

Leu Arg Leu Ile Gly Ser Ser Leu Phe Phe Pro Arg Glu Asn Lys
                165                 170                 175

Gly Asp Lys Asp Leu Phe Thr Tyr Val Ala Ile His Ser Val Gly Arg
            180                 185                 190

Asp Ile Gly Val Ala Gly Ser Tyr Glu Ser His Ile Glu Pro Ile Ser
        195                 200                 205

Asp Leu Thr Tyr Gln Leu Phe Ile Asn Asn Glu Lys Arg Leu Leu Tyr
    210                 215                 220

Ala Tyr Lys Pro Lys Gln Asn Lys Ile Ile Glu Leu Lys Glu Asn Leu
225                 230                 235                 240

Trp Asn Leu Lys Lys Glu Lys Lys Pro Leu Asp Leu Glu Phe Thr Lys
                245                 250                 255

Pro Leu Glu Lys Ser Ile Thr Phe Ser Val Lys Asn Asp Lys Leu Phe
            260                 265                 270

Lys Val Ser Lys Asp Leu Met Leu Arg Gln Ala Lys Phe Asn Ile Gln
        275                 280                 285

Gly Lys Glu Lys Leu Ser Lys Glu Glu Arg Gln Ile Asn Arg Asp Phe
    290                 295                 300

Ser Lys Ile Lys Ser Asn Val Ile Ser Leu Ser Tyr Gly Arg Phe Glu
305                 310                 315                 320

Glu Leu Lys Lys Glu Lys Asn Ile Trp Ser Pro His Ile Tyr Arg Glu
                325                 330                 335

Val Lys Gln Lys Glu Ile Lys Pro Cys Ile Val Arg Lys Gly Asp Arg
            340                 345                 350

Ile Glu Leu Phe Glu Gln Leu Lys Arg Lys Met Asp Lys Leu Lys Lys
        355                 360                 365

Phe Arg Lys Glu Arg Gln Lys Lys Ile Ser Lys Asp Leu Asn Phe Ala
```

```
                370                 375                 380
Glu Arg Ile Ala Tyr Asn Phe His Thr Lys Ser Ile Lys Asn Thr Ser
385                 390                 395                 400

Asn Lys Ile Asn Ile Asp Gln Glu Ala Lys Arg Gly Lys Ala Ser Tyr
                405                 410                 415

Met Arg Lys Arg Ile Gly Asn Glu Ser Phe Arg Lys Tyr Cys Glu
                420                 425                 430

Gln Cys Phe Ser Val Gly Asn Val Tyr His Asn Val Gln Asn Gly Cys
                435                 440                 445

Ser Cys Phe Asp Asn Pro Ile Glu Leu Ile Lys Lys Gly Asp Glu Gly
                450                 455                 460

Leu Ile Pro Lys Gly Lys Glu Asp Arg Lys Tyr Lys Gly Ala Leu Arg
465                 470                 475                 480

Asp Asp Asn Leu Gln Met Gln Ile Ile Arg Val Ala Phe Asn Ile Ala
                485                 490                 495

Lys Gly Tyr Glu Asp Phe Tyr Asn Asn Leu Lys Glu Lys Thr Glu Lys
                500                 505                 510

Asp Leu Lys Leu Lys Phe Lys Ile Gly Thr Thr Ile Ser Thr Gln Glu
                515                 520                 525

Ser Asn Asn Lys Glu Met
                530
```

<210> SEQ ID NO 189
<211> LENGTH: 577
<212> TYPE: PRT
<213> ORGANISM: Artificial sequence
<220> FEATURE:
<223> OTHER INFORMATION: Synthetic sequence

<400> SEQUENCE: 189

```
Ser Asn Leu Ile Lys Leu Gly Lys Gln Ala Ile Asn Phe Ala Ala Asn
1               5                   10                  15

Tyr Asp Ala Asn Leu Glu Val Gly Cys Lys Asn Cys Lys Phe Leu Ser
                20                  25                  30

Ser Thr Asn Lys Tyr Pro Arg Gln Thr Asn Val His Leu Asp Asn Lys
                35                  40                  45

Met Ala Cys Arg Ser Cys Asn Gln Ser Thr Met Glu Pro Ala Ile Tyr
                50                  55                  60

Ile Val Arg Ile Gly Glu Lys Lys Ala Lys Tyr Asp Ile Tyr Asn Ser
65                  70                  75                  80

Leu Thr Lys Phe Asn Phe Gln Ser Leu Lys Tyr Lys Ala Lys Arg Ser
                85                  90                  95

Gln Arg Phe Lys Pro Lys Gln Pro Lys Glu Leu Gln Glu Leu Ser Ile
                100                 105                 110

Ala Val Arg Lys Glu Lys Ala Leu Asp Ile Ile Gln Lys Ser Ile Asp
                115                 120                 125

His Leu Ile Gln Asp Ile Arg Pro Glu Ile Pro Arg Ile Lys Gln Gln
                130                 135                 140

Lys Arg Tyr Lys Asn His Val Gly Lys Leu Phe Tyr Leu Gln Lys Arg
145                 150                 155                 160

Arg Lys Asn Lys Leu Asn Leu Ile Gly Lys Gly Ser Phe Phe Lys Val
                165                 170                 175

Phe Ser Pro Lys Glu Lys Lys Asn Glu Leu Leu Val Ile Cys Ala Leu
                180                 185                 190

Thr Asn Ile Gly Arg Asp Ile Gly Leu Ile Gly Asn Tyr Asn Thr Ile
```

```
                195                 200                 205
Ile Asn Pro Leu Phe Glu Val Thr Tyr Gln Leu Tyr Tyr Asp Tyr Ile
210                 215                 220

Pro Lys Lys Asn Asn Lys Asn Val Gln Arg Arg Leu Leu Tyr Ala Tyr
225                 230                 235                 240

Lys Ser Lys Asn Glu Lys Ile Leu Lys Leu Lys Glu Ala Phe Phe Lys
                245                 250                 255

Arg Gly His Glu Asn Ala Val Asn Leu Gly Ser Phe Ser Tyr Glu Lys
            260                 265                 270

Pro Leu Glu Lys Ser Leu Thr Leu Lys Ile Lys Asn Asp Lys Asp Asp
        275                 280                 285

Phe Gln Val Ser Pro Ser Leu Arg Ile Arg Thr Gly Arg Phe Phe Val
290                 295                 300

Pro Ser Lys Arg Asn Leu Ser Arg Gln Glu Arg Glu Ile Asn Arg Arg
305                 310                 315                 320

Leu Val Lys Ile Lys Ser Lys Ile Lys Asn Met Thr Tyr Gly Lys Phe
                325                 330                 335

Glu Thr Ala Arg Asp Lys Gln Ser Val His Ile Phe Arg Leu Glu Arg
            340                 345                 350

Gln Lys Glu Lys Leu Pro Leu Gln Phe Arg Lys Asp Glu Lys Glu Phe
        355                 360                 365

Met Glu Glu Phe Gln Lys Leu Lys Arg Arg Thr Asn Ser Leu Lys Lys
370                 375                 380

Leu Arg Lys Ser Arg Gln Lys Lys Leu Ala Asp Leu Leu Gln Leu Ser
385                 390                 395                 400

Glu Lys Val Val Tyr Asn Asn His Thr Gly Thr Leu Lys Lys Thr Ser
                405                 410                 415

Asn Phe Leu Asn Phe Ser Ser Ser Val Lys Arg Gly Lys Thr Ala Tyr
            420                 425                 430

Ile Lys Glu Leu Leu Gly Gln Glu Gly Phe Glu Thr Leu Tyr Cys Ser
        435                 440                 445

Asn Cys Ile Asn Lys Gly Gln Lys Thr Arg Tyr Asn Ile Glu Thr Lys
450                 455                 460

Glu Lys Cys Phe Ser Cys Lys Asp Val Pro Phe Val Trp Lys Lys Lys
465                 470                 475                 480

Ser Thr Asp Lys Asp Arg Lys Gly Ala Phe Leu Phe Pro Ala Lys Leu
                485                 490                 495

Lys Asp Val Ile Lys Ala Thr Phe Thr Val Ala Lys Ala Tyr Glu Asp
            500                 505                 510

Phe Tyr Asp Asn Leu Lys Ser Ile Asp Glu Lys Lys Pro Tyr Ile Lys
        515                 520                 525

Phe Lys Ile Gly Leu Ile Leu Ala His Val Arg His Glu His Lys Ala
530                 535                 540

Arg Ala Lys Glu Glu Ala Gly Gln Lys Asn Ile Tyr Asn Lys Pro Ile
545                 550                 555                 560

Lys Ile Asp Lys Asn Cys Lys Glu Cys Phe Phe Lys Glu Glu Ala
                565                 570                 575

Met

<210> SEQ ID NO 190
<211> LENGTH: 613
<212> TYPE: PRT
<213> ORGANISM: Artificial sequence
<220> FEATURE:
```

<223> OTHER INFORMATION: Synthetic sequence

<400> SEQUENCE: 190

```
Asn Thr Thr Arg Lys Lys Phe Arg Lys Arg Thr Gly Phe Pro Gln Ser
1               5                   10                  15

Asp Asn Ile Lys Leu Ala Tyr Cys Ser Ala Ile Val Arg Ala Ala Asn
            20                  25                  30

Leu Asp Ala Asp Ile Gln Lys Lys His Asn Gln Cys Asn Pro Asn Leu
        35                  40                  45

Cys Val Gly Ile Lys Ser Asn Glu Gln Ser Arg Lys Tyr Glu His Ser
    50                  55                  60

Asp Arg Gln Ala Leu Leu Cys Tyr Ala Cys Asn Gln Ser Thr Gly Ala
65                  70                  75                  80

Pro Lys Val Asp Tyr Ile Gln Ile Gly Glu Ile Gly Ala Lys Tyr Lys
                85                  90                  95

Ile Leu Gln Met Val Asn Ala Tyr Asp Phe Leu Ser Leu Ala Tyr Asn
                100                 105                 110

Leu Thr Lys Leu Arg Asn Gly Lys Ser Arg Gly His Gln Arg Met Ser
            115                 120                 125

Gln Leu Asp Glu Val Val Ile Val Ala Asp Tyr Glu Lys Ala Thr Glu
    130                 135                 140

Val Ile Lys Arg Ser Ile Asn His Leu Leu Asp Asp Ile Arg Gly Gln
145                 150                 155                 160

Leu Ser Lys Leu Lys Lys Arg Thr Gln Asn Glu His Ile Thr Glu His
                165                 170                 175

Lys Gln Ser Lys Ile Arg Arg Lys Leu Arg Lys Leu Ser Arg Leu Leu
                180                 185                 190

Lys Arg Arg Arg Trp Lys Trp Gly Thr Ile Pro Asn Pro Tyr Leu Lys
            195                 200                 205

Asn Trp Val Phe Thr Lys Lys Asp Pro Glu Leu Val Thr Val Ala Leu
        210                 215                 220

Leu His Lys Leu Gly Arg Asp Ile Gly Leu Val Asn Arg Ser Lys Arg
225                 230                 235                 240

Arg Ser Lys Gln Lys Leu Leu Pro Lys Val Gly Phe Gln Leu Tyr Tyr
                245                 250                 255

Lys Trp Glu Ser Pro Ser Leu Asn Asn Ile Lys Lys Ser Lys Ala Lys
                260                 265                 270

Lys Leu Pro Lys Arg Leu Leu Ile Pro Tyr Lys Asn Val Lys Leu Phe
            275                 280                 285

Asp Asn Lys Gln Lys Leu Glu Asn Ala Ile Lys Ser Leu Leu Glu Ser
        290                 295                 300

Tyr Gln Lys Thr Ile Lys Val Glu Phe Asp Gln Phe Gln Asn Arg
305                 310                 315                 320

Thr Glu Glu Ile Ile Ala Glu Glu Gln Gln Thr Leu Glu Arg Gly Leu
                325                 330                 335

Leu Lys Gln Leu Glu Lys Lys Asn Glu Phe Ala Ser Gln Lys Lys
                340                 345                 350

Ala Leu Lys Glu Glu Lys Lys Lys Ile Lys Glu Pro Arg Lys Ala Lys
            355                 360                 365

Leu Leu Met Glu Glu Ser Arg Ser Leu Gly Phe Leu Met Ala Asn Val
        370                 375                 380

Ser Tyr Ala Leu Phe Asn Thr Thr Ile Glu Asp Leu Tyr Lys Lys Ser
385                 390                 395                 400
```

```
Asn Val Val Ser Gly Cys Ile Pro Gln Glu Pro Val Val Phe Pro
                405                 410                 415

Ala Asp Ile Gln Asn Lys Gly Ser Leu Ala Lys Ile Leu Phe Ala Pro
            420                 425                 430

Lys Asp Gly Phe Arg Ile Lys Phe Ser Gly Gln His Leu Thr Ile Arg
            435                 440                 445

Thr Ala Lys Phe Lys Ile Arg Gly Lys Glu Ile Lys Ile Leu Thr Lys
        450                 455                 460

Thr Lys Arg Glu Ile Leu Lys Asn Ile Glu Lys Leu Arg Arg Val Trp
465                 470                 475                 480

Tyr Arg Glu Gln His Tyr Lys Leu Lys Leu Phe Gly Lys Glu Val Ser
                485                 490                 495

Ala Lys Pro Arg Phe Leu Asp Lys Arg Lys Thr Ser Ile Glu Arg Arg
            500                 505                 510

Asp Pro Asn Lys Leu Ala Asp Gln Thr Asp Asp Arg Gln Ala Glu Leu
        515                 520                 525

Arg Asn Lys Glu Tyr Glu Leu Arg His Lys Gln His Lys Met Ala Glu
    530                 535                 540

Arg Leu Asp Asn Ile Asp Thr Asn Ala Gln Asn Leu Gln Thr Leu Ser
545                 550                 555                 560

Phe Trp Val Gly Glu Ala Asp Lys Pro Pro Lys Leu Asp Glu Lys Asp
                565                 570                 575

Ala Arg Gly Phe Gly Val Arg Thr Cys Ile Ser Ala Trp Lys Trp Phe
            580                 585                 590

Met Glu Asp Leu Leu Lys Lys Gln Glu Glu Asp Pro Leu Leu Lys Leu
        595                 600                 605

Lys Leu Ser Ile Met
        610

<210> SEQ ID NO 191
<211> LENGTH: 615
<212> TYPE: PRT
<213> ORGANISM: Artificial sequence
<220> FEATURE:
<223> OTHER INFORMATION: Synthetic sequence

<400> SEQUENCE: 191

Pro Lys Lys Pro Lys Phe Gln Lys Arg Thr Gly Phe Pro Gln Pro Asp
1               5                   10                  15

Asn Leu Arg Lys Glu Tyr Cys Leu Ala Ile Val Arg Ala Ala Asn Leu
            20                  25                  30

Asp Ala Asp Phe Glu Lys Lys Cys Thr Lys Cys Glu Gly Ile Lys Thr
        35                  40                  45

Asn Lys Lys Gly Asn Ile Val Lys Gly Arg Thr Tyr Asn Ser Ala Asp
    50                  55                  60

Lys Asp Asn Leu Leu Cys Tyr Ala Cys Asn Ile Ser Thr Gly Ala Pro
65                  70                  75                  80

Ala Val Asp Tyr Val Phe Val Gly Ala Leu Glu Ala Lys Tyr Lys Ile
                85                  90                  95

Leu Gln Met Val Lys Ala Tyr Asp Phe His Ser Leu Ala Tyr Asn Leu
            100                 105                 110

Ala Lys Leu Trp Lys Gly Arg Gly Arg Gly His Gln Arg Met Gly Gly
        115                 120                 125

Leu Asn Glu Val Val Ile Val Ser Asn Glu Lys Ala Leu Asp Val
    130                 135                 140
```

```
Ile Glu Lys Ser Leu Asn His Phe His Asp Glu Ile Arg Gly Glu Leu
145                 150                 155                 160

Ser Arg Leu Lys Ala Lys Phe Gln Asn Glu His Leu His Val His Lys
            165                 170                 175

Glu Ser Lys Leu Arg Arg Lys Leu Arg Lys Ile Ser Arg Leu Leu Lys
            180                 185                 190

Arg Arg Arg Trp Lys Trp Asp Val Ile Pro Asn Ser Tyr Leu Arg Asn
        195                 200                 205

Phe Thr Phe Thr Lys Thr Arg Pro Asp Phe Ile Ser Val Ala Leu Leu
    210                 215                 220

His Arg Val Gly Arg Asp Ile Gly Leu Val Thr Lys Thr Lys Ile Pro
225                 230                 235                 240

Lys Pro Thr Asp Leu Leu Pro Gln Phe Gly Phe Gln Ile Tyr Tyr Thr
            245                 250                 255

Trp Asp Glu Pro Lys Leu Asn Lys Leu Lys Lys Ser Arg Leu Arg Ser
            260                 265                 270

Glu Pro Lys Arg Leu Leu Val Pro Tyr Lys Lys Ile Glu Leu Tyr Lys
            275                 280                 285

Asn Lys Ser Val Leu Glu Glu Ala Ile Arg His Leu Ala Glu Val Tyr
            290                 295                 300

Thr Glu Asp Leu Thr Ile Cys Phe Lys Asp Phe Phe Glu Thr Gln Lys
305                 310                 315                 320

Arg Lys Phe Val Ser Lys Glu Lys Glu Ser Leu Lys Arg Glu Leu Leu
            325                 330                 335

Lys Glu Leu Thr Lys Leu Lys Lys Asp Phe Ser Glu Arg Lys Thr Ala
            340                 345                 350

Leu Lys Arg Asp Arg Lys Glu Ile Lys Glu Pro Lys Lys Ala Lys Leu
            355                 360                 365

Leu Met Glu Glu Ser Arg Ser Leu Gly Phe Leu Ala Ala Asn Thr Ser
            370                 375                 380

Tyr Ala Leu Phe Asn Leu Ile Ala Ala Asp Leu Tyr Thr Lys Ser Lys
385                 390                 395                 400

Lys Ala Cys Ser Thr Lys Leu Pro Arg Gln Leu Ser Thr Ile Leu Pro
            405                 410                 415

Leu Glu Ile Lys Glu His Lys Ser Thr Thr Ser Leu Ala Ile Lys Pro
            420                 425                 430

Glu Glu Gly Phe Lys Ile Arg Phe Ser Asn Thr His Leu Ser Ile Arg
            435                 440                 445

Thr Pro Lys Phe Lys Met Lys Gly Ala Asp Ile Lys Ala Leu Thr Lys
            450                 455                 460

Arg Lys Arg Glu Ile Leu Lys Asn Ala Thr Lys Leu Glu Lys Ser Trp
465                 470                 475                 480

Tyr Gly Leu Lys His Tyr Lys Leu Lys Leu Tyr Gly Lys Glu Val Ala
            485                 490                 495

Ala Lys Pro Arg Phe Leu Asp Lys Arg Asn Pro Ser Ile Asp Arg Arg
            500                 505                 510

Asp Pro Lys Glu Leu Met Glu Gln Ile Glu Asn Arg Arg Asn Glu Val
            515                 520                 525

Lys Asp Leu Glu Tyr Glu Ile Arg Lys Gly Gln His Gln Met Ala Lys
            530                 535                 540

Arg Leu Asp Asn Val Asp Thr Asn Ala Gln Asn Leu Gln Thr Lys Ser
545                 550                 555                 560

Phe Trp Val Gly Glu Ala Asp Lys Pro Pro Glu Leu Asp Ser Met Glu
```

565                 570                 575
Ala Lys Lys Leu Gly Leu Arg Thr Cys Ile Ser Ala Trp Lys Trp Phe
                580                 585                 590

Met Lys Asp Leu Val Leu Leu Gln Glu Lys Ser Pro Asn Leu Lys Leu
            595                 600                 605

Lys Leu Ser Leu Thr Glu Met
        610                 615

<210> SEQ ID NO 192
<211> LENGTH: 775
<212> TYPE: PRT
<213> ORGANISM: Artificial sequence
<220> FEATURE:
<223> OTHER INFORMATION: Synthetic sequence

<400> SEQUENCE: 192

Lys Phe Ser Lys Arg Gln Glu Gly Phe Leu Ile Pro Asp Asn Ile Asp
1               5                   10                  15

Leu Tyr Lys Cys Leu Ala Ile Val Arg Ser Ala Asn Leu Asp Ala Asp
            20                  25                  30

Val Gln Gly His Lys Ser Cys Tyr Gly Val Lys Lys Asn Gly Thr Tyr
        35                  40                  45

Arg Val Lys Gln Asn Gly Lys Lys Gly Val Lys Glu Lys Gly Arg Lys
    50                  55                  60

Tyr Val Phe Asp Leu Ile Ala Phe Lys Gly Asn Ile Glu Lys Ile Pro
65                  70                  75                  80

His Glu Ala Ile Glu Glu Lys Asp Gln Gly Arg Val Ile Val Leu Gly
                85                  90                  95

Lys Phe Asn Tyr Lys Leu Ile Leu Asn Ile Glu Lys Asn His Asn Asp
            100                 105                 110

Arg Ala Ser Leu Glu Ile Lys Asn Lys Ile Lys Lys Leu Val Gln Ile
        115                 120                 125

Ser Ser Leu Glu Thr Gly Glu Phe Leu Ser Asp Leu Leu Ser Gly Lys
    130                 135                 140

Ile Gly Ile Asp Glu Val Tyr Gly Ile Ile Glu Pro Asp Val Phe Ser
145                 150                 155                 160

Gly Lys Glu Leu Val Cys Lys Ala Cys Gln Gln Ser Thr Tyr Ala Pro
                165                 170                 175

Leu Val Glu Tyr Met Pro Val Gly Glu Leu Asp Ala Lys Tyr Lys Ile
            180                 185                 190

Leu Ser Ala Ile Lys Gly Tyr Asp Phe Leu Ser Leu Ala Tyr Asn Leu
        195                 200                 205

Ser Arg Asn Arg Ala Asn Lys Lys Arg Gly His Gln Lys Leu Gly Gly
    210                 215                 220

Gly Glu Leu Ser Glu Val Val Ile Ser Ala Asn Tyr Asp Lys Ala Leu
225                 230                 235                 240

Asn Val Ile Lys Arg Ser Ile Asn His Tyr His Val Glu Ile Lys Pro
                245                 250                 255

Glu Ile Ser Lys Leu Lys Lys Met Gln Asn Glu Pro Leu Lys Val
            260                 265                 270

Met Lys Gln Ala Arg Ile Arg Arg Glu Leu His Gln Leu Ser Arg Lys
        275                 280                 285

Val Lys Arg Leu Lys Trp Lys Trp Gly Met Ile Pro Asn Pro Glu Leu
    290                 295                 300

Gln Asn Ile Ile Phe Glu Lys Lys Glu Lys Asp Phe Val Ser Tyr Ala

```
            305                 310                 315                 320
        Leu Leu His Thr Leu Gly Arg Asp Ile Gly Leu Phe Lys Asp Thr Ser
                        325                 330                 335
        Met Leu Gln Val Pro Asn Ile Ser Asp Tyr Gly Phe Gln Ile Tyr Tyr
                        340                 345                 350
        Ser Trp Glu Asp Pro Lys Leu Asn Ser Ile Lys Lys Ile Lys Asp Leu
                        355                 360                 365
        Pro Lys Arg Leu Leu Ile Pro Tyr Lys Arg Leu Asp Phe Tyr Ile Asp
                        370                 375                 380
        Thr Ile Leu Val Ala Lys Val Ile Lys Asn Leu Ile Glu Leu Tyr Arg
        385                 390                 395                 400
        Lys Ser Tyr Val Tyr Glu Thr Phe Gly Glu Tyr Gly Tyr Ala Lys
                        405                 410                 415
        Lys Ala Glu Asp Ile Leu Phe Asp Trp Asp Ser Ile Asn Leu Ser Glu
                        420                 425                 430
        Gly Ile Glu Gln Lys Ile Gln Lys Ile Lys Asp Glu Phe Ser Asp Leu
                        435                 440                 445
        Leu Tyr Glu Ala Arg Glu Ser Lys Arg Gln Asn Phe Val Glu Ser Phe
                450                 455                 460
        Glu Asn Ile Leu Gly Leu Tyr Asp Lys Asn Phe Ala Ser Asp Arg Asn
        465                 470                 475                 480
        Ser Tyr Gln Glu Lys Ile Gln Ser Met Ile Ile Lys Lys Gln Gln Glu
                        485                 490                 495
        Asn Ile Glu Gln Lys Leu Lys Arg Glu Phe Lys Glu Val Ile Glu Arg
                        500                 505                 510
        Gly Phe Glu Gly Met Asp Gln Asn Lys Lys Tyr Tyr Lys Val Leu Ser
                        515                 520                 525
        Pro Asn Ile Lys Gly Gly Leu Leu Tyr Thr Asp Thr Asn Asn Leu Gly
                        530                 535                 540
        Phe Phe Arg Ser His Leu Ala Phe Met Leu Leu Ser Lys Ile Ser Asp
        545                 550                 555                 560
        Asp Leu Tyr Arg Lys Asn Asn Leu Val Ser Lys Gly Gly Asn Lys Gly
                        565                 570                 575
        Ile Leu Asp Gln Thr Pro Glu Thr Met Leu Thr Leu Glu Phe Gly Lys
                        580                 585                 590
        Ser Asn Leu Pro Asn Ile Ser Ile Lys Arg Lys Phe Asn Ile Lys
                        595                 600                 605
        Tyr Asn Ser Ser Trp Ile Gly Ile Arg Lys Pro Lys Phe Ser Ile Lys
                        610                 615                 620
        Gly Ala Val Ile Arg Glu Ile Thr Lys Lys Val Arg Asp Glu Gln Arg
        625                 630                 635                 640
        Leu Ile Lys Ser Leu Glu Gly Val Trp His Lys Ser Thr His Phe Lys
                        645                 650                 655
        Arg Trp Gly Lys Pro Arg Phe Asn Leu Pro Arg His Pro Asp Arg Glu
                        660                 665                 670
        Lys Asn Asn Asp Asp Asn Leu Met Glu Ser Ile Thr Ser Arg Arg Glu
                        675                 680                 685
        Gln Ile Gln Leu Leu Arg Glu Lys Gln Lys Gln Glu Lys Met
                        690                 695                 700
        Ala Gly Arg Leu Asp Lys Ile Asp Lys Glu Ile Gln Asn Leu Gln Thr
        705                 710                 715                 720
        Ala Asn Phe Gln Ile Lys Gln Ile Asp Lys Lys Pro Ala Leu Thr Glu
                        725                 730                 735
```

```
Lys Ser Glu Gly Lys Gln Ser Val Arg Asn Ala Leu Ser Ala Trp Lys
                740                 745                 750

Trp Phe Met Glu Asp Leu Ile Lys Tyr Gln Lys Arg Thr Pro Ile Leu
        755                 760                 765

Gln Leu Lys Leu Ala Lys Met
        770                 775

<210> SEQ ID NO 193
<211> LENGTH: 777
<212> TYPE: PRT
<213> ORGANISM: Artificial sequence
<220> FEATURE:
<223> OTHER INFORMATION: Synthetic sequence

<400> SEQUENCE: 193

Lys Phe Ser Lys Arg Gln Glu Gly Phe Val Ile Pro Glu Asn Ile Gly
1               5                   10                  15

Leu Tyr Lys Cys Leu Ala Ile Val Arg Ser Ala Asn Leu Asp Ala Asp
            20                  25                  30

Val Gln Gly His Val Ser Cys Tyr Gly Val Lys Lys Asn Gly Thr Tyr
        35                  40                  45

Val Leu Lys Gln Asn Gly Lys Lys Ser Ile Arg Glu Lys Gly Arg Lys
    50                  55                  60

Tyr Ala Ser Asp Leu Val Ala Phe Lys Gly Asp Ile Glu Lys Ile Pro
65                  70                  75                  80

Phe Glu Val Ile Glu Glu Lys Lys Lys Glu Gln Ser Ile Val Leu Gly
                85                  90                  95

Lys Phe Asn Tyr Lys Leu Val Leu Asp Val Met Lys Gly Glu Lys Asp
            100                 105                 110

Arg Ala Ser Leu Thr Met Lys Asn Lys Ser Lys Lys Leu Val Gln Val
        115                 120                 125

Ser Ser Leu Gly Thr Asp Glu Phe Leu Leu Thr Leu Leu Asn Glu Lys
    130                 135                 140

Phe Gly Ile Glu Glu Ile Tyr Gly Ile Ile Glu Pro Glu Val Phe Ser
145                 150                 155                 160

Gly Lys Lys Leu Val Cys Lys Ala Cys Gln Gln Ser Thr Tyr Ala Pro
                165                 170                 175

Leu Val Glu Tyr Met Pro Val Gly Glu Leu Asp Ser Lys Tyr Lys Ile
            180                 185                 190

Leu Ser Ala Ile Lys Gly Tyr Asp Phe Leu Ser Leu Ala Tyr Asn Leu
        195                 200                 205

Ala Arg His Arg Ser Asn Lys Lys Arg Gly His Gln Lys Leu Gly Gly
    210                 215                 220

Gly Glu Leu Ser Glu Val Val Ile Ser Ala Asn Ala Lys Ala Leu
225                 230                 235                 240

Asn Val Ile Lys Arg Ser Leu Asn His Tyr Tyr Ser Glu Ile Lys Pro
                245                 250                 255

Glu Ile Ser Lys Leu Arg Lys Lys Met Gln Asn Glu Pro Leu Lys Val
            260                 265                 270

Gly Lys Gln Ala Arg Met Arg Arg Glu Leu His Gln Leu Ser Arg Lys
        275                 280                 285

Val Lys Arg Leu Lys Trp Lys Trp Gly Lys Ile Pro Asn Leu Glu Leu
    290                 295                 300

Gln Asn Ile Thr Phe Lys Glu Ser Asp Arg Asp Phe Ile Ser Tyr Ala
305                 310                 315                 320
```

```
Leu Leu His Thr Leu Gly Arg Asp Ile Gly Met Phe Asn Lys Thr Glu
            325                 330                 335

Ile Lys Met Pro Ser Asn Ile Leu Gly Tyr Gly Phe Gln Ile Tyr Tyr
            340                 345                 350

Asp Trp Glu Glu Pro Lys Leu Asn Thr Ile Lys Lys Ser Lys Asn Thr
            355                 360                 365

Pro Lys Arg Ile Leu Ile Pro Tyr Lys Lys Leu Asp Phe Tyr Asn Asp
            370                 375                 380

Ser Ile Leu Val Ala Arg Ala Ile Lys Glu Leu Val Gly Leu Phe Gln
385                 390                 395                 400

Glu Ser Tyr Glu Trp Glu Ile Phe Gly Asn Tyr Asn Tyr Ala Lys
            405                 410                 415

Glu Ala Glu Val Glu Leu Ile Lys Leu Asp Glu Glu Ser Ile Asn Gly
            420                 425                 430

Asn Val Glu Lys Lys Leu Gln Arg Ile Lys Glu Asn Phe Ser Asn Leu
            435                 440                 445

Leu Glu Lys Ala Arg Glu Lys Lys Arg Gln Asn Phe Ile Glu Ser Phe
            450                 455                 460

Glu Ser Ile Ala Arg Leu Tyr Asp Glu Ser Phe Thr Ala Asp Arg Asn
465                 470                 475                 480

Glu Tyr Gln Arg Glu Ile Gln Ser Phe Ile Ile Glu Lys Gln Lys Gln
            485                 490                 495

Ser Ile Glu Lys Lys Leu Lys Asn Glu Phe Lys Lys Ile Val Glu Lys
            500                 505                 510

Lys Phe Asn Glu Gln Glu Gln Gly Lys Lys His Tyr Arg Val Leu Asn
            515                 520                 525

Pro Thr Ile Ile Asn Glu Phe Leu Pro Lys Asp Lys Asn Asn Leu Gly
            530                 535                 540

Phe Leu Arg Ser Lys Ile Ala Phe Ile Leu Leu Ser Lys Ile Ser Asp
545                 550                 555                 560

Asp Leu Tyr Lys Lys Ser Asn Ala Val Ser Lys Gly Gly Glu Lys Gly
            565                 570                 575

Ile Ile Lys Gln Gln Pro Glu Thr Ile Leu Asp Leu Glu Phe Ser Lys
            580                 585                 590

Ser Lys Leu Pro Ser Ile Asn Ile Lys Lys Leu Phe Asn Ile Lys
            595                 600                 605

Tyr Thr Ser Ser Trp Leu Gly Ile Arg Lys Pro Lys Phe Asn Ile Lys
            610                 615                 620

Gly Ala Lys Ile Arg Glu Ile Thr Arg Arg Val Arg Asp Val Gln Arg
625                 630                 635                 640

Thr Leu Lys Ser Ala Glu Ser Ser Trp Tyr Ala Ser Thr His Phe Arg
            645                 650                 655

Arg Trp Gly Phe Pro Arg Phe Asn Gln Pro Arg His Pro Asp Lys Glu
            660                 665                 670

Lys Lys Ser Asp Asp Arg Leu Ile Glu Ser Ile Thr Leu Leu Arg Glu
            675                 680                 685

Gln Ile Gln Ile Leu Leu Arg Glu Lys Gln Lys Gly Gln Lys Glu Met
            690                 695                 700

Ala Gly Arg Leu Asp Asp Val Asp Lys Lys Ile Gln Asn Leu Gln Thr
705                 710                 715                 720

Ala Asn Phe Gln Ile Lys Gln Thr Gly Asp Lys Pro Ala Leu Thr Glu
            725                 730                 735
```

```
Lys Ser Ala Gly Lys Gln Ser Phe Arg Asn Ala Leu Ser Ala Trp Lys
            740                 745                 750

Trp Phe Met Glu Asn Leu Leu Lys Tyr Gln Asn Lys Thr Pro Asp Leu
            755                 760                 765

Lys Leu Lys Ile Ala Arg Thr Val Met
            770                 775

<210> SEQ ID NO 194
<211> LENGTH: 610
<212> TYPE: PRT
<213> ORGANISM: Artificial sequence
<220> FEATURE:
<223> OTHER INFORMATION: Synthetic sequence

<400> SEQUENCE: 194

Lys Trp Ile Glu Pro Asn Asn Ile Asp Phe Asn Lys Cys Leu Ala Ile
  1               5                  10                  15

Thr Arg Ser Ala Asn Leu Asp Ala Asp Val Gln Gly His Lys Met Cys
             20                  25                  30

Tyr Gly Ile Lys Thr Asn Gly Thr Tyr Lys Ala Ile Gly Lys Ile Asn
             35                  40                  45

Lys Lys His Asn Thr Gly Ile Ile Glu Lys Arg Arg Thr Tyr Val Tyr
 50                  55                  60

Asp Leu Ile Val Thr Lys Glu Lys Asn Glu Lys Ile Val Lys Lys Thr
 65                  70                  75                  80

Asp Phe Met Ala Ile Asp Glu Glu Ile Glu Phe Asp Glu Lys Lys Glu
                 85                  90                  95

Lys Leu Leu Lys Lys Tyr Ile Lys Ala Glu Val Leu Gly Thr Gly Glu
            100                 105                 110

Leu Ile Arg Lys Asp Leu Asn Asp Gly Glu Lys Phe Asp Asp Leu Cys
            115                 120                 125

Ser Ile Glu Glu Pro Gln Ala Phe Arg Arg Ser Glu Leu Val Cys Lys
130                 135                 140

Ala Cys Asn Gln Ser Thr Tyr Ala Ser Asp Ile Arg Tyr Ile Pro Ile
145                 150                 155                 160

Gly Glu Ile Glu Ala Lys Tyr Lys Ile Leu Lys Ala Ile Lys Gly Tyr
                165                 170                 175

Asp Phe Leu Ser Leu Lys Tyr Asn Leu Gly Arg Leu Arg Asp Ser Lys
            180                 185                 190

Lys Arg Gly His Gln Lys Met Gly Gln Gly Glu Leu Lys Glu Phe Val
            195                 200                 205

Ile Cys Ala Asn Lys Glu Lys Ala Leu Asp Val Ile Lys Arg Ser Leu
210                 215                 220

Asn His Tyr Leu Asn Glu Val Lys Asp Glu Ile Ser Arg Leu Asn Lys
225                 230                 235                 240

Lys Met Gln Asn Glu Pro Leu Lys Val Asn Asp Gln Ala Arg Trp Arg
                245                 250                 255

Arg Glu Leu Asn Gln Ile Ser Arg Arg Leu Lys Arg Leu Lys Trp Lys
            260                 265                 270

Trp Gly Glu Ile Pro Asn Pro Glu Leu Lys Asn Leu Ile Phe Lys Ser
            275                 280                 285

Ser Arg Pro Glu Phe Val Ser Tyr Ala Leu Ile His Thr Leu Gly Arg
            290                 295                 300

Asp Ile Gly Leu Ile Asn Glu Thr Glu Leu Lys Pro Asn Asn Ile Gln
305                 310                 315                 320
```

Glu Tyr Gly Phe Gln Ile Tyr Tyr Lys Trp Glu Asp Pro Glu Leu Asn
                325                 330                 335

His Ile Lys Lys Val Lys Asn Ile Pro Lys Arg Phe Ile Ile Pro Tyr
            340                 345                 350

Lys Asn Leu Asp Leu Phe Gly Lys Tyr Thr Ile Leu Ser Arg Ala Ile
        355                 360                 365

Glu Gly Ile Leu Lys Leu Tyr Ser Ser Ser Phe Gln Tyr Lys Ser Phe
    370                 375                 380

Lys Asp Pro Asn Leu Phe Ala Lys Glu Gly Lys Lys Ile Thr Asn
385                 390                 395                 400

Glu Asp Phe Glu Leu Gly Tyr Asp Glu Lys Ile Lys Lys Ile Lys Asp
                405                 410                 415

Asp Phe Lys Ser Tyr Lys Lys Ala Leu Leu Glu Lys Lys Asn Thr
            420                 425                 430

Leu Glu Asp Ser Leu Asn Ser Ile Leu Ser Val Tyr Glu Gln Ser Leu
        435                 440                 445

Leu Thr Glu Gln Ile Asn Val Lys Lys Trp Lys Glu Gly Leu Leu
    450                 455                 460

Lys Ser Lys Glu Ser Ile His Lys Gln Lys Lys Ile Glu Asn Ile Glu
465                 470                 475                 480

Asp Ile Ile Ser Arg Ile Glu Glu Leu Lys Asn Val Glu Gly Trp Ile
                485                 490                 495

Arg Thr Lys Glu Arg Asp Ile Val Asn Lys Glu Thr Asn Leu Lys
            500                 505                 510

Arg Glu Ile Lys Lys Glu Leu Lys Asp Ser Tyr Tyr Glu Glu Val Arg
        515                 520                 525

Lys Asp Phe Ser Asp Leu Lys Lys Gly Glu Glu Ser Glu Lys Lys Pro
    530                 535                 540

Phe Arg Glu Glu Pro Lys Pro Ile Val Ile Lys Asp Tyr Ile Lys Phe
545                 550                 555                 560

Asp Val Leu Pro Gly Glu Asn Ser Ala Leu Gly Phe Phe Leu Ser His
                565                 570                 575

Leu Ser Phe Asn Leu Phe Asp Ser Ile Gln Tyr Glu Leu Phe Glu Lys
            580                 585                 590

Ser Arg Leu Ser Ser Ser Lys His Pro Gln Ile Pro Glu Thr Ile Leu
        595                 600                 605

Asp Leu
    610

<210> SEQ ID NO 195
<211> LENGTH: 632
<212> TYPE: PRT
<213> ORGANISM: Artificial sequence
<220> FEATURE:
<223> OTHER INFORMATION: Synthetic sequence

<400> SEQUENCE: 195

Phe Arg Lys Phe Val Lys Arg Ser Gly Ala Pro Gln Pro Asp Asn Leu
1               5                   10                  15

Asn Lys Tyr Lys Cys Ile Ala Ile Val Arg Ala Ala Asn Leu Asp Ala
            20                  25                  30

Asp Ile Met Ser Asn Glu Ser Ser Asn Cys Val Met Cys Lys Gly Ile
        35                  40                  45

Lys Met Asn Lys Arg Lys Thr Ala Lys Gly Ala Ala Lys Thr Thr Glu
    50                  55                  60

-continued

```
Leu Gly Arg Val Tyr Ala Gly Gln Ser Gly Asn Leu Leu Cys Thr Ala
 65                  70                  75                  80

Cys Thr Lys Ser Thr Met Gly Pro Leu Val Asp Tyr Val Pro Ile Gly
                 85                  90                  95

Arg Ile Arg Ala Lys Tyr Thr Ile Leu Arg Ala Val Lys Glu Tyr Asp
            100                 105                 110

Phe Leu Ser Leu Ala Tyr Asn Leu Ala Arg Thr Arg Val Ser Lys Lys
        115                 120                 125

Gly Gly Arg Gln Lys Met His Ser Leu Ser Glu Leu Val Ile Ala Ala
130                 135                 140

Glu Tyr Glu Ile Ala Trp Asn Ile Ile Lys Ser Ser Val Ile His Tyr
145                 150                 155                 160

His Gln Glu Thr Lys Glu Ile Ser Gly Leu Arg Lys Lys Leu Gln
                165                 170                 175

Ala Glu His Ile His Lys Asn Lys Glu Ala Arg Ile Arg Arg Glu Met
            180                 185                 190

His Gln Ile Ser Arg Arg Ile Lys Arg Leu Lys Trp Lys Trp His Met
        195                 200                 205

Ile Pro Asn Ser Glu Leu His Asn Phe Leu Phe Lys Gln Gln Asp Pro
210                 215                 220

Ser Phe Val Ala Val Ala Leu Leu His Thr Leu Gly Arg Asp Ile Gly
225                 230                 235                 240

Met Ile Asn Lys Pro Lys Gly Ser Ala Lys Arg Glu Phe Ile Pro Glu
                245                 250                 255

Tyr Gly Phe Gln Ile Tyr Tyr Lys Trp Met Asn Pro Lys Leu Asn Asp
            260                 265                 270

Ile Asn Lys Gln Lys Tyr Arg Lys Met Pro Lys Arg Ser Leu Ile Pro
        275                 280                 285

Tyr Lys Asn Leu Asn Val Phe Gly Asp Arg Glu Leu Ile Glu Asn Ala
290                 295                 300

Met His Lys Leu Leu Lys Leu Tyr Asp Glu Asn Leu Glu Val Lys Gly
305                 310                 315                 320

Ser Lys Phe Phe Lys Thr Arg Val Val Ala Ile Ser Ser Lys Glu Ser
                325                 330                 335

Glu Lys Leu Lys Arg Asp Leu Leu Trp Lys Gly Glu Leu Ala Lys Ile
            340                 345                 350

Lys Lys Asp Phe Asn Ala Asp Lys Asn Lys Met Gln Glu Leu Phe Lys
        355                 360                 365

Glu Val Lys Glu Pro Lys Lys Ala Asn Ala Leu Met Lys Gln Ser Arg
370                 375                 380

Asn Met Gly Phe Leu Leu Gln Asn Ile Ser Tyr Gly Ala Leu Gly Leu
385                 390                 395                 400

Leu Ala Asn Arg Met Tyr Glu Ala Ser Ala Lys Gln Ser Lys Gly Asp
                405                 410                 415

Ala Thr Lys Gln Pro Ser Ile Val Ile Pro Leu Glu Met Glu Phe Gly
            420                 425                 430

Asn Ala Phe Pro Lys Leu Leu Leu Arg Ser Gly Lys Phe Ala Met Asn
        435                 440                 445

Val Ser Ser Pro Trp Leu Thr Ile Arg Lys Pro Lys Phe Val Ile Lys
450                 455                 460

Gly Asn Lys Ile Lys Asn Ile Thr Lys Leu Met Lys Asp Glu Lys Ala
465                 470                 475                 480

Lys Leu Lys Arg Leu Glu Thr Ser Tyr His Arg Ala Thr His Phe Arg
```

```
                485                 490                 495
Pro Thr Leu Arg Gly Ser Ile Asp Trp Asp Ser Pro Tyr Phe Ser Ser
            500                 505                 510

Pro Lys Gln Pro Asn Thr His Arg Arg Ser Pro Asp Arg Leu Ser Ala
            515                 520                 525

Asp Ile Thr Glu Tyr Arg Gly Arg Leu Lys Ser Val Glu Ala Glu Leu
        530                 535                 540

Arg Glu Gly Gln Arg Ala Met Ala Lys Lys Leu Asp Ser Val Asp Met
545                 550                 555                 560

Thr Ala Ser Asn Leu Gln Thr Ser Asn Phe Gln Leu Glu Lys Gly Glu
                565                 570                 575

Asp Pro Arg Leu Thr Glu Ile Asp Glu Lys Gly Arg Ser Ile Arg Asn
            580                 585                 590

Cys Ile Ser Ser Trp Lys Lys Phe Met Glu Asp Leu Met Lys Ala Gln
                595                 600                 605

Glu Ala Asn Pro Val Ile Lys Ile Lys Ile Ala Leu Lys Asp Glu Ser
            610                 615                 620

Ser Val Leu Ser Glu Asp Ser Met
625                 630

<210> SEQ ID NO 196
<211> LENGTH: 625
<212> TYPE: PRT
<213> ORGANISM: Artificial sequence
<220> FEATURE:
<223> OTHER INFORMATION: Synthetic sequence

<400> SEQUENCE: 196

Lys Phe His Pro Glu Asn Leu Asn Lys Ser Tyr Cys Leu Ala Ile Val
1               5                   10                  15

Arg Ala Ala Asn Leu Asp Ala Asp Ile Gln Gly His Ile Asn Cys Ile
            20                  25                  30

Gly Ile Lys Ser Asn Lys Ser Asp Arg Asn Tyr Glu Asn Lys Leu Glu
        35                  40                  45

Ser Leu Gln Asn Val Glu Leu Leu Cys Lys Ala Cys Thr Lys Ser Thr
50                  55                  60

Tyr Lys Pro Asn Ile Asn Ser Val Pro Val Gly Glu Lys Lys Ala Lys
65                  70                  75                  80

Tyr Ser Ile Leu Ser Glu Ile Lys Lys Tyr Asp Phe Asn Ser Leu Val
                85                  90                  95

Tyr Asn Leu Lys Lys Tyr Arg Lys Gly Lys Ser Arg Gly His Gln Lys
            100                 105                 110

Leu Asn Glu Leu Arg Glu Leu Val Ile Thr Ser Glu Tyr Lys Lys Ala
        115                 120                 125

Leu Asp Val Ile Asn Lys Ser Val Asn His Tyr Leu Val Asn Ile Lys
130                 135                 140

Asn Lys Met Ser Lys Leu Lys Lys Ile Leu Gln Asn Glu His Ile His
145                 150                 155                 160

Val Gly Thr Leu Ala Arg Ile Arg Arg Glu Arg Asn Arg Ile Ser Arg
                165                 170                 175

Lys Leu Asp His Tyr Arg Lys Lys Trp Lys Phe Val Pro Asn Lys Ile
            180                 185                 190

Leu Lys Asn Tyr Val Phe Lys Asn Gln Ser Pro Asp Phe Val Ser Val
        195                 200                 205

Ala Leu Leu His Lys Leu Gly Arg Asp Ile Gly Leu Ile Thr Lys Thr
```

```
              210                 215                 220
Ala Ile Leu Gln Lys Ser Phe Pro Glu Tyr Ser Leu Gln Leu Tyr Tyr
225                 230                 235                 240

Lys Tyr Asp Thr Pro Lys Leu Asn Tyr Leu Lys Lys Ser Lys Phe Lys
                245                 250                 255

Ser Leu Pro Lys Arg Ile Leu Ile Ser Tyr Lys Tyr Pro Lys Phe Asp
                260                 265                 270

Ile Asn Ser Asn Tyr Ile Glu Glu Ser Ile Asp Lys Leu Leu Lys Leu
            275                 280                 285

Tyr Glu Glu Ser Pro Ile Tyr Lys Asn Asn Ser Lys Ile Ile Glu Phe
        290                 295                 300

Phe Lys Lys Ser Glu Asp Asn Leu Ile Lys Ser Glu Asn Asp Ser Leu
305                 310                 315                 320

Lys Arg Gly Ile Met Lys Glu Phe Glu Lys Val Thr Lys Asn Phe Ser
                325                 330                 335

Ser Lys Lys Lys Lys Leu Lys Glu Glu Leu Lys Leu Lys Asn Glu Asp
                340                 345                 350

Lys Asn Ser Lys Met Leu Ala Lys Val Ser Arg Pro Ile Gly Phe Leu
            355                 360                 365

Lys Ala Tyr Leu Ser Tyr Met Leu Phe Asn Ile Ile Ser Asn Arg Ile
        370                 375                 380

Phe Glu Phe Ser Arg Lys Ser Ser Gly Arg Ile Pro Gln Leu Pro Ser
385                 390                 395                 400

Cys Ile Ile Asn Leu Gly Asn Gln Phe Glu Asn Phe Lys Asn Glu Leu
                405                 410                 415

Gln Asp Ser Asn Ile Gly Ser Lys Lys Asn Tyr Lys Tyr Phe Cys Asn
                420                 425                 430

Leu Leu Leu Lys Ser Ser Gly Phe Asn Ile Ser Tyr Glu Glu Glu His
            435                 440                 445

Leu Ser Ile Lys Thr Pro Asn Phe Phe Ile Asn Gly Arg Lys Leu Lys
        450                 455                 460

Glu Ile Thr Ser Glu Lys Lys Ile Arg Lys Glu Asn Glu Gln Leu
465                 470                 475                 480

Ile Lys Gln Trp Lys Lys Leu Thr Phe Phe Lys Pro Ser Asn Leu Asn
                485                 490                 495

Gly Lys Lys Thr Ser Asp Lys Ile Arg Phe Lys Ser Pro Asn Asn Pro
                500                 505                 510

Asp Ile Glu Arg Lys Ser Glu Asp Asn Ile Val Glu Asn Ile Ala Lys
            515                 520                 525

Val Lys Tyr Lys Leu Glu Asp Leu Leu Ser Glu Gln Arg Lys Glu Phe
        530                 535                 540

Asn Lys Leu Ala Lys Lys His Asp Gly Val Asp Val Glu Ala Gln Cys
545                 550                 555                 560

Leu Gln Thr Lys Ser Phe Trp Ile Asp Ser Asn Ser Pro Ile Lys Lys
                565                 570                 575

Ser Leu Glu Lys Lys Asn Glu Lys Val Ser Val Lys Lys Met Lys
                580                 585                 590

Ala Ile Arg Ser Cys Ile Ser Ala Trp Lys Trp Phe Met Ala Asp Leu
            595                 600                 605

Ile Glu Ala Gln Lys Glu Thr Pro Met Ile Lys Leu Lys Leu Ala Leu
        610                 615                 620

Met
625
```

<210> SEQ ID NO 197
<211> LENGTH: 517
<212> TYPE: PRT
<213> ORGANISM: Artificial sequence
<220> FEATURE:
<223> OTHER INFORMATION: Synthetic sequence

<400> SEQUENCE: 197

```
Thr Thr Leu Val Pro Ser His Leu Ala Gly Ile Glu Val Met Asp Glu
1               5                   10                  15

Thr Thr Ser Arg Asn Glu Asp Met Ile Gln Lys Glu Thr Ser Arg Ser
            20                  25                  30

Asn Glu Asp Glu Asn Tyr Leu Gly Val Lys Asn Lys Cys Gly Ile Asn
        35                  40                  45

Val His Lys Ser Gly Arg Gly Ser Ser Lys His Glu Pro Asn Met Pro
    50                  55                  60

Pro Glu Lys Ser Gly Glu Gly Gln Met Pro Lys Gln Asp Ser Thr Glu
65                  70                  75                  80

Met Gln Gln Arg Phe Asp Glu Ser Val Thr Gly Glu Thr Gln Val Ser
                85                  90                  95

Ala Gly Ala Thr Ala Ser Ile Lys Thr Asp Ala Arg Ala Asn Ser Gly
            100                 105                 110

Pro Arg Val Gly Thr Ala Arg Ala Leu Ile Val Lys Ala Ser Asn Leu
        115                 120                 125

Asp Arg Asp Ile Lys Leu Gly Cys Lys Pro Cys Glu Tyr Ile Arg Ser
    130                 135                 140

Glu Leu Pro Met Gly Lys Lys Asn Gly Cys Asn His Cys Glu Lys Ser
145                 150                 155                 160

Ser Asp Ile Ala Ser Val Pro Lys Val Glu Ser Gly Phe Arg Lys Ala
                165                 170                 175

Lys Tyr Glu Leu Val Arg Arg Phe Glu Ser Phe Ala Ala Asp Ser Ile
            180                 185                 190

Ser Arg His Leu Gly Lys Glu Gln Ala Arg Thr Arg Gly Lys Arg Gly
        195                 200                 205

Lys Lys Asp Lys Lys Glu Gln Met Gly Lys Val Asn Leu Asp Glu Ile
    210                 215                 220

Ala Ile Leu Lys Asn Glu Ser Leu Ile Glu Tyr Thr Glu Asn Gln Ile
225                 230                 235                 240

Leu Asp Ala Arg Ser Asn Arg Ile Lys Glu Trp Leu Arg Ser Leu Arg
                245                 250                 255

Leu Arg Leu Arg Thr Arg Asn Lys Gly Leu Lys Lys Ser Lys Ser Ile
            260                 265                 270

Arg Arg Gln Leu Ile Thr Leu Arg Arg Asp Tyr Arg Lys Trp Ile Lys
        275                 280                 285

Pro Asn Pro Tyr Arg Pro Asp Glu Asp Pro Asn Glu Asn Ser Leu Arg
    290                 295                 300

Leu His Thr Lys Leu Gly Val Asp Ile Gly Val Gln Gly Gly Asp Asn
305                 310                 315                 320

Lys Arg Met Asn Ser Asp Asp Tyr Glu Thr Ser Phe Ser Ile Thr Trp
                325                 330                 335

Arg Asp Thr Ala Thr Lys Ile Cys Phe Thr Lys Pro Lys Gly Leu
            340                 345                 350

Leu Pro Arg His Met Lys Phe Lys Leu Arg Gly Tyr Pro Glu Leu Ile
        355                 360                 365
```

Leu Tyr Asn Glu Glu Leu Arg Ile Gln Asp Ser Gln Lys Phe Pro Leu
                370                 375                 380

Val Asp Trp Glu Arg Ile Pro Ile Phe Lys Leu Arg Gly Val Ser Leu
385                 390                 395                 400

Gly Lys Lys Val Lys Ala Leu Asn Arg Ile Thr Glu Ala Pro Arg
                405                 410                 415

Leu Val Val Ala Lys Arg Ile Gln Val Asn Ile Glu Ser Lys Lys Lys
                420                 425                 430

Lys Val Leu Thr Arg Tyr Val Tyr Asn Asp Lys Ser Ile Asn Gly Arg
                435                 440                 445

Leu Val Lys Ala Glu Asp Ser Asn Lys Asp Pro Leu Leu Glu Phe Lys
                450                 455                 460

Lys Gln Ala Glu Glu Ile Asn Ser Asp Ala Lys Tyr Tyr Glu Asn Gln
465                 470                 475                 480

Glu Ile Ala Lys Asn Tyr Leu Trp Gly Cys Glu Gly Leu His Lys Asn
                485                 490                 495

Leu Leu Glu Glu Gln Thr Lys Asn Pro Tyr Leu Ala Phe Lys Tyr Gly
                500                 505                 510

Phe Leu Asn Ile Val
                515

<210> SEQ ID NO 198
<211> LENGTH: 410
<212> TYPE: PRT
<213> ORGANISM: Artificial sequence
<220> FEATURE:
<223> OTHER INFORMATION: Synthetic sequence

<400> SEQUENCE: 198

Leu Asp Phe Lys Arg Thr Cys Ser Gln Glu Leu Val Leu Leu Pro Glu
1               5                   10                  15

Ile Glu Gly Leu Lys Leu Ser Gly Thr Gln Gly Val Thr Ser Leu Ala
                20                  25                  30

Lys Lys Leu Ile Asn Lys Ala Ala Asn Val Asp Arg Asp Glu Ser Tyr
                35                  40                  45

Gly Cys His His Cys Ile His Thr Arg Thr Ser Leu Ser Lys Pro Val
50                  55                  60

Lys Lys Asp Cys Asn Ser Cys Asn Gln Ser Thr Asn His Pro Ala Val
65                  70                  75                  80

Pro Ile Thr Leu Lys Gly Tyr Lys Ile Ala Phe Tyr Glu Leu Trp His
                85                  90                  95

Arg Phe Thr Ser Trp Ala Val Asp Ser Ile Ser Lys Ala Leu His Arg
                100                 105                 110

Asn Lys Val Met Gly Lys Val Asn Leu Asp Glu Tyr Ala Val Val Asp
                115                 120                 125

Asn Ser His Ile Val Cys Tyr Ala Val Arg Lys Cys Tyr Glu Lys Arg
                130                 135                 140

Gln Arg Ser Val Arg Leu His Lys Arg Ala Tyr Arg Cys Arg Ala Lys
145                 150                 155                 160

His Tyr Asn Lys Ser Gln Pro Val Gly Arg Ile Tyr Lys Lys Ser
                165                 170                 175

Lys Arg Arg Asn Ala Arg Asn Leu Lys Lys Glu Ala Lys Arg Tyr Phe
                180                 185                 190

Gln Pro Asn Glu Ile Thr Asn Gly Ser Ser Asp Ala Leu Phe Tyr Lys
                195                 200                 205

```
Ile Gly Val Asp Leu Gly Ile Ala Lys Gly Thr Pro Glu Thr Glu Val
        210                 215                 220

Lys Val Asp Val Ser Ile Cys Phe Gln Val Tyr Tyr Gly Asp Ala Arg
225                 230                 235                 240

Arg Val Leu Arg Val Arg Lys Met Asp Glu Leu Gln Ser Phe His Leu
                245                 250                 255

Asp Tyr Thr Gly Lys Leu Lys Leu Lys Gly Ile Gly Asn Lys Asp Thr
            260                 265                 270

Phe Thr Ile Ala Lys Arg Asn Glu Ser Leu Lys Trp Gly Ser Thr Lys
        275                 280                 285

Tyr Glu Val Ser Arg Ala His Lys Lys Phe Lys Pro Phe Gly Lys Lys
    290                 295                 300

Gly Ser Val Lys Arg Lys Cys Asn Asp Tyr Phe Arg Ser Ile Ala Ser
305                 310                 315                 320

Trp Ser Cys Glu Ala Ala Ser Gln Arg Ala Gln Ser Asn Leu Lys Asn
                325                 330                 335

Ala Phe Pro Tyr Gln Lys Ala Leu Val Lys Cys Tyr Lys Asn Leu Asp
            340                 345                 350

Tyr Lys Gly Val Lys Lys Asn Asp Met Trp Tyr Arg Leu Cys Ser Asn
        355                 360                 365

Arg Ile Phe Arg Tyr Ser Arg Ile Ala Glu Asp Ile Ala Gln Tyr Gln
    370                 375                 380

Ser Asp Lys Gly Lys Ala Lys Phe Glu Phe Val Ile Leu Ala Gln Ser
385                 390                 395                 400

Val Ala Glu Tyr Asp Ile Ser Ala Ile Met
                405                 410

<210> SEQ ID NO 199
<211> LENGTH: 602
<212> TYPE: PRT
<213> ORGANISM: Artificial sequence
<220> FEATURE:
<223> OTHER INFORMATION: Synthetic sequence

<400> SEQUENCE: 199

Val Phe Leu Thr Asp Asp Lys Arg Lys Thr Ala Leu Arg Lys Ile Arg
1               5                   10                  15

Ser Ala Phe Arg Lys Thr Ala Glu Ile Ala Leu Val Arg Ala Gln Glu
            20                  25                  30

Ala Asp Ser Leu Asp Arg Gln Ala Lys Lys Leu Thr Ile Glu Thr Val
        35                  40                  45

Ser Phe Gly Ala Pro Gly Ala Lys Asn Ala Phe Ile Gly Ser Leu Gln
50                  55                  60

Gly Tyr Asn Trp Asn Ser His Arg Ala Asn Val Pro Ser Ser Gly Ser
65                  70                  75                  80

Ala Lys Asp Val Phe Arg Ile Thr Glu Leu Gly Leu Gly Ile Pro Gln
                85                  90                  95

Ser Ala His Glu Ala Ser Ile Gly Lys Ser Phe Glu Leu Val Gly Asn
            100                 105                 110

Val Val Arg Tyr Thr Ala Asn Leu Leu Ser Lys Gly Tyr Lys Lys Gly
        115                 120                 125

Ala Val Asn Lys Gly Ala Lys Gln Gln Arg Glu Ile Lys Gly Lys Glu
    130                 135                 140

Gln Leu Ser Phe Asp Leu Ile Ser Asn Gly Pro Ile Ser Gly Asp Lys
145                 150                 155                 160
```

-continued

```
Leu Ile Asn Gly Gln Lys Asp Ala Leu Ala Trp Trp Leu Ile Asp Lys
                165                 170                 175

Met Gly Phe His Ile Gly Leu Ala Met Glu Pro Leu Ser Ser Pro Asn
            180                 185                 190

Thr Tyr Gly Ile Thr Leu Gln Ala Phe Trp Lys Arg His Thr Ala Pro
        195                 200                 205

Arg Arg Tyr Ser Arg Gly Val Ile Arg Gln Trp Gln Leu Pro Phe Gly
    210                 215                 220

Arg Gln Leu Ala Pro Leu Ile His Asn Phe Phe Arg Lys Lys Gly Ala
225                 230                 235                 240

Ser Ile Pro Ile Val Leu Thr Asn Ala Ser Lys Lys Leu Ala Gly Lys
                245                 250                 255

Gly Val Leu Leu Glu Gln Thr Ala Leu Val Asp Pro Lys Lys Trp Trp
            260                 265                 270

Gln Val Lys Glu Gln Val Thr Gly Pro Leu Ser Asn Ile Trp Glu Arg
        275                 280                 285

Ser Val Pro Leu Val Leu Tyr Thr Ala Thr Phe Thr His Lys His Gly
    290                 295                 300

Ala Ala His Lys Arg Pro Leu Thr Leu Lys Val Ile Arg Ile Ser Ser
305                 310                 315                 320

Gly Ser Val Phe Leu Leu Pro Leu Ser Lys Val Thr Pro Gly Lys Leu
                325                 330                 335

Val Arg Ala Trp Met Pro Asp Ile Asn Ile Leu Arg Asp Gly Arg Pro
            340                 345                 350

Asp Glu Ala Ala Tyr Lys Gly Pro Asp Leu Ile Arg Ala Arg Glu Arg
        355                 360                 365

Ser Phe Pro Leu Ala Tyr Thr Cys Val Thr Gln Ile Ala Asp Glu Trp
    370                 375                 380

Gln Lys Arg Ala Leu Glu Ser Asn Arg Asp Ser Ile Thr Pro Leu Glu
385                 390                 395                 400

Ala Lys Leu Val Thr Gly Ser Asp Leu Leu Gln Ile His Ser Thr Val
                405                 410                 415

Gln Gln Ala Val Glu Gln Gly Ile Gly Gly Arg Ile Ser Ser Pro Ile
            420                 425                 430

Gln Glu Leu Leu Ala Lys Asp Ala Leu Gln Leu Val Leu Gln Gln Leu
        435                 440                 445

Phe Met Thr Val Asp Leu Leu Arg Ile Gln Trp Gln Leu Lys Gln Glu
    450                 455                 460

Val Ala Asp Gly Asn Thr Ser Glu Lys Ala Val Gly Trp Ala Ile Arg
465                 470                 475                 480

Ile Ser Asn Ile His Lys Asp Ala Tyr Lys Thr Ala Ile Glu Pro Cys
                485                 490                 495

Thr Ser Ala Leu Lys Gln Ala Trp Asn Pro Leu Ser Gly Phe Glu Glu
            500                 505                 510

Arg Thr Phe Gln Leu Asp Ala Ser Ile Val Arg Lys Arg Ser Thr Ala
        515                 520                 525

Lys Thr Pro Asp Asp Glu Leu Val Ile Val Leu Arg Gln Gln Ala Ala
    530                 535                 540

Glu Met Thr Val Ala Val Thr Gln Ser Val Ser Lys Glu Leu Met Glu
545                 550                 555                 560

Leu Ala Val Arg His Ser Ala Thr Leu His Leu Leu Val Gly Glu Val
                565                 570                 575
```

Ala Ser Lys Gln Leu Ser Arg Ser Ala Asp Lys Asp Arg Gly Ala Met
            580                 585                 590

Asp His Trp Lys Leu Leu Ser Gln Ser Met
            595                 600

<210> SEQ ID NO 200
<211> LENGTH: 494
<212> TYPE: PRT
<213> ORGANISM: Artificial sequence
<220> FEATURE:
<223> OTHER INFORMATION: Synthetic sequence

<400> SEQUENCE: 200

Glu Asp Leu Leu Gln Lys Ala Leu Asn Thr Ala Thr Asn Val Ala Ala
1               5                   10                  15

Ile Glu Arg His Ser Cys Ile Ser Cys Leu Phe Thr Glu Ser Glu Ile
            20                  25                  30

Asp Val Lys Tyr Lys Thr Pro Asp Lys Ile Gly Gln Asn Thr Ala Gly
        35                  40                  45

Cys Gln Ser Cys Thr Phe Arg Val Gly Tyr Ser Gly Asn Ser His Thr
    50                  55                  60

Leu Pro Met Gly Asn Arg Ile Ala Leu Asp Lys Leu Arg Glu Thr Ile
65                  70                  75                  80

Gln Arg Tyr Ala Trp His Ser Leu Leu Phe Asn Val Pro Pro Ala Pro
                85                  90                  95

Thr Ser Lys Arg Val Arg Ala Ile Ser Glu Leu Arg Val Ala Ala Gly
            100                 105                 110

Arg Glu Arg Leu Phe Thr Val Ile Thr Phe Val Gln Thr Asn Ile Leu
        115                 120                 125

Ser Lys Leu Gln Lys Arg Tyr Ala Ala Asn Trp Thr Pro Lys Ser Gln
    130                 135                 140

Glu Arg Leu Ser Arg Leu Arg Glu Gly Gln His Ile Leu Ser Leu
145                 150                 155                 160

Leu Glu Ser Gly Ser Trp Gln Gln Lys Glu Val Val Arg Glu Asp Gln
                165                 170                 175

Asp Leu Ile Val Cys Ser Ala Leu Thr Lys Pro Gly Leu Ser Ile Gly
            180                 185                 190

Ala Phe Cys Arg Pro Lys Tyr Leu Lys Pro Ala Lys His Ala Leu Val
        195                 200                 205

Leu Arg Leu Ile Phe Val Glu Gln Trp Pro Gly Gln Ile Trp Gly Gln
    210                 215                 220

Ser Lys Arg Thr Arg Arg Met Arg Arg Arg Lys Asp Val Glu Arg Val
225                 230                 235                 240

Tyr Asp Ile Ser Val Gln Ala Trp Ala Leu Lys Gly Lys Glu Thr Arg
                245                 250                 255

Ile Ser Glu Cys Ile Asp Thr Met Arg Arg His Gln Gln Ala Tyr Ile
            260                 265                 270

Gly Val Leu Pro Phe Leu Ile Leu Ser Gly Ser Thr Val Arg Gly Lys
        275                 280                 285

Gly Asp Cys Pro Ile Leu Lys Glu Ile Thr Arg Met Arg Tyr Cys Pro
    290                 295                 300

Asn Asn Glu Gly Leu Ile Pro Leu Gly Ile Phe Tyr Arg Gly Ser Ala
305                 310                 315                 320

Asn Lys Leu Leu Arg Val Val Lys Ser Ser Phe Thr Leu Pro Met
                325                 330                 335

Trp Gln Asn Ile Glu Thr Leu Pro His Pro Glu Pro Phe Ser Pro Glu
                340                 345                 350

Gly Trp Thr Ala Thr Gly Ala Leu Tyr Glu Lys Asn Leu Ala Tyr Trp
        355                 360                 365

Ser Ala Leu Asn Glu Ala Val Asp Trp Tyr Thr Gly Gln Ile Leu Ser
    370                 375                 380

Ser Gly Leu Gln Tyr Pro Asn Gln Asn Glu Phe Leu Ala Arg Leu Gln
385                 390                 395                 400

Asn Val Ile Asp Ser Ile Pro Arg Lys Trp Phe Arg Pro Gln Gly Leu
                405                 410                 415

Lys Asn Leu Lys Pro Asn Gly Gln Glu Asp Ile Val Pro Asn Glu Phe
        420                 425                 430

Val Ile Pro Gln Asn Ala Ile Arg Ala His His Val Ile Glu Trp Tyr
            435                 440                 445

His Lys Thr Asn Asp Leu Val Ala Lys Thr Leu Leu Gly Trp Gly Ser
        450                 455                 460

Gln Thr Thr Leu Asn Gln Thr Arg Pro Gln Gly Asp Leu Arg Phe Thr
465                 470                 475                 480

Tyr Thr Arg Tyr Tyr Phe Arg Glu Lys Glu Val Pro Glu Val
                485                 490

<210> SEQ ID NO 201
<211> LENGTH: 649
<212> TYPE: PRT
<213> ORGANISM: Artificial sequence
<220> FEATURE:
<223> OTHER INFORMATION: Synthetic sequence

<400> SEQUENCE: 201

Val Pro Lys Lys Leu Met Arg Glu Leu Ala Lys Lys Ala Val Phe
1               5                   10                  15

Glu Ala Ile Phe Asn Asp Pro Ile Pro Gly Ser Phe Gly Cys Lys Arg
                20                  25                  30

Cys Thr Leu Ile Asp Gly Ala Arg Val Thr Asp Ala Ile Glu Lys Lys
            35                  40                  45

Gln Gly Ala Lys Arg Cys Ala Gly Cys Glu Pro Cys Thr Phe His Thr
    50                  55                  60

Leu Tyr Asp Ser Val Lys His Ala Leu Pro Ala Ala Thr Gly Cys Asp
65                  70                  75                  80

Arg Thr Ala Ile Asp Thr Gly Leu Trp Glu Ile Leu Thr Ala Leu Arg
                85                  90                  95

Ser Tyr Asn Trp Met Ser Phe Arg Arg Asn Ala Val Ser Asp Ala Ser
                100                 105                 110

Gln Lys Gln Val Trp Ser Ile Glu Leu Ala Ile Trp Ala Asp Lys
    115                 120                 125

Glu Arg Ala Leu Arg Val Ile Leu Ser Ala Leu Thr His Thr Ile Gly
130                 135                 140

Lys Leu Lys Asn Gly Phe Ser Arg Asp Gly Val Trp Lys Gly Lys
145                 150                 155                 160

Gln Leu Tyr Glu Asn Leu Ala Gln Lys Asp Leu Ala Lys Gly Leu Phe
                165                 170                 175

Ala Asn Gly Glu Ile Phe Gly Lys Glu Leu Val Glu Ala Asp His Asp
                180                 185                 190

Met Leu Ala Trp Thr Ile Val Pro Asn His Gln Phe His Ile Gly Leu
            195                 200                 205

```
Ile Arg Gly Asn Trp Lys Pro Ala Ala Val Glu Ala Ser Thr Ala Phe
    210                 215                 220

Asp Ala Arg Trp Leu Thr Asn Gly Ala Pro Leu Arg Asp Thr Arg Thr
225                 230                 235                 240

His Gly His Arg Gly Arg Arg Phe Asn Arg Thr Glu Lys Leu Thr Val
                245                 250                 255

Leu Cys Ile Lys Arg Asp Gly Val Ser Glu Glu Phe Arg Gln Glu
            260                 265                 270

Arg Asp Tyr Glu Leu Ser Val Met Leu Leu Gln Pro Lys Asn Lys Leu
        275                 280                 285

Lys Pro Glu Pro Lys Gly Glu Leu Asn Ser Phe Glu Asp Leu His Asp
290                 295                 300

His Trp Trp Phe Leu Lys Gly Asp Glu Ala Thr Ala Leu Val Gly Leu
305                 310                 315                 320

Thr Ser Asp Pro Thr Val Gly Asp Phe Ile Gln Leu Gly Leu Tyr Ile
                325                 330                 335

Arg Asn Pro Ile Lys Ala His Gly Glu Thr Lys Arg Arg Leu Leu Ile
            340                 345                 350

Cys Phe Glu Pro Pro Ile Lys Leu Pro Leu Arg Arg Ala Phe Pro Ser
        355                 360                 365

Glu Ala Phe Lys Thr Trp Glu Pro Thr Ile Asn Val Phe Arg Asn Gly
    370                 375                 380

Arg Arg Asp Thr Glu Ala Tyr Tyr Asp Ile Asp Arg Ala Arg Val Phe
385                 390                 395                 400

Glu Phe Pro Glu Thr Arg Val Ser Leu Glu His Leu Ser Lys Gln Trp
                405                 410                 415

Glu Val Leu Arg Leu Glu Pro Asp Arg Glu Asn Thr Asp Pro Tyr Glu
            420                 425                 430

Ala Gln Gln Asn Glu Gly Ala Glu Leu Gln Val Tyr Ser Leu Leu Gln
        435                 440                 445

Glu Ala Ala Gln Lys Met Ala Pro Lys Val Val Ile Asp Pro Phe Gly
    450                 455                 460

Gln Phe Pro Leu Glu Leu Phe Ser Thr Phe Val Ala Gln Leu Phe Asn
465                 470                 475                 480

Ala Pro Leu Ser Asp Thr Lys Ala Lys Ile Gly Lys Pro Leu Asp Ser
                485                 490                 495

Gly Phe Val Val Glu Ser His Leu His Leu Leu Glu Glu Asp Phe Ala
            500                 505                 510

Tyr Arg Asp Phe Val Arg Val Thr Phe Met Gly Thr Glu Pro Thr Phe
        515                 520                 525

Arg Val Ile His Tyr Ser Asn Gly Glu Gly Tyr Trp Lys Lys Thr Val
    530                 535                 540

Leu Lys Gly Lys Asn Asn Ile Arg Thr Ala Leu Ile Pro Glu Gly Ala
545                 550                 555                 560

Lys Ala Ala Val Asp Ala Tyr Lys Asn Lys Arg Cys Pro Leu Thr Leu
                565                 570                 575

Glu Ala Ala Ile Leu Asn Glu Glu Lys Asp Arg Arg Leu Val Leu Gly
            580                 585                 590

Asn Lys Ala Leu Ser Leu Leu Ala Gln Thr Ala Arg Gly Asn Leu Thr
        595                 600                 605

Ile Leu Glu Ala Leu Ala Ala Glu Val Leu Arg Pro Leu Ser Gly Thr
    610                 615                 620

Glu Gly Val Val His Leu His Ala Cys Val Thr Arg His Ser Thr Leu
```

Thr Glu Ser Thr Glu Thr Asp Asn Met
625                 630                 635                 640
                645

<210> SEQ ID NO 202
<211> LENGTH: 414
<212> TYPE: PRT
<213> ORGANISM: Artificial sequence
<220> FEATURE:
<223> OTHER INFORMATION: Synthetic sequence

<400> SEQUENCE: 202

Val Glu Lys Leu Phe Ser Glu Arg Leu Lys Arg Ala Met Trp Leu Lys
1               5                   10                  15

Asn Glu Ala Gly Arg Ala Pro Pro Ala Glu Thr Leu Thr Leu Lys His
            20                  25                  30

Lys Arg Val Ser Gly Gly His Glu Lys Val Lys Glu Glu Leu Gln Arg
        35                  40                  45

Val Leu Arg Ser Leu Ser Gly Thr Asn Gln Ala Ala Trp Asn Leu Gly
    50                  55                  60

Leu Ser Gly Gly Arg Glu Pro Lys Ser Ser Asp Ala Leu Lys Gly Glu
65                  70                  75                  80

Lys Ser Arg Val Val Leu Glu Thr Val Val Phe His Ser Gly His Asn
                85                  90                  95

Arg Val Leu Tyr Asp Val Ile Glu Arg Asp Gln Val His Gln Arg
            100                 105                 110

Ser Ser Ile Met His Met Arg Arg Lys Gly Ser Asn Leu Leu Arg Leu
        115                 120                 125

Trp Gly Arg Ser Gly Lys Val Arg Arg Lys Met Arg Glu Glu Val Ala
    130                 135                 140

Glu Ile Lys Pro Val Trp His Lys Asp Ser Arg Trp Leu Ala Ile Val
145                 150                 155                 160

Glu Glu Gly Arg Gln Ser Val Val Gly Ile Ser Ser Ala Gly Leu Ala
                165                 170                 175

Val Phe Ala Val Gln Glu Ser Gln Cys Thr Thr Ala Glu Pro Lys Pro
            180                 185                 190

Leu Glu Tyr Val Val Ser Ile Trp Phe Arg Gly Ser Lys Ala Leu Asn
        195                 200                 205

Pro Gln Asp Arg Tyr Leu Glu Phe Lys Lys Leu Lys Thr Thr Glu Ala
    210                 215                 220

Leu Arg Gly Gln Gln Tyr Asp Pro Ile Pro Phe Ser Leu Lys Arg Gly
225                 230                 235                 240

Ala Gly Cys Ser Leu Ala Ile Arg Gly Glu Gly Ile Lys Phe Gly Ser
                245                 250                 255

Arg Gly Pro Ile Lys Gln Phe Phe Gly Ser Asp Arg Ser Arg Pro Ser
            260                 265                 270

His Ala Asp Tyr Asp Gly Lys Arg Arg Leu Ser Leu Phe Ser Lys Tyr
        275                 280                 285

Ala Gly Asp Leu Ala Asp Leu Thr Glu Glu Gln Trp Asn Arg Thr Val
    290                 295                 300

Ser Ala Phe Ala Glu Asp Glu Val Arg Arg Ala Thr Leu Ala Asn Ile
305                 310                 315                 320

Gln Asp Phe Leu Ser Ile Ser His Glu Lys Tyr Ala Glu Arg Leu Lys
                325                 330                 335

Lys Arg Ile Glu Ser Ile Glu Glu Pro Val Ser Ala Ser Lys Leu Glu

```
                    340                 345                 350
Ala Tyr Leu Ser Ala Ile Phe Glu Thr Phe Val Gln Gln Arg Glu Ala
                355                 360                 365

Leu Ala Ser Asn Phe Leu Met Arg Leu Val Glu Ser Val Ala Leu Leu
            370                 375                 380

Ile Ser Leu Glu Glu Lys Ser Pro Arg Val Glu Phe Arg Val Ala Arg
385                 390                 395                 400

Tyr Leu Ala Glu Ser Lys Glu Gly Phe Asn Arg Lys Ala Met
                405                 410

<210> SEQ ID NO 203
<211> LENGTH: 413
<212> TYPE: PRT
<213> ORGANISM: Artificial sequence
<220> FEATURE:
<223> OTHER INFORMATION: Synthetic sequence

<400> SEQUENCE: 203

Val Val Ile Thr Gln Ser Glu Leu Tyr Lys Glu Arg Leu Leu Arg Val
1               5                   10                  15

Met Glu Ile Lys Asn Asp Arg Gly Arg Lys Glu Pro Arg Glu Ser Gln
            20                  25                  30

Gly Leu Val Leu Arg Phe Thr Gln Val Thr Gly Gly Gln Glu Lys Val
        35                  40                  45

Lys Gln Lys Leu Trp Leu Ile Phe Glu Gly Phe Ser Gly Thr Asn Gln
    50                  55                  60

Ala Ser Trp Asn Phe Gly Gln Pro Ala Gly Gly Arg Lys Pro Asn Ser
65                  70                  75                  80

Gly Asp Ala Leu Lys Gly Pro Lys Ser Arg Val Thr Tyr Glu Thr Val
                85                  90                  95

Val Phe His Phe Gly Leu Arg Leu Leu Ser Ala Val Ile Glu Arg His
            100                 105                 110

Asn Leu Lys Gln Gln Arg Gln Thr Met Ala Tyr Met Lys Arg Arg Ala
        115                 120                 125

Ala Ala Arg Lys Lys Trp Ala Arg Ser Gly Lys Lys Cys Ser Arg Met
    130                 135                 140

Arg Asn Glu Val Glu Lys Ile Lys Pro Lys Trp His Lys Asp Pro Arg
145                 150                 155                 160

Trp Phe Asp Ile Val Lys Glu Gly Glu Pro Ser Ile Val Gly Ile Ser
                165                 170                 175

Ser Ala Gly Phe Ala Ile Tyr Ile Val Glu Glu Pro Asn Phe Pro Arg
            180                 185                 190

Gln Asp Pro Leu Glu Ile Glu Tyr Ala Ile Ser Ile Trp Phe Arg Arg
        195                 200                 205

Asp Arg Ser Gln Tyr Leu Thr Phe Lys Lys Ile Gln Lys Ala Glu Lys
    210                 215                 220

Leu Lys Glu Leu Gln Tyr Asn Pro Ile Pro Phe Arg Leu Lys Gln Glu
225                 230                 235                 240

Lys Thr Ser Leu Val Phe Glu Ser Gly Asp Ile Lys Phe Gly Ser Arg
                245                 250                 255

Gly Ser Ile Glu His Phe Arg Asp Glu Ala Arg Gly Lys Pro Pro Lys
            260                 265                 270

Ala Asp Met Asp Asn Asn Arg Arg Leu Thr Met Phe Ser Val Phe Ser
        275                 280                 285

Gly Asn Leu Thr Asn Leu Thr Glu Glu Gln Tyr Ala Arg Pro Val Ser
```

```
            290                 295                 300
Gly Leu Leu Ala Pro Asp Glu Lys Arg Met Pro Thr Leu Leu Lys Lys
305                 310                 315                 320

Leu Gln Asp Phe Phe Thr Pro Ile His Glu Lys Tyr Gly Glu Arg Ile
                325                 330                 335

Lys Gln Arg Leu Ala Asn Ser Glu Ala Ser Lys Arg Pro Phe Lys Lys
                340                 345                 350

Leu Glu Glu Tyr Leu Pro Ala Ile Tyr Leu Glu Phe Arg Ala Arg Arg
            355                 360                 365

Glu Gly Leu Ala Ser Asn Trp Val Leu Val Leu Ile Asn Ser Val Arg
    370                 375                 380

Thr Leu Val Arg Ile Lys Ser Glu Asp Pro Tyr Ile Glu Phe Lys Val
385                 390                 395                 400

Ser Gln Tyr Leu Leu Glu Lys Glu Asp Asn Lys Ala Leu
                405                 410

<210> SEQ ID NO 204
<211> LENGTH: 449
<212> TYPE: PRT
<213> ORGANISM: Artificial sequence
<220> FEATURE:
<223> OTHER INFORMATION: Synthetic sequence

<400> SEQUENCE: 204

Lys Gln Asp Ala Leu Phe Glu Glu Arg Leu Lys Lys Ala Ile Phe Ile
1               5                   10                  15

Lys Arg Gln Ala Asp Pro Leu Gln Arg Glu Glu Leu Ser Leu Leu Pro
                20                  25                  30

Pro Asn Arg Lys Ile Val Thr Gly Gly His Glu Ser Ala Lys Asp Thr
            35                  40                  45

Leu Lys Gln Ile Leu Arg Ala Ile Asn Gly Thr Asn Gln Ala Ser Trp
        50                  55                  60

Asn Pro Gly Thr Pro Ser Gly Lys Arg Asp Ser Lys Ser Ala Asp Ala
65                  70                  75                  80

Leu Ala Gly Pro Lys Ser Arg Val Lys Leu Glu Thr Val Val Phe His
                85                  90                  95

Val Gly His Arg Leu Lys Lys Val Val Glu Tyr Gln Gly His Gln
            100                 105                 110

Lys Gln Gln His Gly Leu Lys Ala Phe Met Arg Thr Cys Ala Ala Met
        115                 120                 125

Arg Lys Lys Trp Lys Arg Ser Gly Lys Val Val Gly Glu Leu Arg Glu
130                 135                 140

Gln Leu Ala Asn Ile Gln Pro Lys Trp His Tyr Asp Ser Arg Pro Leu
145                 150                 155                 160

Asn Leu Cys Phe Glu Gly Lys Pro Ser Val Val Gly Leu Arg Ser Ala
                165                 170                 175

Gly Ile Ala Leu Tyr Thr Ile Gln Lys Ser Val Val Pro Val Lys Glu
            180                 185                 190

Pro Lys Pro Ile Glu Tyr Ala Val Ser Ile Trp Phe Arg Gly Pro Lys
        195                 200                 205

Ala Met Asp Arg Glu Asp Arg Cys Leu Glu Phe Lys Lys Leu Lys Ile
    210                 215                 220

Ala Thr Glu Leu Arg Lys Leu Gln Phe Glu Pro Ile Val Ser Thr Leu
225                 230                 235                 240

Thr Gln Gly Ile Lys Gly Phe Ser Leu Tyr Ile Gln Gly Asn Ser Val
```

-continued

```
                245                 250                 255
Lys Phe Gly Ser Arg Gly Pro Ile Lys Tyr Phe Ser Asn Glu Ser Val
            260                 265                 270
Arg Gln Arg Pro Pro Lys Ala Asp Pro Asp Gly Asn Lys Arg Leu Ala
        275                 280                 285
Leu Phe Ser Lys Phe Ser Gly Asp Leu Ser Asp Leu Thr Glu Glu Gln
        290                 295                 300
Trp Asn Arg Pro Ile Leu Ala Phe Glu Gly Ile Ile Arg Arg Ala Thr
305                 310                 315                 320
Leu Gly Asn Ile Gln Asp Tyr Leu Thr Val Gly His Glu Gln Phe Ala
                325                 330                 335
Ile Ser Leu Glu Gln Leu Leu Ser Glu Lys Glu Ser Val Leu Gln Met
            340                 345                 350
Ser Ile Glu Gln Gln Arg Leu Lys Lys Asn Leu Gly Lys Lys Ala Glu
        355                 360                 365
Asn Glu Trp Val Glu Ser Phe Gly Ala Glu Gln Ala Arg Lys Lys Ala
    370                 375                 380
Gln Gly Ile Arg Glu Tyr Ile Ser Gly Phe Phe Gln Glu Tyr Cys Ser
385                 390                 395                 400
Gln Arg Glu Gln Trp Ala Glu Asn Trp Val Gln Leu Asn Lys Ser
                405                 410                 415
Val Arg Leu Phe Leu Thr Ile Gln Asp Ser Thr Pro Phe Ile Glu Phe
            420                 425                 430
Arg Val Ala Arg Tyr Leu Pro Lys Gly Glu Lys Lys Gly Lys Ala
        435                 440                 445
Met
```

<210> SEQ ID NO 205
<211> LENGTH: 711
<212> TYPE: PRT
<213> ORGANISM: Artificial sequence
<220> FEATURE:
<223> OTHER INFORMATION: Synthetic sequence

<400> SEQUENCE: 205

```
Ala Asn His Ala Glu Arg His Lys Arg Leu Arg Lys Glu Ala Asn Arg
1               5                   10                  15
Ala Ala Asn Arg Asn Arg Pro Leu Val Ala Asp Cys Asp Thr Gly Asp
            20                  25                  30
Pro Leu Val Gly Ile Cys Arg Leu Leu Arg Arg Gly Asp Lys Met Gln
        35                  40                  45
Pro Asn Lys Thr Gly Cys Arg Ser Cys Glu Gln Val Glu Pro Glu Leu
    50                  55                  60
Arg Asp Ala Ile Leu Val Ser Gly Pro Gly Arg Leu Asp Asn Tyr Lys
65                  70                  75                  80
Tyr Glu Leu Phe Gln Arg Gly Arg Ala Met Ala Val His Arg Leu Leu
                85                  90                  95
Lys Arg Val Pro Lys Leu Asn Arg Pro Lys Lys Ala Ala Gly Asn Asp
            100                 105                 110
Glu Lys Lys Ala Glu Asn Lys Lys Ser Glu Ile Gln Lys Glu Lys Gln
        115                 120                 125
Lys Gln Arg Arg Met Met Pro Ala Val Ser Met Lys Gln Val Ser Val
    130                 135                 140
Ala Asp Phe Lys His Val Ile Glu Asn Thr Val Arg His Leu Phe Gly
145                 150                 155                 160
```

```
Asp Arg Arg Asp Arg Glu Ile Ala Glu Cys Ala Ala Leu Arg Ala Ala
                165                 170                 175

Ser Lys Tyr Phe Leu Lys Ser Arg Arg Val Arg Pro Arg Lys Leu Pro
            180                 185                 190

Lys Leu Ala Asn Pro Asp His Gly Lys Glu Leu Lys Gly Leu Arg Leu
        195                 200                 205

Arg Glu Lys Arg Ala Lys Leu Lys Lys Glu Lys Glu Lys Gln Ala Glu
    210                 215                 220

Leu Ala Arg Ser Asn Gln Lys Gly Ala Val Leu His Val Ala Thr Leu
225                 230                 235                 240

Lys Lys Asp Ala Pro Pro Met Pro Tyr Glu Lys Thr Gln Gly Arg Asn
                245                 250                 255

Asp Tyr Thr Thr Phe Val Ile Ser Ala Ala Ile Lys Val Gly Ala Thr
            260                 265                 270

Arg Gly Thr Lys Pro Leu Leu Thr Pro Gln Pro Arg Glu Trp Gln Cys
        275                 280                 285

Ser Leu Tyr Trp Arg Asp Gly Gln Arg Trp Ile Arg Gly Gly Leu Leu
    290                 295                 300

Gly Leu Gln Ala Gly Ile Val Leu Gly Pro Lys Leu Asn Arg Glu Leu
305                 310                 315                 320

Leu Glu Ala Val Leu Gln Arg Pro Ile Glu Cys Arg Met Ser Gly Cys
                325                 330                 335

Gly Asn Pro Leu Gln Val Arg Gly Ala Ala Val Asp Phe Phe Met Thr
            340                 345                 350

Thr Asn Pro Phe Tyr Val Ser Gly Ala Ala Tyr Ala Gln Lys Lys Phe
        355                 360                 365

Lys Pro Phe Gly Thr Lys Arg Ala Ser Glu Asp Gly Ala Ala Ala Lys
    370                 375                 380

Ala Arg Glu Lys Leu Met Thr Gln Leu Ala Lys Val Leu Asp Lys Val
385                 390                 395                 400

Val Thr Gln Ala Ala His Ser Pro Leu Asp Gly Ile Trp Glu Thr Arg
                405                 410                 415

Pro Glu Ala Lys Leu Arg Ala Met Ile Met Ala Leu Glu His Glu Trp
            420                 425                 430

Ile Phe Leu Arg Pro Gly Pro Cys His Asn Ala Ala Glu Glu Val Ile
        435                 440                 445

Lys Cys Asp Cys Thr Gly Gly His Ala Ile Leu Trp Ala Leu Ile Asp
    450                 455                 460

Glu Ala Arg Gly Ala Leu Glu His Lys Glu Phe Tyr Ala Val Thr Arg
465                 470                 475                 480

Ala His Thr His Asp Cys Glu Lys Gln Lys Leu Gly Gly Arg Leu Ala
                485                 490                 495

Gly Phe Leu Asp Leu Leu Ile Ala Gln Asp Val Pro Leu Asp Asp Ala
            500                 505                 510

Pro Ala Ala Arg Lys Ile Lys Thr Leu Leu Glu Ala Thr Pro Pro Ala
        515                 520                 525

Pro Cys Tyr Lys Ala Ala Thr Ser Ile Ala Thr Cys Asp Cys Glu Gly
    530                 535                 540

Lys Phe Asp Lys Leu Trp Ala Ile Ile Asp Ala Thr Arg Ala Gly His
545                 550                 555                 560

Gly Thr Glu Asp Leu Trp Ala Arg Thr Leu Ala Tyr Pro Gln Asn Val
                565                 570                 575
```

Asn Cys Lys Cys Lys Ala Gly Lys Asp Leu Thr His Arg Leu Ala Asp
            580                 585                 590

Phe Leu Gly Leu Leu Ile Lys Arg Asp Gly Pro Phe Arg Glu Arg Pro
        595                 600                 605

Pro His Lys Val Thr Gly Asp Arg Lys Leu Val Phe Ser Gly Asp Lys
        610                 615                 620

Lys Cys Lys Gly His Gln Tyr Val Ile Leu Ala Lys Ala His Asn Glu
625                 630                 635                 640

Glu Val Val Arg Ala Trp Ile Ser Arg Trp Gly Leu Lys Ser Arg Thr
                645                 650                 655

Asn Lys Ala Gly Tyr Ala Ala Thr Glu Leu Asn Leu Leu Asn Trp
            660                 665                 670

Leu Ser Ile Cys Arg Arg Trp Met Asp Met Leu Thr Val Gln Arg
        675                 680                 685

Asp Thr Pro Tyr Ile Arg Met Lys Thr Gly Arg Leu Val Val Asp Asp
        690                 695                 700

Lys Lys Glu Arg Lys Ala Met
705                 710

<210> SEQ ID NO 206
<211> LENGTH: 574
<212> TYPE: PRT
<213> ORGANISM: Artificial sequence
<220> FEATURE:
<223> OTHER INFORMATION: Synthetic sequence

<400> SEQUENCE: 206

Ala Lys Gln Arg Glu Ala Leu Arg Val Ala Leu Glu Arg Gly Ile Val
1               5                   10                  15

Arg Ala Ser Asn Arg Thr Tyr Thr Leu Val Thr Asn Cys Thr Lys Gly
            20                  25                  30

Gly Pro Leu Pro Glu Gln Cys Arg Met Ile Glu Arg Gly Lys Ala Arg
        35                  40                  45

Ala Met Lys Trp Glu Pro Lys Leu Val Gly Cys Gly Ser Cys Ala Ala
    50                  55                  60

Ala Thr Val Asp Leu Pro Ala Ile Glu Glu Tyr Ala Gln Pro Gly Arg
65                  70                  75                  80

Leu Asp Val Ala Lys Tyr Lys Leu Thr Thr Gln Ile Leu Ala Met Ala
                85                  90                  95

Thr Arg Arg Met Met Val Arg Ala Ala Lys Leu Ser Arg Arg Lys Gly
            100                 105                 110

Gln Trp Pro Ala Lys Val Gln Glu Glu Lys Glu Pro Glu Pro
        115                 120                 125

Lys Lys Met Leu Lys Ala Val Glu Met Arg Pro Val Ala Ile Val Asp
    130                 135                 140

Phe Asn Arg Val Ile Gln Thr Thr Ile Glu His Leu Trp Ala Glu Arg
145                 150                 155                 160

Ala Asn Ala Asp Glu Ala Glu Leu Lys Ala Leu Lys Ala Ala Ala Ala
                165                 170                 175

Tyr Phe Gly Pro Ser Leu Lys Ile Arg Ala Arg Gly Pro Pro Lys Ala
            180                 185                 190

Ala Ile Gly Arg Glu Leu Lys Lys Ala His Arg Lys Lys Ala Tyr Ala
        195                 200                 205

Glu Arg Lys Lys Ala Arg Arg Lys Arg Ala Glu Leu Ala Arg Ser Gln
    210                 215                 220

```
Ala Arg Gly Ala Ala Ala His Ala Ala Ile Arg Glu Arg Asp Ile Pro
225                 230                 235                 240

Pro Met Ala Tyr Glu Arg Thr Gln Gly Arg Asn Asp Val Thr Thr Ile
            245                 250                 255

Pro Ile Ala Ala Ala Ile Lys Ile Ala Ala Thr Arg Gly Ala Arg Pro
        260                 265                 270

Leu Pro Ala Pro Lys Pro Met Lys Trp Gln Cys Ser Leu Tyr Trp Asn
    275                 280                 285

Glu Gly Gln Arg Trp Ile Arg Gly Gly Met Leu Thr Ala Gln Ala Tyr
290                 295                 300

Ala His Ala Ala Asn Ile His Arg Pro Met Arg Cys Glu Met Trp Gly
305                 310                 315                 320

Val Gly Asn Pro Leu Lys Val Arg Ala Phe Glu Gly Arg Val Ala Asp
            325                 330                 335

Pro Asp Gly Ala Lys Gly Arg Lys Ala Glu Phe Arg Leu Gln Thr Asn
        340                 345                 350

Ala Phe Tyr Val Ser Gly Ala Ala Tyr Arg Asn Lys Lys Phe Lys Pro
    355                 360                 365

Phe Gly Thr Asp Arg Gly Ile Gly Ser Ala Arg Lys Lys Arg Glu
370                 375                 380

Arg Leu Met Ala Gln Leu Ala Lys Ile Leu Asp Lys Val Val Ser Gln
385                 390                 395                 400

Ala Ala His Ser Pro Leu Asp Asp Ile Trp His Thr Arg Pro Ala Gln
            405                 410                 415

Lys Leu Arg Ala Met Ile Lys Gln Leu Glu His Glu Trp Met Phe Leu
        420                 425                 430

Arg Pro Gln Ala Pro Thr Val Glu Gly Thr Lys Pro Asp Val Asp Val
    435                 440                 445

Ala Gly Asn Met Gln Arg Gln Ile Lys Ala Leu Met Ala Pro Asp Leu
450                 455                 460

Pro Pro Ile Glu Lys Gly Ser Pro Ala Lys Arg Phe Thr Gly Asp Lys
465                 470                 475                 480

Arg Lys Lys Gly Glu Arg Ala Val Arg Val Ala Glu Ala His Ser Asp
            485                 490                 495

Glu Val Val Thr Ala Trp Ile Ser Arg Trp Gly Ile Gln Thr Arg Arg
        500                 505                 510

Asn Glu Gly Ser Tyr Ala Ala Gln Glu Leu Glu Leu Leu Asn Trp
    515                 520                 525

Leu Gln Ile Cys Arg Arg Arg Trp Leu Asp Met Thr Ala Ala Gln Arg
530                 535                 540

Val Ser Pro Tyr Ile Arg Met Lys Ser Gly Arg Met Ile Thr Asp Ala
545                 550                 555                 560

Ala Asp Glu Gly Val Ala Pro Ile Pro Leu Val Glu Asn Met
            565                 570

<210> SEQ ID NO 207
<211> LENGTH: 743
<212> TYPE: PRT
<213> ORGANISM: Artificial sequence
<220> FEATURE:
<223> OTHER INFORMATION: Synthetic sequence

<400> SEQUENCE: 207

Lys Ser Ile Ser Gly Arg Ser Ile Lys His Met Ala Cys Leu Lys Asp
1               5                   10                  15
```

Met Leu Lys Ser Glu Ile Thr Glu Ile Glu Lys Gln Lys Lys Glu
            20              25              30

Ser Leu Arg Lys Trp Asp Tyr Tyr Ser Lys Phe Ser Asp Glu Ile Leu
        35              40              45

Phe Arg Arg Asn Leu Asn Val Ser Ala Asn His Asp Ala Asn Ala Cys
    50              55              60

Tyr Gly Cys Asn Pro Cys Ala Phe Leu Lys Glu Val Tyr Gly Phe Arg
65              70              75              80

Ile Glu Arg Arg Asn Asn Glu Arg Ile Ile Ser Tyr Arg Gly Leu
                85              90              95

Ala Gly Cys Lys Ser Cys Val Gln Ser Thr Gly Tyr Pro Pro Ile Glu
            100             105             110

Phe Val Arg Arg Lys Phe Gly Ala Asp Lys Ala Met Glu Ile Val Arg
        115             120             125

Glu Val Leu His Arg Arg Asn Trp Gly Ala Leu Ala Arg Asn Ile Gly
    130             135             140

Arg Glu Lys Glu Ala Asp Pro Ile Leu Gly Glu Leu Asn Glu Leu Leu
145             150             155             160

Leu Val Asp Ala Arg Pro Tyr Phe Gly Asn Lys Ser Ala Ala Asn Glu
            165             170             175

Thr Asn Leu Ala Phe Asn Val Ile Thr Arg Ala Ala Lys Lys Phe Arg
        180             185             190

Asp Glu Gly Met Tyr Asp Ile His Lys Gln Leu Asp Ile His Ser Glu
    195             200             205

Glu Gly Lys Val Pro Lys Gly Arg Lys Ser Arg Leu Ile Arg Ile Glu
210             215             220

Arg Lys His Lys Ala Ile His Gly Leu Asp Pro Gly Glu Thr Trp Arg
225             230             235             240

Tyr Pro His Cys Gly Lys Gly Glu Lys Tyr Gly Val Trp Leu Asn Arg
            245             250             255

Ser Arg Leu Ile His Ile Lys Gly Asn Glu Tyr Arg Cys Leu Thr Ala
        260             265             270

Phe Gly Thr Thr Gly Arg Arg Met Ser Leu Asp Val Ala Cys Ser Val
    275             280             285

Leu Gly His Pro Leu Val Lys Lys Arg Lys Lys Gly Lys Lys Thr
290             295             300

Val Asp Gly Thr Glu Leu Trp Gln Ile Lys Lys Ala Thr Glu Thr Leu
305             310             315             320

Pro Glu Asp Pro Ile Asp Cys Thr Phe Tyr Leu Tyr Ala Ala Lys Pro
            325             330             335

Thr Lys Asp Pro Phe Ile Leu Lys Val Gly Ser Leu Lys Ala Pro Arg
        340             345             350

Trp Lys Lys Leu His Lys Asp Phe Phe Glu Tyr Ser Asp Thr Glu Lys
    355             360             365

Thr Gln Gly Gln Glu Lys Gly Lys Arg Val Val Arg Gly Lys Val
370             375             380

Pro Arg Ile Leu Ser Leu Arg Pro Asp Ala Lys Phe Lys Val Ser Ile
385             390             395             400

Trp Asp Asp Pro Tyr Asn Gly Lys Asn Lys Gly Thr Leu Leu Arg
            405             410             415

Met Glu Leu Ser Gly Leu Asp Gly Ala Lys Lys Pro Leu Ile Leu Lys
        420             425             430

Arg Tyr Gly Glu Pro Asn Thr Lys Pro Lys Asn Phe Val Phe Trp Arg

```
                435                 440                 445
Pro His Ile Thr Pro His Pro Leu Thr Phe Thr Pro Lys His Asp Phe
    450                 455                 460

Gly Asp Pro Asn Lys Lys Thr Lys Arg Arg Val Phe Asn Arg Glu
465                 470                 475                 480

Tyr Tyr Gly His Leu Asn Asp Leu Ala Lys Met Glu Pro Asn Ala Lys
                485                 490                 495

Phe Phe Glu Asp Arg Glu Val Ser Asn Lys Lys Asn Pro Lys Ala Lys
            500                 505                 510

Asn Ile Arg Ile Gln Ala Lys Glu Ser Leu Pro Asn Ile Val Ala Lys
        515                 520                 525

Asn Gly Arg Trp Ala Ala Phe Asp Pro Asn Asp Ser Leu Trp Lys Leu
    530                 535                 540

Tyr Leu His Trp Arg Gly Arg Lys Thr Ile Lys Gly Gly Ile Ser
545                 550                 555                 560

Gln Glu Phe Gln Glu Phe Lys Glu Arg Leu Asp Leu Tyr Lys Lys His
                565                 570                 575

Glu Asp Glu Ser Glu Trp Lys Glu Lys Glu Lys Leu Trp Glu Asn His
            580                 585                 590

Glu Lys Glu Trp Lys Lys Thr Leu Glu Ile His Gly Ser Ile Ala Glu
        595                 600                 605

Val Ser Gln Arg Cys Val Met Gln Ser Met Met Gly Pro Leu Asp Gly
    610                 615                 620

Leu Val Gln Lys Lys Asp Tyr Val His Ile Gly Gln Ser Ser Leu Lys
625                 630                 635                 640

Ala Ala Asp Asp Ala Trp Thr Phe Ser Ala Asn Arg Tyr Lys Lys Ala
                645                 650                 655

Thr Gly Pro Lys Trp Gly Lys Ile Ser Val Ser Asn Leu Leu Tyr Asp
            660                 665                 670

Ala Asn Gln Ala Asn Ala Glu Leu Ile Ser Gln Ser Ile Ser Lys Tyr
        675                 680                 685

Leu Ser Lys Gln Lys Asp Asn Gln Gly Cys Glu Gly Arg Lys Met Lys
    690                 695                 700

Phe Leu Ile Lys Ile Ile Glu Pro Leu Arg Glu Asn Phe Val Lys His
705                 710                 715                 720

Thr Arg Trp Leu His Glu Met Thr Gln Lys Asp Cys Glu Val Arg Ala
                725                 730                 735

Gln Phe Ser Arg Val Ser Met
            740

<210> SEQ ID NO 208
<211> LENGTH: 769
<212> TYPE: PRT
<213> ORGANISM: Artificial sequence
<220> FEATURE:
<223> OTHER INFORMATION: Synthetic sequence

<400> SEQUENCE: 208

Phe Pro Ser Asp Val Gly Ala Asp Ala Leu Lys His Val Arg Met Leu
1               5                   10                  15

Gln Pro Arg Leu Thr Asp Glu Val Arg Lys Val Ala Leu Thr Arg Ala
            20                  25                  30

Pro Ser Asp Arg Pro Ala Leu Ala Arg Phe Ala Ala Val Ala Gln Asp
        35                  40                  45

Gly Leu Ala Phe Val Arg His Leu Asn Val Ser Ala Asn His Asp Ser
```

```
                50                  55                  60
Asn Cys Thr Phe Pro Arg Asp Pro Arg Asp Pro Arg Arg Gly Pro Cys
 65                  70                  75                  80

Glu Pro Asn Pro Cys Ala Phe Leu Arg Glu Val Trp Gly Phe Arg Ile
                 85                  90                  95

Val Ala Arg Gly Asn Glu Arg Ala Leu Ser Tyr Arg Arg Gly Leu Ala
                100                 105                 110

Gly Cys Lys Ser Cys Val Gln Ser Thr Gly Phe Pro Ser Val Pro Phe
                115                 120                 125

His Arg Ile Gly Ala Asp Asp Cys Met Arg Lys Leu His Glu Ile Leu
                130                 135                 140

Lys Ala Arg Asn Trp Arg Leu Leu Ala Arg Asn Ile Gly Arg Glu Arg
145                 150                 155                 160

Glu Ala Asp Pro Leu Leu Thr Glu Leu Ser Glu Tyr Leu Leu Val Asp
                165                 170                 175

Ala Arg Thr Tyr Pro Asp Gly Ala Ala Pro Asn Ser Gly Arg Leu Ala
                180                 185                 190

Glu Asn Val Ile Lys Arg Ala Ala Lys Lys Phe Arg Asp Glu Gly Met
                195                 200                 205

Arg Asp Ile His Ala Gln Leu Arg Val His Ser Arg Glu Gly Lys Val
210                 215                 220

Pro Lys Gly Arg Leu Gln Arg Leu Arg Arg Ile Glu Arg Lys His Arg
225                 230                 235                 240

Ala Ile His Ala Leu Asp Pro Gly Pro Ser Trp Glu Ala Glu Gly Ser
                245                 250                 255

Ala Arg Ala Glu Val Gln Gly Val Ala Val Tyr Arg Ser Gln Leu Leu
                260                 265                 270

Arg Val Gly His His Thr Gln Gln Ile Glu Pro Val Gly Ile Val Ala
                275                 280                 285

Arg Thr Leu Phe Gly Val Gly Arg Thr Asp Leu Asp Val Ala Val Ser
                290                 295                 300

Val Leu Gly Ala Pro Leu Thr Lys Arg Lys Gly Ser Lys Thr Leu
305                 310                 315                 320

Glu Ser Thr Glu Asp Phe Arg Ile Ala Lys Ala Arg Glu Thr Arg Ala
                325                 330                 335

Glu Asp Lys Ile Glu Val Ala Phe Val Leu Tyr Pro Thr Ala Ser Leu
                340                 345                 350

Leu Arg Asp Glu Ile Pro Lys Asp Ala Phe Pro Ala Met Arg Ile Asp
                355                 360                 365

Arg Phe Leu Leu Lys Val Gly Ser Val Gln Ala Asp Arg Glu Ile Leu
                370                 375                 380

Leu Gln Asp Asp Tyr Tyr Arg Phe Gly Asp Ala Glu Val Lys Ala Gly
385                 390                 395                 400

Lys Asn Lys Gly Arg Thr Val Thr Arg Pro Val Lys Val Pro Arg Leu
                405                 410                 415

Gln Ala Leu Arg Pro Asp Ala Lys Phe Arg Val Asn Val Trp Ala Asp
                420                 425                 430

Pro Phe Gly Ala Gly Asp Ser Pro Gly Thr Leu Leu Arg Leu Glu Val
                435                 440                 445

Ser Gly Val Thr Arg Arg Ser Gln Pro Leu Arg Leu Leu Arg Tyr Gly
                450                 455                 460

Gln Pro Ser Thr Gln Pro Ala Asn Phe Leu Cys Trp Arg Pro His Arg
465                 470                 475                 480
```

```
Val Pro Asp Pro Met Thr Phe Thr Pro Arg Gln Lys Phe Gly Glu Arg
            485                 490                 495

Arg Lys Asn Arg Arg Thr Arg Arg Pro Arg Val Phe Glu Arg Leu Tyr
        500                 505                 510

Gln Val His Ile Lys His Leu Ala His Leu Glu Pro Asn Arg Lys Trp
            515                 520                 525

Phe Glu Glu Ala Arg Val Ser Ala Gln Lys Trp Ala Lys Ala Arg Ala
    530                 535                 540

Ile Arg Arg Lys Gly Ala Glu Asp Ile Pro Val Val Ala Pro Pro Ala
545                 550                 555                 560

Lys Arg Arg Trp Ala Ala Leu Gln Pro Asn Ala Glu Leu Trp Asp Leu
                565                 570                 575

Tyr Ala His Asp Arg Glu Ala Arg Lys Arg Phe Arg Gly Gly Arg Ala
                580                 585                 590

Ala Glu Gly Glu Glu Phe Lys Pro Arg Leu Asn Leu Tyr Leu Ala His
            595                 600                 605

Glu Pro Glu Ala Glu Trp Glu Ser Lys Arg Asp Arg Trp Glu Arg Tyr
    610                 615                 620

Glu Lys Lys Trp Thr Ala Val Leu Glu Glu His Ser Arg Met Cys Ala
625                 630                 635                 640

Val Ala Asp Arg Thr Leu Pro Gln Phe Leu Ser Asp Pro Leu Gly Ala
                645                 650                 655

Arg Met Asp Asp Lys Asp Tyr Ala Phe Val Gly Lys Ser Ala Leu Ala
                660                 665                 670

Val Ala Glu Ala Phe Val Glu Glu Gly Thr Val Glu Arg Ala Gln Gly
            675                 680                 685

Asn Cys Ser Ile Thr Ala Lys Lys Phe Ala Ser Asn Ala Ser Arg
    690                 695                 700

Lys Arg Leu Ser Val Ala Asn Leu Leu Asp Val Ser Asp Lys Ala Asp
705                 710                 715                 720

Arg Ala Leu Val Phe Gln Ala Val Arg Gln Tyr Val Gln Arg Gln Ala
                725                 730                 735

Glu Asn Gly Gly Val Gly Arg Arg Met Ala Phe Leu Arg Lys Leu
            740                 745                 750

Leu Ala Pro Leu Arg Gln Asn Phe Val Cys His Thr Arg Trp Leu His
        755                 760                 765

Met

<210> SEQ ID NO 209
<211> LENGTH: 564
<212> TYPE: PRT
<213> ORGANISM: Artificial sequence
<220> FEATURE:
<223> OTHER INFORMATION: Synthetic sequence

<400> SEQUENCE: 209

Ala Ala Arg Lys Lys Arg Gly Lys Ile Gly Ile Thr Val Lys Ala
1               5                   10                  15

Lys Glu Lys Ser Pro Pro Ala Ala Gly Pro Phe Met Ala Arg Lys Leu
            20                  25                  30

Val Asn Val Ala Ala Asn Val Asp Gly Val Glu Val His Leu Cys Val
        35                  40                  45

Glu Cys Glu Ala Asp Ala His Gly Ser Ala Ser Ala Arg Leu Leu Gly
    50                  55                  60
```

```
Gly Cys Arg Ser Cys Thr Gly Ser Ile Gly Ala Glu Gly Arg Leu Met
 65                  70                  75                  80

Gly Ser Val Asp Val Asp Arg Glu Arg Val Ile Ala Glu Pro Val His
                 85                  90                  95

Thr Glu Thr Glu Arg Leu Gly Pro Asp Val Lys Ala Phe Glu Ala Gly
            100                 105                 110

Thr Ala Glu Ser Lys Tyr Ala Ile Gln Arg Gly Leu Glu Tyr Trp Gly
            115                 120                 125

Val Asp Leu Ile Ser Arg Asn Arg Ala Arg Thr Val Arg Lys Met Glu
            130                 135                 140

Glu Ala Asp Arg Pro Glu Ser Ser Thr Met Glu Lys Thr Ser Trp Asp
145                 150                 155                 160

Glu Ile Ala Ile Lys Thr Tyr Ser Gln Ala Tyr His Ala Ser Glu Asn
                165                 170                 175

His Leu Phe Trp Glu Arg Gln Arg Arg Val Arg Gln His Ala Leu Ala
            180                 185                 190

Leu Phe Arg Arg Ala Arg Glu Arg Asn Arg Gly Glu Ser Pro Leu Gln
            195                 200                 205

Ser Thr Gln Arg Pro Ala Pro Leu Val Leu Ala Leu His Ala Glu
            210                 215                 220

Ala Ala Ala Ile Ser Gly Arg Ala Arg Ala Glu Tyr Val Leu Arg Gly
225                 230                 235                 240

Pro Ser Ala Asn Val Arg Ala Ala Ala Asp Ile Asp Ala Lys Pro
                245                 250                 255

Leu Gly His Tyr Lys Thr Pro Ser Pro Lys Val Ala Arg Gly Phe Pro
            260                 265                 270

Val Lys Arg Asp Leu Leu Arg Ala Arg His Arg Ile Val Gly Leu Ser
            275                 280                 285

Arg Ala Tyr Phe Lys Pro Ser Asp Val Val Arg Gly Thr Ser Asp Ala
            290                 295                 300

Ile Ala His Val Ala Gly Arg Asn Ile Gly Val Ala Gly Gly Lys Pro
305                 310                 315                 320

Lys Glu Ile Glu Lys Thr Phe Thr Leu Pro Phe Val Ala Tyr Trp Glu
                325                 330                 335

Asp Val Asp Arg Val Val His Cys Ser Ser Phe Lys Ala Asp Gly Pro
            340                 345                 350

Trp Val Arg Asp Gln Arg Ile Lys Ile Arg Gly Val Ser Ser Ala Val
            355                 360                 365

Gly Thr Phe Ser Leu Tyr Gly Leu Asp Val Ala Trp Ser Lys Pro Thr
370                 375                 380

Ser Phe Tyr Ile Arg Cys Ser Asp Ile Arg Lys Lys Phe His Pro Lys
385                 390                 395                 400

Gly Phe Gly Pro Met Lys His Trp Arg Gln Trp Ala Lys Glu Leu Asp
                405                 410                 415

Arg Leu Thr Glu Gln Arg Ala Ser Cys Val Val Arg Ala Leu Gln Asp
            420                 425                 430

Asp Glu Glu Leu Leu Gln Thr Met Glu Arg Gly Gln Arg Tyr Tyr Asp
            435                 440                 445

Val Phe Ser Cys Ala Ala Thr His Ala Thr Arg Gly Glu Ala Asp Pro
            450                 455                 460

Ser Gly Gly Cys Ser Arg Cys Glu Leu Val Ser Cys Gly Val Ala His
465                 470                 475                 480

Lys Val Thr Lys Lys Ala Lys Gly Asp Thr Gly Ile Glu Ala Val Ala
```

485                 490                 495
Val Ala Gly Cys Ser Leu Cys Glu Ser Lys Leu Val Gly Pro Ser Lys
                500                 505                 510

Pro Arg Val His Arg Gln Met Ala Ala Leu Arg Gln Ser His Ala Leu
            515                 520                 525

Asn Tyr Leu Arg Arg Leu Gln Arg Glu Trp Glu Ala Leu Glu Ala Val
        530                 535                 540

Gln Ala Pro Thr Pro Tyr Leu Arg Phe Lys Tyr Ala Arg His Leu Glu
545                 550                 555                 560

Val Arg Ser Met

<210> SEQ ID NO 210
<211> LENGTH: 565
<212> TYPE: PRT
<213> ORGANISM: Artificial sequence
<220> FEATURE:
<223> OTHER INFORMATION: Synthetic sequence

<400> SEQUENCE: 210

Ala Ala Lys Lys Lys Gln Arg Gly Lys Ile Gly Ile Ser Val Lys
1               5                   10                  15

Pro Lys Glu Gly Ser Ala Pro Ala Asp Gly Pro Phe Met Ala Arg
            20                  25                  30

Lys Leu Val Asn Val Ala Ala Asn Val Asp Gly Val Glu Val Asn Leu
        35                  40                  45

Cys Ile Glu Cys Glu Ala Asp Ala His Gly Ser Ala Pro Ala Arg Leu
    50                  55                  60

Leu Gly Gly Cys Lys Ser Cys Thr Gly Ser Ile Gly Ala Glu Gly Arg
65                  70                  75                  80

Leu Met Gly Ser Val Asp Val Asp Arg Ala Asp Ala Ile Ala Lys Pro
                85                  90                  95

Val Asn Thr Glu Thr Glu Lys Leu Gly Pro Asp Val Gln Ala Phe Glu
            100                 105                 110

Ala Gly Thr Ala Glu Thr Lys Tyr Ala Leu Gln Arg Gly Leu Glu Tyr
        115                 120                 125

Trp Gly Val Asp Leu Ile Ser Arg Asn Arg Ser Arg Thr Val Arg Arg
    130                 135                 140

Thr Glu Glu Gly Gln Pro Glu Ser Ala Thr Met Glu Lys Thr Ser Trp
145                 150                 155                 160

Asp Glu Ile Ala Ile Lys Ser Tyr Thr Arg Ala Tyr His Ala Ser Glu
                165                 170                 175

Asn His Leu Phe Trp Glu Arg Gln Arg Arg Val Arg Gln His Ala Leu
            180                 185                 190

Ala Leu Phe Lys Arg Ala Lys Glu Arg Asn Arg Gly Asp Ser Thr Leu
        195                 200                 205

Pro Arg Glu Pro Gly His Gly Leu Val Ala Ile Ala Ala Leu Ala Cys
    210                 215                 220

Glu Ala Tyr Ala Val Gly Gly Arg Asn Leu Ala Glu Thr Val Val Arg
225                 230                 235                 240

Gly Pro Thr Phe Gly Thr Ala Arg Ala Val Arg Asp Val Glu Ile Ala
                245                 250                 255

Ser Leu Gly Arg Tyr Lys Thr Pro Ser Pro Lys Val Ala His Gly Ser
            260                 265                 270

Pro Val Lys Arg Asp Phe Leu Arg Ala Arg His Arg Ile Val Gly Leu
        275                 280                 285

Ala Arg Ala Tyr Tyr Arg Pro Ser Asp Val Val Arg Gly Thr Ser Asp
        290                 295                 300

Ala Ile Ala His Val Ala Gly Arg Asn Ile Gly Val Ala Gly Gly Lys
305                 310                 315                 320

Pro Arg Ala Val Glu Ala Val Phe Thr Leu Pro Phe Val Ala Tyr Trp
                325                 330                 335

Glu Asp Val Asp Arg Val Val His Cys Ser Ser Phe Gln Val Ser Ala
            340                 345                 350

Pro Trp Asn Arg Asp Gln Arg Met Lys Ile Ala Gly Val Thr Thr Ala
        355                 360                 365

Ala Gly Thr Phe Ser Leu His Gly Gly Glu Leu Lys Trp Ala Lys Pro
    370                 375                 380

Thr Ser Phe Tyr Ile Arg Cys Ser Asp Thr Arg Arg Lys Phe Arg Pro
385                 390                 395                 400

Lys Gly Phe Gly Pro Met Lys Arg Trp Arg Gln Trp Ala Lys Asp Leu
                405                 410                 415

Asp Arg Leu Val Glu Gln Arg Ala Ser Cys Val Val Arg Ala Leu Gln
            420                 425                 430

Asp Asp Ala Ala Leu Leu Glu Thr Met Glu Arg Gly Gln Arg Tyr Tyr
        435                 440                 445

Asp Val Phe Ala Cys Ala Val Thr His Ala Thr Arg Gly Glu Ala Asp
    450                 455                 460

Arg Leu Ala Gly Cys Ser Arg Cys Ala Leu Thr Pro Cys Gln Glu Ala
465                 470                 475                 480

His Arg Val Thr Thr Lys Pro Arg Gly Asp Ala Gly Val Glu Gln Val
                485                 490                 495

Gln Thr Ser Asp Cys Ser Leu Cys Glu Gly Lys Leu Val Gly Pro Ser
            500                 505                 510

Lys Pro Arg Leu His Arg Thr Leu Thr Leu Leu Arg Gln Glu His Gly
        515                 520                 525

Leu Asn Tyr Leu Arg Arg Leu Gln Arg Glu Trp Glu Ser Leu Glu Ala
    530                 535                 540

Val Gln Val Pro Thr Pro Tyr Leu Arg Phe Lys Tyr Ala Arg His Leu
545                 550                 555                 560

Glu Val Arg Ser Met
                565

<210> SEQ ID NO 211
<211> LENGTH: 499
<212> TYPE: PRT
<213> ORGANISM: Artificial sequence
<220> FEATURE:
<223> OTHER INFORMATION: Synthetic sequence

<400> SEQUENCE: 211

Thr Asp Ser Gln Ser Glu Ser Val Pro Glu Val Val Tyr Ala Leu Thr
1               5                   10                  15

Gly Gly Glu Val Pro Gly Arg Val Pro Pro Asp Gly Gly Ser Ala Glu
            20                  25                  30

Gly Ala Arg Asn Ala Pro Thr Gly Leu Arg Lys Gln Arg Gly Lys Ile
        35                  40                  45

Lys Ile Ser Ala Lys Pro Ser Lys Pro Gly Ser Pro Ala Ser Ser Leu
    50                  55                  60

Ala Arg Thr Leu Val Asn Glu Ala Ala Asn Val Asp Gly Val Gln Ser
65                  70                  75                  80

```
Ser Gly Cys Ala Thr Cys Arg Met Arg Ala Asn Gly Ser Ala Pro Arg
                85                  90                  95

Ala Leu Pro Ile Gly Cys Val Ala Cys Ala Ser Ser Ile Gly Arg Ala
                100                 105                 110

Pro Gln Glu Glu Thr Val Cys Ala Leu Pro Thr Thr Gln Gly Pro Asp
                115                 120                 125

Val Arg Leu Leu Glu Gly Gly His Ala Leu Arg Lys Tyr Asp Ile Gln
    130                 135                 140

Arg Ala Leu Glu Tyr Trp Gly Val Asp Leu Ile Gly Arg Asn Leu Asp
145                 150                 155                 160

Arg Gln Ala Gly Arg Gly Met Glu Pro Ala Glu Gly Ala Thr Ala Thr
                165                 170                 175

Met Lys Arg Val Ser Met Asp Glu Leu Ala Val Leu Asp Phe Gly Lys
                180                 185                 190

Ser Tyr Tyr Ala Ser Glu Gln His Leu Phe Ala Ala Arg Gln Arg Arg
                195                 200                 205

Val Arg Gln His Ala Lys Ala Leu Lys Ile Arg Ala Lys His Ala Asn
    210                 215                 220

Arg Ser Gly Ser Val Lys Arg Ala Leu Asp Arg Ser Arg Lys Gln Val
225                 230                 235                 240

Thr Ala Leu Ala Arg Glu Phe Phe Lys Pro Ser Asp Val Val Arg Gly
                245                 250                 255

Asp Ser Asp Ala Leu Ala His Val Val Gly Arg Asn Leu Gly Val Ser
                260                 265                 270

Arg His Pro Ala Arg Glu Ile Pro Gln Thr Phe Thr Leu Pro Leu Cys
                275                 280                 285

Ala Tyr Trp Glu Asp Val Asp Arg Val Ile Ser Cys Ser Ser Leu Leu
                290                 295                 300

Ala Gly Glu Pro Phe Ala Arg Asp Gln Glu Ile Arg Ile Glu Gly Val
305                 310                 315                 320

Ser Ser Ala Leu Gly Ser Leu Arg Leu Tyr Arg Gly Ala Ile Glu Trp
                325                 330                 335

His Lys Pro Thr Ser Leu Tyr Ile Arg Cys Ser Asp Thr Arg Arg Lys
                340                 345                 350

Phe Arg Pro Arg Gly Gly Leu Lys Lys Arg Trp Arg Gln Trp Ala Lys
                355                 360                 365

Asp Leu Asp Arg Leu Val Glu Gln Arg Ala Cys Cys Ile Val Arg Ser
    370                 375                 380

Leu Gln Ala Asp Val Glu Leu Gln Thr Met Glu Arg Ala Gln Arg
385                 390                 395                 400

Phe Tyr Asp Val His Asp Cys Ala Ala Thr His Val Gly Pro Val Ala
                405                 410                 415

Val Arg Cys Ser Pro Cys Ala Gly Lys Gln Phe Asp Trp Asp Arg Tyr
                420                 425                 430

Arg Leu Leu Ala Ala Leu Arg Gln Glu His Ala Leu Asn Tyr Leu Arg
                435                 440                 445

Arg Leu Gln Arg Glu Trp Glu Ser Leu Glu Ala Gln Gln Val Lys Met
    450                 455                 460

Pro Tyr Leu Arg Phe Lys Tyr Ala Arg Lys Leu Glu Val Ser Gly Pro
465                 470                 475                 480

Leu Ile Gly Leu Glu Val Arg Arg Glu Pro Ser Met Gly Thr Ala Ile
                485                 490                 495
```

Ala Glu Met

<210> SEQ ID NO 212
<211> LENGTH: 358
<212> TYPE: PRT
<213> ORGANISM: Artificial sequence
<220> FEATURE:
<223> OTHER INFORMATION: Synthetic sequence

<400> SEQUENCE: 212

```
Ala Gly Thr Ala Gly Arg Arg His Gly Ser Leu Gly Ala Arg Arg Ser
1               5                   10                  15
Ile Asn Ile Ala Gly Val Thr Asp Arg His Gly Arg Trp Gly Cys Glu
            20                  25                  30
Ser Cys Val Tyr Thr Arg Asp Gln Ala Gly Asn Arg Ala Arg Cys Ala
        35                  40                  45
Pro Cys Asp Gln Ser Thr Tyr Ala Pro Asp Val Gln Glu Val Thr Ile
    50                  55                  60
Gly Gln Arg Gln Ala Lys Tyr Thr Ile Phe Leu Thr Leu Gln Ser Phe
65                  70                  75                  80
Ser Trp Thr Asn Thr Met Arg Asn Asn Lys Arg Ala Ala Gly Arg
                85                  90                  95
Ser Lys Arg Thr Thr Gly Lys Arg Ile Gly Gln Leu Ala Glu Ile Lys
            100                 105                 110
Ile Thr Gly Val Gly Leu Ala His Ala His Asn Val Ile Gln Arg Ser
        115                 120                 125
Leu Gln His Asn Ile Thr Lys Met Trp Arg Ala Glu Lys Gly Lys Ser
130                 135                 140
Lys Arg Val Ala Arg Leu Lys Lys Ala Lys Gln Leu Thr Lys Arg Arg
145                 150                 155                 160
Ala Tyr Phe Arg Arg Met Ser Arg Gln Ser Arg Gly Asn Gly Phe
                165                 170                 175
Phe Arg Thr Gly Lys Gly Gly Ile His Ala Val Ala Pro Val Lys Ile
            180                 185                 190
Gly Leu Asp Val Gly Met Ile Ala Ser Gly Ser Ser Glu Pro Ala Asp
        195                 200                 205
Glu Gln Thr Val Thr Leu Asp Ala Ile Trp Lys Gly Arg Lys Lys Lys
    210                 215                 220
Ile Arg Leu Ile Gly Ala Lys Gly Glu Leu Ala Val Ala Ala Cys Arg
225                 230                 235                 240
Phe Arg Glu Gln Gln Thr Lys Gly Asp Lys Cys Ile Pro Leu Ile Leu
                245                 250                 255
Gln Asp Gly Glu Val Arg Trp Asn Gln Asn Asn Trp Gln Cys His Pro
            260                 265                 270
Lys Lys Leu Val Pro Leu Cys Gly Leu Glu Val Ser Arg Lys Phe Val
        275                 280                 285
Ser Gln Ala Asp Arg Leu Ala Gln Asn Lys Val Ala Ser Pro Leu Ala
    290                 295                 300
Ala Arg Phe Asp Lys Thr Ser Val Lys Gly Thr Leu Val Glu Ser Asp
305                 310                 315                 320
Phe Ala Ala Val Leu Val Asn Val Thr Ser Ile Tyr Gln Gln Cys His
                325                 330                 335
Ala Met Leu Leu Arg Ser Gln Glu Pro Thr Pro Ser Leu Arg Val Gln
            340                 345                 350
Arg Thr Ile Thr Ser Met
```

<210> SEQ ID NO 213
<211> LENGTH: 369
<212> TYPE: PRT
<213> ORGANISM: Artificial sequence
<220> FEATURE:
<223> OTHER INFORMATION: Synthetic sequence

<400> SEQUENCE: 213

```
Gly Val Arg Phe Ser Pro Ala Gln Ser Gln Val Phe Phe Arg Thr Val
1               5                   10                  15

Ile Pro Gln Ser Val Glu Ala Arg Phe Ala Ile Asn Met Ala Ala Ile
            20                  25                  30

His Asp Ala Ala Gly Ala Phe Gly Cys Ser Val Cys Arg Phe Glu Asp
        35                  40                  45

Arg Thr Pro Arg Asn Ala Lys Ala Val His Gly Cys Ser Pro Cys Thr
    50                  55                  60

Arg Ser Thr Asn Arg Pro Asp Val Phe Val Leu Pro Val Gly Ala Ile
65                  70                  75                  80

Lys Ala Lys Tyr Asp Val Phe Met Arg Leu Leu Gly Phe Asn Trp Thr
                85                  90                  95

His Leu Asn Arg Arg Gln Ala Lys Arg Val Thr Val Arg Asp Arg Ile
            100                 105                 110

Gly Gln Leu Asp Glu Leu Ala Ile Ser Met Leu Thr Gly Lys Ala Lys
        115                 120                 125

Ala Val Leu Lys Lys Ser Ile Cys His Asn Val Asp Lys Ser Phe Lys
    130                 135                 140

Ala Met Arg Gly Ser Leu Lys Lys Leu His Arg Lys Ala Ser Lys Thr
145                 150                 155                 160

Gly Lys Ser Gln Leu Arg Ala Lys Leu Ser Asp Leu Arg Glu Arg Thr
                165                 170                 175

Asn Thr Thr Gln Glu Gly Ser His Val Glu Gly Asp Ser Asp Val Ala
            180                 185                 190

Leu Asn Lys Ile Gly Leu Asp Val Gly Leu Val Gly Lys Pro Asp Tyr
        195                 200                 205

Pro Ser Glu Glu Ser Val Glu Val Val Cys Leu Tyr Phe Val Gly
    210                 215                 220

Lys Val Leu Ile Leu Asp Ala Gln Gly Arg Ile Arg Asp Met Arg Ala
225                 230                 235                 240

Lys Gln Tyr Asp Gly Phe Lys Ile Pro Ile Ile Gln Arg Gly Gln Leu
                245                 250                 255

Thr Val Leu Ser Val Lys Asp Leu Gly Lys Trp Ser Leu Val Arg Gln
            260                 265                 270

Asp Tyr Val Leu Ala Gly Asp Leu Arg Phe Glu Pro Lys Ile Ser Lys
        275                 280                 285

Asp Arg Lys Tyr Ala Glu Cys Val Lys Arg Ile Ala Leu Ile Thr Leu
    290                 295                 300

Gln Ala Ser Leu Gly Phe Lys Glu Arg Ile Pro Tyr Tyr Val Thr Lys
305                 310                 315                 320

Gln Val Glu Ile Lys Asn Ala Ser His Ile Ala Phe Val Thr Glu Ala
                325                 330                 335

Ile Gln Asn Cys Ala Glu Asn Phe Arg Glu Met Thr Glu Tyr Leu Met
            340                 345                 350

Lys Tyr Gln Glu Lys Ser Pro Asp Leu Lys Val Leu Leu Thr Gln Leu
```

355                 360                 365
Met

<210> SEQ ID NO 214
<211> LENGTH: 486
<212> TYPE: PRT
<213> ORGANISM: Artificial sequence
<220> FEATURE:
<223> OTHER INFORMATION: Synthetic sequence

<400> SEQUENCE: 214

Arg Ala Val Val Gly Lys Val Phe Leu Glu Gln Ala Arg Ala Leu
1               5                   10                  15

Asn Leu Ala Thr Asn Phe Gly Thr Asn His Arg Thr Gly Cys Asn Gly
                20                  25                  30

Cys Tyr Val Thr Pro Gly Lys Leu Ser Ile Pro Gln Asp Gly Glu Lys
            35                  40                  45

Asn Ala Ala Gly Cys Thr Ser Cys Leu Met Lys Ala Thr Ala Ser Tyr
50                  55                  60

Val Ser Tyr Pro Lys Pro Leu Gly Glu Lys Val Ala Lys Tyr Ser Thr
65                  70                  75                  80

Leu Asp Ala Leu Lys Gly Phe Pro Trp Tyr Ser Leu Arg Leu Asn Leu
                85                  90                  95

Arg Pro Asn Tyr Arg Gly Lys Pro Ile Asn Gly Val Gln Glu Val Ala
            100                 105                 110

Pro Val Ser Lys Phe Arg Leu Ala Glu Glu Val Ile Gln Ala Val Gln
        115                 120                 125

Arg Tyr His Phe Thr Glu Leu Glu Gln Ser Phe Pro Gly Gly Arg Arg
    130                 135                 140

Arg Leu Arg Glu Leu Arg Ala Phe Tyr Thr Lys Glu Tyr Arg Arg Ala
145                 150                 155                 160

Pro Glu Gln Arg Gln His Val Val Asn Gly Asp Arg Asn Ile Val Val
                165                 170                 175

Val Thr Val Leu His Glu Leu Gly Phe Ser Val Gly Met Phe Asn Glu
            180                 185                 190

Val Glu Leu Leu Pro Lys Thr Pro Ile Glu Cys Ala Val Asn Val Phe
        195                 200                 205

Ile Arg Gly Asn Arg Val Leu Leu Glu Val Arg Lys Pro Gln Phe Asp
    210                 215                 220

Lys Glu Arg Leu Leu Val Glu Ser Leu Trp Lys Lys Asp Ser Arg Arg
225                 230                 235                 240

His Thr Ala Lys Trp Thr Pro Pro Asn Asn Glu Gly Arg Ile Phe Thr
                245                 250                 255

Ala Glu Gly Trp Lys Asp Phe Gln Leu Pro Leu Leu Gly Ser Thr
            260                 265                 270

Ser Arg Ser Leu Arg Ala Ile Glu Lys Glu Gly Phe Val Gln Leu Ala
        275                 280                 285

Pro Gly Arg Asp Pro Asp Tyr Asn Asn Thr Ile Asp Glu Gln His Ser
    290                 295                 300

Gly Arg Pro Phe Leu Pro Leu Tyr Leu Tyr Leu Gln Gly Thr Ile Ser
305                 310                 315                 320

Gln Glu Tyr Cys Val Phe Ala Gly Thr Trp Val Ile Pro Phe Gln Asp
                325                 330                 335

Gly Ile Ser Pro Tyr Ser Thr Lys Asp Thr Phe Gln Pro Asp Leu Lys
            340                 345                 350

```
Arg Lys Ala Tyr Ser Leu Leu Asp Ala Val Lys His Arg Leu Gly
            355                 360                 365

Asn Lys Val Ala Ser Gly Leu Gln Tyr Gly Arg Phe Pro Ala Ile Glu
    370                 375                 380

Glu Leu Lys Arg Leu Val Arg Met His Gly Ala Thr Arg Lys Ile Pro
385                 390                 395                 400

Arg Gly Glu Lys Asp Leu Leu Lys Lys Gly Asp Pro Asp Thr Pro Glu
                405                 410                 415

Trp Trp Leu Leu Glu Gln Tyr Pro Glu Phe Trp Arg Leu Cys Asp Ala
            420                 425                 430

Ala Ala Lys Arg Val Ser Gln Asn Val Gly Leu Leu Ser Leu Lys
                435                 440                 445

Lys Gln Pro Leu Trp Gln Arg Arg Trp Leu Glu Ser Arg Thr Arg Asn
    450                 455                 460

Glu Pro Leu Asp Asn Leu Pro Leu Ser Met Ala Leu Thr Leu His Leu
465                 470                 475                 480

Thr Asn Glu Glu Ala Leu
                485

<210> SEQ ID NO 215
<211> LENGTH: 400
<212> TYPE: PRT
<213> ORGANISM: Artificial sequence
<220> FEATURE:
<223> OTHER INFORMATION: Synthetic sequence

<400> SEQUENCE: 215

Ala Ala Val Tyr Ser Lys Phe Tyr Ile Glu Asn His Phe Lys Met Gly
1               5                   10                  15

Ile Pro Glu Thr Leu Ser Arg Ile Arg Gly Pro Ser Ile Ile Gln Gly
            20                  25                  30

Phe Ser Val Asn Glu Asn Tyr Ile Asn Ile Ala Gly Val Gly Asp Arg
        35                  40                  45

Asp Phe Ile Phe Gly Cys Lys Lys Cys Lys Tyr Thr Arg Gly Lys Pro
    50                  55                  60

Ser Ser Lys Lys Ile Asn Lys Cys His Pro Cys Lys Arg Ser Thr Tyr
65                  70                  75                  80

Pro Glu Pro Val Ile Asp Val Arg Gly Ser Ile Ser Glu Phe Lys Tyr
                85                  90                  95

Lys Ile Tyr Asn Lys Leu Lys Gln Glu Pro Asn Gln Ser Ile Lys Gln
            100                 105                 110

Asn Thr Lys Gly Arg Met Asn Pro Ser Asp His Thr Ser Ser Asn Asp
        115                 120                 125

Gly Ile Ile Asn Gly Ile Asp Asn Arg Ile Ala Tyr Asn Val Ile
    130                 135                 140

Phe Ser Ser Tyr Lys His Leu Met Glu Lys Gln Ile Asn Leu Leu Arg
145                 150                 155                 160

Asp Thr Thr Lys Arg Lys Ala Arg Gln Ile Lys Lys Tyr Asn Asn Ser
                165                 170                 175

Gly Lys Lys Lys His Ser Leu Arg Ser Gln Thr Lys Gly Asn Leu Lys
            180                 185                 190

Asn Arg Tyr His Met Leu Gly Met Phe Lys Lys Gly Ser Leu Thr Ile
        195                 200                 205

Thr Asn Glu Gly Asp Phe Ile Thr Ala Val Arg Lys Val Gly Leu Asp
    210                 215                 220
```

Ile Ser Leu Tyr Lys Asn Glu Ser Leu Asn Lys Gln Glu Val Glu Thr
225                 230                 235                 240

Glu Leu Cys Leu Asn Ile Lys Trp Gly Arg Thr Lys Ser Tyr Thr Val
            245                 250                 255

Ser Gly Tyr Ile Pro Leu Pro Ile Asn Ile Asp Trp Lys Leu Tyr Leu
        260                 265                 270

Phe Glu Lys Glu Thr Gly Leu Thr Leu Arg Leu Phe Gly Asn Lys Tyr
    275                 280                 285

Lys Ile Gln Ser Lys Lys Phe Leu Ile Ala Gln Leu Phe Lys Pro Lys
290                 295                 300

Arg Pro Pro Cys Ala Asp Pro Val Val Lys Ala Gln Lys Trp Ser
305                 310                 315                 320

Ala Leu Asn Ala His Val Gln Gln Met Ala Gly Leu Phe Ser Asp Ser
            325                 330                 335

His Leu Leu Lys Arg Glu Leu Lys Asn Arg Met His Lys Gln Leu Asp
        340                 345                 350

Phe Lys Ser Leu Trp Val Gly Thr Glu Asp Tyr Ile Lys Trp Phe Glu
    355                 360                 365

Glu Leu Ser Arg Ser Tyr Val Glu Gly Ala Glu Lys Ser Leu Glu Phe
370                 375                 380

Phe Arg Gln Asp Tyr Phe Cys Phe Asn Tyr Thr Lys Gln Thr Thr Met
385                 390                 395                 400

<210> SEQ ID NO 216
<211> LENGTH: 666
<212> TYPE: PRT
<213> ORGANISM: Artificial sequence
<220> FEATURE:
<223> OTHER INFORMATION: Synthetic sequence

<400> SEQUENCE: 216

Pro Gln Gln Gln Arg Asp Leu Met Leu Met Ala Ala Asn Tyr Asp Gln
1               5                   10                  15

Asp Tyr Gly Asn Gly Cys Gly Pro Cys Thr Val Val Ala Ser Ala Ala
            20                  25                  30

Tyr Arg Pro Asp Pro Gln Ala Gln His Gly Cys Lys Arg His Leu Arg
        35                  40                  45

Thr Leu Gly Ala Ser Ala Val Thr His Val Gly Leu Gly Asp Arg Thr
    50                  55                  60

Ala Thr Ile Thr Ala Leu His Arg Leu Arg Gly Pro Ala Ala Leu Ala
65                  70                  75                  80

Ala Arg Ala Arg Ala Ala Gln Ala Ala Ser Ala Pro Met Thr Pro Asp
            85                  90                  95

Thr Asp Ala Pro Asp Asp Arg Arg Leu Glu Ala Ile Asp Ala Asp
        100                 105                 110

Asp Val Val Leu Val Gly Ala His Arg Ala Leu Trp Ser Ala Val Arg
    115                 120                 125

Arg Trp Ala Asp Asp Arg Arg Ala Ala Leu Arg Arg Leu His Ser
130                 135                 140

Glu Arg Glu Trp Leu Leu Lys Asp Gln Ile Arg Trp Ala Glu Leu Tyr
145                 150                 155                 160

Thr Leu Ile Glu Ala Ser Gly Thr Pro Pro Gln Gly Arg Trp Arg Asn
            165                 170                 175

Thr Leu Gly Ala Leu Arg Gly Gln Ser Arg Trp Arg Arg Val Leu Ala
        180                 185                 190

-continued

```
Pro Thr Met Arg Ala Thr Cys Ala Glu Thr His Ala Glu Leu Trp Asp
        195                 200                 205
Ala Leu Ala Glu Leu Val Pro Glu Met Ala Lys Asp Arg Arg Gly Leu
        210                 215                 220
Leu Arg Pro Pro Val Glu Ala Asp Ala Leu Trp Arg Ala Pro Met Ile
225                 230                 235                 240
Val Glu Gly Trp Arg Gly His Ser Val Val Asp Ala Val Ala
                245                 250                 255
Pro Pro Leu Asp Leu Pro Gln Pro Cys Ala Trp Thr Ala Val Arg Leu
                260                 265                 270
Ser Gly Asp Pro Arg Gln Arg Trp Gly Leu His Leu Ala Val Pro Pro
        275                 280                 285
Leu Gly Gln Val Gln Pro Pro Asp Pro Leu Lys Ala Thr Leu Ala Val
        290                 295                 300
Ser Met Arg His Arg Gly Gly Val Arg Val Arg Thr Leu Gln Ala Met
305                 310                 315                 320
Ala Val Asp Ala Asp Ala Pro Met Gln Arg His Leu Gln Val Pro Leu
                325                 330                 335
Thr Leu Gln Arg Gly Gly Gly Leu Gln Trp Gly Ile His Ser Arg Gly
                340                 345                 350
Val Arg Arg Arg Glu Ala Arg Ser Met Ala Ser Trp Glu Gly Pro Pro
        355                 360                 365
Ile Trp Thr Gly Leu Gln Leu Val Asn Arg Trp Lys Gly Gln Gly Ser
        370                 375                 380
Ala Leu Leu Ala Pro Asp Arg Pro Asp Thr Pro Pro Tyr Ala Pro
385                 390                 395                 400
Asp Ala Ala Val Ala Pro Ala Gln Pro Asp Thr Lys Arg Ala Arg Arg
                405                 410                 415
Thr Leu Lys Glu Ala Cys Thr Val Cys Arg Cys Ala Pro Gly His Met
                420                 425                 430
Arg Gln Leu Gln Val Thr Leu Thr Gly Asp Gly Thr Trp Arg Arg Phe
        435                 440                 445
Arg Leu Arg Ala Pro Gln Gly Ala Lys Arg Lys Ala Glu Val Leu Lys
        450                 455                 460
Val Ala Thr Gln His Asp Glu Arg Ile Ala Asn Tyr Thr Ala Trp Tyr
465                 470                 475                 480
Leu Lys Arg Pro Glu His Ala Ala Gly Cys Asp Thr Cys Asp Gly Asp
                485                 490                 495
Ser Arg Leu Asp Gly Ala Cys Arg Gly Cys Arg Pro Leu Leu Val Gly
                500                 505                 510
Asp Gln Cys Phe Arg Arg Tyr Leu Asp Lys Ile Glu Ala Asp Arg Asp
        515                 520                 525
Asp Gly Leu Ala Gln Ile Lys Pro Lys Ala Gln Glu Ala Val Ala Ala
        530                 535                 540
Met Ala Ala Lys Arg Asp Ala Arg Ala Gln Lys Val Ala Ala Arg Ala
545                 550                 555                 560
Ala Lys Leu Ser Glu Ala Thr Gly Gln Arg Thr Ala Ala Thr Arg Asp
                565                 570                 575
Ala Ser His Glu Ala Arg Ala Gln Lys Glu Leu Glu Ala Val Ala Thr
                580                 585                 590
Glu Gly Thr Thr Val Arg His Asp Ala Ala Ala Val Ser Ala Phe Gly
        595                 600                 605
```

```
Ser Trp Val Ala Arg Lys Gly Asp Glu Tyr Arg His Gln Val Gly Val
    610                 615                 620

Leu Ala Asn Arg Leu Glu His Gly Leu Arg Leu Gln Glu Leu Met Ala
625                 630                 635                 640

Pro Asp Ser Val Val Ala Asp Gln Gln Arg Ala Ser Gly His Ala Arg
                645                 650                 655

Val Gly Tyr Arg Tyr Val Leu Thr Ala Met
                660                 665

<210> SEQ ID NO 217
<211> LENGTH: 560
<212> TYPE: PRT
<213> ORGANISM: Artificial sequence
<220> FEATURE:
<223> OTHER INFORMATION: Synthetic sequence

<400> SEQUENCE: 217

Ala Val Ala His Pro Val Gly Arg Gly Asn Ala Gly Ser Pro Gly Ala
1               5                   10                  15

Arg Gly Pro Glu Glu Leu Pro Arg Gln Leu Val Asn Arg Ala Ser Asn
                20                  25                  30

Val Thr Arg Pro Ala Thr Tyr Gly Cys Ala Pro Cys Arg His Val Arg
            35                  40                  45

Leu Ser Ile Pro Lys Pro Val Leu Thr Gly Cys Arg Ala Cys Glu Gln
    50                  55                  60

Thr Thr His Pro Ala Pro Lys Arg Ala Val Arg Gly Ala Asp Ala
65                  70                  75                  80

Ala Lys Tyr Asp Leu Ala Ala Phe Phe Ala Gly Trp Ala Ala Asp Leu
                85                  90                  95

Glu Gly Arg Asn Arg Arg Gln Val His Ala Pro Leu Asp Pro Gln
                100                 105                 110

Pro Asp Pro Asn His Glu Pro Ala Val Thr Leu Gln Lys Ile Asp Leu
            115                 120                 125

Ala Glu Val Ser Ile Glu Glu Phe Gln Arg Val Leu Ala Arg Ser Val
    130                 135                 140

Lys His Arg His Asp Gly Arg Ala Ser Arg Glu Arg Glu Lys Ala Arg
145                 150                 155                 160

Ala Tyr Ala Gln Val Ala Lys Lys Arg Arg Asn Ser His Ala His Gly
                165                 170                 175

Ala Arg Thr Arg Arg Ala Val Arg Arg Gln Thr Arg Ala Val Arg Arg
            180                 185                 190

Ala His Arg Met Gly Ala Asn Ser Gly Glu Ile Leu Val Ala Ser Gly
    195                 200                 205

Ala Glu Asp Pro Val Pro Glu Ala Ile Asp His Ala Ala Gln Leu Arg
210                 215                 220

Arg Arg Ile Arg Ala Cys Ala Arg Asp Leu Glu Gly Leu Arg His Leu
225                 230                 235                 240

Ser Arg Arg Tyr Leu Lys Thr Leu Glu Lys Pro Cys Arg Arg Pro Arg
                245                 250                 255

Ala Pro Asp Leu Gly Arg Ala Arg Cys His Ala Leu Val Glu Ser Leu
            260                 265                 270

Gln Ala Ala Glu Arg Glu Leu Glu Glu Leu Arg Arg Cys Asp Ser Pro
    275                 280                 285

Asp Thr Ala Met Arg Arg Leu Asp Ala Val Leu Ala Ala Ala Ser
    290                 295                 300
```

Thr Asp Ala Thr Phe Ala Thr Gly Trp Thr Val Gly Met Asp Leu
305                 310                 315                 320

Gly Val Ala Pro Arg Gly Ser Ala Ala Pro Glu Val Ser Pro Met Glu
            325                 330                 335

Met Ala Ile Ser Val Phe Trp Arg Lys Gly Ser Arg Arg Val Ile Val
            340                 345                 350

Ser Lys Pro Ile Ala Gly Met Pro Ile Arg Arg His Glu Leu Ile Arg
            355                 360                 365

Leu Glu Gly Leu Gly Thr Leu Arg Leu Asp Gly Asn His Tyr Thr Gly
    370                 375                 380

Ala Gly Val Thr Lys Gly Arg Gly Leu Ser Glu Gly Thr Glu Pro Asp
385                 390                 395                 400

Phe Arg Glu Lys Ser Pro Ser Thr Leu Gly Phe Thr Leu Ser Asp Tyr
                405                 410                 415

Arg His Glu Ser Arg Trp Arg Pro Tyr Gly Ala Lys Gln Gly Lys Thr
                420                 425                 430

Ala Arg Gln Phe Phe Ala Ala Met Ser Arg Glu Leu Arg Ala Leu Val
            435                 440                 445

Glu His Gln Val Leu Ala Pro Met Gly Pro Pro Leu Leu Glu Ala His
    450                 455                 460

Glu Arg Arg Phe Glu Thr Leu Leu Lys Gly Gln Asp Asn Lys Ser Ile
465                 470                 475                 480

His Ala Gly Gly Gly Arg Tyr Val Trp Arg Gly Pro Pro Asp Ser
                485                 490                 495

Lys Lys Arg Pro Ala Ala Asp Gly Asp Trp Phe Arg Phe Gly Arg Gly
            500                 505                 510

His Ala Asp His Arg Gly Trp Ala Asn Lys Arg His Glu Leu Ala Ala
            515                 520                 525

Asn Tyr Leu Gln Ser Ala Phe Arg Leu Trp Ser Thr Leu Ala Glu Ala
    530                 535                 540

Gln Glu Pro Thr Pro Tyr Ala Arg Tyr Lys Tyr Thr Arg Val Thr Met
545                 550                 555                 560

<210> SEQ ID NO 218
<211> LENGTH: 404
<212> TYPE: PRT
<213> ORGANISM: Artificial sequence
<220> FEATURE:
<223> OTHER INFORMATION: Synthetic sequence

<400> SEQUENCE: 218

Trp Asp Phe Leu Thr Leu Gln Val Tyr Glu Arg His Thr Ser Pro Glu
1               5                   10                  15

Val Cys Val Ala Gly Asn Ser Thr Lys Cys Ala Ser Gly Thr Arg Lys
            20                  25                  30

Ser Asp His Thr His Gly Val Gly Val Lys Leu Gly Ala Gln Glu Ile
        35                  40                  45

Asn Val Ser Ala Asn Asp Asp Arg Asp His Glu Val Gly Cys Asn Ile
    50                  55                  60

Cys Val Ile Ser Arg Val Ser Leu Asp Ile Lys Gly Trp Arg Tyr Gly
65                  70                  75                  80

Cys Glu Ser Cys Val Gln Ser Thr Pro Glu Trp Arg Ser Ile Val Arg
                85                  90                  95

Phe Asp Arg Asn His Lys Glu Ala Lys Gly Glu Cys Leu Ser Arg Phe
            100                 105                 110

Glu Tyr Trp Gly Ala Gln Ser Ile Ala Arg Ser Leu Lys Arg Asn Lys
            115                 120                 125

Leu Met Gly Gly Val Asn Leu Asp Glu Leu Ala Ile Val Gln Asn Glu
130                 135                 140

Asn Val Val Lys Thr Ser Leu Lys His Leu Phe Asp Lys Arg Lys Asp
145                 150                 155                 160

Arg Ile Gln Ala Asn Leu Lys Ala Val Lys Val Arg Met Arg Glu Arg
            165                 170                 175

Arg Lys Ser Gly Arg Gln Arg Lys Ala Leu Arg Arg Gln Cys Arg Lys
            180                 185                 190

Leu Lys Arg Tyr Leu Arg Ser Tyr Asp Pro Ser Asp Ile Lys Glu Gly
            195                 200                 205

Asn Ser Cys Ser Ala Phe Thr Lys Leu Gly Leu Asp Ile Gly Ile Ser
210                 215                 220

Pro Asn Lys Pro Pro Lys Ile Glu Pro Lys Val Glu Val Val Phe Ser
225                 230                 235                 240

Leu Phe Tyr Gln Gly Ala Cys Asp Lys Ile Val Thr Val Ser Ser Pro
            245                 250                 255

Glu Ser Pro Leu Pro Arg Ser Trp Lys Ile Lys Ile Asp Gly Ile Arg
            260                 265                 270

Ala Leu Tyr Val Lys Ser Thr Lys Val Lys Phe Gly Gly Arg Thr Phe
            275                 280                 285

Arg Ala Gly Gln Arg Asn Asn Arg Arg Lys Val Arg Pro Pro Asn Val
            290                 295                 300

Lys Lys Gly Lys Arg Lys Gly Ser Arg Ser Gln Phe Phe Asn Lys Phe
305                 310                 315                 320

Ala Val Gly Leu Asp Ala Val Ser Gln Gln Leu Pro Ile Ala Ser Val
            325                 330                 335

Gln Gly Leu Trp Gly Arg Ala Glu Thr Lys Lys Ala Gln Thr Ile Cys
            340                 345                 350

Leu Lys Gln Leu Glu Ser Asn Lys Pro Leu Lys Glu Ser Gln Arg Cys
            355                 360                 365

Leu Phe Leu Ala Asp Asn Trp Val Val Arg Val Cys Gly Phe Leu Arg
            370                 375                 380

Ala Leu Ser Gln Arg Gln Gly Pro Thr Pro Tyr Ile Arg Tyr Arg Tyr
385                 390                 395                 400

Arg Cys Asn Met

<210> SEQ ID NO 219
<211> LENGTH: 392
<212> TYPE: PRT
<213> ORGANISM: Artificial sequence
<220> FEATURE:
<223> OTHER INFORMATION: Synthetic sequence

<400> SEQUENCE: 219

Ala Arg Asn Val Gly Gln Arg Asn Ala Ser Arg Gln Ser Lys Arg Glu
1               5                   10                  15

Ser Ala Lys Ala Arg Ser Arg Arg Val Thr Gly Gly His Ala Ser Val
            20                  25                  30

Thr Gln Gly Val Ala Leu Ile Asn Ala Ala Asn Ala Asp Arg Asp
            35                  40                  45

His Thr Thr Gly Cys Glu Pro Cys Thr Trp Glu Arg Val Asn Leu Pro
50                  55                  60

Leu Gln Glu Val Ile His Gly Cys Asp Ser Cys Thr Lys Ser Ser Pro

```
                65                  70                  75                  80
        Phe Trp Arg Asp Ile Lys Val Val Asn Lys Gly Tyr Arg Glu Ala Lys
                        85                  90                  95

Glu Glu Ile Met Arg Ile Ala Ser Gly Ile Ser Ala Asp His Leu Ser
                    100                 105                 110

Arg Ala Leu Ser His Asn Lys Val Met Gly Arg Leu Asn Leu Asp Glu
                    115                 120                 125

Val Cys Ile Leu Asp Phe Arg Thr Val Leu Asp Thr Ser Leu Lys His
                130                 135                 140

Leu Thr Asp Ser Arg Ser Asn Gly Ile Lys Glu His Ile Arg Ala Val
        145                 150                 155                 160

His Arg Lys Ile Arg Met Arg Arg Lys Ser Gly Lys Thr Ala Arg Ala
                        165                 170                 175

Leu Arg Lys Gln Tyr Phe Ala Leu Arg Arg Gln Trp Lys Ala Gly His
                    180                 185                 190

Lys Pro Asn Ser Ile Arg Glu Gly Asn Ser Leu Thr Ala Leu Arg Ala
                    195                 200                 205

Val Gly Phe Asp Val Gly Val Ser Glu Gly Thr Glu Pro Met Pro Ala
                210                 215                 220

Pro Gln Thr Glu Val Val Leu Ser Val Phe Tyr Lys Gly Ser Ala Thr
        225                 230                 235                 240

Arg Ile Leu Arg Ile Ser Ser Pro His Pro Ile Ala Lys Arg Ser Trp
                        245                 250                 255

Lys Val Lys Ile Ala Gly Ile Lys Ala Leu Lys Leu Ile Arg Arg Glu
                    260                 265                 270

His Asp Phe Ser Phe Gly Arg Glu Thr Tyr Asn Ala Ser Gln Arg Ala
                    275                 280                 285

Glu Lys Arg Lys Phe Ser Pro His Ala Ala Arg Lys Asp Phe Phe Asn
                290                 295                 300

Ser Phe Ala Val Gln Leu Asp Arg Leu Ala Gln Gln Leu Cys Val Ser
        305                 310                 315                 320

Ser Val Glu Asn Leu Trp Val Thr Glu Pro Gln Gln Lys Leu Leu Thr
                        325                 330                 335

Leu Ala Lys Asp Thr Ala Pro Tyr Gly Ile Arg Glu Gly Ala Arg Phe
                    340                 345                 350

Ala Asp Thr Arg Ala Arg Leu Ala Trp Asn Trp Val Phe Arg Val Cys
                    355                 360                 365

Gly Phe Thr Arg Ala Leu His Gln Glu Gln Glu Pro Thr Pro Tyr Cys
                370                 375                 380

Arg Phe Thr Trp Arg Ser Lys Met
        385                 390

<210> SEQ ID NO 220
<211> LENGTH: 59
<212> TYPE: DNA
<213> ORGANISM: Artificial sequence
<220> FEATURE:
<223> OTHER INFORMATION: Synthetic sequence

<400> SEQUENCE: 220
ctacgccgat tatcttctga caactttcgc aagcggtgta aggtaaaaaa tgcgggcac          59

<210> SEQ ID NO 221
<211> LENGTH: 59
<212> TYPE: DNA
<213> ORGANISM: Artificial sequence
```

<220> FEATURE:
<223> OTHER INFORMATION: Synthetic sequence

<400> SEQUENCE: 221
gtgcccgcat tttttacctt acaccgcttg cgaaagttgt cagaagataa tcggcgtag    59

<210> SEQ ID NO 222
<211> LENGTH: 90
<212> TYPE: DNA
<213> ORGANISM: Artificial sequence
<220> FEATURE:
<223> OTHER INFORMATION: Synthetic sequence

<400> SEQUENCE: 222
tttatatgtt tctcctggag ataacgcaat cgtgacaact ttcgcaagcg gtgtaaggta    60
gcaggcttcc gaattccgcg tttttacggc                                    90

<210> SEQ ID NO 223
<211> LENGTH: 90
<212> TYPE: DNA
<213> ORGANISM: Artificial sequence
<220> FEATURE:
<223> OTHER INFORMATION: Synthetic sequence

<400> SEQUENCE: 223
gccgtaaaaa cgcggaattc ggaagcctgc taccttacac cgcttgcgaa agttgtcacg    60
attgcgttat ctccaggaga aacatataaa                                    90

<210> SEQ ID NO 224
<211> LENGTH: 56
<212> TYPE: DNA
<213> ORGANISM: Artificial sequence
<220> FEATURE:
<223> OTHER INFORMATION: Synthetic sequence

<400> SEQUENCE: 224
gatcttcagc tatacattat tgcaccaaca ctaaggcaga gtatgtttac ctggac       56

<210> SEQ ID NO 225
<211> LENGTH: 56
<212> TYPE: DNA
<213> ORGANISM: Artificial sequence
<220> FEATURE:
<223> OTHER INFORMATION: Synthetic sequence

<400> SEQUENCE: 225
gatcttcagc tttgtattac tggaaggatg cttgcttgag gtgtaaaaac ctggac       56

<210> SEQ ID NO 226
<211> LENGTH: 5
<212> TYPE: DNA
<213> ORGANISM: Artificial sequence
<220> FEATURE:
<223> OTHER INFORMATION: Synthetic sequence

<400> SEQUENCE: 226 ttttt                                                                5

<210> SEQ ID NO 227
<211> LENGTH: 6
<212> TYPE: DNA
<213> ORGANISM: Artificial sequence
<220> FEATURE:
<223> OTHER INFORMATION: Synthetic sequence

```
<400> SEQUENCE: 227 tttttt                                                              6

<210> SEQ ID NO 228
<211> LENGTH: 7
<212> TYPE: DNA
<213> ORGANISM: Artificial sequence
<220> FEATURE:
<223> OTHER INFORMATION: Synthetic sequence

<400> SEQUENCE: 228 ttttttt                                                             7

<210> SEQ ID NO 229
<211> LENGTH: 8
<212> TYPE: DNA
<213> ORGANISM: Artificial sequence
<220> FEATURE:
<223> OTHER INFORMATION: Synthetic sequence

<400> SEQUENCE: 229 tttttttt                                                            8

<210> SEQ ID NO 230
<211> LENGTH: 9
<212> TYPE: DNA
<213> ORGANISM: Artificial sequence
<220> FEATURE:
<223> OTHER INFORMATION: Synthetic sequence

<400> SEQUENCE: 230 ttttttttt                                                           9

<210> SEQ ID NO 231
<211> LENGTH: 10
<212> TYPE: DNA
<213> ORGANISM: Artificial sequence
<220> FEATURE:
<223> OTHER INFORMATION: Synthetic sequence

<400> SEQUENCE: 231
tttttttttt                                                         10

<210> SEQ ID NO 232
<211> LENGTH: 11
<212> TYPE: DNA
<213> ORGANISM: Artificial sequence
<220> FEATURE:
<223> OTHER INFORMATION: Synthetic sequence

<400> SEQUENCE: 232
tttttttttt t                                                       11

<210> SEQ ID NO 233
<211> LENGTH: 12
<212> TYPE: DNA
<213> ORGANISM: Artificial sequence
<220> FEATURE:
<223> OTHER INFORMATION: Synthetic sequence

<400> SEQUENCE: 233
tttttttttt tt                                                      12

<210> SEQ ID NO 234
<211> LENGTH: 55
```

```
<212> TYPE: DNA
<213> ORGANISM: Artificial sequence
<220> FEATURE:
<223> OTHER INFORMATION: Synthetic sequence

<400> SEQUENCE: 234
gccggggtgg tgcccatcct ggtcgagctg gacggcgacg taaacggcca caagc      55

<210> SEQ ID NO 235
<211> LENGTH: 55
<212> TYPE: DNA
<213> ORGANISM: Artificial sequence
<220> FEATURE:
<223> OTHER INFORMATION: Synthetic sequence

<400> SEQUENCE: 235
gccggggtgg tgcccatcct ggtcgagctg gacggcgacg tgctcggcca caagc      55

<210> SEQ ID NO 236
<211> LENGTH: 55
<212> TYPE: DNA
<213> ORGANISM: Artificial sequence
<220> FEATURE:
<223> OTHER INFORMATION: Synthetic sequence

<400> SEQUENCE: 236
gccggggtgg tgcccatcct ggtcgagctg gacggcgagc taaacggcca caagc      55

<210> SEQ ID NO 237
<211> LENGTH: 55
<212> TYPE: DNA
<213> ORGANISM: Artificial sequence
<220> FEATURE:
<223> OTHER INFORMATION: Synthetic sequence

<400> SEQUENCE: 237
gccggggtgg tgcccatcct ggtcgagctg gacggcctcg taaacggcca caagc      55

<210> SEQ ID NO 238
<211> LENGTH: 55
<212> TYPE: DNA
<213> ORGANISM: Artificial sequence
<220> FEATURE:
<223> OTHER INFORMATION: Synthetic sequence

<400> SEQUENCE: 238
gccggggtgg tgcccatcct ggtcgagctg gacgcggacg taaacggcca caagc      55

<210> SEQ ID NO 239
<211> LENGTH: 55
<212> TYPE: DNA
<213> ORGANISM: Artificial sequence
<220> FEATURE:
<223> OTHER INFORMATION: Synthetic sequence

<400> SEQUENCE: 239
gccggggtgg tgcccatcct ggtcgagctg gagcgcgacg taaacggcca caagc      55

<210> SEQ ID NO 240
<211> LENGTH: 55
<212> TYPE: DNA
<213> ORGANISM: Artificial sequence
<220> FEATURE:
<223> OTHER INFORMATION: Synthetic sequence

<400> SEQUENCE: 240
```

```
gccggggtgg tgcccatcct ggtcgagctg ctcggcgacg taaacggcca caagc      55
```

<210> SEQ ID NO 241
<211> LENGTH: 55
<212> TYPE: DNA
<213> ORGANISM: Artificial sequence
<220> FEATURE:
<223> OTHER INFORMATION: Synthetic sequence

<400> SEQUENCE: 241

```
gccggggtgg tgcccatcct ggtcgagcac gacggcgacg taaacggcca caagc      55
```

<210> SEQ ID NO 242
<211> LENGTH: 55
<212> TYPE: DNA
<213> ORGANISM: Artificial sequence
<220> FEATURE:
<223> OTHER INFORMATION: Synthetic sequence

<400> SEQUENCE: 242

```
gccggggtgg tgcccatcct ggtcgacgtg gacggcgacg taaacggcca caagc      55
```

<210> SEQ ID NO 243
<211> LENGTH: 55
<212> TYPE: DNA
<213> ORGANISM: Artificial sequence
<220> FEATURE:
<223> OTHER INFORMATION: Synthetic sequence

<400> SEQUENCE: 243

```
gccggggtgg tgcccatcct ggtcctgctg gacggcgacg taaacggcca caagc      55
```

<210> SEQ ID NO 244
<211> LENGTH: 55
<212> TYPE: DNA
<213> ORGANISM: Artificial sequence
<220> FEATURE:
<223> OTHER INFORMATION: Synthetic sequence

<400> SEQUENCE: 244

```
gccggggtgg tgcccatcct ggaggagctg gacggcgacg taaacggcca caagc      55
```

<210> SEQ ID NO 245
<211> LENGTH: 55
<212> TYPE: DNA
<213> ORGANISM: Artificial sequence
<220> FEATURE:
<223> OTHER INFORMATION: Synthetic sequence

<400> SEQUENCE: 245

```
gccggggtgg tgcccatcct cctcgagctg gacggcgacg taaacggcca caagc      55
```

<210> SEQ ID NO 246
<211> LENGTH: 34
<212> TYPE: DNA
<213> ORGANISM: Artificial sequence
<220> FEATURE:
<223> OTHER INFORMATION: Synthetic sequence

<400> SEQUENCE: 246

```
gtgttaatac aaaggtacag gaacaaagaa tttg                              34
```

<210> SEQ ID NO 247
<211> LENGTH: 18
<212> TYPE: DNA
<213> ORGANISM: Artificial sequence

```
<220> FEATURE:
<223> OTHER INFORMATION: Synthetic sequence

<400> SEQUENCE: 247
caaagagaag cctcggcc                                                    18

<210> SEQ ID NO 248
<211> LENGTH: 55
<212> TYPE: DNA
<213> ORGANISM: Artificial sequence
<220> FEATURE:
<223> OTHER INFORMATION: Synthetic sequence

<400> SEQUENCE: 248
tttattcaag gcaatcacta tcagctgtgg aacacccagg taaactaaca caact          55

<210> SEQ ID NO 249
<211> LENGTH: 55
<212> TYPE: DNA
<213> ORGANISM: Artificial sequence
<220> FEATURE:
<223> OTHER INFORMATION: Synthetic sequence

<400> SEQUENCE: 249
tttattcaag gcaatcacta tcagctgtgg aacacccagg tgctctaaca caact          55

<210> SEQ ID NO 250
<211> LENGTH: 55
<212> TYPE: DNA
<213> ORGANISM: Artificial sequence
<220> FEATURE:
<223> OTHER INFORMATION: Synthetic sequence

<400> SEQUENCE: 250
tttattcaag gcaatcacta tcagctgtgg aacacccacc taaactaaca caact          55

<210> SEQ ID NO 251
<211> LENGTH: 55
<212> TYPE: DNA
<213> ORGANISM: Artificial sequence
<220> FEATURE:
<223> OTHER INFORMATION: Synthetic sequence

<400> SEQUENCE: 251
tttattcaag gcaatcacta tcagctgtgg aacaccgtgg taaactaaca caact          55

<210> SEQ ID NO 252
<211> LENGTH: 55
<212> TYPE: DNA
<213> ORGANISM: Artificial sequence
<220> FEATURE:
<223> OTHER INFORMATION: Synthetic sequence

<400> SEQUENCE: 252
tttattcaag gcaatcacta tcagctgtgg aacaggcagg taaactaaca caact          55

<210> SEQ ID NO 253
<211> LENGTH: 55
<212> TYPE: DNA
<213> ORGANISM: Artificial sequence
<220> FEATURE:
<223> OTHER INFORMATION: Synthetic sequence

<400> SEQUENCE: 253
tttattcaag gcaatcacta tcagctgtgg aagtcccagg taaactaaca caact          55
```

<210> SEQ ID NO 254
<211> LENGTH: 55
<212> TYPE: DNA
<213> ORGANISM: Artificial sequence
<220> FEATURE:
<223> OTHER INFORMATION: Synthetic sequence

<400> SEQUENCE: 254
tttattcaag gcaatcacta tcagctgtgg ttcacccagg taaactaaca caact        55

<210> SEQ ID NO 255
<211> LENGTH: 55
<212> TYPE: DNA
<213> ORGANISM: Artificial sequence
<220> FEATURE:
<223> OTHER INFORMATION: Synthetic sequence

<400> SEQUENCE: 255
tttattcaag gcaatcacta tcagctgtcc aacacccagg taaactaaca caact        55

<210> SEQ ID NO 256
<211> LENGTH: 55
<212> TYPE: DNA
<213> ORGANISM: Artificial sequence
<220> FEATURE:
<223> OTHER INFORMATION: Synthetic sequence

<400> SEQUENCE: 256
tttattcaag gcaatcacta tcagctcagg aacacccagg taaactaaca caact        55

<210> SEQ ID NO 257
<211> LENGTH: 55
<212> TYPE: DNA
<213> ORGANISM: Artificial sequence
<220> FEATURE:
<223> OTHER INFORMATION: Synthetic sequence

<400> SEQUENCE: 257
tttattcaag gcaatcacta tcaggagtgg aacacccagg taaactaaca caact        55

<210> SEQ ID NO 258
<211> LENGTH: 55
<212> TYPE: DNA
<213> ORGANISM: Artificial sequence
<220> FEATURE:
<223> OTHER INFORMATION: Synthetic sequence

<400> SEQUENCE: 258
tttattcaag gcaatcacta tctcctgtgg aacacccagg taaactaaca caact        55

<210> SEQ ID NO 259
<211> LENGTH: 55
<212> TYPE: DNA
<213> ORGANISM: Artificial sequence
<220> FEATURE:
<223> OTHER INFORMATION: Synthetic sequence

<400> SEQUENCE: 259
tttattcaag gcaatcacta agagctgtgg aacacccagg taaactaaca caact        55

<210> SEQ ID NO 260
<211> LENGTH: 59
<212> TYPE: DNA
<213> ORGANISM: Artificial sequence
<220> FEATURE:
<223> OTHER INFORMATION: Synthetic sequence

```
<400> SEQUENCE: 260
ctacgccgat tatcttctga caactttcgc aagcggtgta aggcgaaaaa tgcgggcac      59

<210> SEQ ID NO 261
<211> LENGTH: 59
<212> TYPE: DNA
<213> ORGANISM: Artificial sequence
<220> FEATURE:
<223> OTHER INFORMATION: Synthetic sequence

<400> SEQUENCE: 261
ctacgccgat tatcttctga caactttcgc aagcggtgta aaataaaaaa tgcgggcac      59

<210> SEQ ID NO 262
<211> LENGTH: 59
<212> TYPE: DNA
<213> ORGANISM: Artificial sequence
<220> FEATURE:
<223> OTHER INFORMATION: Synthetic sequence

<400> SEQUENCE: 262
ctacgccgat tatcttctga caactttcgc aagcggtgtg gggtaaaaaa tgcgggcac      59

<210> SEQ ID NO 263
<211> LENGTH: 59
<212> TYPE: DNA
<213> ORGANISM: Artificial sequence
<220> FEATURE:
<223> OTHER INFORMATION: Synthetic sequence

<400> SEQUENCE: 263
ctacgccgat tatcttctga caactttcgc aagcggtaca aggtaaaaaa tgcgggcac      59

<210> SEQ ID NO 264
<211> LENGTH: 59
<212> TYPE: DNA
<213> ORGANISM: Artificial sequence
<220> FEATURE:
<223> OTHER INFORMATION: Synthetic sequence

<400> SEQUENCE: 264
ctacgccgat tatcttctga caactttcgc aagcgacgta aggtaaaaaa tgcgggcac      59

<210> SEQ ID NO 265
<211> LENGTH: 59
<212> TYPE: DNA
<213> ORGANISM: Artificial sequence
<220> FEATURE:
<223> OTHER INFORMATION: Synthetic sequence

<400> SEQUENCE: 265
ctacgccgat tatcttctga caactttcgc aagtagtgta aggtaaaaaa tgcgggcac      59

<210> SEQ ID NO 266
<211> LENGTH: 59
<212> TYPE: DNA
<213> ORGANISM: Artificial sequence
<220> FEATURE:
<223> OTHER INFORMATION: Synthetic sequence

<400> SEQUENCE: 266
ctacgccgat tatcttctga caactttcgc agacggtgta aggtaaaaaa tgcgggcac      59

<210> SEQ ID NO 267
```

```
<210> SEQ ID NO 267
<211> LENGTH: 59
<212> TYPE: DNA
<213> ORGANISM: Artificial sequence
<220> FEATURE:
<223> OTHER INFORMATION: Synthetic sequence

<400> SEQUENCE: 267
ctacgccgat tatcttctga caactttcgt gagcggtgta aggtaaaaaa tgcgggcac        59

<210> SEQ ID NO 268
<211> LENGTH: 59
<212> TYPE: DNA
<213> ORGANISM: Artificial sequence
<220> FEATURE:
<223> OTHER INFORMATION: Synthetic sequence

<400> SEQUENCE: 268
ctacgccgat tatcttctga caactttac aagcggtgta aggtaaaaaa tgcgggcac        59

<210> SEQ ID NO 269
<211> LENGTH: 59
<212> TYPE: DNA
<213> ORGANISM: Artificial sequence
<220> FEATURE:
<223> OTHER INFORMATION: Synthetic sequence

<400> SEQUENCE: 269
ctacgccgat tatcttctga caactcccgc aagcggtgta aggtaaaaaa tgcgggcac        59

<210> SEQ ID NO 270
<211> LENGTH: 59
<212> TYPE: DNA
<213> ORGANISM: Artificial sequence
<220> FEATURE:
<223> OTHER INFORMATION: Synthetic sequence

<400> SEQUENCE: 270
ctacgccgat tatcttctga caatcttcgc aagcggtgta aggtaaaaaa tgcgggcac        59

<210> SEQ ID NO 271
<211> LENGTH: 59
<212> TYPE: DNA
<213> ORGANISM: Artificial sequence
<220> FEATURE:
<223> OTHER INFORMATION: Synthetic sequence

<400> SEQUENCE: 271
ctacgccgat tatcttctga cggctttcgc aagcggtgta aggtaaaaaa tgcgggcac        59

<210> SEQ ID NO 272
<211> LENGTH: 59
<212> TYPE: DNA
<213> ORGANISM: Artificial sequence
<220> FEATURE:
<223> OTHER INFORMATION: Synthetic sequence

<400> SEQUENCE: 272
ctacgccgat tatcttctgg taactttcgc aagcggtgta aggtaaaaaa tgcgggcac        59

<210> SEQ ID NO 273
<211> LENGTH: 49
<212> TYPE: DNA
<213> ORGANISM: Artificial sequence
<220> FEATURE:
<223> OTHER INFORMATION: Synthetic sequence

<400> SEQUENCE: 273
```

```
tatcttctga caactttcgc aagcggtgta aggtaaaaaa tgcgggcac        49

<210> SEQ ID NO 274
<211> LENGTH: 44
<212> TYPE: DNA
<213> ORGANISM: Artificial sequence
<220> FEATURE:
<223> OTHER INFORMATION: Synthetic sequence

<400> SEQUENCE: 274
tctgacaact tcgcaagcg gtgtaaggta aaaaatgcgg gcac              44

<210> SEQ ID NO 275
<211> LENGTH: 39
<212> TYPE: DNA
<213> ORGANISM: Artificial sequence
<220> FEATURE:
<223> OTHER INFORMATION: Synthetic sequence

<400> SEQUENCE: 275
caactttcgc aagcggtgta aggtaaaaaa tgcgggcac                   39

<210> SEQ ID NO 276
<211> LENGTH: 34
<212> TYPE: DNA
<213> ORGANISM: Artificial sequence
<220> FEATURE:
<223> OTHER INFORMATION: Synthetic sequence

<400> SEQUENCE: 276
ttcgcaagcg gtgtaaggta aaaaatgcgg gcac                        34

<210> SEQ ID NO 277
<211> LENGTH: 54
<212> TYPE: DNA
<213> ORGANISM: Artificial sequence
<220> FEATURE:
<223> OTHER INFORMATION: Synthetic sequence

<400> SEQUENCE: 277
ctacgccgat tatcttctga caactttcgc aagcggtgta aggtaaaaaa tgcg  54

<210> SEQ ID NO 278
<211> LENGTH: 49
<212> TYPE: DNA
<213> ORGANISM: Artificial sequence
<220> FEATURE:
<223> OTHER INFORMATION: Synthetic sequence

<400> SEQUENCE: 278
ctacgccgat tatcttctga caactttcgc aagcggtgta aggtaaaaa        49

<210> SEQ ID NO 279
<211> LENGTH: 40
<212> TYPE: DNA
<213> ORGANISM: Artificial sequence
<220> FEATURE:
<223> OTHER INFORMATION: Synthetic sequence

<400> SEQUENCE: 279
ctacgccgat tatcttctga caactttcgc aagcggtgta                  40

<210> SEQ ID NO 280
<211> LENGTH: 35
<212> TYPE: DNA
```

```
<213> ORGANISM: Artificial sequence
<220> FEATURE:
<223> OTHER INFORMATION: Synthetic sequence

<400> SEQUENCE: 280
ctacgccgat tatcttctga caactttcgc aagcg                            35

<210> SEQ ID NO 281
<211> LENGTH: 30
<212> TYPE: DNA
<213> ORGANISM: Artificial sequence
<220> FEATURE:
<223> OTHER INFORMATION: Synthetic sequence

<400> SEQUENCE: 281
ctacgccgat tatcttctga caactttcgc                                  30

<210> SEQ ID NO 282
<211> LENGTH: 25
<212> TYPE: DNA
<213> ORGANISM: Artificial sequence
<220> FEATURE:
<223> OTHER INFORMATION: Synthetic sequence

<400> SEQUENCE: 282
ctacgccgat tatcttctga caact                                       25

<210> SEQ ID NO 283
<211> LENGTH: 20
<212> TYPE: DNA
<213> ORGANISM: Artificial sequence
<220> FEATURE:
<223> OTHER INFORMATION: Synthetic sequence

<400> SEQUENCE: 283
ctacgccgat tatcttctga                                             20

<210> SEQ ID NO 284
<211> LENGTH: 34
<212> TYPE: DNA
<213> ORGANISM: Artificial sequence
<220> FEATURE:
<223> OTHER INFORMATION: Synthetic sequence

<400> SEQUENCE: 284
caactttcgc aagcggtgta aggtaaaaaa tgcg                             34

<210> SEQ ID NO 285
<211> LENGTH: 63
<212> TYPE: DNA
<213> ORGANISM: Artificial sequence
<220> FEATURE:
<223> OTHER INFORMATION: Synthetic sequence

<400> SEQUENCE: 285
atggaatgtg gcgaacgctt tcaacgaaac aactttcgca agcggtgtaa ggtaaaaaat  60
gcg                                                               63

<210> SEQ ID NO 286
<211> LENGTH: 63
<212> TYPE: DNA
<213> ORGANISM: Artificial sequence
<220> FEATURE:
<223> OTHER INFORMATION: Synthetic sequence

<400> SEQUENCE: 286
```

```
atggaatgtg gcgaacgctt agttggaaac aactttcgca agcggtgtaa ggtaaaaaat    60
gcg                                                                  63

<210> SEQ ID NO 287
<211> LENGTH: 63
<212> TYPE: DNA
<213> ORGANISM: Artificial sequence
<220> FEATURE:
<223> OTHER INFORMATION: Synthetic sequence

<400> SEQUENCE: 287
atggaatgtg gcgaagcgaa agttggaaac aactttcgca agcggtgtaa ggtaaaaaat    60
gcg                                                                  63

<210> SEQ ID NO 288
<211> LENGTH: 63
<212> TYPE: DNA
<213> ORGANISM: Artificial sequence
<220> FEATURE:
<223> OTHER INFORMATION: Synthetic sequence

<400> SEQUENCE: 288
atggaatgtg cgcttgcgaa agttggaaac aactttcgca agcggtgtaa ggtaaaaaat    60
gcg                                                                  63

<210> SEQ ID NO 289
<211> LENGTH: 63
<212> TYPE: DNA
<213> ORGANISM: Artificial sequence
<220> FEATURE:
<223> OTHER INFORMATION: Synthetic sequence

<400> SEQUENCE: 289
atggatacac cgcttgcgaa agttggaaac aactttcgca agcggtgtaa ggtaaaaaat    60
gcg                                                                  63

<210> SEQ ID NO 290
<211> LENGTH: 63
<212> TYPE: DNA
<213> ORGANISM: Artificial sequence
<220> FEATURE:
<223> OTHER INFORMATION: Synthetic sequence

<400> SEQUENCE: 290
taccttacac cgcttgcgaa agttggaaac aactttcgca agcggtgtaa ggtaaaaaat    60
gcg                                                                  63

<210> SEQ ID NO 291
<211> LENGTH: 40
<212> TYPE: DNA
<213> ORGANISM: Artificial sequence
<220> FEATURE:
<223> OTHER INFORMATION: Synthetic sequence

<400> SEQUENCE: 291
gttttatctt ctgctggtgg ttcgttcggt attttttaatg                         40

<210> SEQ ID NO 292
<211> LENGTH: 40
<212> TYPE: DNA
<213> ORGANISM: Artificial sequence
<220> FEATURE:
```

<223> OTHER INFORMATION: Synthetic sequence

<400> SEQUENCE: 292
cattaaaaat accgaacgaa ccaccagcag aagataaaac                     40

<210> SEQ ID NO 293
<211> LENGTH: 43
<212> TYPE: DNA
<213> ORGANISM: Artificial sequence
<220> FEATURE:
<223> OTHER INFORMATION: Synthetic sequence

<400> SEQUENCE: 293
gaccatttgc gaaatgtatc taatggtcaa actaaatcta ctc                 43

<210> SEQ ID NO 294
<211> LENGTH: 43
<212> TYPE: DNA
<213> ORGANISM: Artificial sequence
<220> FEATURE:
<223> OTHER INFORMATION: Synthetic sequence

<400> SEQUENCE: 294
gagtagattt agtttgacca ttagatacat ttcgcaaatg gtc                 43

<210> SEQ ID NO 295
<211> LENGTH: 37
<212> TYPE: DNA
<213> ORGANISM: Artificial sequence
<220> FEATURE:
<223> OTHER INFORMATION: Synthetic sequence

<400> SEQUENCE: 295
cttgcagaac ccggatagac gaatgaagga atgcaac                       37

<210> SEQ ID NO 296
<211> LENGTH: 37
<212> TYPE: DNA
<213> ORGANISM: Artificial sequence
<220> FEATURE:
<223> OTHER INFORMATION: Synthetic sequence

<400> SEQUENCE: 296
cttgcaggcc ttgaatagag gagttaagga atgcaac                       37

<210> SEQ ID NO 297
<211> LENGTH: 37
<212> TYPE: DNA
<213> ORGANISM: Artificial sequence
<220> FEATURE:
<223> OTHER INFORMATION: Synthetic sequence

<400> SEQUENCE: 297
gttgcacagt gctaattaga gaaactagga atgcaac                       37

<210> SEQ ID NO 298
<211> LENGTH: 37
<212> TYPE: DNA
<213> ORGANISM: Artificial sequence
<220> FEATURE:
<223> OTHER INFORMATION: Synthetic sequence

<400> SEQUENCE: 298
ctagcatatt cagaacaaag ggattaagga atgcaac                       37

```
<210> SEQ ID NO 299
<211> LENGTH: 37
<212> TYPE: DNA
<213> ORGANISM: Artificial sequence
<220> FEATURE:
<223> OTHER INFORMATION: Synthetic sequence

<400> SEQUENCE: 299
ctttcatatt cagaaactag gggttaagga ctgcaac                              37

<210> SEQ ID NO 300
<211> LENGTH: 37
<212> TYPE: DNA
<213> ORGANISM: Artificial sequence
<220> FEATURE:
<223> OTHER INFORMATION: Synthetic sequence

<400> SEQUENCE: 300
gttgcatccc tacgtcgtga gcaccggtga gtgcaac                              37

<210> SEQ ID NO 301
<211> LENGTH: 31
<212> TYPE: DNA
<213> ORGANISM: Artificial sequence
<220> FEATURE:
<223> OTHER INFORMATION: Synthetic sequence

<400> SEQUENCE: 301
ggaaaggaat cccctgaagg aaacgagggg g                                    31

<210> SEQ ID NO 302
<211> LENGTH: 36
<212> TYPE: DNA
<213> ORGANISM: Artificial sequence
<220> FEATURE:
<223> OTHER INFORMATION: Synthetic sequence

<400> SEQUENCE: 302
gtgtccatca atcagatttg cgttggccgg tgcaat                               36

<210> SEQ ID NO 303
<211> LENGTH: 37
<212> TYPE: DNA
<213> ORGANISM: Artificial sequence
<220> FEATURE:
<223> OTHER INFORMATION: Synthetic sequence

<400> SEQUENCE: 303
gtttcagcgc acgaattaac gagatgagag atgcaac                              37

<210> SEQ ID NO 304
<211> LENGTH: 500
<212> TYPE: PRT
<213> ORGANISM: Artificial sequence
<220> FEATURE:
<223> OTHER INFORMATION: Synthetic sequence

<400> SEQUENCE: 304
```

Lys Glu Pro Leu Asn Ile Gly Lys Thr Ala Lys Ala Val Phe Lys Glu
1               5                   10                  15

Ile Asp Pro Thr Ser Leu Asn Arg Ala Ala Asn Tyr Asp Ala Ser Ile
            20                  25                  30

Glu Leu Asn Cys Lys Glu Cys Lys Phe Lys Pro Phe Lys Asn Val Lys
        35                  40                  45

Arg Tyr Glu Phe Asn Phe Tyr Asn Asn Trp Tyr Arg Cys Asn Pro Asn

-continued

```
              50                  55                  60
Ser Cys Leu Gln Ser Thr Tyr Lys Ala Gln Val Arg Lys Val Glu Ile
 65                  70                  75                  80

Gly Tyr Glu Lys Leu Lys Asn Glu Ile Leu Thr Gln Met Gln Tyr Tyr
                 85                  90                  95

Pro Trp Phe Gly Arg Leu Tyr Gln Asn Phe Phe His Asp Glu Arg Asp
                    100                 105                 110

Lys Met Thr Ser Leu Asp Glu Ile Gln Val Ile Gly Val Gln Asn Lys
                    115                 120                 125

Val Phe Phe Asn Thr Val Glu Lys Ala Trp Arg Glu Ile Ile Lys Lys
    130                 135                 140

Arg Phe Lys Asp Asn Lys Glu Thr Met Glu Thr Ile Pro Glu Leu Lys
145                 150                 155                 160

His Ala Ala Gly His Gly Lys Arg Lys Leu Ser Asn Lys Ser Leu Leu
                    165                 170                 175

Arg Arg Arg Phe Ala Phe Val Gln Lys Ser Phe Lys Phe Val Asp Asn
                    180                 185                 190

Ser Asp Val Ser Tyr Arg Ser Phe Ser Asn Asn Ile Ala Cys Val Leu
                195                 200                 205

Pro Ser Arg Ile Gly Val Asp Leu Gly Gly Val Ile Ser Arg Asn Pro
210                 215                 220

Lys Arg Glu Tyr Ile Pro Gln Glu Ile Ser Phe Asn Ala Phe Trp Lys
225                 230                 235                 240

Gln His Glu Gly Leu Lys Lys Gly Arg Asn Ile Glu Ile Gln Ser Val
                    245                 250                 255

Gln Tyr Lys Gly Glu Thr Val Lys Arg Ile Glu Ala Asp Thr Gly Glu
                260                 265                 270

Asp Lys Ala Trp Gly Lys Asn Arg Gln Arg Arg Phe Thr Ser Leu Ile
                275                 280                 285

Leu Lys Leu Val Pro Lys Gln Gly Gly Lys Lys Val Trp Lys Tyr Pro
    290                 295                 300

Glu Lys Arg Asn Glu Gly Asn Tyr Glu Tyr Phe Pro Ile Pro Ile Glu
305                 310                 315                 320

Phe Ile Leu Asp Ser Gly Glu Thr Ser Ile Arg Phe Gly Gly Asp Glu
                    325                 330                 335

Gly Glu Ala Gly Lys Gln Lys His Leu Val Ile Pro Phe Asn Asp Ser
                340                 345                 350

Lys Ala Thr Pro Leu Ala Ser Gln Gln Thr Leu Leu Glu Asn Ser Arg
                355                 360                 365

Phe Asn Ala Glu Val Lys Ser Cys Ile Gly Leu Ala Ile Tyr Ala Asn
370                 375                 380

Tyr Phe Tyr Gly Tyr Ala Arg Asn Tyr Val Ile Ser Ser Ile Tyr His
385                 390                 395                 400

Lys Asn Ser Lys Asn Gly Gln Ala Ile Thr Ala Ile Tyr Leu Glu Ser
                    405                 410                 415

Ile Ala His Asn Tyr Val Lys Ala Ile Glu Arg Gln Leu Gln Asn Leu
                420                 425                 430

Leu Leu Asn Leu Arg Asp Phe Ser Phe Met Glu Ser His Lys Lys Glu
                435                 440                 445

Leu Lys Lys Tyr Phe Gly Gly Asp Leu Glu Gly Thr Gly Gly Ala Gln
                450                 455                 460

Lys Arg Arg Glu Lys Glu Glu Lys Ile Glu Lys Glu Ile Glu Gln Ser
465                 470                 475                 480
```

Tyr Leu Pro Arg Leu Ile Arg Leu Ser Leu Thr Lys Met Val Thr Lys
                485                 490                 495

Gln Val Glu Met
            500

<210> SEQ ID NO 305
<211> LENGTH: 507
<212> TYPE: PRT
<213> ORGANISM: Artificial sequence
<220> FEATURE:
<223> OTHER INFORMATION: Synthetic sequence

<400> SEQUENCE: 305

Glu Leu Ile Val Asn Glu Asn Lys Asp Pro Leu Asn Ile Gly Lys Thr
1               5                   10                  15

Ala Lys Ala Val Phe Lys Glu Ile Asp Pro Thr Ser Ile Asn Arg Ala
            20                  25                  30

Ala Asn Tyr Asp Ala Ser Ile Glu Leu Ala Cys Lys Glu Cys Lys Phe
        35                  40                  45

Lys Pro Phe Asn Asn Thr Lys Arg His Asp Phe Ser Phe Tyr Ser Asn
    50                  55                  60

Trp His Arg Cys Ser Pro Asn Ser Cys Leu Gln Ser Thr Tyr Arg Ala
65                  70                  75                  80

Lys Ile Arg Lys Thr Glu Ile Gly Tyr Glu Lys Leu Lys Asn Glu Ile
                85                  90                  95

Leu Asn Gln Met Gln Tyr Tyr Pro Trp Phe Gly Arg Leu Tyr Gln Asn
            100                 105                 110

Phe Phe Asn Asp Gln Arg Asp Lys Met Thr Ser Leu Asp Glu Ile Gln
        115                 120                 125

Val Thr Gly Val Gln Asn Lys Ile Phe Phe Asn Thr Val Glu Lys Ala
    130                 135                 140

Trp Arg Glu Ile Ile Lys Lys Arg Phe Arg Asp Asn Lys Glu Thr Met
145                 150                 155                 160

Arg Thr Ile Pro Asp Leu Lys Asn Lys Ser Gly His Gly Ser Arg Lys
                165                 170                 175

Leu Ser Asn Lys Ser Leu Leu Arg Arg Arg Phe Ala Phe Ala Gln Lys
            180                 185                 190

Ser Phe Lys Leu Val Asp Asn Ser Asp Val Ser Tyr Arg Ala Phe Ser
        195                 200                 205

Asn Asn Val Ala Cys Val Leu Pro Ser Lys Ile Gly Val Asp Ile Gly
    210                 215                 220

Gly Ile Ile Asn Lys Asp Leu Lys Arg Glu Tyr Ile Pro Gln Glu Ile
225                 230                 235                 240

Thr Phe Asn Val Phe Trp Lys Gln His Asp Gly Leu Lys Lys Gly Arg
                245                 250                 255

Asn Ile Glu Ile His Ser Val Gln Tyr Lys Gly Glu Ile Val Lys Arg
            260                 265                 270

Ile Glu Ala Asp Thr Gly Glu Asp Lys Ala Trp Gly Lys Asn Arg Gln
        275                 280                 285

Arg Arg Phe Thr Ser Leu Ile Leu Lys Ile Thr Pro Lys Gln Gly Gly
    290                 295                 300

Lys Lys Ile Trp Lys Phe Pro Glu Lys Lys Asn Ala Ser Asp Tyr Glu
305                 310                 315                 320

Tyr Phe Pro Ile Pro Ile Glu Phe Ile Leu Asp Asn Gly Asp Ala Ser
                325                 330                 335

```
Ile Lys Phe Gly Gly Glu Gly Glu Val Gly Lys Gln Lys His Leu
            340                 345                 350

Leu Ile Pro Phe Asn Asp Ser Lys Ala Thr Pro Leu Ser Ser Lys Gln
            355                 360                 365

Met Leu Leu Glu Thr Ser Arg Phe Asn Ala Glu Val Lys Ser Thr Ile
370                 375                 380

Gly Leu Ala Leu Tyr Ala Asn Tyr Phe Val Ser Tyr Ala Arg Asn Tyr
385                 390                 395                 400

Val Ile Lys Ser Thr Tyr His Lys Asn Ser Lys Gly Gln Ile Val
                405                 410                 415

Thr Glu Ile Tyr Leu Glu Ser Ile Ser Gln Asn Phe Val Arg Ala Ile
            420                 425                 430

Gln Arg Gln Leu Gln Ser Leu Met Leu Asn Leu Lys Asp Trp Gly Phe
            435                 440                 445

Met Gln Thr His Lys Lys Glu Leu Lys Tyr Phe Gly Ser Asp Leu
            450                 455                 460

Glu Gly Ser Lys Gly Gly Gln Lys Arg Arg Glu Lys Glu Glu Lys Ile
465                 470                 475                 480

Glu Lys Glu Ile Glu Ala Ser Tyr Leu Pro Arg Leu Ile Arg Leu Ser
                485                 490                 495

Leu Thr Lys Ser Val Thr Lys Ala Glu Glu Met
            500                 505

<210> SEQ ID NO 306
<211> LENGTH: 529
<212> TYPE: PRT
<213> ORGANISM: Artificial sequence
<220> FEATURE:
<223> OTHER INFORMATION: Synthetic sequence

<400> SEQUENCE: 306

Pro Glu Glu Lys Thr Ser Lys Leu Lys Pro Asn Ser Ile Asn Leu Ala
1               5                   10                  15

Ala Asn Tyr Asp Ala Asn Glu Lys Phe Asn Cys Lys Glu Cys Lys Phe
            20                  25                  30

His Pro Phe Lys Asn Lys Arg Tyr Glu Phe Asn Phe Tyr Asn Asn
        35                  40                  45

Leu His Gly Cys Lys Ser Cys Thr Lys Ser Thr Asn Asn Pro Ala Val
    50                  55                  60

Lys Arg Ile Glu Ile Gly Tyr Gln Lys Leu Lys Phe Glu Ile Lys Asn
65                  70                  75                  80

Gln Met Glu Ala Tyr Pro Trp Phe Gly Arg Leu Arg Ile Asn Phe Tyr
                85                  90                  95

Ser Asp Glu Lys Arg Lys Met Ser Glu Leu Asn Glu Met Gln Val Thr
            100                 105                 110

Gly Val Lys Asn Lys Ile Phe Phe Asp Ala Ile Glu Cys Ala Trp Arg
        115                 120                 125

Glu Ile Leu Lys Lys Arg Phe Arg Glu Ser Lys Glu Thr Leu Ile Thr
    130                 135                 140

Ile Pro Lys Leu Lys Asn Lys Ala Gly His Gly Ala Arg Lys His Arg
145                 150                 155                 160

Asn Lys Lys Leu Leu Ile Arg Arg Ala Phe Met Lys Lys Asn Phe
                165                 170                 175

His Phe Leu Asp Asn Asp Ser Ile Ser Tyr Arg Ser Phe Ala Asn Asn
            180                 185                 190
```

```
Ile Ala Cys Val Leu Pro Ser Lys Val Gly Asp Ile Gly Gly Ile
        195                 200                 205

Ile Ser Pro Asp Val Gly Lys Asp Ile Lys Pro Val Asp Ile Ser Leu
210                 215                 220

Asn Leu Met Trp Ala Ser Lys Glu Gly Ile Lys Ser Gly Arg Lys Val
225                 230                 235                 240

Glu Ile Tyr Ser Thr Gln Tyr Asp Gly Asn Met Val Lys Lys Ile Glu
                245                 250                 255

Ala Glu Thr Gly Glu Asp Lys Ser Trp Gly Lys Asn Arg Lys Arg Arg
            260                 265                 270

Gln Thr Ser Leu Leu Ser Ile Pro Lys Pro Ser Lys Gln Val Gln
        275                 280                 285

Glu Phe Asp Phe Lys Glu Trp Pro Arg Tyr Lys Asp Ile Glu Lys Lys
290                 295                 300

Val Gln Trp Arg Gly Phe Pro Ile Lys Ile Ile Phe Asp Ser Asn His
305                 310                 315                 320

Asn Ser Ile Glu Phe Gly Thr Tyr Gln Gly Gly Lys Gln Lys Val Leu
                325                 330                 335

Pro Ile Pro Phe Asn Asp Ser Lys Thr Thr Pro Leu Gly Ser Lys Met
            340                 345                 350

Asn Lys Leu Glu Lys Leu Arg Phe Asn Ser Lys Ile Lys Ser Arg Leu
        355                 360                 365

Gly Ser Ala Ile Ala Ala Asn Lys Phe Leu Glu Ala Ala Arg Thr Tyr
370                 375                 380

Cys Val Asp Ser Leu Tyr His Glu Val Ser Ala Asn Ala Ile Gly
385                 390                 395                 400

Lys Gly Lys Ile Phe Ile Glu Tyr Tyr Leu Glu Ile Leu Ser Gln Asn
                405                 410                 415

Tyr Ile Glu Ala Ala Gln Lys Gln Leu Gln Arg Phe Ile Glu Ser Ile
            420                 425                 430

Glu Gln Trp Phe Val Ala Asp Pro Phe Gln Gly Arg Leu Lys Gln Tyr
        435                 440                 445

Phe Lys Asp Asp Leu Lys Arg Ala Lys Cys Phe Leu Cys Ala Asn Arg
450                 455                 460

Glu Val Gln Thr Thr Cys Tyr Ala Ala Val Lys Leu His Lys Ser Cys
465                 470                 475                 480

Ala Glu Lys Val Lys Asp Lys Asn Lys Glu Leu Ala Ile Lys Glu Arg
                485                 490                 495

Asn Asn Lys Glu Asp Ala Val Ile Lys Glu Val Glu Ala Ser Asn Tyr
            500                 505                 510

Pro Arg Val Ile Arg Leu Lys Leu Thr Lys Thr Ile Thr Asn Lys Ala
        515                 520                 525

Met

<210> SEQ ID NO 307
<211> LENGTH: 35
<212> TYPE: DNA
<213> ORGANISM: Artificial sequence
<220> FEATURE:
<223> OTHER INFORMATION: Synthetic sequence

<400> SEQUENCE: 307
cttttagaca gtttaaattc taagggtat aaaac                          35
```

```
<210> SEQ ID NO 308
<211> LENGTH: 36
<212> TYPE: DNA
<213> ORGANISM: Artificial sequence
<220> FEATURE:
<223> OTHER INFORMATION: Synthetic sequence

<400> SEQUENCE: 308
gtcgaaatgc ccgcgcgggg gcgtcgtacc cgcgac                              36

<210> SEQ ID NO 309
<211> LENGTH: 37
<212> TYPE: DNA
<213> ORGANISM: Artificial sequence
<220> FEATURE:
<223> OTHER INFORMATION: Synthetic sequence

<400> SEQUENCE: 309
gttgcagcgg ccgacggagc gcgagcgtgg atgccac                             37

<210> SEQ ID NO 310
<211> LENGTH: 35
<212> TYPE: DNA
<213> ORGANISM: Artificial sequence
<220> FEATURE:
<223> OTHER INFORMATION: Synthetic sequence

<400> SEQUENCE: 310
ctttagactt ctccggaagt cgaattaatg gaaac                               35

<210> SEQ ID NO 311
<211> LENGTH: 28
<212> TYPE: DNA
<213> ORGANISM: Artificial sequence
<220> FEATURE:
<223> OTHER INFORMATION: Synthetic sequence

<400> SEQUENCE: 311
gggcgccccg cgcgagcggg ggttgaag                                       28

<210> SEQ ID NO 312
<211> LENGTH: 136
<212> TYPE: DNA
<213> ORGANISM: Artificial Sequence
<220> FEATURE:
<223> OTHER INFORMATION: Synthetic sequence

<400> SEQUENCE: 312
gaaggatgct tgcttgaggt gtagttgtca ttccttcatt cgtctattcg ggttctgcaa    60
ctatacatta ttgcaccaac actaaggcag agtatggttg cattccttca ttcgtctatt   120
cgggttctgc aacggg                                                  136

<210> SEQ ID NO 313
<211> LENGTH: 102
<212> TYPE: DNA
<213> ORGANISM: Artificial Sequence
<220> FEATURE:
<223> OTHER INFORMATION: Synthetic sequence

<400> SEQUENCE: 313
agaatgcttg cttgaggtgt agttgcattc cttcattcgt ctattcgggt aattgcacca    60
acactaaggc agagtatggt tgcattcctt cattcgtcta gg                      102

<210> SEQ ID NO 314
```

```
<211> LENGTH: 75
<212> TYPE: DNA
<213> ORGANISM: Artificial Sequence
<220> FEATURE:
<223> OTHER INFORMATION: Synthetic sequence

<400> SEQUENCE: 314
cgatgcttgc ttgaggtgta gttgcattgc accaacacta aggcagagta tggttgcatt    60
ccttcattcg tctag                                                     75

<210> SEQ ID NO 315
<211> LENGTH: 90
<212> TYPE: DNA
<213> ORGANISM: Artificial Sequence
<220> FEATURE:
<223> OTHER INFORMATION: Synthetic sequence

<400> SEQUENCE: 315
gatgcttgct tgaggtgtag ttgcattcct tcattctgca ccaacactaa ggcagagtat    60
ggttgcattc cttttcgggt tctgcaacgg                                     90

<210> SEQ ID NO 316
<211> LENGTH: 73
<212> TYPE: DNA
<213> ORGANISM: Artificial Sequence
<220> FEATURE:
<223> OTHER INFORMATION: Synthetic sequence

<400> SEQUENCE: 316
gcttgcttga ggtgtagttg cattccttca ttccacctac actaaggcag agtatggttg    60
cattccttca ttc                                                       73

<210> SEQ ID NO 317
<211> LENGTH: 73
<212> TYPE: DNA
<213> ORGANISM: Artificial Sequence
<220> FEATURE:
<223> OTHER INFORMATION: Synthetic sequence

<400> SEQUENCE: 317
gcttgcttga ggtgtagttg cattccttca ttccacctac actaaggcag agtatggttg    60
cattccttca ttc                                                       73

<210> SEQ ID NO 318
<211> LENGTH: 63
<212> TYPE: DNA
<213> ORGANISM: Artificial Sequence
<220> FEATURE:
<223> OTHER INFORMATION: Synthetic sequence

<400> SEQUENCE: 318
gcttgcttga ggtgtagttg cattcgcaac actaaggcag agtatggttg cattccttca    60
ttc                                                                  63

<210> SEQ ID NO 319
<211> LENGTH: 66
<212> TYPE: DNA
<213> ORGANISM: Artificial Sequence
<220> FEATURE:
<223> OTHER INFORMATION: Synthetic sequence

<400> SEQUENCE: 319
cttgcttgag gtgtagttgc cgacactaag gcagagtatg gttgcattat cgggttctg     60
``` caacgg 66

<210> SEQ ID NO 320
<211> LENGTH: 69
<212> TYPE: DNA
<213> ORGANISM: Artificial Sequence
<220> FEATURE:
<223> OTHER INFORMATION: Synthetic sequence

<400> SEQUENCE: 320
cttgcttgag gtgtagttgc attccttcat tcaaacacta aggcagagta tggttgcatt 60
ccttcattc 69

<210> SEQ ID NO 321
<211> LENGTH: 73
<212> TYPE: DNA
<213> ORGANISM: Artificial Sequence
<220> FEATURE:
<223> OTHER INFORMATION: Synthetic sequence

<400> SEQUENCE: 321
ttgcttgagg tgtagttgca ttccttcatt ctaacactaa ggcagagtat ggttgcattc 60
cttcattcgt cta 73

<210> SEQ ID NO 322
<211> LENGTH: 58
<212> TYPE: DNA
<213> ORGANISM: Artificial Sequence
<220> FEATURE:
<223> OTHER INFORMATION: Synthetic sequence

<400> SEQUENCE: 322
ttgcttgagg tgtagttgca tccacactaa ggcagagtat ggttgcattc cttcattc 58

<210> SEQ ID NO 323
<211> LENGTH: 67
<212> TYPE: DNA
<213> ORGANISM: Artificial Sequence
<220> FEATURE:
<223> OTHER INFORMATION: Synthetic sequence

<400> SEQUENCE: 323
tgcttaaggt gtagttgcat tccttcattc caacactaag gcagagtatg gttgcattcc 60
ttcattc 67

<210> SEQ ID NO 324
<211> LENGTH: 66
<212> TYPE: DNA
<213> ORGANISM: Artificial Sequence
<220> FEATURE:
<223> OTHER INFORMATION: Synthetic sequence

<400> SEQUENCE: 324
tgcttgaggt gtagttgcat tccttcattc cacactaagg cagagtatgg ttgcattcct 60
tcattc 66

<210> SEQ ID NO 325
<211> LENGTH: 72
<212> TYPE: DNA
<213> ORGANISM: Artificial Sequence
<220> FEATURE:
<223> OTHER INFORMATION: Synthetic sequence

<400> SEQUENCE: 325
tgcttgaggt gtagttgcat tccttcattc aacactaagg cagagtatgg ttgcattcct     60
tcattcgtct at     72

<210> SEQ ID NO 326
<211> LENGTH: 64
<212> TYPE: DNA
<213> ORGANISM: Artificial Sequence
<220> FEATURE:
<223> OTHER INFORMATION: Synthetic sequence

<400> SEQUENCE: 326
cttgaggtgt agttgcattc cttcattcaa cactaaggca gagtatggtt gcattccttc     60
attc     64

<210> SEQ ID NO 327
<211> LENGTH: 59
<212> TYPE: DNA
<213> ORGANISM: Artificial Sequence
<220> FEATURE:
<223> OTHER INFORMATION: Synthetic sequence

<400> SEQUENCE: 327
cttgaggtgt agttgcattc cttaacacta aggcagagta tggttgcatt ccttcattc     59

<210> SEQ ID NO 328
<211> LENGTH: 63
<212> TYPE: DNA
<213> ORGANISM: Artificial Sequence
<220> FEATURE:
<223> OTHER INFORMATION: Synthetic sequence

<400> SEQUENCE: 328
ttgaggtgta gttgcattcc ttcattcaac actaaggcag agtatggttg cattccttca     60
ttc     63

<210> SEQ ID NO 329
<211> LENGTH: 62
<212> TYPE: DNA
<213> ORGANISM: Artificial Sequence
<220> FEATURE:
<223> OTHER INFORMATION: Synthetic sequence

<400> SEQUENCE: 329
tgaggtgtag ttgcattcct tcattcaaca ctaaggcaga gtatggttgc attccttcat     60
tc     62

<210> SEQ ID NO 330
<211> LENGTH: 61
<212> TYPE: DNA
<213> ORGANISM: Artificial Sequence
<220> FEATURE:
<223> OTHER INFORMATION: Synthetic sequence

<400> SEQUENCE: 330
tgaggtgtag ttgcattcct tcgttcacac taaggcagag tatggttgca ttccttcatt     60
c     61

<210> SEQ ID NO 331
<211> LENGTH: 61
<212> TYPE: DNA
<213> ORGANISM: Artificial Sequence
<220> FEATURE:
<223> OTHER INFORMATION: Synthetic sequence

<400> SEQUENCE: 331
tgaggtgtag ttgcattcct tcattcacac taaggcagag tatggttgca ttccttcatt    60
c    61

<210> SEQ ID NO 332
<211> LENGTH: 61
<212> TYPE: DNA
<213> ORGANISM: Artificial Sequence
<220> FEATURE:
<223> OTHER INFORMATION: Synthetic sequence

<400> SEQUENCE: 332
ctacgccgat tatcttctga caactttcgc aagcggtgta aggtaaaaaa tgcgggcacc    60
c    61

<210> SEQ ID NO 333
<211> LENGTH: 30
<212> TYPE: DNA
<213> ORGANISM: Artificial Sequence
<220> FEATURE:
<223> OTHER INFORMATION: Synthetic sequence

<400> SEQUENCE: 333
ggaatgcaac taccttacac cgcttgcgaa    30

<210> SEQ ID NO 334
<211> LENGTH: 140
<212> TYPE: DNA
<213> ORGANISM: Artificial Sequence
<220> FEATURE:
<223> OTHER INFORMATION: Synthetic sequence

<400> SEQUENCE: 334
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt    140

<210> SEQ ID NO 335
<211> LENGTH: 40
<212> TYPE: DNA
<213> ORGANISM: Artificial Sequence
<220> FEATURE:
<223> OTHER INFORMATION: Synthetic sequence

<400> SEQUENCE: 335
gacgaatgaa ggaatgcaac taccttacac cgcttgcgaa    40

<210> SEQ ID NO 336
<211> LENGTH: 40
<212> TYPE: DNA
<213> ORGANISM: Artificial Sequence
<220> FEATURE:
<223> OTHER INFORMATION: Synthetic sequence

<400> SEQUENCE: 336
gacgaatgaa ggaatgcaac ccttacaccg cttgcgaaag    40

<210> SEQ ID NO 337
<211> LENGTH: 40
<212> TYPE: DNA

```
<213> ORGANISM: Artificial Sequence
<220> FEATURE:
<223> OTHER INFORMATION: Synthetic sequence

<400> SEQUENCE: 337
gacgaatgaa ggaatgcaac ttacaccgct tgcgaaagtt                              40

<210> SEQ ID NO 338
<211> LENGTH: 40
<212> TYPE: DNA
<213> ORGANISM: Artificial Sequence
<220> FEATURE:
<223> OTHER INFORMATION: Synthetic sequence

<400> SEQUENCE: 338
gacgaatgaa ggaatgcaac acaccgcttg cgaaagttgt                              40

<210> SEQ ID NO 339
<211> LENGTH: 41
<212> TYPE: DNA
<213> ORGANISM: Artificial Sequence
<220> FEATURE:
<223> OTHER INFORMATION: Synthetic sequence

<400> SEQUENCE: 339
gacgaatgaa ggaatgcaac cgtcgccgtc cagctcgacc a                            41

<210> SEQ ID NO 340
<211> LENGTH: 40
<212> TYPE: DNA
<213> ORGANISM: Artificial Sequence
<220> FEATURE:
<223> OTHER INFORMATION: Synthetic sequence

<400> SEQUENCE: 340
gacgaatgaa ggaatgcaac gatcgttacg ctaactatga                              40

<210> SEQ ID NO 341
<211> LENGTH: 180
<212> TYPE: DNA
<213> ORGANISM: Artificial Sequence
<220> FEATURE:
<223> OTHER INFORMATION: Synthetic sequence

<400> SEQUENCE: 341
ttcactgata aagtggagaa ccgcttcacc aaaagctgtc ccttagggga ttagaacttg        60
agtgaaggtg ggctgcttgc atcagcctaa tgtcgagaag tgctttcttc ggaaagtaac       120
cctcgaaaca aattcatttg aaagaatgaa ggaatgcaac acttgacact taatgctcaa       180

<210> SEQ ID NO 342
<211> LENGTH: 44
<212> TYPE: DNA
<213> ORGANISM: Artificial Sequence
<220> FEATURE:
<223> OTHER INFORMATION: Synthetic sequence

<400> SEQUENCE: 342
gggtaatttc tactaagtgt agatacttga cacttaatgc tcaa                         44

<210> SEQ ID NO 343
<211> LENGTH: 45
<212> TYPE: DNA
<213> ORGANISM: Artificial Sequence
<220> FEATURE:
<223> OTHER INFORMATION: Synthetic sequence
```

```
<400> SEQUENCE: 343
gacgaatgaa ggaatgcaac taccttacac cgcttgcgaa agttg              45

<210> SEQ ID NO 344
<211> LENGTH: 38
<212> TYPE: DNA
<213> ORGANISM: Artificial Sequence
<220> FEATURE:
<223> OTHER INFORMATION: Synthetic sequence

<400> SEQUENCE: 344
gacgaatgaa ggaatgcaac taccttacac cgcttgcg                      38

<210> SEQ ID NO 345
<211> LENGTH: 36
<212> TYPE: DNA
<213> ORGANISM: Artificial Sequence
<220> FEATURE:
<223> OTHER INFORMATION: Synthetic sequence

<400> SEQUENCE: 345
gacgaatgaa ggaatgcaac taccttacac cgcttg                        36

<210> SEQ ID NO 346
<211> LENGTH: 34
<212> TYPE: DNA
<213> ORGANISM: Artificial Sequence
<220> FEATURE:
<223> OTHER INFORMATION: Synthetic sequence

<400> SEQUENCE: 346
gacgaatgaa ggaatgcaac taccttacac cgct                          34

<210> SEQ ID NO 347
<211> LENGTH: 32
<212> TYPE: DNA
<213> ORGANISM: Artificial Sequence
<220> FEATURE:
<223> OTHER INFORMATION: Synthetic sequence

<400> SEQUENCE: 347
gacgaatgaa ggaatgcaac taccttacac cg                            32

<210> SEQ ID NO 348
<211> LENGTH: 30
<212> TYPE: DNA
<213> ORGANISM: Artificial Sequence
<220> FEATURE:
<223> OTHER INFORMATION: Synthetic sequence

<400> SEQUENCE: 348
gacgaatgaa ggaatgcaac taccttacac                               30

<210> SEQ ID NO 349
<211> LENGTH: 57
<212> TYPE: DNA
<213> ORGANISM: Artificial Sequence
<220> FEATURE:
<223> OTHER INFORMATION: Synthetic sequence

<400> SEQUENCE: 349
gttgcagaac ccgaatagac gaatgaagga atgcaactac cttacaccgc ttgcgaa  57

<210> SEQ ID NO 350
```

```
<211> LENGTH: 37
<212> TYPE: DNA
<213> ORGANISM: Artificial Sequence
<220> FEATURE:
<223> OTHER INFORMATION: Synthetic sequence

<400> SEQUENCE: 350
gaatgaagga atgcaactac cttacaccgc ttgcgaa                              37

<210> SEQ ID NO 351
<211> LENGTH: 35
<212> TYPE: DNA
<213> ORGANISM: Artificial Sequence
<220> FEATURE:
<223> OTHER INFORMATION: Synthetic sequence

<400> SEQUENCE: 351
atgaaggaat gcaactacct tacaccgctt gcgaa                                35

<210> SEQ ID NO 352
<211> LENGTH: 179
<212> TYPE: DNA
<213> ORGANISM: Artificial Sequence
<220> FEATURE:
<223> OTHER INFORMATION: Synthetic sequence

<400> SEQUENCE: 352
cttcactgat aaagtggaga accgcttcac caaaagctgt cccttagggg attagaactt     60
gagtgaaggt gggctgcttg catcagccta atgtcgagaa gtgctttctt cggaaagtaa   120
ccctcgaaac aaattcattt ttcctctcca attctgcaca aaaaaggtg agtccttat     179

<210> SEQ ID NO 353
<211> LENGTH: 110
<212> TYPE: DNA
<213> ORGANISM: Artificial Sequence
<220> FEATURE:
<223> OTHER INFORMATION: Synthetic sequence

<400> SEQUENCE: 353
cttcactgat aaagtggaga accgcttcac caaaagctgt cccttagggg attagaactt     60
gagtgaaggt gggctgcttg catcagccta atgtcgagaa gtgctttctt                110

<210> SEQ ID NO 354
<211> LENGTH: 72
<212> TYPE: DNA
<213> ORGANISM: Artificial Sequence
<220> FEATURE:
<223> OTHER INFORMATION: Synthetic sequence

<400> SEQUENCE: 354
cttcactgat aaagtggaga accgcttcac caaaagctgt cccttagggg attagaactt     60
gagtgaaggt gg                                                         72

<210> SEQ ID NO 355
<211> LENGTH: 136
<212> TYPE: DNA
<213> ORGANISM: Artificial Sequence
<220> FEATURE:
<223> OTHER INFORMATION: Synthetic sequence

<400> SEQUENCE: 355
ttcactgata aagtggagaa ccgcttcacc aaaagctgtc ccttagggga ttagaacttg     60
agtgaaggtg gctgcttgc atcagcctaa tgtcgagaag tgctttcttc ggaaagtaac   120
```

```
cctcgaaaca aattca                                                      136

<210> SEQ ID NO 356
<211> LENGTH: 234
<212> TYPE: DNA
<213> ORGANISM: Artificial Sequence
<220> FEATURE:
<223> OTHER INFORMATION: Synthetic sequence

<400> SEQUENCE: 356
ttcacacttc actgataaag tggagaaccg cttcaccaaa agctgtccct tagggggatta      60 gaacttgagt gaaggtgggc tgcttgcatc agcctaatgt cgagaagtgc tttcttcgga     120
aagtaaccct cgaaacaaat tcattttttcc tctccaattc tgcacaaaaa aaggtgagtc    180
cttataaacc ggcgtgcaga acgccggctc acctttttttc ttcattcgat ttta          234

<210> SEQ ID NO 357
<211> LENGTH: 181
<212> TYPE: DNA
<213> ORGANISM: Artificial Sequence
<220> FEATURE:
<223> OTHER INFORMATION: Synthetic sequence

<400> SEQUENCE: 357
cttcactgat aaagtggaga accgcttcac caaaagctgt cccttagggg attagaactt      60
gagtgaaggt gggctgcttg catcagccta atgtcgagaa gtgctttctt cggaaagtaa     120
ccctcgaaac aaattcattt gaagaatga aggaatgcaa ctaccttaca ccgcttgcga      180
a                                                                     181

<210> SEQ ID NO 358
<211> LENGTH: 222
<212> TYPE: DNA
<213> ORGANISM: Artificial Sequence
<220> FEATURE:
<223> OTHER INFORMATION: Synthetic sequence

<400> SEQUENCE: 358
cttcactgat aaagtggaga accgcttcac caaaagctgt cccttagggg attagaactt      60
gagtgaaggt gggctgcttg catcagccta atgtcgagaa gtgctttctt cggaaagtaa     120
ccctcgaaac aaattcattt ttcctctcca attctgcaca agaaagttgc agaacccgaa     180
tagacgaatg aaggaatgca actaccttac accgcttgcg aa                        222

<210> SEQ ID NO 359
<211> LENGTH: 45
<212> TYPE: DNA
<213> ORGANISM: Artificial Sequence
<220> FEATURE:
<223> OTHER INFORMATION: Synthetic sequence

<400> SEQUENCE: 359
gacgaatgaa ggaatgcaac taccgaacga accaccagca gaaga                      45

<210> SEQ ID NO 360
<211> LENGTH: 45
<212> TYPE: DNA
<213> ORGANISM: Artificial Sequence
<220> FEATURE:
<223> OTHER INFORMATION: Synthetic sequence

<400> SEQUENCE: 360
```
gacgaatgaa ggaatgcaac tcttctgctg gtggttcgtt cggta        45

<210> SEQ ID NO 361
<211> LENGTH: 43
<212> TYPE: DNA
<213> ORGANISM: Artificial Sequence
<220> FEATURE:
<223> OTHER INFORMATION: Synthetic sequence

<400> SEQUENCE: 361
gacgaatgaa ggaatgcaac gtttgaccat tagatacatt tcg          43

<210> SEQ ID NO 362
<211> LENGTH: 43
<212> TYPE: DNA
<213> ORGANISM: Artificial Sequence
<220> FEATURE:
<223> OTHER INFORMATION: Synthetic sequence

<400> SEQUENCE: 362
gacgaatgaa ggaatgcaac cgaaatgtat ctaatggtca aac          43

<210> SEQ ID NO 363
<211> LENGTH: 7580
<212> TYPE: DNA
<213> ORGANISM: Artificial sequence
<220> FEATURE:
<223> OTHER INFORMATION: Synthetic sequence

<400> SEQUENCE: 363
gcaaccgcac ctgtggcgcc ggtgatgccg gccacgatgc gtccggcgta gaggatcgag      60
atctcgatcc cgcgaaatta atacgactca ctatagggag accacaacgg tttccctcta     120
gtgccggctc cggagagctc tttaattaag cggccgccct gcaggactcg agttctagaa     180
ataattttgt ttaactttaa gaaggagata tacatatgaa atcttctcac catcaccatc     240
accatcacca tcaccatggt tcttctatga aaatcgaaga aggtaaactg gtaatctgga     300
ttaacggcga taaaggctat aacggtctcg ctgaagtcgg taagaaattc gagaaagata     360
ccggaattaa agtcaccgtt gagcatccgg ataaactgga agagaaattc ccacaggttg     420
cggcaactgg cgatggccct gacattatct tctgggcaca cgaccgcttt ggtggctacg     480
ctcaatctgg cctgttggct gaaatcaccc cggacaaagc gttccaggac aagctgtatc     540
cgtttacctg ggatgccgta cgttacaacg gcaagctgat tgcttacccg atcgctgttg     600
aagcgttatc gctgatttat aacaaagatc tgctgccgaa cccgccaaaa acctgggaag     660
agatcccggc gctggataaa gaactgaaag cgaaaggtaa gagcgcgctg atgttcaacc     720
tgcaagaacc gtacttcacc tggccgctga ttgctgctga cggggggttat gcgttcaagt     780
atgaaaacgg caagtacgac attaaagacg tgggcgtgga taacgctggc gcgaaagcgg     840
gtctgacctt cctggttgac ctgattaaaa acaaacacat gaatgcagac accgattact     900
ccatcgcaga agctgccttt aataaaggcg aaacagcgat gaccatcaac ggcccgtggg     960
catggtccaa catcgacacc agcaaagtga attatggtgt aacggtactg ccgaccttca    1020
agggtcaacc atccaaaccg ttcgttggcg tgctgagcgc aggtattaac gccgccagtc    1080
cgaacaaaga gctggcaaaa gagttcctcg aaaactatct gctgactgat gaaggtctgg    1140
aagcggttaa taaagacaaa ccgctgggtg ccgtagcgct gaagtcttac gaggaagagt    1200
tggcgaaaga tccacgtatt gccgccacta tggaaaacgc ccagaaaggt gaaatcatgc    1260
cgaacatccc gcagatgtcc gctttctggt atgccgtgcg tactgcggtg atcaacgccg    1320

```
ccagcggtcg tcagactgtc gatgaagccc tgaaagacgc gcagactaat tcgagctcga    1380
acaacaacaa caataacaat aacaacaacc tcgggatcga ggaaaacctg tacttccaat    1440
ccaatgcaat ggaagaaagc attattaccg gtgtgaaatt caaactgcgc atcgataaag    1500
aaaccaccaa aaaactgaac gagtacttcg atgaatatgg caaagcaatt aacttcgccg    1560
tgaagatcat tcagaaagaa ctggcagatg atcgttttgc aggtaaagca aaactggacc    1620
agaataaaaa cccgatcctg gatgaaaacg gcaaaaaaat ctatgaattc ccggatgaat    1680
tttgcagctg tggtaaacag gttaacaagt acgttaacaa caaaccgttt tgccaagagt    1740
gctataaaat ccgctttacc gaaaatggta ttcgcaaacg tatgtatagc gccaaaggtc    1800
gtaaagccga acataaaatc aatatcctga acagcaccaa caagatcagc aaaacccatt    1860
ttaactatgc cattcgcgaa gccttcattc tggataaaag catcaaaaag cagcgcaaaa    1920
aacgtaatga acgtctgcgt gaaagtaaaa aacgtctgca gcagtttatc gatatgcgtg    1980
atggtaaacg tgaaatttgc ccgaccatta aaggtcagaa agtggatcgt tttattcatc    2040
cgagctggat caccaaagat aaaaagctgg aagattttcg cggttatacc ctgagcatta    2100
tcaacagcaa aattaagatt ctggatcgca acatcaaacg cgaagaaaaa agcctgaaag    2160
aaaaaggcca gatcatcttt aaagccaaac gtctgatgct ggataaatcc attcgttttg    2220
ttggtgatcg caaagtgctg tttacaatta gtaaaaccct gccgaaagag tatgaactgg    2280
atctgccgag caaagaaaaa cggctgaatt ggctgaaaga gaagatcgag attatcaaga    2340
accagaaacc gaaatatgcc tatctgctgc gcaaaaacat tgagagcgaa aaaaaaccga    2400
actatgagta ctatctgcag tacaccctgg aaattaaacc ggaactgaaa gatttttatg    2460
atggtgccat tggtattgac cgtggcatta atcatattgc cgtttgcacc tttattagca    2520
acgatggtaa agttacccct ccgaaatttt tcagcagcgg tgaaattctg cgtctgaaaa    2580
atctgcagaa agagcgtgat cgcttttctg tgcgtaaaca caacaaaaat cgcaaaaaag    2640
gcaacatgcg cgtgatcgaa aacaaaatca atctgatcct gcaccgttat agcaagcaga    2700
ttgttgatat ggccaaaaag ctgaatgcca gcattgtttt tgaagaactg ggtcgtattg    2760
gtaaaagccg caccaaaatg aaaaaaagcc agcgttataa actgagcctg ttcatcttca    2820
agaaactgag cgatctggtt gattacaaaa gccgtcgtga aggtattcgt gttacctatg    2880
ttccgcctga atataccagc aaagaatgta gccattgcgg tgaaaaagtt aatacccagc    2940
gtccgttt aa tggcaactat agcctgttta atgcaacaa atgtggcatc cagctgaaca    3000
gcgattataa tgcaagcatc aacattgcga aaagggcct gaaaattccg aatagcacct    3060
aataacattg gaagtggata acggatccgc gatcgcggcg cgccacctgg tggccggccg    3120
gtaccacgcg tgcgcgctga tccggctgct aacaaagccc gaaaggaagc tgagttggct    3180
gctgccaccg ctgagcaata actagcataa ccccttgggg cctctaaacg ggtcttgagg    3240
ggttttttgc tgaaaggagg aactatatcc ggatatccac aggacgggtg tggtcgccat    3300
gatcgcgtag tcgatagtgg ctccaagtag cgaagcgagc aggactgggc ggcggccaaa    3360
gcggtcggac agtgctccga gaacgggtgc gcatagaaat tgcatcaacg catatagcgc    3420
tagcagcacg ccatagtgac tggcgatgct gtcggaatgg acgatatccc gcaagaggcc    3480
cggcagtacc ggcataacca agcctatgcc tacagcatcc agggtgacgg tgccgaggat    3540
gacgatgagc gcattgttag atttcataca cggtgcctga ctgcgttagc aatttaactg    3600
tgataaacta ccgcattaaa gcttatcgat gataagctgt caaacatgag aattcttgaa    3660
```

-continued

```
gacgaaaggg cctcgtgata cgcctatttt tataggttaa tgtcatgata ataatggttt    3720
cttagacgtc aggtggcact tttcggggaa atgtgcgcgg aaccccctatt tgtttatttt   3780
tctaaataca ttcaaatatg tatccgctca tgagacaata accctgataa atgcttcaat   3840
aacattgaaa aaggaagagt atgagtattc aacatttccg tgtcgccctt attccctttt   3900
ttgcggcatt ttgccttcct gttttttgctc acccagaaac gctggtgaaa gtaaaagatg   3960
ctgaagatca gttgggtgca cgagtgggtt acatcgaact ggatctcaac agcggtaaga   4020
tccttgagag ttttcgcccc gaagaacgtt ttccaatgat gagcactttt aaagttctgc   4080
tatgtggcgc ggtattatcc cgtgttgacg ccgggcaaga gcaactcggt cgccgcatac   4140
actattctca gaatgacttg gttgagtact caccagtcac agaaaagcat cttacggatg   4200
gcatgacagt aagagaatta tgcagtgctg ccataaccat gagtgataac actgcggcca   4260
acttacttct gacaacgatc ggaggaccga aggagctaac cgcttttttg cacaacatgg   4320
gggatcatgt aactcgcctt gatcgttggg aaccggagct gaatgaagcc ataccaaacg   4380
acgagcgtga ccaccgatg cctgcagcaa tggcaacaac gttgcgcaaa ctattaactg   4440
gcgaactact tactctagct tcccggcaac aattaataga ctggatggag gcggataaag   4500
ttgcaggacc acttctgcgc tcggcccttc cggctggctg gtttattgct gataaatctg   4560
gagccggtga gcgtgggtct cgcggtatca ttgcagcact ggggccagat ggtaagccct   4620
cccgtatcgt agttatctac acgacgggga gtcaggcaac tatggatgaa cgaaatagac   4680
agatcgctga gataggtgcc tcactgatta gcattggta actgtcagac caagtttact   4740
catatatact ttagattgat ttaaaacttc atttttaatt taaaaggatc taggtgaaga   4800
tcctttttga taatctcatg accaaaatcc cttaacgtga gttttcgttc cactgagcgt   4860
cagacccccg agaaaagatc aaaggatctt cttgagatcc ttttttttctg cgcgtaatct   4920
gctgcttgca acaaaaaaa ccaccgctac cagcggtggt ttgtttgccg atcaagagc    4980
taccaactct ttttccgaag gtaactggct tcagcagagc gcagatacca atactgtcc    5040
ttctagtgta gccgtagtta ggccaccact tcaagaactc tgtagcaccg cctacatacc   5100
tcgctctgct aatcctgtta ccagtggctg ctgccagtgg cgataagtcg tgtcttaccg   5160
ggttggactc aagacgatag ttaccggata aggcgcagcg gtcgggctga acggggggtt   5220
cgtgcacaca gcccagcttg gagcgaacga cctacaccga actgagatac ctacagcgtg   5280
agctatgaga aagcgccacg cttcccgaag ggagaaaggc ggacaggtat ccggtaagcg   5340
gcagggtcgg aacaggagag cgcacgaggg agcttccagg gggaaacgcc tggtatcttt   5400
atagtcctgt cgggtttcgc cacctctgac ttgagcgtcg atttttgtga tgctcgtcag   5460
gggggcggag cctatggaaa aacgccagca acgcggcctt tttacggttc ctggccttt    5520
gctggccttt tgctcacatg ttctttcctg cgttatcccc tgattctgtg ataaccgta    5580
ttaccgccctt tgagtgagct gataccgctc gccgcagccg aacgaccgag cgcagcgagt   5640
cagtgagcga ggaagcggaa gagcgcctga tgcggtattt tctccttacg catctgtgcg   5700
gtatttcaca ccgcaatggt gcactctcag tacaatctgc tctgatgccg catagttaag   5760
ccagtataca ctccgctatc gctacgtgac tgggtcatgg ctgcgccccg acacccgcca   5820
acacccgctg acgcgccctg acgggcttgt ctgctcccgg catccgctta cagacaagct   5880
gtgaccgtct ccgggagctg catgtgtcag aggttttcac cgtcatcacc gaaacgcgcg   5940
aggcagctgc ggtaaagctc atcagcgtgg tcgtgaagcg attcacagat gtctgcctgt   6000
tcatccgcgt ccagctcgtt gagtttctcc agaagcgtta atgtctggct tctgataaag   6060
```

```
cgggccatgt taagggcggt ttttcctgt ttggtcactg atgcctccgt gtaagggga      6120 tttctgttca tggggtaat gataccgatg aaacgagaga ggatgctcac gatacgggtt      6180
actgatgatg aacatgcccg gttactggaa cgttgtgagg gtaaacaact ggcggtatgg     6240
atgcggcggg accagagaaa aatcactcag ggtcaatgcc agcgcttcgt taatacagat    6300
gtaggtgttc cacagggtag ccagcagcat cctgcgatgc agatccggaa cataatggtg    6360
cagggcgctg acttccgcgt ttccagactt tacgaaacac ggaaaccgaa gaccattcat    6420
gttgttgctc aggtcgcaga cgttttgcag cagcagtcgc ttcacgttcg ctcgcgtatc    6480
ggtgattcat tctgctaacc agtaaggcaa ccccgccagc ctagccgggt cctcaacgac    6540
aggagcacga tcatgcgcac ccgtggccag gacccaacgc tgcccgagat gcgccgcgtg    6600
cggctgctgg agatggcgga cgcgatggat atgttctgcc aagggttggt ttgcgcattc    6660
acagttctcc gcaagaattg attggctcca attcttggag tggtgaatcc gttagcgagg    6720
tgccgccggc ttccattcag gtcgaggtgg cccggctcca tgcaccgcga cgcaacgcgg    6780
ggaggcagac aaggtatagg gcggcgccta caatccatgc caacccgttc catgtgctcg    6840
ccgaggcgga taaatcgcc gtgacgatca gcggtccaat gatcgaagtt aggctggtaa     6900
gagccgcgag cgatccttga agctgtccct gatggtcgtc atctacctgc ctggacagca    6960
tggcctgcaa cgcgggcatc ccgatgccgc cggaagcgag aagaatcata atggggaagg    7020
ccatccagcc tcgcgtcgcg aacgccagca agacgtagcc cagcgcgtcg gccgccatgc    7080
cggcgataat ggcctgcttc tcgccgaaac gtttggtggc gggaccagtg acgaaggctt    7140
gagcgagggc gtgcaagatt ccgaataccg caagcgacag gccgatcatc gtcgcgctcc    7200
agcgaaagcg gtcctcgccg aaaatgaccc agagcgctgc cggcacctgt cctacgagtt    7260
gcatgataaa gaagacagtc ataagtgcgg cgacgatagt catgccccgc gcccaccgga    7320
aggagctgac tgggttgaag gctctcaagg gcatcggtcg acgctctccc ttatgcgact    7380
cctgcattag gaagcagccc agtagtaggt tgaggccgtt gagcaccgcc gccgcaagga    7440
atggtgcatg caaggagatg gcgcccaaca gtccccggc cacggggcct gccaccatac     7500
ccacgccgaa acaagcgctc atgagcccga agtggcgagc ccgatcttcc ccatcggtga    7560
tgtcggcgat ataggcgcca                                                7580
```

<210> SEQ ID NO 364
<211> LENGTH: 4715
<212> TYPE: DNA
<213> ORGANISM: Artificial sequence
<220> FEATURE:
<223> OTHER INFORMATION: Synthetic sequence

<400> SEQUENCE: 364

```
atcgttgata gagttatttt accactccct atcagtgata gagaaaagaa ttcaaaagat     60
ctaaagagga gaaaggatct atggaagaaa gcattattac cggtgtgaaa ttcaaactgc    120
gcatcgataa agaaaccacc aaaaaactga acgagtactt cgatgaatat ggcaaagcaa    180
ttaacttcgc cgtgaagatc attcagaaag aactggcaga tgatcgtttt gcaggtaaag    240
caaaactgga ccagaataaa aacccgatcc tggatgaaaa cggcaaaaaa atctatgaat    300
tcccggatga attttgcagc tgtggtaaac aggttaacaa gtacgttaac aacaaaccgt    360
tttgccaaga gtgctataaa atccgctttta ccgaaaatgg tattcgcaaa cgtatgtata    420
gcgccaaagg tcgtaaagcc gaacataaaa tcaatatcct gaacagcacc aacaagatca    480
```

```
gcaaaaccca ttttaactat gccattcgcg aagccttcat tctggataaa agcatcaaaa    540
agcagcgcaa aaaacgtaat gaacgtctgc gtgaaagtaa aaaacgtctg cagcagttta    600
tcgatatgcg tgatggtaaa cgtgaaattt gcccgaccat taaaggtcag aaagtggatc    660
gttttattca tccgagctgg atcaccaaag ataaaaagct ggaagatttt cgcggttata    720
ccctgagcat tatcaacagc aaaattaaga ttctggatcg caacatcaaa cgcgaagaaa    780
aaagcctgaa agaaaaaggc cagatcatct ttaaagccaa acgtctgatg ctggataaat    840
ccattcgttt tgttggtgat cgcaaagtgc tgtttacaat tagtaaaacc ctgccgaaag    900
agtatgaact ggatctgccg agcaagaaaa acggctgaaa ttggctgaaa gagaagatcg    960
agattatcaa gaaccagaaa ccgaaatatg cctatctgct gcgcaaaaac attgagagcg   1020
aaaaaaaacc gaactatgag tactatctgc agtacaccct ggaaattaaa ccggaactga   1080 aagatttta tgatggtgcc attggtattg accgtggcat taatcatatt gccgtttgca   1140
cctttattag caacgatggt aaagttaccc ctccgaaatt tttcagcagc ggtgaaattc   1200
tgcgtctgaa aaatctgcag aaagagcgtg atcgctttct gctgcgtaaa cacaacaaaa   1260
atcgcaaaaa aggcaacatg cgcgtgatcg aaaacaaaat caatctgatc ctgcaccgtt   1320
atagcaagca gattgttgat atggccaaaa agctgaatgc cagcattgtt tttgaagaac   1380
tgggtcgtat tggtaaaagc cgcaccaaaa tgaaaaaaag ccagcgttat aaactgagcc   1440
tgttcatctt caagaaactg agcgatctgg ttgattacaa aagccgtcgt gaaggtattc   1500
gtgttaccta tgttccgcct gaatatacca gcaaagaatg tagccattgc ggtgaaaaag   1560 ttaatacca gcgtccgttt aatggcaact atagcctgtt taaatgcaac aaatgtggca   1620
tccagctgaa cagcgattat aatgcaagca tcaacattgc gaaaaagggc ctgaaaattc   1680
cgaatagcac ctaataatgt tggttaagcc acaatatgga atattgttct tatggacagt   1740
attgacttaa attaataatc ttcgaaggct atatgcggaa gatttggcgt tgttgtaacg   1800
caataagggg taaccctgaa aaggtttgaa atcatataaa cctagtttta tttgagttta   1860
ggctcagata aaatgaacag accaatcttt aattccgttc tgatttaaaa aatcagaatc   1920
tctttataaa tagtattaca aaaagtgtac attccaaaat ccgaaagcag aattgacctt   1980
tttaagccta aaaagccaa atttcaaggc tctttcatac tcagaacaaa gggattaagg   2040
aatgcaacta ccttcacccg cttgcgaaag ttgtcagaag ataatctttc atactcagaa   2100
caaagggatt aaggaatgca actatcttat ccatttcttg acatcaaatt ttcttgcagc   2160
atctgaattg cttaattgct ttccttgctt cagcaggaaa tagccaagat tttccagttc   2220
tgctggcgtt attgcaagca cggggatttt gtgcttgctg tagattttgt tcttcaggac   2280 cttcttttc catgctagag tcacactggc tcaccttcgg gtgggccttt ctgcgtttat   2340
acctagggat atattccgct tcctcgctca ctgactcgct acgctcggtc gttcgactgc   2400
ggcgagcgga atggcttac gaacggggcg gagatttcct ggaagatgcc aggaagatac   2460
ttaacaggga agtgagaggg ccgcggcaaa gccgttttc cataggctcc gcccccctga   2520
caagcatcac gaaatctgac gctcaaatca gtggtggcga acccgacag gactataaag   2580 ataccaggcg tttccccctg gcggctccct cgtgcgctct cctgttcctg cctttcggtt   2640
taccggtgtc attccgctgt tatggccgcg tttgtctcat tccacgcctg acactcagtt   2700
ccgggtaggc agttcgctcc aagctggact gtatgcacga accccccgtt cagtccgacc   2760
gctgcgcctt atccggtaac tatcgtcttg agtccaaccc ggaaagacat gcaaagcac   2820 cactggcagc agccactggt aattgattta gaggagttag tcttgaagtc atgcgccggt   2880
```

```
taaggctaaa ctgaaaggac aagtttttggt gactgcgctc ctccaagcca gttacctcgg    2940
ttcaaagagt tggtagctca gagaaccttc gaaaaaccgc cctgcaaggc ggttttttcg    3000
ttttcagagc aagagattac gcgcagacca aaacgatctc aagaagatca tcttattaat    3060
cagataaaat atttctagat ttcagtgcaa tttatctctt caaatgtagc acctgaagtc    3120
agccccatac gatataagtt gttactagtg cttggattct caccaataaa aaacgcccgg    3180
cggcaaccga gcgttctgaa caaatccaga tggagtctg aggtcattac tggatctatc     3240
aacaggagtc caagcgagct cgatatcaaa ttacgccccg ccctgccact catcgcagta    3300
ctgttgtaat tcattaagca ttctgccgac atggaagcca tcacaaacgg catgatgaac    3360
ctgaatcgcc agcggcatca gcaccttgtc gccttgcgta taatatttgc ccatggtgaa    3420
aacgggggcg aagaagttgt ccatattggc cacgtttaaa tcaaaactgg tgaaactcac    3480
ccagggattg gctgagacga aaacatatt ctcaataaac cctttaggga ataggccag      3540 gttttcaccg taacacgcca catcttgcga atatatgtgt agaaactgcc ggaaatcgtc    3600
gtggtattca ctccagagcg atgaaaacgt ttcagtttgc tcatggaaaa cggtgtaaca    3660
agggtgaaca ctatcccata tcaccagctc accgtctttc attgccatac gaaattccgg    3720
atgagcattc atcaggcggg caagaatgtg aataaaggcc ggataaaact tgtgcttatt    3780
tttctttacg gtctttaaaa aggccgtaat atccagctga acgtctggt tataggtaca     3840 ttgagcaact gactgaaatg cctcaaaatg ttctttacga tgccattggg atatatcaac    3900
ggtggtatat ccagtgattt ttttctccat tttagcttcc ttagctcctg aaaatctcga    3960
taactcaaaa aatcgcccg gtagtgatct tatttcatta tggtgaaagt tggaacctct    4020
tacgtgccga tcaacgtctc attttcgcca gatatcgacg tcttaagacc cacttttcaca  4080 tttaagttgt ttttctaatc cgcatatgat caattcaagg ccgaataaga aggctggctc    4140
tgcaccttgg tgatcaaata attcgatagc ttgtcgtaat aatggcggca tactatcagt    4200
agtaggtgtt tcccttcttt ctttagcgac ttgatgctct tgatcttcca atacgcaacc    4260
taaagtaaaa tgccccacag cgctgagtgc atataatgca ttctctagtg aaaaaccttg    4320
ttggcataaa aaggctaatt gattttcgag agtttcatac tgttttttctg taggccgtgt   4380 acctaaatgt acttttgctc catcgcgatg acttagtaaa gcacatctaa aacttttagc    4440
gttattacgt aaaaaatctt gccagctttc cccttctaaa gggcaaaagt gagtatggtg    4500
cctatctaac atctcaatgg ctaaggcgtc gagcaaagcc cgcttatttt ttacatgcca    4560
atacaatgta ggctgctcta cacctagctt ctgggcgagt ttacgggttg ttaaaccttc    4620
gattccgacc tcattaagca gctctaatgc gctgttaatc actttacttt tatctaatct    4680
agacatcatt aattcctaat ttttgttgac actct                                4715
```

<210> SEQ ID NO 365
<211> LENGTH: 4670
<212> TYPE: DNA
<213> ORGANISM: Artificial sequence
<220> FEATURE:
<223> OTHER INFORMATION: Synthetic sequence

<400> SEQUENCE: 365

```
taattcctaa ttttgttga cactctatcg ttgatagagt tatttacca ctccctatca       60 gtgatagaga aaagaattca aaagatctaa agaggagaaa ggatctatga aatctcacca    120
tcaccatcac catgaaaacc tgtacttcca atccaatatt ggaagtggaa tggccaaaaa    180
```

```
caccattacc aaaacactga aactgcgtat tgtgcgtccg tataatagcg cagaagtgga    240
aaaaattgtt gccgacgaaa aaaacaaccg cgaaaaaatc gcactggaaa agaacaaaga    300
caaagtgaaa gaagcctgca gcaaacatct gaaagttgca gcatattgta ccacacaggt    360
tgaacgtaat gcatgcctgt tttgtaaagc acgtaaactg gatgacaaat tctaccaaaa    420
actgcgtggt cagtttccgg atgcagtttt ttggcaagaa atcagcgaaa ttttttcgcca   480 gctgcagaaa caggcagcag aaatctataa tcagagcctg atcgaactgt actacgagat    540
ttttatcaaa ggcaaaggta ttgcaaatgc cagcagcgtt gaacattatc tgagtgatgt    600
ttgttatacc cgtgcagcag aactgtttaa aaacgcagca attgcaagcg gtctgcgtag    660
caaaatcaaa agcaattttc gtctgaaaga actgaaaaac atgaaaagtg gtctgccgac    720
caccaaaagc gataattttc cgattccgct ggttaaacag aaaggtggtc agtataccgg    780
ttttgaaatt agcaatcata atagcgactt catcatcaag attccgtttg tcgttggca    840 ggtcaaaaaa gagattgata atatcgtcc gtgggagaaa tttgactttg aacaggttca    900
gaaaagcccg aaaccgatta gcctgctgct gagcacccca cgtcgtaaac gtaataaagg    960
ttggagcaaa gatgaaggca ccgaagccga aatcaaaaaa gttatgaatg gcgattatca    1020
gaccagctac attgaagtta aacgtggcag caaaatcggt gaaaaaagcg catggatgct    1080
gaatctgagc attgatgttc cgaaaattga taaaggtgtg gatccgagca ttattggtgg    1140
tattgatgtt ggtgttaaat caccgctggt ttgcgcaatt aacaatgcat ttagccgtta    1200
tagcatcagc gataacgacc tgtttcactt caacaagaaa atgtttgcac gtcgtcgtat    1260
cctgctgaaa aaaaccgtc ataaacgtgc aggtcatggt gcaaaaaaca aactgaaacc    1320
gatcaccatt ctgaccgaaa aaagtgaacg ttttcgcaaa aagctgattg aacgttgggc    1380
atgtgaaatc gcggatttct tcattaaaaa caaagttggc accgtgcaga tggaaaatct    1440
ggaaagcatg aaacgtaaag aggacagcta ttttaacatt cgcctgcgtg cttttggcc    1500 gtatgcagaa atgcagaaca aaatcgaatt caaactgaag cagtatggca tcgaaattcg    1560
taaagttgca ccgaataata ccagcaaaac ctgtagcaaa tgtggccatc tgaacaacta    1620
tttcaacttc gagtaccgca agaaaaacaa attcccgcac tttaaatgcg aaaaatgcaa    1680
cttcaaagaa aacgccgatt ataatgcagc cctgaatatt tcaaacccga aactgaaaag    1740
caccaaagag gaaccgtaaa tatttatact ttattatcct tcattgacaa aaatgagaat    1800
gttatcccag ataacatttg atgtacacag attcacactt cactgataaa gtggagaacc    1860
gcttcaccaa aagctgtccc ttaggggatt agaacttgag tgaaggtggg ctgcttgcat    1920
cagcctaatg tcgagaagtg ctttcttcgg aaagtaaccc tcgaaacaaa ttcatttttc    1980
ctctccaatt ctgcacaaaa aaaggtgagt ccttataaac cggcgtgcag aacgccggct    2040
cacctttttt cttcattcga ttttatgctt aaaagccgta aaaacgcgga attcggcgcc    2100
gttgcagaac ccgaatagac gaatgaagga atgcaactac cttacaccgc ttgcgaaagt    2160
tgtcagaaga taatcttgca gaacccgaat agacgaatga aggaatgcaa tcttgacaga    2220
gcccgattgc gttatctcca ggagaaacat ataaaagcat caaccgctga tcggactaga    2280
gtcacactgg ctcaccttcg ggtgggcctt tctgcgttta tacctaggga tatattccgc    2340
ttcctcgctc actgactcgc tacgctcggt cgttcgactg cggcgagcgg aaatggctta    2400
cgaacggggc ggagatttcc tggaagatgc caggaagata cttaacaggg aagtgagagg    2460
gccgcggcaa agccgttttt ccataggctc cgccccctg acaagcatca cgaaatctga    2520
cgctcaaatc agtggtggcg aaacccgaca ggactataaa gataccaggc gtttcccct    2580
```

```
ggcggctccc tcgtgcgctc tcctgttcct gcctttcggt ttaccggtgt cattccgctg    2640
ttatggccgc gtttgtctca ttccacgcct gacactcagt tccgggtagg cagttcgctc    2700
caagctggac tgtatgcacg aaccccccgt tcagtccgac cgctgcgcct tatccggtaa    2760
ctatcgtctt gagtccaacc cggaaagaca tgcaaaagca ccactggcag cagccactgg    2820
taattgattt agaggagtta gtcttgaagt catgcgccgg ttaaggctaa actgaaagga    2880
caagttttgg tgactgcgct cctccaagcc agttacctcg gttcaaagag ttggtagctc    2940
agagaacctt cgaaaaaccg ccctgcaagg cggttttttc gttttcagag caagagatta    3000
cgcgcagacc aaaacgatct caagaagatc atcttattaa tcagataaaa tatttctaga    3060
tttcagtgca atttatctct tcaaatgtag cacctgaagt cagccccata cgatataagt    3120
tgttactagt gcttggattc tcaccaataa aaaacgcccg gcggcaaccg agcgttctga    3180
acaaatccag atggagttct gaggtcatta ctggatctat caacaggagt ccaagcgagc    3240
tcgatatcaa attacgcccc gccctgccac tcatcgcagt actgttgtaa ttcattaagc    3300
attctgccga catggaagcc atcacaaacg gcatgatgaa cctgaatcgc cagcggcatc    3360
agcaccttgt cgccttgcgt ataatatttg cccatggtga aaacggggc gaagaagttg    3420 tccatattgg ccacgtttaa atcaaaactg gtgaaactca cccagggatt ggctgagacg    3480
aaaaacatat tctcaataaa ccctttaggg aataggcca ggttttcacc gtaacacgcc    3540
acatcttgcg aatatatgtg tagaaactgc cggaaatcgt cgtggtattc actccagagc    3600
gatgaaaacg tttcagtttg ctcatggaaa acggtgtaac aagggtgaac actatcccat    3660
atcaccagct caccgtcttt cattgccata cgaaattccg gatgagcatt catcaggcgg    3720
gcaagaatgt gaataaaggc cggataaaac ttgtgcttat ttttctttac ggtctttaaa    3780
aaggccgtaa tatccagctg aacggtctgg ttataggtac attgagcaac tgactgaaat    3840
gcctcaaaat gttctttacg atgccattgg gatatatcaa cggtggtata ccagtgatt    3900 tttttctcca ttttagcttc cttagctcct gaaaatctcg ataactcaaa aaatacgccc    3960
ggtagtgatc ttatttcatt atggtgaaag ttggaacctc ttacgtgccg atcaacgtct    4020
cattttcgcc agatatcgac gtcttaagac ccactttcac atttaagttg tttttctaat    4080
ccgcatatga tcaattcaag gccgaataag aaggctggct ctgcaccttg gtgatcaaat    4140
aattcgatag cttgtcgtaa taatggcggc atactatcag tagtaggtgt ttccctttct    4200
tctttagcga cttgatgctc ttgatcttcc aatacgcaac ctaaagtaaa atgccccaca    4260
gcgctgagtg catataatgc attctctagt gaaaaaccett gttggcataa aaaggctaat    4320
tgattttcga gagtttcata ctgttttct gtaggccgtg tacctaaatg tacttttgat    4380
ccatcgcgat gacttagtaa agcacatcta aaacttttag cgttattacg taaaaatct    4440 tgccagcttt cccttctaa agggcaaaag tgagtatggt gcctatctaa catctcaatg    4500
gctaaggcgt cgagcaaagc ccgcttattt tttacatgcc aatacaatgt aggctgctct    4560
acacctagct tctgggcgag tttacgggtt gttaaccett cgattccgac ctcattaagc    4620
agctctaatg cgctgttaat cactttactt ttatctaatc tagacatcat                4670
```

<210> SEQ ID NO 366
<211> LENGTH: 4607
<212> TYPE: DNA
<213> ORGANISM: Artificial sequence
<220> FEATURE:
<223> OTHER INFORMATION: Synthetic sequence

<400> SEQUENCE: 366

```
ttacttttat ctaatctaga catcattaat tcctaatttt tgttgacact ctatcgttga      60
tagagttatt ttaccactcc ctatcagtga tagagaaaag aattcaaaag atctaaagag     120
gagaaaggat ctatggccaa aaacaccatt accaaaacac tgaaactgcg tattgtgcgt     180
ccgtataata gcgcagaagt ggaaaaaatt gttgccgacg aaaaaaacaa ccgcgaaaaa     240
atcgcactgg aaaagaacaa agacaaagtg aaagaagcct gcagcaaaca tctgaaagtt     300
gcagcatatt gtaccacaca ggttgaacgt aatgcatgcc tgttttgtaa agcacgtaaa     360
ctggatgaca aattctacca aaaactgcgt ggtcagtttc cggatgcagt ttttttggcaa    420
gaaatcagcg aaattttttcg ccagctgcag aaacaggcag cagaaatcta taatcagagc    480
ctgatcgaac tgtactacga gatttttatc aaaggcaaag gtattgcaaa tgccagcagc    540
gttgaacatt atctgagtga tgtttgttat acccgtgcag cagaactgtt taaaaacgca    600
gcaattgcaa gcggtctgcg tagcaaaatc aaaagcaatt ttcgtctgaa agaactgaaa    660
aacatgaaaa gtggtctgcc gaccaccaaa agcgataatt ttccgattcc gctggttaaa    720
cagaaaggtg gtcagtatac cggttttgaa attagcaatc ataatagcga cttcatcatc    780
aagattccgt ttggtcgttg gcaggtcaaa aaagagatta taaatatcg tccgtgggag     840
aaatttgact ttgaacaggt tcagaaaagc ccgaaaccga ttagcctgct gctgagcacc    900
cagcgtcgta acgtaataa aggttggagc aaagatgaag gcaccgaagc cgaaatcaaa    960
aaagttatga atggcgatta tcagaccagc tacattgaag ttaaacgtgg cagcaaaatc    1020
ggtgaaaaaa gcgcatggat gctgaatctg agcattgatg ttccgaaaat tgataaaggt    1080
gtggatccga gcattattgg tggtattgat gttggtgtta aatcaccgct ggtttgcgca    1140
attaacaatg catttagccg ttatagcatc agcgataacg acctgtttca cttcaacaag    1200
aaaatgtttg cacgtcgtcg tatcctgctg aaaaaaaacc gtcataaacg tgcaggtcat    1260
ggtgcaaaaa acaaactgaa accgatcacc attctgaccg aaaaaagtga acgttttcgc    1320
aaaaagctga ttgaacgttg ggcatgtgaa atcgcggatt tcttcattaa aaacaaagtt    1380
ggcaccgtgc agatggaaaa tctggaaagc atgaaacgta aagaggacag ctatttttaac    1440
attcgcctgc gtggcttttg gccgtatgca gaaatgcaga acaaaatcga attcaaactg    1500
aagcagtatg gcatcgaaat tcgtaaagtt gcaccgaata ataccagcaa aacctgtagc    1560
aaatgtggcc atctgaacaa ctatttcaac ttcgagtacc gcaagaaaaa caaattcccg    1620
cactttaaat gcgaaaaatg caacttcaaa gaaaacgccg attataatgc agccctgaat    1680
atttcaaacc cgaaactgaa aagcaccaaa gaggaaccgt aaatattttat actttattat    1740
ccttcattga caaaatgag aatgttatcc cagataacat ttgatgtaca cagattcaca    1800
cttcactgat aaagtggaga accgcttcac caaaagctgt cccttagggg attagaactt    1860
gagtgaaggt gggctgcttg catcagccta atgtcgagaa gtgctttctt cggaaagtaa    1920
ccctcgaaac aaattcattt ttcctctcca attctgcaca aaaaaggtg agtccttata    1980
aaccggcgtg cagaacgccg gctcaccttt tttcttcatt cgatttatg cttaaaagcc    2040
gtaaaaacgc ggaattcggc gccgttgcag aacccgaata gacgaatgaa ggaatgcaac    2100
taccttacac cgcttgcgaa agttgtcaga agataatctt gcagaacccg aatagacgaa    2160
tgaaggaatg caatcttgac agagcccgat tgcgttatct ccaggagaaa catataaaag    2220
catcaaccgc tgatcggact agagtcacac tggctcacct tcgggtgggc ctttctgcgt    2280
ttatacctag ggatatattc cgcttcctcg ctcactgact cgctacgctc ggtcgttcga    2340
```

```
ctgcggcgag cggaaatggc ttacgaacgg ggcggagatt tcctggaaga tgccaggaag    2400
atacttaaca gggaagtgag agggccgcgg caaagccgtt tttccatagg ctccgccccc    2460
ctgacaagca tcacgaaatc tgacgctcaa atcagtggtg gcgaaacccg acaggactat    2520
aaagatacca ggcgtttccc cctggcggct ccctcgtgcg ctctcctgtt cctgcctttc    2580
ggtttaccgg tgtcattccg ctgttatggc cgcgtttgtc tcattccacg cctgacactc    2640
agttccgggt aggcagttcg ctccaagctg gactgtatgc acgaaccccc cgttcagtcc    2700
gaccgctgcg ccttatccgg taactatcgt cttgagtcca acccggaaag acatgcaaaa    2760
gcaccactgg cagcagccac tggtaattga tttagaggag ttagtcttga agtcatgcgc    2820
cggttaaggc taaactgaaa ggacaagttt tggtgactgc gctcctccaa gccagttacc    2880
tcggttcaaa gagttggtag ctcagagaac cttcgaaaaa ccgccctgca aggcggtttt    2940
ttcgttttca gagcaagaga ttacgcgcag accaaaacga tctcaagaag atcatcttat    3000
taatcagata aaatatttct agatttcagt gcaatttatc tcttcaaatg tagcacctga    3060
agtcagcccc atacgatata agttgttact agtgcttgga ttctcaccaa taaaaaacgc    3120
ccggcggcaa ccgagcgttc tgaacaaatc cagatggagt tctgaggtca ttactggatc    3180
tatcaacagg agtccaagcg agctcgatat caaattacgc cccgccctgc cactcatcgc    3240
agtactgttg taattcatta agcattctgc cgacatggaa gccatcacaa acggcatgat    3300
gaacctgaat cgccagcggc atcagcacct tgtcgccttg cgtataatat ttgcccatgg    3360
tgaaaacggg ggcgaagaag ttgtccatat tggccacgtt taaatcaaaa ctggtgaaac    3420
tcacccaggg attggctgag acgaaaaaca tattctcaat aaacccttta gggaaatagg    3480
ccaggttttc accgtaacac gccacatctt gcgaatatat gtgtagaaac tgccggaaat    3540
cgtcgtggta ttcactccag agcgatgaaa acgtttcagt ttgctcatgg aaaacggtgt    3600
aacaagggtg aacactatcc catatccacca gctcaccgtc tttcattgcc atacgaaatt    3660
ccggatgagc attcatcagg cgggcaagaa tgtgaataaa ggccggataa aacttgtgct    3720 tattttctt tacggtcttt aaaaaggccg taatatccag ctgaacggtc tggttatagg    3780
tacattgagc aactgactga aatgcctcaa aatgttcttt acgatgccat gggatatat    3840 caacggtggt atatccagtg attttttttct ccattttagc ttccttagct cctgaaaatc    3900
tcgataactc aaaaaatacg cccggtagtg atcttatttc attatggtga agttggaac    3960 ctcttacgtg ccgatcaacg tctcatttc gccagatatc gacgtcttaa gacccacttt    4020
cacatttaag ttgttttct aatccgcata tgatcaattc aaggccgaat aagaaggctg    4080
gctctgcacc ttggtgatca ataattcga tagcttgtcg taataatggc ggcatactat    4140
cagtagtagg tgtttcccttt tcttctttag cgacttgatg ctcttgatct tccaatacgc    4200
aacctaaagt aaaatgcccc acagcgctga gtgcatataa tgcattctct agtgaaaaac    4260
cttgttggca taaaaggct aattgatttt cgagagtttc atactgttt tctgtaggcc    4320 gtgtacctaa atgtactttt gctccatcgc gatgacttag taaagcacat ctaaaacttt    4380
tagcgttatt acgtaaaaaa tcttgccagc tttcccttc taaagggcaa aagtgagtat    4440
ggtgcctatc taacatctca atggctaagg cgtcgagcaa agcccgctta ttttttacat    4500
gccaatacaa tgtaggctgc tctacaccta gcttctgggc gagtttacgg gttgttaaac    4560
cttcgattcc gacctcatta agcagctcta atgcgctgtt aatcact               4607
```

<210> SEQ ID NO 367

<211> LENGTH: 7556
<212> TYPE: DNA
<213> ORGANISM: Artificial sequence
<220> FEATURE:
<223> OTHER INFORMATION: Synthetic sequence

<400> SEQUENCE: 367

| | |
|---|---|
| acccacgccg aaacaagcgc tcatgagccc gaagtggcga gcccgatctt ccccatcggt | 60 |
| gatgtcggcg atataggcgc cagcaaccgc acctgtggcg ccggtgatgc cggccacgat | 120 |
| gcgtccggcg tagaggatcg agatctcgat cccgcgaaat taatacgact cactataggg | 180 |
| agaccacaac ggtttccctc tagtgccggt ccggagagc tctttaatta agcggccgcc | 240 |
| ctgcaggact cgagttctag aaataatttt gtttaacttt aagaaggaga tatacatatg | 300 |
| aaatcttctc accatcacca tcaccatcac catcaccatg gttcttctat gaaaatcgaa | 360 |
| gaaggtaaac tggtaatctg gattaacggc gataaaggct ataacggtct cgctgaagtc | 420 |
| ggtaagaaat tcgagaaaga taccggaatt aaagtcaccg ttgagcatcc ggataaactg | 480 |
| gaagagaaat tcccacaggt tgcggcaact ggcgatggcc ctgacattat cttctgggca | 540 |
| cacgaccgct ttggtggcta cgctcaatct ggcctgttgg ctgaaatcac cccggacaaa | 600 |
| gcgttccagg acaagctgta tccgtttacc tgggatgccg tacgttacaa cggcaagctg | 660 |
| attgcttacc cgatcgctgt tgaagcgtta tcgctgatttt ataacaaaga tctgctgccg | 720 |
| aacccgccaa aaacctggga agagatcccg gcgctggata agaactgaa agcgaaaggt | 780 |
| aagagcgcgc tgatgttcaa cctgcaagaa ccgtacttca cctggccgct gattgctgct | 840 |
| gacgggggtt atgcgttcaa gtatgaaaac ggcaagtacg acattaaaga cgtgggcgtg | 900 |
| gataacgctg gcgcgaaagc gggtctgacc ttcctggttg acctgattaa aaacaaacac | 960 |
| atgaatgcag acaccgatta ctccatcgca gaagctgcct taataaagg cgaaacagcg | 1020 |
| atgaccatca acggcccgtg ggcatggtcc aacatcgaca ccagcaaagt gaattatggt | 1080 |
| gtaacggtac tgccgacctt caagggtcaa ccatccaaac cgttcgttgg cgtgctgagc | 1140 |
| gcaggtatta acgccgccag tccgaacaaa gagctggcaa agagttcct cgaaaactat | 1200 |
| ctgctgactg atgaaggtct ggaagcggtt aataaagaca aaccgctggg tgccgtagcg | 1260 |
| ctgaagtctt acgaggaaga gttggcgaaa gatccacgta ttgccgccac tatggaaaac | 1320 |
| gcccagaaag tgaaatcat gccgaacatc ccgcagatgt ccgctttctg gtatgccgtg | 1380 |
| cgtactgcgg tgatcaacgc cgccagcggt cgtcagactg tcgatgaagc cctgaaagac | 1440 |
| gcgcagacta attcgagctc gaacaacaac aacaataaca ataacaacaa cctcgggatc | 1500 |
| gaggaaaacc tgtacttcca atccaatgca atggccaaaa acaccattac caaaacactg | 1560 |
| aaactgcgta ttgtgcgtcc gtataatagc gcagaagtgg aaaaaattgt tgccgacgaa | 1620 |
| aaaacaacc gcgaaaaaat cgcactggaa aagaacaaag acaaagtgaa agaagcctgc | 1680 |
| agcaaacatc tgaaagttgc agcatattgt accacacagg ttgaacgtaa tgcatgcctg | 1740 |
| ttttgtaaag cacgtaaact ggatgacaaa ttctaccaaa aactgcgtgg tcagttccg | 1800 |
| gatgcagttt tttggcaaga atcagcgaa attttcgcc agctgcagaa acaggcagca | 1860 |
| gaaatctata atcagagcct gatcgaactg tactacgaga tttttatcaa aggcaaaggt | 1920 |
| attgcaaatg ccagcagcgt tgaacattat ctgagtgatg tttgttatac ccgtgcagca | 1980 |
| gaactgtttta aaaacgcagc aattgcaagc ggtctgcgta gcaaaatcaa aagcaatttt | 2040 |
| cgtctgaaag aactgaaaaa catgaaagt ggtctgccga ccaccaaaag cgataatttt | 2100 |
| ccgattccgc tggttaaaca gaaaggtggt cagtataccg gttttgaaat tagcaatcat | 2160 |

```
aatagcgact tcatcatcaa gattccgttt ggtcgttggc aggtcaaaaa agagattgat    2220
aaatatcgtc cgtgggagaa atttgacttt gaacaggttc agaaaagccc gaaaccgatt    2280
agcctgctgc tgagcaccca gcgtcgtaaa cgtaataaag gttggagcaa agatgaaggc    2340
accgaagccg aaatcaaaaa agttatgaat ggcgattatc agaccagcta cattgaagtt    2400
aaacgtggca gcaaaatctg tgaaaaaagc gcatggatgc tgaatctgag cattgatgtt    2460
ccgaaaattg ataaaggtgt ggatccgagc attattggtg gtattgatgt tggtgttaaa    2520
tcaccgctgg tttgcgcaat taacaatgca tttagccgtt atagcatcag cgataacgac    2580
ctgtttcact tcaacaagaa aatgtttgca cgtcgtcgta tcctgctgaa aaaaaaccgt    2640
cataaacgtg caggtcatgg tgcaaaaaac aaactgaaac cgatcaccat tctgaccgaa    2700
aaaagtgaac gttttcgcaa aaagctgatt gaacgttggg catgtgaaat cgcggatttc    2760
ttcattaaaa acaaagttgg caccgtgcag atggaaaatc tggaaagcat gaaacgtaaa    2820
gaggacagct attttaacat tcgcctgcgt ggcttttggc cgtatgcaga atgcagaac     2880 aaaatcgaat tcaaactgaa gcagtatggc atcgaaattc gtaaagttgc accgaataat    2940
accagcaaaa cctgtagcaa atgtggccat ctgaacaact atttcaactt cgagtaccgc    3000
aagaaaaaca aattcccgca cttaaatgc gaaaaatgca acttcaaaga aacgccgat     3060 tataatgcag ccctgaatat ttcaaacccg aaactgaaaa gcaccaaaga ggaaccgtaa    3120
taacattgga agtggataac ggatccgcga tcgcggcgcg ccacctggtg gccggccggt    3180
accacgcgtg cgcgctgatc cggctgctaa caaagcccga aaggaagctg agttggctgc    3240
tgccaccgct gagcaataac tagcataacc ccttggggcc tctaaacggg tcttgagggg    3300 tttttgctg aaaggaggaa ctatatccgg atatccacag gacgggtgtg gtcgccatga     3360
tcgcgtagtc gatagtggct ccaagtagcg aagcgagcag gactgggcgg cggccaaagc    3420
ggtcggacag tgctccgaga acgggtgcgc atagaaattg catcaacgca tatagcgcta    3480
gcagcacgcc atagtgactg gcgatgctgt cggaatggac gatatccgc aagaggcccg     3540 gcagtaccgg cataaccaag cctatgccta cagcatccag ggtgacggtg ccgaggatga    3600
cgatgagcgc attgttagat tcatacacg gtgcctgact gcgttagcaa tttaactgtg     3660
ataaactacc gcattaaagc ttatcgatga taagctgtca acatgagaa ttcttgaaga    3720 cgaaagggcc tcgtgatacg cctatttta taggttaatg tcatgataat aatggtttct    3780
tagacgtcag gtggcacttt tcggggaaat gtgcgcggaa cccctatttg tttatttttc    3840
taaatacatt caaatatgta tccgctcatg agacaataac cctgataaat gcttcaataa    3900
cattgaaaaa ggaagagtat gagtattcaa catttccgtg tcgcccttat ccctttttt    3960 gcggcatttt gccttcctgt ttttgctcac ccagaaacgc tggtgaaagt aaaagatgct    4020
gaagatcagt tgggtgcacg agtgggttac atcgaactgg atctcaacag cggtaagatc    4080
cttgagagtt ttcgccccga agaacgtttt ccaatgatga gcacttttaa agttctgcta    4140
tgtggcgcgg tattatcccg tgttgacgcc gggcaagagc aactcggtcg ccgcatacac    4200
tattctcaga atgacttggt tgagtactca ccagtcacag aaaagcatct tacggatggc    4260
atgacagtaa gagaattatg cagtgctgcc ataaccatga gtgataacac tgcggccaac    4320
ttacttctga caacgatcgg aggaccgaag gagctaaccg ctttttttgca caacatgggg    4380 gatcatgtaa ctcgccttga tcgttgggaa ccggagctga atgaagccat accaaacgac    4440
gagcgtgaca ccacgatgcc tgcagcaatg gcaacaacgt tgcgcaaact attaactggc    4500
```

```
gaactactta ctctagcttc ccggcaacaa ttaatagact ggatggaggc ggataaagtt    4560
gcaggaccac ttctgcgctc ggcccttccg gctggctggt ttattgctga taaatctgga    4620
gccggtgagc gtgggtctcg cggtatcatt gcagcactgg ggccagatgg taagccctcc    4680
cgtatcgtag ttatctacac gacggggagt caggcaacta tggatgaacg aaatagacag    4740
atcgctgaga taggtgcctc actgattaag cattggtaac tgtcagacca agtttactca    4800
tatatacttt agattgattt aaaacttcat ttttaattta aaaggatcta ggtgaagatc    4860 cttttttgata atctcatgac caaaatccct taacgtgagt tttcgttcca ctgagcgtca    4920
gaccccgtag aaaagatcaa aggatcttct tgagatcctt ttttctgcg cgtaatctgc     4980 tgcttgcaaa caaaaaaacc accgctacca gcggtggttt gtttgccgga tcaagagcta    5040
ccaactcttt ttccgaaggt aactggcttc agcagagcgc agataccaaa tactgtcctt    5100
ctagtgtagc cgtagttagg ccaccacttc aagaactctg tagcaccgcc tacatacctc    5160
gctctgctaa tcctgttacc agtggctgct gccagtggcg ataagtcgtg tcttaccggg    5220
ttggactcaa gacgatagtt accggataag gcgcagcggt cgggctgaac ggggggttcg    5280
tgcacacagc ccagcttgga gcgaacgacc tacaccgaac tgagatacct acagcgtgag    5340
ctatgagaaa gcgccacgct tcccgaaggg agaaaggcgg acaggtatcc ggtaagcggc    5400
agggtcggaa caggagagcg cacgagggag cttccagggg gaaacgcctg gtatctttat    5460
agtcctgtcg ggtttcgcca cctctgactt gagcgtcgat ttttgtgatg ctcgtcaggg    5520
gggcggagcc tatggaaaaa cgccagcaac gcggcctttt tacggttcct ggccttttgc    5580
tggccttttg ctcacatgtt ctttcctgcg ttatccctg attctgtgga taaccgtatt    5640
accgcctttg agtgagctga taccgctcgc cgcagccgaa cgaccgagcg cagcgagtca    5700
gtgagcgagg aagcggaaga gcgcctgatg cggtattttc tccttacgca tctgtgcggt    5760
atttcacacc gcaatggtgc actctcagta caatctgctc tgatgccgca tagttaagcc    5820
agtatacact ccgctatcgc tacgtgactg ggtcatggct gcgccccgac acccgccaac    5880
acccgctgac gcgccctgac gggcttgtct gctcccggca tccgcttaca gacaagctgt    5940
gaccgtctcc gggagctgca tgtgtcagag gttttcaccg tcatcaccga aacgcgcgag    6000
gcagctgcgg taaagctcat cagcgtggtc gtgaagcgat tcacagatgt ctgcctgttc    6060
atccgcgtcc agctcgttga gtttctccag aagcgttaat gtctggcttc tgataaagcg    6120
ggccatgtta agggcggttt tttcctgttt ggtcactgat gcctccgtgt aagggggatt    6180
tctgttcatg ggggtaatga taccgatgaa acgagagagg atgctcacga tacgggttac    6240
tgatgatgaa catgcccggt tactggaacg ttgtgagggt aaacaactgg cggtatggat    6300
gcggcgggac cagagaaaaa tcactcaggg tcaatgccag cgcttcgtta atacagatgt    6360
aggtgttcca cagggtagcc agcagcatcc tgcgatgcag atccggaaca taatggtgca    6420
gggcgctgac ttccgcgttt ccagacttta cgaaacacgg aaaccgaaga ccattcatgt    6480
tgttgctcag gtcgcagacg ttttgcagca gcagtcgctt cacgttcgct cgcgtatcgg    6540
tgattcattc tgctaaccag taaggcaacc ccgccagcct agccgggtcc tcaacgacag    6600
gagcacgatc atgcgcaccc gtggccagga cccaacgctg cccagatgc gccgcgtgcg     6660 gctgctggag atggcggacg cgatggatat gttctgccaa gggttggttt gcgcattcac    6720
agttctccgc aagaattgat tggctccaat tcttggagtg gtgaatccgt tagcgaggtg    6780
ccgccggctt ccattcaggt cgaggtggcc cggctccatg caccgcgacg caacgcgggg    6840
aggcagacaa ggtatagggc ggcgcctaca atccatgcca acccgttcca tgtgctcgcc    6900
```

| | |
|---|---|
| gaggcggcat aaatcgccgt gacgatcagc ggtccaatga tcgaagttag gctggtaaga | 6960 |
| gccgcgagcg atccttgaag ctgtccctga tggtcgtcat ctacctgcct ggacagcatg | 7020 |
| gcctgcaacg cgggcatccc gatgccgccg gaagcgagaa gaatcataat ggggaaggcc | 7080 |
| atccagcctc gcgtcgcgaa cgccagcaag acgtagccca gcgcgtcggc cgccatgccg | 7140 |
| gcgataatgg cctgcttctc gccgaaacgt ttggtggcgg gaccagtgac gaaggcttga | 7200 |
| gcgagggcgt gcaagattcc gaataccgca agcgacaggc cgatcatcgt cgcgctccag | 7260 |
| cgaaagcggt cctcgccgaa aatgacccag agcgctgccg gcacctgtcc tacgagttgc | 7320 |
| atgataaaga agacagtcat aagtgcggcg acgatagtca tgccccgcgc ccaccggaag | 7380 |
| gagctgactg ggttgaaggc tctcaagggc atcggtcgac gctctccctt atgcgactcc | 7440 |
| tgcattagga agcagcccag tagtaggttg aggccgttga gcaccgccgc cgcaaggaat | 7500 |
| ggtgcatgca aggagatggc gcccaacagt cccccggcca cggggcctgc caccat | 7556 |

<210> SEQ ID NO 368
<211> LENGTH: 30
<212> TYPE: DNA
<213> ORGANISM: Artificial sequence
<220> FEATURE:
<223> OTHER INFORMATION: Synthetic sequence

<400> SEQUENCE: 368
ttcatttgag cattaaatgt caagttctgc                                30

<210> SEQ ID NO 369
<211> LENGTH: 30
<212> TYPE: DNA
<213> ORGANISM: Artificial sequence
<220> FEATURE:
<223> OTHER INFORMATION: Synthetic sequence

<400> SEQUENCE: 369
ttcatttgag cattaagtgt caagttctgc                                30

<210> SEQ ID NO 370
<211> LENGTH: 21
<212> TYPE: DNA
<213> ORGANISM: Artificial sequence
<220> FEATURE:
<223> OTHER INFORMATION: Synthetic sequence

<400> SEQUENCE: 370
aaactcgtaa ttcacagttc a                                         21

<210> SEQ ID NO 371
<211> LENGTH: 10
<212> TYPE: DNA
<213> ORGANISM: Artificial Sequence
<220> FEATURE:
<223> OTHER INFORMATION: Synthetic sequence

<400> SEQUENCE: 371
tatatatata                                                      10

<210> SEQ ID NO 372
<211> LENGTH: 6
<212> TYPE: DNA
<213> ORGANISM: Artificial Sequence
<220> FEATURE:
<223> OTHER INFORMATION: Synthetic sequence

```
<400> SEQUENCE: 372 tatata                                                                   6

<210> SEQ ID NO 373
<211> LENGTH: 5
<212> TYPE: DNA
<213> ORGANISM: Artificial Sequence
<220> FEATURE:
<223> OTHER INFORMATION: Synthetic sequence

<400> SEQUENCE: 373 tatat                                                                    5
```

US 11,441,137 B2

CASZ COMPOSITIONS AND METHODS OF USE

CROSS-REFERENCE

This application is a continuation of U.S. patent application Ser. No. 16/694,720, filed Nov. 25, 2019, which is a continuation of PCT/US2018/058545, filed Oct. 31, 2018, which claims the benefit of U.S. Provisional Patent Application No. 62/580,395, filed Nov. 1, 2017, which applications are incorporated herein by reference in their entirety.

GOVERNMENT RIGHTS

This invention was made with government support under 1244557 awarded by the National Science Foundation and under DE-AC02-05CH11231 awarded by the Department of Energy. The government has certain rights in the invention.

INCORPORATION BY REFERENCE OF SEQUENCE LISTING PROVIDED AS A TEXT FILE

A Sequence Listing is provided herewith as a text file, "BERK-374WO_SEQ_LISTING_ST25.txt" created on Oct. 30, 2018 and having a size of 536 KB. The contents of the text file are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

SUMMARY

The present disclosure provides compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ trans activating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

BRIEF DESCRIPTION OF THE DRAWINGS

FIG. 1 depicts examples of naturally occurring CasZ protein sequences.

FIG. 2 depicts schematic representations of CasZ loci, which include a Cas1 protein in addition to the CasZ protein.

FIG. 7 depict the sequences of Cas14 proteins described herein.

FIG. 10 depicts a maximum likelihood tree for Cas1 from known CRISPR systems.

FIG. 20, Panels A-E depict high fidelity ssDNA DNP detection by CRISPR-Cas14a. FIG. 20, panel C provides nucleotide sequences (Top to Bottom: SEQ ID NOs:367-370)

FIG. 21, Panels A-F depict the impact of various activators on Cas14a1 cleavage rate.

FIG. 24 depicts Cas14 nucleotide sequences of plasmids used in the present invention.

DEFINITIONS

Figure 3:
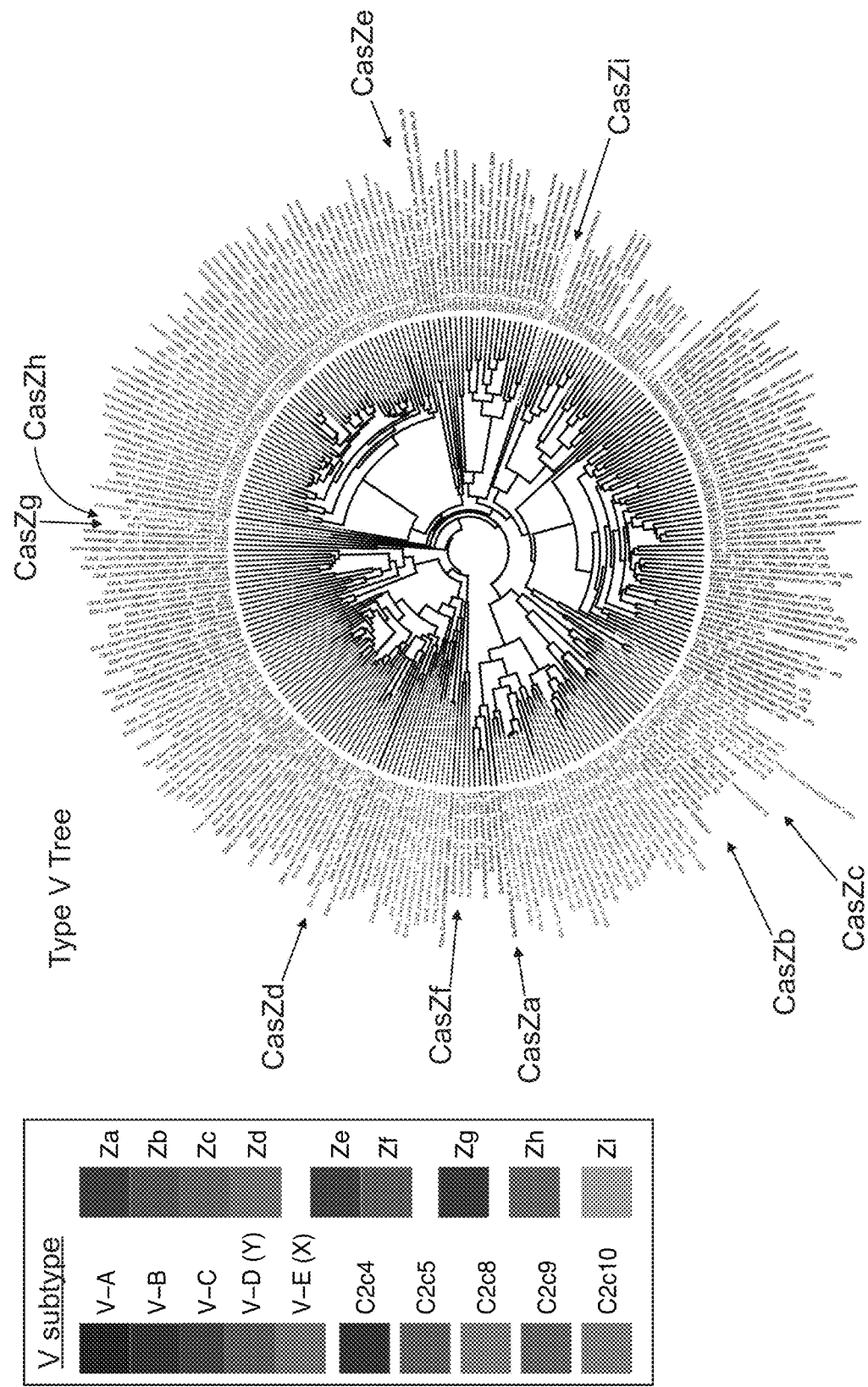
FIG. 3 depicts a phylogenetic tree of CasZ sequences in relation to other Class 2 CRISPR/Cas effector protein sequences.

"Heterologous," as used herein, means a nucleotide or polypeptide sequence that is not found in the native nucleic acid or protein, respectively. For example, relative to a CasZ polypeptide, a heterologous polypeptide comprises an amino acid sequence from a protein other than the CasZ polypeptide. In some cases, a portion of a CasZ protein from one species is fused to a portion of a CasZ protein from a different species. The CasZ sequence from each species could therefore be considered heterologous relative to one another. As another example, a CasZ protein (e.g., a dCasZ protein) can be fused to an active domain from a non-CasZ protein (e.g., a histone deacetylase), and the sequence of the active domain could be considered a heterologous polypeptide (it is heterologous to the CasZ protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasZ polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ trans activating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

Compositions

CRISPR/CasZ Proteins, Guide RNAs, and trancRNA

Class 2 CRISPR-Cas systems are characterized by effector modules that include a single multidomain protein. In the CasZ system, a CRISPR/Cas endonuclease (e.g., a CasZ protein) interacts with (binds to) a corresponding guide RNA (e.g., a CasZ guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasZ protein forms a complex with a CasZ guide RNA and the guide RNA provides sequence specificity to the RNP complex via the guide sequence. The CasZ protein of the complex provides the site-specific activity. In other words, the CasZ protein is guided to a target site (e.g., stabilized at a target site) within a target nucleic acid (e.g. a target nucleotide sequence within a target chromosomal nucleic acid; or a target nucleotide sequence within a target extrachromosomal nucleic acid, e.g., an episomal nucleic acid, a minicircle nucleic acid, a mitochondrial nucleic acid, a chloroplast nucleic acid, etc.) by virtue of its association with the guide RNA.

The present disclosure provides compositions comprising a CasZ polypeptide (and/or a nucleic acid encoding the CasZ polypeptide) (e.g., where the CasZ polypeptide can be a naturally existing CasZ protein, a nickase CasZ protein, a dCasZ protein, a chimeric CasZ protein, etc.)(a CasZa, CasZb, CasZc, CasZd, CasZe, CasZf, CasZg, CasZh, CasZi, CasZj, CasZK, or CasZl protein). The present disclosure provides compositions comprising a CasZ guide RNA (and/or a nucleic acid encoding the CasZ guide RNA). For example, the present disclosure provides compositions comprising (a) a CasZ polypeptide (and/or a nucleic acid encoding the CasZ polypeptide) and (b) a CasZ guide RNA (and/or a nucleic acid encoding the CasZ guide RNA). The present disclosure provides a nucleic acid/protein complex (RNP complex) comprising: (a) a CasZ polypeptide; and (b) a CasZ guide RNA. The present disclosure provides compositions comprising a CasZ trancRNA. The present disclosure provides compositions comprising a CasZ trancRNA and one or more of: (a) a CasZ protein, and (b) a CasZ guide RNA (e.g., comprising a CasZ trancRNA and a CasZ protein, a CasZ trancRNA and a CasZ guide RNA, or a CasZ trancRNA and a CasZ protein and a CasZ guide RNA. The present disclosure provides a nucleic acid/protein complex (RNP complex) comprising: (a) a CasZ polypeptide; (b) a CasZ guide RNA; and (c) a CasZ trancRNA. The present disclosure provides compositions comprising a CasZ protein and one or more of: (a) a CasZ trancRNA, and (b) a CasZ guide RNA.

CasZ Protein

A CasZ polypeptide (this term is used interchangeably with the term "CasZ protein", "Cas14", "Cas14 polypeptide", or "Cas14 protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasZ protein includes a fusion partner with an activity, and in some cases the CasZ protein provides nuclease activity). In some cases, the CasZ protein is a naturally-occurring protein (e.g., naturally occurs in prokaryotic cells). In other cases, the CasZ protein is not a naturally-occurring polypeptide (e.g., the CasZ protein is a variant CasZ protein, a chimeric protein, and the like). A CasZ protein includes 3 partial RuvC domains (RuvC-I, RuvC-II, and RuvC-III, also referred to herein as subdomains) that are not contiguous with respect to the primary amino acid sequence of the CasZ protein, but form a RuvC domain once the protein is produced and folds. A naturally occurring CasZ protein functions as an endonuclease that catalyzes cleavage at a specific sequence in a targeted nucleic acid (e.g., a double stranded DNA (dsDNA)). The sequence specificity is provided by the associated guide RNA, which hybridizes to a target sequence within the target DNA. The naturally occurring CasZ guide RNA is a crRNA, where the crRNA includes (i) a guide sequence that hybridizes to a target sequence in the target DNA and (ii) a protein binding segment that binds to the CasZ protein.

In some embodiments, the CasZ protein of the subject methods and/or compositions is (or is derived from) a naturally occurring (wild type) protein. Examples of naturally occurring CasZ proteins (e.g., CasZa, CasZb, CasZc, CasZd, CasZe, CasZf, CasZg, CasZh, CasZi, CasZj, CasZk, CasZl) are depicted in FIG. 1. In some cases, a subject CasZ protein is a CasZa protein. In some cases, a subject CasZ protein is a CasZb protein. In some cases, a subject CasZ protein is a CasZc protein. In some cases, a subject CasZ protein is a CasZd protein. In some cases, a subject CasZ protein is a CasZe protein. In some cases, a subject CasZ protein is a CasZf protein. In some cases, a subject CasZ protein is a CasZg protein. In some cases, a subject CasZ protein is a CasZh protein. In some cases, a subject CasZ protein is a CasZi protein. In some cases, a subject CasZ protein is a CasZj protein. In some cases, a subject CasZ protein is a CasZk protein. In some cases, a subject CasZ protein is a CasZl protein. In some cases, a subject CasZ protein is a CasZe, CasZf, CasZg, or CasZh protein. In some cases, a subject CasZ protein is a CasZj, CasZk, or CasZl protein.

It is important to note that this newly discovered protein (CasZ) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasZ protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. In addition, in their natural context, the CasZ-encoding DNA sequences are present in loci that also have a Cas1 protein.

In some cases, a subject CasZ protein has a length of 900 amino acids or less (e.g., 850 amino acids or less, 800 amino acids or less, 750 amino acids or less, or 700 amino acids or less). In some cases, a subject CasZ protein has a length of 850 amino acids or less (e.g., 850 amino acids or less). In some cases, a subject CasZ protein length of 800 amino acids or less (e.g., 750 amino acids or less). In some cases, a subject CasZ protein has a length of 700 amino acids or less. In some cases, a subject CasZ protein has a length of 650 amino acids or less.

In some cases, a subject CasZ protein has a length in a range of from 350-900 amino acids (e.g., 350-850, 350-800, 350-750, 350-700, 400-900, 400-850, 400-800, 400-750, or 400-700 amino acids).

In some cases, a subject CasZ protein (e.g., CasZa) has a length in a range of from 350-750 amino acids (e.g., 350-700, 350-550, 450-550, 450-750, 450-650, or 450-550 amino acids). In some cases, a subject CasZ protein (e.g., CasZa) has a length in a range of from 450-750 amino acids (e.g., 500-700 amino acids). In some cases, a subject CasZ protein (e.g., CasZa) has a length in a range of from 350-700 amino acids (e.g., 350-650, 350-600, or 350-550 amino acids). In some cases, a subject CasZ protein (e.g., CasZa) has a length in a range of from 500-700 amino acids. In some cases, a subject CasZ protein (e.g., CasZa) has a length in a range of from 450-550 amino acids. In some cases, a subject CasZ protein (e.g., CasZa) has a length in a range of from 350-550 amino acids.

In some cases, a subject CasZ protein (e.g., CasZb) has a length in a range of from 350-700 amino acids (e.g., 350-650, or 350-620 amino acids). In some cases, a subject CasZ protein (e.g., CasZb) has a length in a range of from 450-700 amino acids (e.g., 450-650, 500-650 or 500-620 amino acids). In some cases, a subject CasZ protein (e.g., CasZb) has a length in a range of from 500-650 amino acids (e.g., 500-620 amino acids). In some cases, a subject CasZ protein (e.g., CasZb) has a length in a range of from 500-620 amino acids.

In some cases, a subject CasZ protein (e.g., CasZc) has a length in a range of from 600-800 amino acids (e.g., 600-650 or 700-800 amino acids). In some cases, a subject CasZ protein (e.g., CasZc) has a length in a range of from 600-650 amino acids. In some cases, a subject CasZ protein (e.g., CasZc) has a length in a range of from 700-800 amino acids.

In some cases, a subject CasZ protein (e.g., CasZd) has a length in a range of from 400-650 amino acids (e.g., 400-600, 400-550, 500-650, 500-600 or 500-550 amino acids). In some cases, a subject CasZ protein (e.g., CasZd) has a length in a range of from 500-600 amino acids. In some cases, a subject CasZ protein (e.g., CasZd) has a length in a range of from 500-550 amino acids. In some cases, a subject CasZ protein (e.g., CasZd) has a length in a range of from 400-550 amino acids.

In some cases, a subject CasZ protein (e.g., CasZe) has a length in a range of from 450-700 amino acids (e.g., 450-650, 450-615, 475-700, 475-650, or 475-615 amino acids). In some cases, a subject CasZ protein (e.g., CasZe) has a length in a range of from 450-675 amino acids. In some cases, a subject CasZ protein (e.g., CasZe) has a length in a range of from 475-675 amino acids.

In some cases, a subject CasZ protein (e.g., CasZf) has a length in a range of from 400-550 amino acids (e.g., 400-520, 400-500, 400-475, 415-550, 415-520, 415-500, or 415-475 amino acids). In some cases, a subject CasZ protein (e.g., CasZf) has a length in a range of from 400-475 amino acids (e.g., 400-450 amino acids).

In some cases, a subject CasZ protein (e.g., CasZg) has a length in a range of from 500-750 amino acids (e.g., 550-750 or 500-700 amino acids). In some cases, a subject CasZ protein (e.g., CasZg) has a length in a range of from 700-750 amino acids. In some cases, a subject CasZ protein (e.g., CasZg) has a length in a range of from 550-600 amino acids.

In some cases, a subject CasZ protein (e.g., CasZh) has a length in a range of from 380-450 amino acids (e.g., 380-420, 400-450, or 400-420 amino acids). In some cases, a subject CasZ protein (e.g., CasZh) has a length in a range of from 400-420 amino acids.

In some cases, a subject CasZ protein (e.g., CasZi) has a length in a range of from 700-800 amino acids (e.g., 700-750, 720-800, or 720-750 amino acids). In some cases, a subject CasZ protein (e.g., CasZi) has a length in a range of from 720-780 amino acids.

In some cases, a subject CasZ protein (e.g., CasZj) has a length in a range of from 600-750 amino acids (e.g., 600-700 or 650-700 amino acids). In some cases, a subject CasZ protein (e.g., CasZj) has a length in a range of from 400-420 amino acids.

In some cases, a subject CasZ protein (e.g., CasZk) has a length in a range of from 450-600 amino acids (e.g., 450-580, 480-600, 480-580, or 500-600 amino acids). In some cases, a subject CasZ protein (e.g., CasZk) has a length in a range of from 480-580 amino acids.

In some cases, a subject CasZ protein (e.g., CasZl) has a length in a range of from 350-500 amino acids (e.g., 350-450, 380-450, 350-420, or 380-420 amino acids). In some cases a subject CasZ protein (e.g., CasZl) has a length in a range of from 380-420 amino acids.

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZa protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZa protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZa protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZa protein of FIG. 1 or FIG. 7. In some cases, a subject CasZ protein includes a CasZa amino acid sequence of FIG. 1 or FIG. 7. In some cases, a subject CasZ protein includes a CasZa amino acid sequence of FIG. 1 or FIG. 7, with the exception that the sequence includes one or more amino acid substitutions (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZa protein of FIG. 1 or FIG. 7 and has a length in a range of from 350-800 amino acids (e.g., 350-800, 350-750, 350-700, 350-550, 450-550, 450-750, 450-650, or 450-550 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZb protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZb protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZb protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZb protein of FIG. 1 or FIG. 7. In some cases, a subject CasZ protein includes a CasZb amino acid sequence of FIG. 1 or FIG. 7. In some cases, a subject CasZ protein includes a CasZb amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZb protein of FIG. 1 or FIG. 7 and has a length in a range of from 350-700 amino acids (e.g., 350-650, or 350-620 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZc protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZc protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZc protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZc protein of FIG. 1 or FIG. 7. In some cases, a subject CasZ protein includes a CasZc amino acid sequence of FIG. 1 or FIG. 7. In some cases, a subject CasZ protein includes a CasZc amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZc protein of FIG. 1 or FIG. 7 and has a length in a range of from 600-800 amino acids (e.g., 600-650 or 700-800 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZd protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZd protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZd protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZd protein of FIG. 1 or FIG. 7. In some cases, a subject CasZ protein includes a CasZd amino acid sequence of FIG. 1 or FIG. 7. In some cases, a subject CasZ protein includes a CasZd amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZd protein of FIG. 1 or FIG. 7 and has a length in a range of from 400-650 amino acids (e.g., 400-600, 400-550, 500-650, 500-600 or 500-550 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZe protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZe protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZe protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZe protein of FIG. 1 or FIG. 7. In some cases, a subject CasZ protein includes a CasZe amino acid sequence of FIG. 1 or FIG. 7. In some cases, a subject CasZ protein includes a CasZe amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZe protein of FIG. 1 or FIG. 7 and has a length in a range of from 450-700 amino acids (e.g., 450-650, 450-615, 475-700, 475-650, or 475-615 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZf protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZf protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZf protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZf protein of FIG. 1 or FIG. 7. In some cases, a subject CasZ protein includes a CasZf amino acid sequence of FIG. 1 or FIG. 7. In some cases, a subject CasZ protein includes a CasZf amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZf protein of FIG. 1 or FIG. 7 and has a length in a range of from 400-750 amino acids (e.g., 400-700, 700-650, 400-620, 400-600, 400-550, 400-520, 400-500, 400-475, 415-550, 415-520, 415-500, or 415-475 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZg protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZg protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZg protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZg protein of FIG. 1 or FIG. 7. In some cases, a subject CasZ protein includes a CasZg amino acid sequence of FIG. 1 or FIG. 7. In some cases, a subject CasZ protein includes a CasZg amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZg protein of FIG. 1 or FIG. 7 and has a length in a range of from 500-750 amino acids (e.g., 500-750 amino acids (e.g., 550-750 amino acids)).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZh protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZh protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZh protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZh protein of FIG. 1 or FIG. 7. In some cases, a subject CasZ protein includes a CasZh amino acid sequence of FIG. 1 or FIG. 7. In some cases, a subject CasZ protein includes a CasZh amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZh protein of FIG. 1 or FIG. 7 and has a length in a range of from 380-450 amino acids (e.g., 380-420, 400-450, or 400-420 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZi protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZi protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZi protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZi protein of FIG. 1 or FIG. 7. In some cases, a subject CasZ protein includes a CasZi amino acid sequence of FIG. 1 or FIG. 7. In some cases, a subject CasZ protein includes a CasZi amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZi protein of FIG. 1 or FIG. 7 and has a length in a range of from 700-800 amino acids (e.g., 700-750, 720-800, or 720-750 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZj protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZj protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZj protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZj protein of FIG. 1 or FIG. 7. In some cases, a subject CasZ protein includes a CasZj amino acid sequence of FIG. 1 or FIG. 7. In some cases, a subject CasZ protein includes a CasZj amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZj protein of FIG. 1 or FIG. 7 and has a length in a range of from 600-750 amino acids (e.g., 600-700 or 650-700 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZk protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZk protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZk protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZk protein of FIG. 1 or FIG. 7. In some cases, a subject CasZ protein includes a CasZk amino acid sequence of FIG. 1 or FIG. 7. In some cases, a subject CasZ protein includes a CasZk amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZk protein of FIG. 1 or FIG. 7 and has a length in a range of from 450-600 amino acids (e.g., 450-580, 480-600, 480-580, or 500-600 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZl protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZl protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZl protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZl protein of FIG. 1 or FIG. 7. In some cases, a subject CasZ protein includes a CasZl amino acid sequence of FIG. 1 or FIG. 7. In some cases, a subject CasZ protein includes a CasZl amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZl protein of FIG. 1 or FIG. 7 and has a length in a range of from 450-600 amino acids (e.g., 450-580, 480-600, 480-580, or 500-600 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZe, CasZf, CasZg, or CasZh protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having a CasZe, CasZf, CasZg, or CasZh protein sequence of FIG. 1 or FIG. 7. In some cases, a subject CasZ protein includes an amino acid sequence having a CasZe, CasZf, CasZg, or CasZh protein sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions). In some cases, a subject CasZ protein includes an amino acid sequence having 90% or more sequence identity (e.g., 95% or more, 97% or more, 98% or more, 99% or more, or 100% sequence identity) with a CasZe, CasZf, CasZg, or CasZh protein of FIG. 1 or FIG. 7 and has a length in a range of from 350-900 amino acids (e.g., 350-850, 350-800, 400-900, 400-850, or 400-800 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having a CasZa, CasZb, CasZc, CasZd, CasZe, CasZf, CasZg, CasZh, CasZi, CasZj, CasZK, or CasZl protein sequence of FIG. 1 or FIG. 7. In some cases, a subject CasZ protein includes an amino acid sequence having a CasZa, CasZb, CasZc, CasZd, CasZe, CasZf, CasZg, CasZh, CasZi, CasZj, CasZK, or CasZl protein sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions). In some cases, a subject CasZ protein includes an amino acid sequence having 90% or more sequence identity (e.g., 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7 and has a length in a range of from 350-900 amino acids (e.g., 350-850, 350-800, 400-900, 400-850, or 400-800 amino acids).

CasZ Variants

A variant CasZ protein has an amino acid sequence that is different by at least one amino acid (e.g., has a deletion, insertion, substitution, fusion) when compared to the amino acid sequence of the corresponding wild type CasZ protein. A CasZ protein that cleaves one strand but not the other of a double stranded target nucleic acid is referred to herein as a "nickase" (e.g., a "nickase CasZ"). A CasZ protein that has substantially no nuclease activity is referred to herein as a dead CasZ protein ("dCasZ") (with the caveat that nuclease activity can be provided by a heterologous polypeptide—a fusion partner—in the case of a chimeric CasZ protein, which is described in more detail below). For any of the CasZ variant proteins described herein (e.g., nickase CasZ, dCasZ, chimeric CasZ), the CasZ variant can include a CasZ protein sequence with the same parameters described above (e.g., domains that are present, percent identity, length, and the like).

Variants—Catalytic Activity

In some cases, the CasZ protein is a variant CasZ protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasZ protein is a catalytically 'dead' protein (has substantially no cleavage activity) and can be referred to as a 'dCasZ.' In some cases, the variant CasZ protein is a nickase (cleaves only one strand of a double stranded target nucleic acid, e.g., a double stranded target DNA). As described in more detail herein, in some cases, a CasZ protein (in some case a CasZ protein with wild type cleavage activity and in some cases a variant CasZ with reduced cleavage activity, e.g., a dCasZ or a nickase CasZ) is fused (conjugated) to a heterologous polypeptide that has an activity of interest (e.g., a catalytic activity of interest) to form a fusion protein (a chimeric CasZ protein).

Catalytic residues of CasZ include D405, E586 and D684 when numbered according to CasZi.1 (e.g., see FIG. 1). Thus, in some cases, the CasZ protein has reduced activity and one or more of the above described amino acids (or one or more corresponding amino acids of any CasZ protein) are mutated (e.g., substituted with an alanine). In some cases, the variant CasZ protein is a catalytically 'dead' protein (is catalytically inactive) and is referred to as 'dCasZ.' A dCasZ protein can be fused to a fusion partner that provides an activity, and in some cases, the dCasZ (e.g., one without a fusion partner that provides catalytic activity—but which can have an NLS when expressed in a eukaryotic cell) can bind to target DNA and can be used for imaging (e.g., the protein can be tagged/labeled) and/or can block RNA polymerase from transcribing from a target DNA. In some cases, the variant CasZ protein is a nickase (cleaves only one strand of a double stranded target nucleic acid, e.g., a double stranded target DNA).

Variants—Chimeric CasZ (i.e., Fusion Proteins)

As noted above, in some cases, a CasZ protein (in some cases a CasZ protein with wild type cleavage activity and in some cases a variant CasZ with reduced cleavage activity, e.g., a dCasZ or a nickase CasZ) is fused (conjugated) to a heterologous polypeptide that has an activity of interest (e.g., a catalytic activity of interest) to form a fusion protein (a chimeric CasZ protein). A heterologous polypeptide to which a CasZ protein can be fused is referred to herein as a 'fusion partner.'

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasZ protein includes a heterologous polypeptide that has enzymatic activity that modifies a target nucleic acid (e.g., nuclease activity such as FokI nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasZ protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the KrUppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifyies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragement of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable chimeric CasZ protein), and a chloroplast transit peptide. Suitable chloroplast transit peptides include, but are not limited to:

(SEQ ID NO: 101)
MASMISSSAVTTVSRASRGQSAAMAPFGGLKSMTGFPVRKVNTDITSITS

NGGRVKCMQVWPPIGKKKFETLSYLPPLTRDSRA;

(SEQ ID NO: 102)
MASMISSSAVTTVSRASRGQSAAMAPFGGLKSMTGFPVRKVNTDITSITS

NGGRVKS;

(SEQ ID NO: 103)
MASSMLSSATMVASPAQATMVAPFNGLKSSAAFPATRKANNDITSITSNG

GRVNCMQVWPPIEKKKFETLSYLPDLTDSGGRVNC;

(SEQ ID NO: 104)
MAQVSRICNGVQNPSLISNLSKSSQRKSPLSVSLKTQQHPRAYPISSSWG

LKKSGMTLIGSELRPLKVMSSVSTAC;

(SEQ ID NO: 105)
MAQVSRICNGVWNPSLISNLSKSSQRKSPLSVSLKTQQHPRAYPISSSWG

LKKSGMTLIGSELRPLKVMSSVSTAC;

(SEQ ID NO: 106)
MAQINNMAQGIQTLNPNSNFHKPQVPKSSSFLVFGSKKLKNSANSMLVLK

KDSIFMQLFCSFRISASVATAC;

(SEQ ID NO: 107)
MAALVTSQLATSGTVLSVTDRFRRPGFQGLRPRNPADAALGMRTVGASAA

PKQSRKPHRFDRRCLSMVV;

(SEQ ID NO: 108)
MAALTTSQLATSATGFGIADRSAPSSLLRHGFQGLKPRSPAGGDATSLSV

TTSARATPKQQRSVQRGSRRFPSVVVC;

(SEQ ID NO: 109)
MASSVLSSAAVATRSNVAQANMVAPFTGLKSAASFPVSRKQNLDITSIAS

NGGRVQC;

(SEQ ID NO: 110)
MESLAATSVFAPSRVAVPAARALVRAGTVVPTRRTSSTSGTSGVKCSAAV

TPQASPVISRSAAAA;

and (SEQ ID NO: 111)
MGAAATSMQSLKFSNRLVPPSRRLSPVPNNVTCNNLPKSAAPVRTVKCCA

SSWNSTINGAAATTNGASAASS.

In some case, a CasZ fusion polypeptide of the present disclosure comprises: a) a CasZ polypeptide of the present disclosure; and b) a chloroplast transit peptide. Thus, for example, a CRISPR-CasZ complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasZ fusion polypeptide of the present disclosure can comprise: a) a CasZ polypeptide of the present disclosure; and b) an endosomal escape peptide. In some cases, an endosomal escape polypeptide comprises the amino acid sequence GLFXALLXLLXSLWXLLLXA (SEQ ID NO: 112), wherein each X is independently selected from lysine, histidine, and arginine. In some cases, an endosomal escape polypeptide comprises the amino acid sequence GLFHALLHLLHSLWHLLLHA (SEQ ID NO: 113).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et. al., J Virol. 2006 February; 80(4):1939-48; Tan et al., Proc Natl Acad Sci USA. 2003 Oct. 14; 100(21): 11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptides include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasZ polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasZ polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasZ polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cis-elements that are located in either the core exon region or the exon extension region (i.e., between the two alternative 5' splice sites). For more examples, see WO2010075303, which is hereby incorporated by reference in its entirety.

Further suitable fusion partners include, but are not limited to, proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject chimeric CasZ polypeptide include, but are not limited to those described in the following applications (which publications are related to other CRISPR endonucleases such as Cas9, but the described fusion partners can also be used with CasZ instead): PCT patent applications: WO2010075303, WO2012068627, and WO2013155555, and can be found, for example, in U.S. patent applications and U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140278938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasZ fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) a nuclear localization signal (NLS) (e.g, in some cases 2 or more, 3 or more, 4 or more, or 5 or more NLSs). Thus, in some cases, a CasZ polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 114); the NLS from nucleoplasmin (e.g., the nucleoplasmin bipartite NLS with the sequence KRPAATKKAGQAKKKK (SEQ ID NO: 115)); the c-myc NLS having the amino acid sequence PAAKRVKLD (SEQ ID NO: 116) or RQRR- NELKRSP (SEQ ID NO: 117); the hRNPA1 M9 NLS having the sequence NQSSNFGPMKGGNFG-GRSSGPYGGGGQYFAKPRNQGGY (SEQ ID NO: 118); the sequence RMRIZFKNKGKDTAELRRRRVEVS-VELRKAKKDEQILKRRNV (SEQ ID NO: 119) of the IBB domain from importin-alpha; the sequences VSRKRPRP (SEQ ID NO: 120) and PPKKARED (SEQ ID NO: 121) of the myoma T protein; the sequence PQPKKKPL (SEQ ID NO: 122) of human p53; the sequence SALIKKKKMAP (SEQ ID NO: 123) of mouse c-abl IV; the sequences DRLRR (SEQ ID NO: 124) and PKQKKRK (SEQ ID NO: 125) of the influenza virus NS1; the sequence RKLKK-KIKKL (SEQ ID NO: 126) of the Hepatitis virus delta antigen; the sequence REKKKFLKRR (SEQ ID NO: 127) of the mouse Mx1 protein; the sequence KRKGDEVDGVDEVAKKKSKK (SEQ ID NO: 128) of the human poly(ADP-ribose) polymerase; and the sequence RKCLQAGMNLEARKTKK (SEQ ID NO: 129) of the steroid hormone receptors (human) glucocorticoid. In general, NLS (or multiple NLSs) are of sufficient strength to drive accumulation of the CasZ protein in a detectable amount in the nucleus of a eukaryotic cell. Detection of accumulation in the nucleus may be performed by any suitable technique. For example, a detectable marker may be fused to the CasZ protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasZ fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasZ to generate a fusino protein, or linked to a variant CasZ protein such as a dCasZ, nickase CasZ, or chimeric CasZ protein to generate a fusion protein). In some embodiments, a PTD is covalently linked to the carboxyl terminus of a polypeptide (e.g., linked to a wild type CasZ to generate a fusino protein, or linked to a variant CasZ protein such as a dCasZ, nickase CasZ, or chimeric CasZ protein to generate a fusion protein). In some cases, the PTD is inserted interally in the CasZ fusion polypeptide (i.e., is not at the N- or C-terminus of the CasZ fusion polypeptide) at a suitable insertion site. In some cases, a subject CasZ fusion polypeptide includes (is conjugated to, is fused to) one or more PTDs (e.g., two or more, three or more, four or more PTDs). In some cases, a PTD includes a nuclear localization signal (NLS) (e.g, in some cases 2 or more, 3 or more, 4 or more, or 5 or more NLSs). Thus, in some cases, a CasZ fusion polypeptide includes one or more NLSs (e.g., 2 or more, 3 or more, 4 or more, or 5 or more NLSs). In some cases, a PTD is covalently linked to a nucleic acid (e.g., a CasZ guide nucleic acid, a polynucleotide encoding a CasZ guide nucleic acid, a polynucleotide encoding a CasZ fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 130); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO: 131); Transportan GWTLNSAGYLLGKINLKA-LAALAKKIL (SEQ ID NO: 132); KALAWEAKLAKA-LAKALAKHLAKALAKALKCEA (SEQ ID NO: 133); and RQIKIWFQNRRMKWKK (SEQ ID NO: 134). Exemplary PTDs include but are not limited to, YGRKKRRQRRR (SEQ ID NO: 130), RKKRRQRRR (SEQ ID NO: 135); an arginine homopolymer of from 3 arginine residues to 50 arginine residues; Exemplary PTD domain amino acid sequences include, but are not limited to, any of the following: YGRKKRRQRRR (SEQ ID NO: 130); RKKRRQRR (SEQ ID NO: 136); YARAAARQARA (SEQ ID NO: 137); THRLPRRRRRR (SEQ ID NO: 138); and GGR-RARRRRRR (SEQ ID NO: 139). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some instances, a subject CasZ protein is fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 140), $GGSGGS_n$ (SEQ ID NO: 141), and $GGGS_n$ (SEQ ID NO: 142), where n is an integer of at least one), glycine-alanine polymers, alanine-serine polymers. Exemplary linkers can comprise amino acid sequences including, but not limited to, GGSG (SEQ ID NO: 143), GGSGG (SEQ ID NO: 144), GSGSG (SEQ ID NO: 145), GSGGG (SEQ ID NO: 146), GGGSG (SEQ ID NO: 147), GSSSG (SEQ ID NO: 148), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasZ polypeptide of the present disclosure comprises (e.g., can be attached/fused to) a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrapel, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A natural CasZ protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some cases, the PAM for a CasZ protein is immediately 5' of the target sequence of the non-complementary strand of the target DNA (also referred to as the non-target strand; the complementary strand hybridizes to the guide sequence of the guide RNA while the non-complementary strand does not directly hybridize with the guide RNA and is the reverse complement of the non-complementary strand). In some cases (e.g., for CasZc), the PAM sequence of the non-complementary strand is 5'-TTA-3'. In some cases (e.g., for CasZb), the PAM sequence of the non-complementary strand is 5'-TTTN-3'. In some cases (e.g., for CasZb), the PAM sequence of the non-complementary strand is 5'-TTTA-3'.

In some cases, different CasZ proteins (i.e., CasZ proteins from various species) may be advantageous to use in the various provided methods in order to capitalize on various enzymatic characteristics of the different CasZ proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasZ proteins from different species may require different PAM sequences in the target DNA. Thus, for a particular CasZ protein of choice, the PAM sequence preference may be different than the sequence(s) described above. Various methods (including in silico and/or wet lab methods) for identification of the appropriate PAM sequence are known in the art and are routine, and any convenient method can be used.

CasZ Guide RNA

A nucleic acid molecule that binds to a CasZ protein, forming a ribonucleoprotein complex (RNP), and targets the complex to a specific location within a target nucleic acid (e.g., a target DNA) is referred to herein as a "CasZ guide RNA" or simply as a "guide RNA." It is to be understood that in some cases, a hybrid DNA/RNA can be made such that a CasZ guide RNA includes DNA bases in addition to RNA bases, but the term "CasZ guide RNA" is still used to encompass such a molecule herein.

A CasZ guide RNA can be said to include two segments, a targeting segment and a protein-binding segment. The targeting segment of a CasZ guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasZ polypeptide. The protein-binding segment of a subject CasZ guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasZ guide RNA (the guide sequence of the CasZ guide RNA) and the target nucleic acid.

A CasZ guide RNA and a CasZ protein, e.g., a fusion CasZ polypeptide, form a complex (e.g., bind via non-covalent interactions). The CasZ guide RNA provides target specificity to the complex by including a targeting segment, which includes a guide sequence (a nucleotide sequence that is complementary to a sequence of a target nucleic acid). The CasZ protein of the complex provides the site-specific activity (e.g., cleavage activity provided by the CasZ protein and/or an activity provided by the fusion partner in the case of a chimeric CasZ protein). In other words, the CasZ protein is guided to a target nucleic acid sequence (e.g. a target sequence) by virtue of its association with the CasZ guide RNA.

The "guide sequence" also referred to as the "targeting sequence" of a CasZ guide RNA can be modified so that the CasZ guide RNA can target a CasZ protein (e.g., a naturally occurring CasZ protein, a fusion CasZ polypeptide (chimeric CasZ), and the like) to any desired sequence of any desired target nucleic acid, with the exception (e.g., as described herein) that the PAM sequence can be taken into account. Thus, for example, a CasZ guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some cases, a CasZ guide RNA has a length of 30 nucleotides (nt) or more (e.g., 35 nt or more, 40 nt or more, 45 nt or more, 50 nt or more, 55 nt or more, or 60 nt or more). In some embodiments, a CasZ guide RNA has a length of 40 nucleotides (nt) or more (e.g., 45 nt or more, 50 nt or more, 55 nt or more, or 60 nt or more). In some cases, a CasZ guide RNA has a length of from 30 nucleotides (nt) to 100 nt (e.g., 30-90, 30-80, 30-75, 30-70, 30-65, 40-100, 40-90, 40-80, 40-75, 40-70, or 40-65 nt). In some cases, a CasZ guide RNA has a length of from 40 nucleotides (nt) to 100 nt (e.g., 40-90, 40-80, 40-75, 40-70, or 40-65 nt).

Guide Sequence of a CasZ Guide RNA

A subject CasZ guide RNA includes a guide sequence (i.e., a targeting sequence), which is a nucleotide sequence that is complementary to a sequence (a target site) in a target nucleic acid. In other words, the guide sequence of a CasZ guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasZ guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt.

Protein-Binding Segment of a CasZ Guide RNA

The protein-binding segment of a subject CasZ guide RNA interacts with a CasZ protein. The CasZ guide RNA guides the bound CasZ protein to a specific nucleotide sequence within target nucleic acid via the above-mentioned guide sequence. The protein-binding segment of a CasZ guide RNA comprises two stretches of nucleotides that are complementary to one another and hybridize to form a double stranded RNA duplex (dsRNA duplex). Thus, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide or multiple nucleotides) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject CasZ guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject CasZ guide RNA includes more paired bases, less paired bases, a smaller bulge, a larger bulge, fewer bulges, more bulges, or any convenient combination thereof, as compared to a naturally occurring duplex region (of a naturally occurring CasZ guide RNA).

Examples of various Cas9 guide RNAs and cpf1 guide RNAs can be found in the art, and in some cases variations similar to those introduced into Cas9 guide RNAs can also be introduced into CasZ guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patent applications and U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

A CasZ guide RNA comprises both the guide sequence and two stretches ("duplex-forming segments") of nucleotides that hybridize to form the dsRNA duplex of the protein-binding segment. The particular sequence of a given CasZ guide RNA can be characteristic of the species in which a crRNA is found. Examples of suitable CasZ guide RNAs are provided herein.

Example Guide RNA Sequences

Repeat sequences (non-guide sequence portion of a CasZ guide RNA) of crRNAs for naturally existing CasZ proteins (e.g., see FIG. 1 and FIG. 7) are shown in Table 1 and Table 3.

TABLE 1 crRNA repeat sequences for CasZ proteins

| CasZ Protein | Repeat sequence | SEQ ID NO: |
|---|---|---|
| Za.1 | GTTGCATTCCTTCATTCGTCTATTCGGGTTCTGCAAC | 51 |
| Za.2 | GTTGCATTCCTTCATTCGTCTATCCGGGTTCTGCAAG | 52 |
| Za.3 | GTTGCAGAACCCGAATAGACGAATGAAGGAATGCAAC | 53 |
| Za.4 | CTATCATATTCAGAACAAAGGGATTAAGGAATGCAAC | 54 |
| Za.5 | CTTTCATACTCAGAACAAAGGGATTAAGGAATGCAAC | 55 |
| Za.6 | GTCTACAACTCATTGATAGAAATCAATGAGTTAGACA | 56 |
| Za.7 | GTTATAAAGGCGGGGATCGCGACCGAGCGATTGAAAG | 57 |
| Zb.1 | GTTGCATTCCTTAATTCATTTTCTCAATATCGGAAAC | 58 |
| Zb.2 | GTTGCAGAAATAGAATAAAGGAATTAAGGAATGCAAC | 59 |
| Zb.3 | CTTTCATACTCAGAACAAAGGGATTAAGGAATGCAAC | 55 |
| Zb.4 | ATTTCATACTCAGAACAAAGGGATTAAGGAATGCAAC | 61 |
| Zb.5 | GTTTCAGCGCACGAATTAACGAGATGAGAGATGCAACT | 62 |
| Zb.6 | CTTGCAGAAGCTGAATAGACGAATCAAGGAATGCAAC | 63 |
| Zb.7 | CACTTGCAGGCCTTGAATAGAGGAGTTAAGGAATGCAAC | 64 |
| Zb.8 | GTCTCCATGACTGAAAAGTCGTGGCCGAATTGAAAC | 65 |
| Zb.9 | GTTGCAGCGCCCGAACTGACGAGACGAGAGATGCAAC | 66 |
| Zb.10 | GTTGCGCGAATAGAATAAAGGAATTAAGGAATGCAAC | 67 |
| Zb.11 | AGTTGCATTCCTTAATCCCTCTGTTCAGTTTGTGCAAT | 68 |
| Zc.1 | GTTGCATTCCTAGTTTCTCTAATTAGCACTGTGCAAC | 69 |
| Zc.2 | GTTGCGGCGCGCGAATAAACGAGACTAGGAATGCAAC | 70 |
| Zc.3 | ACTAGTTGCATTCCTTAATCCCTTTGTTCTGAATATGCTAG | 71 |
| Zc.4 | CTTTCATATTCAGAACAAAGGGATTAAGGAATGCAAC | 72 |
| Zc.5 | GTTGCAGTCCTTAACCCCTAGTTTCTGAATATGAAAGAT | 73 |
| Zc.6 | GTTGCAGCCCCGAACTAACGAGATGAGAGATGCAAC | 74 |
| Zc.7 | CTTGCAGAACAATCATATATGACTAATCAGACTGCAAC | 75 |
| Zd.1 | GTTGCACTCACCGGTGCTCACGACGTAGGGATGCAAC | 76 |
| Zd.2 | GTCCCTACTCGCTAGGGAAACTAATTGAATGGAAAC | 77 |
| Ze.1 | GTTGCATTCGGGTGCAAAACAGGGAGTAGAGTGTAAC | 78 |
| Ze.2 | CTTCCAAACTCGAGCCAGTGGGGAGAGAAGTGGCA | 79 |
| Ze.3 | CCTGTAGACCGGTCTCATTCTGAGAGGGGTATGCAACT | 80 |
| Ze.4 | GTCTCGAGACCCTACAGATTTTGGAGAGGGGTGGGAC | 81 |
| Ze.4b | GTCCCACCCCTCTCCAAAATCTGTAGGGTCTCGAGAC | 82 |
| Zf.1 | GTAGCAGGACTCTCCTCGAGAGAAACAGGGGTATGCT | 83 |
| Zf.2 | GTACAATACCTCTCCTTTAAGAGAGGGAGGGGTACGCTAC | 84 |

TABLE 1 -continued crRNA repeat sequences for CasZ proteins

| CasZ Protein | Repeat sequence | SEQ ID NO: |
|---|---|---|
| Zf.3 | CCCCCTCGTTTCCTTCAGGGGATTCCTTTCC | 85 |
| Zg.1 | GGTTCCCCCGGGCGCGGGTGGGGTGGCG | 86 |
| Zg.2 | GGCTGCTCCGGGTGCGCGTGGAGCGAGG | 87 |
| Zh.1 | GTTTTATACCCTTTAGAATTTAAACTGTCTAAAAG | 88 |
| Zi.1 | ATTGCACCGGCCAACGCAAATCTGATTGATGGACAC | 89 |
| Zi.2 | GCCGCAGCGGCCGACGCGGCCCTGATCGATGGACAC | 90 |
| Zj.1 | GTCGAAATGCCCGCGCGGGGCGTCGTACCCGCGAC | 91 |
| Zk.1 | GGCTAGCCCGTGCGCGCAGGGACGAGTGG | 92 |
| Zk.2 | GCCCGTGCGCGCAGGGACGAGTGG | 93 |
| Zk.3 | GTTGCAGCGGCCGACGGAGCGCGAGCGTGGATGCCAC | 94 |
| Zk.4 | CCATCGCCCCGCGCGCACGTGGATGAGCC | 95 |
| Zl.1 | CTTTAGACTTCTCCGGAAGTCGAATTAATGGAAAC | 96 |
| Zl.2 | GGGCGCCCCGCGCGAGCGGGGGTTGAAG | 97 |
| Za.8 | CTTGCAGAACCCGGATAGACGAATGAAGGAATGCAAC | 295 |
| Zb.12 | CTTGCAGGCCTTGAATAGAGGAGTTAAGGAATGCAAC | 296 |
| Zb.13 | GTTGCACAGTGCTAATTAGAGAAACTAGGAATGCAAC | 297 |
| Zb.14 | CTAGCATATTCAGAACAAAGGGATTAAGGAATGCAAC | 298 |
| Zb.15 | CTTTCATATTCAGAAACTAGGGGTTAAGGACTGCAAC | 299 |
| Zc.8 | GTTGCATCCCTACGTCGTGAGCACCGGTGAGTGCAAC | 300 |
| Ze.5 | GGAAAGGAATCCCCTGAAGGAAACGAGGGGG | 301 |
| Zg.3 | GTGTCCATCAATCAGATTTGCGTTGGCCGGTGCAAT | 302 |
| Zb.16 | GTTTCAGCGCACGAATTAACGAGATGAGAGATGCAAC | 303 |
| Zj.2 | CTTTTAGACAGTTTAAATTCTAAAGGGTATAAAAC | 307 |

In some cases, a subject CasZ guide RNA comprises (e.g., in addition to a guide sequence, e.g., as part of the protein-binding region) a crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a crRNA sequence of Table 1 or Table 3.

In some cases, a subject CasZ guide RNA comprises (e.g., in addition to a guide sequence, e.g., as part of the protein-binding region) a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3.

In some cases, a subject CasZ guide RNA comprises (e.g., in addition to a guide sequence, e.g., as part of the protein-binding region) a CasZa crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZa crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZa crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZa crRNA sequence of Table 1 or Table 3.

In some cases, a subject CasZ guide RNA comprises (e.g., in addition to a guide sequence, e.g., as part of the protein-binding region) a CasZb crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZb crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZb crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZb crRNA sequence of Table 1 or Table 3.

In some cases, a subject CasZ guide RNA comprises (e.g., in addition to a guide sequence, e.g., as part of the protein-binding region) a CasZc crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZc crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZc crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZc crRNA sequence of Table 1 or Table 3.

In some cases, a subject CasZ guide RNA comprises (e.g., in addition to a guide sequence, e.g., as part of the protein-binding region) a CasZd crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZd crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZd crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZd crRNA sequence of Table 1 or Table 3.

In some cases, a subject CasZ guide RNA comprises (e.g., in addition to a guide sequence, e.g., as part of the protein-binding region) a CasZe crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZe crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZe crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZe crRNA sequence of Table 1 or Table 3.

In some cases, a subject CasZ guide RNA comprises (e.g., in addition to a guide sequence, e.g., as part of the protein-binding region) a CasZf crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZf crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZf crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZf crRNA sequence of Table 1 or Table 3.

In some cases, a subject CasZ guide RNA comprises (e.g., in addition to a guide sequence, e.g., as part of the protein-binding region) a CasZg crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZg crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZg crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZg crRNA sequence of Table 1 or Table 3.

In some cases, a subject CasZ guide RNA comprises (e.g., in addition to a guide sequence, e.g., as part of the protein-binding region) a CasZh crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZh crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZh crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZh crRNA sequence of Table 1 or Table 3.

In some cases, a subject CasZ guide RNA comprises (e.g., in addition to a guide sequence, e.g., as part of the protein-binding region) a CasZi crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZi crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZi crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZi crRNA sequence of Table 1 or Table 3.

In some cases, a subject CasZ guide RNA comprises (e.g., in addition to a guide sequence, e.g., as part of the protein-binding region) a CasZj crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZj crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZj crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZj crRNA sequence of Table 1 or Table 3.

In some cases, a subject CasZ guide RNA comprises (e.g., in addition to a guide sequence, e.g., as part of the protein-binding region) a CasZk crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZk crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZk crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZk crRNA sequence of Table 1 or Table 3.

In some cases, a subject CasZ guide RNA comprises (e.g., in addition to a guide sequence, e.g., as part of the protein-binding region) a CasZl crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZl crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZl crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZl crRNA sequence of Table 1 or Table 3.

In some cases, a subject CasZ guide RNA comprises (e.g., in addition to a guide sequence, e.g., as part of the protein-binding region) a CasZj, CasZl, or CasZk crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZj, CasZl, or CasZk crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZj, CasZl, or CasZk crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZj, CasZl, or CasZk crRNA sequence of Table 1 or Table 3.

CasZ Transactivating Noncoding RNA (TrancRNA)

Compositions and methods of the present disclosure include a CasZ transactivating noncoding RNA ("trancRNA"; also referred to herein as a "CasZ trancRNA"). In some cases, a trancRNA forms a complex with a CasZ polypeptide of the present disclosure and a CasZ guide RNA. A trancRNA can be identified as a highly transcribed RNA encoded by a nucleotide sequence present in a CasZ locus. The sequence encoding a trancRNA is usually located between the cas genes and the array of the CasZ locus (the repeats) (e.g., can be located adjacent to the repeat sequences). Examples below demonstrate detection of a CasZ trancRNA. In some cases, a CasZ trancRNA co-immunoprecipitates (forms a complex with) with a CasZ polypeptide. In some cases, the presence of a CasZ trancRNA is required for function of the system. Data related to trancRNAs (e.g., their expression and their location on naturally occurring arrays) is presented in the examples section below.

In some cases, a CasZ trancRNA has a length of from 60 nucleotides (nt) to 270 nt (e.g., 60-260, 70-270, 70-260, or 75-255 nt). In some cases, a CasZ trancRNA (e.g., a CasZa trancRNA) has a length of from 60-150 nt (e.g., 60-140, 60-130, 65-150, 65-140, 65-130, 70-150, 70-140, or 70-130 nt). In some cases, a CasZ trancRNA (e.g., a CasZa trancRNA) has a length of from 70-130 nt. In some cases, a CasZ trancRNA (e.g., a CasZa trancRNA) has a length of about 80 nt. In some cases, a CasZ trancRNA (e.g., a CasZa trancRNA) has a length of about 90 nt. In some cases, a CasZ trancRNA (e.g., a CasZa trancRNA) has a length of about 120 nt.

In some cases, a CasZ trancRNA (e.g., a CasZb trancRNA) has a length of from 85-240 nt (e.g., 85-230, 85-220, 85-150, 85-130, 95-240, 95-230, 95-220, 95-150, or 95-130 nt). In some cases, a CasZ trancRNA (e.g., a CasZb trancRNA) has a length of from 95-120 nt. In some cases, a CasZ trancRNA (e.g., a CasZb trancRNA) has a length of about 105 nt. In some cases, a CasZ trancRNA (e.g., a CasZb trancRNA) has a length of about 115 nt. In some cases, a CasZ trancRNA (e.g., a CasZb trancRNA) has a length of about 215 nt.

In some cases, a CasZ trancRNA (e.g., a CasZc trancRNA) has a length of from 80-275 nt (e.g., 85-260 nt). In some cases, a CasZ trancRNA (e.g., a CasZc trancRNA) has a length of from 80-110 nt (e.g., 85-105 nt). In some cases, a CasZ trancRNA (e.g., a CasZc trancRNA) has a length of from 235-270 nt (e.g., 240-260 nt). In some cases, a CasZ trancRNA (e.g., a CasZc trancRNA) has a length of about 95 nt. In some cases, a CasZ trancRNA (e.g., a CasZc trancRNA) has a length of about 250 nt.

Example trancRNA Sequences

Examples of trancRNA sequences for naturally existing CasZ proteins are shown in Table 2.

TABLE 2

CasZ trancRNA sequences

| CasZ Protein | trancRNA sequence | SEQ ID NO |
|---|---|---|
| Za.1 | CGATTCCTCCCTACAGTAGTTAGGTATAGCCGAAAGGTAG AGACTAAATCTGTAGTTGGAGTGGGCCGCTTGCATCGGCC | 151 |
| Za.2 | TCGTCTCGAGGGTTACCAAAATTGGCACTTCTCGACTTTA GGCCGATGCAAGCGGCCCACTCCACTACAGATTTAGTCTC TACCTTGCGGCTATACCTAACTTACTGTAGGGAGGAATCG TG | 152 |
| Za.3 | CTTCACTGATAAAGTGGAGAACCGCTTCACCAAAAGCTGT CCCTTAGGGGATTAGAACTTGAGTGAAGGTGGGCTGCTTG CATCAGCCTAA | 153 |
| Zb.2 | CAGAATAATACTGACTTACTAAGATATCTTGAGGGTATAC CCGAAAAGATTGGCGTTGTTGCAACGCAATAAGATGTAAA TCTGAAAAGGTTTGGAATCATATAAATAATTTTA | 154 |
| Zb.4 | AAGCCAAGATATGGAATGCCATTGTAATATTATGGTGTTG ACTTAGTTTAGATTTAAACAATCTTCGATGGCTATATGCG GAAGGTTTGGCGTCGTTGTAACGC | 155 |
| Zb.6 | CAGTGTGCATAGCTATAACACTACGCAAAGACTGCTAAAG AGCGATGTGCTCTATCGCAGTCTCACCTTTAATGGACTTA CGGATCTTTTGGAGCACTAAGCTCCGCTGCGGTGCAACAC CGCCCTTTTCTTGCCTCTGCTTGCCCTTTCCGGTTATTAT AGCCGGGAGAGTGCGGAAGATTACCGCTCTAGCTCGCAGC ATGTTACTGAGTC | 156 |
| Zc.3 | GCAAGTCATTCGGGGACACTTTTTGTTATTTAAAGTGTTT TAGATAAATCAGTGTCATGCTGAATAACGACCCGACCTAT AAATAACATAATCC | 157 |
| Zc.5 | GTCCTTAAGGTACTACACATTACATGTGAACGTGGAGCTA ATAATAGAAATATTATTAGACTACACCTTATTAATAACGG TAGGAGATCTATATGGTCTTGAATGGAATAGTAATTGTGA AATTATAATTTCTGTTCTTAGCTACTTAAGATGGCTCGTT GCAAGCCACTCGGGGGCTCTCTTGAAGTCAAAGAGCTTTA GACAAATCAGTGTCAAACTGAATAACGACCCGACCATGAC TTCATAATCCCG | 158 |

In some cases, a subject CasZ trancRNA comprises a CasZa trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZa trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa trancRNA sequence above. In some cases, a subject CasZ trancRNA comprises a nucleotide sequence having 90% or more identity (e.g., 93% or more, 95% or more, 97% or more, 98% or more, or 100% identity) with a CasZa trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa trancRNA sequence above, and has a length of from 60-150 nt (e.g., 60-140, 60-130, 65-150, 65-140, 65-130, 70-150, 70-140, or 70-130 nt).

In some cases, a subject CasZ trancRNA comprises a CasZb trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZb trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZb trancRNA sequence above. In some cases, a subject CasZ trancRNA comprises a nucleotide sequence having 90% or more identity (e.g., 93% or more, 95% or more, 97% or more, 98% or more, or 100% identity) with a CasZb trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZb trancRNA sequence above, and has a length of from 85-240 nt (e.g., 85-230, 85-220, 85-150, 85-130, 95-240, 95-230, 95-220, 95-150, or 95-130 nt).

In some cases, a subject CasZ trancRNA comprises a CasZc trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZc trancRNA sequence above. In some cases, a subject CasZ trancRNA comprises a nucleotide sequence having 90% or more identity (e.g., 93% or more, 95% or more, 97% or more, 98% or more, or 100% identity) with a CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZc trancRNA sequence above, and has a length of from 80-110 nt (e.g., 85-105 nt) or from 235-270 nt (e.g., 240-260 nt).

In some cases, a subject CasZ trancRNA comprises a CasZa, CasZb, or CasZc trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZa, CasZb, or CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa, CasZb, or CasZc trancRNA sequence above. In some cases, a subject CasZ trancRNA comprises a nucleotide sequence having 90% or more identity (e.g., 93% or more, 95% or more, 97% or more, 98% or more, or 100% identity) with a CasZa, CasZb, or CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa, CasZb, or CasZc trancRNA sequence above, and has a length of from 60 nucleotides (nt) to 270 nt (e.g., 60-260, 70-270, 70-260, or 75-255 nt).

In some cases, a CasZ trancRNA comprises a modified nucleotide (e.g., methylated). In some cases, a CasZ trancRNA comprises one or more of: i) a base modification or substitution; ii) a backbone modification; iii) a modified internucleoside linkage; and iv) a modified sugar moiety. Possible nucleic acid modifications are described below.

Casz Systems

The present disclosure provides a CasZ system. A CasZ system of the present disclosure can comprise one or more of: (1) a CasZ transactivating noncoding RNA (trancRNA) (referred to herein as a "CasZ trancRNA") or a nucleic acid encoding the CasZ trancRNA (e.g., an expression vector); (2) a CasZ protein (e.g., a wild type protein, a variant, a catalytically compromised variant, a CasZ fusion protein, and the like) or a nucleic acid encoding the CasZ protein (e.g., an RNA, an expression vector, and the like); and (3) a CasZ guide RNA (that binds to and provides sequence specificity to the CasZ protein, e.g., a guide RNA that can bind to a target sequence of a eukaryotic genome) or a nucleic acid encoding the CasZ guide RNA)(e.g., an expression vector). A CasZ system can include a host cell (e.g., a eukaryotic cell, a plant cell, a mammalian cell, a human cell) that comprises one or more of (1), (2), and (3) (in any combination), e.g., in some cases the host cell comprises a trancRNA and/or a nucleic acid encoding the trancRNA. In some cases, a CasZ system includes (e.g., in addition to the above) a donor template nucleic acid. In some cases, the CasZ system is a system of one or more nucleic acids (e.g., one or more expression vectors encoding any combination of the above).

Nucleic Acids

The present disclosure provides one or more nucleic acids comprising one or more of: a CasZ trancRNA sequence, a nucleotide sequence encoding a CasZ trancRNA, a nucleotide sequence encoding a CasZ polypeptide (e.g., a wild type CasZ protein, a nickase CasZ protein, a dCasZ protein, chimeric CasZ protein/CasZ fusion protein, and the like), a CasZ guide RNA sequence, a nucleotide sequence encoding a CasZ guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasZ trancRNA, the nucleotide sequence encoding the CasZ protein, and/or the nucleotide sequence encoding the CasZ guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

The present disclosure provides one or more recombinant expression vectors that include (in different recombinant expression vectors in some cases, and in the same recombinant expression vector in some cases): a CasZ trancRNA sequence, a nucleotide sequence encoding a CasZ trancRNA, a nucleotide sequence encoding a CasZ polypeptide (e.g., a wild type CasZ protein, a nickase CasZ protein, a dCasZ protein, chimeric CasZ protein/CasZ fusion protein, and the like), a CasZ guide RNA sequence, a nucleotide sequence encoding a CasZ guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasZ trancRNA, the nucleotide sequence encoding the CasZ protein, and/or the nucleotide sequence encoding the CasZ guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasZ guide RNA is operably linked to a control element, e.g., a transcriptional control element, such as a promoter. In some embodiments, a nucleotide sequence encoding a CasZ protein or a CasZ fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasZ protein, thus resulting in a chimeric CasZ polypeptide.

In some cases, a nucleotide sequence encoding a CasZ guide RNA and/or a CasZ fusion polypeptide is operably linked to an inducible promoter. In some cases, a nucleotide sequence encoding a CasZ guide RNA and/or a CasZ fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasZ guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a CasZ protein (e.g., a wild type CasZ protein, a nickase CasZ protein, a dCasZ protein, a chimeric CasZ protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., DNA or RNA) (e.g., a nucleic acid comprising a donor polynucleotide sequence, one or more nucleic acids encoding a CasZ protein and/or a CasZ guide RNA and/or a CasZ trancRNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some cases, a CasZ protein can be provided as RNA. The RNA can be provided by direct chemical synthesis or may be transcribed in vitro from a DNA (e.g., encoding the CasZ protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasZ guide RNA; recombinant expression vectors encoding the CasZ protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasZ guide RNA and/or a CasZ polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasZ guide RNA and/or a CasZ protein to a cell may include nucleic acid sequences that encode for selectable markers in the target cells, so as to identify cells that have taken up the CasZ guide RNA and/or CasZ protein.

A nucleic acid comprising a nucleotide sequence encoding a CasZ polypeptide, or a CasZ fusion polypeptide, is in some cases an RNA. Thus, a CasZ fusion protein can be introduced into cells as RNA. Methods of introducing RNA into cells are known in the art and may include, for example, direct injection, transfection, or any other method used for the introduction of DNA. A CasZ protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally, or alternatively, a CasZ polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 134). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasZ polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasZ guide RNA, encoding a CasZ fusion protein, etc.) and proteins (e.g., a CasZ fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasZ polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasZ polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasZ polypeptide, or a CasZ fusion polypeptide, of the present disclosure is at least 80% pure, at least 85% pure, at least 90% pure, at least 95% pure, at least 98% pure, or at least 99% pure (e.g., free of contaminants, non-CasZ proteins or other macromolecules, etc.).

To induce cleavage or any desired modification to a target nucleic acid (e.g., genomic DNA), or any desired modification to a polypeptide associated with target nucleic acid, the CasZ guide RNA and/or the CasZ polypeptide and/or the CasZ trancRNA, and/or the donor template sequence, whether they be introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasZ guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasZ guide RNA that does not change when the guide sequence is changed to hybrized to a desired target sequence (e.g., sequences that contribute to the CasZ binding aspect of the guide RNA, e.g, the sequences that contribute to the dsRNA duplex(es) of the CasZ guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasZ guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination-based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasZ guide RNA or trancRNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation.

Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a guide RNA, a tranc RNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a guide RNA, a tranc RNA, etc.) has a combination of modified nucleotides. For example, a subject nucleic acid (e.g., a guide RNA, a tranc RNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasZ guide RNA and/or CasZ trancRNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602, the disclosure of which is incorporated herein by reference in its entirety). In general, the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O—, S—, or N-alkyl; O—, S—, or N-alkenyl; O—, S or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy ($-O-CH_3$), aminopropoxy ($-O$ $CH_2$ $CH_2$ $CH_2NH_2$), allyl ($-CH_2-CH=CH_2$), —O-allyl ($-O-CH_2-CH=CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci.* USA, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., Bioorg. *Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some cases, a PTD is covalently linked to the 3' end of an exogenous polynucleotide. In some cases, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 130); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO: 131); Transportan GWTLNSAGYLLGKINLKALAALAKKIL SEQ ID NO: 132); KALAWEAKLAKALAKALAKHLAKALAKALKCEA SEQ ID NO: 133); and RQIKIWFQNRRMKWKK SEQ ID NO: 134). Exemplary PTDs include but are not limited to, YGRKKRRQRRR SEQ ID NO: 130), RKKRRQRRR SEQ ID NO: 135); an arginine homopolymer of from 3 arginine residues to 50 arginine residues; Exemplary PTD domain amino acid sequences include, but are not limited to, any of the following: YGRKKRRQRRR SEQ ID NO: 130); RKKRRQRR SEQ ID NO: 136); YARAAARQARA SEQ ID NO: 137); THRLPRRRRRR SEQ ID NO: 138); and GGRRARRRRRR SEQ ID NO: 139). In some cases, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components Into a Target Cell

A CasZ guide RNA (or a nucleic acid comprising a nucleotide sequence encoding same) and/or a CasZ polypeptide (or a nucleic acid comprising a nucleotide sequence encoding same) and/or a CasZ trancRNA (or a nucleic acid that includes a nucleotide sequence encoding same) and/or a donor polynucleotide (donor template) can be introduced into a host cell by any of a variety of well-known methods.

Any of a variety of compounds and methods can be used to deliver to a target cell a CasZ system of the present disclosure. As a non-limiting example, a CasZ system of the present disclosure can be combined with a lipid. As another non-limiting example, a CasZ system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a CasZ polypeptide of the present disclosure (e.g., wild type protein, variant protein, chimeric/fusion protein, dCasZ, etc.) is provided as a nucleic acid (e.g., an mRNA, a DNA, a plasmid, an expression vector, a viral vector, etc.) that encodes the CasZ polypeptide. In some cases, the CasZ polypeptide of the present disclosure is provided directly as a protein (e.g., without an associated guide RNA or with an associate guide RNA, i.e., as a ribonucleoprotein complex). A CasZ polypeptide of the present disclosure can be introduced into a cell (provided to the cell) by any convenient method; such methods are known to those of ordinary skill in the art. As an illustrative example, a CasZ polypeptide of the present disclosure can be injected directly into a cell (e.g., with or without a CasZ guide RNA or nucleic acid encoding a CasZ guide RNA, and with or without a donor polynucleotide and with or without a CasZ trancRNA). As another example, a preformed complex of a CasZ polypeptide of the present disclosure and a CasZ guide RNA (an RNP) can be introduced into a cell (e.g, eukaryotic cell) (e.g., via injection, via nucleofection; via a protein transduction domain (PTD) conjugated to one or more components, e.g., conjugated to the CasZ protein, conjugated to a guide RNA, conjugated to a CasZ trancRNA, conjugated to a CasZ polypeptide of the present disclosure and a guide RNA; etc.).

In some cases, a nucleic acid (e.g., a CasZ guide RNA and/or a nucleic acid encoding it, a nucleic acid encoding a CasZ protein, a CasZ trancRNA and/or a nucleic acid encoding it, and the like) and/or a polypeptide (e.g., a CasZ polypeptide; a CasZ fusion polypeptide) is delivered to a cell (e.g., a target host cell) in a particle, or associated with a particle. In some cases, a CasZ system of the present disclosure is delivered to a cell in a particle, or associated with a particle. The terms "particle" and nanoparticle" can be used interchangeable, as appropriate. For example, a recombinant expression vector comprising a nucleotide sequence encoding a CasZ polypeptide of the present disclosure and/or a CasZ guide RNA, an mRNA comprising a nucleotide sequence encoding a CasZ polypeptide of the present disclosure, and guide RNA may be delivered simultaneously using particles or lipid envelopes; for instance, a CasZ polypeptide and/or a CasZ guide RNA and/or a trancRNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasZ polypeptide and a CasZ guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasZ polypeptide of the present disclosure (or an mRNA comprising a nucleotide sequence encoding a CasZ polypeptide of the present disclosure; or a recombinant expression vector comprising a nucleotide sequence encoding a CasZ polypeptide of the present disclosure) and/or CasZ guide RNA (or a nucleic acid such as one or more expression vectors encoding the CasZ guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasZ polypeptide of the present disclosure, a CasZ fusion polypeptide of the present disclosure, an RNP of the present disclosure, a nucleic acid of the present disclosure, or a CasZ system of the present disclosure. In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasZ polypeptide of the present disclosure, a CasZ fusion polypeptide of the present disclosure, an RNP of the present disclosure, a nucleic acid of the present disclosure, or a CasZ system of the present disclosure, to a target cell.

In some cases, lipid nanoparticles (LNPs) are used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o[2"-(methoxypolyethyleneglycol 2000) succinoyl]-1,2-dimyristoyl-sn-glycol (PEG-S-DMG), and R-3-[(.omega.-methoxy-poly(ethylene glycol)2000)carbamoyl]-1,2-dimyristyloxlpropyl-3-amine (PEG-C-DOMG) may be used. A nucleic acid (e.g., a CasZ guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. See, e.g., Cutler et al., J. Am. Chem. Soc. 2011 133:9254-9257, Hao et at, Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of from 25 nm to 200 nm. In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of 100 nm or less In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of from 35 nm to 60 nm.

Nanoparticles suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. A prototype nanoparticle of semi-solid nature is the liposome.

In some cases, an exosome is used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Exosomes are endogenous nano-vesicles that transport RNAs and proteins, and which can deliver RNA to the brain and other target organs.

In some cases, a liposome is used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasZ system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CasZ system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasZ system of the present disclosure, or a component thereof, may be delivered encapsulated in PLGA microspheres such as that further described in US published applications 20130252281 and 20130245107 and 20130244279.

Supercharged proteins can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA) (e.g., a CasZ guide RNA, a nucleic acid encoding a CasZ guide RNA, a nucleic acid encoding CasZ polypeptide, a donor template, and the like), or a CasZ system of the present disclosure, to a target cell (e.g., a target cell in vivo, where the target cell is a target cell in circulation, a target cell in a tissue, a target cell in an organ, etc.). An implantable device suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasZ polypeptide, the CasZ fusion polypeptide, the RNP, or the CasZ system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear-auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasZ polypeptide of the present disclosure and/or a nucleic acid comprising a nucleotide sequence encoding a CasZ polypeptide of the present disclosure. The present disclosure provides a modified cell comprising a CasZ polypeptide of the present disclosure, where the modified cell is a cell that does not normally comprise a CasZ polypeptide of the present disclosure. The present disclosure provides a modified cell (e.g., a genetically modified cell) comprising nucleic acid comprising a nucleotide sequence encoding a CasZ polypeptide of the present disclosure. The present disclosure provides a genetically modified cell that is genetically modified with an mRNA comprising a nucleotide sequence encoding a CasZ polypeptide of the present disclosure. The present disclosure provides a genetically modified cell that is genetically modified with a recombinant expression vector comprising a nucleotide sequence encoding a CasZ polypeptide of the present disclosure. The present disclosure provides a genetically modified cell that is genetically modified with a recombinant expression vector comprising: a) a nucleotide sequence encoding a CasZ polypeptide of the present disclosure; and b) a nucleotide sequence encoding a CasZ guide RNA of the present disclosure. The present disclosure provides a genetically modified cell that is genetically modified with a recombinant expression vector comprising: a) a nucleotide sequence encoding a CasZ polypeptide of the present disclosure; b) a nucleotide sequence encoding a CasZ guide RNA of the present disclosure; and c) a nucleotide sequence encoding a donor template.

A cell that serves as a recipient for a CasZ polypeptide of the present disclosure and/or a nucleic acid comprising a nucleotide sequence encoding a CasZ polypeptide of the present disclosure and/or a CasZ guide RNA of the present disclosure (or a nucleic acid encoding it) and/or a CasZ trancRNA (or a nucleic acid encoding it), can be any of a variety of cells, including, e.g., in vitro cells; in vivo cells; ex vivo cells; primary cells; cancer cells; animal cells; plant cells; algal cells; fungal cells; etc. A cell that serves as a recipient for a CasZ polypeptide of the present disclosure and/or a nucleic acid comprising a nucleotide sequence encoding a CasZ polypeptide of the present disclosure and/or a CasZ guide RNA of the present disclosure is referred to as a "host cell" or a "target cell." A host cell or a target cell can be a recipient of a CasZ system of the present disclosure. A host cell or a target cell can be a recipient of a CasZ RNP of the present disclosure. A host cell or a target cell can be a recipient of a single component of a CasZ system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., a cell in culture, e.g., an established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf— red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota* or *Holometabola, Hymenoptera, Coleoptera, Strepsiptera, Raphidioptera, Megaloptera, Neuroptera, Mecoptera, Siphonaptera, Diptera, Trichoptera,* or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasZ system of the present disclosure, or a component of a CasZ system of the present disclosure.

A kit of the present disclosure can comprise any combination as listed for a CasZ system (e.g., see above). A kit of the present disclosure can comprise: a) a component, as described above, of a CasZ system of the present disclosure, or can comprise a CasZ system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasZ guide RNA; vii) a CasZ trancRNA; and the like. A kit of the present disclosure can comprise: a) a component, as described above, of a CasZ system of the present disclosure, or can comprise a CasZ system of the present disclosure; and b) a therapeutic agent.

A kit of the present disclosure can comprise a recombinant expression vector comprising: a) an insertion site for inserting a nucleic acid comprising a nucleotide sequence encoding a portion of a CasZ guide RNA that hybridizes to a target nucleotide sequence in a target nucleic acid; and b) a nucleotide sequence encoding the CasZ-binding portion of a CasZ guide RNA. A kit of the present disclosure can comprise a recombinant expression vector comprising: a) an insertion site for inserting a nucleic acid comprising a nucleotide sequence encoding a portion of a CasZ guide RNA that hybridizes to a target nucleotide sequence in a target nucleic acid; b) a nucleotide sequence encoding the CasZ-binding portion of a CasZ guide RNA; and c) a nucleotide sequence encoding a CasZ polypeptide of the present disclosure. A kit of the present disclosure can comprise a recombinant expression vector comprising a nucleotide sequence encoding a CasZ trancRNA.

Detection of SSDNA

A CasZ (Cas14) polypeptide of the present disclosure, once activated by detection of a target DNA (double or single stranded), can promiscuously cleave non-targeted single stranded DNA (ssDNA). Once a CasZ (Cas14) is activated by a guide RNA, which occurs when the guide RNA hybridizes to a target sequence of a target DNA (i.e., the sample includes the target DNA, e.g., target ssDNA), the protein becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA). In some cases, a CasZ polypeptide requires, in addition to a CasZ guide RNA, a tranc RNA for activation.

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a CasZ polypeptide; (ii) a guide RNA comprising: a region that binds to the CasZ polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the CasZ polypeptide, thereby detecting the target DNA. In some cases, the methods include can include (a) contacting the sample with: (i) a CasZ polypeptide; (ii) a guide RNA comprising: a region that binds to the CasZ polypeptide, and a guide sequence that hybridizes with the target DNA; (iii) a CasZ tranc RNA; and (iv) a detector DNA that is single stranded and does not hybridize with the guide sequence of the guide RNA; and (b) measuring a detectable signal produced by cleavage of the single stranded detector DNA by the CasZ polypeptide, thereby detecting the target DNA. As noted above, once a subject CasZ polypeptide protein is activated by a guide RNA, which occurs when the sample includes a target DNA to which the guide RNA hybridizes (i.e., the sample includes the targeted target DNA), the CasZ polypeptide is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a CasZ polypeptide; and (ii) a guide RNA comprising: a region that binds to the CasZ polypeptide, and a guide sequence that hybridizes with the target DNA, wherein the CasZ polypeptide cleaves non-target ssDNAs of said plurality. Such methods can include contacting a population of nucleic acids, wherein said population comprises a target DNA and a plurality of non-target ssDNAs, with: (i) a CasZ polypeptide; (ii) a guide RNA comprising: a region that binds to the CasZ polypeptide, and a guide sequence that hybridizes with the target DNA, and (iii) a CasZ tranc RNA, wherein the CasZ polypeptide cleaves non-target ssDNAs of said plurality. Such methods can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The tranc RNA can be provided as RNA or as a nucleic acid encoding the guide RNA (e.g., a DNA such as a recombinant expression vector). The CasZ polypeptide can be provided as a protein per se or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided. In some cases, a single-molecule RNA comprising: i) a CasZ guide RNA; and ii) a tranc RNA (or a nucleic acid comprising a nucleotide sequence encoding the single-molecule RNA) is used.

In some cases (e.g., when contacting a sample with a guide RNA and a CasZ polypeptide; or when contacting a sample with a guide RNA, a CasZ polypeptide, and a tranc RNA), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

In some cases, a method of the present disclosure for detecting a target DNA comprises: a) contacting a sample with a guide RNA, a CasZ polypeptide, and a detector DNA), where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasZ polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a method of the present disclosure for detecting a target DNA comprises: a) contacting a sample with a guide RNA, a tranc RNA, a CasZ polypeptide, and a detector DNA (or contacting a sample with: i) a single-molecule RNA comprising a guide RNA and a tranc RNA; i) a CasZ polypeptide; and iii) a detector DNA), where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasZ polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a detectable signal produced by cleavage of a single-stranded detector DNA is produced for no more than 60 minutes. For example, in some cases, a detectable signal produced by cleavage of a single-stranded detector DNA is produced for no more than 60 minutes, no more than 45 minutes, no more than 30 minutes, no more than 15 minutes, no more than 10 minutes, or no more than 5 minutes. For example, in some cases, a detectable signal produced by cleavage of a single-stranded detector DNA is produced for a period of time of from 1 minute to 60 minutes, e.g., from 1 minute to 5 minutes, from 5 minutes to 10 minutes, from 10 minutes to 15 minutes, from 15 minutes to 30 minutes, from 30 minutes to 45 minutes, or from 45 minutes to 60 minutes. In some cases, after the detectable signal is produced (e.g., produced for no more than 60 minutes), production of the detectable signal can be stopped, e.g., by lowering the temperature of the sample (e.g., lowering the temperature to 10° C. or less, 5° C. or less, 4° C. or less, or 0° C.), by adding an inhibitor to the sample, by lyophilizing the sample, by heating the sample to over 40° C., and the like. The measuring step can occur at any time after production of the detectable signal has been stopped. For example, the measuring step can occur from 5 minutes to 48 hours after production of the detectable signal has been stopped. For example, the measuring step can occur from 5 minutes to 15 minutes, from 15 minutes to 30 minutes, from 30 minutes to 60 minutes, from 1 hour to 4 hours, from 4 hours to 8 hours, from 8 hours to 12 hours, from 12 hours to 24 hours, from 24 hours to 36 hours, or from 36 hours to 48 hours, after production of the detectable signal has been stopped. The measuring step can occur more than 48 hours after production of the detectable signal has been stopped.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. Thus, e.g., the target DNA can be present in the sample in a concentration of 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, a target DNA is present in a sample in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 800 aM. In some cases, a target DNA is present in a sample in a range of from 50 aM to 1 pM. In some cases, a target DNA is present in a sample in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM. In some cases, the minimum concentration at which a target DNA can be detected in a sample is in a range of from 100 aM to 500 pM.

In some cases, a target DNA is present in a sample in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 500 pM. In some cases, a target DNA is present in a sample in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases, the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to 10' DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5 \times 10^3$ non-target DNAs, one copy per $10^4$ non-target DNAs, one copy per $5 \times 10^4$ non-target DNAs, one copy per $10^5$ non-target DNAs, one copy per $5 \times 10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5 \times 10^3$ non-target DNAs, from 1 copy per $5 \times 10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc; animal-like members of Protista, e.g., flagellates (e.g., Euglena), amoeboids (e.g., amoeba), sporozoans (e.g., Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., Saccharomyces); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Ayes (birds); and Mammalian (mammals) Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, Plasmodium parasites, Toxoplasma parasites, Schistosoma parasites, and the like. "Helminths" include roundworms, heartworms, and phytophagous nematodes (Nematoda), flukes (Tematoda), Acanthocephala, and tapeworms (Cestoda). Protozoan infections include infections from *Giardia* spp., *Trichomonas* spp., *African trypanosomiasis*, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis,* and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNA viruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae,* methicillin-resistant *Staphylococcus aureus, Legionella pneumophila, Streptococcus pyogenes, Escherichia coli, Neisseria gonorrhoeae, Neisseria meningitidis, Pneumococcus, Cryptococcus neoformans, Histoplasma capsulatum,* Hemophilus influenzae B, *Treponema pallidum,* Lyme disease spirochetes, *Pseudomonas aeruginosa, Mycobacterium leprae, Brucella abortus,* rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae.*

Measuring a Detectable Signal

In some cases, a subject method includes a step of measuring (e.g., measuring a detectable signal produced by CasZ-mediated ssDNA cleavage). Because a CasZ polypeptide cleaves non-targeted ssDNA once activated, which occurs when a guide RNA hybridizes with a target DNA in the presence of a CasZ polypeptide (and, in some cases, also including a tranc RNA), a detectable signal can be any signal that is produced when ssDNA is cleaved. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24): 10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of CasZ polypeptide, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X'). Non-limiting examples of applications of/uses for the compositions and methods of the disclosure include single-nucleotide polymorphism (SNP) detection, cancer screening, detection of bacterial infection, detection of antibiotic resistance, detection of viral infection, and the like. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence. A method of the present disclosure in some cases does not include an amplification step. A method of the present disclosure in some cases includes an amplification step.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasZ polypeptide that cleaves DNAs present in the sample, and (iii) a detector ssDNA; b) measuring a detectable signal produced by CasZ polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasZ polypeptide that cleaves DNAs present in the sample, (iii) a tranc RNA; (iv) a detector ssDNA; b) measuring a detectable signal produced by CasZ polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a CasZ polypeptide that cleaves ssDNA (e.g., amplification of nucleic acids in the sample can begin prior to contact with a CasZ polypeptide). In some cases, the nucleic acids in a sample are amplified simultaneous with contact with a CasZ polypeptide. For example, in some cases a subject method includes amplifying nucleic acids of a sample (e.g., by contacting the sample with amplification components) prior to contacting the amplified sample with a CasZ polypeptide. In some cases, a subject method includes contacting a sample with amplification components at the same time (simultaneous with) that the sample is contacted with a CasZ polypeptide. If all components are added simultaneously (amplification components and detection components such as a CasZ polypeptide, a guide RNA, and a detector DNA), it is possible that the trans-cleavage activity of the CasZ polypeptide, will begin to degrade the nucleic acids of the sample at the same time the nucleic acids are undergoing amplification. However, even if this is the case, amplifying and detecting simultaneously can still increase sensitivity compared to performing the method without amplification.

In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted, in some cases the nucleic acids are amplified (e.g., by contact with amplification components) prior to contacting the amplified nucleic acids with a CasZ polypeptide. In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with an enzymatically active CasZ polypeptide. In some cases, amplification occurs for 2 minutes or more (e.g., 3 minutes or more, 4 minutes or more, 5 minutes or more, 7.5 minutes or more, 10 minutes or more, etc.) prior to contact with an active CasZ polypeptide. In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a CasZ polypeptide. In some such cases, the CasZ polypeptide is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP),co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium actetate, 10 mM Magnesium acetate, 2 mM DTT, 5% PEG compound (Carbowax-20M), 3 mM ATP, 30 mM Phosphocreatine, 100 ng/µl creatine kinase, 420 ng/µl gp32, 140 ng/µl UvsX, 35 ng/µl UvsY, 2000M dNTPs, 300 nM each oligonucleotide, 35 ng/µl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a CasZ polypeptide; ii) a guide RNA; and iii) a detector DNA that is single stranded and does not hybridize with the guide sequence of the guide RNA.

A suitable single-stranded detector DNA has a length of from 7 nucleotides to 25 nucleotides. For example, a suitable single-stranded detector DNA has a length of from 7 nucleotides to nucleotides, from 11 nucleotides to 15 nucleotides, from 15 nucleotides to 20 nucleotides, or from 20 nucleotides to 25 nucleotides. In some cases, a suitable single-stranded detector DNA has a length of from 10 nucleotides to 15 nucleotides. In some cases, a suitable single-stranded detector DNA has a length of 10 nucleotides. In some cases, a suitable single-stranded detector DNA has a length of 11 nucleotides. In some cases, a suitable single-stranded detector DNA has a length of 12 nucleotides. In some cases, a suitable single-stranded detector DNA has a length of 13 nucleotides. In some cases, a suitable single-stranded detector DNA has a length of 14 nucleotides. In some cases, a suitable single-stranded detector DNA has a length of 15 nucleotides.

In some cases, a subject method includes: a) contacting a sample with a labeled single stranded detector DNA (detector ssDNA) that includes a fluorescence-emitting dye pair; a CasZ polypeptide that cleaves the labeled detector ssDNA after it is activated (by binding to the guide RNA in the context of the guide RNA hybridizing to a target DNA); and b) measuring the detectable signal that is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a CasZ polypeptide).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: B ajar et al. Sensors (Basel). 2016 Sep. 14; 16(9); and Abraham et al. PLoS One. 2015 Aug. 3; 10(8):e0134436.

TABLE 6

Examples of FRET pairs (donor and acceptor FRET moieties)

| Donor | Acceptor |
| --- | --- |
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a CasZ polypeptide. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a CasZ polypeptide), but the signal will be quenched when the partners are in close proximity (e.g., prior to cleavage of the detector ssDNA by a CasZ polypeptide).

A quencher moiety can quench a signal from the signal moiety (e.g., prior to cleavage of the detector ssDNA by a CasZ polypeptide) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

Kits for Detecting Target DNA

The present disclosure provides a kit for detecting a target DNA, e.g., in a sample comprising a plurality of DNAs. In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; and ii) a CasZ polypeptide, and/or a nucleic acid encoding said CasZ polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; ii) a tranc RNA and/or a nucleic acid encoding said guide RNA; and iii) a CasZ polypeptide, and/or a nucleic acid encoding said CasZ polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a single-molecule RNA comprising a guide RNA and a tranc RNA, and/or a nucleic acid encoding single-molecule RNA; and iii) a CasZ polypeptide, and/or a nucleic acid encoding said CasZ polypeptide. In some cases, a nucleic acid encoding a single-molecule RNA includes sequence insertion sites for the insertion of guide sequences by a user.

In some cases, a subject kit comprises: (a) a labeled detector ssDNA comprising a fluorescence-emitting dye pair, e.g., a FRET pair and/or a quencher/fluor pair; and (b) one or more of: (i) a guide RNA, and/or a nucleic acid encoding said guide RNA; and/or i) a CasZ polypeptide.

Positive Conrols

A kit of the present disclosure (e.g., one that comprises a labeled detector ssDNA and a CasZ polypeptide) can also include a positive control target DNA. In some cases, the kit also includes a positive control guide RNA that comprises a nucleotide sequence that hybridizes to the control target DNA. In some cases, the positive control target DNA is provided in various amounts, in separate containers. In some cases, the positive control target DNA is provided in various known concentrations, in separate containers, along with control non-target DNAs.

Nucleic Acids

While the RNAs of the disclosure (e.g., guide RNAs, tranc RNAs, single-molecule RNAs comprising a guide RNA and a tranc RNA) can be synthesized using any convenient method (e.g., chemical synthesis, in vitro using an RNA polymerase enzyme, e.g., T7 polymerase, T3 polymerase, SP6 polymerase, etc.), nucleic acids encoding such RNAs are also envisioned. Additionally, while a CasZ polypeptide of the disclosure can be provided (e.g., as part of a kit) in protein form, nucleic acids (such as mRNA and/or DNA) encoding the CasZ polypeptide can also be provided.

In some cases, a kit of the present disclosure comprises a nucleic acid (e.g., a DNA, e.g., a recombinant expression vector) that comprises a nucleotide sequence encoding a single-molecule RNA comprising: i) a guide RNA; and ii) a tranc RNA. In some cases, the nucleotide sequence encodes the guide RNA portion of the single-molecule RNA without a guide sequence. For example, in some cases, the nucleic acid comprises a nucleotide sequence encoding: i) a constant region of a guide RNA (a guide RNA without a guide sequence), and comprises an insertion site for a nucleic acid encoding a guide sequence; and ii) a tranc RNA.

For example, in some cases, a kit of the present disclosure comprises a nucleic acid (e.g., a DNA, e.g., a recombinant expression vector) that comprises a nucleotide sequence encoding a guide RNA. In some cases, the nucleotide sequence encodes a guide RNA without a guide sequence. For example, in some cases, the nucleic acid comprises a nucleotide sequence encoding a constant region of a guide RNA (a guide RNA without a guide sequence), and comprises an insertion site for a nucleic acid encoding a guide sequence. In some cases, a kit of the present disclosure comprises a nucleic acid (e.g., an mRNA, a DNA, e.g., a recombinant expression vector) that comprises a nucleotide sequence encoding a CasZ polypeptide.

In some cases, the guide RNA-encoding nucleotide sequence is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a CasZ polypeptide is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like.

Utility

CasZ compositions (e.g., expression vectors, kits, compositions, nucleic acids, and the like) find use in a variety of methods. For example, a CasZ compositions of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasZ polypeptide of the present disclosure; and b) one or more (e.g., two) CasZ guide RNAs. In some cases, a method of the present disclosure for modifying a target nucleic acid comprises contacting the target nucleic acid with: a) a CasZ polypeptide, and b) one or more (e.g., two) CasZ guide RNAs, and c) a CasZ trancRNA. In some cases, a method of the present disclosure for modifying a target nucleic acid comprises contacting the target nucleic acid with: a) a CasZ polypeptide of the present disclosure; b) a CasZ guide RNA; and c)

a donor nucleic acid (e.g, a donor template). In some cases, a method of the present disclosure for modifying a target nucleic acid comprises contacting the target nucleic acid with: a) a CasZ polypeptide; b) a CasZ guide RNA; c) a CasZ trancRNA, and d) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasZ polypeptide includes binding of the CasZ polypeptide to a particular region in a target nucleic acid (by virtue of being targeted there by an associated CasZ guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods (e.g., that are used with CRISPR/Cas9 systems), see, for example, Jinek et al., Science. 2012 Aug. 17; 3 37(6096):816-21; Chylinski et al., RNA Biol. 2013 May; 10(5):726-37; Ma et al., Biomed Res Int. 2013; 2 013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patent applications and U.S. Pat. Nos. 8,906,616; 8,895,308; 8,889, 418; 8,889,356; 8,871,445; 8,865,406; 8,795,965; 8,771, 945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140335625; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasZ polypeptide or with a CasZ fusion polypeptide, etc., encompass all methods for contacting the target nucleic acid. For example, a CasZ polypeptide can be provided to a cell as protein, RNA (encoding the CasZ polypeptide), or DNA (encoding the CasZ polypeptide); while a CasZ guide RNA can be provided as a guide RNA or as a nucleic acid encoding the guide RNA and a CasZ trancRNA can be provided as a trancRNA or as a nucleic acid encoding the trancRNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasZ polypeptide; in the form of a protein for a CasZ fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasZ polypeptide or a CasZ fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a CasZ locus, e.g., a nucleic acid comprising a nucleotide sequence encoding a CasZ polypeptide as well as nucleotide sequences of about 1 kilobase (kb) to 5 kb in length surrounding the CasZ-encoding nucleotide sequence from a cell (e.g., in some cases a cell that in its natural state (the state in which it occurs in nature) comprises a CasZ locus) comprising a CasZ locus, where the target cell does not normally (in its natural state) comprise a CasZ locus (e.g., in some cases the locus includes a CasZ trancRNA. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a CasZ locus, e.g., a nucleic acid obtained from a source cell (e.g., in some cases a cell that in its natural state (the state in which it occurs in nature) comprises a CasZ locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a CasZ polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a CasZ locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a CasZ polypeptide of the present disclosure, or with a CasZ fusion polypeptide of the present disclosure. In some cases, abmethod of the present disclosure for modifying a target nucleic acid comprises contacting a target nucleic acid with a CasZ polypeptide and a CasZ guide RNA. In some cases, abmethod of the present disclosure for modifying a target nucleic acid comprises contacting a target nucleic acid with a CasZ polypeptide, a CasZ guide RNA, and a CasZ trancRNA. In some cases, abmethod of the present disclosure for modifying a target nucleic acid comprises contacting a target nucleic acid with a CasZ polypeptide, a first CasZ guide RNA, and a second CasZ guide RNA (and in some cases a CasZ trancRNA). In some cases, a method of the present disclosure for modifying a target nucleic acid comprises contacting a target nucleic acid with a CasZ polypeptide of the present disclosure and a CasZ guide RNA and a donor DNA template. In some cases, a method of the present disclosure for modifying a target nucleic acid comprises contacting a target nucleic acid with a CasZ polypeptide of the present disclosure and a CasZ guide RNA and a CasZ trancRNA and a donor DNA template.

In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

Target Nucleic Acids and Target Cells of Interest

A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasZ guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to geneically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasZ protein (and/or nucleic acid encoding the protein such as DNA and/or RNA), and/or CasZ guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some cases, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Donor Polynucleotide (Donor Template)

Guided by a CasZ guide RNA, a CasZ protein in some cases generates site-specific double strand breaks (DSBs) or single strand breaks (SSBs) (e.g., when the CasZ protein is a nickase variant) within double-stranded DNA (dsDNA) target nucleic acids, which are repaired either by non-homologous end joining (NHEJ) or homology-directed recombination (HDR).

In some cases, contacting a target DNA (with a CasZ protein and a CasZ guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, a CasZ trancRNA (or nucleic acid encoding same), a CasZ guide RNA (or nucleic acid encoding same), and/or a CasZ protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasZ guide RNA and CasZ protein (or CasZ guide RNA and CasZ trancRNA and CasZ protein) is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasZ protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair of a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasZ guide RNA and/or a CasZ fusion polypeptide and/or donor polynucleotide.

Transgenic, Non-Human Animals

As described above, in some cases, a nucleic acid (e.g., a recombinant expression vector) of the present disclosure (e.g., a nucleic acid comprising a nucleotide sequence encoding a CasZ polypeptide; a nucleic acid comprising a nucleotide sequence encoding a CasZ fusion polypeptide; etc.), is used as a transgene to generate a transgenic non-human organism that produces a CasZ polypeptide, or a CasZ fusion polypeptide, of the present disclosure. The present disclosure provides a transgenic-non-human organism comprising a nucleotide sequence encoding a CasZ polypeptide, or a CasZ fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasZ polypeptide or a CasZ fusion polypeptide. In some embodiments, the genome of the transgenic non-human animal comprises a nucleotide sequence encoding a CasZ polypeptide, or a CasZ fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a a CasZ polypeptide, e or a CasZ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasZ polypeptide of the present disclosure; a nucleic acid comprising a nucleotide sequence encoding a CasZ fusion polypeptide of the present disclosure; etc.), is used as a transgene to generate a transgenic plant that produces a CasZ polypeptide, or a CasZ fusion polypeptide, of the present disclosure. The present disclosure provides a transgenic plant comprising a nucleotide sequence encoding a CasZ polypeptide, or a CasZ fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasZ polypeptide, or a CasZ fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize Agrobacterium.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasZ polypeptide, or a CasZ fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasZ polypeptide, or a CasZ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure, numbered 1-36 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspects

Aspect 1. A method of guiding a CasZ polypeptide to a target sequence of a target nucleic acid, the method comprising contacting the target nucleic acid with an engineered and/or non-naturally occurring complex comprising: (a) a CasZ polypeptide; and (b) a CasZ guide RNA that comprises a guide sequence that hybridizes to a target sequence of the target nucleic acid, and comprises a region that binds to the CasZ polypeptide.

Aspect 2. The method of aspect 1, wherein the method results in modification of the target nucleic acid, modulation of transcription from the target nucleic acid, or modification of a polypeptide associated with a target nucleic acid.

Aspect 3. The method of aspect 2, wherein the target nucleic acid is modified by being cleaved.

Aspect 4. The method of any one of aspects 1-3, wherein the target nucleic acid is selected from: double stranded DNA, single stranded DNA, RNA, genomic DNA, and extrachromosomal DNA.

Aspect 5. The method of any one of aspects 1-4, wherein the guide sequence and the region that binds to the CasZ polypeptide are heterologous to one another.

Aspect 6. The method of any one of aspects 1-5, wherein said contacting results in genome editing.

Aspect 7. The method of any one of aspects 1-5, wherein said contacting takes place outside of a bacterial cell and outside of an archaeal cell.

Aspect 8. The method of any one of aspects 1-5, wherein said contacting takes place in vitro outside of a cell.

Aspect 9. The method of any one of aspects 1-7, wherein said contacting takes place inside of a target cell.

Aspect 10. The method of aspect 9, wherein said contacting comprises: introducing into the target cell at least one of: (a) the CasZ polypeptide, or a nucleic acid encoding the CasZ polypeptide; and (b) the CasZ guide RNA, or a nucleic acid encoding the CasZ guide RNA.

Aspect 11. The method of aspect 10, wherein the nucleic acid encoding the CasZ polypeptide is a non-naturally sequence that is codon optimized for expression in the target cell.

Aspect 12. The method of any one of aspects 9-11, wherein the target cell is a eukaryotic cell.

Aspect 13. The method of any one of aspects 9-12, wherein the target cell is in culture in vitro.

Aspect 14. The method of any one of aspects 9-12, wherein the target cell is in vivo.

Aspect 15. The method of any one of aspects 9-12, wherein the target cell is ex vivo.

Aspect 16. The method of aspect 12, wherein the eukaryotic cell is selected from the group consisting of: a plant cell, a fungal cell, a single cell eukaryotic organism, a mammalian cell, a reptile cell, an insect cell, an avian cell, a fish cell, a parasite cell, an arthropod cell, an arachnid cell, a cell of an invertebrate, a cell of a vertebrate, a rodent cell, a mouse cell, a rat cell, a primate cell, a non-human primate cell, and a human cell.

Aspect 17. The method of any one of aspects 9-16, wherein said contacting further comprises: introducing a DNA donor template into the target cell.

Aspect 18. The method of any one of aspects 1-17, wherein the method comprises contacting the target nucleic acid with a CasZ transactivating noncoding RNA (trancRNA).

Aspect 19. The method of any one of aspects 9-17, wherein said contacting comprises: introducing a CasZ transactivating noncoding RNA (trancRNA) and/or a nucleic acid encoding the CasZ trancRNA into the target cell.

Aspect 20. The method of aspect 18 or aspect 19, wherein the trancRNA comprises a nucleotide sequence having 70% or more (at least 70%, at least 75%, at least 80%, at least 85%, at least 90%, at least 95%, at least 98%, at least 99%, or 100%) nucleotide sequence identity with a trancRNA sequence of Table 2.

Aspect 21. A composition comprising an engineered and/or non-naturally occurring complex comprising: (a) a CasZ polypeptide, or a nucleic acid encoding said CasZ polypeptide; and (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide.

Aspect 22. The composition of aspect 21, further comprising a CasZ transactivating noncoding RNA (trancRNA), or a nucleic acid encoding said CasZ trancRNA.

Aspect 23. A kit comprising an engineered and/or non-naturally occurring complex comprising: (a) a CasZ polypeptide, or a nucleic acid encoding said CasZ polypeptide; (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide.

Aspect 24. The kit of aspect 23, further comprising a CasZ transactivating noncoding RNA (trancRNA), or a nucleic acid encoding said CasZ trancRNA.

Aspect 25. A genetically modified eukaryotic cell, comprising at least one of: (a) a CasZ polypeptide, or a nucleic acid encoding said CasZ polypeptide; (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide; and (c) a CasZ transactivating noncoding RNA (trancRNA), or a nucleic acid encoding said CasZ trancRNA.

Aspect 26. The composition, kit, or eukaryotic cell of any one of the preceding aspects, characterized by at least one of: (a) the nucleic acid encoding said CasZ polypeptide comprises a nucleotide sequence that: (i) encodes the CasZ polypeptide and, (ii) is operably linked to a heterologous promoter; (b) the nucleic acid encoding said CasZ guide RNA comprises a nucleotide sequence that: (i) encodes the CasZ guide RNA and, (ii) is operably linked to a heterologous promoter; and (c) the nucleic acid encoding said CasZ trancRNA comprises a nucleotide sequence that: (i) encodes the CasZ trancRNA and, (ii) is operably linked to a heterologous promoter.

Aspect 27. The composition, kit, or eukaryotic cell of any one of the preceding aspects, for use in a method of therapeutic treatment of a patient.

Aspect 28. The method, composition, kit, or eukaryotic cell of any one of the preceding aspects, wherein at least one of: the nucleic acid encoding said CasZ polypeptide, the nucleic acid encoding said CasZ guide RNA, and the nucleic acid encoding said CasZ trancRNA, is a recombinant expression vector.

Aspect 29. The method, composition, kit, or eukaryotic cell of any one of the preceding aspects, wherein the CasZ guide RNA and/or the CasZ trancRNA comprises one or more of: a modified nucleobase, a modified backbone or non-natural internucleoside linkage, a modified sugar moiety, a Locked Nucleic Acid, a Peptide Nucleic Acid, and a deoxyribonucleotide.

Aspect 30. The method, composition, kit, or eukaryotic cell of any one of the preceding aspects, wherein the CasZ polypeptide is a variant CasZ polypeptide with reduced nuclease activity compared to a corresponding wild type CasZ protein.

Aspect 31. The method, composition, kit, or eukaryotic cell of any one of the preceding aspects, wherein at least one of: the CasZ polypeptide, the nucleic acid encoding the CasZ polypeptide, the CasZ guide RNA, the nucleic acid encoding the CasZ guide RNA, the CasZ trancRNA, and the nucleic acid encoding the CasZ trancRNA; is conjugated to a heterologous moiety.

Aspect 32. The method, composition, kit, or eukaryotic cell of aspect 31, wherein the heterologous moiety is a heterologous polypeptide.

Aspect 33. The method, composition, kit, or eukaryotic cell of any one of the preceding aspects, wherein the CasZ polypeptide has reduced nuclease activity compared to a corresponding wild type CasZ protein, and is fused to a heterologous polypeptide.

Aspect 34. The method, composition, kit, or eukaryotic cell of aspect 33, wherein the heterologous polypeptide: (i) has DNA modifying activity, (ii) exhibits the ability to increase or decrease transcription, and/or (iii) has enzymatic activity that modifies a polypeptide associated with DNA.

Aspect 35. The method, composition, kit, or eukaryotic cell of any one of the preceding aspects, wherein the CasZ polypeptide comprises an amino acid sequence having 70% or more (at least 70%, at least 75%, at least 80%, at least 85%, at least 90%, at least 95%, at least 98%, at least 99%, or 100%) amino acid sequence identity with a CasZ protein of FIG. 1 or FIG. 7.

Aspect 36. The method, composition, kit, or eukaryotic cell of any one of the preceding aspects, wherein the guide sequence and the region that binds to the CasZ polypeptide are heterologous to one another.

Aspect 37. A method of detecting a target DNA in a sample, the method comprising: (a) contacting the sample with: (i) a CasZ polypeptide; (ii) a guide RNA comprising: a region that binds to the CasZ polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the CasZ, thereby detecting the target DNA.

Aspect 38. The method of aspect 37, wherein the target DNA is single stranded.

Aspect 39. The method of aspect 37 or 38, wherein the target DNA is double stranded.

Aspect 40. The method of any one of aspects 37-39, wherein the target DNA is viral DNA.

Aspect 41. The method of any one of aspects 37-40, wherein the target DNA is papovavirus, hepdnavirus, herpesvirus, adenovirus, poxvirus, or parvovirus DNA.

Aspect 42. The method of any one of aspects 37-41, wherein the CasZ polypeptide comprises an amino acid sequence having at least 85% amino acid sequence identity to the CasZ amino acid sequence set forth in any one of FIGS. 1 and 7.

Aspect 43. The method of any one of aspects 37-41, wherein the CasZ polypeptide is a Cas14a polypeptide.

Aspect 44. The method according to any one of aspects 37-43, wherein the sample comprises DNA molecules from a cell lysate.

Aspect 45. The method according to any one of aspects 37-44, wherein the sample comprises cells.

Aspect 46. The method according to any one of aspects 37-45, wherein said contacting is carried out inside of a cell in vitro, ex vivo, or in vivo.

Aspect 47. The method according to aspect 46, wherein the cell is a eukaryotic cell.

Aspect 48. The method according to any one of aspects 37-47, wherein the target DNA can be detected at a concentration as low as 10 aM.

Aspect 49. The method according to any one of aspects 37-48, comprising determining an amount of the target DNA present in the sample.

Aspect 50. The method according to aspect 49, wherein said determining comprises: measuring the detectable signal to generate a test measurement; measuring a detectable signal produced by a reference sample or cell to generate a reference measurement; and comparing the test measurement to the reference measurement to determine an amount of target DNA present in the sample.

Aspect 51. The method according to any one of aspects 37-50, wherein measuring a detectable signal comprises one or more of: gold nanoparticle based detection, fluorescence polarization, colloid phase transition/dispersion, electrochemical detection, and semiconductor-based sensing.

Aspect 52. The method according to any one of aspects 37-51, wherein the single stranded detector DNA comprises a fluorescence-emitting dye pair.

Aspect 53. The method according to aspect 52, wherein the fluorescence-emitting dye pair produces an amount of detectable signal prior to cleavage of the single stranded detector DNA, and the amount of detectable signal is reduced after cleavage of the single stranded detector DNA.

Aspect 54. The method according to aspect 52, wherein the single stranded detector DNA produces a first detectable signal prior to being cleaved and a second detectable signal after cleavage of the single stranded detector DNA.

Aspect 55. The method according to any one of aspects 52-54, wherein the fluorescence-emitting dye pair is a fluorescence resonance energy transfer (FRET) pair.

Aspect 56. The method according to aspect 18, wherein an amount of detectable signal increases after cleavage of the single stranded detector DNA.

Aspect 57. The method according to aspect 52 or aspect 56, wherein the fluorescence-emitting dye pair is a quencher/fluor pair.

Aspect 58. The method according to any one of aspects 52-57, wherein the single stranded detector DNA comprises two or more fluorescence-emitting dye pairs.

Aspect 59. The method according to aspect 58, wherein said two or more fluorescence-emitting dye pairs include a fluorescence resonance energy transfer (FRET) pair and a quencher/fluor pair.

Aspect 60. The method according to any one of aspects 37-59, wherein the single stranded detector DNA comprises a modified nucleobase, a modified sugar moiety, and/or a modified nucleic acid linkage.

Aspect 61. The method according to any one of aspects 37-60, wherein the method comprises amplifying nucleic acids in the sample.

Aspect 62. The method according to aspect 61, wherein said amplifying comprises isothermal amplification.

Aspect 63. The method according to aspect 62, wherein the isothermal amplification comprises recombinase polymerase amplification (RPA).

Aspect 64. The method according to any one of aspects 61-63, wherein said amplifying begins prior to the contacting of step (a).

Aspect 65. The method according to any one of aspects 61-63, wherein said amplifying begins together with the contacting of step (a).

Aspect 66. A kit for detecting a target DNA in a sample, the kit comprising: (a) a guide RNA, or a nucleic acid encoding the guide RNA; wherein the guide RNA comprises: a region that binds to a CasZ polypeptide, and a guide sequence that is complementary to a target DNA; and (b) a labeled detector DNA that is single stranded and does not hybridize with the guide sequence of the guide RNA.

Aspect 67. The kit of aspect 66, further comprising a CasZ polypeptide.

Aspect 68. The kit of aspect 67, wherein the CasZ polypeptide comprises an amino acid sequence having at least 85% amino acid sequence identity to the CasZ amino acid sequence set forth in any one of FIGS. 1 and 7.

Aspect 69. The kit of aspect 67, wherein the CasZ polypeptide is a Cas14a polypeptide.

Aspect 70. The kit of any one of aspects 66-69, wherein the single stranded detector DNA comprises a fluorescence-emitting dye pair.

Aspect 71. The kit of aspect 70, wherein the fluorescence-emitting dye pair is a FRET pair.

Aspect 72. The kit of aspect 70, wherein the fluorescence-emitting dye pair is a quencher/fluor pair.

Aspect 73. The kit of any one of aspects 70-72, wherein the single stranded detector DNA comprises two or more fluorescence-emitting dye pairs.

Aspect 74. The kit of aspect 73, wherein said two or more fluorescence-emitting dye pairs include a first fluorescence-emitting dye pair that produces a first detectable signal and a second fluorescence-emitting dye pair that produces a second detectable signal.

Aspect 75. The kit of any one of aspects 66-74, further comprising nucleic acid amplification components.

Aspect 76. The kit of aspect 75, wherein the nucleic acid amplification components are components for recombinase polymerase amplification (RPA).

Aspect 77. A method of cleaving single stranded DNAs (ssDNAs), the method comprising: contacting a population of nucleic acids, wherein said population comprises a target DNA and a plurality of non-target ssDNAs, with: (i) a CasZ polypeptide; and (ii) a guide RNA comprising: a region that binds to the CasZ polypeptide, and a guide sequence that hybridizes with the target DNA, wherein the CasZ polypeptide cleaves non-target ssDNAs of said plurality.

Aspect 78. The method of aspect 77, wherein said contacting is inside of a cell in vitro, ex vivo, or in vivo.

Aspect 79. The method of aspect 78, wherein the cell is a eukaryotic cell.

Aspect 80. The method of aspect 79, wherein the eukaryotic cell is a plant cell.

Aspect 81. The method of any one of aspects 78-80, wherein the non-target ssDNAs are foreign to the cell.

Aspect 82. The method of aspect 81, wherein the non-target ssDNAs are viral DNAs.

Aspect 83. The method of any one of aspects 77-82, wherein the target DNA is single stranded.

Aspect 84. The method of any one of aspects 77-82, wherein the target DNA is double stranded.

Aspect 85. The method of any one of aspects 77-84, wherein the target DNA is viral DNA.

Aspect 86. The method of any one of aspects 77-84, wherein the target DNA is papovavirus, hepdnavirus, herpesvirus, adenovirus, poxvirus, or parvovirus DNA.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following materials and methods generally apply to the results presented in the Examples described herein except where noted otherwise.

Metagenomics and Metatranscriptomics

The initial analysis was performed on previously assembled and binned metagenomes from two sites: the Rifle Integrated Field Research (IFRC) site, adjacent to the Colorado River near Rifle, Colorado and Crystal Geyser, a cold, $CO_2$-driven geyser on the Colorado Plateau in Utah. Metatranscriptomic data from IFRC site was used to detect transcription of non-coding elements in nature. Further mining of CRISPR-Cas14 systems was then performed on public metagenomes from IMG/M.

CRISPR-Cas Computation Analysis

The assembled contigs from the various samples were scanned with the HMMer suite for known Cas proteins using Hidden Markov Model (HMMs) profiles. Additional HMMs were constructed for Cas14 proteins based on the MAFFT alignments of putative type V effectors that contained less than 800 aa, and were adjacent to acquisition cas genes and CRISPR arrays. These HMMs were iteratively refined by augmenting them with manually selected novel putative Cas14 sequences that were found using the existing Cas14 HMM models. The sequence of Cas14 repeat sequences are provided in Table 3. CRISPR arrays were identified using a local version of the CrisprFinder software and CRISPRDetect. Phylogenetic trees of Cas1 and type V effector proteins were constructed using RAxML with PROTGAMMALG as the substitution model and 100 bootstrap samplings. Trees were visualized using FigTree 1.4.1 (on the internet at tree(dot)bio(dot)ed(dot)ac(dot)uk/software/figtree/). Metatranscriptomic reads were mapped to assembled contigs using Bowtie2. RNase presence analysis was based on HMMs that were built from alignment of KEGG orthologous groups (KOs) downloaded from KEGG database.

TABLE 3

Repeat sequences (non-guide sequence portion of a Cas14 guide RNA) of all Cas14 proteins used herein (e.g., see FIG. 7) are shown in Table 3.

| Cas14 Protein | Repeat sequence | SEQ ID No: | Scaffold Accession NO: |
|---|---|---|---|
| Cas14a.1 (CasZa.3) | GTTGCAGAACCCGAATAGACGAATGAAGGAATGCAAC | 53 | NCBI: MK005734 |
| Cas14a.2 (Za.8) | CTTGCAGAACCCGGATAGACGAATGAAGGAATGCAAC | 295 | NCBI: MK005733 |
| Cas14a.3 (CasZa.3) | GTTGCAGAACCCGAATAGACGAATGAAGGAATGCAAC | 53 | NCBI: MK005732 |
| Cas14a.4 (CasZa.4) | CTATCATATTCAGAACAAAGGGATTAAGGAATGCAAC | 54 | NCBI: MK005735 |
| Cas14a.5 (CasZa.5, CasZb.3) | CTTTCATACTCAGAACAAAGGGATTAAGGAATGCAAC | 55 | NCBI: MK005736 |
| Cas14a.6 (CasZa.6) | GTCTACAACTCATTGATAGAAATCAATGAGTTAGACA | 56 | IMG/M: Ga0137385_10000156 |
| Cas14b.1 (Cas Zb.2) | GTTGCAGAAATAGAATAAAGGAATTAAGGAATGCAAC | 59 | NCBI: MK005737 |
| Cas14b.2 (CasZa.5, CasZb.3) | CTTTCATACTCAGAACAAAGGGATTAAGGAATGCAAC | 55 | NCBI: MK005738 |
| Cas14b.3 (CasZb.4) | ATTTCATACTCAGAACAAAGGGATTAAGGAATGCAAC | 61 | NCBI: MK005739 |
| Cas14b.4 (CasZb.16) | GTTTCAGCGCACGAATTAACGAGATGAGAGATGCAAC | 303 | NCBI: MK005740 |
| Cas14b.5 (CasZb.6) | CTTGCAGAAGCTGAATAGACGAATCAAGGAATGCAAC | 63 | NCBI: MK005741 |
| Cas14b.6 (Za.12) | CTTGCAGGCCTTGAATAGAGGAGTTAAGGAATGCAAC | 296 | NCBI: MK005742 |
| Cas14b.7 (CasZb.9) | GTTGCAGCGCCCGAACTGACGAGACGAGAGATGCAAC | 66 | IMG/M: Ga0172369_10000737 |
| Cas14b.8 (CasZb.10) | GTTGCGCGAATAGAATAAAGGAATTAAGGAATGCAAC | 67 | IMG/M: Ga0172369 |
| Cas14b.9 (CasZb.11) | AGTTGCATTCCTTAATCCCTCTGTTCAGTTTGTGCAAT | 68 | IMG/M: Ga0172365_10004421 |
| Cas14b.10 (Zb.13) | GTTGCACAGTGCTAATTAGAGAAACTAGGAATGCAAC | 297 | NCBI: MK005743 |
| Cas14b.11 (CasZc.2) | GTTGCGGCGCGCGAATAAACGAGACTAGGAATGCAAC | 70 | NCBI: MK005744 |

TABLE 3 -continued

Repeat sequences (non-guide sequence portion of a Cas14 guide RNA) of all Cas14 proteins used herein (e.g., see FIG. 7) are shown in Table 3.

| Cas14 Protein | Repeat sequence | SEQ ID No: | Scaffold Accession NO: |
|---|---|---|---|
| Cas14b.12 (Zb.14) | CTAGCATATTCAGAACAAAGGGATTAAGGAATGCAAC | 298 | NCBI: MK005745 |
| Cas14b.13 (CasZc.4) | CTTTCATATTCAGAACAAAGGGATTAAGGAATGCAAC | 72 | NCBI: MK005746 |
| Cas14b.14 (Zb.15) | CTTTCATATTCAGAAACTAGGGGTTAAGGACTGCAAC | 299 | NCBI: MK005747 |
| Cas14b.15 (CasZc.6) | GTTGCAGCCCCCGAACTAACGAGATGAGAGATGCAAC | 74 | IMG/M: Ga0116204_1008574 |
| Cas14b.16 (casZc.7) | CTTGCAGAACAATCATATATGACTAATCAGACTGCAAC | 75 | IMG/M: Ga0078972_1001015a |
| Cas14c.1 (Zb.8) | GTTGCATCCCTACGTCGTGAGCACCGGTGAGTGCAAC | 300 | NCBI: MK005748 |
| Cas14c.2 (CasZd.2) | GTCCCTACTCGCTAGGGAAACTAATTGAATGGAAAC | 77 | IMG/M: JGI12048 J13642_10201286 |
| Cas14d.1 (CasZe.2) | CTTCCAAACTCGAGCCAGTGGGGAGAGAAGTGGCA | 79 | NCBI: MK005750 |
| Cas14d.2 (CasZe.3) | CCTGTAGACCGGTCTCATTCTGAGAGGGGTATGCAACT | 80 | NCBI: MK005751 |
| Cas14d.3 (CasZe.4) | GTCTCGAGACCCTACAGATTTTGGAGAGGGGTGGGAC | 81 | NCBI: MK005752 |
| Cas14e.1 (CasZt 1) | GTAGCAGGACTCTCCTCGAGAGAAACAGGGGTATGCT | 83 | NCBI: MK005753 |
| Cas14e.2 (CasZt 2) | GTACAATACCTCTCCTTTAAGAGAGGGAGGGGTACGCTAC | 84 | NCBI: MK005754 |
| Cas14e.3 (Zc.5) | GGAAAGGAATCCCCTGAAGGAAACGAGGGGG | 301 | NCBI: MK005755 |
| Cas14f.1 (CasZg.1) | GGTTCCCCCGGGCGCGGGTGGGGTGGCG | 86 | NCBI: MK005756 |
| Cas14f.2 (CasZg.2) | GGCTGCTCCGGGTGCGCGTGGAGCGAGG | 87 | IMG/M: Ga0105042_100140 |
| Cas14g.1 (Ze.3) | GTGTCCATCAATCAGATTTGCGTTGGCCGGTGCAAT | 302 | NCBI: MK005758 |
| Cas14g.2 (CasZi.2) | GCCGCAGCGGCCGACGCGGCCCTGATCGATGGACAC | 90 | IMG/M: Ga0123330_1010394 |
| Cas14h.1 (CasZk.1) | GGCTAGCCCGTGCGCGCAGGGACGAGTGG | 92 | IMG/M: Ga0070762_10001740 |
| Cas14h.2 (CasZk.2) | GCCCGTGCGCGCAGGGACGAGTGG | 93 | IMG/M: Ga0070766_10011912 |
| Cas14h.3 (CasZk.4) | CCATCGCCCCGCGCGCACGTGGATGAGCC | 95 | IMG/M: Ga0116216_10000905 |

TABLE 3 -continued

Repeat sequences (non-guide sequence portion of
a Cas14 guide RNA) of all Cas14 proteins used herein
(e.g., see FIG. 7) are shown in Table 3.

| Cas14 Protein | Repeat sequence | SEQ ID No: | Scaffold Accession NO: |
|---|---|---|---|
| Cas14u.1 (CasZa.7) | GTTATAAAGGCGGGGATCGCGACCGAGCGATTGAAAG | 57 | IMG/M: Ga0066793_10010091 |
| Cas14u.2 (CasZb.8) | GTCTCCATGACTGAAAAGTCGTGGCCGAATTGAAAC | 65 | IMG/M: JGI24730 J26740_1002785 |
| Cas14u.3 (CasZe.1) | GTTGCATTCGGGTGCAAAACAGGGAGTAGAGTGTAAC | 78 | NCBI: MK005749 |
| Cas14u.4 (CasZj.2) | CTTTTAGACAGTTTAAATTCTAAAGGGTATAAAAC | 307 | NCBI: MK005757 |
| Cas14u.5 (CasZj.1) | GTCGAAATGCCCGCGCGGGGCGTCGTACCCGCGAC | 308 | IMG/M: Ga0137373_10000316 |
| Cas14u.6 (CasZk.3) | GTTGCAGCGGCCGACGGAGCGCGAGCGTGGATGCCAC | 309 | IMG/M: Ga0070717_10000077 |
| Cas14u.7 (CasZl.1) | CTTTAGACTTCTCCGGAAGTCGAATTAATGGAAAC | 310 | IMG/M: JGI12210 IMG/M: J13797_10004690 |
| Cas14u.8 (CasZl.2) | GGGCGCCCCGCGCGAGCGGGGGTTGAAG | 311 | IMG/M: Ga0073904_10021651 |

Generation of Expression Plasmids, RNA and DNA Substrates

Minimal CRISPR loci for putative systems were designed by removing acquisition proteins and generating minimal arrays with a single spacer. These minimal loci were ordered as gBlocks (IDT) and assembled into a plasmid with a tetracycline inducible promoter driving expression of the locus. Plasmid maps were available on Addgene and in the figures. All RNA was in vitro transcribed using T7 polymerase and PCR products as dsDNA template. Resulting IVTs were gel extracted and ethanol precipitated. DNA substrates were obtained from IDT and their sequences are available in Table 4. For radiolabeled cleavage assays DNA oligos were gel extracted from a PAGE gel before radiolabeling. For FQ assays, DNA substrates were used without further purification.

E. coli RNAseq

Small RNA sequencing was conducted as described previously with modification in Harrington et al. (2017). E. coli NEB Stable3 was transformed with a plasmid expressing Cas14a1 system with a tetracycline inducible promoter upstream of the Cas14a1 ORF or the same plasmid with an N-terminal 10x-histidine tag fused to Cas14. Starters were grown up overnight in SOB, diluted 1:100 in 5 mL fresh SOB containing 214 nM anhydrotetracycline and grown up overnight at 25° C. For sequencing of RNA pulled down with Cas14a, the plasmid containing an N-terminal His-tag fused to Cas14a1 was grown up at 18° C. before lysis and purification as described in "Protein purification", stopping after the Ni-NTA elution. Cells were pelleted and RNA was extracted using hot phenol as previously described. Total nucleic acids were treated with TURBO DNase and phenol extracted. The resulting RNA was treated with rSAP which was heat inactivated before addition of T4 PNK. Adapters were ligated onto the small RNA using the NEBnext small RNA kit and gel-extracted on an 8% native PAGE gel. RNA was sequenced on a MiSeq with single end 300 bp reads. For analysis, the resulting reads were trimmed using Cutadapt, discarding sequences<8 nt and mapped to the plasmid reference using Bowtie2.

PAM Depletion Assays

PAM depletion assays were conducted as previously described in Burstein et al. (2017). Randomized plasmid libraries were generated using a primer containing a randomized PAM region adjacent to the target sequence. The randomized primers were hybridized with a primer that was complementary to the 3' end of the primer and the duplex was extended using Klenow Fragment (NEB). The dsDNA containing the target and were digested with EcoRI and NcoI, ligated into pUC19 backbone and transformed into E. coli DH5α and >107 cells were harvested. Next E. coli NEBstable was transformed with either a CRISPR plasmid or an empty vector control and these transformed E. coli were made electrocompetent by repeated washing with 10% glycerol. These electrocompetent cells were transformed with 200 ng of the target library and plated on bioassay dishes containing selection for the target (carbenicillin, 100 mg l-1) and CRISPR plasmid (chloramphenicol, 30 mg l-1). Cells were harvested and prepared for amplicon sequencing on an Illumina MiSeq. The PAM region was extracted using Cutadapt and depletion values were calculated in python. PAMs were visualized using WebLogo.

Transcriptomic RNA Mapping

RNA was extracted from 0.2 mm filters using the Invitrogen TRIzol reagent, followed by genomic DNA removal and cleaning using the Qiagen RNase-Free DNase Set kit and the Qiagen Mini RNeasy kit. An Agilent 2100 Bioanalyzer (Agilent Technologies) was used to assess the integrity of the RNA samples. The Applied Biosystems SOLiD Total RNA-Seq kit was used to generate the cDNA template library. The SOLiD EZ Bead system (Life Technologies) was used to perform emulsion clonal bead amplification to generate bead templates for SOLiD platform sequencing. Samples were sequenced at Pacific Northwest National Laboratory on the 5500XL SOLiD platform. The 50 bp single reads were trimmed using Sickle as in Brown et al. (2015).

Protein Purification

Cas14a1 was purified as described previously with modification. *E. coli* BL21(DE3) RIL were transformed with 10×His-MBP-Cas14a1 expression plasmid and grown up to OD600=0.5 in Terrific Broth (TB) and induced with 0.5 mM IPTG. Cells were grown overnight at 18° C., collected by centrifugation, resuspended in Lysis Buffer (50 mM Tris-HCl, pH 7.5, 20 mM imidazole, 0.5 mM TCEP, 500 mM NaCl) and broken by sonication. Lysate was batch loaded on to Ni-NTA resin, washed with the above buffer before elution with Elution Buffer (50 mM Tris-HCl, pH 7.5, 300 mM imidazole, 0.5 mM TCEP, 500 mM NaCl). The MBP and His-tag were removed by overnight incubation with TEV at 4° C. The resulting protein exchanged into Buffer A (20 mM HEPES, pH 7.5, 0.5 mM TCEP, 150 mM NaCl) and loaded over tandem MBP, heparin columns (GE, Hi-Trap) and eluted with a linear gradient from Buffer A to Buffer B (20 mM HEPES, pH 7.5, 0.5 mM TCEP, 1250 mM NaCl). The resulting fractions containing Cas14a1 were loaded onto an 5200 gel filtration column, flash frozen and stored at −80° C. until use.

In Vitro Cleavage Assays

Radiolabeled

Radiolabeled cleavage assays were conducted in 1× Cleavage Buffer (25 mM NaCl, 20 mM HEPES, pH 7.5, 1 mM DTT, 5% glycerol). 100 nM Cas14a1 was complexed with 125 nM crRNA and 125 nM tracrRNA for 10 min at RT. ~1 nM radiolabeled DNA or RNA substrate was added and allowed to react for 30 min at 37° C. The reaction was stopped by adding 2× Quench Buffer (90% formamide, 25 mM EDTA and trace bromophenol blue), heated to 95° C. for 2 min and run on a 10% polyacrylamide gel containing 7M Urea and 0.5×TBE. Products were visualized by phosphorimaging.

M13 DNA Cleavage

M13 DNA cleavage assays were conducted in 100 mM NaCl, 20 mM HEPES, pH 7.5, 1 mM DTT, 5% glycerol. 250 nM Cas14a1 was complexed with 250 nM crRNA and 250 nM tracrRNA and 250 nM ssDNA activator. The reaction was initiated by addition of 5 nM M13 ssDNA plasmid and was quenched by addition of loading buffer supplemented with 10 mM EDTA. Products were separated on a 1.5% agarose TAE gel prestained with SYBR gold (Thermofisher).

FQ Detection of Trans-Cleavage

FQ detection was conducted as previously described in Chen et al. (2018) with modification. 100 nM Cas14a1 was complexed with 125 nM crRNA, 125 nM tracrRNA, 50 nM FQ probe and 2 nM ssDNA activator in 1× Cleavage Buffer at 37° C. for 10 min. The reaction was then initiated by addition of activator DNA when for all reactions except for the RNA optimization experiments where the variable RNA component was used to initiate. The reaction was monitored in a fluorescence plate reader for up to 120 minutes at 37° C. with fluorescence measurements taken every 1 min ($\lambda$ex: 485 nm; $\lambda$em: 535 nm). The resulting data were background subtracted using the readings taken in the absence of activator and fit using a single exponential decay curve.

Data Availability

Figure 24O:
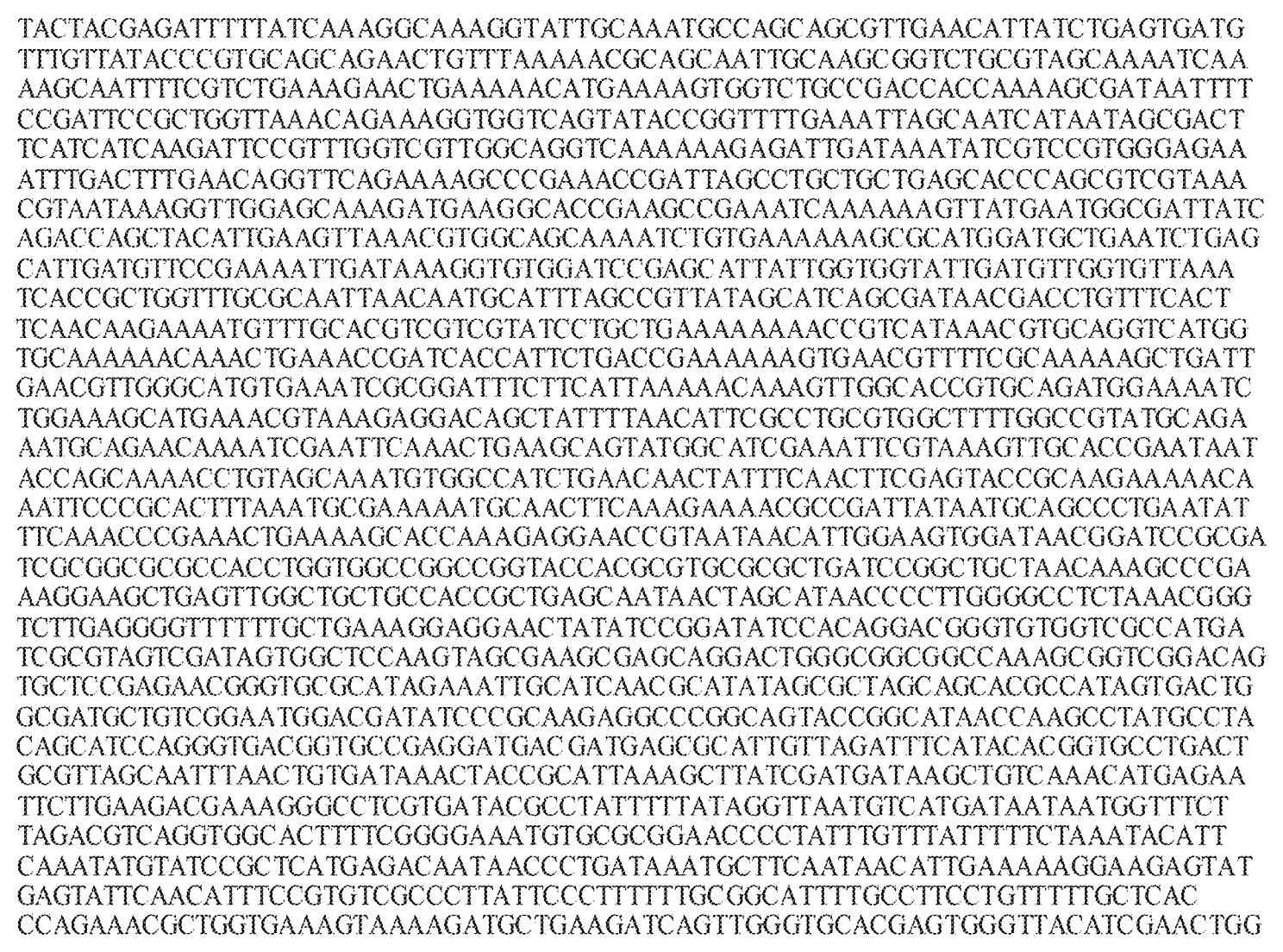

Plasmids used herein are available on Addgene (plasmid numbers 112500, 112501, 112502, 112503, 112504, 112505, 112506). Oligonucleotides used herein are provided in Table 4 and Table 5. The plasmids used herein are provided in FIG. 24. The Cas14 protein sequences used herein are provided in FIG. 7.

TABLE 4

Oligonucleotides and plasmids used herein.

| DNA Name | Sequence | SEQ ID NO: |
|---|---|---|
| Radiolabeld DNA activator 1 strand | cTACGCCGattatcttctgacaactttcgcaagcggtgtaaggtaAAA AAtgCGGGCACT | 220 |
| Radiolabeld DNA activator 1 NT strand | GTGCCCGcaTTTTTtaccttacaccgcttgcgaaagttgtcagaagat aatCGGCGTAg | 221 |
| Radiolabeld DNA activator 2 strand | tttatatgtttctcctggagataacgcaatcgtgacaactttcgcaag cggtgtaaggtaGCAGGCTTCcgaattccgcgttttacggcT | 222 |
| Radiolabeld DNA activator 2 NT strand | gccgtaaaaacgcggaattcgGAAGCCTGCtaccttacaccgcttgcg aaagttgtcacgattgcgttatctccaggagaaacatataaa | 223 |
| Radiolabeld Activator 3 | gatcttcagcTATACATTATTGCACCAACACTAAGGCAGAGTATGt tacctggac | 224 |

TABLE 4-continued

Oligonucleotides and plasmids used herein.

| DNA Name | Sequence | SEQ ID NO: |
|---|---|---|
| Radiolabeld Activator 4 | gatcttcagcTTTGTATTACTGGAAGGATGCTTGCTTGAGGTGTAaaaacctggac | 225 |
| F-Q 5nt | /56-FAM/TTTTT/3IABkFQ/ | 226 |
| F-Q 6nt | /56-FAM/TTTTTT/3IABkFQ/ | 227 |
| F-Q 7nt | /56-FAM/TTTTTTT/3IABkFQ/ | 228 |
| F-Q 8nt | /56-FAM/TTTTTTTT/3IABkFQ/ | 229 |
| F-Q 9nt | /56-FAM/TTTTTTTTT/3IABkFQ/ | 230 |
| F-Q 10nt | /56-FAM/TTTTTTTTTT/3IABkFQ/ | 231 |
| F-Q 11nt | /56-FAM/TTTTTTTTTTT/3IABkFQ/ | 232 |
| F-Q 12nt | /56-FAM/TTTTTTTTTTTT/3IABkFQ/ | 233 |
| F-Q 10nt A/T | /56-FAM/TATATATATA/3IABkFQ/ | 371 |
| F-Q 6nt ALT | /56-FAM/TATATA/3IABkFQ/ | 372 |
| F-Q 5nt ALT | /56-FAM/TATAT/3IABkFQ/ | 373 |
| Target 2, Perfect AAAT 3' | GCCGGGGTGGTGCCCATCCTGGTCGAGCTGGACGGCGACGTAAACGGCCACAAGC | 234 |
| Target 2, Perfect TCGT 3' | GCCGGGGTGGTGCCCATCCTGGTCGAGCTGGACGGCGACGTGCTCGGCCACAAGC | 235 |
| Target 2, 1-2 MM | GCCGGGGTGGTGCCCATCCTGGTCGAGCTGGACGGCGAGCTAAACGGCCACAAGC | 236 |
| Target 2, 3-4 MM | GCCGGGGTGGTGCCCATCCTGGTCGAGCTGGACGGCCTCGTAAACGGCCACAAGC | 237 |
| Target 2, 5-6 MM | GCCGGGGTGGTGCCCATCCTGGTCGAGCTGGACGCGGACGTAAACGGCCACAAGC | 238 |
| Target 2, 7-8 MM | GCCGGGGTGGTGCCCATCCTGGTCGAGCTGGAGCGCGACGTAAACGGCCACAAGC | 239 |
| Target 2, 9-10 MM | GCCGGGGTGGTGCCCATCCTGGTCGAGCTGCTCGGCGACGTAAACGGCCACAAGC | 240 |
| Target 2, 11-12 MM | GCCGGGGTGGTGCCCATCCTGGTCGAGCACGACGGCGACGTAAACGGCCACAAGC | 241 |
| Target 2, 13-14 MM | GCCGGGGTGGTGCCCATCCTGGTCGACGTGGACGGCGACGTAAACGGCCACAAGC | 242 |
| Target 2, 15-16 MM | GCCGGGGTGGTGCCCATCCTGGTCCTGCTGGACGGCGACGTAAACGGCCACAAGC | 243 |
| Target 2, 17-18 MM | GCCGGGGTGGTGCCCATCCTGGAGGAGCTGGACGGCGACGTAAACGGCCACAAGC | 244 |
| Target 2, 19-20 MM | GCCGGGGTGGTGCCCATCCTCCTCGAGCTGGACGGCGACGTAAACGGCCACAAGC | 245 |
| HERC2 Amp Fwd | G*T*G*T*TAATACAAAGGTACAGGAACAAAGAATTTG | 246 |
| HERC2 Amp Rev | CAAAGAGAAGCCTCGGCC | 247 |
| Target 1, Perfect AAAT 3' | TTTATTCAAGGCAATCACTATACAGCTGTGGAACACCCAGGTAAACTAACACAACT | 248 |

TABLE 4-continued

Oligonucleotides and plasmids used herein.

| DNA Name | Sequence | SEQ ID NO: |
|---|---|---|
| Target 1, Perfect TCGT 3' | TTTATTCAAGGCAATCACTATCAGCTGTGGAACACCCAGGT GCTCTAACACAACT | 249 |
| Target 1, 1-2 MM | TTTATTCAAGGCAATCACTATCAGCTGTGGAACACCCACCTA AACTAACACAACT | 250 |
| Target 1, 3-4 MM | TTTATTCAAGGCAATCACTATCAGCTGTGGAACACCGTGGT AAACTAACACAACT | 251 |
| Target 1, 5-6 MM | TTTATTCAAGGCAATCACTATCAGCTGTGGAACAGGCAGGT AAACTAACACAACT | 252 |
| Target 1, 7-8 MM | TTTATTCAAGGCAATCACTATCAGCTGTGGAAGTCCCAGGT AAACTAACACAACT | 253 |
| Target 1, 9-10 MM | TTTATTCAAGGCAATCACTATCAGCTGTGGTTCACCCAGGTA AACTAACACAACT | 254 |
| Target 1, 11-12 MM | TTTATTCAAGGCAATCACTATCAGCTGTCCAACACCCAGGTA AACTAACACAACT | 255 |
| Target 1, 13-14 MM | TTTATTCAAGGCAATCACTATCAGCTCAGGAACACCCAGGT AAACTAACACAACT | 256 |
| Target 1, 15-16 MM | TTTATTCAAGGCAATCACTATCAGGAGTGGAACACCCAGGT AAACTAACACAACT | 257 |
| Target 1, 17-18 MM | TTTATTCAAGGCAATCACTATCTCCTGTGGAACACCCAGGTA AACTAACACAACT | 258 |
| Target 1, 19-20 MM | TTTATTCAAGGCAATCACTAAGAGCTGTGGAACACCCAGGT AAACTAACACAACT | 259 |
| Target 3, Perfect | cTACGCCGattatcttctgacaactttcgcaagcggtgtaaggtaAAA AAtgCGGGCAC | 220 |
| Target 3, 1-2 MM | cTACGCCGattatcttctgacaactttcgcaagcggtgtaaggCGAAA AAtgCGGGCAC | 260 |
| Target 3, 3-4 MM | cTACGCCGattatcttctgacaactttcgcaagcggtgtaaAAtaAAA AAtgCGGGCAC | 261 |
| Target 3, 5-6 MM | cTACGCCGattatcttctgacaactttcgcaagcggtgtGGggtaAAA AAtgCGGGCAC | 262 |
| Target 3, 7-8 MM | cTACGCCGattatcttctgacaactttcgcaagcggtACaaggtaAAA AAtgCGGGCAC | 263 |
| Target 3, 9-10 MM | cTACGCCGattatcttctgacaactttcgcaagcgACgtaaggtaAAA AAtgCGGGCAC | 264 |
| Target 3, 11-12 MM | cTACGCCGattatcttctgacaactttcgcaagTAgtgtaaggtaAAA AAtgCGGGCAC | 265 |
| Target 3, 13-14 MM | cTACGCCGattatcttctgacaactttcgcaGAcggtgtaaggtaAAA AAtgCGGGCAC | 266 |
| Target 3, 15-16 MM | cTACGCCGattatcttctgacaactttcgTGagcggtgtaaggtaAAA AAtgCGGGCAC | 267 |
| Target 3, 17-18 MM | cTACGCCGattatcttctgacaactttTAcaagcggtgtaaggtaAAA AAtgCGGGCAC | 268 |
| Target 3, 19-20 MM | cTACGCCGattatcttctgacaactCCcgcaagcggtgtaaggtaAAA AAtgCGGGCAC | 269 |
| Target 3, 21-22 MM | cTACGCCGattatcttctgacaaTCttcgcaagcggtgtaaggtaAAA AAtgCGGGCAC | 270 |
| Target 3, 23-24 MM | cTACGCCGattatcttctgacGGctttcgcaagcggtgtaaggtaAAA AAtgCGGGCAC | 271 |

TABLE 4 -continued

Oligonucleotides and plasmids used herein.

| DNA Name | Sequence | SEQ ID NO: |
|---|---|---|
| Target 3, 25-26 MM | cTACGCCGattatcttctgGTaactttcgcaagcggtgtaaggtaAAAAAtgCGGGCAC | 272 |
| Full Length Activator | cTACGCCGattatcttctgacaactttcgcaagcggtgtaaggtaAAAAAtgCGGGCAC | 220 |
| -20 5' activator target | tatcttctgacaactttcgcaagcggtgtaaggtaAAAAAtgCGGGCAC | 273 |
| -25 5' activator target | tctgacaactttcgcaagcggtgtaaggtaAAAAAtgCGGGCAC | 274 |
| -30 5' activator target | caactttcgcaagcggtgtaaggtaAAAAAtgCGGGCAC | 275 |
| -35 5' activator target | ttcgcaagcggtgtaaggtaAAAAAtgCGGGCAC | 276 |
| -5 3' activator target | cTACGCCGattatcttctgacaactttcgcaagcggtgtaaggtaAAAAAtgCG | 277 |
| -9 3' activator target | cTACGCCGattatcttctgacaactttcgcaagcggtgtaaggtaAAAA | 278 |
| -14 3' activator target | cTACGCCGattatcttctgacaactttcgcaagcggtgta | 279 |
| -19 3' activator target | cTACGCCGattatcttctgacaactttcgcaagcg | 280 |
| -24 3' activator target | cTACGCCGattatcttctgacaactttcgc | 281 |
| -29 3' activator target | cTACGCCGattatcttctgacaact | 282 |
| -34 3' activator target | cTACGCCGattatcttctga | 283 |
| No loop | caactttcgcaagcggtgtaaggtaAAAAAtgCG | 284 |
| 0nt SL | atggaatgtggcgaacgctttcaacGAAAcaactttcgcaagcggtgtaaggtaAAAAAtgCG | 285 |
| 5nt SL | atggaatgtggcgaacgcttagttgGAAAcaactttcgcaagcggtgtaaggtaAAAAAtgCG | 286 |
| 10nt SL | atggaatgtggcgaagcgaaagttgGAAAcaactttcgcaagcggtgtaaggtaAAAAAtgCG | 287 |
| 15nt SL | atggaatgtgcgcttgcgaaagttgGAAAcaactttcgcaagcggtgtaaggtaAAAAAtgCG | 288 |
| 20nt SL | atggatacaccgcttgcgaaagttgGAAAcaactttcgcaagcggtgtaaggtaAAAAAtgCG | 289 |
| 25nt SL | taccttacaccgcttgcgaaagttgGAAAcaactttcgcaagcggtgtaaggtaAAAAAtgCG | 290 |
| M13_1 Oligo | GTTTTATCTTCTGCTGGTGGTTCGTTCGGTATTTTTAATG | 291 |
| M13_2 Oligo | CATTAAAAATACCGAACGAACCACCAGCAGAAGATAAAAC | 292 |

TABLE 4 -continued

Oligonucleotides and plasmids used herein.

| DNA Name | Sequence | SEQ ID NO: |
|---|---|---|
| M13_3 Oligo | GACCATTTGCGAAATGTATCTAATGGTCAAACTAAATCTACTC | 293 |
| M13_4 Oligo | GAGTAGATTTAGTTTGACCATTAGATACATTTCGCAAATGGTC | 294 |

TABLE 5

RNA Oligonucleotides.

| RNA Name | Sequence | SEQ ID NO: |
|---|---|---|
| ssRNA target | cTACGCCGattatcttctgacaactttcgcaagcggtgtaaggt aAAAAAtgCGGGCACcc | 332 |
| crRNA | GGAATGCAACtaccttacaccgcagcgaa | 333 |
| tracrRNA | CTTCACTGATAAAGTGGAGAACCGCTTCACCAAAAGCTGTC CCTTAGGGCATTAGAACTTGAGTGAAGGTGGGCTGCTTGCA TCAGCCTAATGTCGAGAAGTGCTTTCTTCGGAAAGTAACCCT CGAAACAAATTCATTT | 334 |
| crRNA 1 | GACGAATGAAGGAATGCAACtaccttacaccgcttgcgaa | 335 |
| crRNA 2 | GACGAATGAAGGAATGCAACccttacaccgcttgcgaaag | 336 |
| crRNA 3 | GACGAATGAAGGAATGCAACttacaccgcttgcgaaagtt | 337 |
| crRNA 4 | GACGAATGAAGGAATGCAACacaccgcttgcgaaagttgt | 338 |
| crRNA MM target 2 | GACGAATGAAGGAATGCAACCGTCGCCGTCCAGCTCGACCA | 339 |
| crRNA MM target 3 | GACGAATGAAGGAATGCAACGATCGTTACGCTAACTATGA | 340 |
| HERC2 A sgRNA | TTCACTGATAAAGTGGAGAACCGCTTCACCAAAAGCTGTCC CTTAGGGGATTAGAACTTGAGTGAAGGTGGGCTGCTTGCAT CAGCCTAATGTCGAGAAGTGCTTTCTTCGGAAAGTAACCCT CGAAACAAATTCATTTgaaaGAATGAAGGAATGCAACacttgacac ttaatgctcaa | 341 |
| LbCas12a HERC2 crRNA | GGGTAATTTCTACTAAGTGTAGATacttgacacttaatgctcaa | 342 |
| 25nt spacer crRNA target 4 | GACGAATGAAGGAATGCAACtaccttacaccgcttgcgaaagttg | 343 |
| 20nt spacer crRNA target 4 | GACGAATGAAGGAATGCAACtaccttacaccgcttgcgaa | 335 |
| 18nt spacer crRNA target 4 | GACGAATGAAGGAATGCAACtaccttacaccgcttgcg | 344 |
| 16nt spacer crRNA target 4 | GACGAATGAAGGAATGCAACtaccttacaccgcttg | 345 |
| 14nt spacer crRNA target 4 | GACGAATGAAGGAATGCAACtaccttacaccgct | 346 |
| 12nt spacer crRNA target 4 | GACGAATGAAGGAATGCAACtaccttacaccg | 347 |

TABLE 5 -continued

RNA Oligonucleotides.

| RNA Name | Sequence | SEQ ID NO: |
|---|---|---|
| 10nt spacer crRNA target 4 | GACGAATGAAGGAATGCAACtaccttacac | 348 |
| Full repeat crRNA target 4 | GTTGCAGAACCCGAATAGACOAATGAAGGAATGCAACtaccttacaccgcttgcgaa | 349 |
| 20nt repeat crRNA target 4 | GACGAATGAAGGAATGCAACtaccttacaccgcttgcgaa | 335 |
| 17nt repeat crRNA target 4 | GAATGAAGGAATGCAACtaccttacaccgcttgcgaa | 350 |
| 15nt repeat crRNA target 4 | ATGAAGGAATGCAACtaccttacaccgcttgcgaa | 351 |
| 10nt repeat crRNA target 4 | GGAATGCAACtaccttacaccgcttgcgaa | 333 |
| tracrRNA +41nt | CTTCACTGATAAAGTGGAGAACCGCTTCACCAAAAGCTGTCCCITAGGGGATTAGAACTTGAGTGAAGGTGGGCTGCTTGCATCAGCCTAATGTCGAGAAGTGCTTTCTTCGGAAAGTAACCGTCGAAACAAATTCATTTTTCCTCTCCAATTCTGCACAAAAAAAGGTGAGTCCTTAT | 352 |
| tracrRNA +3nt | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTT | 334 |
| tracrRNA -26 | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTT | 353 |
| tracrRNA -65 | CTTCACTGATAAAGTGGAGAACCGCTTCACCAAAAGCTGTCCCTTAGGGGATTAGAACTTGAGTGAAGGTGG | 354 |
| tracrRNA +0 | TTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCA | 355 |
| tracrRNA +90nt | ttcacacTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCAttttcctctccaattctgcacaaaaaaaggtgagtcct-tataaaccggcgtgcagaacgccggctcaccttattcttcattcga-tata | 356 |
| sgRNA 1 | CTTCACTGATAAAGTGGAGAACCGCTTCACCAAAAGGTGTCCCTTAGGGGATTAGAACTTGAGTGAAGGTGGGCTGCTTGCATCAGCCTAATGTCGAGAAGTGCTTTCTICGGAAAGTAACCCTCGAAACAAATTCATTTgaaaGAATGAAGGAATGCAACtaccttacaccgcttgcgaa | 357 |
| sgRNA 2 | CTTCACTGATAAAGTGGAGAACCGCTICACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTTTCCTCTCCAATTCTGCACAAgaaaGTTGCAGAACCCGAATAGACGAATGAAGGAATGCAACtaccttacacCGcttgcgaa | 358 |
| M13 target 1 crRNA | GACGAATGAAGGAATGCAACTACCGAACGAACCACCAGCAGAAGA | 359 |
| M13 target 2 crRNA | GACGAATGAAGGAATGCAACTCTTCTGCTGGTGGTTCGTTCGGTA | 360 |

TABLE 5 -continued

RNA Oligonucleotides.

| RNA Name | Sequence | SEQ ID NO: |
|---|---|---|
| M13 target 3 crRNA | GACGAATGAAGGAATGCAACGTTTGACCATTAGATACATTTCG | 361 |
| M13 target 4 crRNA | GACGAATGAAGGAATGCAACCGAAATGTATCTAATGGTCAAAC | 362 |

Example 1

FIG. 1 depicts examples of naturally occurring CasZ protein sequences.

FIG. 2 depicts schematic representations of CasZ loci, which include a Cas1 protein in addition to the CasZ protein.

FIG. 3 depicts a phylogenetic tree of CasZ sequences in relation to other Class 2 CRISPR/Cas effector protein sequences.

Figure 4:
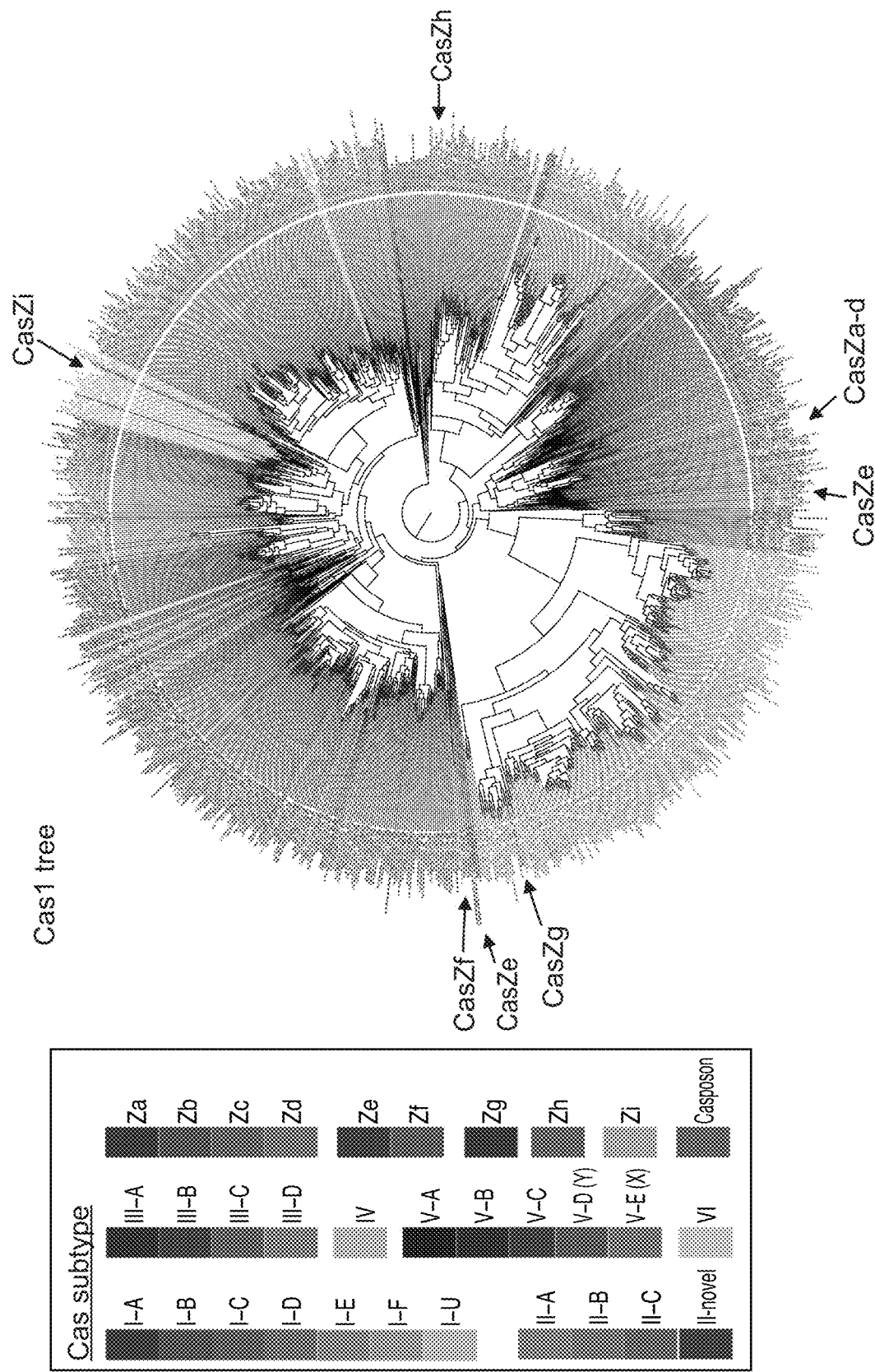
FIG. 4 depicts a phylogenetic tree of Cas1 sequences from CasZ loci in relation to Cas1 sequences from other Class 2 CRISPR/Cas loci.
Figure 5B:
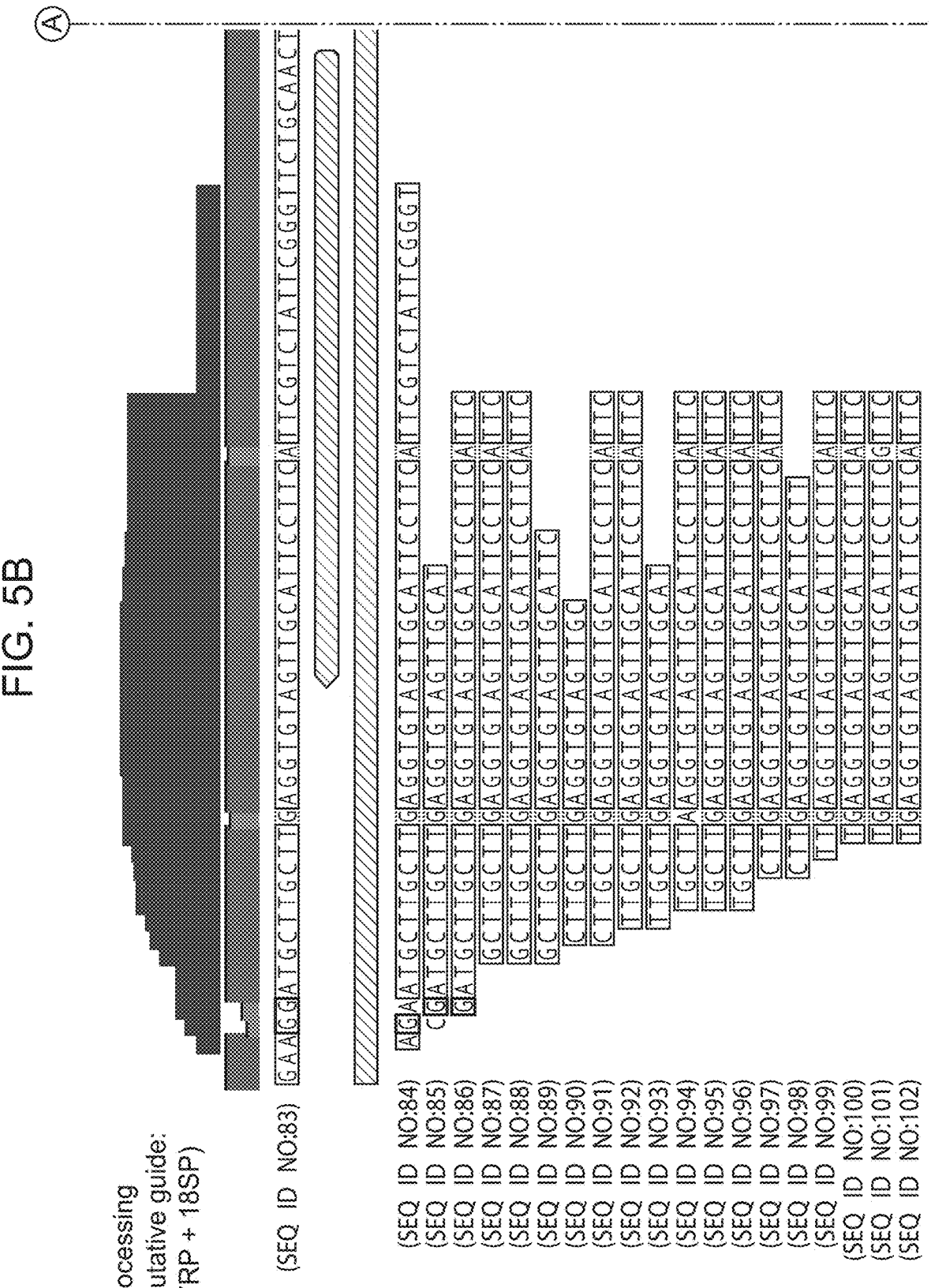
FIG. 5 depicts transcriptomic RNA mapping data demonstrating expression of trancRNA from CasZ loci. The trancRNAs are adjacent to the CasZ repeat array, but do not include the repeat sequence and are not complementary to the repeat sequence. Shown are RNA mapping data for the following loci: CasZa3, CasZb4, CasZc5, CasZd1, and CasZe3. Small repeating aligned arrows represent the repeats of the CRISPR array (indicating the presence of guide RNA-encoding sequence); The peaks outside and adjacent to the repeat arrays represent highly transcribed trancRNAs.
Figure 5C:
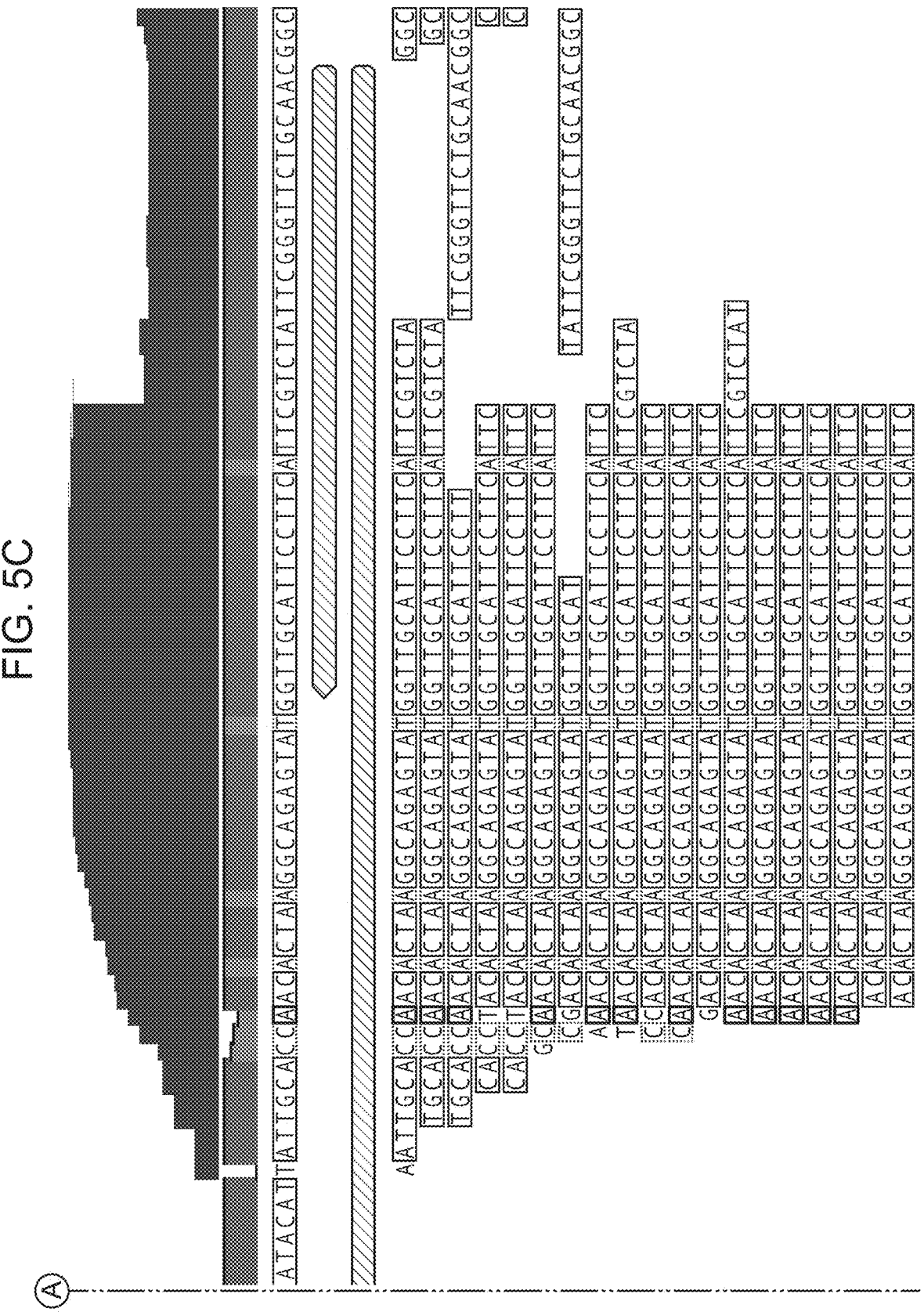
Figure 5D:
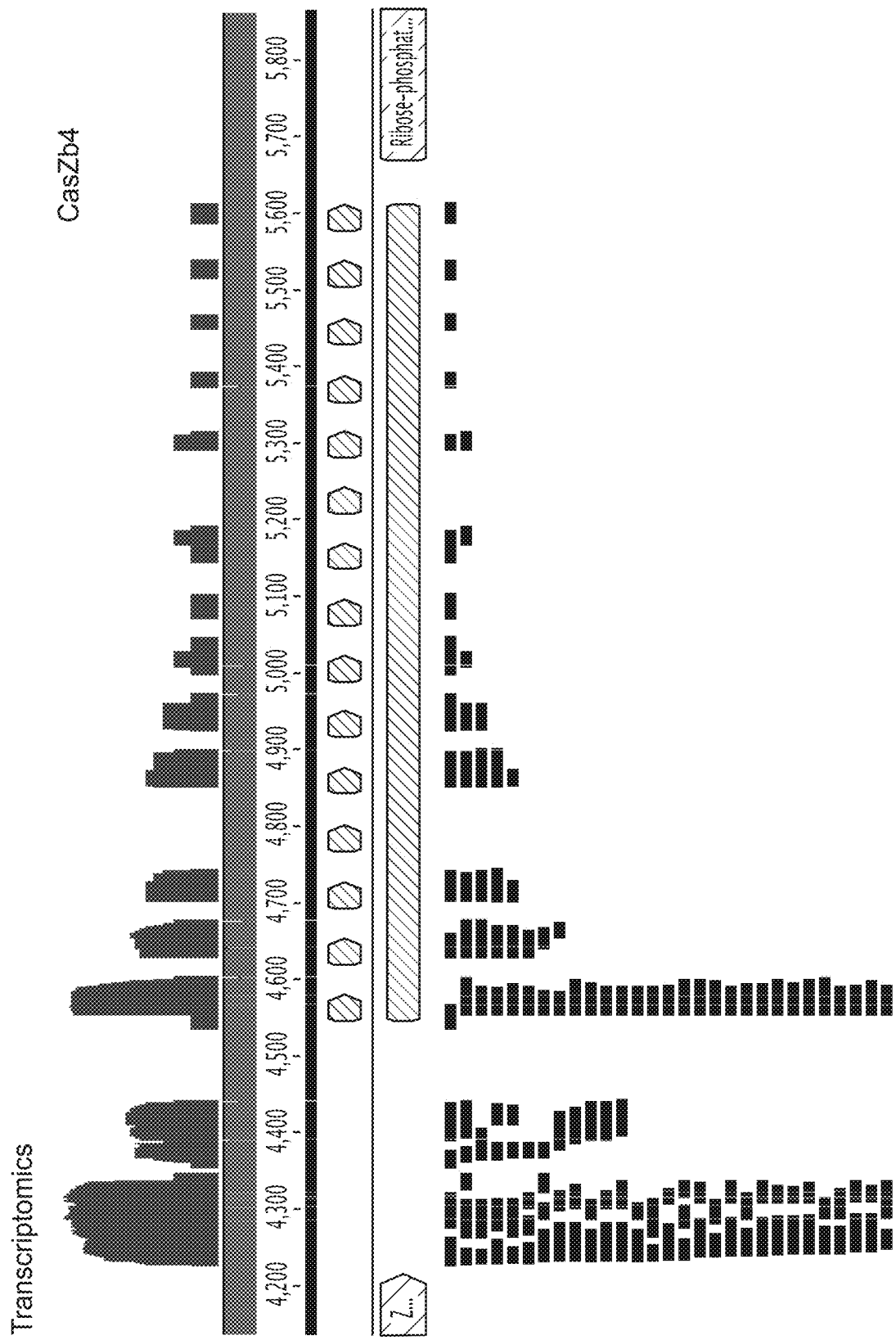
Figure 5E:
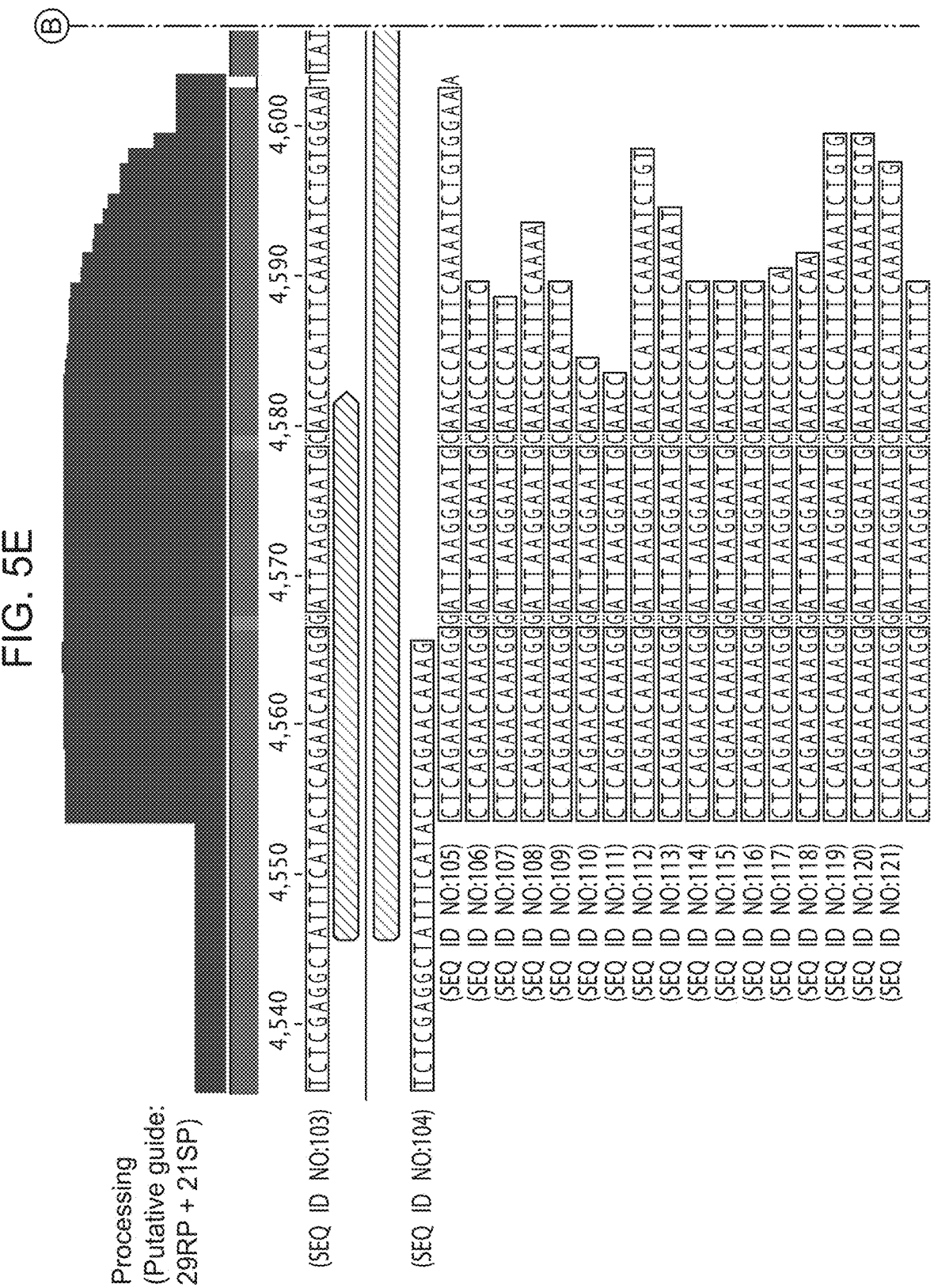
Figure 5F:
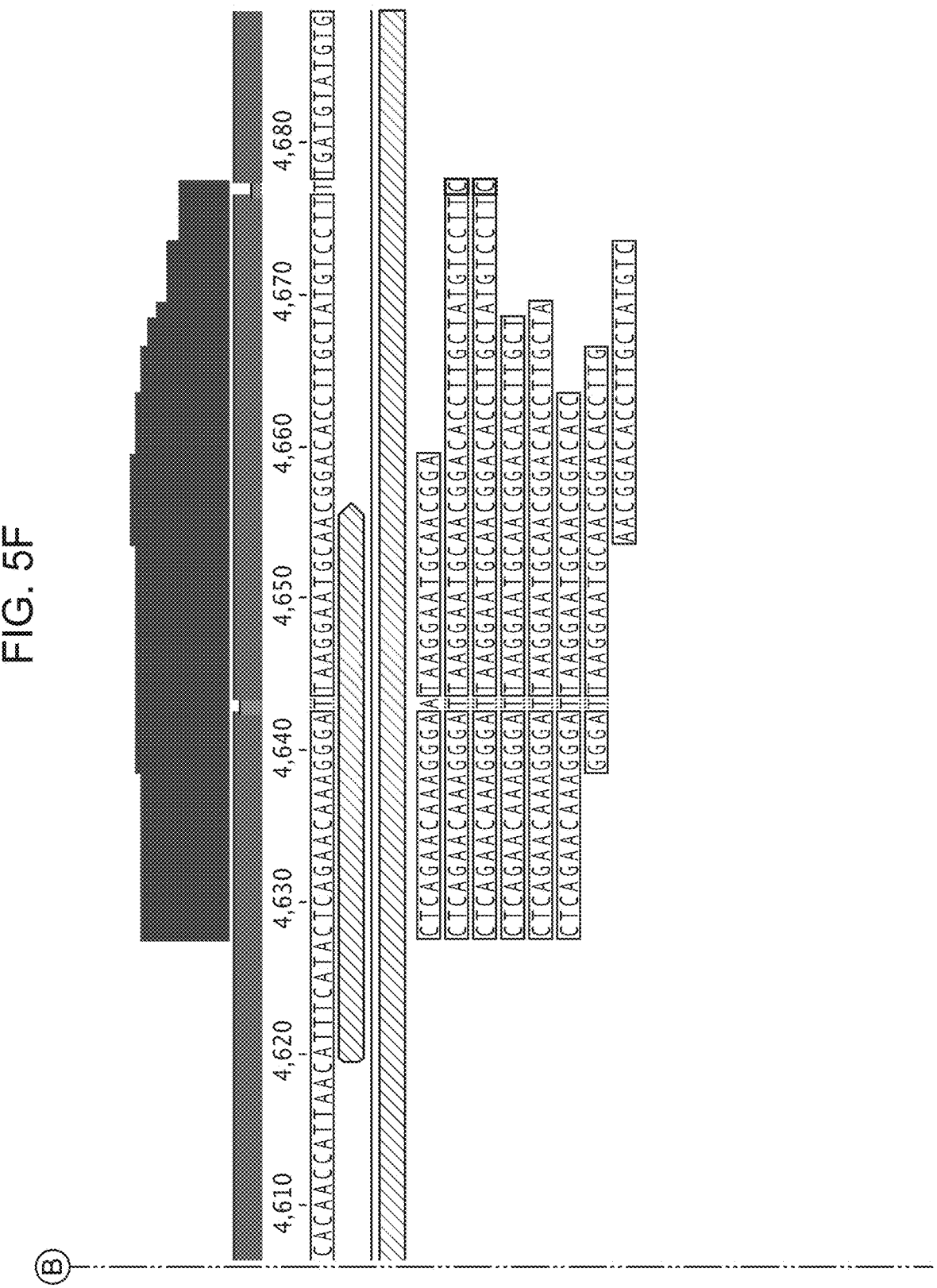
Figure 5G:
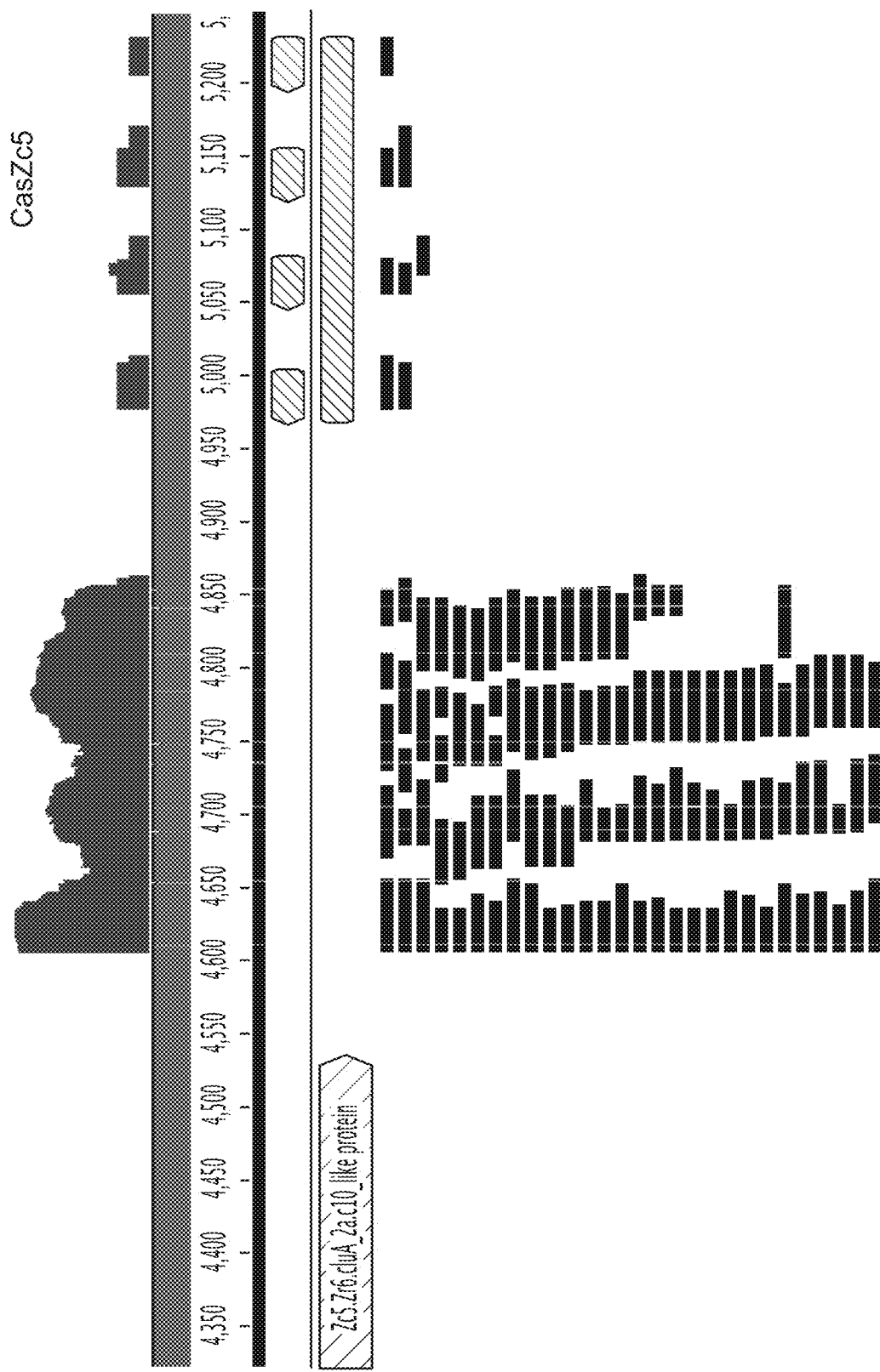
Figure 5H:
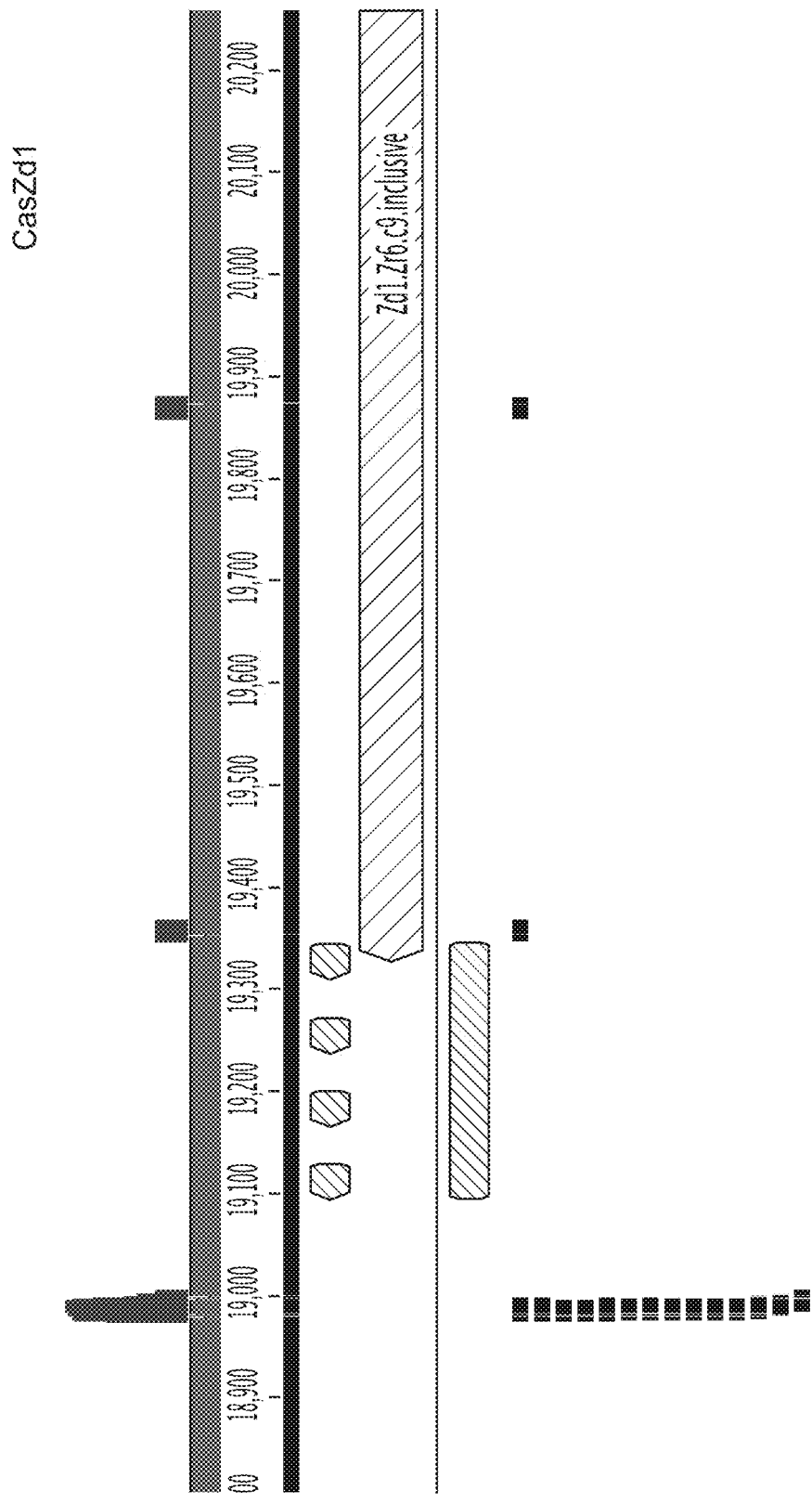
Figure 5I:
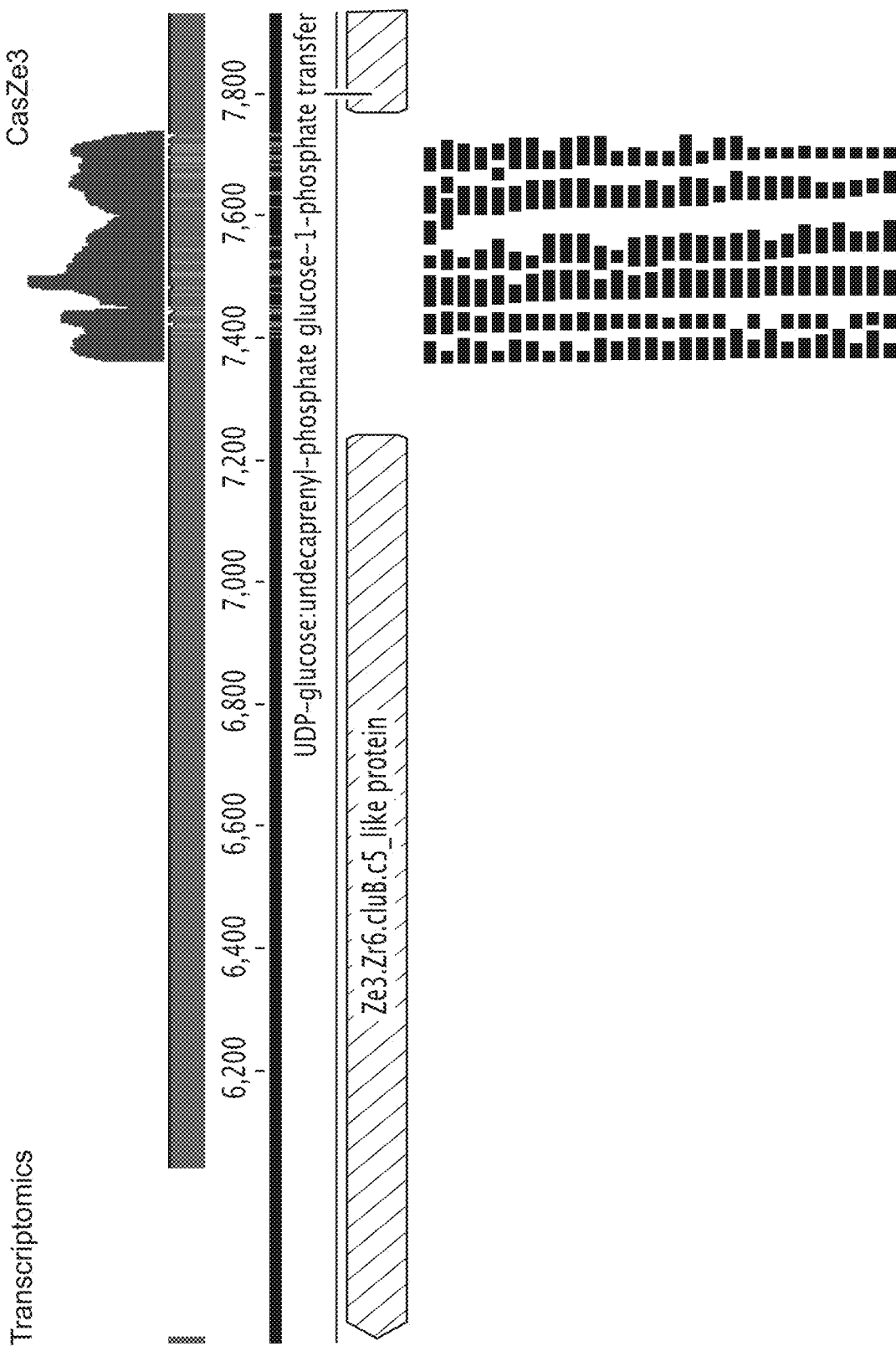
Figure 6:
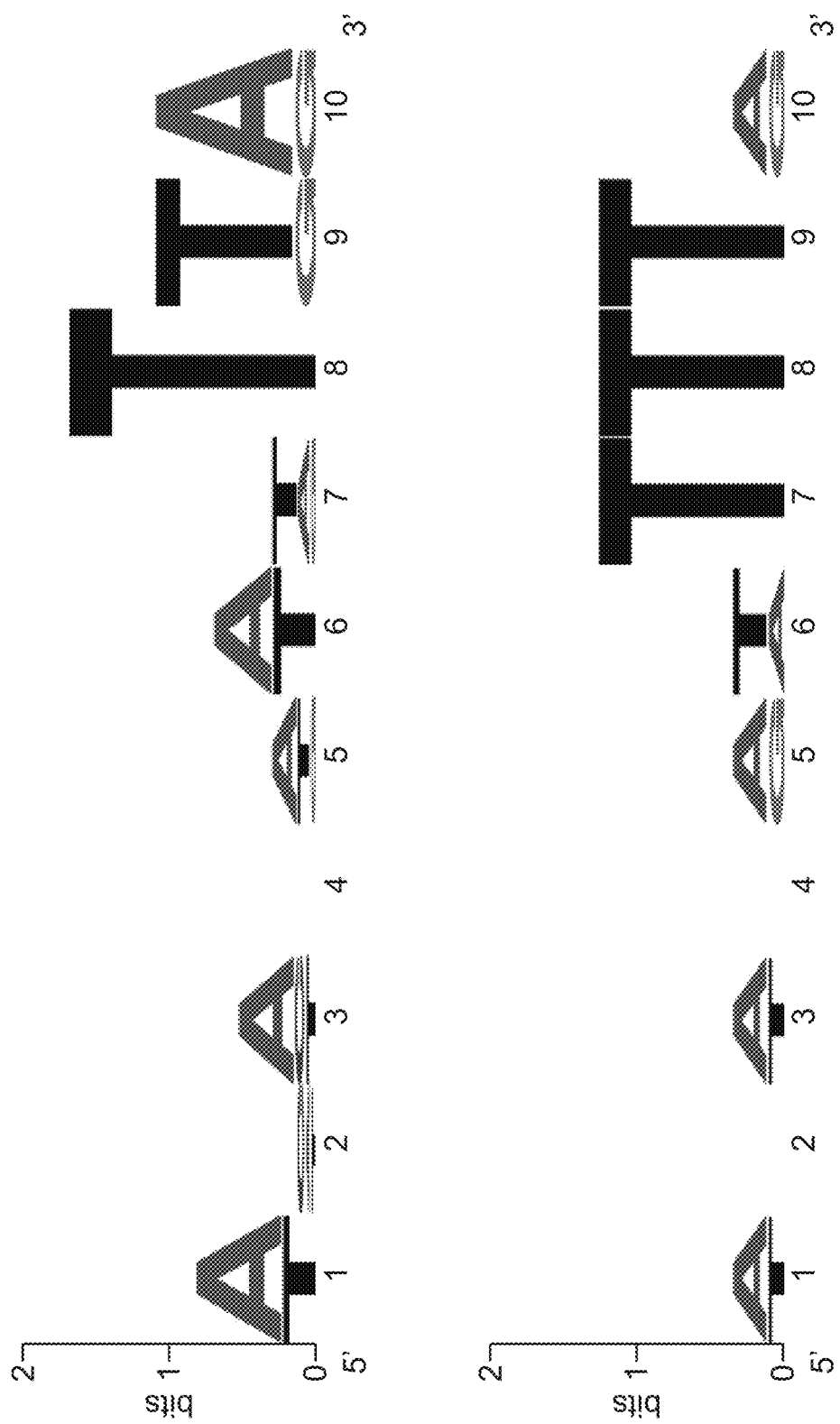
FIG. 6 depicts results for PAM preferences as assayed using PAM depletion assays for CasZc (top) and CasZb (bottom).
Figure 8A:
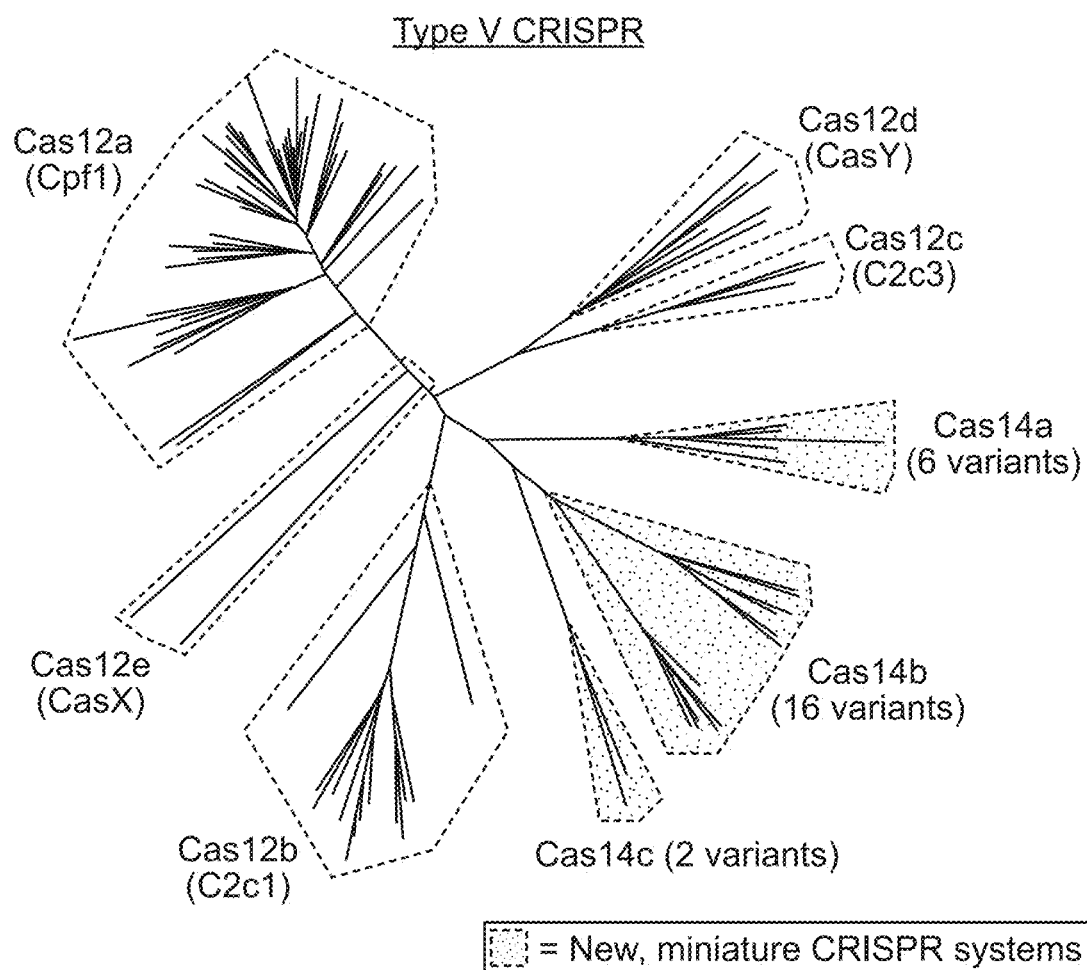
FIG. 8, Panels A-D depict the architecture and phylogeny of CRISPR-Cas14 genomic loci.
Figure 8B:
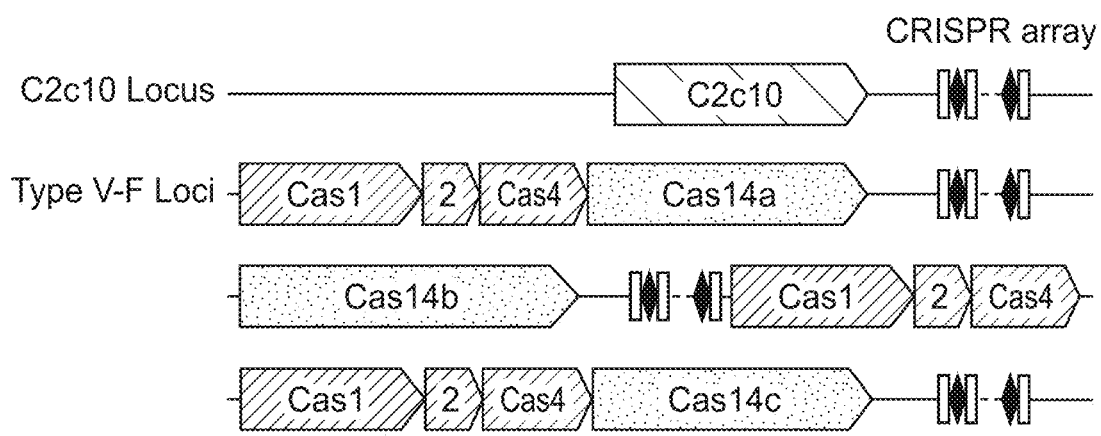
Figure 8C:
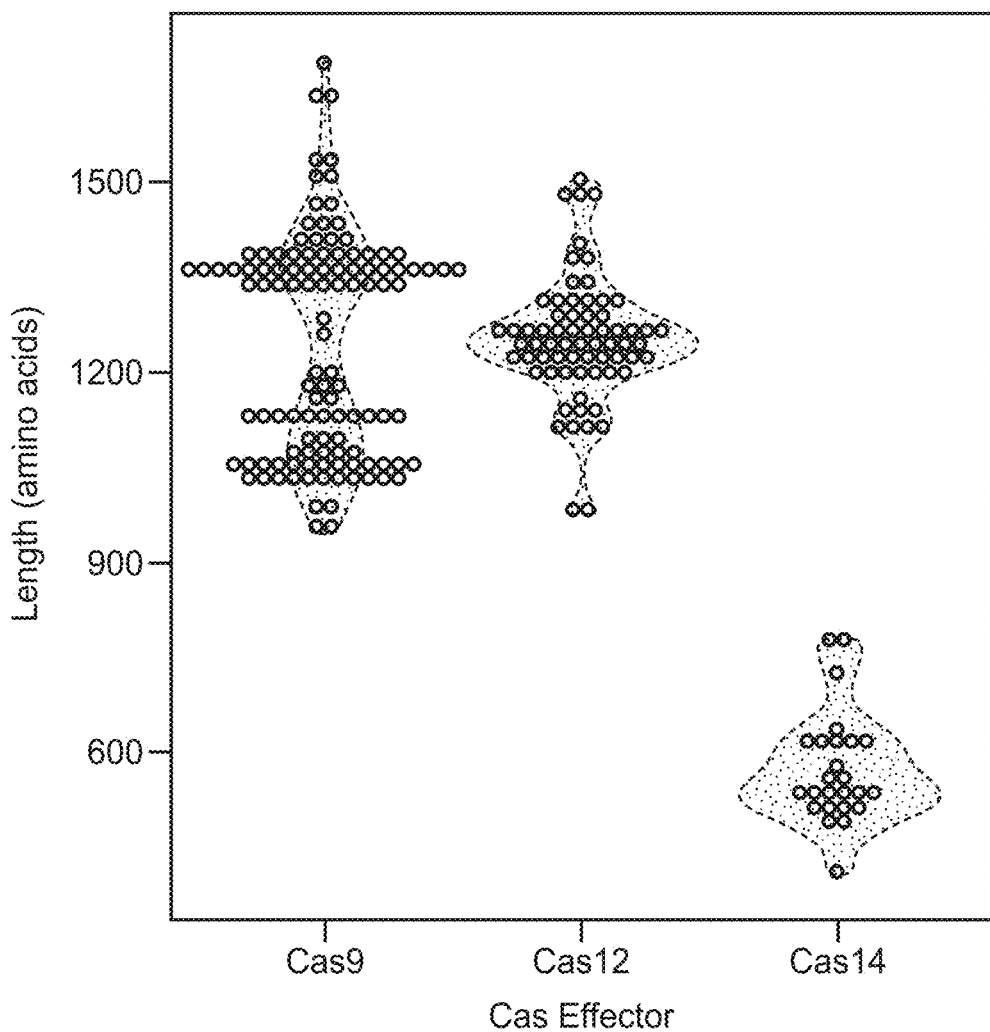
Figure 8D:
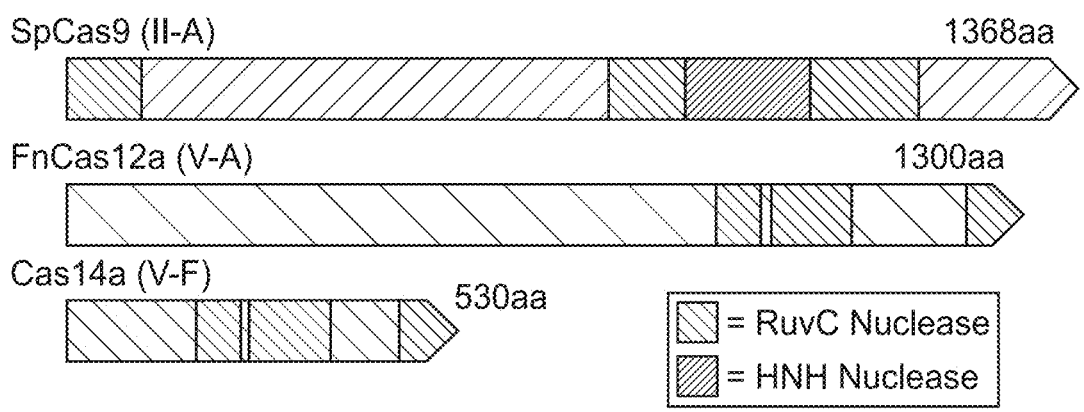

FIG. 4 depicts a phylogenetic tree of Cas1 sequences from CasZ loci in relation to Cas1 sequences from other Class 2 CRISPR/Cas loci.

FIG. 5 depicts transcriptomic RNA mapping data demonstrating expression of trancRNA from CasZ loci. The trancRNAs are adjacent to the CasZ repeat array, but do not include the repeat sequence and are not complementary to the repeat sequence. Shown are RNA mapping data for the following loci: CasZa3, CasZb4, CasZc5, CasZd1, and CasZe3. Small repeating aligned arrows represent the repeats of the CRISPR array (indicating the presence of guide RNA-encoding sequence); the peaks outside and adjacent to the repeat arrays represent highly transcribed trancRNAs.

This metatranscriptomic data was not 16S depleted, and hence large portions of the data were mapped to 16S, and mRNA, for example, was almost not represented at all in these reads. Nonetheless, RNA mapping to the predicted trancRNA regions was observed.

Example 2

A set of CRISPR-Cas systems from uncultivated archaea that contained Cas14, a family of exceptionally compact RNA-guided nucleases of just 400-700 amino acids were disclosed herein, including Cas1 and Cas2 proteins that are responsible for integrating DNA into CRISPR genomic loci and showed evidence of actively adapting their CRISPR arrays to new infections. Despite their small size, Cas14 proteins were capable of RNA-guided single-stranded DNA (ssDNA) cleavage without restrictive sequence requirements. Moreover, target recognition by Cas14 triggered non-specific cutting of ssDNA molecules. Metagenomic data showed that multiple CRISPR-Cas14 systems evolved independently and suggested a potential evolutionary origin of single-effector CRISPR-based adaptive immunity.

Figure 9:
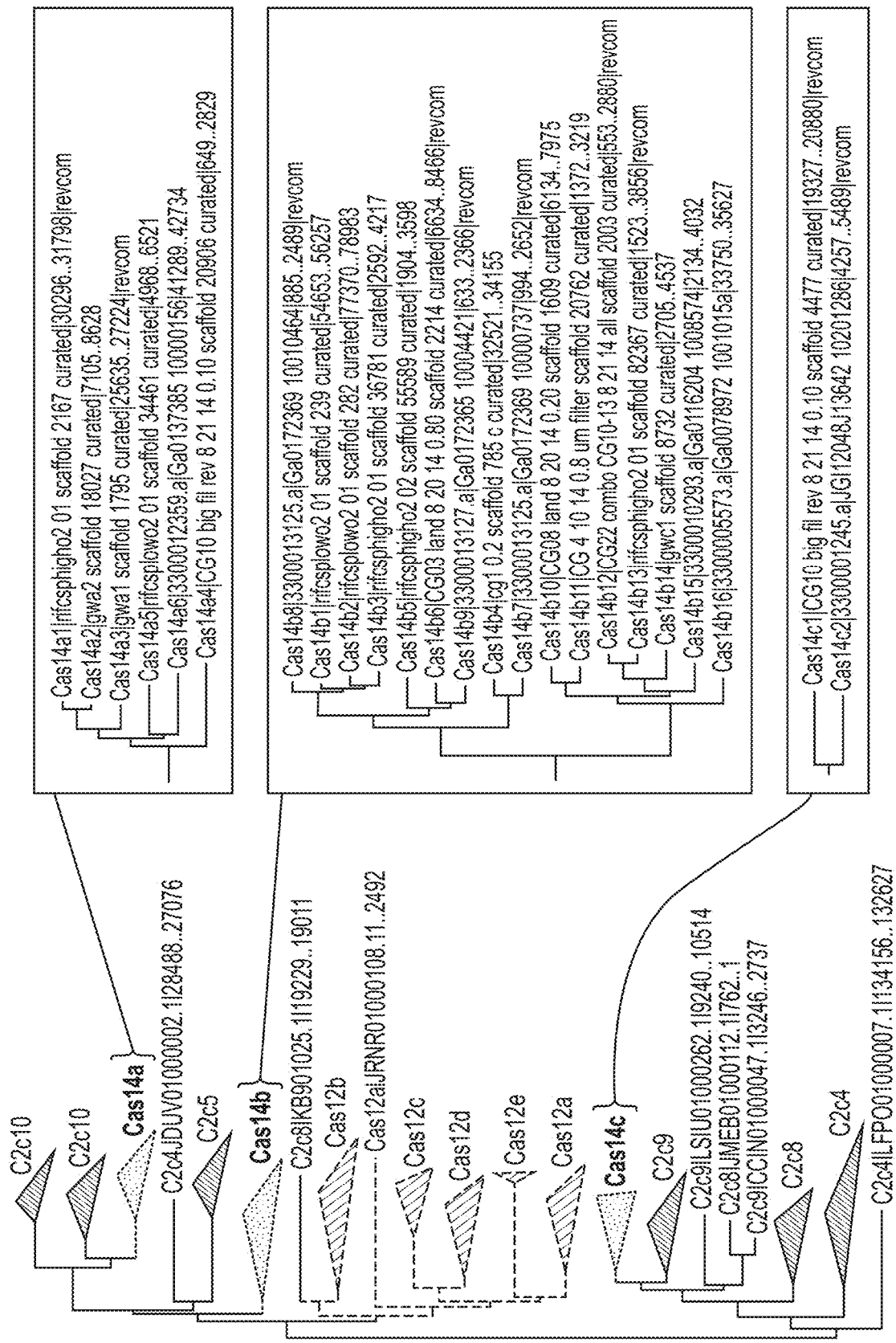
FIG. 9 depicts a phylogenetic analysis of Cas14 orthologs.
Figure 11A:
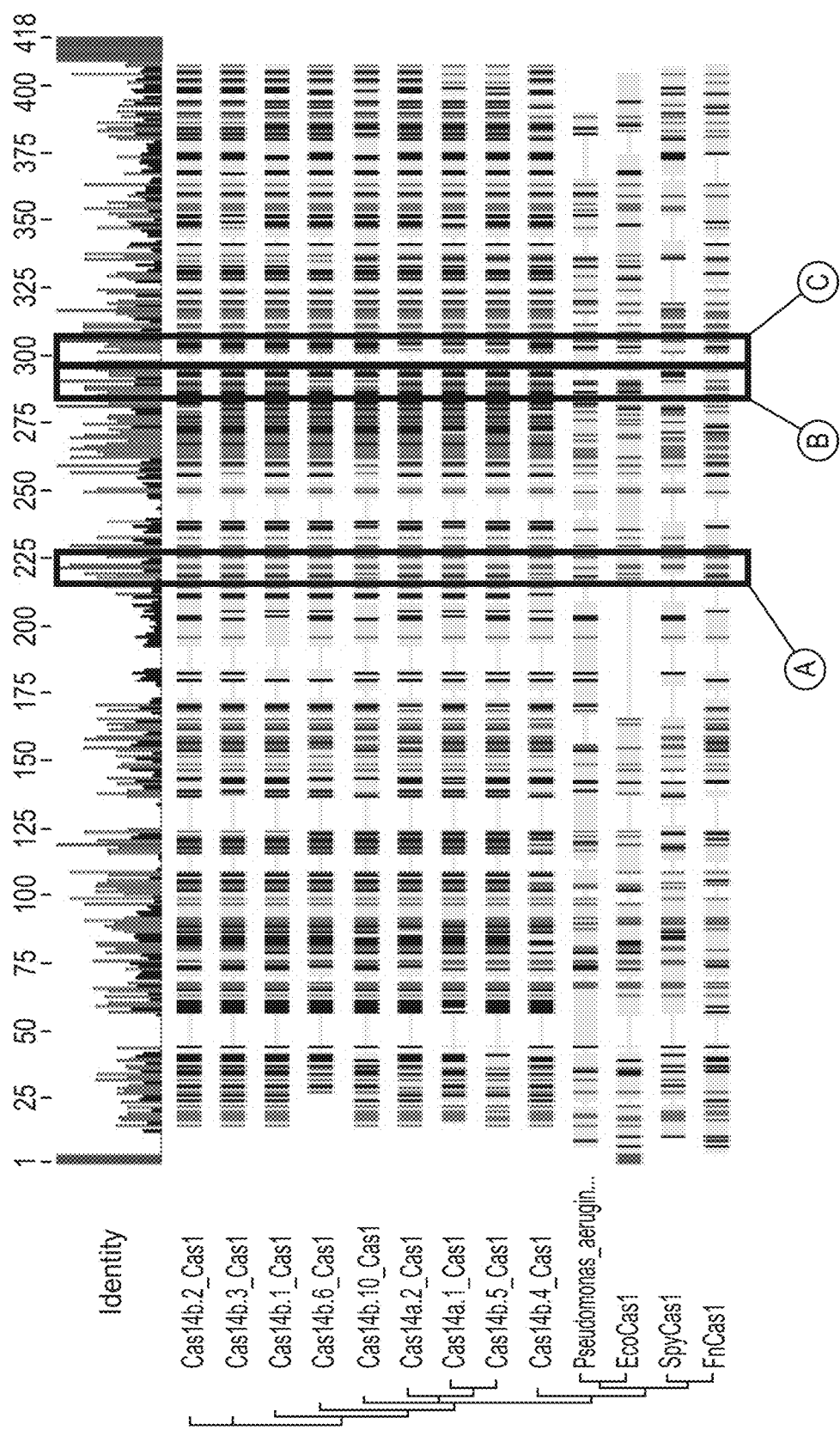
FIG. 11, Panels A-B depict the acquisition of new spacers by CRISPR-Cas14 systems.
Figure 11B:
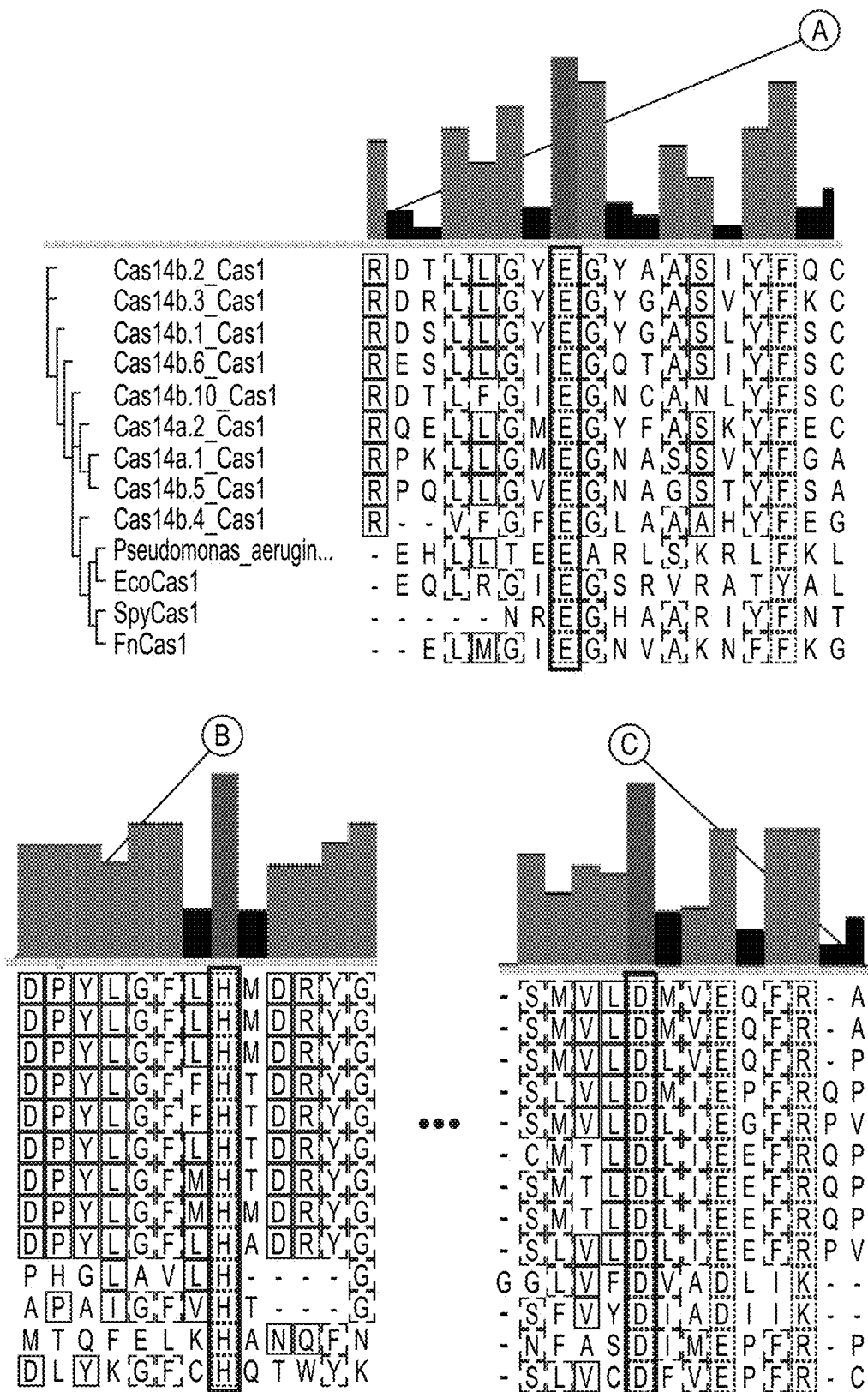
Figure 11C:
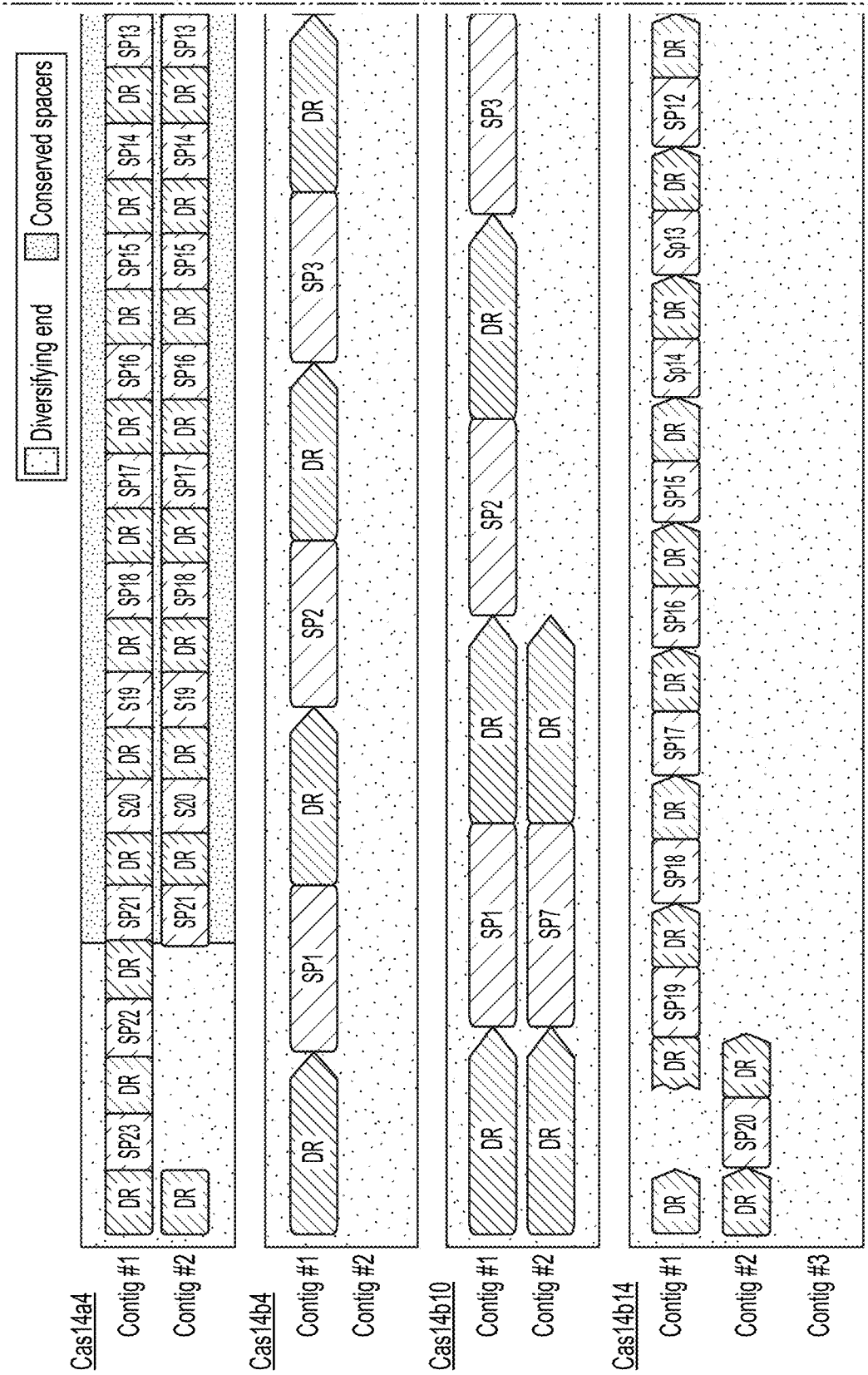
Figure 11D:
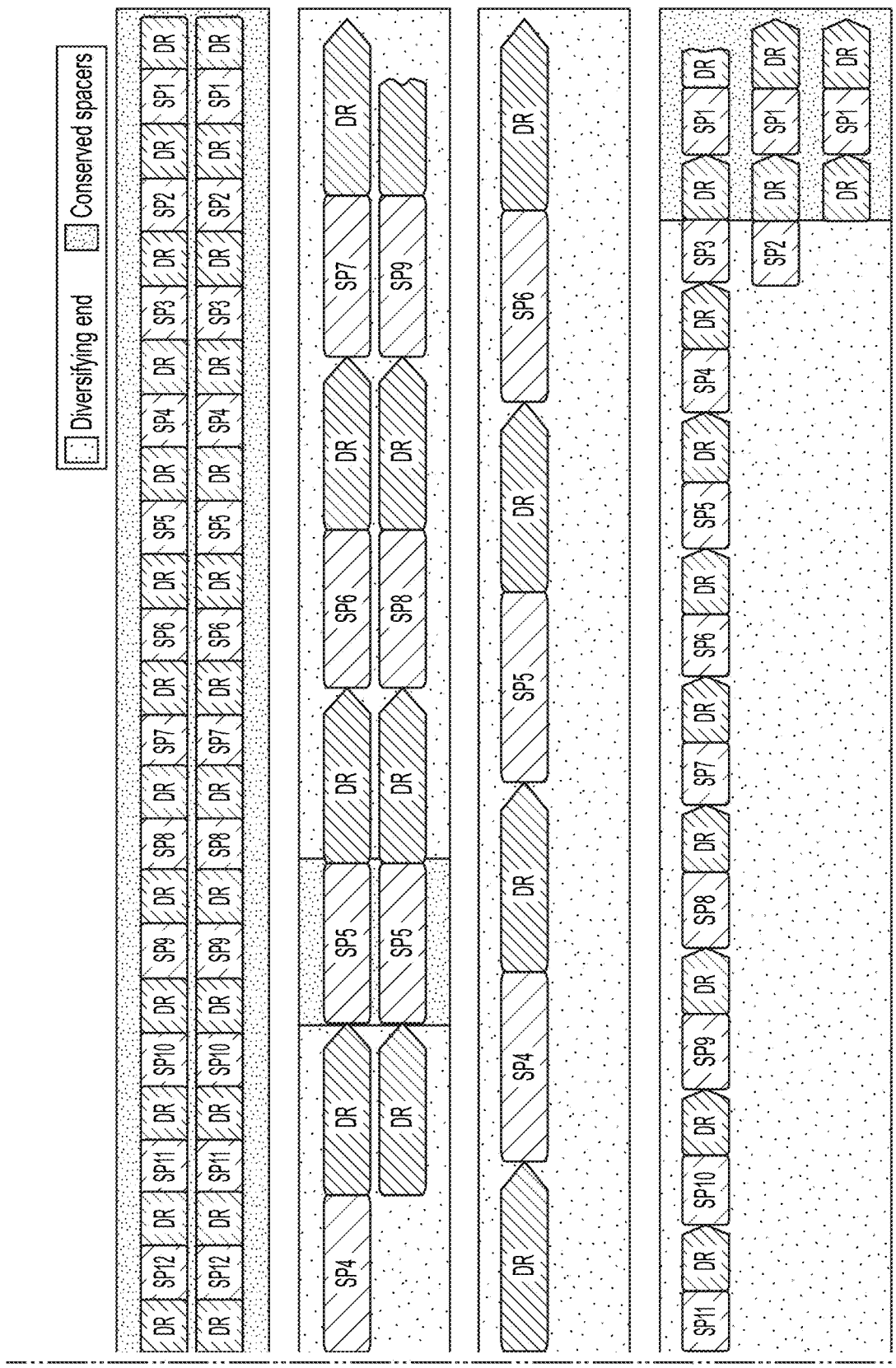
Figure 12A:
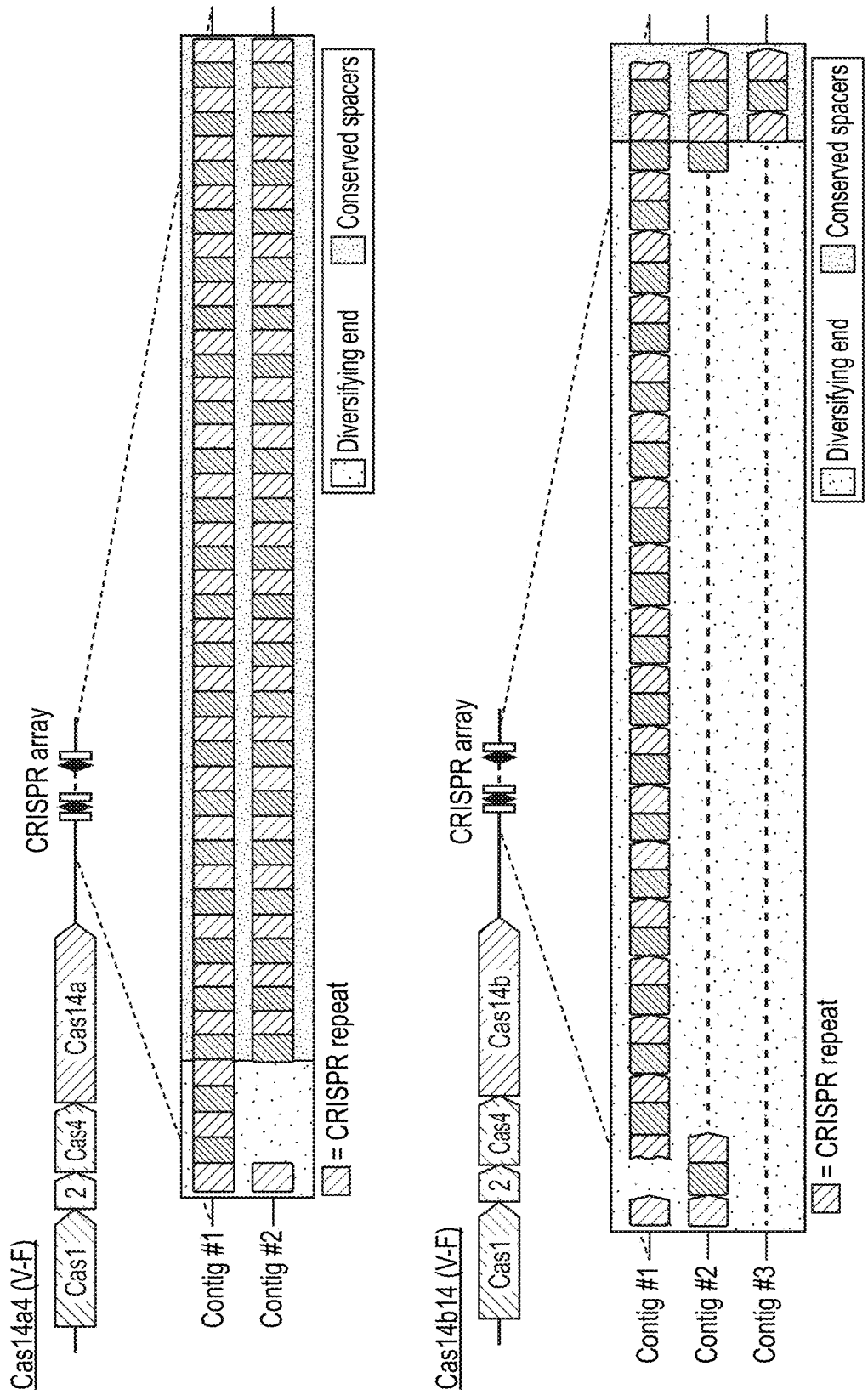
FIG. 12, Panels A-D depict that CRISPR-Cas14a actively adapts and encodes a tracrRNA.
Figure 12B:
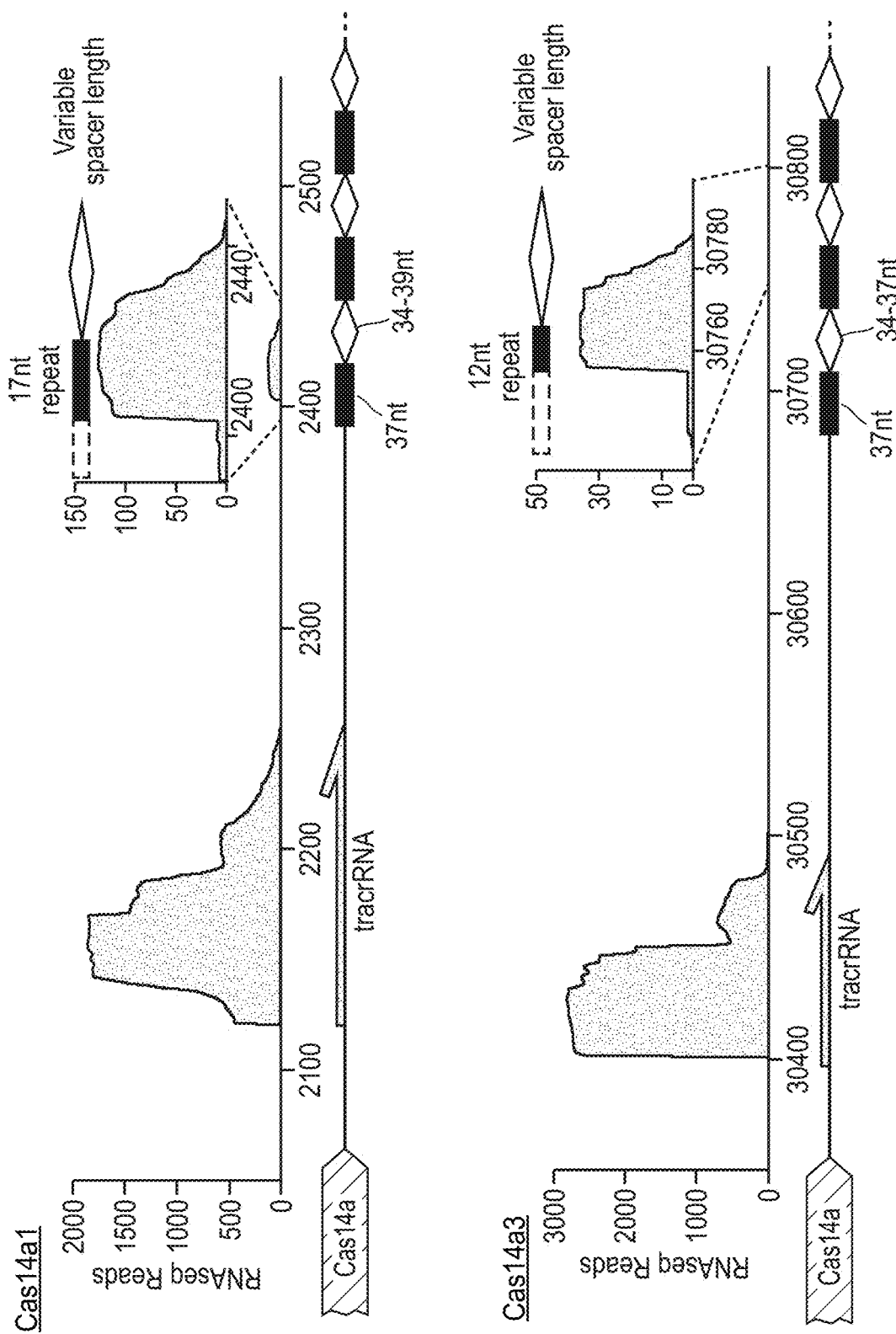
Figure 12C:
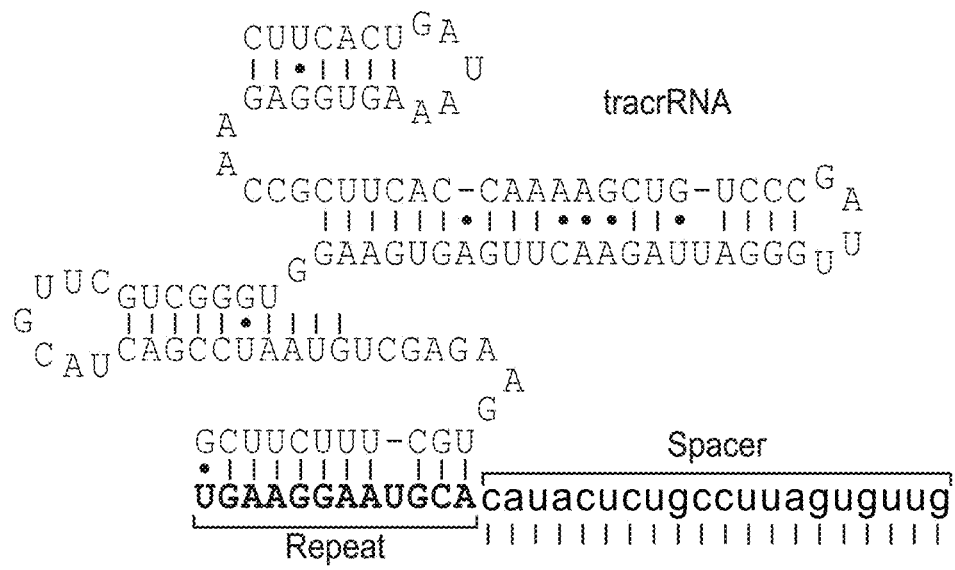
Figure 12D:
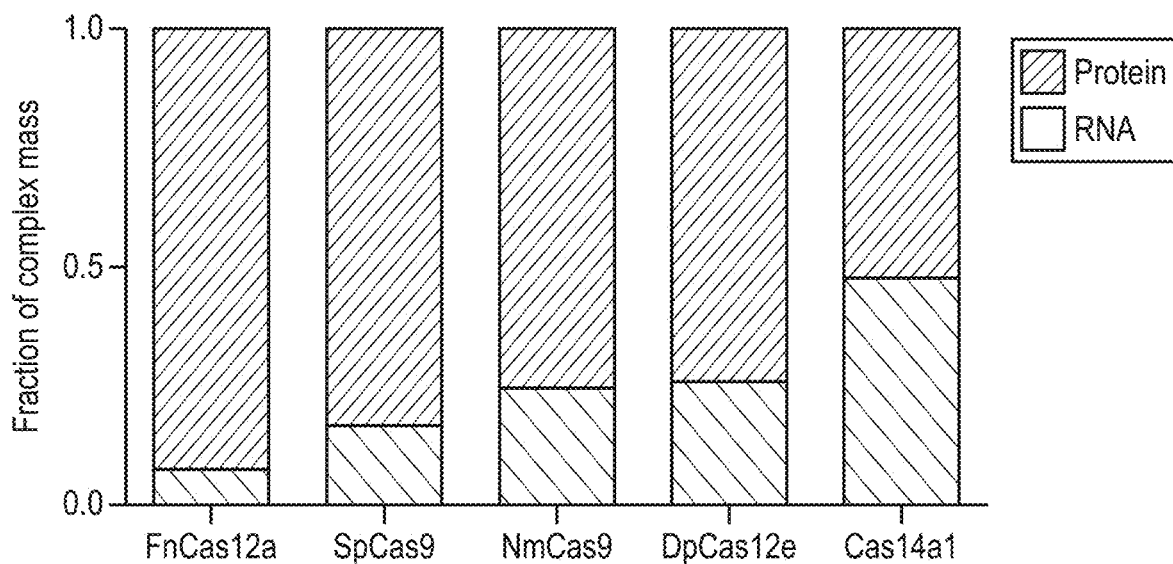
Figure 13A:
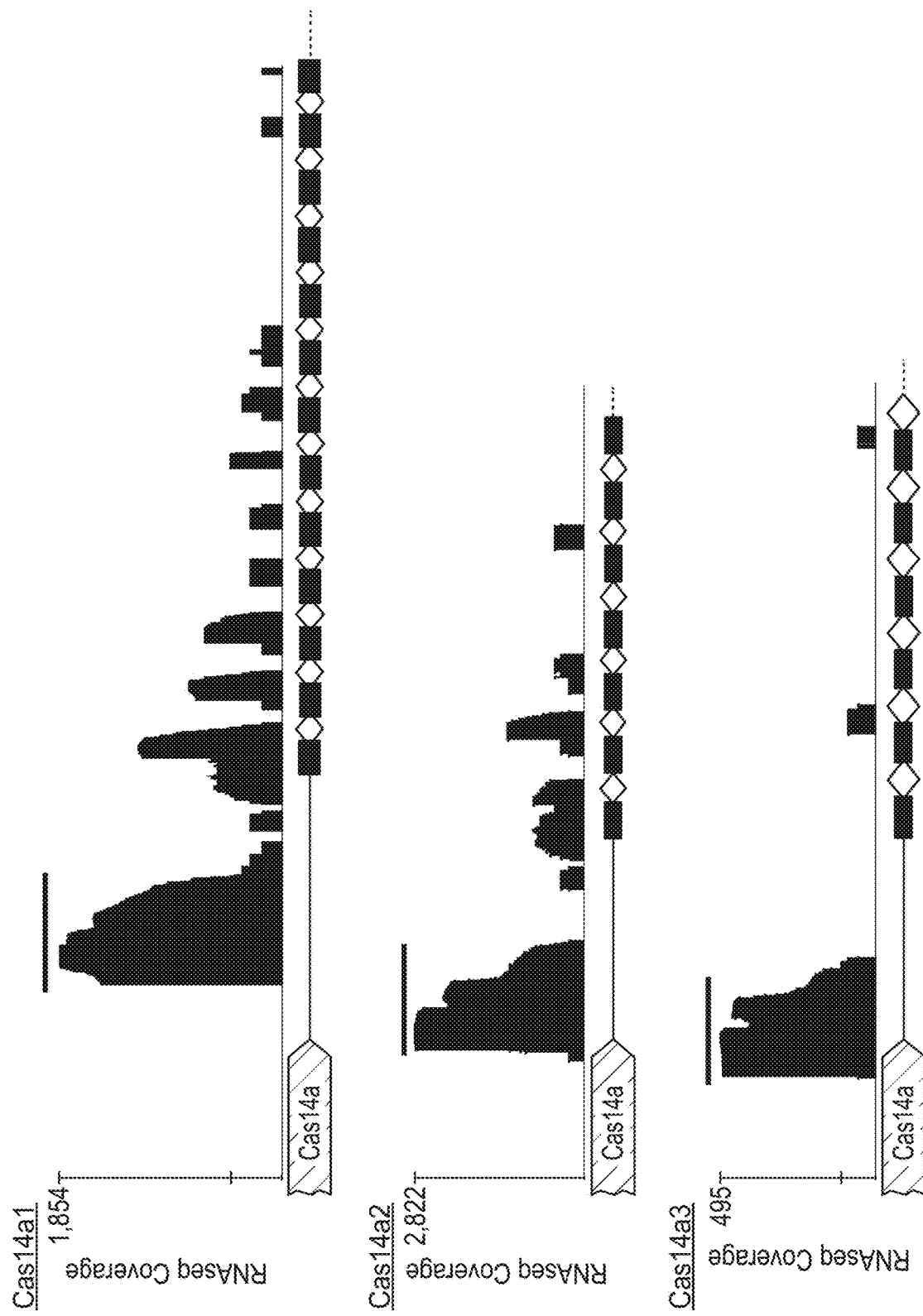
FIG. 13, Panels A-B depict metatranscriptomics for CRISPR-Cas14 loci.
Figure 13B:
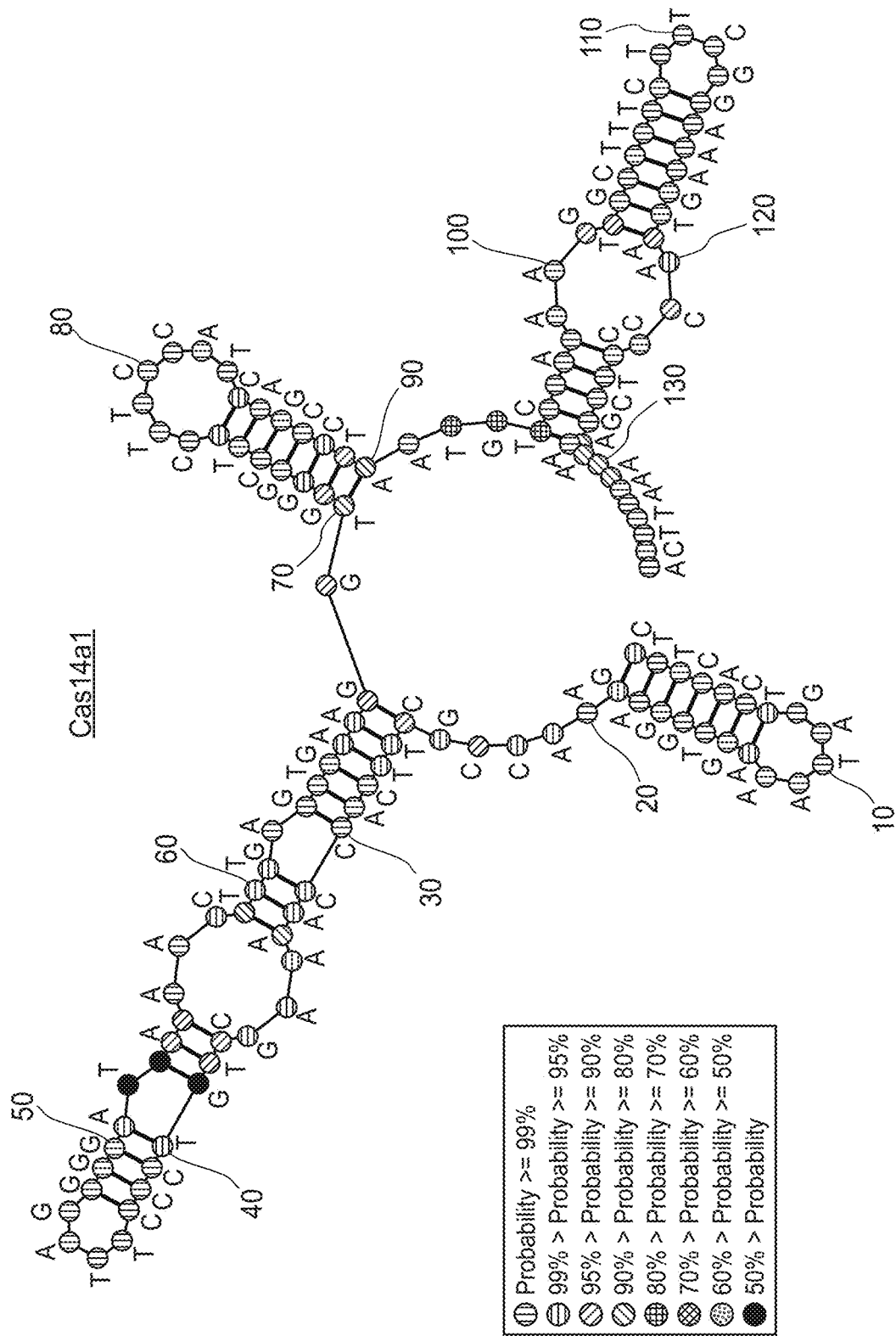
Figure 13C:
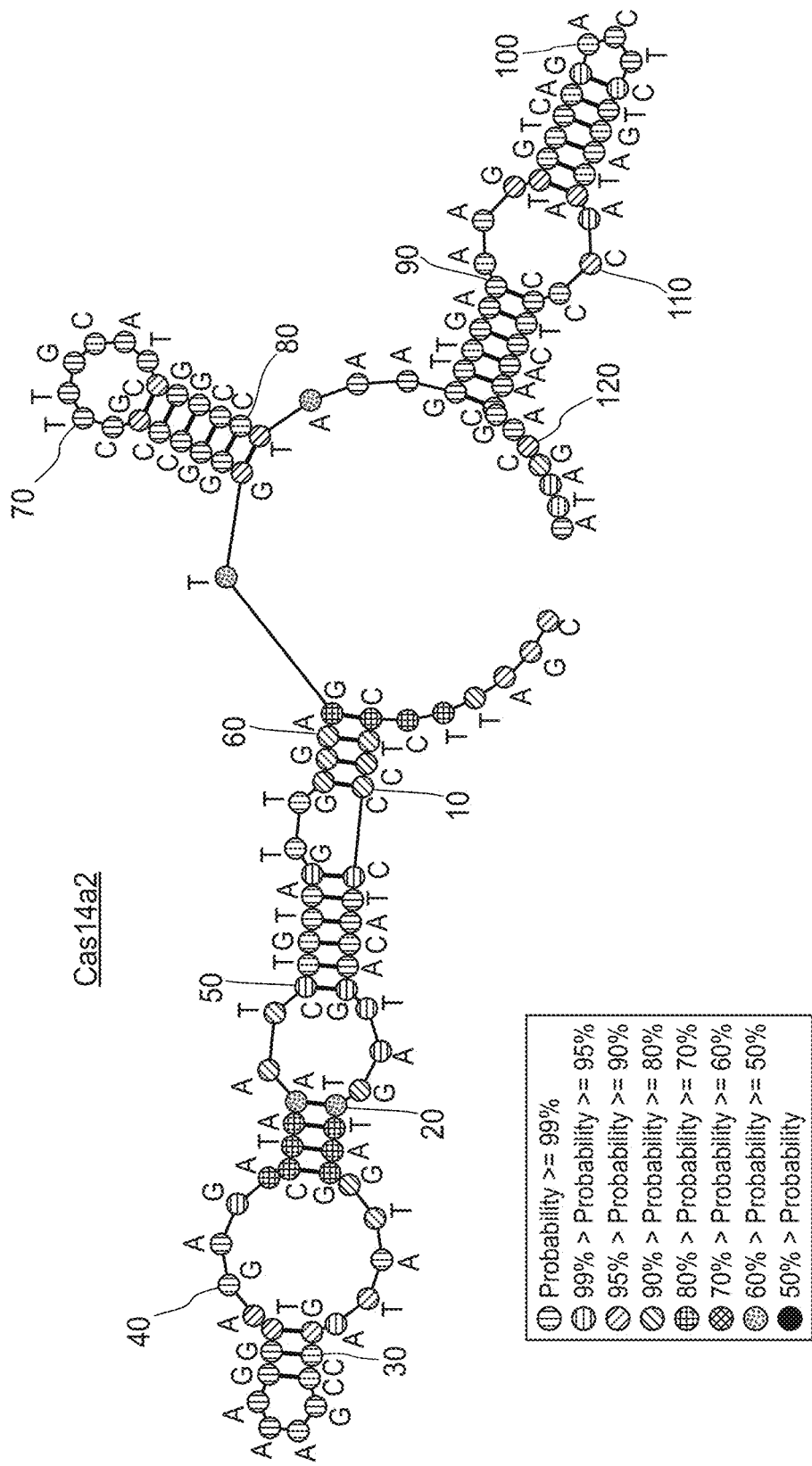
Figure 13D:
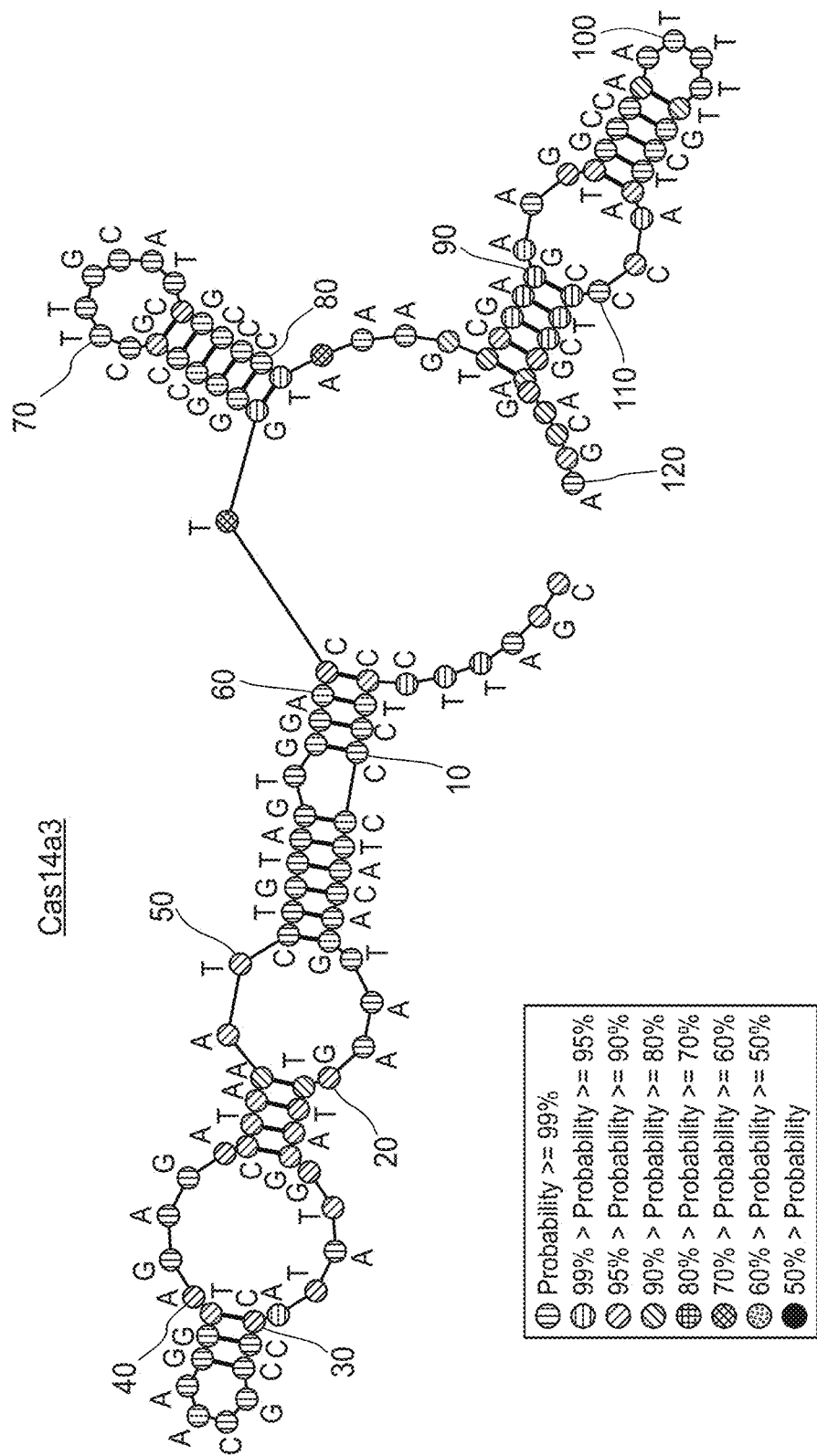
Figure 13E:
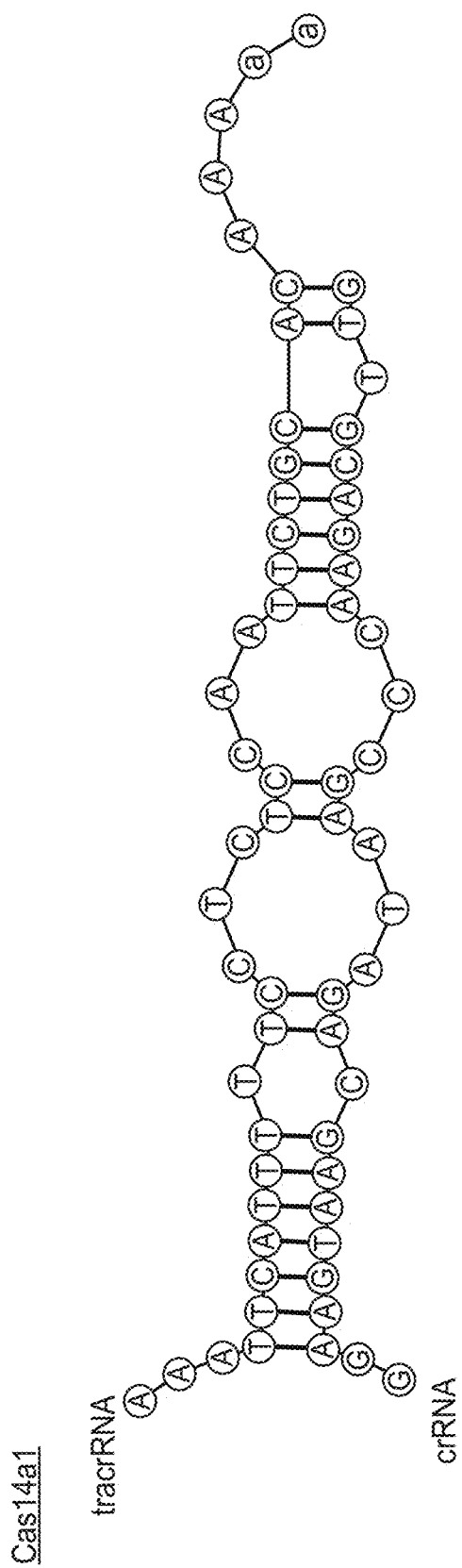

Competition between microbes and viruses stimulated the evolution of CRISPR-based adaptive immunity to provide protection against infectious agents. In class 2 CRISPR-Cas systems, a single 100-200 kilodalton (kD) CRISPR-associated (Cas) protein with multiple functional domains carried out RNA-guided binding and cutting of DNA or RNA substrates. To determine whether simpler, smaller RNA-guided proteins occurred in nature, terabase-scale metagenomic datasets were queried for uncharacterized genes proximal to both a CRISPR array and cas1, the gene that encoded the universal CRISPR integrase. This analysis identified a diverse family of CRISPR-Cas systems that contain cas1, cas2, cas4, and cas14, described herein, encoding a 40-70 kD polypeptide (FIG. 8, Panel A). Twenty-four (24) different cas14 gene variants have been identified that cluster into three subgroups (Cas14a-c) based on comparative sequence analysis (FIG. 8, Panels A-B, FIG. 9, FIG. 10). Cas14 proteins were ~400-700 amino acids (aa), about half the size of previously known class 2 CRISPR RNA-guided enzymes (FIG. 8, Panels C-D). While the identified Cas14 proteins exhibited considerable sequence diversity, all were united by the presence of a predicted RuvC nuclease domain, whose organization was characteristic of Type V CRISPR-Cas DNA-targeting enzymes (FIG. 8, Panel D).

The identified Cas14 proteins occurred almost exclusively within DPANN, a super-phylum of symbiotic archaea characterized by small cell and genome sizes. Phylogenetic comparisons showed that Cas14 proteins were widely diverse with similarities to C2c10 and C2c9, families of bacterial RuvC-domain-containing proteins that were sometimes found near a CRISPR array but never together with other cas genes (FIG. 8, Panel B and FIG. 9). This observation and the small size of c2c10 and cas14 genes made it improbable that these systems could function as standalone CRISPR effectors.

FIG. 8, Panels A-D depict architecture and phylogeny of CRISPR-Cas14 genomic loci. FIG. 8, Panel A depicts a phylogenetic tree of Type V CRISPR systems. Newly identified miniature CRISPR systems are highlighted in orange. FIG. 8, Panel B depicts representative loci architectures for C2c10 and CRISPR-Cas14 systems. FIG. 8, Panel C depicts the length distribution of Cas14a-c systems compared to Cas12a-e and Cas9. FIG. 8, Panel D depicts the domain organization of Cas14a compared to Cas9 and Cas12a. Protein lengths are drawn to scale.

FIG. 9 depicts the maximum likelihood tree for known Type V CRISPR effectors and class 2 candidates containing a RuvC domain Inset shows individual orthologs for each newly identified subtype. FIG. 10 depicts a maximum likelihood tree for Cas1 from known CRISPR systems.

Example 3

Figure 14B:
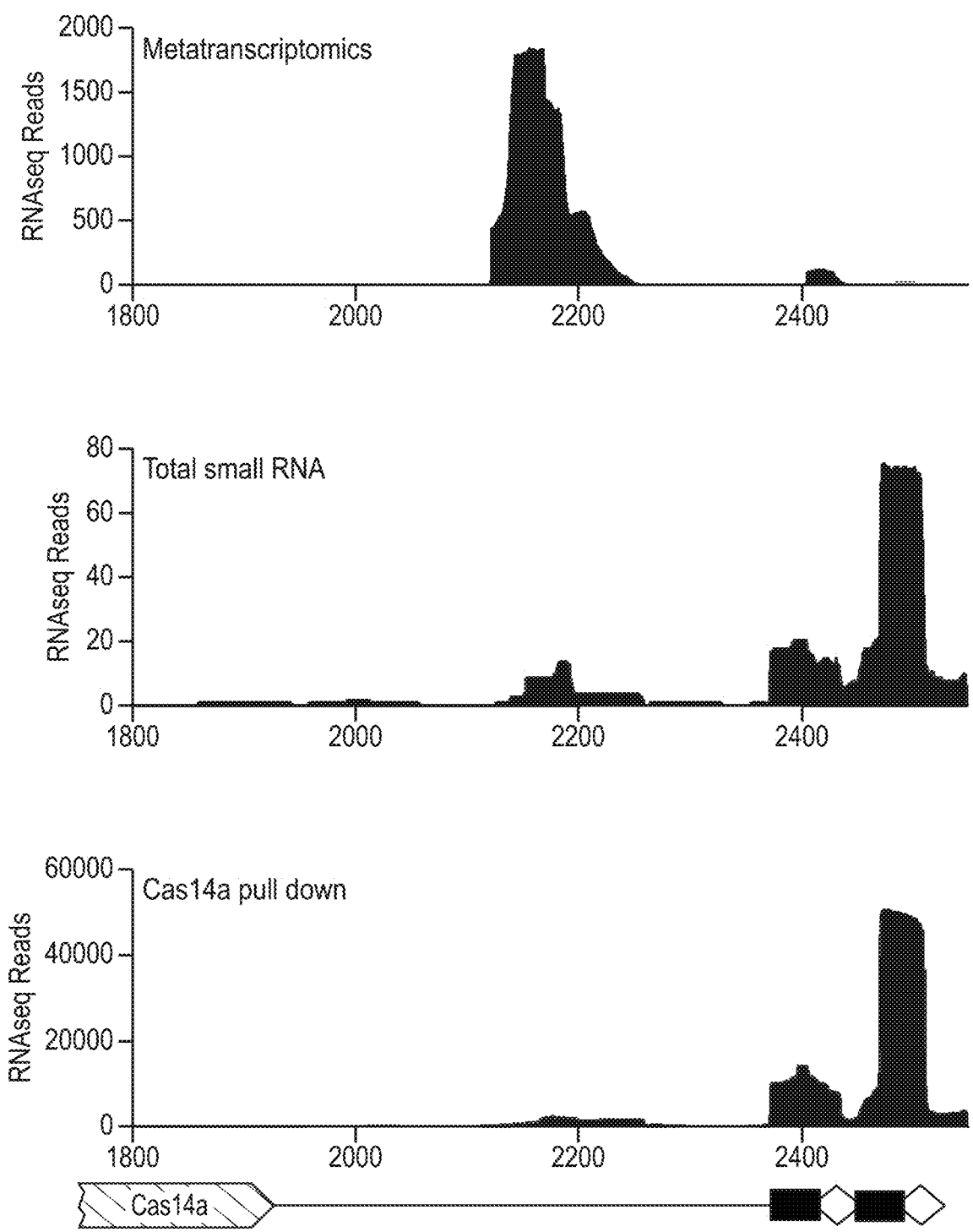
FIG. 14, Panels A-B depict RNA processing and heterologous expression by CRISPR-Cas14.

Based on their proximity to conserved genes responsible for creating genetic memory of infection (cas1, cas2, cas4) (FIG. 11, Panel A), it was explored whether CRISPR-Cas14 systems actively acquired DNA sequences into their CRISPR arrays. Assembled metagenomic contiguous DNA sequences (contigs) for multiple CRISPR-Cas14 loci revealed that otherwise identical CRISPR systems showed diversity in their CRISPR arrays, suggesting active adaptation to new infections (FIG. 11, Panel B and FIG. 12, Panel A). Without intending to be bound by any particular theory, it is proposed that the active acquisition of new DNA sequences indicated that these CRISPR-Cas14 loci encoded functional enzymes with nucleic acid targeting activity despite their small size. To test this possibility, it was investigated whether RNA components were produced from CRISPR-Cas14 loci. Environmental metatranscriptomic sequencing data were analyzed for the presence of RNA from the native archaeal host that contains CRISPR-Cas14a (FIG. 12, Panel B and FIG. 13, Panel A). In addition to CRISPR RNAs (crRNAs), a highly abundant non-coding RNA was mapped to about a 130-base pair sequence located between cas14a and the adjacent CRISPR array. The 20 nucleotides (nts) at the 3' end of this transcript were mostly complementary to the repeat segment of the crRNA (FIG. 12, Panel C and FIG. 13, Panel B), as observed for trans-activating CRISPR RNAs (tracrRNAs) found in association with Cas9, Cas12b and Cas12e CRISPR systems. In these previously studied systems, the double-stranded-RNA-cutting enzyme Ribonuclease III (RNase III) generated mature tracrRNAs and crRNAs, but no genes encoding RNase III were present in cas14-containing reconstructed genomes (FIG. 14, Panel A). This observation implied that an alternative mechanism for CRISPR-associated RNA processing existed in these hosts.

Figure 15A:
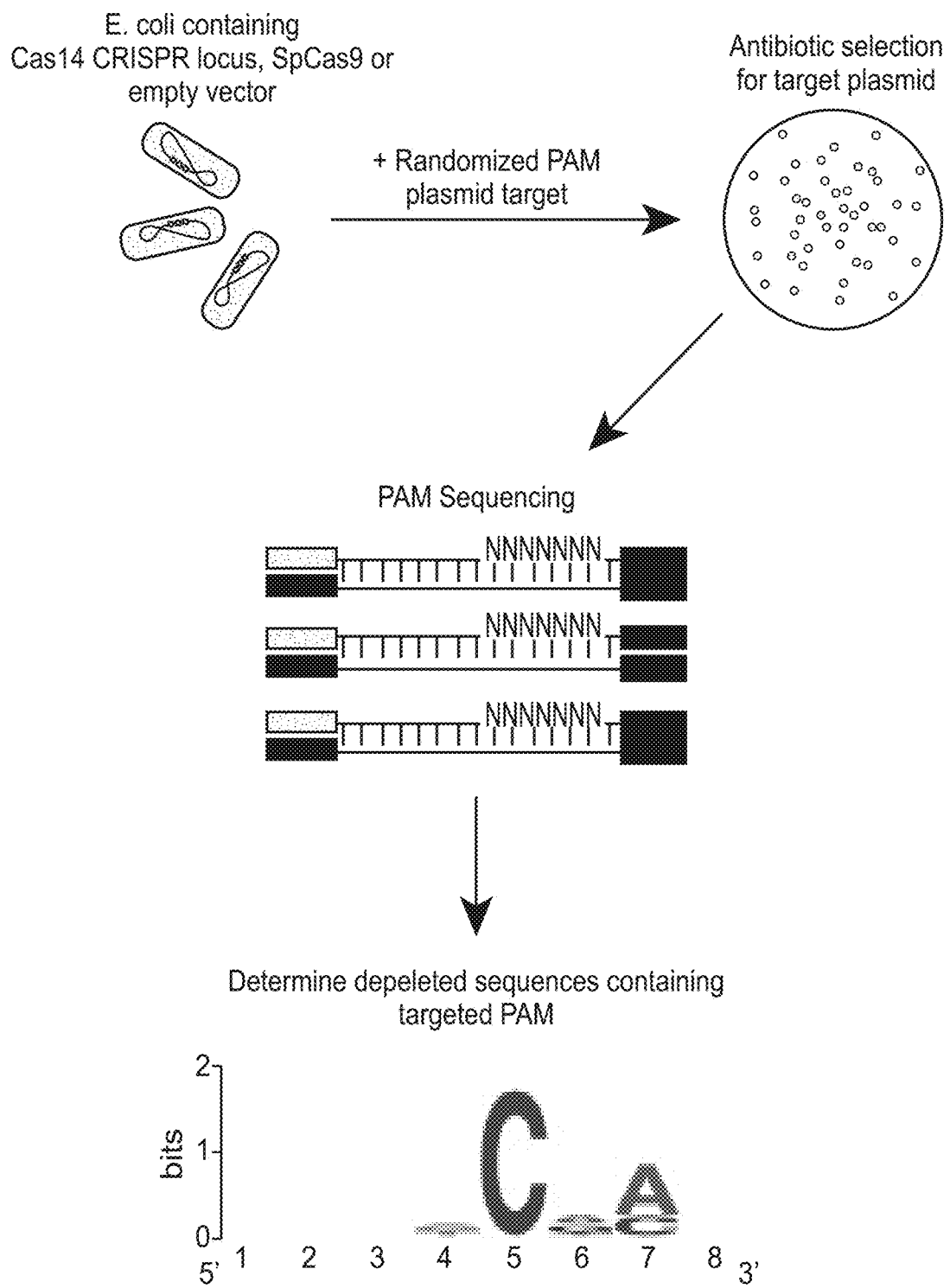
FIG. 15, Panels A-D depict plasmid depletion by Cas14a1 and SpCas9.
Figure 15D:
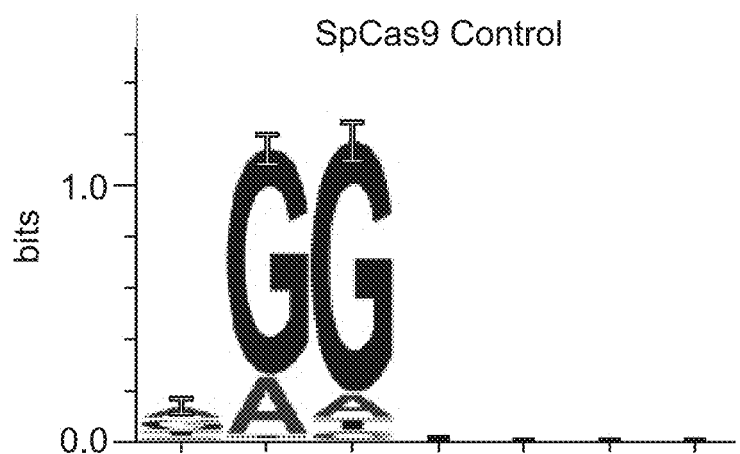

To test whether the Cas14a proteins and associated RNA components could assemble in a heterologous organism, a plasmid was introduced into *E. coli* containing a minimal CRISPR-Cas14a locus that included the Cas14 gene, the CRISPR array and intergenic regions containing the putative tracrRNA. Affinity purification of the Cas14a protein from cell lysate and sequencing of co-purifying RNA revealed a highly abundant mature crRNA as well as the putative tracrRNA, suggesting that Cas14 associated with both crRNA and tracrRNA (FIG. 14, Panel B). The calculated mass of the assembled Cas14a protein-tracrRNA-crRNA particle was 48% RNA by weight compared to just 17% for *S. pyogenes* Cas9 (SpCas9) (FIG. 12, Panel D) and 8% for *F. novicida* Cas12a (FnCas12a), hinting at a central role of the RNA in the architecture of the Cas14a complex. Known class 2 CRISPR systems required a short sequence called a protospacer adjacent motif (PAM) to target double-stranded DNA (dsDNA). To test whether Cas14a required a PAM and could conduct dsDNA interference, *E. coli* was transformed expressing a minimal Cas14a locus with a dsDNA plasmid containing a randomized PAM region next to a sequence matching the target-encoding sequence (spacer) in the Cas14 array. No depletion of a PAM sequence was detected among *E. coli* transformants, suggesting that the CRISPR-Cas14a system was either unable to target dsDNA, could do so without requiring a PAM, or was inactive in this heterologous host (FIG. 15, Panels A-D).

FIG. 11, Panels A-B depict acquisition of new spacers by CRISPR-Cas14 systems. FIG. 11, Panel A depicts alignment of Cas14 Cas1 orthologs. Expansion shows conservation of previously implicated active site residues highlighted in red boxes. FIG. 11, Panel B depicts multiple CRISPR arrays assembled for various CRISPR-Cas14 systems revealing spacer diversity for these CRISPR systems. Orange arrows indicate repeats while variously colored boxes indicate unique spacers.

FIG. 12, Panels A-D depict that CRISPR-Cas14a actively adapts and encodes a tracrRNA. FIG. 12, Panel A depicts pacer diversity for Cas14a and Cas14b with CRISPR repeats diagramed in orange and unique spacers shown in different colors. FIG. 12, Panel B depicts metatranscriptomics reads mapped to Cas14a1 and Cas14a3. Inset shows expansion of most abundant repeat and spacer sequence. FIG. 12, Panel C depicts in silico predicted structure of Cas14a1 crRNA and tracrRNA. RNase III orthologs were not identified in host genomes (FIG. 14, Panel A). FIG. 12, Panel D depicts fraction of various CRISPR complexes mass made up of by RNA and protein.

FIG. 13, Panels A-B depict metatranscriptomics for CRISPR-Cas14 loci. FIG. 13, Panel A depicts environmental RNA sequencing reads for Cas14a orthologs. Location of Cas14 and the CRISPR array indicated below. RNA structures to the right show the in silico predicted structure of the tracrRNA identified from metatranscriptomics. FIG. 13, Panel B depicts predicted hybridization for Cas14a1 crRNA:tracrRNA duplex.

FIG. 14, Panels A-B depict RNA processing and heterologous expression by CRISPR-Cas14. FIG. 14, Panel A depicts the presence of common RNase orthologs in Cas14 containing genomes. Light purple represents hits that were significantly shorter than the expected length for the given RNase. Note that RNase III is absent in all investigated genomes. FIG. 14, Panel B depicts small RNAseq reads from heterologous expression of Cas14a1 locus in *E. coli* (FIG. 14, Panel B, bottom two graphs) compared to metatranscriptomic reads (FIG. 14, Panel B, top graph). Pull down refers to RNA that copurified with Ni-NTA affinity purified Cas14a1.

FIG. 15, Panels A-D depict plasmid depletion by Cas14a1 and SpCas9. FIG. 15, Panel A depicts a diagram outlining a PAM discovery experiment. *E. coli* expressing the CRISPR system of interest was challenged with a plasmid containing a randomized PAM sequence flanking the target. The surviving (transformed) cells were harvested and sequenced along with a control harboring an empty vector. The depleted sequences were then sequenced and PAMs depleted more than the PAM Depletion Value Threshold (PDVT) were used to generate a Weblogo. FIG. 15, Panels B-D depict PAM sequences depleted by heterologously expressed Cas14a1 transformed with a target plasmid containing a randomized PAM sequence 5' (FIG. 15, Panel B) or 3' (FIG. 15, Panel C) of the target. "No sequences" indicated that no sequences were found to be depleted at or above the given PDVT.

Example 4

Figure 16A:
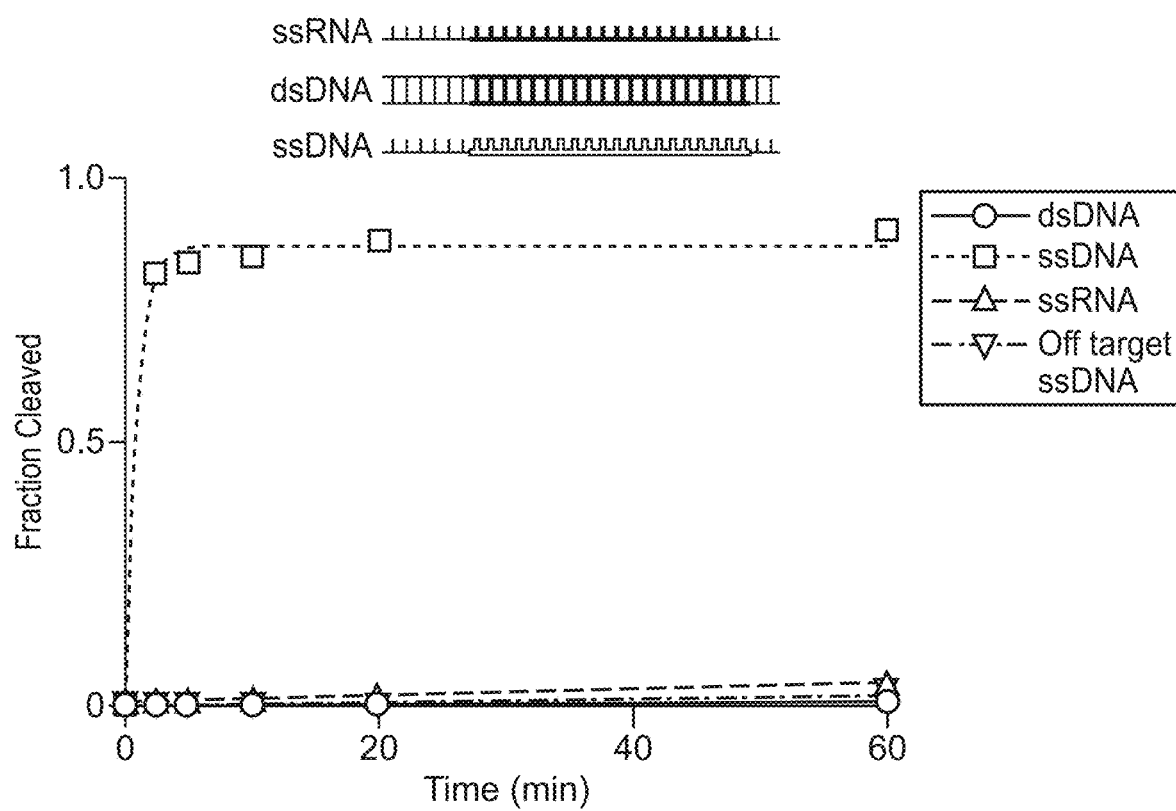
FIG. 16, Panels A-D depict CRISPR-Cas14a is an RNA-guided DNA-endonuclease.
Figure 16D:
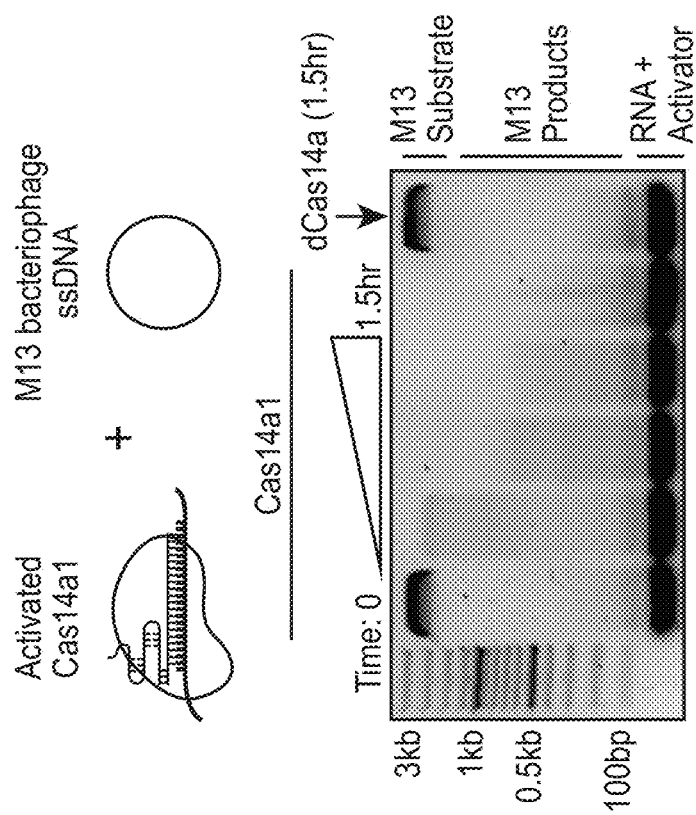
Figure 16C:
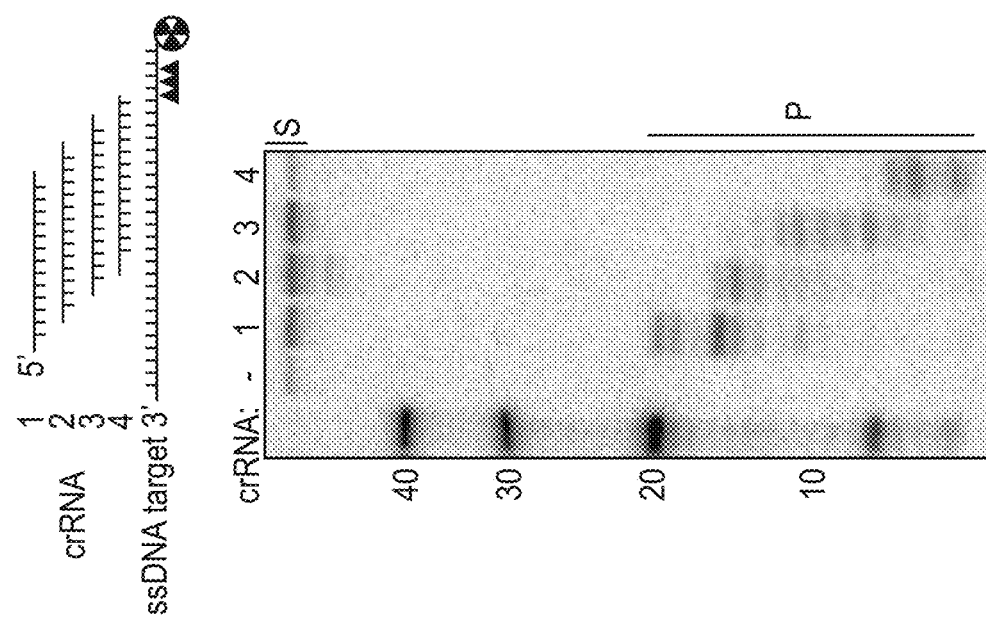
Figure 17B:
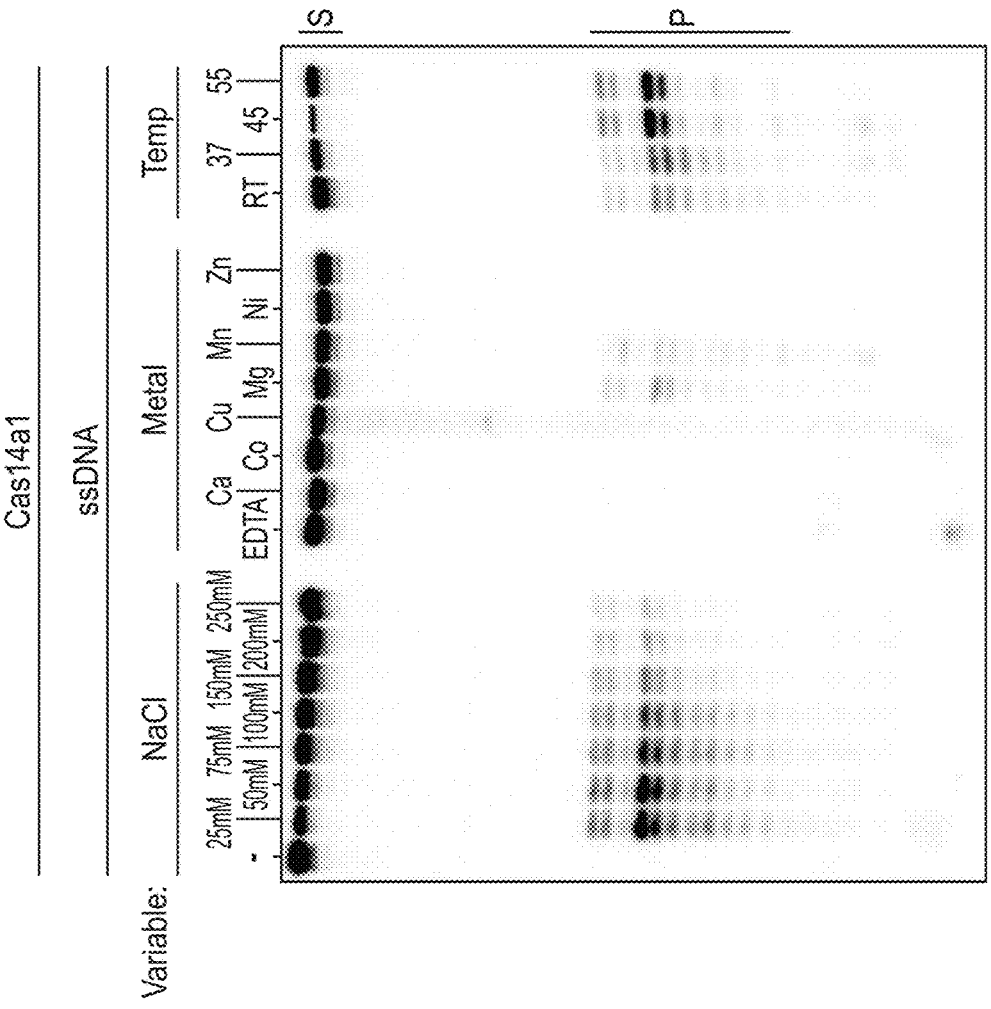
FIG. 17, Panels A-E depict degradation of ssDNA by Cas14a1.
Figure 17A:
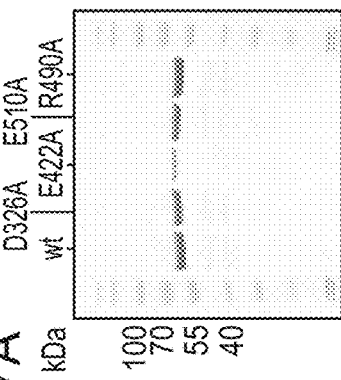
Figure 17C:
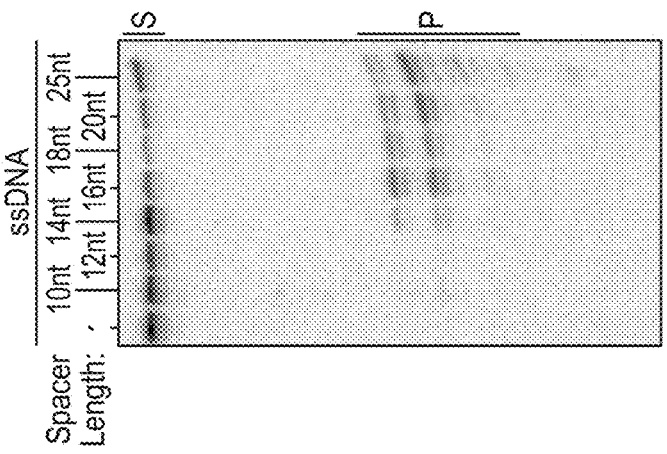
Figure 17D:
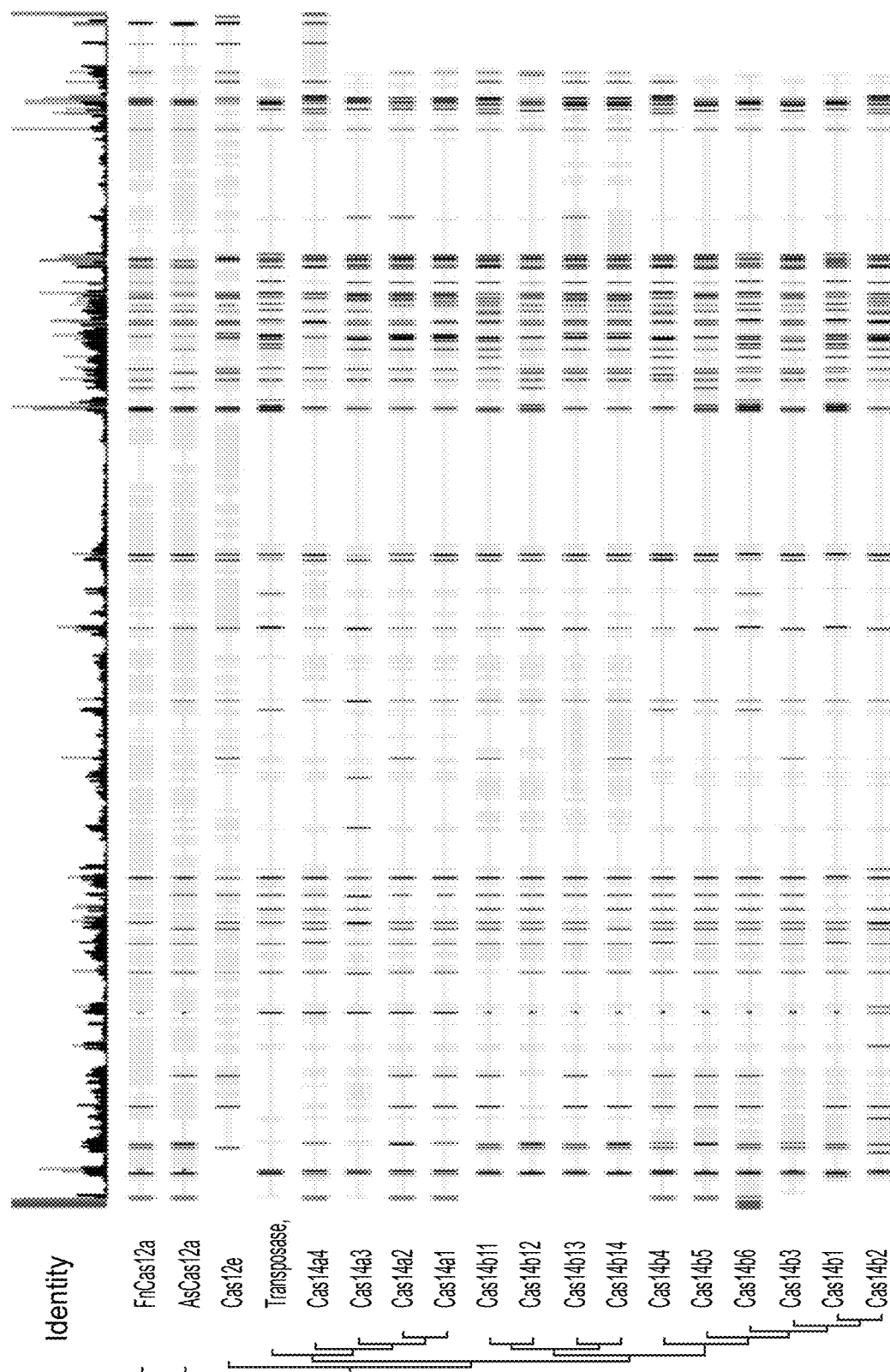
Figure 17E:
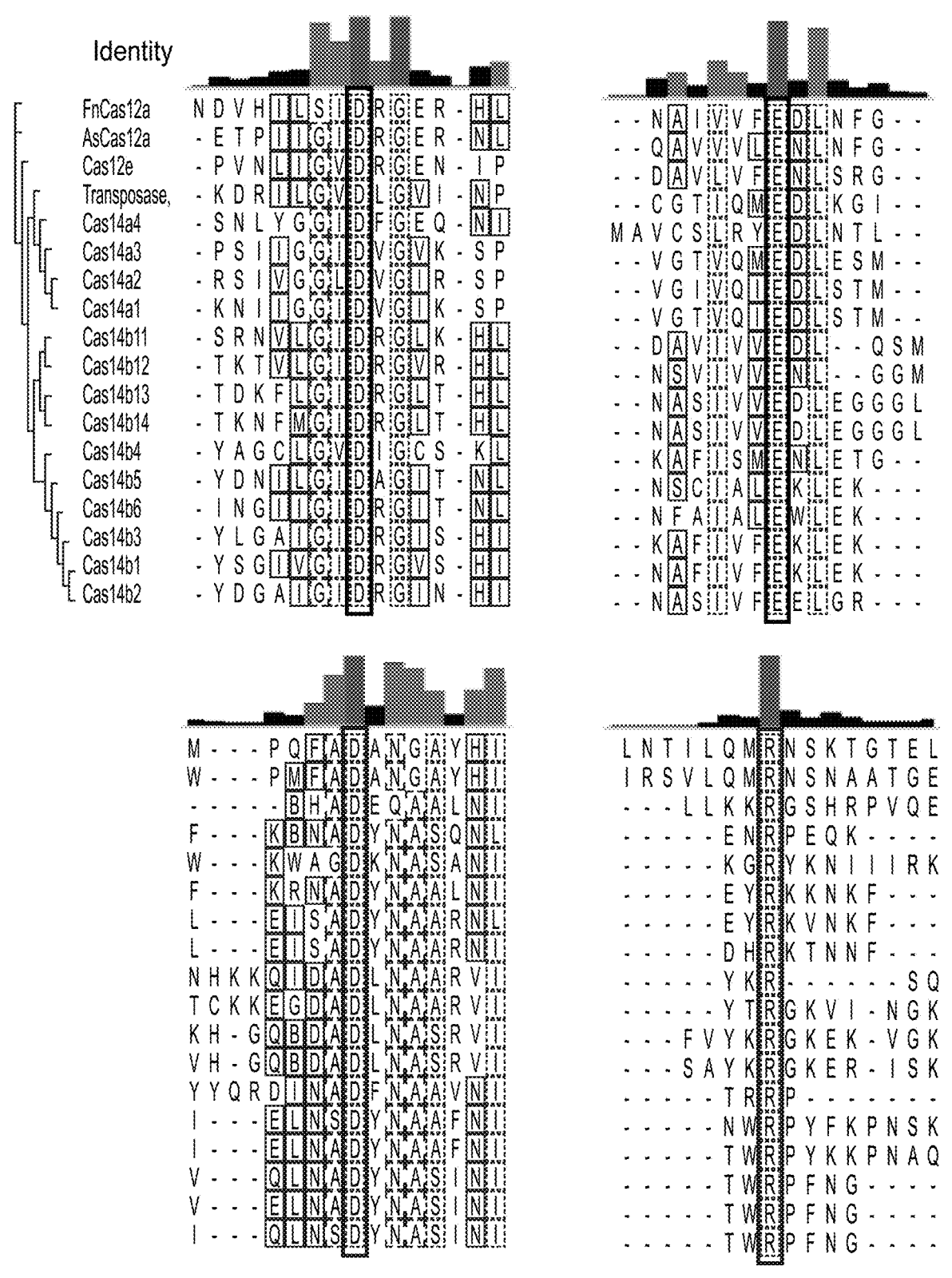
Figure 18:
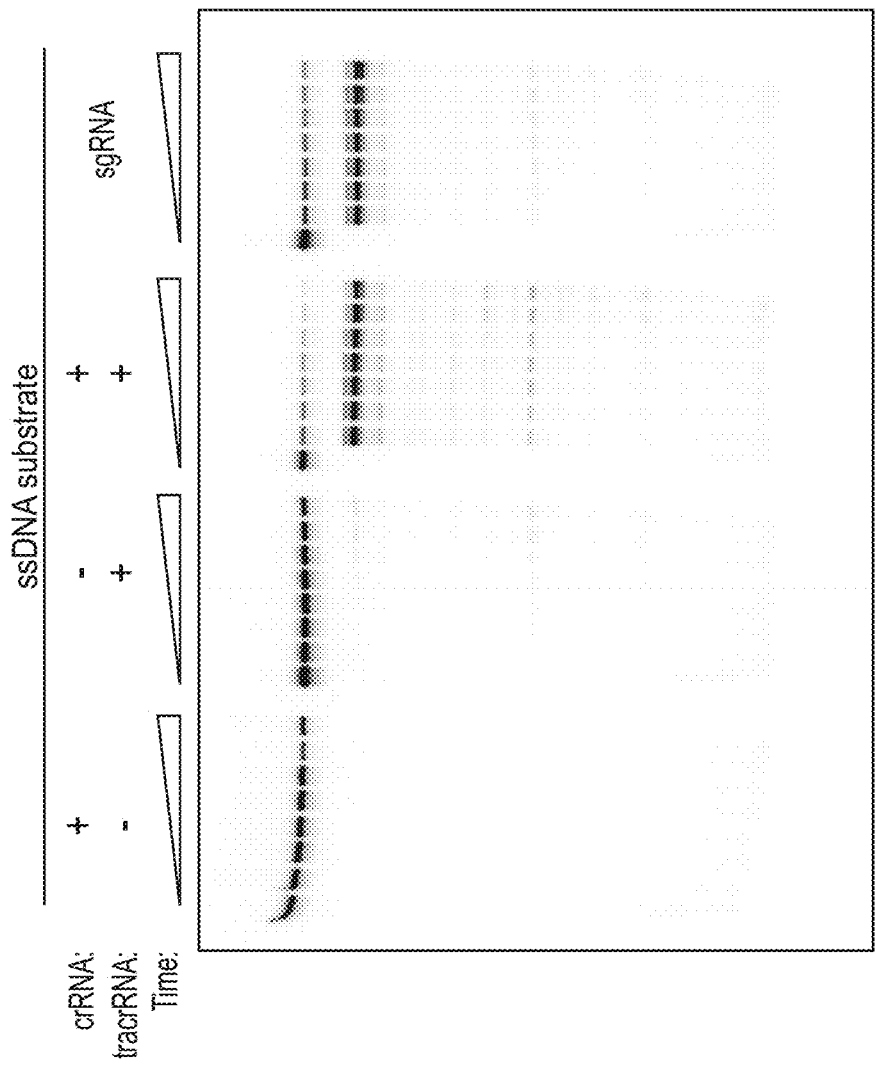
FIG. 18 depicts kinetics of Cas14a1 cleavage of ssDNA with various guide RNA components.
Figure 17F:
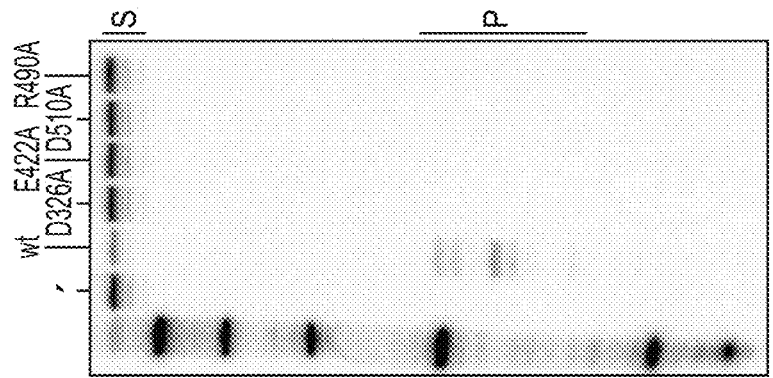
Figure 19E:
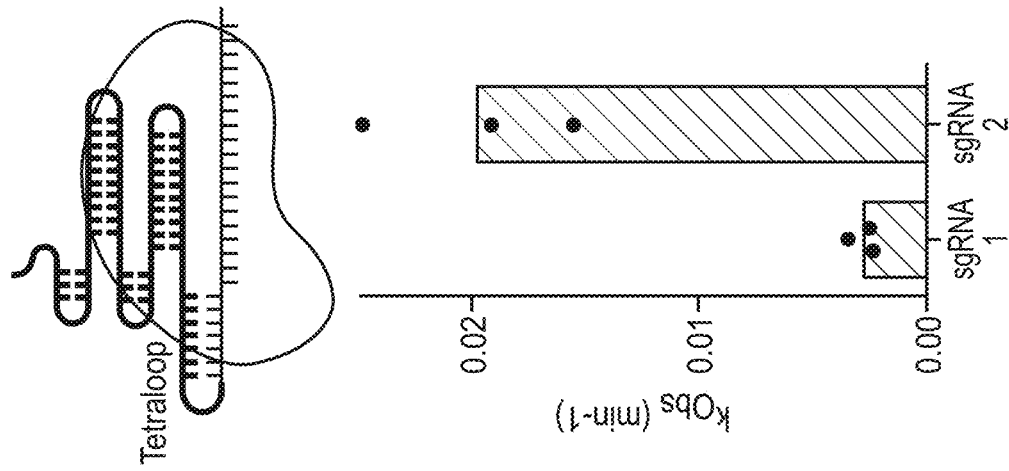
FIG. 19, Panels A-F depict optimization of Cas14a1 guide RNA components.
Figure 19D:
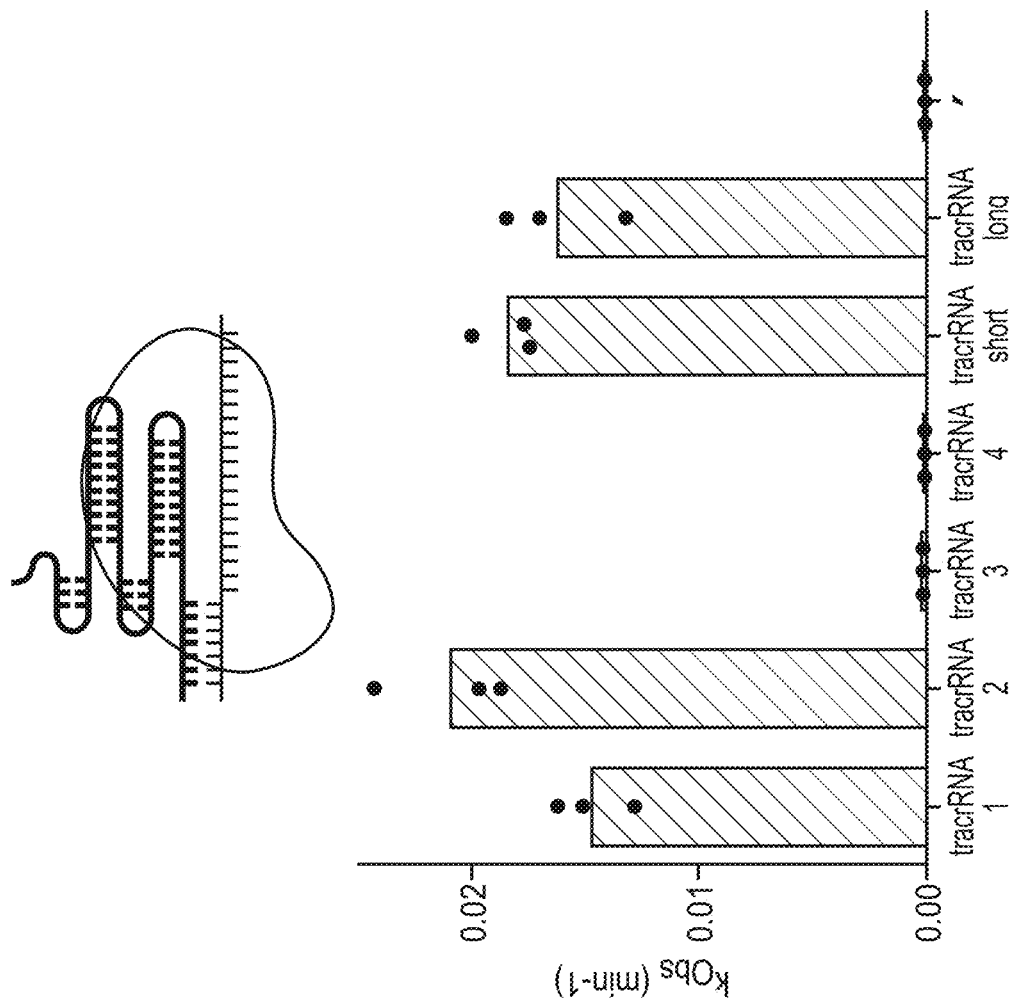
Figure 20B:
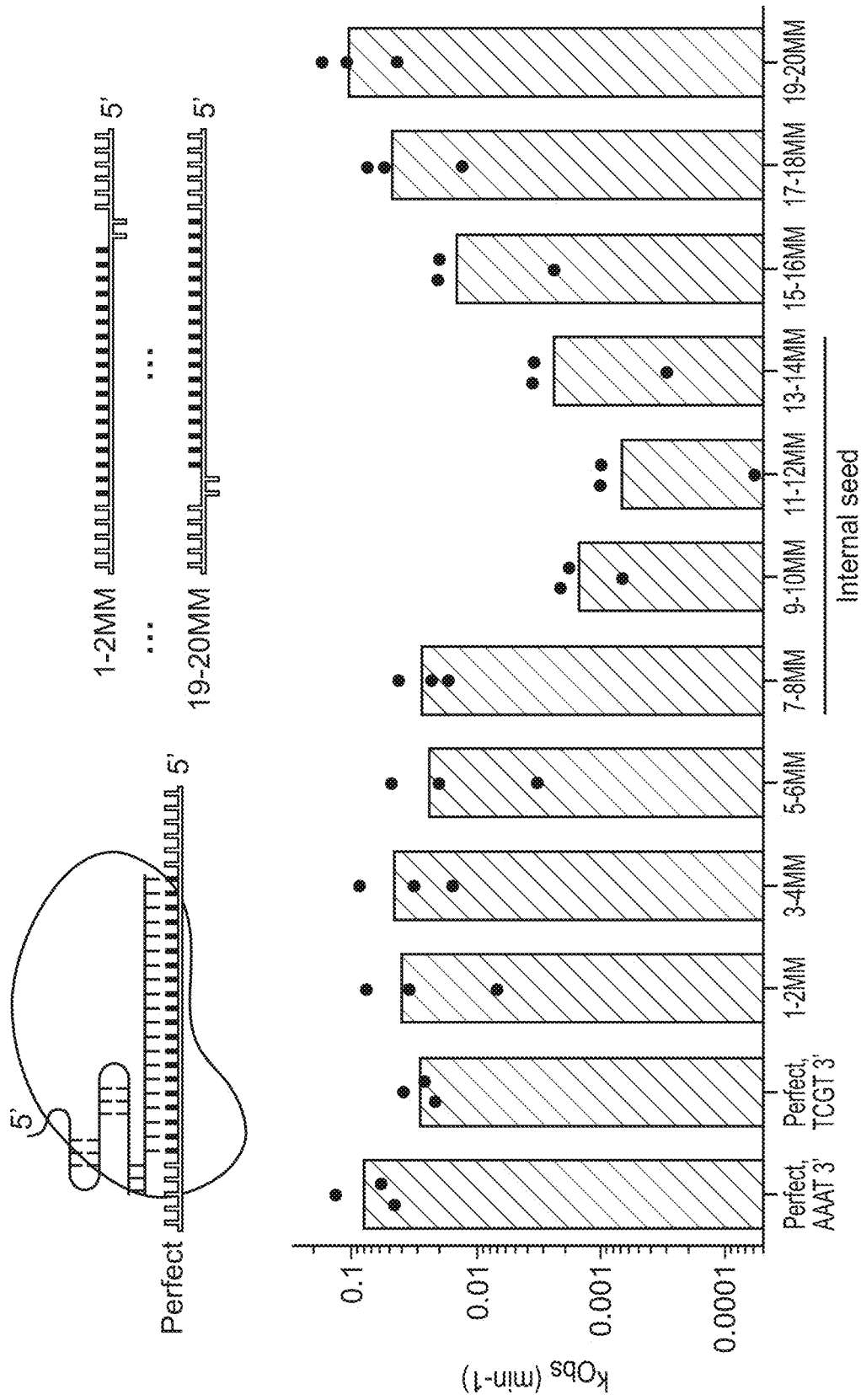
Figure 20C:
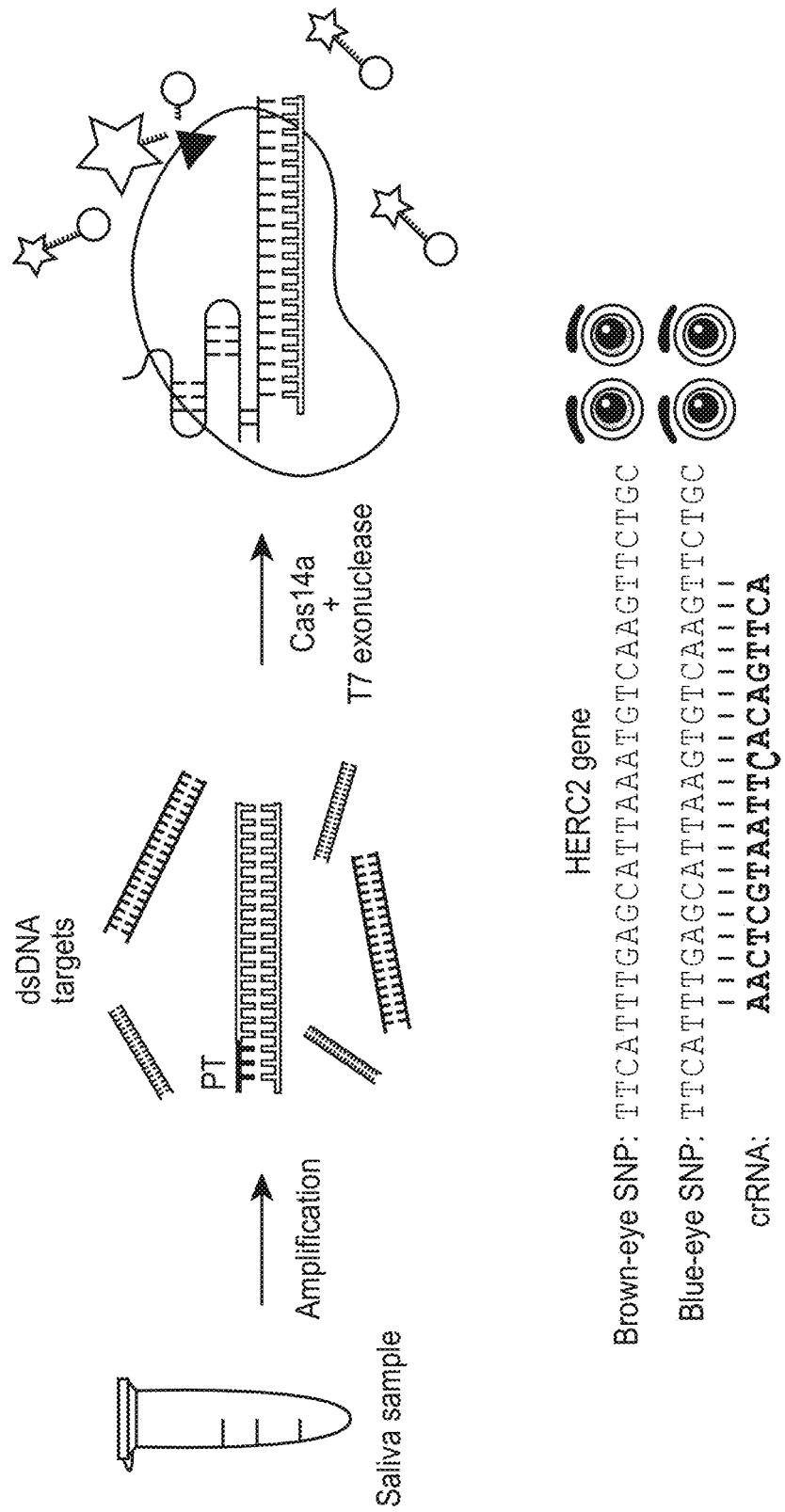
Figure 20E:
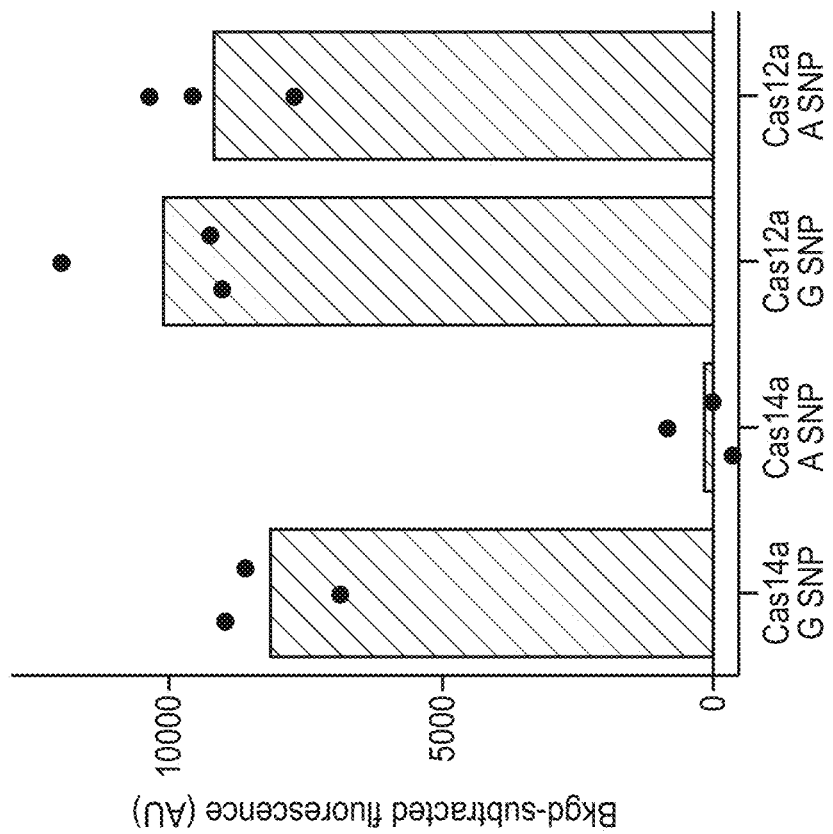
Figure 20D:
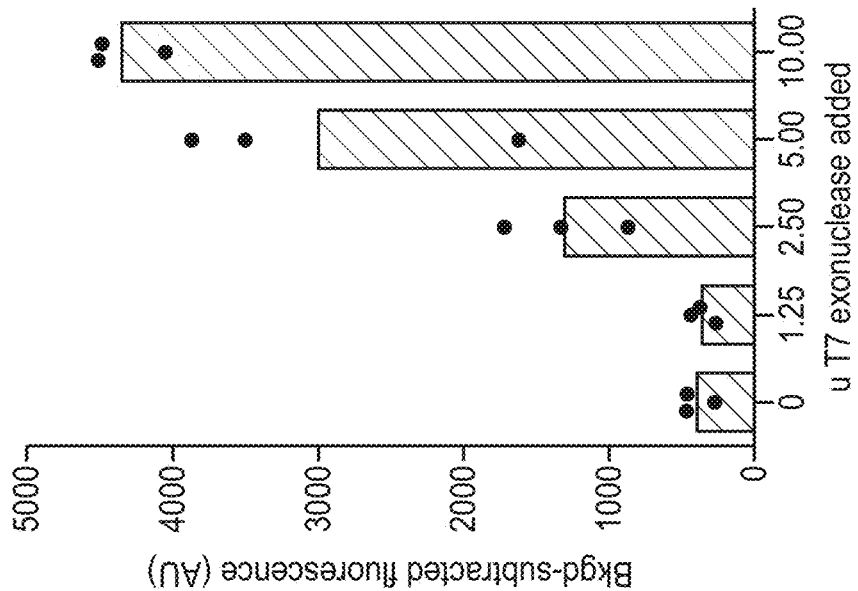

It was tested whether purified Cas14a-tracrRNA-crRNA complexes were capable of RNA-guided nucleic acid cleavage in vitro. All currently reconstituted DNA-targeting class 2 interference complexes were able to recognize both dsDNA and ssDNA substrates. Purified Cas14a-tracrRNA-crRNA complexes were incubated with radiolabeled target oligonucleotides (ssDNA, dsDNA, and ssRNA) bearing 20-nucleotide sequence complementary to the crRNA guide sequence, or a non-complementary ssDNA, and these substrates were analyzed for Cas14a-mediated cleavage. Only in the presence of a complementary ssDNA substrate was any cleavage product detected (FIG. 16, Panel A and FIG. 17, Panels A-C), and cleavage was dependent on the presence of both tracrRNA and crRNA, which could also be combined into a single-guide RNA (sgRNA) (FIG. 16, Panel B and FIG. 18). The lack of detectable dsDNA cleavage suggested that Cas14a targeted ssDNA selectively, although it was possible that some other factor or sequence requirement could enable dsDNA recognition in the native host. Mutation of the conserved active site residues in the Cas14a RuvC domain eliminated cleavage activity (FIG. 17, Panel A), implicating RuvC as the domain responsible for DNA cutting. Moreover, Cas14a DNA cleavage was sensitive to truncation of the RNA components to lengths shorter than the naturally produced sequences (FIG. 16, Panel B and FIG. 19, Panels A-D). These results established Cas14a as the smallest class 2 CRISPR effector demonstrated to conduct programmable RNA-guided DNA cleavage.

It was tested whether Cas14a required a PAM for ssDNA cleavage in vitro by tiling Cas14a guides across a ssDNA substrate (FIG. 16, Panel C). Despite sequence variation adjacent to the targets of these different guides, cleavage was observed for all four sequences. The cleavage sites occurred beyond the guide-complementary region of the ssDNA and shifted in response to guide binding position (FIG. 16, Panel C). These data demonstrated Cas14a was an ssDNA-targeting CRISPR endonuclease that did not require a PAM for activation.

Based on the observation that Cas14a cut outside of the crRNA/DNA targeting heteroduplex, it was proposed that Cas14a may possess target-activated non-specific ssDNA cleavage activity, similar to the RuvC-containing enzyme Cas12a. To test this possibility, Cas14a-tracrRNA-crRNA was incubated with a complementary activator DNA and an aliquot of M13 bacteriophage ssDNA bearing no sequence complementarity to the Cas14a crRNA or activator (FIG. 16, Panel D). The M13 ssDNA was rapidly degraded to small fragments, an activity that was eliminated by mutation of the conserved Cas14a RuvC active site, suggesting that activation of Cas14a resulted in non-specific ssDNA degradation.

To investigate the specificity of target-dependent non-specific DNA cutting activity by Cas14a, a fluorophore-quencher (FQ) assay was adapted in which cleavage of dye-labeled ssDNA generates a fluorescent signal (FIG. 20, Panel A). When Cas14a was incubated with various guide RNA-target ssDNA pairs, a fluorescent signal was observed only in the presence of the cognate target and showed strong preference for longer FQ-containing substrates (FIG. 19, Panel F and FIG. 20, Panel A). Cas14a mismatch tolerance was tested by tiling 2-nt mismatches across the targeted region in various ssDNA substrates. Mismatches near the middle of the ssDNA target strongly inhibited Cas14a activity, revealing an internal seed sequence that was distinct from the PAM-proximal seed region observed for dsDNA-targeting CRISPR-Cas systems (FIG. 20, Panel B and FIG. 21, Panels A-D). Moreover, DNA substrates containing strong secondary structure resulted in reduced activation of Cas14a (FIG. 21, Panel E). Truncation of ssDNA substrates also resulted in reduced or undetectable trans cleavage (FIG. 21, Panel F). These results suggested a mechanism of fidelity distinct from dsDNA-targeting class 2 CRISPR systems, possibly utilizing a preordered region of the crRNA to gate cleavage activity similarly to the RNA-targeting Cas13a enzymes.

Further investigation of compact Type V systems in metagenomic data revealed a large diversity of systems that, like Cas14a-c, include a gene encoding a short RuvC-containing protein adjacent to acquisition-associated cas genes and a CRISPR array. Twenty (20) additional such systems were found that cluster into five main families (Cas14d-h). These families seemed to have evolved from independent domestication events of TnpB, the transposase-associated protein implicated as the evolutionary parent of type V CRISPR effectors. Excluding cas14g, which was related to cas12b, the cas14-like genes formed separate clades on the type V effector phylogeny (FIG. 22, Panels A-B), and their cas1 genes had different origins (FIG. 10, Panel A). Altogether 38 CRISPR-Cas14 systems belonging to eight families (Cas14a-h) were identified and eight additional systems that could not be clustered with the analysis (termed Cas14u, Table 3).

The small size of the Cas14 proteins described herein and their resemblance to type V effector proteins suggested that RNA-guided ssDNA cleavage may have existed as an ancestral class 2 CRISPR system. In this scenario, a small, domesticated TnpB-like ssDNA interference complex may have gained additional domains over time, gradually improving dsDNA recognition and cleavage. Smaller Cas9 orthologs exhibited weaker dsDNA-targeting activity than their larger counterparts but retained the ability to robustly cleave ssDNA. Aside from the evolutionary implications, the ability of Cas14 to specifically target ssDNA suggested a role in defense against ssDNA viruses or mobile genetic elements (MGEs) that propagated through ssDNA intermediates. Without intending to be bound by any particular theory, an ssDNA-targeting CRISPR system may be particularly advantageous in certain marine environments where ssDNA viruses comprised the vast majority of viral abundance.

FIG. 16, Panels A-D depict CRISPR-Cas14a as an RNA-guided DNA-endonuclease. FIG. 16, Panel A depicts cleavage kinetics of Cas14a1 targeting ssDNA, dsDNA, ssRNA and off-target ssDNA. FIG. 16, Panel B depicts a diagram of Cas14a RNP bound to target ssDNA and Cas14a1 cleavage kinetics of radiolabeled ssDNA in the presence of various RNA components. FIG. 16, Panel C depicts tiling of a ssDNA substrate by Cas14a1 guide sequences. FIG. 16, Panel D depicts cleavage of the ssDNA viral M13 genome with activated Cas14a1.

FIG. 17, Panels A-E depict degradation of ssDNA by Cas14a1. FIG. 17, Panel A depicts SDS-PAGE of purified Cas14a1 and Cas14a1 point mutants. FIG. 17, Panel B depicts optimization of salt, cation and temperature for Cas14a1 cleavage of ssDNA targets. FIG. 17, Panel C depicts radiolabled cleavage of ssDNA by Cas14a1 with spacer sequences of various lengths. FIG. 17, Panel D depicts alignment of Cas14 with previously studied Cas12 proteins to identify RuvC active site residues and FIG. 17, Panel E depicts cleavage of ssDNA by purified Cas14a1 RuvC point mutants.

FIG. 18 depicts the kinetics of Cas14a1 cleavage of ssDNA with various guide RNA components.

FIG. 19, Panels A-F depict optimization of Cas14a1 guide RNA components. FIG. 19, Panel A depicts a diagram of Cas14a1 targeting ssDNA. Impact on Cas14a1 cleavage of an FQ ssDNA substrate by varying the spacer length (FIG. 19, Panel B), repeat length (FIG. 19, Panel C), tracrRNA (FIG. 19, Panel D), and fusing the crRNA and tracrRNA together (FIG. 19, Panel E). FIG. 19, Panel F depicts a heat map showing the background subtracted fluorescence resulting from cleavage of an ssDNA FQ reporter in the presence of various guide and target combinations.

FIG. 20, Panels A-E depict high fidelity ssDNA SNP detection by CRISPR-Cas14a. FIG. 20, Panel A depicts a fluorescent-quencher (FQ) assay for detection of ssDNA by Cas14a1 and the cleavage kinetics for various length FQ substrates. FIG. 20, Panel B depicts cleavage kinetics for Cas14a1 with mismatches tiled across the substrate (individual points represent replicate measurements). FIG. 20, panel C depicts a diagram of Cas14-DETECTR strategy and HERC2 eye color SNP. FIG. 20, panel D depicts titration of T7 exonuclease and impact on Cas14a-DETECTR. FIG. 20, panel E, depicts SNP detection using Cas14a-DETECTR with a blue-eye targeting guide for a blue-eyed and brown-eyed saliva sample compared to ssDNA detection using Cas12a.

FIG. 21, Panels A-F depict the impact of various activators on Cas14a1 cleavage rate FIG. 21, Panel A depicts a diagram of Cas14a1 targeting of ssDNA with position of mismatches used in panels A-D and raw rates for representative replicates of mismatch (MM) position for Target 1. Cleavage rates for Cas14a targeting substrates with mutations tiled across three different substrates (FIG. 21, Panels B-D). FIG. 21, Panel E depicts trans cleavage rates for substrates with increasing amounts of secondary structure. FIG. 21, Panel F depicts trans leavage rates with truncated substrates. Points represent individual measurements.

Figure 22A:
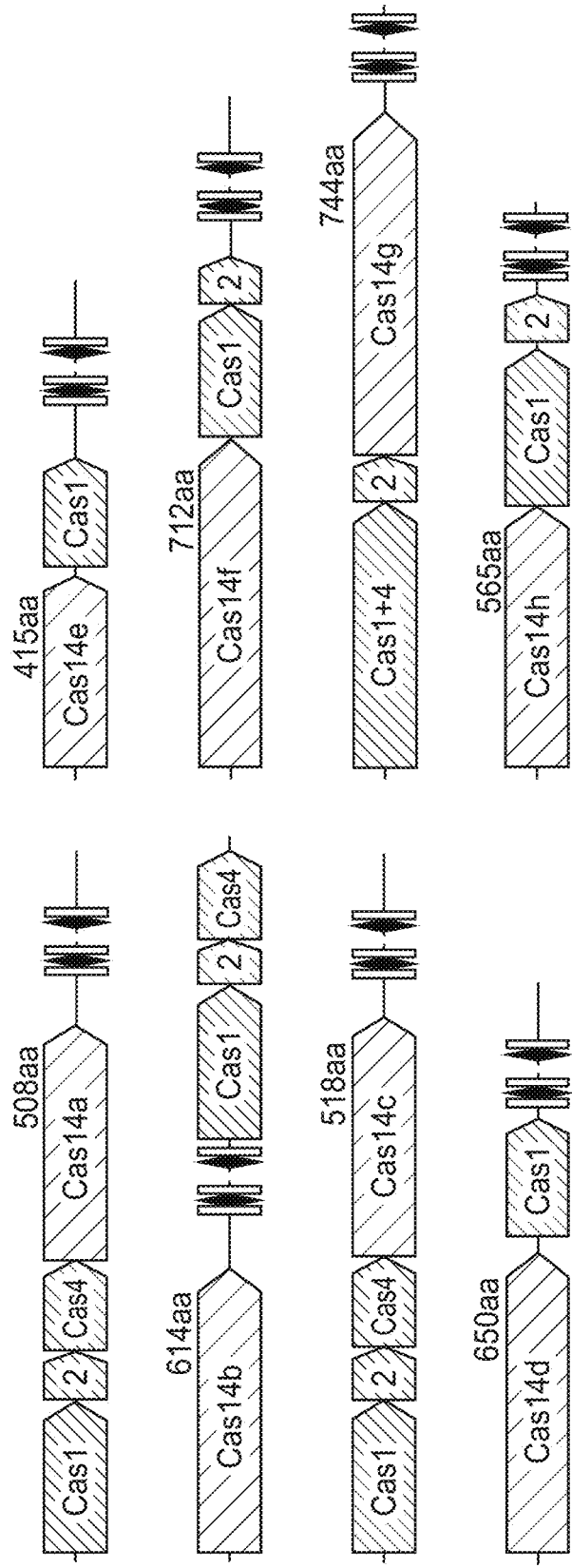
FIG. 22, Panels A-B depict diversity of CRISPR-Cas14 systems.

FIG. 22, Panels A-B depict diversity of CRISPR-Cas14 systems. FIG. 22, Panel A depicts representative locus architecture for indicated Cas14 systems. Protein lengths are drawn to scale. FIG. 22, Panel B depicts a maximum likelihood tree for Type V effectors including all eight identified subtypes of Cas14.

Figure 23A:
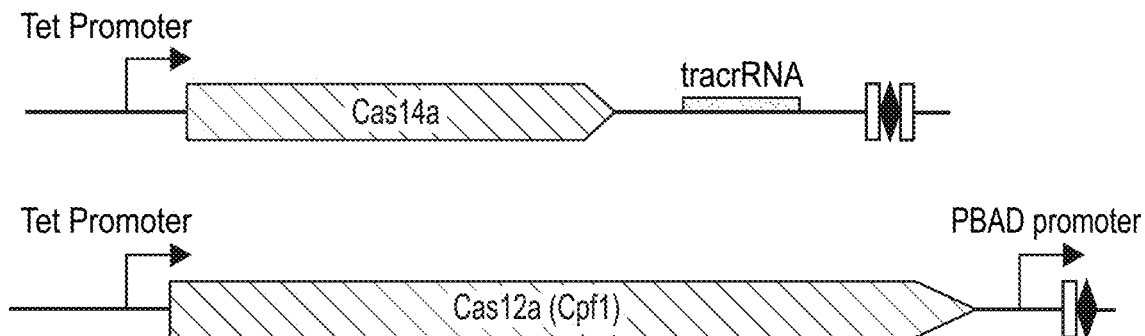
FIG. 23, Panels A-C depict a test of Cas14a1 mediated interference in a heterologous host. Diagram of Cas14a1 and LbCas12a constructs to test interference in *E. coli*.
Figure 23B:
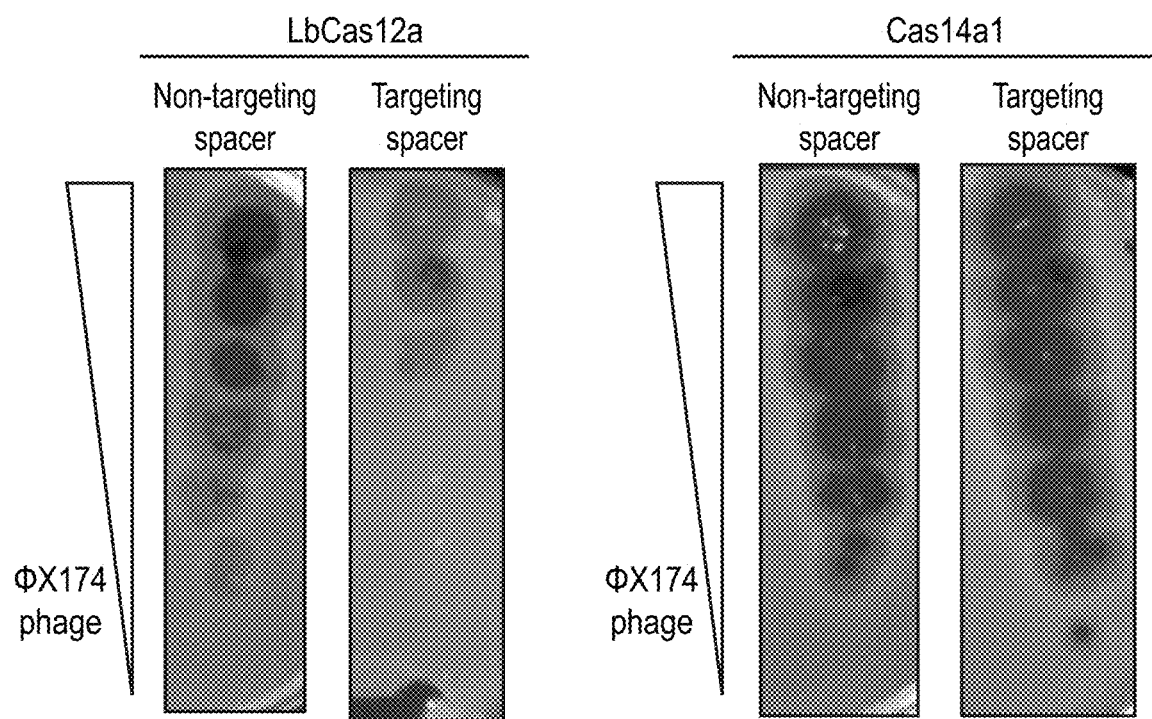
Figure 23C:
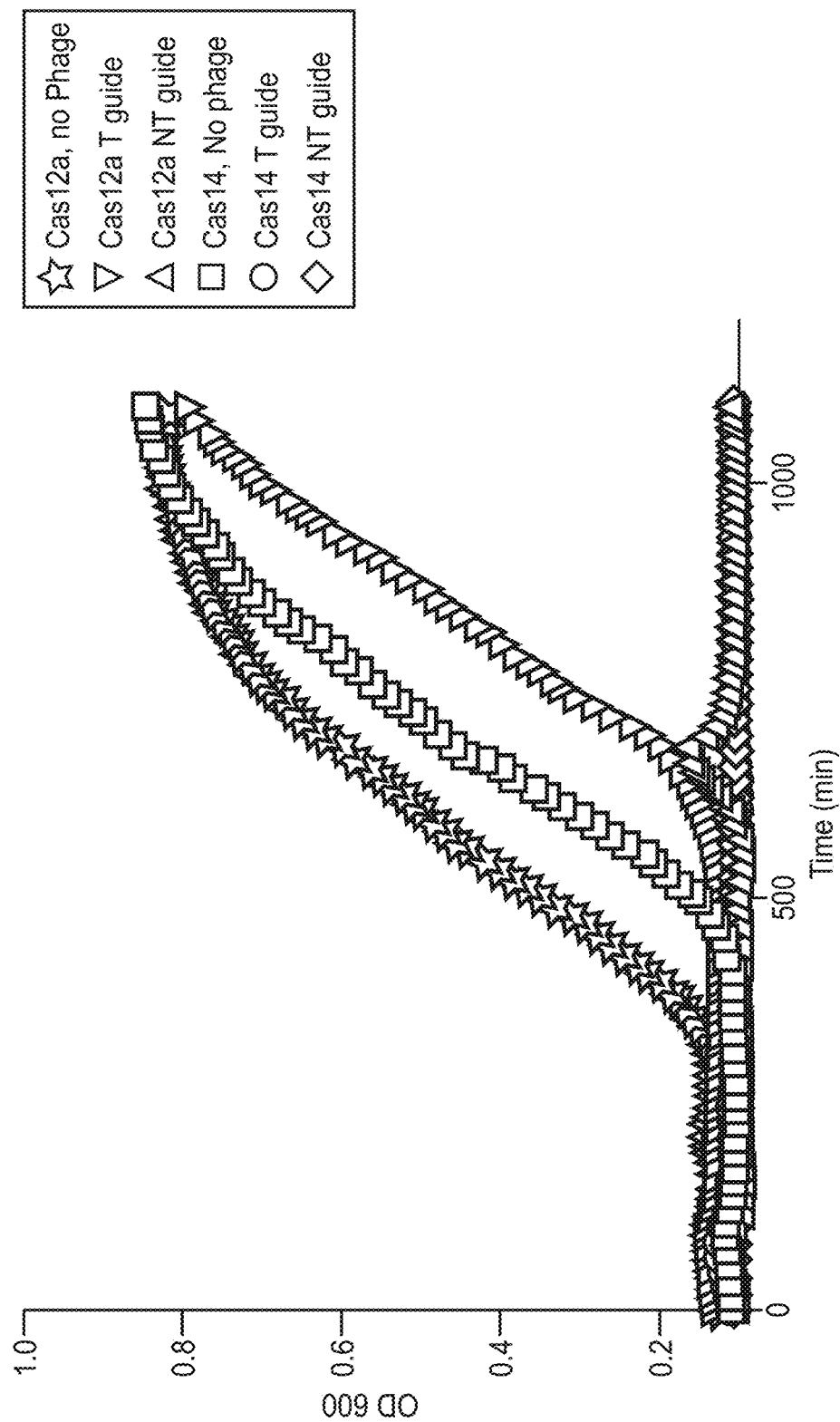
Figure 25A:
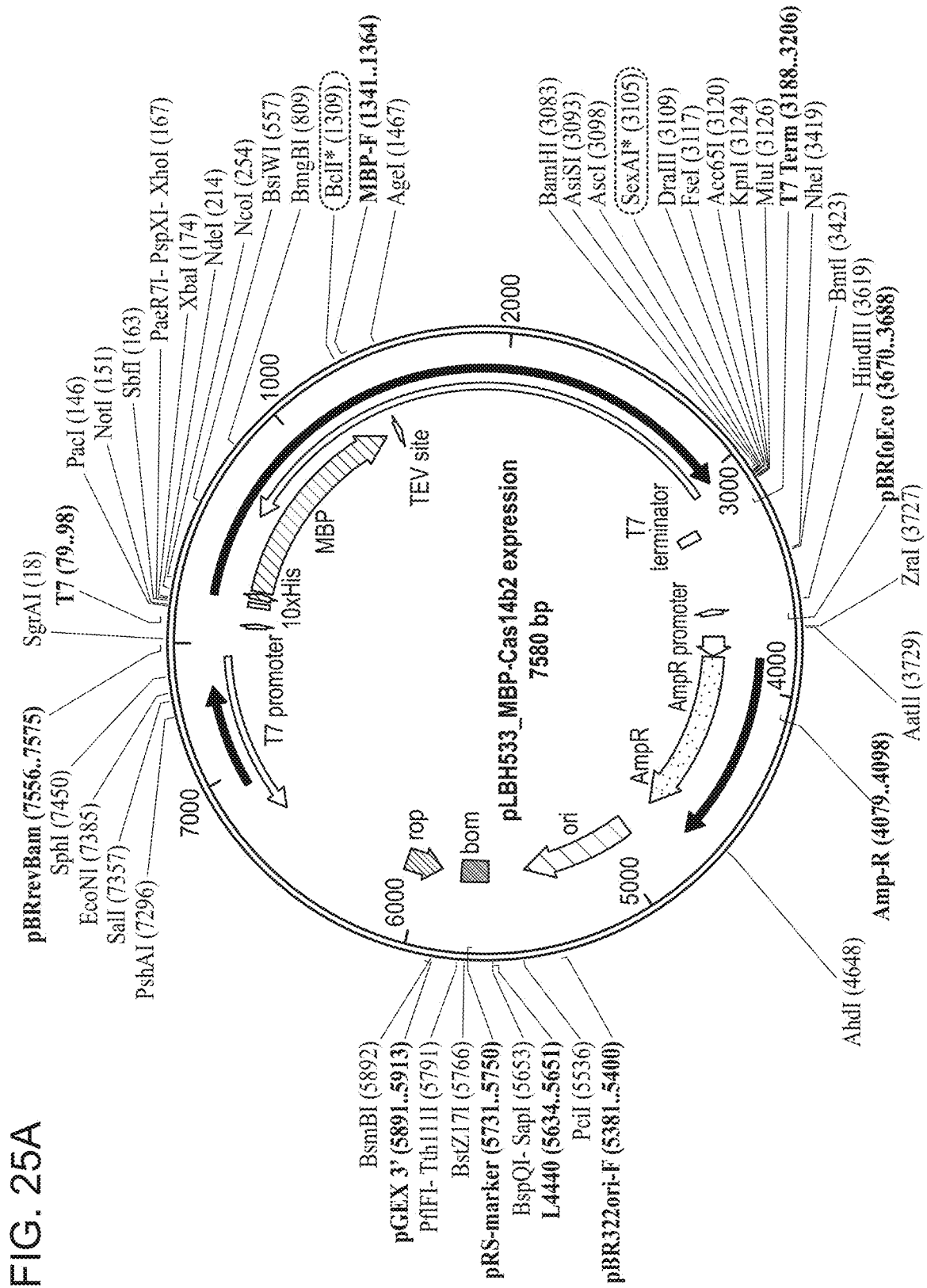
FIG. 25, Panels A-E depict a sequence map of each of the plasmids disclosed in FIG. 24.
Figure 25B:
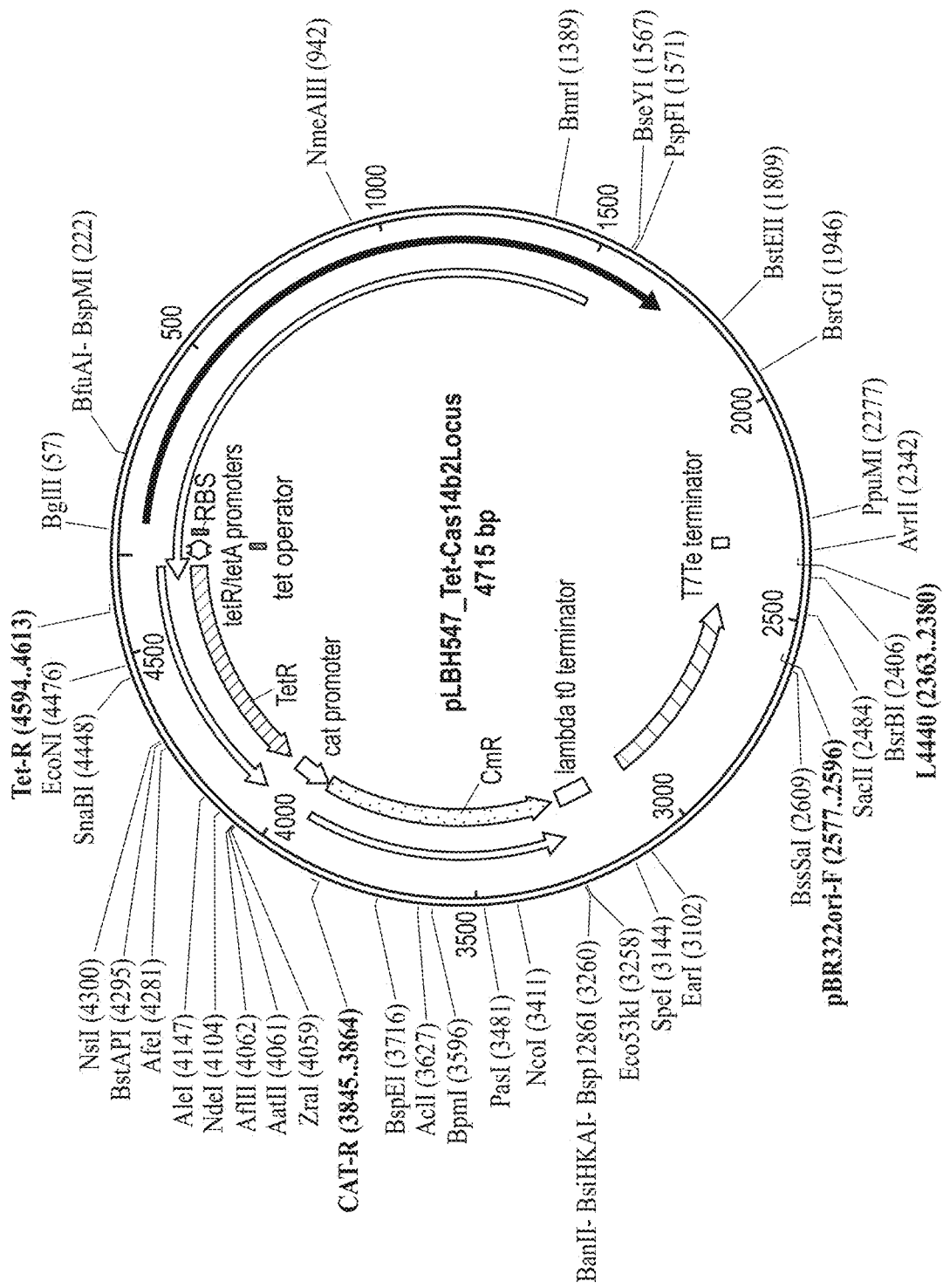
Figure 25C:
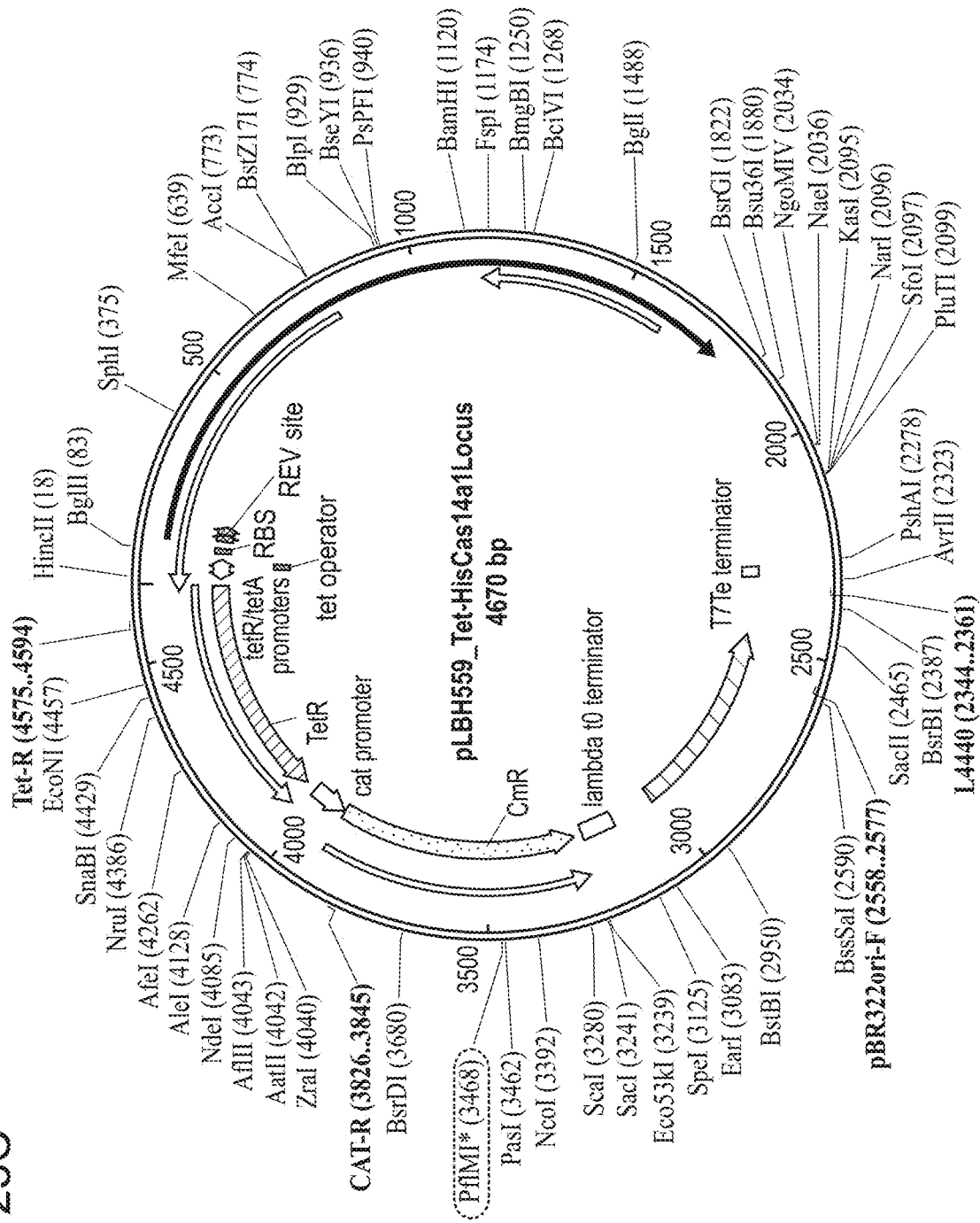
Figure 25D:
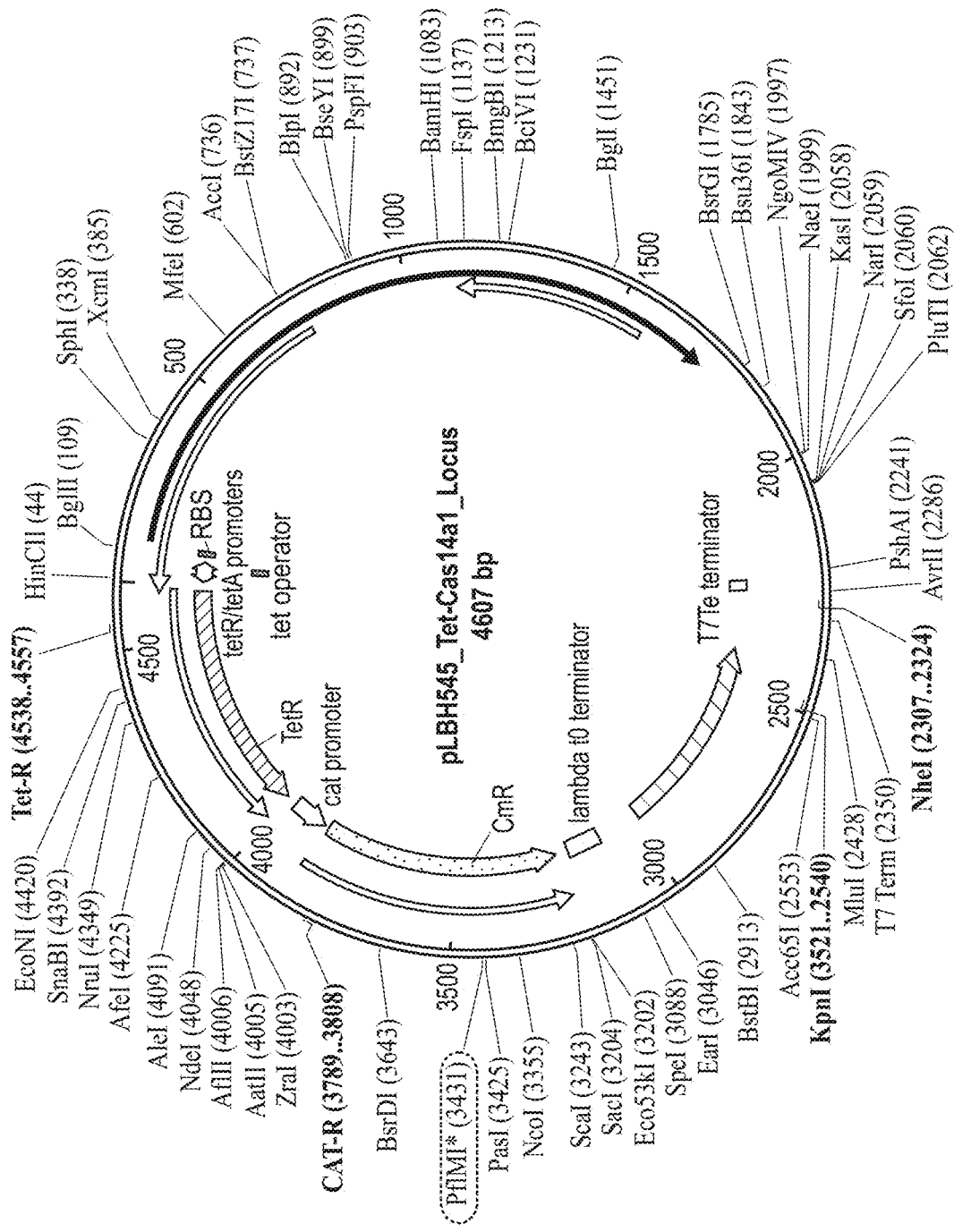
Figure 25E:
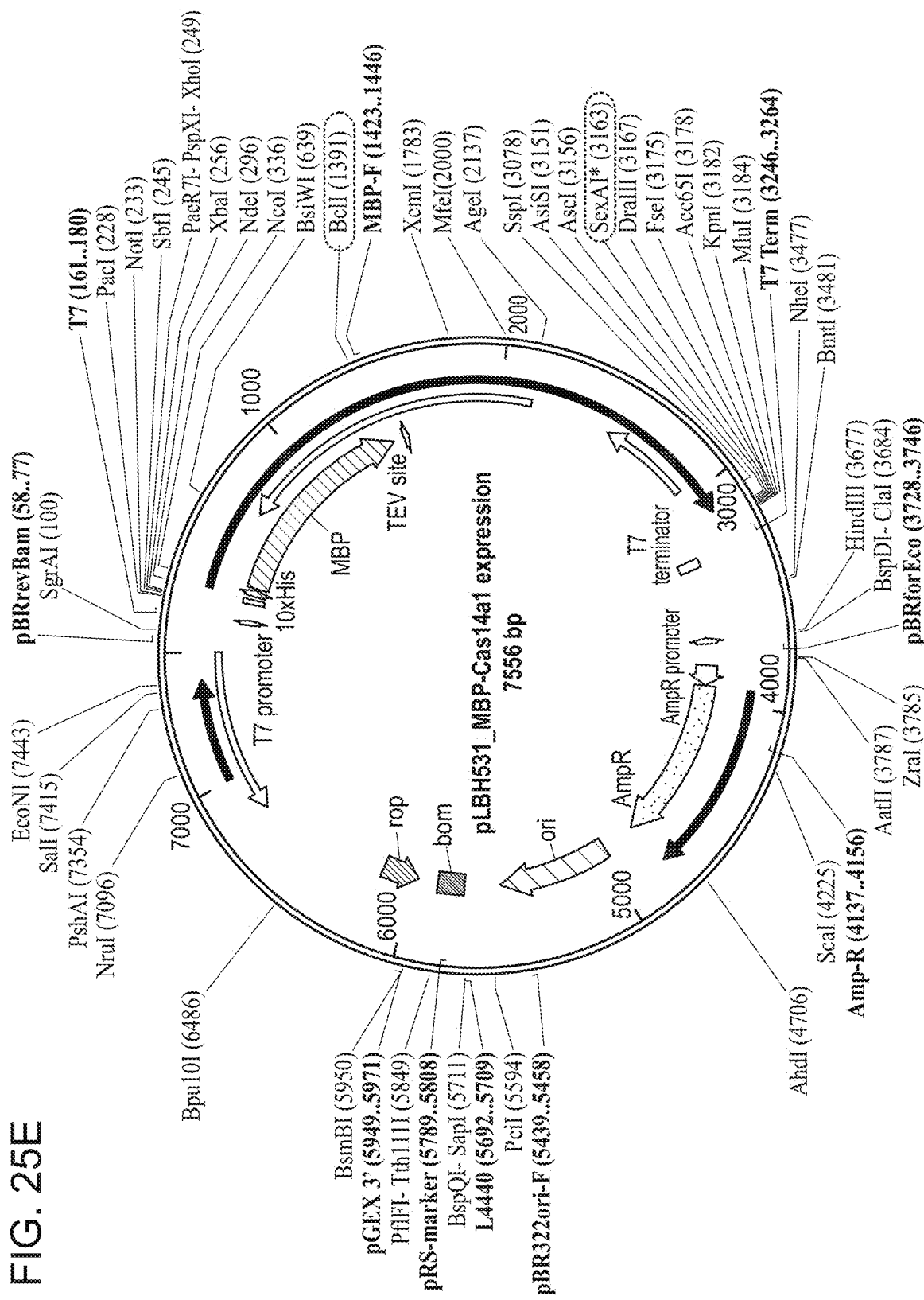

FIG. 23, Panels A-C depict a test of Cas14a1 mediated interference in a heterologous host. Diagram of Cas14a1 and LbCas12a constructs to test interference in *E. coli*. (B) Plaques of ΦX174 spotted on *E. coli* revealing Cas12a—but not Cas14a1-mediated interference. Each spot represents a 10-fold dilution of the ΦX174 stock. (C) Growth curves of *E. coli* expressing Cas14a1 or LbCas12a infected with ΦX174 (T, targeting; NT, non-targeting). FIG. 19, Panel F shows a heat map showing the background-subtracted fluorescence resulting from cleavage of a ssDNA FQ reporter in the presence of various guide and target combinations after a 30-minute incubation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. R. Barrangou et al., CRISPR provides acquired resistance against viruses in prokaryotes. *Science*. 315, 1709-12 (2007).
2. S. A. Jackson et al., CRISPR-Cas: Adapting to change. *Science*. 356 (6333), pp. 1-9 (2017).
3. S. Shmakov et al., Diversity and evolution of class 2 CRISPR-Cas systems. *Nat. Rev. Microbiol*. 15, 169-182 (2017).
4. J. S. Chen, J. A. Doudna, The chemistry of Cas9 and its CRISPR colleagues. *Nat. Rev. Chem*. 1, 0078 (2017).
5. C. T. Brown et al., Unusual biology across a group comprising more than 15% of domain Bacteria. *Nature*. 523, 208-211 (2015).
6. K. Anantharaman et al., Thousands of microbial genomes shed light on interconnected biogeochemical processes in an aquifer system. *Nat. Commun*. 7, 13219 (2016).
7. V. M. Markowitz et al., IMG/M 4 version of the integrated metagenome comparative analysis system. *Nucleic Acids Res*. 42, 568-573 (2014).
8. V. M. Markowitz et al., IMG: The integrated microbial genomes database and comparative analysis system. *Nucleic Acids Res*. 40, 115-122 (2012).
9. A. J. Probst et al., Genomic resolution of a cold subsurface aquifer community provides metabolic insights for novel microbes adapted to high $CO_2$ concentrations. *Environ. Microbiol*. 19, 459-474 (2017).
10. I. Yosef, M. G. Goren, U. Qimron, Proteins and DNA elements essential for the CRISPR adaptation process in *Escherichia coli*. *Nucleic Acids Res*. 40, 5569-5576 (2012).
11. J. K. Nuñez, A. S. Y. Lee, A. Engelman, J. a. Doudna, Integrase-mediated spacer acquisition during CRISPR-Cas adaptive immunity. *Nature*. 519, 193-198 (2015).
12. S. Shmakov et al., Discovery and Functional Characterization of Diverse Class 2 CRISPR-Cas Systems. *Mol. Cell*. 60, 385-397 (2015).
13. D. Burstein et al., New CRISPR-Cas systems from uncultivated microbes. *Nature*. 542, 237-241 (2017).
14. C. Rinke et al., Insights into the phylogeny and coding potential of microbial dark matter. *Nature*. 499, 431-437 (2013).
15. C. J. Castelle et al., Genomic expansion of domain archaea highlights roles for organisms from new phyla in anaerobic carbon cycling. *Curr. Biol*. 25, 690-701 (2015).
16. E. Deltcheva et al., CRISPR RNA maturation by trans-encoded small RNA and host factor RNase III. *Nature*. 471, 602-607 (2011).
17. K. E. Savell, J. J. Day, Applications of CRISPR/CAS9 in the mammalian central nervous system. *Yale J. Biol. Med*. 90 (2017), pp. 567-581.
18. F. J. M. Mojica, C. Díez-Villaseñor, J. Garcia-Martinez, C. Almendros, Short motif sequences determine the targets of the prokaryotic CRISPR defence system. *Microbiology*. 155, 733-740 (2009).
19. Y. Zhang, R. Raj an, H. S. Seifert, A. Mondragon, E. J. Sontheimer, DNase H Activity of *Neisseria meningitidis* Cas9. *Mol. Cell*. 60, 242-255 (2015).
20. E. Ma, L. B. Harrington, M. R. O'Connell, K. Zhou, J. A. Doudna, Single-Stranded DNA Cleavage by Divergent CRISPR-Cas9 Enzymes. *Mol. Cell*. 60, 398-407 (2015).
21. J. S. Chen et al., CRISPR-Cas12a target binding unleashes indiscriminate single-stranded DNase activity. *Science*. 360, 436-439 (2018).
22. B. Zetsche et al., Cpf1 Is a Single RNA-Guided Endonuclease of a Class 2 CRISPR-Cas System. *Cell*. 163, 759-771 (2015).
23. A. East-Seletsky et al., Two distinct RNase activities of CRISPR-C2c2 enable guide-RNA processing and RNA detection. *Nature*. 538, 270-273 (2016).
24. L. Liu et al., The Molecular Architecture for RNA-Guided RNA Cleavage by Cas13a. *Cell*. 170, 714-726.e10 (2017).
25. O. O. Abudayyeh et al., C2c2 is a single-component programmable RNA-guided RNA-targeting CRISPR effector. *Science* (80-.). 353, 1-9 (2016).
26. G. J. Knott et al., Guide-bound structures of an RNA-targeting A-cleaving CRISPR-Cas13a enzyme. *Nat. Struct. Mol. Biol*. 24, 825-833 (2017).
27. S. Y. Li et al., CRISPR-Cas12a has both cis- and trans-cleavage activities on single-stranded DNA. *Cell Res*. 28, 491-493 (2018).
28. H. Eiberg et al., Blue eye color in humans may be caused by a perfectly associated founder mutation in a regulatory element located within the HERC2 gene inhibiting OCA2 expression. *Hum. Genet*. 123, 177-187 (2008).
29. S. Shmakov et al., Diversity and evolution of class 2 CRISPR-Cas systems. *Nat. Rev. Microbiol*. 15, 169-182 (2017).

30. E. V Koonin, K. S. Makarova, F. Zhang, Diversity, classification and evolution of CRISPR-Cas systems. *Curr. Opin. Microbiol.* 37, 67-78 (2017).
31. K. S. Makarova et al., An updated evolutionary classification of CRISPR-Cas systems. *Nat Rev Microbiol,* 1-15 (2015).
32. O. Barabas et al., Mechanism of IS 200/IS 605 Family DNA Transposases: Activation and Transposon-Directed Target Site Selection, 208-220 (2008).
33. M. Yoshida et al., Quantitative viral community DNA analysis reveals the dominance of single-stranded DNA viruses in offshore upper bathyal sediment from Tohoku, Japan. *Front. Microbiol.* 9, 1-10 (2018).
34. C. T. Brown et al., Unusual biology across a group comprising more than 15% of domain Bacteria. *Nature.* 523, 208-211 (2015).
35. K. Anantharaman et al., Thousands of microbial genomes shed light on interconnected biogeochemical processes in an aquifer system. *Nat. Commun.* 7, 13219 (2016).
36. A. J. Probst et al., Genomic resolution of a cold subsurface aquifer community provides metabolic insights for novel microbes adapted to high $CO_2$ concentrations. *Environ. Microbiol.* 19, 459-474 (2017).
37. V. M. Markowitz et al., IMG/M 4 version of the integrated metagenome comparative analysis system. *Nucleic Acids Res.* 42, 568-573 (2014).
38. V. M. Markowitz et al., IMG: The integrated microbial genomes database and comparative analysis system. *Nucleic Acids Res.* 40, 115-122 (2012).
39. R. D. Finn, J. Clements, S. R. Eddy, HMMER web server: interactive sequence similarity searching. *Nucleic Acids Res.* 39, W29-W37 (2011).
40. D. Burstein et al., New CRISPR-Cas systems from uncultivated microbes. *Nature.* 542, 237-241 (2017).
41. I. Grissa, G. Vergnaud, C. Pourcel, CRISPRFinder: a web tool to identify clustered regularly interspaced short palindromic repeats. *Nucleic Acids Res.* 35, W52-W57 (2007).
42. A. Biswas, R. H. J. Staals, S. E. Morales, P. C. Fineran, C. M. Brown, CRISPRDetect: A flexible algorithm to define CRISPR arrays. *BMC Genomics.* 17, 1-14 (2016).
43. A. Stamatakis, RAxML version 8: A tool for phylogenetic analysis and post-analysis of large phylogenies. *Bioinformatics.* 30, 1312-1313 (2014).
44. B. Langmead, S. L. Salzberg, Fast gapped-read alignment with Bowtie 2. *Nat Methods.* 9, 357-359 (2012).
45. H. Ogata et al., KEGG: Kyoto encyclopedia of genes and genomes. *Nucleic Acids Res.* 27, 29-34 (1999).
46. L. B. Harrington et al., A thermostable Cas9 with increased lifetime in human plasma. *Nat. Commun.* 8, 1-7 (2017).
47. G. Crooks, G. Hon, J. Chandonia, S. Brenner, NCBI GenBank FTP Site\nWebLogo: a sequence logo generator. *Genome Res.* 14, 1188-1190 (2004).
48. L. B. Harrington et al., A Broad-Spectrum Inhibitor of CRISPR-Cas9. *Cell.* 170, 1224-1233.e15 (2017).
49. J. S. Chen et al., CRISPR-Cas12a target binding unleashes indiscriminate single-stranded DNase activity. *Science.* 360, 436-439 (2018).
50. Brown et al., Unusual biology across a group comprising more than 15% of domain Bacteria. *Nature.* 523, 208-211 (2015), doi:10.1038/nature14486.

The invention claimed is:

1. A method of assaying for a target nucleic acid in a sample, the method comprising:
   A) contacting the sample with:
      1) a detector nucleic acid; and
      2) a composition comprising
         a) a polypeptide comprising an amino acid sequence that is at least 95% identical to an amino acid sequence selected from SEQ ID NO:1 and SEQ ID NO:3; and
         b) a non-naturally occurring guide nucleic acid, at least a portion of which hybridizes to a segment of the target nucleic acid,
      wherein the polypeptide cleaves the detector nucleic acid upon hybridization of the non-naturally occurring guide nucleic acid to the segment of the target nucleic acid; and
   B) assaying for a change in a signal,
      wherein the change in the signal is produced by cleavage of the detector nucleic acid.

2. The method of claim 1, wherein the length of the polypeptide is not greater than 550 amino acids.

3. The method of claim 1, wherein the guide nucleic acid comprises a transactivating noncoding RNA (trancRNA).

4. The method of claim 1, wherein the detector nucleic acid comprises single stranded DNA.

5. The method of claim 1, wherein the detector nucleic acid comprises at least one component of a fluorescence-emitting dye pair.

6. The method of claim 5, wherein the fluorescence-emitting dye pair is selected from a FRET pair; and a quencher and a fluorophore pair.

7. The method of claim 1, wherein the change in the signal is selected from the group consisting of: a decrease in intensity of the signal, an increase in intensity of the signal, and a change in the wavelength of the signal.

8. The method of claim 1, wherein the change in the signal persists for at least one minute.

9. The method of claim 1, wherein the assaying comprises nanoparticle-based detection, fluorescence, fluorescence polarization, colloid phase transition, colloid phase dispersion, electrochemical detection, or any combination thereof.

10. The method of claim 1, wherein the assaying comprises measuring a detectable signal produced by a reference sample or cell to generate a reference measurement.

11. The method of claim 1, wherein the polypeptide cleaves single stranded DNA in a non-sequence specific manner upon hybridization of the non-naturally occurring guide nucleic acid to the segment of the target nucleic acid.

12. The method of claim 1, wherein the detector nucleic acid does not comprise a sequence that is complementary to the portion of the guide nucleic acid that hybridizes to the segment of the target nucleic acid.

13. The method of claim 1, wherein the target nucleic acid is present in the sample at less than one copy per $10^{18}$ non-target DNAs.

14. The method of claim 1, wherein the target nucleic acid is present in the sample at less than one copy per $10^{12}$ non-target DNAs.

15. The method of claim 1, wherein the target nucleic acid is present in the sample at less than one copy per $10^{7}$ non-target DNAs.

16. The method of claim 1, wherein the target nucleic acid is present in the sample at 1 nM or less.

17. The method of claim 1, wherein the target nucleic acid is present in the sample at 100 fM or less.

18. The method of claim 1, wherein the target nucleic acid is single stranded DNA.

19. The method of claim 1, wherein the target nucleic acid is a bacterial nucleic acid.

20. The method of claim 1, wherein the sample comprises a cell lysate.

21. The method of claim 1, wherein the reference sample comprises a positive control target nucleic acid.

22. The method of claim 1, wherein the reference sample comprises a control non-target nucleic acid.

23. The method of claim 1, wherein the polypeptide has an amino acid sequence identity of at least 98% to SEQ ID NO:1 or SEQ ID NO:3.

24. The method of claim 1, wherein the target nucleic acid is a eukaryotic nucleic acid.

25. The method of claim 1, wherein the target nucleic acid is viral nucleic acid.

26. The method of claim 1, wherein the amino acid sequence of the polypeptide is at least 99% identical to SEQ ID NO: 1 or SEQ ID NO: 3.

27. The method of claim 1, wherein the target nucleic acid is double stranded DNA.

28. The method of claim 1, wherein the guide nucleic acid comprises a transactivating CRISPR RNA (tracrRNA).

29. The method of claim 1, wherein the detector nucleic acid consists of single stranded DNA.

* * * * *

UNITED STATES PATENT AND TRADEMARK OFFICE
CERTIFICATE OF CORRECTION

PATENT NO. : 11,441,137 B2
APPLICATION NO. : 16/884766
DATED : September 13, 2022
INVENTOR(S) : Jennifer A. Doudna et al.

It is certified that error appears in the above-identified patent and that said Letters Patent is hereby corrected as shown below:

In the Specification

In Column 49, Line 42, delete "Minis" and insert --Mirus--.

In Column 63, Line 32, delete "at," and insert --al.,--.

In Column 80, Line 23, delete "10'" and insert --$10^7$--.

In Column 82, Line 40, delete "Ayes" and insert --Aves--.

In Column 93, Line 52, delete "Conrols" and insert --Controls--.

In Column 104, Line 30, delete "Animals" and insert --Organisms--.

In Column 119, Line 35, delete "5200" and insert --S200--.

Signed and Sealed this
Fourteenth Day of February, 2023

*Katherine Kelly Vidal*
*Director of the United States Patent and Trademark Office*